US011155620B2

(12) United States Patent
Sabatos-Peyton et al.

(10) Patent No.: US 11,155,620 B2
(45) Date of Patent: Oct. 26, 2021

(54) METHOD OF DETECTING TIM-3 USING ANTIBODY MOLECULES TO TIM-3

(71) Applicants: Novartis AG, Basel (CH); DANA-FARBER CANCER INSTITUTE, INC., Boston, MA (US); Children's Medical Center Corporation, Boston, MA (US)

(72) Inventors: Catherine Anne Sabatos-Peyton, Cambridge, MA (US); Barbara Brannetti, Cambridge, MA (US); Alan S. Harris, Cambridge, MA (US); Thomas Huber, Basel (CH); Thomas Pietzonka, Basel (CH); Jennifer Marie Mataraza, Cambridge, MA (US); Walter A. Blattler, Brookline, MA (US); Daniel J. Hicklin, Montclair, NJ (US); Maximiliano Vasquez, Palo Alto, CA (US); Rosemarie H. DeKruyff, Portola Valley, CA (US); Dale T. Umetsu, Portola Valley, CA (US); Gordon James Freeman, Brookline, MA (US); Tiancen Hu, Cambridge, MA (US); John A. Taraszka, Cambridge, MA (US); Fangmin Xu, Cambridge, MA (US)

(73) Assignees: Novartis AG, Basel (CH); DANA-FARBER CANCER INSTITUTE, INC., Boston, MA (US); The Children's Medical Center Corporation, Boston, MA (US)

(*) Notice: Subject to any disclaimer, the term of this patent is extended or adjusted under 35 U.S.C. 154(b) by 21 days.

(21) Appl. No.: 16/588,063

(22) Filed: Sep. 30, 2019

(65) Prior Publication Data
US 2020/0223917 A1 Jul. 16, 2020

Related U.S. Application Data

(62) Division of application No. 15/432,819, filed on Feb. 14, 2017, now Pat. No. 10,472,419, which is a division of application No. 14/610,837, filed on Jan. 30, 2015, now Pat. No. 9,605,070.

(60) Provisional application No. 62/094,912, filed on Dec. 19, 2014, provisional application No. 61/934,469, filed on Jan. 31, 2014.

(51) Int. Cl.
C07K 16/28 (2006.01)
G01N 33/574 (2006.01)
A61K 39/395 (2006.01)
A61K 45/06 (2006.01)
G01N 33/68 (2006.01)

(52) U.S. Cl.
CPC ........ *C07K 16/2803* (2013.01); *A61K 39/395* (2013.01); *A61K 39/3955* (2013.01); *A61K 39/39558* (2013.01); *A61K 45/06* (2013.01); *G01N 33/57492* (2013.01); *G01N 33/6893* (2013.01); *C07K 2299/00* (2013.01); *C07K 2317/24* (2013.01); *C07K 2317/31* (2013.01); *C07K 2317/34* (2013.01); *C07K 2317/51* (2013.01); *C07K 2317/515* (2013.01); *C07K 2317/52* (2013.01); *C07K 2317/55* (2013.01); *C07K 2317/56* (2013.01); *C07K 2317/565* (2013.01); *C07K 2317/76* (2013.01); *C07K 2317/92* (2013.01); *C07K 2317/94* (2013.01); *G01N 2333/70596* (2013.01)

(58) Field of Classification Search
CPC ............ C07K 16/2803; C07K 2317/51; C07K 2317/515; C07K 2317/52; C07K 2317/92; C07K 2299/00; C07K 2317/34; C07K 2317/76; C07K 2317/94; C07K 2317/24; C07K 2317/31; C07K 2317/55; C07K 2317/56; C07K 2317/565; G01N 33/57492; G01N 33/6893; G01N 2333/70596; A61K 39/395; A61K 39/39558; A61K 39/3955; A61K 45/06; Y02A 50/30; A61P 7/00
See application file for complete search history.

(56) References Cited

U.S. PATENT DOCUMENTS

| 5,324,514 A | 6/1994 | Sipos |
| 5,434,131 A | 7/1995 | Linsley et al. |
| 5,629,204 A | 5/1997 | Honjo et al. |
| 5,698,520 A | 12/1997 | Honjo et al. |
| 5,811,097 A | 9/1998 | Allison et al. |
| 5,897,862 A | 4/1999 | Hardy et al. |
| 5,968,511 A | 10/1999 | Akita et al. |
| 6,051,227 A | 4/2000 | Allison et al. |
| 6,084,083 A | 7/2000 | Levinson |

(Continued)

FOREIGN PATENT DOCUMENTS

| AU | 774391 B2 | 6/2004 |
| CN | 102492038 A | 6/2012 |

(Continued)

OTHER PUBLICATIONS

[No Author Listed] "Crean un ADN sintético capaz de evolucionar," retrieved from www.nationalgeographic.es/ciencia/crean-un-adn-sintetico-capaz-de-evolucionar, Apr. 25, 2012, last accessed Oct. 18, 2019.

(Continued)

*Primary Examiner* — Sharon X Wen
(74) *Attorney, Agent, or Firm* — Lando & Anastasi LLP

(57) ABSTRACT

Antibody molecules that specifically bind to TIM-3 are disclosed. The anti-TIM-3 antibody molecules can be used to treat, prevent and/or diagnose immune, cancerous, or infectious conditions and/or disorders.

20 Claims, 23 Drawing Sheets
Specification includes a Sequence Listing.

(56) References Cited

U.S. PATENT DOCUMENTS

| | | |
|---|---|---|
| 6,204,371 B1 | 3/2001 | Levinson |
| 6,288,218 B1 | 9/2001 | Levinson |
| 6,414,117 B1 | 7/2002 | Levinson |
| 6,562,343 B1 | 5/2003 | Levinson |
| 6,632,927 B2 | 10/2003 | Adair et al. |
| 6,632,976 B1 | 10/2003 | Tomizuka et al. |
| 6,803,192 B1 | 10/2004 | Chen |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,041,474 B2 | 5/2006 | Kingsbury |
| 7,101,550 B2 | 9/2006 | Wood et al. |
| 7,105,328 B2 | 9/2006 | Wood et al. |
| 7,122,372 B2 | 10/2006 | Hardy et al. |
| 7,169,791 B2 | 1/2007 | Breitenstein et al. |
| 7,172,750 B2 | 2/2007 | Levinson |
| 7,329,639 B2 | 2/2008 | Hardy et al. |
| 7,332,582 B2 | 2/2008 | Hardy et al. |
| 7,414,171 B2 | 8/2008 | Honjo et al. |
| 7,423,128 B2 | 9/2008 | Gazit-Bornstein et al. |
| 7,449,300 B2 | 11/2008 | Chen et al. |
| 7,470,428 B2 | 12/2008 | Kuchroo et al. |
| 7,488,802 B2 | 2/2009 | Collins et al. |
| 7,521,051 B2 | 4/2009 | Collins et al. |
| 7,524,498 B2 | 4/2009 | Hardy et al. |
| 7,553,939 B2 | 6/2009 | McIntire et al. |
| 7,563,869 B2 | 7/2009 | Honjo et al. |
| 7,595,048 B2 | 9/2009 | Honjo et al. |
| 7,598,257 B2 | 10/2009 | Rodgers et al. |
| 7,635,757 B2 | 12/2009 | Freeman et al. |
| 7,695,715 B2 | 4/2010 | Hardy et al. |
| 7,722,868 B2 | 5/2010 | Freeman et al. |
| 7,767,675 B2 | 8/2010 | Zhuo et al. |
| 7,794,710 B2 | 9/2010 | Chen et al. |
| 7,838,220 B2 | 11/2010 | McIntire et al. |
| 7,858,746 B2 | 12/2010 | Honjo et al. |
| 7,943,743 B2 | 5/2011 | Korman et al. |
| 8,008,449 B2 | 8/2011 | Korman et al. |
| 8,039,273 B2 | 10/2011 | Jeffrey |
| 8,039,479 B2 | 10/2011 | Michellys et al. |
| 8,088,905 B2 | 1/2012 | Collins et al. |
| 8,101,176 B2 | 1/2012 | Kuchroo et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,287,856 B2 | 10/2012 | Li et al. |
| 8,329,660 B2 | 12/2012 | Kuchroo et al. |
| 8,354,509 B2 | 1/2013 | Carven et al. |
| 8,361,736 B2 | 1/2013 | Majeti et al. |
| 8,415,355 B2 | 4/2013 | Brain et al. |
| 8,460,886 B2 | 6/2013 | Shibayama et al. |
| 8,460,927 B2 | 6/2013 | Chen |
| 8,461,330 B2 | 6/2013 | Zhuo et al. |
| 8,501,758 B2 | 8/2013 | Huang et al. |
| 8,546,336 B2 | 10/2013 | Chen et al. |
| 8,552,002 B2 | 10/2013 | Ding et al. |
| 8,552,154 B2 | 10/2013 | Freeman et al. |
| 8,552,156 B2 | 10/2013 | Takayanagi et al. |
| 8,568,728 B2 | 10/2013 | Jeffrey |
| 8,580,247 B2 | 11/2013 | Li et al. |
| 8,609,089 B2 | 12/2013 | Langermann et al. |
| 8,617,546 B2 | 12/2013 | Kang et al. |
| 8,647,623 B2 | 2/2014 | Takayanagi et al. |
| 8,685,980 B2 | 4/2014 | Besong et al. |
| 8,697,069 B2 | 4/2014 | Kuchroo et al. |
| 8,709,412 B2 | 4/2014 | Jones et al. |
| 8,709,416 B2 | 4/2014 | Langermann et al. |
| 8,709,429 B2 | 4/2014 | Majeti et al. |
| 8,715,619 B2 | 5/2014 | Karsunky |
| 8,728,474 B2 | 5/2014 | Honjo et al. |
| 8,735,551 B2 | 5/2014 | Garner et al. |
| 8,735,553 B1 | 5/2014 | Li et al. |
| 8,779,105 B2 | 7/2014 | Korman et al. |
| 8,779,108 B2 | 7/2014 | Queva et al. |
| 8,841,418 B2 | 9/2014 | Karsunky et al. |
| 8,900,587 B2 | 12/2014 | Carven et al. |
| 8,927,697 B2 | 1/2015 | Davis et al. |
| 8,952,136 B2 | 2/2015 | Carven et al. |
| 9,045,545 B1 | 6/2015 | Clube |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,727 B2 | 8/2015 | Freeman et al. |
| 9,103,832 B2 | 8/2015 | Takayanagi et al. |
| 9,109,034 B1 | 8/2015 | Clube |
| 9,132,281 B2 | 9/2015 | Zeng et al. |
| 9,175,082 B2 | 11/2015 | Zhou et al. |
| 9,333,256 B2 | 5/2016 | Kuchroo et al. |
| 9,358,289 B2 | 6/2016 | Korman et al. |
| 9,387,247 B2 | 7/2016 | Korman et al. |
| 9,409,970 B2 | 8/2016 | Mikesell et al. |
| 9,457,080 B2 | 10/2016 | Freeman et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,605,070 B2 | 3/2017 | Sabatos-Peyton et al. |
| 9,683,048 B2 | 6/2017 | Freeman et al. |
| 9,815,898 B2 | 11/2017 | Freeman et al. |
| 9,815,901 B2 | 11/2017 | Brogdon et al. |
| 9,834,605 B2 | 12/2017 | Carven et al. |
| 9,884,913 B2 | 2/2018 | Sabatos-Peyton et al. |
| 9,908,936 B2 | 3/2018 | Triebel et al. |
| 9,944,645 B2 | 4/2018 | Zhuo et al. |
| 9,988,452 B2 | 6/2018 | Freeman et al. |
| 10,005,832 B2 | 6/2018 | Yoshida et al. |
| 10,472,419 B2 | 11/2019 | Sabatos-Peyton et al. |
| 10,513,558 B2 | 12/2019 | Tipton et al. |
| 10,561,653 B2 | 2/2020 | Bilic et al. |
| 10,570,204 B2 | 2/2020 | Johnson et al. |
| 10,711,060 B2 | 7/2020 | Triebel et al. |
| 10,851,165 B2 | 12/2020 | Freeman et al. |
| 10,981,990 B2 | 4/2021 | Sabatos-Peyton et al. |
| 2002/0164660 A1 | 11/2002 | Spaulding et al. |
| 2003/0039653 A1 | 2/2003 | Chen et al. |
| 2003/0232323 A1 | 12/2003 | Freeman et al. |
| 2004/0073957 A1 | 4/2004 | Tomizuka et al. |
| 2004/0241745 A1 | 12/2004 | Honjo et al. |
| 2005/0191721 A1 | 9/2005 | Kuchroo et al. |
| 2005/0276756 A1 | 12/2005 | Hoo et al. |
| 2006/0110383 A1 | 5/2006 | Honjo et al. |
| 2006/0210567 A1 | 9/2006 | Collins et al. |
| 2007/0041982 A1 | 2/2007 | Ponath et al. |
| 2007/0065427 A1 | 3/2007 | Freeman et al. |
| 2007/0071675 A1 | 3/2007 | Wu et al. |
| 2007/0122378 A1 | 5/2007 | Freeman et al. |
| 2007/0202100 A1 | 8/2007 | Wood et al. |
| 2008/0025979 A1 | 1/2008 | Honjo et al. |
| 2008/0167287 A1 | 7/2008 | Zhuo et al. |
| 2008/0311117 A1 | 12/2008 | Collins et al. |
| 2009/0055944 A1 | 2/2009 | Korman et al. |
| 2009/0076250 A1 | 3/2009 | Honjo et al. |
| 2009/0155275 A1 | 6/2009 | Wu et al. |
| 2009/0304693 A1 | 12/2009 | Ghayur et al. |
| 2009/0311253 A1 | 12/2009 | Ghayur et al. |
| 2010/0028330 A1 | 2/2010 | Collins et al. |
| 2010/0056576 A1 | 3/2010 | Burger et al. |
| 2010/0061992 A1 | 3/2010 | Anderson et al. |
| 2010/0074900 A1 | 3/2010 | Ghayur et al. |
| 2010/0076178 A1 | 3/2010 | Ghayur et al. |
| 2010/0105667 A1 | 4/2010 | Furet et al. |
| 2010/0136009 A1 | 6/2010 | Papkoff et al. |
| 2010/0203056 A1 | 8/2010 | Irving et al. |
| 2010/0233079 A1 | 9/2010 | Jakob et al. |
| 2010/0233183 A1 | 9/2010 | Triebel et al. |
| 2010/0260668 A1 | 10/2010 | Ghayur et al. |
| 2010/0266531 A1 | 10/2010 | Hsieh et al. |
| 2010/0266617 A1 | 10/2010 | Carven et al. |
| 2011/0008766 A1 | 1/2011 | Ghayur et al. |
| 2011/0044894 A1 | 2/2011 | Karsunky |
| 2011/0044980 A1 | 2/2011 | Ghayur et al. |
| 2011/0054151 A1 | 3/2011 | Lazar et al. |
| 2011/0059106 A1 | 3/2011 | Kuchroo et al. |
| 2011/0081341 A1 | 4/2011 | Honjo et al. |

(56) References Cited

U.S. PATENT DOCUMENTS

| | | |
|---|---|---|
| 2011/0091372 A1 | 4/2011 | Ghayur et al. |
| 2011/0091463 A1 | 4/2011 | Ghayur et al. |
| 2011/0110852 A1 | 5/2011 | Miller et al. |
| 2011/0123550 A1 | 5/2011 | Shibayama et al. |
| 2011/0136781 A1 | 6/2011 | Zhuo et al. |
| 2011/0150892 A1 | 6/2011 | Thudium et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0209230 A1 | 8/2011 | Korman et al. |
| 2011/0212094 A1 | 9/2011 | Ghayur et al. |
| 2011/0229461 A1 | 9/2011 | Tyson |
| 2011/0236375 A1 | 9/2011 | Lazar et al. |
| 2011/0263827 A1 | 10/2011 | Ghayur et al. |
| 2011/0271358 A1 | 11/2011 | Freeman et al. |
| 2011/0280800 A1 | 11/2011 | Wu et al. |
| 2011/0280877 A1 | 11/2011 | Tamada |
| 2011/0287009 A1 | 11/2011 | Scheer et al. |
| 2012/0014957 A1 | 1/2012 | Ghayur et al. |
| 2012/0034160 A1 | 2/2012 | Ghayur et al. |
| 2012/0039870 A9 | 2/2012 | Dolk et al. |
| 2012/0039906 A1 | 2/2012 | Olive |
| 2012/0070450 A1 | 3/2012 | Ishikawa et al. |
| 2012/0076805 A1 | 3/2012 | Sharpe et al. |
| 2012/0087858 A1 | 4/2012 | Ghayur et al. |
| 2012/0100131 A1 | 4/2012 | Takayanagi et al. |
| 2012/0107234 A1 | 5/2012 | Pedersen et al. |
| 2012/0114649 A1 | 5/2012 | Langermann et al. |
| 2012/0141501 A1 | 6/2012 | Yoshida et al. |
| 2012/0195900 A1 | 8/2012 | Ghayur et al. |
| 2012/0201746 A1 | 8/2012 | Liu et al. |
| 2012/0201824 A1 | 8/2012 | Wasik |
| 2012/0258108 A1 | 10/2012 | Ghayur et al. |
| 2012/0263722 A1 | 10/2012 | Ghayur et al. |
| 2013/0005216 A1 | 1/2013 | Rittberger |
| 2013/0017199 A1 | 1/2013 | Langermann |
| 2013/0022623 A1 | 1/2013 | Karsunky et al. |
| 2013/0095098 A1 | 4/2013 | Tyson |
| 2013/0109843 A1 | 5/2013 | Carven et al. |
| 2013/0133091 A1 | 5/2013 | Korman et al. |
| 2013/0156774 A1 | 6/2013 | Kuchroo et al. |
| 2013/0183688 A1 | 7/2013 | Kuchroo et al. |
| 2013/0202623 A1 | 8/2013 | Chomont et al. |
| 2013/0230514 A1 | 9/2013 | Langermann et al. |
| 2013/0324515 A1 | 12/2013 | Zhuo et al. |
| 2014/0044728 A1 | 2/2014 | Takayanagi et al. |
| 2014/0044738 A1 | 2/2014 | Langermann et al. |
| 2014/0065142 A1 | 3/2014 | Roschke et al. |
| 2014/0155678 A1 | 6/2014 | Zeng et al. |
| 2014/0178370 A1 | 6/2014 | Freeman et al. |
| 2014/0212422 A1 | 7/2014 | Korman et al. |
| 2014/0234320 A1 | 8/2014 | Croft et al. |
| 2014/0242094 A1 | 8/2014 | Kuchroo et al. |
| 2014/0274788 A1 | 9/2014 | Ishikawa et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341902 A1 | 11/2014 | Maecker et al. |
| 2014/0348743 A1 | 11/2014 | Korman et al. |
| 2015/0017185 A1 | 1/2015 | Akbar et al. |
| 2015/0023986 A1 | 1/2015 | Jones et al. |
| 2015/0079109 A1 | 3/2015 | Li et al. |
| 2015/0086574 A1 | 3/2015 | Karsunky et al. |
| 2015/0093380 A1 | 4/2015 | Honjo et al. |
| 2015/0210769 A1 | 7/2015 | Freeman et al. |
| 2015/0218274 A1 | 8/2015 | Sabatos-Peyton et al. |
| 2015/0232555 A1 | 8/2015 | Carven et al. |
| 2015/0259420 A1 | 9/2015 | Triebel et al. |
| 2015/0290316 A1 | 10/2015 | Graziano et al. |
| 2015/0307609 A1 | 10/2015 | Lonberg et al. |
| 2016/0002334 A1 | 1/2016 | Kuchroo et al. |
| 2016/0068601 A1 | 3/2016 | Brogdon et al. |
| 2016/0108123 A1 | 4/2016 | Freeman et al. |
| 2016/0222121 A1 | 8/2016 | Johnson et al. |
| 2016/0326178 A1 | 11/2016 | Zhuo et al. |
| 2017/0044259 A1 | 2/2017 | Tipton et al. |
| 2017/0088615 A1 | 3/2017 | Korman et al. |
| 2017/0137514 A1 | 5/2017 | Lonberg et al. |
| 2017/0190777 A1 | 7/2017 | Sabatos-Peyton et al. |
| 2017/0198041 A1 | 7/2017 | Sabatos-Peyton et al. |
| 2017/0209574 A1 | 7/2017 | Cao et al. |
| 2017/0210804 A1 | 7/2017 | Triebel et al. |
| 2017/0247456 A1 | 8/2017 | Freeman et al. |
| 2017/0281624 A1 | 10/2017 | Peters et al. |
| 2017/0296659 A1 | 10/2017 | Lebwohl et al. |
| 2017/0304443 A1 | 10/2017 | Lebwohl et al. |
| 2017/0340733 A1 | 11/2017 | Cao |
| 2018/0066054 A1 | 3/2018 | Thudium et al. |
| 2018/0086830 A1 | 3/2018 | Triebel et al. |
| 2018/0155427 A1 | 6/2018 | Freeman et al. |
| 2018/0186882 A1 | 7/2018 | Freeman et al. |
| 2018/0207273 A1 | 7/2018 | Dranoff et al. |
| 2018/0222982 A1 | 8/2018 | Dranoff et al. |
| 2018/0282340 A1 | 10/2018 | Zhuo et al. |
| 2018/0340025 A1 | 11/2018 | Dranoff et al. |
| 2018/0371093 A1 | 12/2018 | Bilic et al. |
| 2020/0030442 A1 | 1/2020 | Cao |
| 2020/0172617 A1 | 6/2020 | Stein et al. |
| 2020/0223917 A1 | 7/2020 | Sabatos-Peyton et al. |
| 2020/0223924 A1 | 7/2020 | Stein et al. |
| 2020/0277378 A1 | 9/2020 | Sabatos-Peyton et al. |
| 2020/0308277 A1 | 10/2020 | Sabatos-Peyton et al. |
| 2020/0339689 A1 | 10/2020 | Freeman et al. |
| 2020/0377600 A1 | 12/2020 | Johnson et al. |
| 2021/0000951 A1 | 1/2021 | Cao et al. |

FOREIGN PATENT DOCUMENTS

| | | |
|---|---|---|
| CN | 103079644 A | 5/2013 |
| CN | 103242448 A | 8/2013 |
| EP | 0670369 A2 | 9/1995 |
| EP | 0742795 A1 | 11/1996 |
| EP | 1165616 A1 | 1/2002 |
| EP | 1210424 A1 | 6/2002 |
| EP | 1334659 A1 | 8/2003 |
| EP | 1385533 A1 | 2/2004 |
| EP | 1445264 A1 | 8/2004 |
| EP | 1537878 A1 | 6/2005 |
| EP | 1576014 A1 | 9/2005 |
| EP | 1591527 A1 | 11/2005 |
| EP | 1870399 A1 | 12/2007 |
| EP | 1896582 A1 | 3/2008 |
| EP | 2161336 A1 | 3/2010 |
| EP | 2195347 A1 | 6/2010 |
| EP | 2206517 A1 | 7/2010 |
| EP | 2243493 A1 | 10/2010 |
| EP | 2270051 A2 | 1/2011 |
| EP | 2307050 A1 | 4/2011 |
| EP | 2328920 A2 | 6/2011 |
| EP | 2342228 A1 | 7/2011 |
| EP | 2342229 A1 | 7/2011 |
| EP | 2360254 A1 | 8/2011 |
| EP | 2370593 A2 | 10/2011 |
| EP | 2397155 A1 | 12/2011 |
| EP | 2397156 A1 | 12/2011 |
| EP | 2412825 A1 | 2/2012 |
| EP | 2417984 A1 | 2/2012 |
| EP | 2418278 A2 | 2/2012 |
| EP | 2439272 A2 | 4/2012 |
| EP | 2439273 A2 | 4/2012 |
| EP | 2482849 A2 | 8/2012 |
| EP | 2504364 A1 | 10/2012 |
| EP | 2099447 B1 | 11/2012 |
| EP | 2535354 A1 | 12/2012 |
| EP | 2545076 A1 | 1/2013 |
| EP | 2545078 A1 | 1/2013 |
| EP | 2051990 B1 | 2/2013 |
| EP | 2581113 A1 | 4/2013 |
| EP | 2170959 B1 | 10/2013 |
| EP | 2691112 A1 | 2/2014 |
| EP | 2699264 A1 | 2/2014 |
| EP | 2723381 A2 | 4/2014 |
| EP | 2320940 B1 | 3/2015 |
| EP | 2905030 A1 | 8/2015 |

(56) References Cited

FOREIGN PATENT DOCUMENTS

| | | |
|---|---|---|
| EP | 2344474 B1 | 9/2015 |
| EP | 2927240 A1 | 10/2015 |
| EP | 2474545 B1 | 11/2016 |
| EP | 3222634 A1 | 9/2017 |
| JP | H07291996 A | 11/1995 |
| JP | 2002194491 A | 7/2002 |
| JP | 2003029846 A | 1/2003 |
| JP | 2004512005 A | 4/2004 |
| RU | 2494107 C2 | 9/2013 |
| WO | WO-8808135 A1 | 10/1988 |
| WO | WO-9520605 A1 | 8/1995 |
| WO | WO-1996027603 A1 | 9/1996 |
| WO | WO-9707671 A1 | 3/1997 |
| WO | WO-0032231 A1 | 6/2000 |
| WO | WO-0058363 A1 | 10/2000 |
| WO | WO-0071078 A2 | 11/2000 |
| WO | WO-0073498 A1 | 12/2000 |
| WO | WO-0114424 A2 | 3/2001 |
| WO | WO-0114556 A1 | 3/2001 |
| WO | WO-0114557 A1 | 3/2001 |
| WO | WO-0139722 A2 | 6/2001 |
| WO | WO-01077342 A1 | 10/2001 |
| WO | WO-01083750 A2 | 11/2001 |
| WO | WO-200194413 A2 | 12/2001 |
| WO | WO-0200692 A2 | 1/2002 |
| WO | WO-0200730 A2 | 1/2002 |
| WO | WO-0224891 A2 | 3/2002 |
| WO | WO-2002022577 A2 | 3/2002 |
| WO | WO-0232378 A2 | 4/2002 |
| WO | WO-0234205 A2 | 5/2002 |
| WO | WO-0239813 A1 | 5/2002 |
| WO | WO-02078731 A1 | 10/2002 |
| WO | WO-02079499 A1 | 10/2002 |
| WO | WO-02086083 A2 | 10/2002 |
| WO | WO-03000066 A1 | 1/2003 |
| WO | WO-03002722 A2 | 1/2003 |
| WO | WO-03011911 A1 | 2/2003 |
| WO | WO-03033644 A2 | 4/2003 |
| WO | WO-03042402 A2 | 5/2003 |
| WO | WO-03063792 A2 | 8/2003 |
| WO | WO-03077914 A1 | 9/2003 |
| WO | WO-03099196 A2 | 12/2003 |
| WO | WO-2004004771 A1 | 1/2004 |
| WO | WO-2004005281 A1 | 1/2004 |
| WO | WO-2004007679 A2 | 1/2004 |
| WO | WO-2004056875 A1 | 7/2004 |
| WO | WO-2004072286 A1 | 8/2004 |
| WO | WO-2004078928 A2 | 9/2004 |
| WO | WO-2005027854 A2 | 3/2005 |
| WO | WO-2005033144 A2 | 4/2005 |
| WO | WO-2005097211 A2 | 10/2005 |
| WO | WO-2006004988 A2 | 1/2006 |
| WO | WO-2006021955 A2 | 3/2006 |
| WO | WO-2006042237 A2 | 4/2006 |
| WO | WO-2006121168 A1 | 11/2006 |
| WO | WO-2006124269 A2 | 11/2006 |
| WO | WO-2006133396 A2 | 12/2006 |
| WO | WO-2007005874 A2 | 1/2007 |
| WO | WO-2007011968 A2 | 1/2007 |
| WO | WO-2007024705 A2 | 3/2007 |
| WO | WO-2007024715 A2 | 3/2007 |
| WO | WO-2007070514 A1 | 6/2007 |
| WO | WO-2007082154 A2 | 7/2007 |
| WO | WO-2007084786 A1 | 7/2007 |
| WO | WO-2007113648 A2 | 10/2007 |
| WO | WO-2007146968 A2 | 12/2007 |
| WO | WO-2008016893 A1 | 2/2008 |
| WO | WO-2008060617 A2 | 5/2008 |
| WO | WO-2008064157 A1 | 5/2008 |
| WO | WO-2008071447 A2 | 6/2008 |
| WO | WO-2008073687 A2 | 6/2008 |
| WO | WO-2008083174 A2 | 7/2008 |
| WO | WO-2008085562 A2 | 7/2008 |
| WO | WO-2008156712 A1 | 12/2008 |
| WO | WO-2009014708 A2 | 1/2009 |
| WO | WO-2009024531 A1 | 2/2009 |
| WO | WO-2009029342 A2 | 3/2009 |
| WO | WO-2009091547 A1 | 7/2009 |
| WO | WO-2009097394 A2 | 8/2009 |
| WO | WO-2009101611 A1 | 8/2009 |
| WO | WO-2009114335 A2 | 9/2009 |
| WO | WO-2009120905 A2 | 10/2009 |
| WO | WO-2009141386 A1 | 11/2009 |
| WO | WO-2010001617 A1 | 1/2010 |
| WO | WO-2010019570 A2 | 2/2010 |
| WO | WO-2010026124 A1 | 3/2010 |
| WO | WO-2010027423 A2 | 3/2010 |
| WO | WO-2010027827 A2 | 3/2010 |
| WO | WO-2010027828 A2 | 3/2010 |
| WO | WO-2010029082 A1 | 3/2010 |
| WO | WO-2010029434 A1 | 3/2010 |
| WO | WO-2010029435 A1 | 3/2010 |
| WO | WO-2010036959 A2 | 4/2010 |
| WO | WO-2010051502 A2 | 5/2010 |
| WO | WO-2010063011 A2 | 6/2010 |
| WO | WO-2010077634 A1 | 7/2010 |
| WO | WO-2010084999 A1 | 7/2010 |
| WO | WO-2010089411 A2 | 8/2010 |
| WO | WO-2010098788 A2 | 9/2010 |
| WO | WO-2010102278 A1 | 9/2010 |
| WO | WO-2010110346 A1 | 9/2010 |
| WO | WO-2010117057 A1 | 10/2010 |
| WO | WO-2011005481 A1 | 1/2011 |
| WO | WO-2011011027 A1 | 1/2011 |
| WO | WO-2011025927 A1 | 3/2011 |
| WO | WO-2011034605 A2 | 3/2011 |
| WO | WO-2011041613 A2 | 4/2011 |
| WO | WO-2011066342 A2 | 6/2011 |
| WO | WO-2011066389 A1 | 6/2011 |
| WO | WO-2011069104 A2 | 6/2011 |
| WO | WO-2011076786 A1 | 6/2011 |
| WO | WO-2011100841 A1 | 8/2011 |
| WO | WO-2011110604 A1 | 9/2011 |
| WO | WO-2011110621 A1 | 9/2011 |
| WO | WO-2011131472 A1 | 10/2011 |
| WO | WO-2011155607 A1 | 12/2011 |
| WO | WO-2011159877 A2 | 12/2011 |
| WO | WO-2012018538 A2 | 2/2012 |
| WO | WO-2012022814 A1 | 2/2012 |
| WO | WO-2012064733 A2 | 5/2012 |
| WO | WO-2012079000 A1 | 6/2012 |
| WO | WO-2012106587 A1 | 8/2012 |
| WO | WO-2012135408 A1 | 10/2012 |
| WO | WO-2012145493 A1 | 10/2012 |
| WO | WO-2012177624 A2 | 12/2012 |
| WO | WO-2012177788 A1 | 12/2012 |
| WO | WO-2013006490 A2 | 1/2013 |
| WO | WO-2013006727 A1 | 1/2013 |
| WO | WO-2013019906 A1 | 2/2013 |
| WO | WO-2013043647 A1 | 3/2013 |
| WO | WO-2013066761 A1 | 5/2013 |
| WO | WO-2013079174 A1 | 6/2013 |
| WO | WO-2013079945 A1 | 6/2013 |
| WO | WO-2013169693 A1 | 11/2013 |
| WO | WO-2013173223 A1 | 11/2013 |
| WO | WO-2013181452 A1 | 12/2013 |
| WO | WO-2013181634 A2 | 12/2013 |
| WO | WO-2013184757 A1 | 12/2013 |
| WO | WO-2014008218 A1 | 1/2014 |
| WO | WO-2014018632 A1 | 1/2014 |
| WO | WO-2014022138 A2 | 2/2014 |
| WO | WO-2014022332 A1 | 2/2014 |
| WO | WO-2014022758 A1 | 2/2014 |
| WO | WO-2014047350 A1 | 3/2014 |
| WO | WO-2014055648 A1 | 4/2014 |
| WO | WO-2014055897 A2 | 4/2014 |
| WO | WO-2014072493 A1 | 5/2014 |
| WO | WO-2014085318 A1 | 6/2014 |
| WO | WO-2014100079 A1 | 6/2014 |
| WO | WO-2014165082 A2 | 10/2014 |
| WO | WO-2014165422 A1 | 10/2014 |
| WO | WO-2014179664 A2 | 11/2014 |
| WO | WO-2014189805 A1 | 11/2014 |
| WO | WO-2014195852 A1 | 12/2014 |

(56) References Cited

FOREIGN PATENT DOCUMENTS

| | | |
|---|---|---|
| WO | WO-2015009856 A2 | 1/2015 |
| WO | WO-2015026634 A1 | 2/2015 |
| WO | WO-2015026684 A1 | 2/2015 |
| WO | WO-2015035606 A1 | 3/2015 |
| WO | WO-2015036394 A1 | 3/2015 |
| WO | WO-2015036499 A1 | 3/2015 |
| WO | WO-2015036511 A1 | 3/2015 |
| WO | WO-2015042246 A1 | 3/2015 |
| WO | WO-2015048312 A1 | 4/2015 |
| WO | WO-2015048520 A1 | 4/2015 |
| WO | WO-2015061668 A1 | 4/2015 |
| WO | WO-2015070060 A1 | 5/2015 |
| WO | WO-2015081158 A1 | 6/2015 |
| WO | WO-2015085847 A1 | 6/2015 |
| WO | WO-2015088847 A1 | 6/2015 |
| WO | WO-2015095423 A2 | 6/2015 |
| WO | WO-2015095811 A2 | 6/2015 |
| WO | WO-2015103602 A1 | 7/2015 |
| WO | WO-2015109124 A2 | 7/2015 |
| WO | WO-2015109391 A1 | 7/2015 |
| WO | WO-2015112800 A1 | 7/2015 |
| WO | WO-2015112805 A1 | 7/2015 |
| WO | WO-2015112900 A1 | 7/2015 |
| WO | WO-2015117002 A1 | 8/2015 |
| WO | WO-2015118175 A2 | 8/2015 |
| WO | WO-2015119944 A1 | 8/2015 |
| WO | WO-2015120198 A1 | 8/2015 |
| WO | WO-2015138920 A1 | 9/2015 |
| WO | WO-2015181342 A1 | 12/2015 |
| WO | WO-2015195163 A1 | 12/2015 |
| WO | WO-2016000619 A1 | 1/2016 |
| WO | WO-2016028672 A1 | 2/2016 |
| WO | WO-2016040880 A1 | 3/2016 |
| WO | WO-2016040882 A1 | 3/2016 |
| WO | WO-2016040892 A1 | 3/2016 |
| WO | WO-2016054555 A2 | 4/2016 |
| WO | WO-2016061142 A1 | 4/2016 |
| WO | WO-2016069727 A1 | 5/2016 |
| WO | WO-2016079049 A1 | 5/2016 |
| WO | WO-2016100882 A1 | 6/2016 |
| WO | WO-2016161239 A1 | 10/2016 |
| WO | WO-2016161270 A1 | 10/2016 |
| WO | 2017017623 A1 | 2/2017 |
| WO | 2017017624 A1 | 2/2017 |
| WO | WO-2017019894 A1 | 2/2017 |
| WO | WO-2017019896 A1 | 2/2017 |
| WO | WO-2017019897 A1 | 2/2017 |
| WO | WO-2017034916 A1 | 3/2017 |
| WO | WO-2017097407 A1 | 6/2017 |
| WO | WO-2017106656 A1 | 6/2017 |
| WO | WO-2017189433 A1 | 11/2017 |
| WO | WO-2019006007 A1 | 1/2019 |
| WO | WO-2019018640 A1 | 1/2019 |
| WO | WO-2019018730 A1 | 1/2019 |
| WO | WO-2019099838 A1 | 5/2019 |
| WO | WO-2019200229 A1 | 10/2019 |

OTHER PUBLICATIONS

[No Author Listed] Press Release: "Bristol-Myers Squibb Announces Collaboration to Evaludate Opdivo (nivolumab) in Combination with Targeted Therapies from Novartis to Treat Non-Small Cell Lung Cancer (NSCLC)," dated Oct. 6, 2014.

Abbas et al. "Functional diversity of helper T lymphocytes" Nature (1996) vol. 383, pp. 787-793.

Abbas, A.K., et al., Cellular and Molecular Immunobiology, 2nd ed., pp. 8, 47-50, W.B. Saunders Company, United States (1991).

Acquaviva et al: "FGFR3 Translocations in Bladder Cancer: Differential Sensitivity to HSP90 Inhibition Based on Drug Metabolism". Molecular Cancer Research. vol. 12. No. 7. Jul. 1, 2014 (Jul. 1, 2014). pp. 1042-1054.

Adams, G.P. and Weiner, L.M., "Monoclonal antibody therapy of cancer," Nature Biotechnology 23(9):1147-1157, Nature Publishing Group, United States (2005).

Agata, Y., et al., "Expression of the PD-1 antigen on the surface of stimulated mouse T and B lymphocytes," International Immunology 8(5):765-772, Oxford University Press, England (1996).

Allard et al. "Targeting CD73 Enhances the Antitumor Activity of Anti-FD-1 and Anti-CTLA-4 mAbs" Clinical Cancer Research (2013) vol. 19, No. 20, pp. 5626-5635.

Allison, J.P. and Krummel, M.F., "The Yin and Yang of T Cell Costimulation," Science 270(5238):932-933, American Association for the Advancement of Science, United States (1995).

Almagro et al. "Humanization of Antibodies" Frontiers in Bioscience (2008) vol. 13, pp. 1619-1633.

Amin et al: "Nivolumab (anti-PD-1; BMS-936558, ONO-4538) in combination with sunitinib or pazopanib in patients (pts) with metastatic renal cell carcinoma (mRCC)" Journal of Clinical Oncology (2014) vol. 32, No. 15 suppl, Abstract 5010.

Anderson "TIM-3 as a therapeutic target in human inflammatory diseases" Expert Opinion on Therapeutic Targets (2007) vol. 11, issue 8, pp. 1005-1009.

Anderson et al. "Lag-3, Tim-3, and TIGIT: Co-inhibitory Receptors with Specialized Functions in Immune Regulation" Immunity (2016) vol. 44, pp. 989-1004.

Anderson et al. "Promotion of Tissue Inflammation by the Immune Receptor Tim-3 Expressed on Innate Immune Cells" Science (2007) vol. 318, pp. 1141-1143.

Anderson et al. "Tim-3, a negative regulator of anti-tumor immunity" Current Opinion in Immunology (2012) vol. 24, No. 2, pp. 213-216.

Anderson, "Tim-3: An Emerging Target in the Cancer Immunotherapy Landscape" Cancer Immunology Research (2014) vol. 2 No. 5 pp. 393-398.

Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (Feb. 2005).

Ansari, M.J., et al., "The programmed death-1 (PD-1) pathway regulates autoimmune diabetes in nonobese diabetic (NOD) mice," The Journal of Experimental Medicine 198(1):63-69, The Rockefeller University Press, United States (2003).

Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).

Armand, P., et al., "289 Nivolumab in Patients with relapsed or Refractory Hodgkin Lymphoma-Preliminary Safety, Efficacy and Biomarker Results of a Phase I Study," 56th ASH Annual Meeting and Exposition, Abstracts & Program, San Francisco, CA, Dec. 6-9, 2014.

Ascierto et al. "Future perspectives in melanoma research" meeting report from the "Melanoma Bridge", Napoli, Dec. 5-8, 2013 Journal of Translational Medicine (2014) vol. 12, No. 277, pp. 1-29.

Ashworth et al. "Management of a Patient With Advanced BRAF-Mutant Melanoma" Journal of the National Comprehensive Cancer Network (2014) vol. 12, No. 3, pp. 315-319.

Aspeslagh et al. "Rationale for anti-OX40 cancer immunotherapy" European Journal of Cancer (2016) vol. 52, pp. 50-66.

Baixeras et al., "Characterization of the Lymphocyte Activation Gene 3-Encoded Protein. A New Ligand for Human Leukocyte Antigen Class II Antgens," J Exp Med (1992) vol. 176, pp. 327-337.

Barber, Daniel L., et al.; "Restoring function in exhausted CD8 T cells during chronic viral infection"; Nature 439:682-687 (2006).

Batus et al. "Optimal Management of Metastatic Melanoma: Current Strategies and Future Directions" Am. J. Clin. Dermatol. (2013) vol. 14, No. 3, pp. 179-194.

Beckman et al. "Antibody Constructs in Cancer Therapy" Cancer (2007) vol. 109, No. 2, pp. 170-179.

Bellucci et al: "JAK1 and JAK2 Modulate Tumor Cell Susceptibility to Natural Killer (NK) Cells Through Regulation of PDLI Expression", Blood (Nov. 15, 2013), Retrieved from the Internet: URL:http://www.bloodjournal.orgjcontent/122/21/3472.full.pdf [retrieved on Apr. 14, 2016].

(56) References Cited

OTHER PUBLICATIONS

Bennett, F., et al., "Program death-1 engagement upon TCR activation has distinct effects on costimulation and cytokine-driven proliferation: attenuation of ICOS, IL-4, and IL-21, but not CD28, IL-7, and IL-15 responses," The Journal of Immunology170(2):711-718, The American Association of Immunologists, United States (2003).

Benson et al. "The PD-1/PD-L1 axis modulates the natural killer cell versus multiple myeloma effect: a therapeutic target for CT-011, a novel monoclonal anti-PD-1 antibody" Blood (2010) vol. 116, No. 13, pp. 2286-2294.

Berg, J.M., et al., "The Immune System," in Biochemistry 5th ed., pp. 921-950, W.H. Freeman and Company, United States (2002).

Berger, R., et al., "Phase I safety and pharmacokinetic study of CT-011, a humanized antibody interacting with PD-1, in patients with advanced hematologic malignancies," Clinical Cancer Research 14(10):3044-3051, American Association for CancerResearch, United States (2008).

Berrien-Elliott et al., "Durable Adoptive Immunotherapy for Leukemia Produced by Manipulation of Multiple Regulatory Pathways of $CD8_+$ T-Cell Tolerance," Cancer Research (2012) vol. 73, pp. 605-616.

Bigras, et al. "Spatial distribution of DNA ploidy in colorectal carcinoma" Analytic Cellular Pathology (1994) vol. 7, pp. 289-300.

Blank et al "Combination of targeted therapy and immunotherapy in melanoma" Cancer Immunol Immunother (2011) vol. 60, pp. 1359-1371.

Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).

Blank, C., et al., "PD-L1/B7H-1 inhibits the effector phase of tumor rejection by T cell receptor (TCR) transgenic $CD8_+$ T cells," Cancer Research 64(3):1140-1145, American Association for Cancer Research, United States (2004).

Blank, Christian, et al.; "Contribution of the PD-L1/PD-1 pathway to T-cell exhaustion: an update on implications for chronic infections and tumor evasion"; Cancer Immunol. Immunotherapy; 56(5):739-745 (2007).

Blazar, B.R., et al., "Infusion of anti-B7.1 (CD80) and anti-B7.2 (CD86) monoclenal antibodies inhibits murine graft-versus-host disease lethality in part via direct effects on $CD4_+$ and $CD8_+$ T cells," The Journal of Immunology 157(8):3250-3259, TheAmerican Association of Immunologists, United States (1996).

Borate et al., "Phase lb Study of the Anti-TIM-3 Antibody MBG453 in Combination with Decitabine in Patients with High-Risk Myelodysplastic Syndrome (MDS) and Acute Myeloid Leukemia (AML)," Blood (2019) vol. 134, Supp. 1, Abstract 637, 5 pages.

Brahmer et al., "Safety and Activity of Anti-PD-L1 Antibody in Patients with Advanced Cancer," N Engl J Med (2012) vol. 366, pp. 2455-2465.

Brahmer, J.R., et al., "Safety and activity of MDX-1106 (ONO-4538) anti-PD-1 monoclonal antibody in patients with selected refractory or relapsed malignancies," Journal of Clinical Oncology 26:Abstract No. 3006, American Society of ClinicalOncology, United States (2008).

Brahmer., J.R., et al., "Phase I study of single-agent anti-programmed death-1 (MDX-1106) in refractory solid tumors: Safety, clinical activity, pharmacodynamics, and immunologic correlates," Journal of Clinical Oncology 28(19):3167-3175, AmericanSociety of Clinical Oncology, United States (2005).

Brand et al., "Prospect for Anti-HER2 Receptor Therapy in Breast Cancer," Anticancer Research (2006) vol. 26, pp. 463-470.

Brown et al, "Blockade of Programmed Death-1 Ligands on Dendritic Cells Enhances T Cell Activation and Cytokine Production", J. Immunol. (2003) vol. 170, pp. 1257-1266.

Brown et al., "Tolerance to Single, but Not Multiple, Amino Acid Replacements in Antibody $V_H$ CDR2: A Means of Minimizing B Cell Wastage from Somatic Hypermutation?" J Immunol (1996) vol. 156, pp. 3285-3291.

Brown, J.A., et al., "Expression and functional consequences PD-1 ligands on natural APCS and tumors," The FASEB Journal 15(4):A345 (abstract No. 275.23), Federation of American Societies for Experimental Biology, United States (2001).

Brunet et al., "A new member of the immunoglobin superfamily CTLA-4," Nature (1987) vol. 328, pp. 267-270.

Butte et al, "Interaction of human PD-L1 and B7-1", Mol Immunol (2008) vol. 45, pp. 3567-3572.

Butte et al., "Programmed Death-1 Ligand 1 Interacts Specifically with the B7-1 Costimulatory Molecule to Inhibit T Cell Responses," Immunity (2007) vol. 27, pp. 111-122.

Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215,Elsevier, the Netherlands (1984).

Cao et al. "Genetic variations and haplotypes in TIM-3 gene and the risk pf gastric cancer" Cancer Immunol Immunother (2010) vol. 59 pp. 1851-1857.

Carreno, B,M, and Collins, M., "The B7 family of ligands and its receptors: new pathways for costimulation and inhibition of immune responses," Annual Review of Immunology 20:29-53, Annual Reviews, United States (2002).

Carreno, B.M., "BTLA: a new inhibitory receptor with a B7-like ligand," TRENDS in Immunology 24(10):524-527, Elsevier, England (2003).

Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (2003).

Carter, L.L., et al., "PD-1:PD-L inhibitory pathway affects both CD4(+) and CD8(+) T cells and is overcome by IL-2," European Journal of Immunology 32(3):634-643, Wiley-VCH Verlag GmbH, Germany (2002).

Carvalho et al., "Doxorubicin: the good, the bad and the ugly effect," Current Medicinal Chemistry (2009) vol. 16, No. 25, pp. 3267-3285.

Casati et al., "Soluble Human LAG-3 Molecule Amplifies the in vitro Generation of Type 1 Tumor-Specific Immunity," Cancer Res (2006) vol. 66, No. 8, pp. 4450-4460.

Catherine Sabatos-Peyton, MBG453: A high affinity, ligand-blocking anti-TIM-3 monoclonal Ab. American Association for Cancer Research (AACR) Annual Meeting, Apr. 17, 2016, New Orleans, Louisiana.

Ceeraz et al., "B7 family checkpoint regulators in immune regulation and disease," Trends Immunol (2013) vol. 34, No. 11, pp. 556-563.

Cespedes "Mouse models in ocogenesis and cancer therapy" Clin. Tranl. Oncol. (2006) vol. 8, No. 5, pp. 318-329.

Chan et al. "Therapeutic antibodies for autoimmunity and inflammation" Nature Reviews Immunology (2010) vol. 10, pp. 301-316.

Chen, L., "Co-inhibitory molecules of the B7-CD28 family in the control of T-cell immunity," Nature Reviews Immunology 4(5):336-347, Nature Publishing Group, England (2004).

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).

Chervontseva A M et al: "Effect of cytarabine on expression of cell adhesion molecules and on endothelium-leukocyte interaction in vitro.", Terapevticheskii Arkhiv 2006, vol. 78, No. 7, 2006, pp. 67-72.

Chesi et al., "IAP antagonists induce anti-tumor immunity in multiple myeloma," Nat Med (2016) vol. 22, No. 12, pp. 1411-1420.

Christiansen et al: "Eradication of solid tumors using histone deacetylase inhibitors combined with irrmune-stimulating antibodies", Proceedings of the National Academy of Sciences, vol. 108 No. 10, Feb. 22, 2011 (Feb. 22, 2011), pp. 4141-4146.

Christiansson Lisa et al: "The tyrosine kinase inhibitors imatinib and dasatinib reduce myeloid suppressor cells and release effector lymphocyte responses.", Molecular Cancer Therapeutics, vol. 14, No. 5, May 2015 (May 2015), pp. 1181-1191.

(56) References Cited

OTHER PUBLICATIONS

ClincalTrials.gov Identifier: NCT01988896 "A Phase 1b Study of MPDL3280A (an Engineered Anti-PDL1 Antibody) in Combination With Cobimetinib in Patients With Locally Advanced or Metastatic Solid Tumors" Clinicaltrials.gov, last updated Dec. 1, 2014.
ClincalTrials.gov Identifier: NCT02323126 "Study of Efficacy and Safety of Nivolumab in Combination With EGF816 and of Nivolumab in Combination With INC280 in Patients With Previously Treated Non-small Cell Lung Cancer (EGF816)," Clinicaltrials.gov, last updated Jun. 6, 2018.
ClinicalTrials.gov "History of Changes for Study NCT01454102," ClinicalTrials.Gov, latest version submitted on Nov. 3, 2017.
ClinicalTrials.gov Identifier: NCT02040064 "Tolerability and Efficacy of Tremelimumab in Combination With Gefitinib in NSCLC Patients", ClinicalTrials.gov; last updated Jan. 17, 2014.
ClinicalTrials.gov Identifier: NCT02263508 "A Phase 1 b/3, Multicenter, Open-label Trial of Tafimogene Laherparepvec in Combination With Pembrolizumab (MK-3475) for Treatment of Unresected,Stage IIIb to IVM1c Melanoma(MASTERKEY-265)", ClinicalTrials.gov; last updated Jun. 22, 2015.
ClinicalTrials.gov Identifier: NCT02339571 "Randomized Phase II/III Study of Nivolumab Plus Ipilimumab Plus Sargramostim Versus Nivolumab Plus Ipilimumab in Patients With Unresectable Stage III or Stage IV Melanoma", ClinicalTrials.gov; last updated Apr. 9, 2015.
ClinicalTrials.gov Identifier: NCT02608268, Safety and Efficacy of MBG453 as Single Agent and in Combination With PDR001 in Patients With Advanced Malignancies, Information provided by Novartis (Novartis Pharmaceuticals), last updated Oct. 13, 2016.
ClinicalTrials.gov Identifier: NCT02817633, A Phase 1 Study of TSR-022, an Anti-TIM-3 Monoclonal Antibody, in Patients With Advanced Solid Tumors, Information provided by Tesaro, Inc., last updated Aug. 26, 2016.
Cloeckaert, A., et al., "O-Polysaccharide epitopic heterogeneity at the surface of *Brucella* spp.studied by enzyme-linked immunosorbent assay and flow cytometry," Clinical and Diagnostic Laboratory Immunology 5(6):862-870, American Society forMicrobiology, United States (1998).
Cohen et al., "Image Cytometry of Estrogen Receptors in Breaast Carcinomas" Cytometry (1988) vol. 9 pp. 579-587.
Collins et al., "The B7 family of immune-regulatory ligands" Genome Biology (2005) vol. 6 No. 223.
Cragg, M.S. et al., "Complement-mediated lysis by anti-CD20 mAb correlated with segregation into lipid rafts," Blood 101(3):1045-1052, American Society of Hematology, United States (2003).
Creelan, B.C., "Update on Immune Checkpoint Inhibitors in Lung Cancer," Journal of the Moffitt Cancer Center 21(1):80-89, H. Lee Moffitt Cancer Center and Research Institute, United States (2014).
Cruse, J.M. and Lewis, R.E., "Antigens and Immunogens," in Atlas of Immunology, 2nd ed., pp. 105-126, CRC Press, United States (Dec. 29, 2003).
Curigliano et al., "Abstract CT183: Phase (Ph) I/II study of MBG453 +/− spartalizumab (PDR001) in patients (pts) with advanced malignancies," AACR Annual Meeting 2019, Cancer Research, vol. 79, Issue 13, Supplement, 2 pages.
Davies, D.R. and Cohen, G.H., "Interactions of protein antigens with antibodies," Proceedings of the National Academy of Sciences USA 93(1):7-12, National Academy of Sciences, United States (1996).
Davies, Julian, et al.; "Affinity improvement of single antibody VH domains: residues in all three hypervariable regions affect antigen binding"; ; 2:169-179 (1996).
Dekruyff et al., "T Cell/Transmembrane, Ig, and Mucin-3 Allelic Variants Differentially Recognize Phosphatidylserine and MEdiate Phagocytosis of Apoptotic Cells" The Journal of Immunology (2010) vol. 184 pp. 1918-1930.
Del-Rio, Maria-Luisa, et al.; "Antibody-mediated signaling through PD-1 costimulates T cells and enhances CD28-dependent proliferation"; Eur. J. Immunol.; 35(12):3545-3560 (2005).

Demaria et al., "Immune-mediated inhibition of Metastases after Treatment with Local Radiation and CTLA-4 Bloackade in a Mouse Model of Breast Cancer," Clinical Cancer Research (2005) vol. 11, pp. 728-734.
Dennis "Off by a whisker" Nature (2006) vol. 442, pp. 739-741.
Dey et al: "Nutl in-3 inhibits the NF[kappa]B Pathway in a p53 Dependent Manner: Implications in Lung Cancer Therapy". Cell Cycle, vol. 6, No. 17, Sep. 1, 2007 (Sep. 1, 2007), pp. 2178-2185.
Dong et al., "Tumor-associated B7-H1 promotes T-cell apoptosis: A potential mechanism of immune evasion", Nat Med (2002) vol. 8 pp. 793-800.
Dong, H. and Chen, L., "B7-H1 pathway and its role in the evasion of tumor immunity," Journal of Molecular Medicine 81(5):281-287, Springer, Germany (2003).
Dong, H., et al., "Tumor-associated B7-H1 promotes T-cell apoptosis: a potential mechanism of immune evasion," Nature Medicine 8(8):793-800, Nature Publishing Company, United States (2002).
Dorfman et al., "The phosphatidylserine receptors, T cell immunoglobulin mucin proteins 3 and 4, are markers of histiocytic sarcoma and other histiocytic and decdritic cell neoplasms" Hum Pathol (2010) vol. 41 No. 10 pp. 1486-1494.
Dougan et al., "Regulation of innate and adaptive antitumor immunity by IAP antagonists," Immunotherapy (2018) vol. 10, No. 9, pp. 787-796.
Dougan, D.A. et al.,"Effects of subsitutions in the binding surface of an antibody on antigen affinity," Protein Engineering 11(1):65-74, Oxford University Press, England (1998).
Drake et al., "Blocking the regulatory T cell molecule LAG-3 augments in vivo anti-tumor immunity in an autochthonous model of prostate cancer," J Clin Oncol (2006) vol. 24, No. 18S, Abstract 2573.
Du Manoir et al., "Ki-67 Labeling in Postmitotic Cells Defines Different Ki-67 Pathways Within the 2c Compartment" Cytometry (1991) vol. 12 pp. 455-463.
El Mir et al., "A Soluble Lymphocyte Activation Gene-3 Molecule Used as a Vaccine Adjuvant Elicits Greater Humoral and Cellular Immune Responses to Both Particulate and Soluble Antigens," J Immunol (2000) vol. 164, pp. 5583-5589.
Entzminger et al., "*De novo* design of antibody complementarity determining regions binding a FLAG tetrapeptide," Sci Rep (2017), retrived from www.nature.com/ articles/s41598-017-10737-9.pdf?origin=ppub, last accessed Jan. 12, 2018.
Extended European Search Report for European Application No. EP 1484888, dated May 31, 2017.
Extended European Search Report issued in European Application No. 19199437.5, dated Mar. 12, 2020, 8 pages.
Finger, L.R., et al., "The human PD-1 gene: complete cDNA, genomic organization, and developmentally regulated expression in B cell progenitors," Gene 197(1-2):177-187, Elsevier, United States (1997).
Fivash, M., et al., "BIAcore for macromolecular interaction," Current Opinion in Biotechnology 9(1):97-101, Current Biology, England (1998).
Fleischer, Bernhard, et al.; "T cell stimulation by staphylococcal enterotoxins"; J. Exp. Medicine; 167(5):1697-1707 (1988).
Fourcade et al., "Upregulation of Tim-3 and PD-1 expression is associated with tumor antigen-specific CD8+ T cell dysfunction in melanoma patients" The Journal of Experimental Medicine (2010) vol. 207 No. 10 pp. 2175-2186.
Franklin, M.C., et al., "Insights into ErbB signaling from the structure of the ErbB2-pertuzumab complex," Cancer Cell 5(4):317-328, Cell Press, United States (Apr. 2004).
Freeman et al., "Cloning of B7-2: a CTLA-4 counter-receptor that costimulates human T cell proliferation," Science (1999) vol. 262, pp. 909-911.
Freeman et al., "Engagement of the PD-1 immunoinhibitory receptor by a novel B7 family member leads to negative regulation of lymphocyte activation", J Exp Med. (2000) vol. 192, No. 7, pp. 1027-1034.
Freeman et al., "TIM genes: a family of cell surface phosphatidylserine receptors that regulate innate and adaptive immunity" Immunol Rev (2010) vol. 235 No. 1 pp. 172-189.

(56) References Cited

OTHER PUBLICATIONS

Fujimori et al. "A Modeling Analysis of Monoclonal Antibody Percolation Through Tumors: A Binding-Site Barrier" J Mucl Med (1990) vol. 31, pp. 1191-1198.
Fukushima et al.,"Antibodies to T-cell Ig and mucin domain-containing proteins (Tim)-1 and -3 suppress the induction and progression of murine allergic conjunctivitis" Biochemical and Biophysical Research Communications (2006) vol. 353 No. 1 p. 211-16.
Fulda, "Molecular Pathways: Targeting Inhibitor of Apoptosis Proteins in Cancer- From Molecular Mechanism to Therapeutic Application," Clin Cancer Res (2013) vol. 20, No. 2, pp. 289-295.
Gao et al., "TIM-3 Expression Characterizes Regulatory T Cells in Tumor Tissues and Is Associated with Lung Cancer Progression" PLoS ONE (2012) vol. 7 No. 2 e30676.
Garcia et al: "The Pan-PIM Kinase Inhibitor LGH447 Shows Activity in PIM2-Dependent Multiple Myeloma and in AML Models", Blood (2013) Retrieved from the Internet: URL:http://www.bloodjournal.orgjcontent/122/21/1666 [retrieved on Apr. 14, 2016].
Garrison K et al: "The small molecule TGF-[beta] signaling inhibitor SM16 synergizes with agonistic OX40 antibody to suppress established mammary tumors and reduce spontaneous metastasis" Cancer Immunology, Immunotherapy (2012) vol. 61 No. 4 pp. 511-521.
Ge, X., et al., "CD134—Allodepletion Allows Selective Elimination of Alloreactive Human T Cells without Loss of Virus-Specific and Leukemia-Specific Effectors," Biology of Blood and Marrow Transplantation 14(5):518-530, American Society for Bloodand Marrow Transplantation, United States (2008).
Geng et al., "Soluble Form of T Cell Ig Mucin 3 Is an Inhibitory Molecule in T Cell-Mediated Immune Response" The Journal of Immunology (2006) vol. 176 pp. 1411-1420.
Gettinger et al. "Safety and Response 1-98 With Nivolumab (Anti-PD-1; BMS-936558, ONO-4538) Plus Erlotinib in Patients (Pts) With Epidermal Growth Factor Receptor Mutant (EGFR MT) Advanced Non-Small Cell Lung Cancer (NSCLC} Metastatic Non-Small Cell Lung Cancer" International Journal of Radiation: Oncology Biology Physics (2014) vol. 90, No. 5, pp. S34-S35.
Ghebeh et al., "Doxorubicin downregulates cell surface B7-H1 expression and upregulates its nuclear expression in breast cancer cells: role of B7-H1 as an anti-apoptotic molecule," Breast Cancer Research (2010) vol. 12, No. 4, Article R48, 12 pages.
Golden-Mason et al., "Negative Immune Regulator Tim-3 Is Overexpressed on T Cells in Hepatitis C Virus Infection and Its Blockade Rescues Dysfunctional CD4$^+$ and CD8$^+$ T Cells," J Virol (2009) vol. 83, No. 18, pp. 9122-9130.
Greenspan, N.S., "Epitopes, paratopes and other topes: do immunologists know what they are talking about?" Bulletin de l'Institut Pasteur 90(4):267-279, Elsevier, France (1992).
Grygielewicz Paulina et al: "Epithelial-mesenchymal transition confers resistance to selective FGFR inhibitors in SNU-16 gastric cancer cells". Gastric Cancer. Springer Japan. Tokyo. vol. 19. No. 1., Nov. 19, 2014 (Nov. 19, 2014). pp. 53-62.
Haitov, "Immunology: Structure and Functions of the Immune System," Geotar-Media Publishing Group, Moscow (2013) p. 110. Russian.
Hallett et al., "Immunosuppressive Effects of Multiple Myeloma Are Oversome by PD-L1 Blockade" Biol Blood Marrow Transplant (2011) vol. 17, No. 8, pp. 1133-1145.
Hamid et al., "Safety and Tumor Responses with Lambrolizumab (Anti-PD-1) in Melanoma" New England Journal of Medicine (2013) vol. 369 No. 2 pp. 134-144.
Hansen, J.A., et al., "Monoclonal Antibodies Identifying a Novel T-Cell Antigen and la Antigens of Human Lymphocytes," Immunogenetics 10:247-260, Springer-Verlag (1980).
Harlow, E. and Lane, D., "Using Antibodies: A Laboratory Manual," Cold Spring Harbor Laboratory Press, Cold Spring Harbor, United States various pages (1999).

Hastings et al., "TIM-3 is Expressed on Activated Human CD4$_+$ T Cells and Regulates Th1 and Th17 Cytokines" Eur J Immunol (2009) vol. 39 No. 9 pp. 2492-2501.
He, Y-F., et al., "Blocking programmed death-1 ligand-PD-1 interactions by local gene therapy results in enhancement of antitumor effect of secondary lymphoid tissue chemokine," The Journal of Immunology 173(8):4919-4928, The American Association ofImmunologists, United States (2004).
Henry et al., "Structure and evolution of the extended B7 family," Immunol Today (1999) vol. 20, No. 6, pp. 285-288.
Herbst et al., "A study of MPDL3280A, an engineered PD-L1 antibody in patients with locally advanced or metastatic tumors," J Clin Oncol (2013) vol. 31, No. 15 (Supp), Abstract 3000.
Highfill et al., "Disruption of CXCR2-Mediated MDSC Tumor Trafficking Enhances Anti-PD1 Efficacy," Science Translational Medicine (2014) vol. 6, Issue 237, Article 237ra67, 15 pages.
Hirano, F., et al., "Blockade of B7-H1 and PD-1 by monoclonal antibodies potentiates cancer therapeutic immunity," Cancer Research 65(3):1089-1096, American Association for Cancer Research, United States (2005).
Hofstra et al., "Prevention of Th2-like cell responses by coadministration of IL-12 and IL-18 is associated with inhibition of antigen-induced airway hyperresponsiveness, eosinophilia, and serum IgE levels." Journal of Immunology (1998) vol. 161 No. 9 pp. 5054-5060.
Hogenesch et al. "Challenges in pre-clinical testing of anti-cancer drugs in cell culture and in animal models" Journal of Controlled Release (2012) vol. 164, No. 2, pp. 183-186.
Hu Yi et al: "Essential role of AKT in tumor cells addicted to FGFR.", Anti-Cancer Drugs, vol. 25, No. 2, Feb. 2014 (Feb. 2014), pp. 183-188.
Huang et al., "Lymphoma endothelium preferentially expresses Tim-3 and facilitates the progression of lymphoma by mediating immune evasion" The Journal of Experimental Medicine (2010) vol. 207 No. 3 pp. 505-520.
Huang et al., "Role of LAG-3 in Regulatory T Cells," Immunity (2004) vol. 21, pp. 503-513.
Huang, Z., "Structural chemistry and therapeutic intervention of protein-protein interactions in immune response, human immunodeficiency virus entry, and apoptosis," Pharmacology & Therapeutics 86(3):201-215, Pergamon Press, England (2000).
Huard et al., "Lymphocyte-activation gene 3/major histocompatibility complex class II interaction modulates the antigenic response of CD4$^+$ T lymphocytes," Eur J Immunol (1994) vol. 24, pp. 3216-3221.
Huard et al., "T cell major histocompatibilty complex class II molecules down-regulate CD4$^+$ T cell clone responses following LAG-3 binding," Eur J Immunol (1996) vol. 26, pp. 1180-1186.
Hutloff, A., et al.,"ICOS is an inducible T-cell co-stimulator structurally and functionally related to CD28," Nature 397(6716):263-266, Nature Publishing Group, England (1999).
International Search Report and Written Opinion for International Application No. PCT/US2015/049826 dated Dec. 16, 2015.
International Search Report and Written Opinion for International Application No. PCT/US2015/055390, dated Dec. 17, 2015.
International Search Report and Written Opinion for International Application No. PCT/US2015/066812 dated Mar. 23, 2016.
International Search Report and Written Opinion for International Application No. PCT/US2016/044545 dated Oct. 28, 2016.
International Search Report and Written Opinion for International Application No. PCT/US2016/044547 dated Oct. 18, 2016.
International Search Report and Written Opinion for International Application No. PCT/US2016/044549 dated Oct. 14, 2016.
International Search Report and Written Opinion for PCT/US2014/057491 dated Jan. 7, 2015.
International Search Report and Written Opinion for PCT/US2015/012754 dated May 20, 2015.
International Search Report and Written Opinion for PCT/US2015/013913 dated May 4, 2015.
International Search Report and Written Opinion for PCT/US2015/049826 dated Dec. 16, 2015.
International Search Report and Written Opinion for PCT/US2015/053799 dated May 17, 2016.

(56) References Cited

OTHER PUBLICATIONS

International Search Report and Written Opinion issued in International Application No. PCT/US2016/067200, dated Apr. 10, 2017.
International Search Report and Written Opinion issued in International Application No. PCT/US2018/039825, dated Oct. 4, 2018.
International Search Report and Written Opinion issued in PCT/US2007/085100, dated Apr. 28, 2008, 11 pages.
International Search Report and Written Opinion issued in PCT/US2018/061534, dated Apr. 1, 2019, 9 pages.
Iouzalen et al., "LAP, a lymphocyte activation gene-3 (LAG-3)-associated protein that binds to a repeated EP motif in the intracellular region of LAG-3, may participate in the down-regulation of the CD3/TCR activation pathway," Eur J Immunol (2001) vol. 31, pp. 2885-2891.
Ishida et al., "Induced expression of PD-1, a novel member of the immunoglobulin gene superfamily, upon programmed cell death," The EMBO Journal (1992) vol. 11, No. 11, pp. 3887-3895.
Ishima, R. and Torchia, D.A., "Protein Dynamics from NMR," Nature Structural Biology 7(9):740-743, Nature Publishing Company, United States (2000).
Iwai et al, "Involvement of PD-L1 on tumor cells in the escape from host immune system and tumor immunotherapy by PD-L1 blockade" PNAS (2002) vol. 99, pp. 12293-12297.
Iwai et al, "PD-1 blockade inhibits hematogenous spread of poorly immunogenic tumor cells by enhanced recruitment of effector T cells", International Immunology (2005) vol. 17, No. 2, pp. 133-144.
Iwai, Y., et al., "Microanatomical localization of PD-1 in human tonsils," Immunology Letters 83(3):215-220, Elsevier, Netherlands (2002).
Iwai, Y., et al., "PD-1 inhibits antiviral immunity at the effector phase in the liver," The Journal of Experimental Medicine 198(1):39-50, The Rockefeller University Press, United States (2003).
Jan et al., "Prospective separation of normal and leukemic stem cells based on differential expression of TIM3, a human acute myeloid leukemia stem cell marker" PNAS (2011) vol. 108 No. 12 pp. 5009-5014.
Jason-Moller, L., et al., "Overview of Biacore Systems and Their Applications," Current Protocols in Protein Science S45:19.13.1-19.13.14, John Wiley & Sons, Inc., United States (2006).
Jiang et al, "mTOR Kinase Inhibitor AZD8855 Enhances the Immunotherapeutic Activity of an Agonist CD40 Antibody in Cancer Treatment" Cancer Research (2011) vol. 71 No. 12, pp. 4074-4084.
Jiang X et al: "The activation of MAPK in melanoma cells resistant to BRAF inhibition promotes PD-L1 expression that is reversible by MEK and PI3K inhibition", Clinical Cancer Research, The American Association for Cancer Research, US, vol. 19, No. 3, Feb. 1, 2013 (Feb. 1, 2013). pp. 598-609.
Jin et al. "Cooperation of Tim-3 and PD-1 in CD8 T-cell exhaustion during chronic viral infection" PNAS (2010) vol. 107, Issue 33, pp. 14733-14738.
Jing et al., "Combined immune checkpoint protein blockade and low dose whole body irradiation as immunotherapy for melanoma," Journal for ImmunoTherapy of Cancer (2015) vol. 3, No. 2, 15 pages.
Johne, B., "Protocol: Epitope Mapping by Surface Plasmon Resonance in the BIAcore," Molecular Biotechnology 9(1):65-71, Humana Press, United States (1998).
Jones et al., "Tim-3 expression defines a novel population of dysfunctional T cells with highly elevated frequencies in progressive HIV-1 infection," J Exp Med (2008) vol. 205, No. 12, pp. 2763-2779.
Ju et al., "T cell immunoglobulin-and mucin-domain-containing molecule-3 (Tim-3) mediates natural killer cell suppression in chronic hepatitis B" Journal of Hepatology (2010) vol. 52 No. 3 pp. 322-329.
Kanai, T., et al., "Blockade of B7-H1 Suppresses the Development of Chronic Intestinal Inflammation," The Journal of Immunology 171(8):4156-4163, American Association of Immunologists, Inc., United States (2003).
Karu et al., "Recombinant Antibody Technology," ILAR Journal, vol. 37, No. 3, pp. 132-141 (1995).
Kasagi, S., et al., "Anti-programmed cell death 1 antibody reduces $CD4_+PD-1_+$ T cells and relieves the lupus-like nephritis of NZB/W FI mice," The Journal Immunology 184(5):2337-2347, The American Association of Immunologists, United States (2010).
Kaveri, S., "Epitope and idiotope mapping using monoclonal antibodies," Medthods in Molecular Biology 51:171-181, Humana Press, United States (1995).
Kearl et al., "PD-1/PD-L1 Blockade after Transient Lymphodepletion to Treat Myeloma," Presentation from Society for Immunotherapy of Cancer Conference, Oct. 27, 2012, North Bethesda, Maryland, 19 pages.
Kearl et al., "Programmed Death Receptor-1/Programmed Death Receptor Ligand-1 Blockage after transient Lymphodepletion to Treat Myeloma," J Immunol (2013) vol. 190, pp. 5620-5628.
Kearley et al., "Th-2 driven, allergen-induced airway inflammation is reduced after treatment with anti-Tim-3 antibody in vivo" The Journal of Experimental Medicine (2007) vol. 204 No. 6 pp. 1289-1294.
Keytruda (pembrolizumab) Drug Label, Initial U.S. Approval: 2014, Revised Aug. 2016.
Keytruda (pembrolizumab) Drug Label, Initial U.S. Approval: 2014, Revised Oct. 2016.
Khaitov, Immunologia, Moscow, (2011) "GEOTAR-Media", p. 103.
Khalil et al. "The New Era of Cancer Immunotherapy: Manipulating T-Cell Activity to Overcome Malignancy" Immunotherapy of Cancer in: Advances in Cancer Research (2015) vol. 128, pp. 1-68.
Kier et al., "PD-1 and its ligands in tolerance and immunity" Annu. Rev. Immunol. (2008) vol. 26 pp. 677-704.
Kikushige et al. "TIM-3 as a therapeutic target for malignant stem cells in acute myelogenous leukemia" New York Academy of Sciences (2012) vol. 1266, pp. 118-123.
Kikushige et al., "TIM-3 Is a Promising Target to Selectively Kill Acute Myeloid Leukemia Stem Cells" Cell Stem Cell (2010) vol. 7 pp. 708-717.
Kim et al: "Eradication of metastatic mouse cancers resistant to immune checkpoint blockade by suppression of myeloid-derived cells. (Includes Supporting Information)", Proceedings of the National Academy of Sciences of the United States of America, vol. 111, No. 32, Aug. 12, 2014 (Aug. 12, 2014), pp. 11774-11777.
Kirkwood et al, "Immunotherapy of cancer in 2012" CA: A Cancer Journal for Clinicians (2012) vol. 62 No. 5 pp. 309-335.
Klein Jan M et al: "The histone deacetylase inhibitor LBH589 (panobinostat) modulates the crosstalk of lymphocytes with Hodgkin lymphoma cell lines.", PLOS ONE (2013) vol. 8, No. 11, E79502, 2813, pp. 1-6.
Klibi et al. "Blood diffusion and Th1-suppressive effects of galectin-9-containing exosomes released by Epstein-Barr virus-infected nasopharyngeal carcinoma cells" Blood (2009) vol. 113 No. 9 pp. 1957-1966.
Knight et al. "Host immunity contributes to the antimelanoma activity of BRAF inhibitors" The Journal of Clinical Investigation (2013) vol. 123, No. 3, pp. 1371-1381.
Knights et al., "Inhibitor of apoptosis protein (IAP) antagonists demonstrate divergent immunomodulatory properties in human immune subsets with implications for combination therapy" Cancer Immunology and Immunotherapy (2013) vol. 62 No. 2 pp. 321-335.
Koga et al., "Blockade of the Interaction Between PD-1 and PD-L1 Accelerates Graft Arterial Disease in Cardiac Allografts," Arterioscler Thromb Vasc Biol (2004) vol. 24, pp. 2057-2062.
Koga, N., et al., "Blockade of the interaction between PD-1 and PD-L1 accelerates graft arterial disease in cardiac allografts," Arteriosclerosis, Thrombosis, and Vascular Biology 24(11):2057-2062, American Heart Association, Inc., United States(2004).
Konishi, J., et al., "B7-H1 expression on non-small cell lung cancer cells and its relationship with tumor-infiltrating lymphocytes and their PD-1 expression," Clinical Cancer Research 10(15):5094-5100, American Association for Cancer Research,United States (2004).
Korman et al, "Checkpoint Blockade in Cancer Immunotherapy" Adv Immunol (2006) vol. 90 pp. 297-339.

(56) References Cited

OTHER PUBLICATIONS

Koya et al., "BRAF Inhibitor Vemurafenib Improves the Antitumor Activity of Adoptive Cell Immunotherapy," Cancer Res (2012) vol. 72, No. 16, pp. 3928-3937.

Kuchroo et al. "The TIM Gene Family: Emerging Roles in Immunity and Disease" Nature Reviews Immunology (2003) vol. 3, pp. 454-462.

Kuchroo et al., "B7-1 and B7-2 Costimulatory Molecules Activate Differentially the Th1/Th2 Developmental Pathways: Application to Autoimmune Disease Therapy" Cell (1995) vol. 80 No. 707-18.

Kwong et al., "Molecular Analysis of Tumor-Promoting $CD8_+$ Cells in Two-Stage Cutaneous Chemical Carcinogenesis" J Invest Dermatol (2010) vol. 130 No. 6 pp. 1726-1736.

Lack et al. "Nebulized but not parenteral IFN-gamma decreases IgE production and normalizes airways function in a murine model of allergen sensitization" Journal of Immunology (1994) vol. 152, pp. 2546-2554.

Ladner, R.C., "Mapping the epitopes of Antibodies," Biotechnology and Genetic Engineering Reviews 24(1):1-30, Taylor & Francis, England (2007).

Laricchia,Robbio, L., et al., "Mapping of Monoclonal Antibody-and Receptor-Binding Domains on Human Granulocyte-Macrophage Colony-Stimulation Factor (rhGM-CSF) Using a Surface Plasmon Resonance-Based Biosensor," Hybridoma 15(5):343-350, Mary AnnLiebert, Inc. United States (1996).

Latchman et al., "PD-L2 is a second ligand for PD-1 and inhibits T cell activation," Nature Immunol (2001) vol. 2, No. 3, pp. 261-268.

Leach, D.R., et al., "Enhancement of antitumor immunity by CTLA-4 blockade," Science 271(5256):1734-1736, American Association for the Advancement of Science, United States (1996).

Lee et al. "The inhibition of the T-cell immunoglobulin and mucin domain 3 (Tim3) pathway enhances the efficacy of tumor vaccine" Biochemical and Biophysical Reseach Communications (2010) vol. 402, pp. 88-93.

Lehmann et al, "Identification of human triple-negative breast cancer subtypes and preclinical models for selection of targeted therapies", J Clin Invest., 121(7): 2750-2767.

Lenschow et al., "Expression and functional significance of an additional ligand for CTLA-2," PNAS (1993) vol. 90, pp. 11054-11058.

Lenschow et al., "Long-term survival of xenogeneic pancreatic islet grafts induced by CTLA4Ig," Science (1992) vol. 257, Issue 5071, pp. 789-792.

Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, UnitedStates, Dec. 6-9, 2014.

Lewis, D.E., et al., "Tumor Necrosis Factor-.alpha. and CD80 Modulate CD28 Expression through a Similar Mechanism of T-cell Receptor-Independent of Transcription," The Journal of Biological Chemistry 279(28):29130-29138, The American Society forBiochemistry and Molecular Biology, Inc., United States (2004).

Li et al., "Contribution of PD-L1 to oncogenesis of lymphoma and its RNAi-based targeting therapy" Leukemia & Lymphoma (2012) vol. 53, No. 10, pp. 2015-2023.

Li, L., et al., "A pathway regulated by cell cycle inhibitor p27Kip1 and checkpoint inhibitor Smad3 is involved in the induction of T cell tolerance," Nature Immunology 7(11):1157-1165, Nature Publishing, United States (2006).

Li, L., et al., "$CD4_+CD25_+$ regulatory T-cell lines from human cord blood have functional and molecular properties and T-cell anergy," Blood 106(9):3068-3073, American Society of Hematology, United States (Nov. 2005).

Li, L., et al., "IL-1beta-Mediated Signals Preferentially Drive Conversion of Regulatory T Cells but Not Coventional T Cells into IL-17-Producing Cells," The Journal of Immunology 185(7):4148-4153, American Association of Immunologists, Inc., UnitedStates (2010).

Li, L., et al., "Rap1-GTP is a Negative Regulator of Th Cell Function and Promotes the Generation of $CD4_+CD103_+$ Regulatory T Cells In Vivo," The Journal of Immunology 175(5):3133-3139, American Association of Immunologists, Inc., United States (Sep. 2005).

Li, L., et al., "The cyclin dependent kinase inhibitor (R)-roscovitine prevents alloreactive T cell clonal expansion and protects against acute GvHD," Cell Cycle 8(11):1794-1802, Landes Bioscience, United States (2009).

Liblau et al. "Th1 and Th2 $CD4_+$ T cells in the pathogenesis of organ-specific autoimune diseases" Immunology Today (1995) vol. 16, Issue 1, pp. 34-38.

Lin, David Yin-Wei, et al.; "The PD-1/PD-L1 complex resembles the antigen-binding Fv domains of antibodies and T cell receptors"; Proc. Natl. Acad. Sci. USA 105(8):3011-3016 (2008).

Linsley et al., "CTLA-4 Is a Second Receptor for the B Cell Activation Antigen B7," J Exp Med (1991) vol. 174, pp. 561-569.

Linsley et al., "Immunosuppression in Vivo by a Soluble Form of the CTLA-4 T Cell Activation Molecule," Science (1992) vol. 257, pp. 792-795.

Linsley et al., "Intracellular Trafficking of CTLA-4 and Focal Localization Towards Sites of TCR Engagement" Immunity (1996) vol. 4 pp. 535-543.

List of clinical trials identified in ClinicalTrials.gov relating to PDR001 as of Dec. 22, 2016.

Liu et al., "A Novel Kinase Inhibitor, INC28060, Blocks c-MET-Dependent Signaling, Neoplastic Activities, and Cross-Talk with EGFR and HER-3," Clin Cancer Res (2011) vol. 17, No. 22, pp. 7127-7138.

Liu et al., The BRAF and MEK Inhibitors Dabrafenib and Trametinib: Effects on Immune Function and in Combination with Immunomodulatory Antibodies Targeting PD-1, PD-L1, and CTLA-4.

Lonberg, N., et al., "Antigen-specific human antibodies from mice comprising four distinct genetic modifications," Nature 368(6474):856-859, Nature Publishing Group, United States (1994).

Loser et al., "IL-10 Controls Ultraviolet-Induced Carcinogenesis in Mice" The Journal of Immunology (2007) vol. 179 pp. 365-371.

Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).

Mach et al., "Phase (PH) II Study of $MBG453_+$ Spartalizumab in Patients (PTS) with Non-Small Cell Lung Cancer (NSCLC) and Melanoma Pretreated with Anti-PD-1/L1 Therapy," Poster Display Session 3 from ESMO Congress, Sep. 30, 2019, 3 pages.

Mahoney et al. "The Next Immune-Checkpoint Inhibitors: PD-1/PDD-L1 Blockade in Melanoma" Clinical Therapeutics (2015) vol. 37, No. 4, pp. 764-782.

Maier et al., "PD-1: PD-L1 Interactions Contribute to the Functional Suppression of Virus-Specific CD8+ T Lymphocytes in the Liver," J Immunol (2007) vol. 178, pp. 2714-2720.

Makishi et al. "Retracted: A modified version of galectin-9 induces cell cycle arrest and apoptosis of Burkitt and Hodgkin lymphoma cells" British Journal of Hematology (2008) vol. 142 pp. 583-594.

Manning et al, "A model of multiple myeloma: culture of 5T33 murine myeloma cells and evaluation of tumorigenicity in the C57BL/KaLwRij mouse.", Br J Cancer., 66(6): 1088-1093 (1992).

Marri et al., "Human Biochemistry" Mir Publishing, Moscow (1993) vol. 1, p. 34. Russian.

Masters et al., "Abstract 5016: Antitumor activity of anti-PD-1 in combination with tyrosine kinase inhibitors in a preclinical renal cell carcinoma model" AACR Annual Meeting (2014) vol. 74, No. 5016.

May, K.F., Jr., et al., "Anti-human CTLA-4 monoclonal antibody promotes T-cell expansion and immunity it a hu-PBL-SCID model: a new method for preclinical screening of costimulatory monoclonal antibodies," Blood 105(3):1114-1120, American Society ofHematology, United States (2005).

Maçon-Lemaître et al., "The negative regulatory function of the lymphocyte-activation gene-3 co-receptor (CD223) on human T cells," Immunology (2005) vol. 115, pp. 170-178.

(56) References Cited

OTHER PUBLICATIONS

Menzies et al. "Systemic treatment for BRAF-mutant melanoma: where do we go next?" Lancet Oncology (2014) vol. 15, pp. e371-e381.
Menzies et al., "Recent advances in melanoma systemic therapy. BRAF inhibitors, CTLA antibodies and beyond" European Journal of Cancer (2013) vol. 49 No. 15 pp. 3229-3241.
Miska et al., "Autoimmunity-mediated antitumor immunity: Tumor as an immunoprivileged self," Eur J Immunol (2012) vol. 42, pp. 2584-2596.
Mittendorf Elizabeth A et al: "PD-L1 expression in triple-negative breast cancer." Cancer Immunology Research. vol. 2. No. 4. Apr. 2014 (Apr. 2014). pp. 361-370.
Mocellin et al., "CTLA-4 blockade and the renaissance of cancer immunotherapy," Biochim Biophys Acta (2013) vol. 1836, pp. 187-196.
Mokyr et al, "Realization of the Therapeutic Potential of CTLA-4 Blockade in Low-Dose Chemotherapy-treated Tumor-bearing Mice", Cancer Research, 58:5301-5304 (1998).
Monney et al. "Th1-specific cell surface protein Tim-3 regulates macrophage activation and severity of an autoimmune disease" Nature (2002) vol. 415, pp. 536-541.
Moreira Da Silva, "Nivolumab Anti-PD-1 monoclonal antibody cancer immunotherapy" Drugs of the Future (2014) vol. 39 No. 1 pp. 15-24.
Mosmann et al. "The expanding universe of T-cell subsets: Th1, Th2 and more" Immunology Today (1996) vol. 17, Issue 3, pp. 138-146.
Mossman et al. "Two Types of Murine Helper T Cell Clone" Journal of Immunology (1986) vol. 136, Issue 7, pp. 2348-2357).
Mou et al., "Association Between TIM-1 Gene Polymorphisms and Allergic Rhinitis in a Han Chinese Population" J Investig Allergol Clin Immunol (2010) vol. 20 No. 1 pp. 3-8.
Murrey et al., Biokhimiya cheloveka, Mir (1993) vol. 1, p. 34.
Nagahara et al., "Galectin-9 Increases Tim-$3_+$ Dendritic Cells and $CD_+$ T Cells and Enhances Antitumor Immunity via Galectin-9-Tim-3 Interactions" The Journal of Immunology (2008) vol. 181 pp. 7660-7669.
Naing et al. "A first-in-human phase I study of the anti-PD-1 antibody PDR001 in patients with advanced solid tumors" 2016 ASCO Annual Meeting, J Clin Oncol 34, 2016 (suppl; abstr 3060).
Najjar et al., "Myeloid-Derived Suppressor Cell Subset Accumulation in Renal Cell Carcinoma Parenchyma Is Associated with Intratumoral Expression of IL1beta, IL8, CXCL5, and Mip-1alpha," Clinical Cancer Research (2016) vol. 23, No. 9, pp. 2346-2355.
Nakae et al., "Mast cells enhance T cell activation: importance of mast cell costimulatory molecules and secreted TNF" The Journal of Immunology (2006) vol. 176 No. 4 pp. 2238-2248.
Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).
Neubert et al., "T cell-induced CSF1 promotes melanoma resistance to PD1 blockade," Science Translational Medicine (2018) vol. 10, No. 436, Article eaan3311, 14 pages.
Ngiow et al. "Prospects for TIM3-Targeted Antitumor Immunotherapy" Cancer Research (2011) vol. 71, Issue 21, pp. 6567-6571.
Ngiow et al., "Anti-TIM3 Antibody Promotes T Cell IFN-γ-Mediated Antitumor Immunity and Suppresses Established Tumors" Cancer Research (2011) vol. 71 No. 10 pp. 3540-3551.
Ngiow et al., "Prospects for TIM3-Targeted Antitumor Immunotherapy," Cancer Res (2011) vol. 71, No. 21, pp. 6657-6571.
Nicholson et al., "An Altered Peptide Ligand Mediates Immune Deviation and Prevents Autoimmune Encephalomyelitis" Immunity (1995) vol. 3 pp. 397-405.
Nielsen, C., et al., "A putative regulatory polymorphism in PD-1 is associated with nephropathy in a population-based cohort of systemic lupus erythematosus patients," Lupus 13(7):510-516, SAGE, England (2004).
Nirschl et al., "Molecular Pathways: Coexpression of Immune Checkpoint Molecules: Signaling Pathways and Implications for Cancer Immunotherapy," Cancer Res (2013) vol. 19, No. 18, pp. 4917-4924.
Nishimura et al., "Developmentally regulated expression of the PD-1 protein on the surface of double-negative ($CD4^-CD8^-$) thymocytes," Int Immunol (1996) vol. 8, No. 5, pp. 773-780.
Nishimura, H., et al., "Autoimmune dilated cardiomyopathy Science in PD-1 receptor-deficient mice," Science 291(5502):319-322, American Association for the Advancement of Science, United States (2001).
Nishimura, H., et al., "Development of lupus-like autoimmune diseases by disruption of the PD-1gene encoding an ITIM motif-carrying immunoreceptor," Immunity 11(2):141-151, Cell Press, United States (1999).
Nishimura, H., et al., "Immunological studies on PD-1 deficient mice: implication of PD-1 as a negative regulator for B cell responses," International Immunology 10(10):1563-1572, Oxford University Press, England (1998).
Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).
Ohigashi et al, "Clinical Significance of Programmed Death-1 Ligand-1 and Programmed Death-1 Ligand-2 Expression in Human Esophageal Cancer" Clin Cancer Research (2005) vol. 11, pp. 2947-2953.
Ohno et al., "Antigen-binding specificities of antibodies are primarily determined by seven residues of $V_H$," PNAS (1985) vol. 82, pp. 2945-2949.
Okamoto et al., "T-Helper Type 1/T-Helper Type 2 Balance in Malignant Pleural Effusions Compared to Tuberculous Pleural Effusions" Chest (2005) vol. 128 pp. 4030-4035.
Okazaki et al, "PD-1 and PD-1 ligands: from discovery to clinical application" Intern. Immun. (2007) vol. 19, pp. 813-824.
Okazaki, T. et al., "New regulatory co-receptors: inducible co-stimulator and PD-1," Current Opinion in Immunology 14(6):779-782, Elsevier, England (2002).
Okazaki, T., et al., "PD-1 immunoreceptor inhibits B cell receptor-mediated signaling by recruiting src homology 2-domain-containing tyrosine phosphatase 2 to phophotyrosine," Proceeding of the National Academy of Sciences 98(24):13866-13871,National Academy of Sciences, United States (2001).
Oki Y et al: "Immune regulatory effects of panobinostat in patients with Hodgkin lymphoma through modulation of serum cytokine levels and T-cell PD1 expression," Blood Cancer Journal, vol. 4, E236, 2014, pp. 1-4.
Okudaira et al., "A modified version of galectin-9 suppresses cell growth and induces apoptosis of human T-cell leukemia virus type 1-infected T-cell lines" Int. J. Cancer (2007) vol. 120 pp. 2251-2261.
OPDIVO (nivolumab) Drug Label, Initial U.S. Approval: 2014, Revised Oct. 2016.
OPDIVO (nivolumab) Drug Label, Initial U.S. Approval: 2014, Revised Nov. 2016.
Opposition filed by ASILFA AG in corresponding Chilean Application No. 2017-00888 on Oct. 24, 2017, assigned litigation file number by the National Institute of Industrial Property of Chile (INAPI) on Feb. 27, 2018, notified by INAPI to agent on Mar. 2, 2018.
Opposition filed by Laboratorios Legrand S.A. in corresponding Colombian Application No. NC2017/0003490 on Dec. 7, 2017, admitted Dec. 19, 2017, published Dec. 20, 2017.
Opposition filed in Colombian Application No. NC2016/0001001, filed Feb. 15, 2017.
Ozaki, S., et al., "Immunotherapy of Multiple Myeloma with a Monoclonal Antibody Directed Against a Plasma Cell-specific Antigen, HM1.24," Blood 90(8):3179-3186, American Society of Hematology, United States (1997).
Ozkaynak, E., et al., "Programmed death-1 targeting can promote allograft survival," The Journal of Immunology 169(11):6546-6553, The American Association of Immunologists, United States (2002).

(56) References Cited

OTHER PUBLICATIONS

Pal et al. "Programmed Death-1 Inhibition in Renal Cell Carcinoma: Clinical Insights and Future Directions," Clinical Adv Hem Onc (2014) vol. 12, Issue 2, pp. 90-99.
Panka, et al.; "Variable region framework differences result in decreased or increased affinity of variant anti-digoxin antibodies"; Proc. Natl. Acad. Sci. USA; 85:3080-3084 (1988).
Pardoll et al. "The blockade of immune checkpoints in cancer immunotherapy" Nature Reviews Cancer (2012) vol. 12, pp. 252-264.
Park, J.W. and Smolen, J., "Monoclonal antibody therapy," Advances in Protein Chemistry 56:369-421, Academic Press, United States (2001).
Parry, Richard V., et al.; "CTLA-4 and PD-1 Receptors Inhibit T-Cell Activation by Distinct Mechanisms"; Molecular and Cellular Biology; 25(21):9543-9553 (2005).
Patel et al., "Taming dendritic cells with TIM-3: another immunosuppressive strategy used by tumors" Immunotherapy (2012) vol. 4 No. 12 pp. 1795-1798.
Paterson et al., "The Programmed Death-1 Ligand 1:B7-1 Pathway Restrains Diabetogenic Effector T Cells In Vivo," J Immunol (2011) vol. 187, pp. 1097-1105.
Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (Aug. 2013).
Patsoukis, N., et al., "PD-1 inhibits T cell proliferation by upregulating p. 27 and p. 15 and suppressing Cdc25A," Cell Cycle 11(23):1-5, Landes Bioscience, United States (Dec. 2012).
Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement ofScience, United States (Jun. 2012).
Perez-Gracia et al, "Orchestrating immune check-point blockade for cancer inmunotherapy in combinations", Current Opinion in Immunology (2014) vol. 27 pp. 89-97.
Phong et al., "Tim-3 enhances Fc[epsilon]R1-proximal signaling to modulate mast cell activation," J Experimental Medicine (2015) vol. 212, No. 13, pp. 2289-2304.
Pinzon-Ortiz et al: "S710: The combination of JAK inhibitor, ruxolitinib, pan-PIM inhibitor, LGH447, and CDK4/6 inhibitor, LEE011, in a preclinical mouse model of myeloproliferative neoplasia", Haematologica, The Hematology Journal: Official Organ of the European Hematology Association, vol. 99. No. Supp 1 (2014) p. 252.
Polyak, M.J. and Deans, J.P., "Alanine-170 and proline-172 are critical determinants for extracellular CD20 epitopes; heterogeneity in the fine specificity of CD20 monoclonal antibodies is defined by additional requirements imposed by both aminoacid sequence and quaternary structure," Blood 99(9):3256-3262, American Society of Hematology, United States (2002).
Post Grant Opposition filed in Colombian Patent Application No. NC2016/0001001, dated Jul. 31, 2018.
Postel-Vinay et al. "Challenges of phase 1 clinical trials evaluating immune checkpoint-targeted antibodies" Annals of Oncology (2016) vol. 27, pp. 214-224.
Powles et al., "MPDL3280A (anti-PD-L1) treatment leads to clinical activity in metastatic bladder cancer," Nature (2014) vol. 515, pp. 558-562.
Prigent et al., "Lymphocyte activation gene-3 induces tumor regression and antitumor immune responses," Eur J Immunol (1999) vol. 29, pp. 3867-3876.
Prokunina, L. and Alarcon-Riquelme, M., "The genetic basis of systemic lupus erythematosus—knowledge of today and thoughts for tomorrow," Human Molecular Genetics 13(1):R143-R148, Oxford University Press, England (2004).
Quintarelli et al: "Selective strong synergism of Ruxolitinib and second generation tyrosine kinase inhibitors to overcome bone marrow stroma related drug resistance in chronic myelogenous leukemia", Leukemia Research, New York,NY, US, vol. 38, No. 2, Nov. 15, 2013 (Nov. 15, 2013), pp. 236-242.
Raziorrouh et al. "The Immunoregulatory Role of CD244 in Chronic Hepatitis B Infection and its Inhibitory Potential on Virus-Specific $CD8_+$ T-cell Function" Hepatology (2010) vol. 52 pp. 1934-1947.
Richter et al., "On the role of the inhibitory receptor LAG-3 in acute and chronic LCMV infection," Int Immunol (2009) vol. 22, No. 1, pp. 13-23.
Riley, J.L. and June, C.H., "The CD28 family: a T-cell rheostat for therapeutic control of T-cell activation," Blood 105(1):13-21, American Society of Hematology, United States (Jan. 2005).
Rothe et al. "Enhancing dendritic cell-induced T-cell responses by immunomodulating molecules" 13th CIMT Annual Meeting (2015) p. 74.
Rowe et al., "Innate IFN-gamma is essential for programmed death ligand-1-mediated T cell stimulation following *Listeria monocytogenes* infection," J Immunol (2012) vol. 189, No. 2, pp. 876-884.
Rudikoff, et al.; "Single Amino Acid Substitution Altering Antigenbinding Specificity"; Proc. Natl. Acad. Sci. USA; 79:1979-1983 (1982).
Rudnick et al. "Affinity and Avidity in Antibody-Based Tumor Targeting" Cancer Biotherapy and Radiopharmaceuticals (2009) vol. 24, No. 2, pp. 155-160.
Sabatos et al. "Interaction of Tim-3 and Tim-3 ligand regulates T helper type 1 responses and induction of peripheral tolerance" Nature Immunology (2003) vol. 4, pp. 1102-1110.
Sabatos-Peyton et al., "Blockade of Tim-3 binding to phosphatidylserine and CEACAM1 is a shared feature of anti-Tim-3 antibodies that have functional efficacy," Oncoimmunology (2018) vol. 7, No. 2, Article e1385690, 9 pages.
Sachdev et al., "Phase 1/2a study of double immune suppression blockade by combining a CSF1 R inhibitor (pexidartinib/PLX3397) with an anti-PD-1 antibody (pembrolizumab) to treat advanced melanoma and other solid tumors," Gynecologic Oncology (2016) vol. 141, pp. 147-148.
Sakuishi et al., "Emerging Tim-3 functions in anti-microbial and tumor immunity" Trends Immunol (2011) vol. 32 No. 8 pp. 345-349.
Sakuishi et al., "Targeting Tim-3 and PD-1 pathways to reverse T cell exhaustion and restore anti-tumor immunity," J Experimental Medicine (2010) vol. 207, No. 10, pp. 2187-2194.
Sakuishi et al., "TIM3+FOXP3+ regulatory T cells are tissue-specific promoters of T-cell dysfunction in cancer" OncoImmunology (2013) vol. 2 No. 4 pp. e23849-1-e23849-9.
Salama, A.D., et al., "Critical role of the programmed death-I (PD-1) pathway in regulation of experimental autoimmune encephalomyelitis," The Journal of Experimental Medicine 198(1):71-78, The Rockefeller University Press, United States (2003).
Sanmamed et al. "Agonists of Co-stimulation in Cancer Immunotherapy Directed Against CD137, OX40, GITR, CD27, CD28, and ICOS" Seminars in Oncology (2015) vol. 42, No. 4, pp. 640-655.
Santiago et al., "Structures of T Cell Immunoglobulin Mucin Receptors 1 and 2 Reveal Mechanisms for Regulation of Immune Responses by the TIM Receptor Family" Immunity (2007) vol. 26 pp. 299-310.
Schroll, A. et al., "Tim3 Is Upregulated and Protective in Nephrotoxic Serum Nephritis", The American Journal of Pathology, vol. 176, No. 4, Apr. 2010.
Search Report and Written Opinion issued in Singapore Application No. 11201605627T dated Aug. 15, 2017.
Search Report and Written Opinion issued in Singapore Application No. 11201702401R, completed Mar. 29, 2018.
Shakhov et al., "SMUCKLER/TIM4 is a distinct member of TIM family expressed by stromal cells of secondary lymphoid tissues and associated with lymphotoxin signaling" Eur. J. Immunol (2004) vol. 34 pp. 494-503.
Sher et al. "Regulation of Immunity to Parasited by T cells and T Cell-derived Cytokines" Annual Review Immunol (1992) vol. 10, pp. 385-409.
Shinohara, T., et al., "Structure and chromosomal localization of the human PD-1 gene (PDCD1)," Genomics 23(3):704-706, Academic Press, United States (1994).

(56) References Cited

OTHER PUBLICATIONS

Sho, M., et al., "Possibility of Clinical Applications for Novel Cancer Immunotherapy via Inhibition of T-cell Negative Pathway," Magazine of the Japan Society of Clinical Oncology 40(2):590 (PS22-5) (2005).

Simeone et al., "Immunomodulating antibodies in the treatment of metastatic melanoma: The experience with anti-CTLA-4, anti-CD137, and anti-PD1," Journal of Immunotoxicology (2012) vol. 9, No. 3, pp. 241-247.

Simmons et al., "Tim-3+ T-bet+ Tumor-Specific Th1 Cells Colocalize with and Inhibit Development and Growth of Murine Neoplasms" The Journal of Immunology (2005) vol. 174 pp. 1405-1415.

Soares et al. "Recombinant Himan Tumor Antigen MUC1 Expressed in Insect Cells: Structure and Immunogenicity" Protein Expression and Purification (2001) vol. 22, pp. 92-100.

Soh, E.Y., et al., "Neutralizing vascular endothelial growth factor activity inhibits thyroid cancer growth in vivo," Surgery 128(6):1059-1066, Mosby, United States (2000).

Song et al: "3681 Phenotypic and Functional Effects of Novel HDAC Inhibitor LBH589 on Human Lymphocyte Populations", 51st ASH Annual Meeting and Exposition (2009) Retrieved from the Internet: URL:https:jjash.confex.comjash/2889/webprogramjPaper22684.html [retrieved on Apr. 14, 2016].

Song W et al: "HDAC inhibition by LBH589 affects the phenotype and function of human myeloid dendritic cells.", Leukemia Jan. 2811, vol. 25, No. 1, Jan. 2011 (Jan. 2011), pp. 161-168.

Steele et al., "CXCR2 Inhibition Profoundly Suppresses Metastases and Augments Immunotherapy in Pancreatic Ductal Adenocarcinoma," Cancel Cell (2016) vol. 29, pp. 832-845.

Stewart et al., "MED14736: Delivering effective blockade of immunosuppression to enhance tumour rejection: Monoclonal antibody discovery and practical development," Cancer Res (2011) vol. 71, No. 8 (Supp), Abstract LB-158.

Strome et al., "A Mechanistic Perspective of Monoclonal Antibodies in Cancer Therapy Beyond Target-Related Effects," The Oncologist (2007) vol. 12, pp. 1084-1095.

Stromnes et al., "Pancreatic Cancer: Planning Ahead for Metastatic Spread," Cancel Cell (2016) vol. 29, No. 6, pp. 774-776.

Supplementary Partial European Search Report for European Application No. EP 1484888, dated Mar. 1, 2017. 10 pages.

Swallow et al., "B7h, a Novel Costimulatory Homolog of B7.1 and B7.2, Is Induced by TNFa," Immunity (1999) vol. 11, pp. 423-432.

Sánchez-Fueyo et al., "Tim-3 inhibits T helper type 1-mediated auto- and alloimmune responses and promotes immunological tolerance," Nat Immunol (2003) vol. 4, No. 11, pp. 1093-1101.

Takamura et al., "Premature Terminal Exhaustion of Friend Virus-Specific Effector $CD8_+$ T Cells by Rapid Induction of Multiple Inhibitory Receptors" J Immunol (2010) vol. 184 pp. 4696-4707.

Talmadge et al. "Murine Models to Evaluate Novel and Conventional Therapeutic Strategies for Cancer" The American Journal of Pathology (2007) vol. 170, No. 3, pp. 793-804.

Tamura, H., et al., "B7-H1 costimulation preferentially enhances CD28-independent T-helper cell function," Blood 97(6):1809-1816, The American Society of Hematology, United States (2001).

Tang et al. "Immunotherapy and tumor microenvironment" Cancer Letters (2016) vol. 370, pp. 85-90.

Teeling, J.L., et al., "Characterization of new human CD20 monoclonal antibodies with potent cytolytic activity against non-Hodgkin Lymphomas," Blood 104(6):1793-1800, American Society of Hematology, United States (2004).

Thangamathesvaran et al., "Immune checkpoint inhibitors and radiotherapy—concept and review of current literature," Ann Transl Med (2018) vol. 6, No. 8, Article 155, 11 pages.

Thomas et al "Combined Effects of RU486 and Tamoxifen on the Growth and Cell Cycle Phases of the MCF-7 Cell Line" Journal of Clinical Endocrinology and Metabolism (1992) vol. 75, Issue 3, pp. 865-870.

Thomas et al. "Effects of Gossypol on the Cell Cycle Phases in T-47D Human Breast Cancer Cells" Anticancer Research (1991) vol. 11, No. 4, pp. 1469-1476.

Thomas, M.L., "Of ITAMs and ITIMs: turning on and off the B cell antigen receptor," The Journal of Experimental Medicine 181(6):1953-1956, The Rockefeller University Press, United States (1995).

Thompson et al, "Tumor B7-H1 Is Associated with Poor Prognosis in Renal Cell Carcinoma Patients with Long-term Follow-up" Cancer Res. (2006) vol. 66, pp. 3381-3385.

Thompson, R. Houston, et al.; "PD-1 is expressed by tumor-infiltrating immune cells and is associated with poor outcome for patients with renal cell carcinoma"; Clin. Cancer Res. 13(6):1757-1761 (2007).

Thurber et al. "Antibody tumor penetration: Transport opposed by systemic and antigen-mediated clearance" Advanced Drug Delivery Reviews (2008) vol. 60, pp. 1421-1434.

Tomlinson, I.M., et al., "The repertoire of human germline VH sequences reveals about fifty groups of VH segments with different hypervariable loops," Journal of Molecular Biology 227(3):776-798, Elsevier, Netherlands (1992).

Topalian et al., "Safety, Activity, and Immune Correlates of Anti-PD-1 Antibody in Cancer," N Engl J Med (2012) vol. 366, No. 26, pp. 2443-2454.

Topalian, S., "Q&A: Suzanne Topalian on Immune Therapies", Cancer Discovery 3(7):712, American Association for Cancer Research, United States, published online Jun. 27, 2013.

Topalian, S., et al., "Nivolumab (anti-PD-1; BMS-936558; ONO-4538) in patients with advanced solid tumors: Survival and long-term safety in a phase I trial," accessed at http://meetinglibrary.asco.org/content/113543-132, accessed on Jun. 1, 2016, 2pages.

Topalian, S.L., et al., "Safety, Activity, and Immune Correlates of Anti-PD-1 Antibody in Cancer," The New England Journal of Medicine 366(26):2443-2454, Massachusetts Medical Society, United States (2012).

Trautmann, Lydie, et al.; "Upregulation of PD-1 expression on HIV-specific $CD8_+$ T cells leads to reversible immune dysfunction"; Nat. Med.; 12(10):1198-1202 (2006).

Triebel et al., "LAG-3, A Novel Lymphocyte Activation Gene Closely Related to CD4," J Exp Med (1990) vol. 171, pp. 1393-1405.

Triebel, "LAG-3: a regulator of T-cell and DC responses and its use in therapeutc vaccination," Trends Immunol (2003) vol. 24, No. 12, pp. 619-622.

Tsai, C-J., et al., "Protein Allostery, signal transmission and dynamics: a classification scheme of allosteric mechanisms," Molecular BioSystems 5(3):207-216, Royal Society of Chemistry, England (2009).

Tsushima, Fumihiko, et al.; "Predominant expression of B7-H1 and its immunoregulatory roles in oral squamous cell carcinoma"; Oral Oncology; 42:268-274 (2006).

Tuskan et al., "Real-time PCR analysis of candidate imprinted genes on mouse chromosome 11 shows balanced expression from the maternal and paternal chromosomes and strain-specific variation in expression levels" Epigenetics (2008) vol. 3 No. 1 pp. 43-50.

UniProtKB/Swiss-Prot Database entry, PDCD1.sub.--HUMAN, accessed at http://www.uniprot.org/uniprot/Q15116.txt, accessed on Jun. 1, 2016, 5 pages.

Van De Weyer et al. "A highly conserved tyosine of Tim-3 is phosphorylated upon stimulation by its ligand galectin-9" Biochemical and Biophysical Research Communications (2006) vol. 351, pp. 571-576.

Van Regenmortel, M.H.V., "The recognition of Proteins and Peptides by Antibodies," Journal of Immunoassay 21(2-3):85-108, Taylor & Francis, England (2000).

Vanneman et al: "Combining immunotherapy and targeted therapies in cancer treatment" Nature Reviews Cancer (2012) vol. 12 No. 4 pp. 237-251.

Verbrugge et al: "The curative outcome of radioinmunotherapy in a mouse breast cancer model relies on mTOR signaling", Radiation Research. Radiation Research Society, GB, (2014) vol. 182 No. 2 pp. 219-229.

Vietta et al. "Considering Therapeutic Antibodies" Science (2006) vol. 313, pp. 308-309.

(56) References Cited

OTHER PUBLICATIONS

Villalobos, "Primer organismo con ADN artificial logra reproducirse," retrieved from www.fayerwayer.com/2014/05/primer-organismo-con-adn-artificial-logra-reproducirse (2014) last accessed Oct. 18, 2019.

Vivier et al., "Immunoreceptor tyrosine-based inhibition motifs," Immunol Today (1997) vol. 18, No. 6, pp. 286-291.

Voskoglou-Nomikos et al. "Clinical Predictive Value of the in Vitro Cell Line, Human Xenograft, and Mouse Allograft Preclinical Cancer Models" Clinical Cancer Research (2003) vol. 9, pp. 4227-4239.

Waldmann, Thomas A.; "Effective cancer therapy through immunomodulation"; Annual Rev.; 57(1):65-81 (2006).

Walunas et al., "CTLA-4 can function as a negative regulator of T cell activation," Immunity (1994) vol. 1, No. 5, pp. 405-413.

Wang et al. "In Vitro Characterization of the Anti-PD-1 Antibody Nivolumab, BMS-936558, and In Vivo Toxicology in Non-Human Primates" Cancer Immunology Research (2014) vol. 2, No. 9, pp. 846-856.

Wang et al., "The Mdm2 inhibitor, NVP-CGM097, in combination with the BRAF inhibitor NVP-LGX818 elicits synergistic antitumor effects in melanoma" Cancer Research (2014), Abstract 5466, Retrieved from the Internet: URL:http://cancerres.aacrjournals.orgjcontent/74/19 Supplement/5466 [retrieved on Apr. 14, 2016].

Wang et al., "VISTA, a novel mouse Ig superfamily ligand that negatively regulates T cell responses" The Journal of Experimental Medicine (2011) vol. 208 No. 3 pp. 577-592.

Wang et al: "Abstract 2929: The Mdm2 inhibitor NVP-CGM097 enhances the anti-tumor activityof NVP-LDK378 in ALK mutant neuroblastomamodels", Cancer Research (2014) Retrieved from the Internet: URL:http:jjcancerres.aacrjournals.orgjcontent/74/19 Supplement/2929 [retrieved on Apr. 14, 2016].

Wang, "Interaction of TIM4-TIM1 Modulates the Function of CD4+CD25+35 Treg in Food Allergic Mice," Master's Thesis submitted at Zhengzhou University (2010) 65 pages, Chinese with English Abstract.

Watanabe et al., "Current approaches for the treatment of multiple myeloma," Int J Hematol (2013) vol. 97, pp. 333-344.

Weber, J.S., et al., "Safety, Efficacy, and Biomarkers of Nivolumab with Vaccine in Ipilimumab-Refractory or -Naive Melanoma," Journal of Clinical Oncology 31 (34):4311-4318, American Society of Clinical Oncology, United States (2013).

Weisberg et al., "Smac mimetics: implications for enhancement of targeted therapies in leukemia: Treating leukemia with Smac mimetics," Leukemia (2010) vol. 24, No. 12, pp. 2100-2109.

Wiener et al., "TIM-3 Is Expressed in Melanoma Cells and Is Upregulated in TGF-Beta Stimulated Mast Cells" Journal of Investigative Dermatology (2007) vol. 127 pp. 906-914.

Wilson, I.A. and Stanfield, R.L., "Antibody-antigen interactions," Current Opinion in Sturctural Biology 3:113-118, Current Biology, United States (1993).

Winslow, R., "New Cancer Drugs Harness Power of Immune System", The Wall Street Journal, May 15, 2013, accessed at http://www.wsj.com/articles/SB10001424127887323398204578485401089823868, accessed on Jun. 1, 2016, 4 pages.

Wolchok et al., "Nivolumab plus Ipilimumab in Advanced Melanoma," N Engl J Med (2013) vol. 369, pp. 122-133.

Wolchok, J.D., et al., "Nivolumab plus Ipilimumab in Advanced Melanoma," The New England Journal of Medicine 369(2):122-133, Massachusetts Medical Society, United States (2013).

Wong, R.M., et al., "Programmed death-1 blockade enhances expansion and functional capacity of human melanoma antigen-specific CTLs," International Immunology 19(10):1223-1234, Oxford University Press, England (2007).

Woo et al. "Immune Inhibitory Molecules LAG-3 and PD-1 Synergistically Regulate T-cell Function to Promote Tumoral Immune Escape" Cancer Research (2011) vol. 72, No. 4, pp. 917-927.

Woods David M et al: "HDAC Inhibition Upregulates PD-1 Ligands in Melanoma and Augments Immunotherapy with PD-1 Blockade," Cancer Immunology Research, vol. 3, No. 12, Dec. 2015 (Dec. 2015), pp. 1375-1385.

Woods David M et al: "The antimelanoma activity of the histone deacetylase inhibitor panobinostat (LBH589) is mediated by direct tumor cytotoxicity and increased tumor immunogenicity.", Melanoma Research, vol. 23, No. 5, Oct. 2013 (Oct. 2013), pp. 341-348.

Woods et al: "Abstract 4090: Inhibition of class I histone deacetylases promotes robust and durable enhancement of PDL1 expression in melanoma: Rationale for combination therapy", Cancer Research (2014) Retrieved from the Internet: URL:http://cancerres.aacrjournals.orgjcontent/74/19Supplement/4090.short [retrieved on Apr. 14, 2016].

Workman et al., "Negative Regulation of T Cell Homeostasis by Lymphocyte Activation Gene-3 (CD223)," J Immunol (2005) vol. 174, pp. 688-695.

Wu et al., "Endothelial cell-expressed Tim-3 facilitates metastasis of melanoma cells by activating the NF-κB pathway" Oncology Reports (2010) vol. 24 pp. 693-699.

Wu et al., "Immunotherapies: The Blockade of Inhibitory Signals," Int J Biol Sci (2012) vol. 8, No. 10, pp. 1420-1430.

Wu, K-P., et al., "Structural Basis of a Flavivirus Recognized by Its Neutralizing Antibody: Solution Structure of the Domain III of the Japanese Encephalitis Virus Envelope Protein," The Journal of Biological Chemistry 278(46):46007-46013, AmericanSociety for Biochemistry and Molecular Biology, Inc., United States (Nov. 2003).

Yamazaki, T., et al., "Expression of programmed death 1 ligands by murine T cells and APC," The Journal of Immunology 169(10):5538-5545, The American Association of Immunologists, United States (2002).

Yan et al., "Tim-3 Expression Defines Regulatory T Cells in Human Tumors" PLoS ONE (2013) vol. 8 No. 3 e58006.

Yang et al., "Lack of TIM-3 Immunoregulation in Multiple Sclerosis" The Journal of Immunology (2008) vol. 180 No. 7 pp. 4409-4414.

Yervoy (ipilimumab) Drug Label, Initial U.S. Approval: 2011, Revised Oct. 2015.

Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology,Inc., United States (2002).

Youngnak, Pornpan, et al.; "Differential binding properties of B7-H1 and B7-DC to programmed death-1"; Biochem. Biophys. Res. Commun.; 307:672-677 (2003).

Yuan Z et al, "Blockade of inhibitors of apoptosis (IAPs) in combination with tumor-targeted delivery of tumor necrosis factor-[alpha] leads to synergistic antitumor activity" Cancer Gene Therapy (2013) vol. 20 No. 1 pp. 46-56.

Zamarin et al. "Immune checkpoint modulation: Rational design of combindation strategies" Pharmacology & Therapeutics (2015) vol. 150, pp. 23-32.

Zehavi-Willner, Tova, et al.; "The mitogenic activity of staphylococcal enterotoxin B (Seb): a monovalent T cell mitogen that stimulates cytolytic T lymphocytes but cannot mediate their lytic interaction"; J. Immunol.; 137(8):2682-2687 (1986).

Zhang et al., "Tim-3 regulates pro-and anti-inflammatory cytokine expression in human CD14+ monocytes" Journal of Leucyte Biology (2012) vol. 91 pp. 189-196.

Zhang, "Oral 31—PD1 Axis Inhibition," Abstract from Poster Presentation from International Association for the Study of Lung Cancer, Aug. 9, 2015, retrieved from library.iaslc.org/search-speaker?search_speaker=30076.

Zhang, "P2.01-097—Phase 3 Study of Pembrolizumab vs Platinum-Based Chemotherapy for PD-L1 ," (NSCLC ID 2182) Abstract from Poster Presentation from International Association for the Study of Lung Cancer, Aug. 9, 2015, retrieved from library.iaslc.org/search-speaker?search_speaker=30076.

Zhang, Xuewu, et al.; "Structural and Functional Ana ysis of the Costimulatory Receptor Programmed Death-1"; Immunity; 20:337-347 (2004).

(56) References Cited

OTHER PUBLICATIONS

Zhou et al., "Coexpression of Tim-3 and PD-1 identifies a $CD8^+$ T-cell exhaustion phenotype in mice with disseminated acute myelogenous leukemia" Blood (2011) vol. 117 No. 17 pp. 4501-4510.

Zhu et al., "CSF1/CSF1 R Blockade Reprograms Tumor-Infiltrating Macrophages and Improves Response to T-cell Checkpoint Immunotherapy in Pancreatic Cancer Models," Cancer Research (2014) vol. 74, No. 18, pp. 5057-5069.

Zhuang J et al: "Selective IAP inhibition results in sensitization of unstimulated but not CD40-stimulated chronic lymphocytic leukaemia cells to TRAIL-induced apoptosis" Pharmacology Research & Perspectives (2014) vol. 2 Issue 6, Article E00081, 14 pages.

Zou, W. and Chen, L., "Inhibitory B7-family Molecules in the Tumour Microenvironment," Nature Reviews Immunology 8(6):467-477, Nature Publishing Group, England (2008).

Zuberek, K., "The role of in vivo PD-1/PD-L1 interactions in syngeneic and allogeneic antitumor responses in murine tumor models," Blood 98(11):42B (2001).

Zuberek, Krystyna, et al.; "In vitro and in vivo expression regulation of PD-1 and PD-L1 in murine tumor models"; Blood; 98(11 Part 1):25a (2001).

Christensen et al., "c-Met as a target for human cancer and characterization of inhibitors for therapeutic intervention," Cancer Letters (2005) vol. 225, pp. 1-26.

Edwards et al., "The Remarkable Flexibility of the Human Antibody Repertoire; Isolation of Over One Thousand Different Antibodies to a Single Protein, BLyS," J Mol Biol (2003) vol. 334, pp. 103-118.

Extended European Search Report issued in European Patent Application No. 18211373.8, dated Jun. 25, 2019.

Fessas et al., "A molecular and preclinical comparison of the PD-1-targeted T-cell checkpoint inhibitors nivolumab and pembrolizumab," Seminars in Oncology (2017) vol. 44, pp. 136-140.

Lu et al., "Everolimus enhances the cytotoxicity of bendamustine in multiple myeloma cells through a network of pro-apoptotic and cell-cycle-progression regulatory proteins," Acta Biochim Biophys Sin (2013) vol. 45, pp. 683-691.

Marchalonis et al., "The antibody repertoire in evolution: Chance, selection, and continuity," Developmental and Compative Immunology (2006) vol. 30, pp. 223-247.

Miko et al., "Involvement of Galectin-9/TIM-3 Pathway in the Systemic Inflammatory Response in Early-Onset Preeclampsia," PLOS One (2013) vol. 8, No. 8, Article e71811, 9 pages.

OPDIVO (nivolumab) Drug Label, Initial U.S. Approval: 2014, Revised Nov. 2016, 58 pages.

Partial European Search Report issued in European Patent Application No. 19206634.8, dated Apr. 30, 2020.

Variable region sequence of murine antibody ABTIM3
Heavy chain (118 aa; SEQ ID NO: 1)

```
QVQLQQPGAE LVKPGASVKM SCKASGYTFT SYNMHWIKQT PGQGLEWIGD IYPGNGDTSY
NQKFKGKATL TADKSSSTVY MQLSSLTSED SAVYYCARVG GAFPMDTWGQ GTSVTVSS
```

Light chain (111 aa; SEQ ID NO: 2)

```
DIVLTQSPAS LAVSLGQRAT ISCRASESVE YYGTSLMQWY QQKPGQPPKL LIYAASNVES
GVPARFSGSG SGTDFSLNIH PVEEDDIAIY FSQQSRKDPS TFGGGTKLEI K
```

Fig. 1A

Sequence alignment of murine antibody ABTIM3 versus murine germline antibody sequences

Heavy chain (118 aa)
V-gene: 94.1% identity (271/288 nt) with IGHV1-12*01F
J-gene: 90.57% identical (48/53) with IGHJ4*01F
Total of 10 amino acid differences

```
ABTIM3 QVQLQQPGAE LVKPGASVKM SCKASGYTFT SYNMHWIKQT PGQGLEWIGD IYPGNGDTSY
G1     -AY---S--- --R------- ---------- ------V--- -R------A ----------

ABTIM3 NQKFKGKATL TADKSSSTVY MQLSSLTSED SAVYYCARVG GAFPMDYWGQ GTSVTVSS
G1     ---------- -V------A- ---------- ----F---
```

Light chain (111 aa)
V-gene: 99.66% identical (290/291 nt) with IGKV3-1*01F
J-gene: 97.06% identity with IGKJ1*01F
Total of 2 amino acid differences

```
ABTIM3 DIVLTQSPAS LAVSLGQRAT ISCRASESVE YYGTSLMQWY QQKPGQPPKL LIYAASNVES
g1     ---------- ---------- ---------- ---------- ---------- ----------

ABTIM3 GVPARFSGSG SGTDFSLNIH PVEEDDIAIY FCQQSRKDPS TFGGGTKLEI K
g1     ---------- ---------- --------M- ------V--  ---------- -
```

Fig.1B

|  | BIAcore $K_D$ (nM) | TIM-3-300.19 $K_D$ (nM) | Cyno cell $K_D$ (nM) |
|---|---|---|---|
| anti-TIM-3#2 | 0.459 | 1.57 | 7.4 |
| ABTIM3 | 0.042 | 0.16 | 0.68 |
Fig. 2A
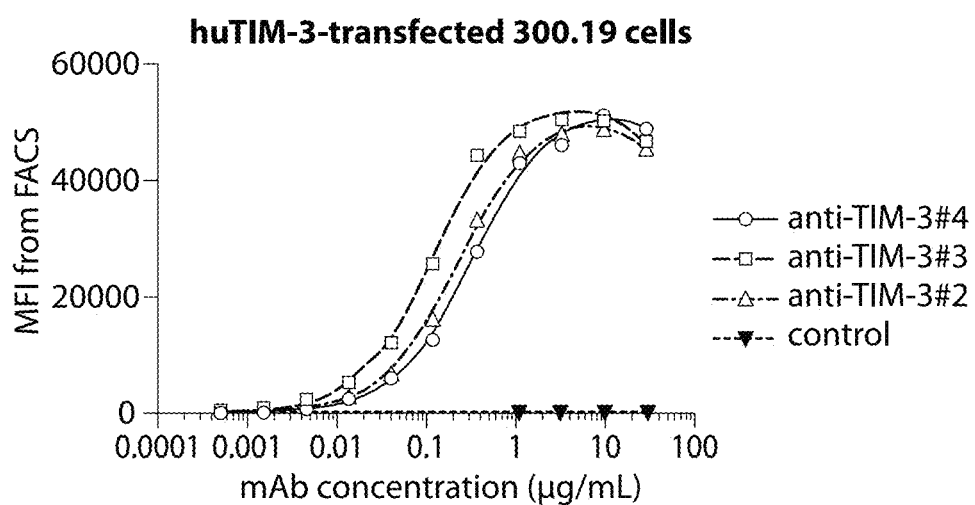
Fig. 2B
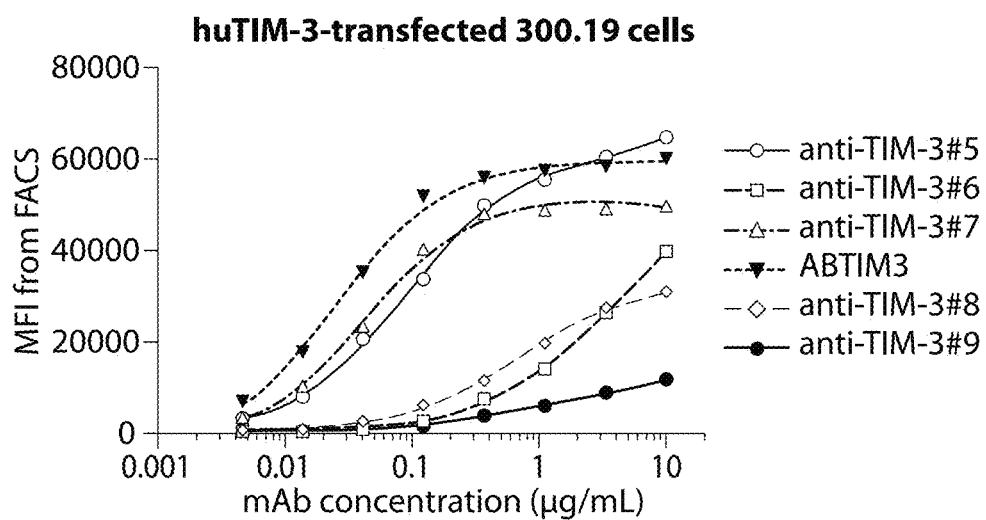
Fig. 2C

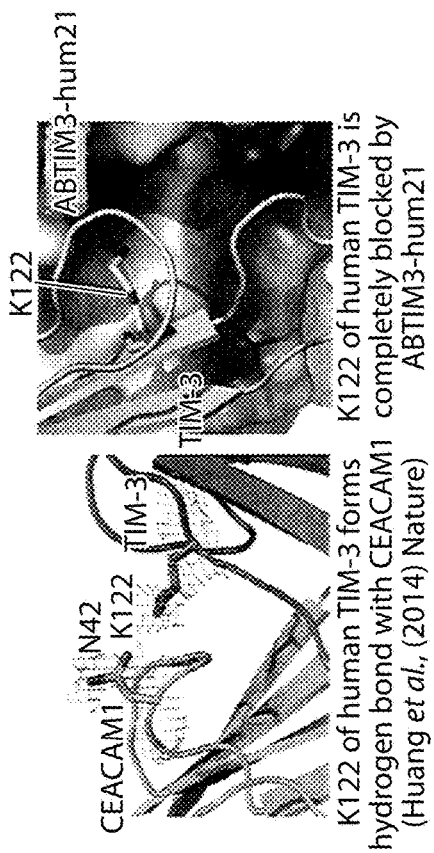
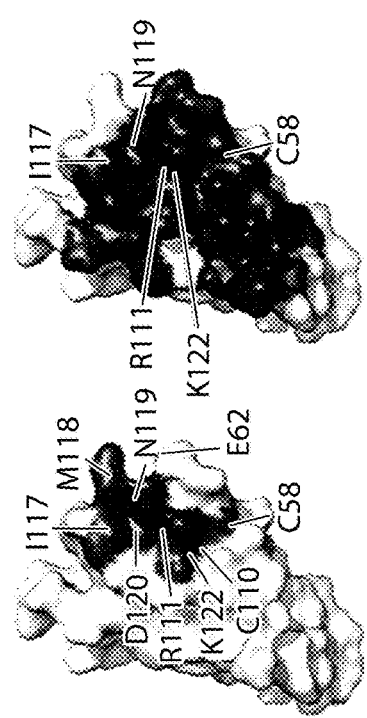
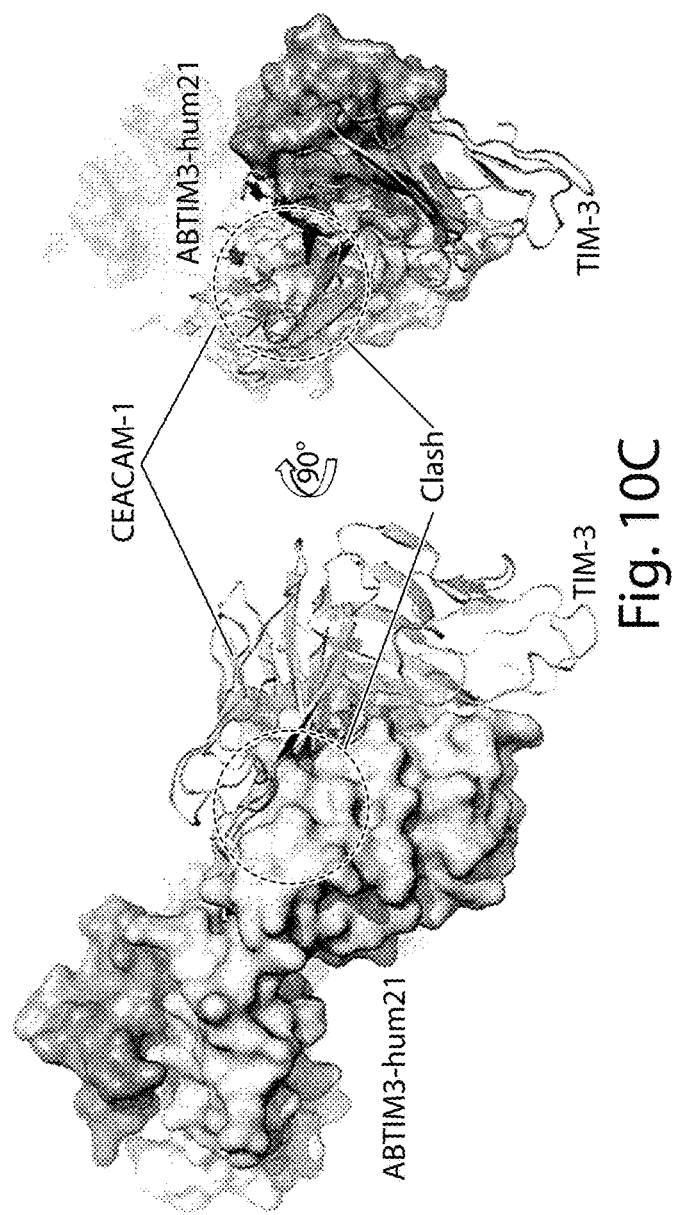
Fig. 10A
Fig. 10B
Fig. 10C

DeKruyff, et al., (2010) J Immunol. 184(4):1918-1930

SEQUENCE LISTING

```
<160> NUMBER OF SEQ ID NOS: 142

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Ile Lys Gln Thr Pro Gly Gln Gly Leu Glu Trp Ile
        35                  40                  45

Gly Asp Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95

Ala Arg Val Gly Gly Ala Phe Pro Met Asp Tyr Trp Gly Gln Gly Thr
            100                 105                 110

Ser Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Leu Thr Gln Ser Pro Ala Ser Leu Ala Val Ser Leu Gly
```

```
                1               5                  10                  15
            Gln Arg Ala Thr Ile Ser Cys Arg Ala Ser Glu Ser Val Glu Tyr Tyr
                        20                  25                  30
            Gly Thr Ser Leu Met Gln Trp Tyr Gln Gln Lys Pro Gly Gln Pro Pro
                    35                  40                  45
            Lys Leu Leu Ile Tyr Ala Ala Ser Asn Val Glu Ser Gly Val Pro Ala
                50                  55                  60
            Arg Phe Ser Gly Ser Gly Ser Gly Thr Asp Phe Ser Leu Asn Ile His
            65                  70                  75                  80
            Pro Val Glu Glu Asp Asp Ile Ala Ile Tyr Phe Cys Gln Gln Ser Arg
                            85                  90                  95
            Lys Asp Pro Ser Thr Phe Gly Gly Gly Thr Lys Leu Glu Ile Lys
                        100                 105                 110
```

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Ser Tyr Asn Met His
1               5
```

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Asp Ile Tyr Pro Gly Asn Gly Asp Thr Ser Tyr Asn Gln Lys Phe Lys
1               5                   10                  15
Gly
```

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Val Gly Gly Ala Phe Pro Met Asp Tyr
1               5
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Arg Ala Ser Glu Ser Val Glu Tyr Tyr Gly Thr Ser Leu Met Gln
1               5                   10                  15
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ser Asn Val Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Ser Arg Lys Asp Pro Ser Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Thr Phe Thr Ser Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Pro Gly Asn Gly Asp
1               5

<210> SEQ ID NO 11
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caggtgcaac tgcagcagcc tggggctgag ctggtgaagc ctggggcctc agtgaagatg      60
tcctgcaagg cttctggcta cacatttacc agttacaata tgcactggat aaagcagaca     120
cctggacagg gcctggaatg gattggagat atttatccag gaaatggtga tacttcctac     180
aatcagaaat tcaaaggcaa ggccacattg actgcagaca atcctccag cacagtctac      240 atgcagctca gcagcctgac atctgaggac tctgcggtct attactgtgc aagagtgggg     300
ggtgcctttc ctatggacta ctggggtcaa ggaacctcag tcaccgtctc ctca           354
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Glu Ser Val Glu Tyr Tyr Gly Thr Ser Leu
1               5                   10

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Ser
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Arg Lys Asp Pro Ser
1               5

<210> SEQ ID NO 15
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gacattgtgc tcacccaatc tccagcttct ttggctgtgt ctctagggca gagagccacc      60
atctcctgca gagccagtga aagtgttgaa tattatggca caagtttaat gcagtggtac     120
caacagaaac caggacagcc acccaaactc ctcatctatg ctgcatccaa cgtagaatct     180
ggggtccctg ccaggtttag tggcagtggg tctgggacag acttcagcct caacatccat     240
cctgtggagg aggatgatat tgcaatatat ttctgtcagc aaagtaggaa ggatccttcg     300
acgttcggtg gaggcaccaa gctggagatc aaa                                  333

<210> SEQ ID NO 16
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                    20                  25                  30

Asn Met His Trp Val Arg Gln Ala Pro Gly Gln Gly Leu Glu Trp Ile
         35                  40                  45

Gly Asp Ile Tyr Pro Gly Asn Gly Asp Thr Ser Tyr Asn Gln Lys Phe
     50                  55                  60

Lys Gly Arg Ala Thr Met Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caggtgcagc tggtgcagtc aggcgccgaa gtgaagaaac ccggcgctag tgtgaaagtc      60
tcttgtaaag ctagtggcta caccttcact agctataata tgcactgggt tcgccaggcc     120
ccagggcagg gcctcgagtg gatcggcgat atctaccccg ggaacggcga cactagttat     180
aatcagaagt ttaagggtag agctactatg accgccgata agtctactag caccgtctat     240
atggaactga gttccctgag gtctgaggac accgccgtct actactgcgc tagagtgggc     300
ggagccttcc ctatggacta ctggggtcaa ggcacccctgg tcaccgtgtc tagc          354

<210> SEQ ID NO 18
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
         35                  40                  45

Gly Asp Ile Tyr Pro Gly Asn Gly Asp Thr Ser Tyr Asn Gln Lys Phe
     50                  55                  60

Lys Gly Arg Ala Thr Met Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 19
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtgcagtc aggcgccgaa gtgaagaaac ccggcgctag tgtgaaagtc      60
tcttgtaaag ctagtggcta caccttcact agctataata tgcactgggt tcgccaggcc     120
ccagggcagg gcctcgagtg gatcggcgat atctaccccg ggaacggcga cactagttat     180
aatcagaagt ttaagggtag agctactatg accgccgata gtctactagc caccgtctat     240
atggaactga gttccctgag gtctgaggac accgccgtct actactgcgc tagagtgggc     300

```
ggagccttcc ctatggacta ctggggtcaa ggcaccctgg tcaccgtgtc tagcgctagc    360
actaagggcc cgtccgtgtt ccccctggca ccttgtagcc ggagcactag cgaatccacc    420
gctgccctcg gctgcctggt caaggattac ttcccggagc ccgtgaccgt gtcctggaac    480
agcggagccc tgacctccgg agtgcacacc ttccccgctg tgctgcagag ctccgggctg    540
tactcgctgt cgtcggtggt cacggtgcct tcatctagcc tgggtaccaa gacctacact    600
tgcaacgtgg accacaagcc ttccaacact aaggtggaca agcgcgtcga atcgaagtac    660
ggcccaccgt gcccgccttg tcccgcgccg gagttcctcg gcggtccctc ggtctttctg    720
ttcccaccga agcccaagga cactttgatg atttcccgca cccctgaagt gacatgcgtg    780
gtcgtggacg tgtcacagga agatccggag gtgcagttca attggtacgt ggatggcgtc    840
gaggtgcaca cgccaaaaac caagccgagg gaggagcagt tcaactccac ttaccgcgtc    900
gtgtccgtgc tgacggtgct gcatcaggac tggctgaacg gaaggagta caagtgcaaa    960 gtgtccaaca agggacttcc tagctcaatc gaaaagacca tctcgaaagc aagggacag   1020 ccccgggaac ccaagtgta taccctgcca ccgagccagg aagaaatgac taagaaccaa   1080
gtctcattga cttgccttgt gaagggcttc tacccatcgg atatcgccgt ggaatgggag   1140
tccaacggcc agccggaaaa caactacaag accacccctc cggtgctgga ctcagacgga   1200
tccttcttcc tctactcgcg gctgaccgtg gataagagca gatggcagga gggaaatgtg   1260
ttcagctgtt ctgtgatgca tgaagccctg cacaaccact acactcagaa gtccctgtcc   1320
ctctccctgg ga                                                      1332
```

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110
```

<210> SEQ ID NO 21
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gatatcgtcc tgactcagtc acccgatagc ctggccgtca gcctgggcga gcgggctact      60
attaactgta gagctagtga atcagtcgag tactacggca ctagcctgat gcagtggtat     120
cagcagaagc ccggtcaacc ccctaagctg ctgatctacg ccgcctctaa cgtggaatca     180
ggcgtgcccg ataggtttag cggtagcggt agtggcaccg acttcaccct gactattagt     240
agcctgcagg ccgaggacgt ggccgtctac tactgtcagc agtctaggaa ggaccctagc     300
accttcggcg gaggcactaa ggtcgagatt aag                                  333
```

<210> SEQ ID NO 22
<211> LENGTH: 218
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 22

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 23
<211> LENGTH: 654
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 23

```
gatatcgtcc tgactcagtc acccgatagc ctggccgtca gcctgggcga gcgggctact      60
```

-continued

```
attaactgta gagctagtga atcagtcgag tactacggca ctagcctgat gcagtggtat      120
cagcagaagc ccggtcaacc ccctaagctg ctgatctacg ccgcctctaa cgtggaatca      180
ggcgtgcccg ataggtttag cggtagcggt agtggcaccg acttcaccct gactattagt      240
agcctgcagg ccgaggacgt ggccgtctac tactgtcagc agtctaggaa ggaccctagc      300
accttcggcg gaggcactaa ggtcgagatt aagcgtacgg tggccgctcc cagcgtgttc      360
atcttccccc ccagcgacga gcagctgaag agcggcaccg ccagcgtggt gtgcctgctg      420
aacaacttct accccgggga ggccaaggtg cagtggaagg tggacaacgc cctgcagagc      480
ggcaacagcc aggagagcgt caccgagcag gacagcaagg actccaccta cagcctgagc      540
agcaccctga ccctgagcaa ggccgactac gagaagcata aggtgtacgc ctgcgaggtg      600
acccaccagg gcctgtccag ccccgtgacc aagagcttca caggggcga gtgc            654
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Ile Tyr Pro Gly Ser Gly Asp Thr Ser Tyr Asn Gln Lys Phe Lys
1               5                   10                  15

Gly

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Pro Gly Ser Gly Asp
1               5

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Ile
            35                  40                  45

Gly Asp Ile Tyr Pro Gly Ser Gly Asp Thr Ser Tyr Asn Gln Lys Phe
        50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 27
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtgcagc tggtgcagtc aggcgccgaa gtgaagaaac ccggcgctag tgtgaaagtt    60
agctgtaaag ctagtggcta caccttcact agctataata tgcactgggt tcgccaggcc   120
ccaggtcaag gcctcgagtg gatcggcgat atctaccccg gtagcggcga cactagttat   180
aatcagaagt ttaagggtag agctactatg accgccgata gtctactagt caccgtctat   240
atggaactga gttccctgag gtctgaagat accgccgtct actactgcgc tagagtgggc   300
ggagccttcc ctatggacta ctggggtcaa ggcaccctgg tcaccgtgtc tagc          354

<210> SEQ ID NO 28
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Ser Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

```
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440

<210> SEQ ID NO 29
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caggtgcagc tggtgcagtc aggcgccgaa gtgaagaaac ccggcgctag tgtgaaagtt      60
agctgtaaag ctagtggcta caccttcact agctataata tgcactgggt tcgccaggcc    120
ccaggtcaag gcctcgagtg gatcggcgat atctaccccg gtagcggcga cactagttat    180
aatcagaagt ttaagggtag agctactatg accgccgata gtctactagc accgtctat    240 atggaactga gttccctgag gtctgaagat accgccgtct actactgcgc tagagtgggc    300
ggagccttcc ctatggacta ctggggtcaa ggcaccctgg tcaccgtgtc tagcgctagc    360
actaagggcc cgtccgtgtt ccccctggca ccttgtagcc ggagcactag cgaatccacc    420
gctgccctcg gctgcctggt caaggattac ttccccgagc ccgtgaccgt gtcctggaac    480
agcggagccc tgacctccgg agtgcacacc ttccccgctg tgctgcagag ctccgggctg    540
tactcgctgt cgtcggtggt cacggtgcct tcatctagcc tgggtaccaa gacctacact    600
tgcaacgtgg accacaagcc ttccaacact aaggtggaca agcgcgtcga atcgaagtac    660
ggcccaccgt gcccgccttg tcccgcgccg gagttcctcg gcggtccctc ggtctttctg    720
```

```
ttcccaccga agcccaagga cactttgatg atttcccgca ccccctgaagt gacatgcgtg    780 gtcgtggacg tgtcacagga agatccggag gtgcagttca attggtacgt ggatggcgtc    840
gaggtgcaca acgccaaaac caagccgagg gaggagcagt tcaactccac ttaccgcgtc    900
gtgtccgtgc tgaccggtgct gcatcaggac tggctgaacg gaaggagta caagtgcaaa    960 gtgtccaaca agggacttcc tagctcaatc gaaaagacca tctcgaaagc caagggacag    1020
ccccgggaac cccaagtgta tacctgcca ccgagccagg aagaaatgac taagaaccaa    1080
gtctcattga cttgccttgt gaagggcttc tacccatcgg atatcgccgt ggaatgggag    1140
tccaacggcc agccggaaaa caactacaag accacccctc cggtgctgga ctcagacgga    1200
tccttcttcc tctactcgcg gctgaccgtg gataagagca gatggcagga gggaaatgtg    1260
ttcagctgtt ctgtgatgca tgaagccctg cacaaccact acactcagaa gtccctgtcc    1320
ctctccctgg ga                                                        1332
```

<210> SEQ ID NO 30  
<211> LENGTH: 17  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 30

Asp Ile Tyr Pro Gly Gln Gly Asp Thr Ser Tyr Asn Gln Lys Phe Lys
1               5                   10                  15

Gly

<210> SEQ ID NO 31  
<211> LENGTH: 6  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 31

Tyr Pro Gly Gln Gly Asp
1               5

<210> SEQ ID NO 32  
<211> LENGTH: 118  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Ile
            35                  40                  45

Gly Asp Ile Tyr Pro Gly Gln Gly Asp Thr Ser Tyr Asn Gln Lys Phe
        50                  55                  60

Lys Gly Arg Ala Thr Met Thr Ala Asp Lys Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115
```

<210> SEQ ID NO 33
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
caggtgcagc tggtgcagtc aggcgccgaa gtgaagaaac ccggcgctag tgtgaaagtt      60
agctgtaaag ctagtggcta tactttcact tcttataata tgcactgggt ccgccaggcc     120
ccaggtcaag gcctcgagtg gatcggcgat atctaccccg gtcaaggcga cacttcctat     180
aatcagaagt ttaagggtag agctactatg accgccgata agtctacttc taccgtctat     240
atggaactga gttccctgag gtctgaggac accgccgtct actactgcgc tagagtgggc     300
ggagccttcc caatggacta ctggggtcaa ggcaccctgg tcaccgtgtc tagc           354
```

<210> SEQ ID NO 34
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 35
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
caggtgcagc tggtgcagtc aggcgccgaa gtgaagaaac ccggcgctag tgtgaaagtt     60
agctgtaaag ctagtggcta tactttcact tcttataata tgcactgggt ccgccaggcc    120
ccaggtcaag gcctcgagtg gatcggcgat atctaccccg gtcaaggcga cacttcctat    180
aatcagaagt ttaagggtag agctactatg accgccgata gtctacttc taccgtctat    240 atggaactga gttccctgag gtctgaggac accgccgtct actactgcgc tagagtgggc    300
ggagccttcc caatggacta ctggggtcaa ggcaccctgg tcaccgtgtc tagcgctagc    360
actaagggcc cgtccgtgtt ccccctggca ccttgtagcc ggagcactag cgaatccacc    420
gctgccctcg gctgcctggt caaggattac ttcccggagc ccgtgaccgt gcctggaac     480 agcggagccc tgacctccgg agtgcacacc ttccccgctg tgctgcagag ctccgggctg    540
tactcgctgt cgtcggtggt cacggtgcct tcatctagcc tgggtaccaa gacctacact    600

```
tgcaacgtgg accacaagcc ttccaacact aaggtggaca agcgcgtcga atcgaagtac      660
ggcccaccgt gcccgccttg tcccgcgccg gagttcctcg gcggtccctc ggtctttctg      720
ttcccaccga agcccaagga cactttgatg atttcccgca cccctgaagt gacatgcgtg      780
gtcgtggacg tgtcacagga agatccggag gtgcagttca attggtacgt ggatggcgtc      840
gaggtgcaca acgccaaaac caagccgagg gaggagcagt tcaactccac ttaccgcgtc      900
gtgtccgtgc tgacggtgct gcatcaggac tggctgaacg gcaaggagta caagtgcaaa      960
gtgtccaaca agggacttcc tagctcaatc gaaaagacca tctcgaaagc caagggacag     1020
ccccgggaac ccaagtgta tatccctgcca ccgagccagg aagaaatgac taagaaccaa     1080
gtctcattga cttgccttgt gaagggcttc tacccatcgg atatcgccgt ggaatgggag     1140
tccaacggcc agccggaaaa caactacaag accacccctc cggtgctgga ctcagacgga     1200
tccttcttcc tctactcgcg gctgaccgtg gataagagca gatggcagga gggaaatgtg     1260
ttcagctgtt ctgtgatgca tgaagccctg cacaaccact acactcagaa gtccctgtcc     1320
ctctccctgg ga                                                         1332
```

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Ile Arg Gln Ala Pro Gly Gln Gly Leu Glu Trp Ile
        35                  40                  45

Gly Asp Ile Tyr Pro Gly Asn Gly Asp Thr Ser Tyr Asn Gln Lys Phe
    50                  55                  60

Lys Gly Arg Ala Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115
```

<210> SEQ ID NO 37
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
caggtgcagc tggtgcagtc aggcgccgaa gtgaagaaac ccggcgctag tgtgaaagtt       60
tcttgtaaag ctagtggcta caccttcact agctataata tgcactggat tagacaggcc      120
ccagggcagg gcctcgagtg gatcggcgat atctaccccg ggaacggcga cactagttat      180
aatcagaagt ttaagggtag agctacccig accgccgata agtctactag caccgtctat      240
```
atggaactga gttccctgag gtctgaggac accgccgtct actactgcgc tagagtgggc    300
ggagccttcc ctatggacta ctgggggcag ggcaccctgg tcaccgtgtc tagc          354

<210> SEQ ID NO 38
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Ile Arg Gln Ala Pro Gly Gln Gly Leu Glu Trp Ile
        35                  40                  45

Gly Asp Ile Tyr Pro Gly Asn Gly Asp Thr Ser Tyr Asn Gln Lys Phe
    50                  55                  60

Lys Gly Arg Ala Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440
```

<210> SEQ ID NO 39
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
caggtgcagc tggtgcagtc aggcgccgaa gtgaagaaac cggcgctag tgtgaaagtt      60
tcttgtaaag ctagtggcta caccttcact agctataata tgcactggat tagacaggcc    120
ccagggcagg gcctcgagtg gatcggcgat atctacccg ggaacggcga cactagttat    180
aatcagaagt ttaagggtag agctaccctg accgccgata agtctactag caccgtctat    240
atggaactga gttccctgag gtctgaggac accgccgtct actactgcgc tagagtgggc    300
ggagccttcc ctatggacta ctgggggcag ggcacccctgg tcaccgtgtc tagcgctagc    360
actaagggcc cgtccgtgtt ccccctggca ccttgtagcc ggagcactag cgaatccacc    420
gctgccctcg gctgcctggt caaggattac ttcccggagc ccgtgaccgt gtcctggaac    480
agcggagccc tgacctccgg agtgcacacc ttccccgctg tgctgcagag ctccgggctg    540
tactcgctgt cgtcggtggt cacggtgcct tcatctagcc tgggtaccaa gacctacact    600
tgcaacgtgg accacaagcc ttccaacact aaggtggaca gcgcgtcga tcgaagtac    660
ggcccaccgt gcccgccttg tcccgcgccg gagttcctcg gcggtccctc ggtctttctg    720
ttcccaccga agcccaagga cactttgatg atttcccgca cccctgaagt gacatgcgtg    780
gtcgtggacg tgtcacagga agatccggag gtgcagttca attggtacgt ggatggcgtc    840
gaggtgcaca acgccaaaac caagccgagg gaggagcagt tcaactccac ttaccgcgtc    900
gtgtccgtgc tgacggtgct gcatcaggac tggctgaacg ggaaggagta caagtgcaaa    960
gtgtccaaca agggacttcc tagctcaatc gaaaagacca tctcgaaagc caagggacag   1020
ccccgggaac ccaagtgta ccctgcca ccgagccagg aagaaatgac taagaaccaa      1080
gtctcattga cttgccttgt gaagggcttc tacccatcgg atatcgccgt ggaatgggag   1140
tccaacggcc agccggaaaa caactacaag accacccctc cggtgctgga ctcagacgga   1200
tccttcttcc tctactcgcg gctgaccgtg gataagagca gatggcagga gggaaatgtg   1260
ttcagctgtt ctgtgatgca tgaagccctg cacaaccact acactcagaa gtccctgtcc   1320
ctctcccctgg ga                                                       1332
```

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Arg
                85                  90                  95

Lys Asp Pro Ser Thr Phe Gly Gly Thr Lys Val Glu Ile Lys
            100                 105                 110
```

<210> SEQ ID NO 41
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
gatatcgtcc tgactcagtc acccgatagc ctggccgtca gcctgggcga gcgggctact        60
attaactgta gagctagtga atcagtcgag tactacggca ctagcctgat gcagtggtat       120
cagcagaagc ccggtcaacc ccctaagctg ctgatctacg ccgcctctaa cgtggaatca       180
ggcgtgcccg ataggtttag cggtagcggt agtggcaccg acttcaccct gactattagt       240
agcctgcagg ccgaggacgt ggccgtctac ttctgtcagc agtctaggaa ggaccctagc       300
accttcggcg gaggcactaa ggtcgagatt aag                                     333
```

<210> SEQ ID NO 42
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80
```

Ser Leu Gln Ala Glu Asp Val Ala Val Tyr Phe Cys Gln Gln Ser Arg
            85                  90                  95

Lys Asp Pro Ser Thr Phe Gly Gly Gly Thr Lys Val Glu Ile Lys Arg
        100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 43
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gatatcgtcc tgactcagtc acccgatagc ctggccgtca gcctgggcga gcgggctact    60
attaactgta gagctagtga atcagtcgag tactacggca ctagcctgat gcagtggtat   120
cagcagaagc ccggtcaacc ccctaagctg ctgatctacg ccgcctctaa cgtggaatca   180
ggcgtgcccg ataggtttag cggtagcggt agtggcaccg acttcaccct gactattagt   240
agcctgcagg ccgaggacgt ggccgtctac ttctgtcagc agtctaggaa ggaccctagc   300
accttcggcg gaggcactaa ggtcgagatt aagcgtacgg tggccgctcc cagcgtgttc   360
atcttccccc ccagcgacga gcagctgaag agcggcaccg ccagcgtggt gtgcctgctg   420
aacaacttct accccgggga ggccaaggtg cagtggaagg tggacaacgc cctgcagagc   480
ggcaacagcc aggagagcgt caccgagcag gacagcaagg actccaccta cagcctgagc   540
agcaccctga ccctgagcaa ggccgactac gagaagcata aggtgtacgc ctgcgaggtg   600
acccaccagg gcctgtccag ccccgtgacc aagagcttca caggggcga gtgc           654

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Ile Arg Gln Ala Pro Gly Gln Gly Leu Glu Trp Ile

```
                35                  40                  45
Gly Asp Ile Tyr Pro Gly Ser Gly Asp Thr Ser Tyr Asn Gln Lys Phe
        50                  55                  60
Lys Gly Arg Ala Thr Leu Thr Ala Asp Lys Ser Thr Ser Thr Val Tyr
 65                 70                  75                  80
Met Glu Leu Ser Ser Leu Arg Ser Glu Asp Thr Ala Val Tyr Tyr Cys
                85                  90                  95
Ala Arg Val Gly Gly Ala Phe Pro Met Asp Tyr Trp Gly Gln Gly Thr
            100                 105                 110
Leu Val Thr Val Ser Ser
            115

<210> SEQ ID NO 45
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
caggtgcagc tggtgcagtc aggcgccgaa gtgaagaaac ccggcgcaag cgttaaagtc    60
tcatgtaaag ctagtggcta caccttcact agctataata tgcactggat tagacaggcc   120
ccagggcaag gcctggagtg gatcggcgat atctaccccg gtagcggcga cactagttat   180
aatcagaagt ttaagggtag agctaccctg accgccgata gtctactagc accgtctat   240 atggaactga gttccctgag gagtgaagac accgccgtct actactgcgc tagagtgggc   300
ggagccttcc ctatggacta ctggggtcaa ggcaccctgg tcaccgtgtc aagc         354

<210> SEQ ID NO 46
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
            20                  25                  30
Asn Met His Trp Ile Arg Gln Ala Pro Gly Gln Gly Leu Glu Trp Ile
        35                  40                  45
Gly Asp Ile Tyr Pro Gly Ser Gly Asp Thr Ser Tyr Asn Gln Lys Phe
    50                  55                  60
Lys Gly Arg Ala Thr Leu Thr Ala Asp Lys Ser Thr Ser Thr Val Tyr
 65                 70                  75                  80
Met Glu Leu Ser Ser Leu Arg Ser Glu Asp Thr Ala Val Tyr Tyr Cys
                85                  90                  95
Ala Arg Val Gly Gly Ala Phe Pro Met Asp Tyr Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Cys Ser Arg Ser Thr Ser Glu Ser Thr Ala Ala Leu Gly
        130                 135                 140
Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly
                435                 440
```

<210> SEQ ID NO 47
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
caggtgcagc tggtgcagtc aggcgccgaa gtgaagaaac ccggcgcaag cgttaaagtc    60
tcatgtaaag ctagtggcta caccttcact agctataata tgcactggat tagacaggcc   120
ccagggcaag gcctggagtg gatcggcgat atctaccccg gtagcggcga cactagttat   180
aatcagaagt ttaagggtag agctaccctg accgccgata gtctactagc accgtctat    240 atggaactga gttccctgag gagtgaagac accgccgtct actactgcgc tagagtgggc   300
ggagccttcc ctatggacta ctggggtcaa ggcacccctg gtcaccgtgt caagcgctagc   360
```

```
actaagggcc cgtccgtgtt ccccctggca ccttgtagcc ggagcactag cgaatccacc    420
gctgccctcg gctgcctggt caaggattac ttcccggagc ccgtgaccgt gtcctggaac    480
agcggagccc tgacctccgg agtgcacacc ttccccgctg tgctgcagag ctccgggctg    540
tactcgctgt cgtcggtggt cacggtgcct tcatctagcc tgggtaccaa gacctacact    600
tgcaacgtgg accacaagcc ttccaacact aaggtggaca gcgcgtcga atcgaagtac     660
ggcccaccgt gcccgccttg tcccgcgccg gagttcctcg gcggtccctc ggtctttctg    720
ttcccaccga agcccaagga cactttgatg atttcccgca cccctgaagt gacatgcgtg    780
gtcgtggacg tgtcacagga agatccggag gtgcagttca attggtacgt ggatggcgtc    840
gaggtgcaca acgccaaaac caagccgagg gaggagcagt tcaactccac ttaccgcgtc    900
gtgtccgtgc tgacggtgct gcatcaggac tggctgaacg gcaaggagta caagtgcaaa    960
gtgtccaaca agggacttcc tagctcaatc gaaaagacca tctcgaaagc caagggacag   1020
ccccgggaac ccaagtgta ccctgcca ccgagccagg aagaaatgac taagaaccaa       1080
gtctcattga cttgccttgt gaagggcttc tacccatcgg atatcgccgt ggaatgggag   1140
tccaacggcc agccggaaaa caactacaag accacccctc cggtgctgga ctcagacgga   1200
tccttcttcc tctactcgcg gctgaccgtg gataagagca gatggcagga gggaaatgtg   1260
ttcagctgtt ctgtgatgca tgaagccctg cacaaccact acactcagaa gtccctgtcc   1320
ctctccctgg ga                                                       1332
```

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Ile Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115

<210> SEQ ID NO 49
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
caggtgcagc tggtgcagtc aggcgccgaa gtgaagaaac ccggcgctag tgtgaaagtc      60
tcttgtaaag ctagtggcta caccttcact agctataata tgcactggat tagacaggcc     120
ccaggtcaag gcctcgagtg gatcggcgat atctacccg gtcaaggcga cactagttat      180
aatcagaagt ttaagggtag agctaccctg accgccgata agtctactag caccgtctat     240
atggaactga gttccctgag gtctgaggac accgccgtct actactgcgc tagagtgggc     300
ggagccttcc ctatggacta ctggggtcaa ggcaccctgg tcaccgtgtc tagc           354
```

<210> SEQ ID NO 50
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Ile Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
```

```
                290                 295                 300
Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly
                435                 440

<210> SEQ ID NO 51
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
caggtgcagc tggtgcagtc aggcgccgaa gtgaagaaac ccggcgctag tgtgaaagtc      60
tcttgtaaag ctagtggcta caccttcact agctataata tgcactggat tagacaggcc    120
ccaggtcaag gcctcgagtg gatcggcgat atctaccccg gtcaaggcga cactagttat    180
aatcagaagt ttaagggtag agctaccctg accgccgata gtctactagt caccgtctat    240
atggaactga gttccctgag gtctgaggac accgccgtct actactgcgc tagagtgggc    300
ggagccttcc ctatggacta ctggggtcaa ggcaccctgg tcaccgtgtc tagcgctagc    360
actaagggcc cgtccgtgtt ccccctggca ccttgtagcc ggagcactag cgaatccacc    420
gctgccctcg gctgcctggt caaggattac ttcccggagc ccgtgaccgt gtcctggaac    480
agcggagccc tgacctccgg agtgcacacc ttccccgctg tgctgcagag ctccgggctg    540
tactcgctgt cgtcggtggt cacggtgcct tcatctagcc tgggtaccaa gacctacact    600
tgcaacgtgg accacaagcc ttccaacact aaggtggaca gcgcgtcga atcgaagtac    660 ggcccaccgt gcccgccttg tccgcgccg gagttcctcg gcggtccctc ggtctttctg    720
ttcccaccga agcccaagga cactttgatg atttcccgca cccctgaagt gacatgcgtg    780
gtcgtggacg tgtcacagga agatccggag gtgcagttca attggtacgt ggatggcgtc    840
gaggtgcaca cgccaaaac caagccgagg gaggagcagt tcaactccac ttaccgcgtc    900
gtgtccgtgc tgacggtgct gcatcaggac tggctgaacg gcaaggagta caagtgcaaa    960
gtgtccaaca agggacttcc tagctcaatc gaaaagacca tctcgaaagc caagggacag    1020
ccccgggaac ccaagtgta cccctgcca ccgagccagg aagaaatgac taagaaccaa    1080
gtctcattga cttgccttgt gaagggcttc taccatcgg atatcgccgt ggaatgggag    1140
tccaacggcc agccggaaaa caactacaag accacccctc cggtgctgga ctcagacgga    1200
```

```
tccttcttcc tctactcgcg gctgaccgtg gataagagca gatggcagga gggaaatgtg   1260
ttcagctgtt ctgtgatgca tgaagccctg cacaaccact acactcagaa gtccctgtcc   1320
ctctccctgg ga                                                        1332
```

<210> SEQ ID NO 52
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115
```

<210> SEQ ID NO 53
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
caggtgcagc tggtgcagtc aggcgccgaa gtgaagaaac ccggctctag cgtgaaagtt   60
tcttgtaaag ctagtggcta caccttcact agctataata tgcactgggt tcgccaggcc   120
ccagggcaag gcctcgagtg gatgggcgat atctaccccg gaacggcga cactagttat   180 aatcagaagt ttaagggtag agtcactatc accgccgata agtctactag caccgtctat   240
atggaactga gttccctgag gtctgaggac accgccgtct actactgcgc tagagtgggc   300
ggagccttcc ctatggacta ctggggtcaa ggcactaccg tgaccgtgtc tagc        354
```

<210> SEQ ID NO 54
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Tyr Thr Phe Thr Ser Tyr
             20                  25                  30

Asn Met His Trp Val Arg Gln Ala Pro Gly Gln Gly Leu Glu Trp Met
             35                  40                  45

Gly Asp Ile Tyr Pro Gly Asn Gly Asp Thr Ser Tyr Asn Gln Lys Phe
 50                  55                  60

Lys Gly Arg Val Thr Ile Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
```

<210> SEQ ID NO 55
<211> LENGTH: 1332
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
caggtgcagc tggtgcagtc aggcgccgaa gtgaagaaac ccggctctag cgtgaaagtt      60
tcttgtaaag ctagtggcta caccttcact agctataata tgcactgggt tcgccaggcc     120
ccagggcaag gcctcgagtg gatgggcgat atctaccccg gaacggcga cactagttat      180
aatcagaagt ttaagggtag agtcactatc accgccgata gtctactag caccgtctat      240
atggaactga gttccctgag gtctgaggac accgccgtct actactgcgc tagagtgggc     300
ggagccttcc ctatggacta ctggggtcaa ggcactaccg tgaccgtgtc tagcgctagc     360
actaagggcc cgtccgtgtt ccccctggca ccttgtagcc ggagcactag cgaatccacc     420
gctgccctcg gctgcctggt caaggattac ttcccggagc ccgtgaccgt gtcctggaac     480
agcggagccc tgacctccgg agtgcacacc ttccccgctg tgctgcagag ctccgggctg     540
tactcgctgt cgtcggtggt cacggtgcct tcatctagcc tgggtaccaa gacctacact     600
tgcaacgtgg accacaagcc ttccaacact aaggtggaca gcgcgtcga atcgaagtac      660
ggcccaccgt gcccgccttg tcccgcgccg gagttcctcg gcggtccctc ggtctttctg     720
ttcccaccga agcccaagga cactttgatg atttcccgca cccctgaagt gacatgcgtg     780
gtcgtggacg tgtcacagga agatcccgag gtgcagttca attggtacgt ggatggcgtc     840
gaggtgcaca cgccaaaac caagccgagg gaggagcagt tcaactccac ttaccgcgtc     900
gtgtccgtgc tgacggtgct gcatcaggac tggctgaacg gaaggagta caagtgcaaa     960
gtgtccaaca agggacttcc tagctcaatc gaaaagacca tctcgaaagc caagggacag    1020
ccccgggaac ccaagtgta cccctgcca ccgagccagg aagaaatgac taagaaccaa     1080
gtctcattga cttgccttgt gaagggcttc tacccatcgg atatcgccgt ggaatgggag    1140
tccaacggcc agccggaaaa caactacaag accacccctc cggtgctgga ctcagacgga    1200
tccttcttcc tctactcgcg gctgaccgtg gataagagca gatggcagga gggaaatgtg    1260
ttcagctgtt ctgtgatgca tgaagccctg cacaaccact acactcagaa gtccctgtcc    1320
ctctccctgg ga                                                        1332
```

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Glu Ser Val Glu Tyr Tyr
                20                  25                  30
Gly Thr Ser Leu Met Gln Trp Tyr Gln Gln Lys Pro Gly Gln Ala Pro
            35                  40                  45
```

Arg Leu Leu Ile Tyr Ala Ala Ser Asn Val Glu Ser Gly Ile Pro Ala
            50                  55                  60

Arg Phe Ser Gly Ser Gly Ser Gly Thr Asp Phe Thr Leu Thr Ile Ser
65                  70                  75                  80

Ser Leu Glu Pro Glu Asp Ile Ala Val Tyr Phe Cys Gln Gln Ser Arg
                85                  90                  95

Lys Asp Pro Ser Thr Phe Gly Gly Gly Thr Lys Val Glu Ile Lys
            100                 105                 110

<210> SEQ ID NO 57
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gagatcgtcc tgactcagtc acccgctacc ctgagcctga gccctggcga gagagctaca      60
ctgagctgta gagctagtga atcagtcgag tactacggca ctagcctgat gcagtggtat     120
cagcagaagc ccggtcaagc ccctagactg ctgatctacg ccgcctctaa cgtggaatca     180
gggatccccg ctaggtttag cggtagcggt agtggcaccg acttcaccct gactatctct     240
agcctggaac ccgaggatat cgccgtctac ttctgtcagc agtctaggaa ggaccctagc     300
accttcggcg gaggcactaa ggtcgagatt aag                                  333

<210> SEQ ID NO 58
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Glu Tyr Tyr
            20                  25                  30

Gly Thr Ser Leu Met Gln Trp Tyr Gln Gln Lys Pro Gly Gln Ala Pro
        35                  40                  45

Arg Leu Leu Ile Tyr Ala Ala Ser Asn Val Glu Ser Gly Ile Pro Ala
            50                  55                  60

Arg Phe Ser Gly Ser Gly Ser Gly Thr Asp Phe Thr Leu Thr Ile Ser
65                  70                  75                  80

Ser Leu Glu Pro Glu Asp Ile Ala Val Tyr Phe Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 59
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gagatcgtcc tgactcagtc acccgctacc ctgagcctga gccctggcga gagagctaca    60
ctgagctgta gagctagtga atcagtcgag tactacggca ctagcctgat gcagtggtat   120
cagcagaagc ccggtcaagc ccctagactg ctgatctacg ccgcctctaa cgtggaatca   180
gggatccccg ctaggtttag cggtagcggt agtggcaccg acttcaccct gactatctct   240
agcctggaac ccgaggatat cgccgtctac ttctgtcagc agtctaggaa ggaccctagc   300
accttcggcg aggcactaa ggtcgagatt aagcgtacgg tggccgctcc cagcgtgttc    360
atcttccccc ccagcgacga gcagctgaag agcggcaccg ccagcgtggt gtgcctgctg   420
aacaacttct acccccggga ggccaaggtg cagtggaagg tggacaacgc cctgcagagc   480
ggcaacagcc aggagagcgt caccgagcag gacagcaagg actccaccta cagcctgagc   540
agcaccctga ccctgagcaa ggccgactac gagaagcata aggtgtacgc ctgcgaggtg   600
acccaccagg gcctgtccag ccccgtgacc aagagcttca caggggcga gtgc          654
```

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Asn Met His Trp Val Arg Gln Met Pro Gly Lys Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115
```

<210> SEQ ID NO 61

-continued

```
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaagtgcagc tggtgcagtc aggcgccgaa gtgaagaagc ccggcgagtc actgaagatt      60
agctgtaaag gttcaggcta caccttcact agctataata tgcactgggt ccgccagatg     120
cccgggaaag gcctcgagtg gatgggcgat atctaccccg gaacggcga cactagttat     180 aatcagaagt ttaaggggca agtcacaatt agcgccgata agtctattag caccgtctac     240
ctgcagtggt ctagcctgaa ggctagtgac accgctatgt actactgcgc tagagtgggc     300
ggagccttcc ctatggacta ctggggtcaa ggcactaccg tgaccgtgtc tagc            354

<210> SEQ ID NO 62
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Asn Met His Trp Val Arg Gln Met Pro Gly Lys Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 63
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
gaagtgcagc tggtgcagtc aggcgccgaa gtgaagaagc ccggcgagtc actgaagatt    60
agctgtaaag gttcaggcta caccttcact agctataata tgcactgggt ccgccagatg   120
cccgggaaag gcctcgagtg gatgggcgat atctaccccg gaacggcga cactagttat    180 aatcagaagt ttaagggca gtcacaatt agcgccgata gtctattag caccgtctac     240 ctgcagtggt ctagcctgaa ggctagtgac accgctatgt actactgcgc tagagtgggc   300
ggagccttcc ctatggacta ctggggtcaa ggcactaccg tgaccgtgtc tagcgctagc   360
actaagggcc cgtccgtgtt cccccctggca ccttgtagcc ggagcactag cgaatccacc   420
gctgccctcg gctgcctggt caaggattac ttcccggagc ccgtgaccgt gtcctggaac   480
agcggagccc tgacctccgg agtgcacacc ttccccgctg tgctgcagag ctccgggctg   540
tactcgctgt cgtcggtggt cacggtgcct tcatctagcc tgggtaccaa gacctacact   600
tgcaacgtgg accacaagcc ttccaacact aaggtggaca gcgcgtcga atcgaagtac   660 ggcccaccgt gcccgccttg tcccgcgccg gagttcctcg gcggtccctc ggtctttctg   720
ttcccaccga agcccaagga cactttgatg atttcccgca cccctgaagt gacatgcgtg   780
gtcgtggacg tgtcacagga agatccggag gtgcagttca attggtacgt ggatggcgtc   840
gaggtgcaca cgccaaaac caagccgagg gaggagcagt tcaactccac ttaccgcgtc   900
gtgtccgtgc tgacggtgct gcatcaggac tggctgaacg gaaggagta caagtgcaaa   960
```

```
gtgtccaaca agggacttcc tagctcaatc gaaaagacca tctcgaaagc caagggacag    1020
ccccgggaac cccaagtgta taccctgcca ccgagccagg aagaaatgac taagaaccaa    1080
gtctcattga cttgccttgt gaagggcttc tacccatcgg atatcgccgt ggaatgggag    1140
tccaacggcc agccggaaaa caactacaag accacccctc cggtgctgga ctcagacgga    1200
tccttcttcc tctactcgcg gctgaccgtg gataagagca gatggcagga gggaaatgtg    1260
ttcagctgtt ctgtgatgca tgaagccctg cacaaccact acactcagaa gtccctgtcc    1320
ctctccctgg ga                                                       1332
```

<210> SEQ ID NO 64
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys
            100                 105                 110
```

<210> SEQ ID NO 65
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gctattcagc tgactcagtc acctagtagc ctgagcgcta gtgtgggcga tagagtgact    60
atcacctgta gagctagtga atcagtcgag tactacggca ctagcctgat gcagtggtat    120
cagcagaagc ccgggaaagc ccctaagctg ctgatctacg ccgcctctaa cgtggaatca    180
ggcgtgccct ctaggtttag cggtagcggt agtggcaccg acttcaccct gactatctct    240
agcctgcagc ccgaggactt cgctacctac ttctgtcagc agtctaggaa ggaccctagc    300
accttcggcg gaggcactaa ggtcgagatt aag                                 333
```

<210> SEQ ID NO 66
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Ala Ile Gln Leu Thr Gln Ser Pro Ser Leu Ser Ala Ser Val Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
                35                  40                  45

Lys Leu Leu Ile Tyr Ala Ala Ser Asn Val Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 67
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gctattcagc tgactcagtc acctagtagc ctgagcgcta gtgtgggcga tagagtgact      60
atcacctgta gagctagtga atcagtcgag tactacggca ctagcctgat gcagtggtat     120
cagcagaagc ccgggaaagc ccctaagctg ctgatctacg ccgcctctaa cgtggaatca     180
ggcgtgccct ctaggtttag cggtagcggt agtggcaccg acttcaccct gactatctct     240
agcctgcagc ccgaggactt cgctacctac ttctgtcagc agtctaggaa ggaccctagc     300
accttcggcg gaggcactaa ggtcgagatt aagcgtacgg tggccgctcc cagcgtgttc     360
atcttccccc ccagcgacga gcagctgaag agcggcaccg ccagcgtggt gtgcctgctg     420
aacaacttct acccccggga ggccaaggtg cagtggaagg tggacaacgc cctgcagagc     480
ggcaacagcc aggagagcgt caccgagcag gacagcaagg actccaccta cagcctgagc     540
agcaccctga ccctgagcaa ggccgactac gagaagcata aggtgtacgc ctgcgaggtg     600
acccaccagg gcctgtccag ccccgtgacc aagagcttca caggggcga gtgc            654
```

<210> SEQ ID NO 68

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
            35                  40                  45

Gly Asp Ile Tyr Pro Gly Ser Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
                100                 105                 110

Thr Val Thr Val Ser Ser
        115

<210> SEQ ID NO 69
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgcaat tggttcagtc aggagcagaa gttaagaagc caggatcatc cgtcaaggtg      60
tcctgcaaag catctggcta caccttcacc agctacaata tgcactgggt ccgacaagcc     120
cctgggcagg gcttggagtg gatgggagac atttaccccg gcagtggtga cacttcctat     180
aaccagaagt tcaagggccg agtcactatt accgctgaca gtccacctc cacagtctac      240 atggaactct cttctctgag atccgaggac actgccgtct attactgcgc tcgcgtgggc     300
ggtgctttcc caatggacta ttggggacag ggcacaaccg tgaccgtcag ctca           354

<210> SEQ ID NO 70
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Asn Met His Trp Val Arg Gln Ala Pro Gly Gln Gly Leu Glu Trp Met
            35                  40                  45

Gly Asp Ile Tyr Pro Gly Ser Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 71
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
caggtgcaat tggttcagtc aggagcagaa gttaagaagc caggatcatc cgtcaaggtg      60
tcctgcaaag catctggcta caccttcacc agctacaata tgcactgggt ccgacaagcc     120
cctgggcagg gcttggagtg gatgggagac atttaccccg gcagtggtga cacttcctat     180
aaccagaagt tcaagggccg agtcactatt accgctgaca gtccacctc cacagtctac      240
atggaactct cttctctgag atccgaggac actgccgtct attactgcgc tcgcgtgggc     300
ggtgctttcc caatggacta ttggggacag ggcacaaccg tgaccgtcag ctcagcctct     360
acaaagggcc cctccgtctt tccactcgcg ccgtgctctc gctccacctc agagtcaact     420
gccgctctgg gttgcctggt caaggactac ttcccagagc cggtgacagt gagctggaac     480
agtggggccc tgacatccgg cgttcatacc ttccccgcag tcctccagtc ctcaggcctg     540
tattccctga gcagcgttgt cacagtgccc tccagctctc ttggcacgaa aacctacaca     600
tgcaacgttg atcataagcc gtctaatacc aaggtggata aaagagtgga gagcaagtac     660
ggcccaccct gcccgccttg cccagctccg gagttcctgg gcggaccatc cgttttcttg     720
tttccaccca aacctaaaga cactctgatg atttcccgaa cccctgaagt gacttgcgtt     780
gtggtggacg tctcccagga ggacccagaa gtgcaattca actggtacgt ggacggggtg     840
gaggtgcaca atgcaaaaac caaaccaagg gaggaacagt taattcaac atataggggtt      900
gtgtctgtgc tgacggttct gcatcaggac tggctgaacg gaaaggaata caagtgcaag     960
gtgtccaaca aaggactgcc aagctctatc gagaaaacaa tctctaaggc caagggacaa    1020
cctagagagc cccaagttta caccctgcca ccatcacagg aagagatgac caaaaatcag    1080
gtgagcttga catgcctggt gaagggcttc taccctagcg atattgcggt tgagtgggag    1140
tcaaatggcc agcctgagaa caactataag actactcctc ccgtgctgga ctccgacggg    1200
agctttttcc tgtattccag gcttacagtc gataagagca gatggcaaga ggggaatgtg    1260
ttttcctgct ccgtgatgca cgaggctctc cataaccatt atactcagaa aagtctctct    1320
ctgtcactgg gcaaa                                                     1335
```

<210> SEQ ID NO 72
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Gln Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Val Gly Gly Ala Phe Pro Met Asp Tyr Trp Gly Gln Gly Thr
            100                 105                 110

Thr Val Thr Val Ser Ser
        115

<210> SEQ ID NO 73
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
caggtgcaat tggttcagtc aggagcagaa gttaagaagc caggatcatc cgtcaaggtg      60
tcctgcaaag catctggcta caccttcacc agctacaata tgcactgggt ccgacaagcc     120
cctgggcagg gcttggagtg gatgggagac atttaccccg gccagggtga cacttcctat     180
aaccagaagt tcaagggccg agtcactatt accgctgaca gtccacctc cacagtctac      240 atggaactct cttctctgag atccgaggac actgccgtct attactgcgc tcgcgtgggc     300
ggtgctttcc caatggacta ttggggacag ggcacaaccg tgaccgtcag ctca           354

<210> SEQ ID NO 74
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Gln Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 75
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
caggtgcaat tggttcagtc aggagcagaa gttaagaagc caggatcatc cgtcaaggtg      60
tcctgcaaag catctggcta caccttcacc agctacaata tgcactgggt ccgacaagcc     120
cctgggcagg gcttggagtg gatgggagac atttaccccg ccagggtga cacttcctat      180 aaccagaagt tcaagggccg agtcactatt accgctgaca gtccacctc cacagtctac      240 atggaactct cttctctgag atccgaggac actgccgtct attactgcgc tcgcgtgggc     300
ggtgctttcc caatggacta ttggggacag ggcacaaccg tgaccgtcag ctcagcctct     360
acaaagggcc cctccgtctt tccactcgcg ccgtgctctc gctccacctc agagtcaact     420
gccgctctgg gttgcctggt caaggactac ttcccagagc cggtgacagt gagctggaac     480
agtggggccc tgacatccgg cgttcatacc ttccccgcag tcctccagtc ctcaggcctg     540
tattccctga gcagcgttgt cacagtgccc tccagctctc ttggcacgaa aacctacaca     600
tgcaacgttg atcataagcc gtctaatacc aaggtggata aaagagtgga gagcaagtac     660
ggcccaccct gcccgccttg cccagctccg gagttcctgg gcggaccatc cgttttcttg     720

```
tttccaccca aacctaaaga cactctgatg atttcccgaa cccctgaagt gacttgcgtt      780
gtggtggacg tctcccagga ggacccagaa gtgcaattca actggtacgt ggacggggtg      840
gaggtgcaca atgcaaaaac caaaccaagg gaggaacagt ttaattcaac atatagggtt      900
gtgtctgtgc tgacggttct gcatcaggac tggctgaacg gaaaggaata caagtgcaag      960
gtgtccaaca aggactgcc aagctctatc gagaaaacaa tctctaaggc caagggacaa     1020
cctagagagc cccaagttta caccctgcca ccatcacagg aagagatgac caaaaatcag     1080
gtgagcttga catgcctggt gaagggcttc taccctagcg atattgcggt tgagtgggag     1140
tcaaatggcc agcctgagaa caactataag actactcctc ccgtgctgga ctccgacggg     1200 agcttttcc tgtattccag gcttacagtc gataagagca gatggcaaga ggggaatgtg     1260 tttcctgct ccgtgatgca cgaggctctc cataaccatt atactcagaa aagtctctct     1320
ctgtcactgg gcaaa                                                     1335
```

<210> SEQ ID NO 76
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Asn Met His Trp Val Arg Gln Met Pro Gly Lys Gly Leu Glu Trp Met
        35                  40                  45

Gly Asp Ile Tyr Pro Gly Ser Gly Asp Thr Ser Tyr Asn Gln Lys Phe
    50                  55                  60

Lys Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115
```

<210> SEQ ID NO 77
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
gaagttcaat tggtacagtc tggcgcagaa gtaaagaaac caggagagag tttgaaaatt       60
tcctgcaagg gcagtgggta cacattcacg tcctacaata tgcactgggt gagacagatg      120
ccaggcaagg gcctggagtg gatgggagac atatacccag gcagtggaga cacaagctat      180
aatcagaaat tcaaaggaca ggtgacgatc tccgcagaca aatccatatc tacggtctac      240
ctccagtggt cctcacttaa agcctccgac accgccatgt actattgcgc tcgggtaggt      300
```
ggcgcgtttc aatggacta ttggggccaa gggaccacag taaccgtcag ctca    354

<210> SEQ ID NO 78
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Asn Met His Trp Val Arg Gln Met Pro Gly Lys Gly Leu Glu Trp Met
        35                  40                  45

Gly Asp Ile Tyr Pro Gly Ser Gly Asp Thr Ser Tyr Asn Gln Lys Phe
    50                  55                  60

Lys Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

| Gln | Glu | Glu | Met | Thr | Lys | Asn | Gln | Val | Ser | Leu | Thr | Cys | Leu | Val | Lys |
|---|---|---|---|---|---|---|---|---|---|---|---|---|---|---|---|
| | | | | 355 | | | | | 360 | | | | | 365 | |

Gly Phe Tyr Pro Ser Asp Ile Ala Val Glu Trp Glu Ser Asn Gly Gln
    370                        375                    380

Pro Glu Asn Asn Tyr Lys Thr Thr Pro Pro Val Leu Asp Ser Asp Gly
385                        390                    395               400

Ser Phe Phe Leu Tyr Ser Arg Leu Thr Val Asp Lys Ser Arg Trp Gln
                405                    410                    415

Glu Gly Asn Val Phe Ser Cys Ser Val Met His Glu Ala Leu His Asn
            420                    425                    430

His Tyr Thr Gln Lys Ser Leu Ser Leu Ser Leu Gly Lys
            435                    440                    445

<210> SEQ ID NO 79
<211> LENGTH: 1335
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 79

```
gaagttcaat tggtacagtc tggcgcagaa gtaaagaaac caggagagag tttgaaaatt      60
tcctgcaagg gcagtgggta cacattcacg tcctacaata tgcactgggt gagacagatg     120
ccaggcaagg gcctggagtg gatgggagac atatacccag gcagtggaga cacaagctat     180
aatcagaaat tcaaaggaca ggtgacgatc tccgcagaca atccatatc tacggtctac      240 ctccagtggt cctcacttaa agcctccgac accgccatgt actattgcgc tcgggtaggt     300
ggcgcgtttc caatggacta ttggggccaa gggaccacag taaccgtcag ctcagcctct     360
acaaagggcc cctccgtctt ccactcgcg ccgtgctctc gctccacctc agagtcaact      420
gccgctctgg gttgcctggt caaggactac ttcccagagc cggtgacagt gagctggaac     480
agtggggccc tgacatccgg cgttcatacc ttccccgcag tcctcagtc ctcaggcctg      540 tattccctga gcagcgttgt cacagtgccc tccagctctc ttggcacgaa aacctacaca     600
tgcaacgttg atcataagcc gtctaatacc aaggtggata aaagagtgga gagcaagtac     660
ggcccaccct gcccgccttg cccagctccg gagttcctgg gcggaccatc cgttttcttg     720
tttccaccca aacctaaaga cactctgatg atttcccgaa cccctgaagt gacttgcgtt     780
gtggtggacg tctcccagga ggacccagaa gtgcaattca actggtacgt ggacggggtg     840
gaggtgcaca atgcaaaaac caaaccaagg gaggaacagt ttaattcaac atataggtt      900 gtgtctgtgc tgacggttct gcatcaggac tggctgaacg gaaaggaata caagtgcaag     960
gtgtccaaca aggactgcc aagtctatc gagaaaacaa tctctaaggc caagggacaa      1020
cctagagagc ccaagtttta caccctgcca ccatcacagg aagagatgac caaaaatcag    1080
gtgagcttga catgcctggt gaagggcttc taccctagcg atattgcggt tgagtgggag    1140
tcaaatggcc agcctgagaa caactataag actactcctc ccgtgctgga ctccgacggg    1200 agcttttcc tgtattccag gcttacagtc gataagagca gatggcaaga ggggaatgtg     1260
ttttcctgct ccgtgatgca cgaggctctc ataaccatt atactcagaa aagtctctct    1320
ctgtcactgg gcaaa                                                    1335
```

<210> SEQ ID NO 80
<211> LENGTH: 118
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 80

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Thr Phe Thr Ser Tyr
            20                  25                  30
Asn Met His Trp Val Arg Gln Met Pro Gly Lys Gly Leu Glu Trp Met
        35                  40                  45
Gly Asp Ile Tyr Pro Gly Gln Gly Asp Thr Ser Tyr Asn Gln Lys Phe
    50                  55                  60
Lys Gly Gln Val Thr Ile Ser Ala Asp Lys Ser Ile Ser Thr Val Tyr
65                  70                  75                  80
Leu Gln Trp Ser Ser Leu Lys Ala Ser Asp Thr Ala Met Tyr Tyr Cys
                85                  90                  95
Ala Arg Val Gly Gly Ala Phe Pro Met Asp Tyr Trp Gly Gln Gly Thr
            100                 105                 110
Thr Val Thr Val Ser Ser
        115
```

<210> SEQ ID NO 81
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81

```
gaagttcaat tggtacagtc tggcgcagaa gtaaagaaac caggagagag tttgaaaatt    60
tcctgcaagg gcagtgggta cacattcacg tcctacaata tgcactgggt gagacagatg   120
ccaggcaagg gcctggagtg gatgggagac atatacccag gccagggaga cacaagctat   180
aatcagaaat tcaaaggaca ggtgacgatc tccgcagaca atccatatc tacggtctac   240
ctccagtggt cctcacttaa agcctccgac accgccatgt actattgcgc tcgggtaggt   300
ggcgcgtttc caatggacta ttggggccaa gggaccacag taaccgtcag ctca         354
```

<210> SEQ ID NO 82
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Thr Phe Thr Ser Tyr
            20                  25                  30
Asn Met His Trp Val Arg Gln Met Pro Gly Lys Gly Leu Glu Trp Met
        35                  40                  45
Gly Asp Ile Tyr Pro Gly Gln Gly Asp Thr Ser Tyr Asn Gln Lys Phe
    50                  55                  60
Lys Gly Gln Val Thr Ile Ser Ala Asp Lys Ser Ile Ser Thr Val Tyr
65                  70                  75                  80
```

```
Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 83
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 83

```
gaagttcaat tggtacagtc tggcgcagaa gtaaagaaac caggagagag tttgaaaatt     60
tcctgcaagg gcagtgggta cacattcacg tcctacaata tgcactgggt gagacagatg    120
ccaggcaagg gcctggagtg gatgggagac atatacccag ccagggaga cacaagctat    180
aatcagaaat tcaaaggaca ggtgacgatc tccgcagaca atccatatc tacggtctac    240
ctccagtggt cctcacttaa agcctccgac accgccatgt actattgcgc tcggtaggt    300
ggcgcgtttc caatggacta ttggggccaa gggaccacag taaccgtcag ctcagcctct    360
acaaagggcc cctccgtctt tccactcgcg ccgtgctctc gctccacctc agagtcaact    420
gccgctctgg gttgcctggt caaggactac ttcccagagc cggtgacagt gagctggaac    480
agtggggccc tgacatccgg cgttcatacc ttccccgcag tcctccagtc tcaggcctg    540
tattccctga gcagcgttgt cacagtgccc tccagctctc ttggcacgaa aacctacaca    600
tgcaacgttg atcataagcc gtctaatacc aaggtggata aaagagtgga gagcaagtac    660
ggcccaccct gcccgccttg cccagctccg gagttcctgg gcggaccatc cgttttcttg    720
tttccaccca aacctaaaga cactctgatg atttcccgaa cccctgaagt gacttgcgtt    780
gtggtggacg tctcccagga ggacccagaa gtgcaattca actggtacgt ggacggggtg    840
gaggtgcaca atgcaaaaac caaaccaagg gaggaacagt ttaattcaac atatagggtt    900
gtgtctgtgc tgacggttct gcatcaggac tggctgaacg gaaaggaata caagtgcaag    960
gtgtccaaca aaggactgcc aagctctatc gagaaaacaa tctctaaggc caagggacaa   1020
cctagagagc cccaagttta caccctgcca ccatcacagg aagagatgac caaaaatcag   1080
gtgagcttga catgcctggt gaagggcttc taccctagcg atattgcggt tgagtgggag   1140
tcaaatggcc agcctgagaa caactataag actactcctc ccgtgctgga ctccgacggg   1200
agctttttcc tgtattccag gcttacagtc gataagagca gatggcaaga ggggaatgtg   1260
ttttcctgct ccgtgatgca cgaggctctc cataaccatt atactcagaa aagtctctct   1320
ctgtcactgg gcaaa                                                    1335
```

<210> SEQ ID NO 84
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110
```

Leu Val Thr Val Ser Ser
        115

<210> SEQ ID NO 85
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
caggtgcaat tggtgcagag cggagcagag gtcaaaaagc ccggagcaag cgtgaaggtc      60
tcatgcaaag caagcggata cacatttaca tcatacaaca tgcactgggt caggcaggct     120
ccaggacagg gactggagtg gatcggggac atctaccctg gacagggcga tactagctat     180
aatcagaagt tcaaaggccg ggccaccatg acagctgaca agtctactag taccgtgtat     240
atggaactga gctccctgcg gtctgaagat accgcagtgt actattgcgc cagagtcggg     300
ggggcatttc ctatggatta ttgggggcag gggactctgg tcactgtcag ctca           354

<210> SEQ ID NO 86
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Ala Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Ala Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 87
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
caggtgcaat tggtgcagag cggagcagag gtcaaaaagc ccggagcaag cgtgaaggtc     60
tcatgcaaag caagcggata cacatttaca tcatacaaca tgcactgggt caggcaggct    120
ccaggacagg gactggagtg gatcggggac atctaccctg acagggcga tactagctat    180 aatcagaagt tcaaaggccg ggccaccatg acagctgaca gtctactag taccgtgtat    240 atggaactga gctccctgcg gtctgaagat accgcagtgt actattgcgc cagagtcggg    300
ggggcatttc ctatggatta ttgggggcag gggactctgg tcactgtcag ctcagctagc    360
accaagggcc ccagcgtgtt cccctggcc cccagcagca gagcaccag cggcggcaca    420 gccgccctgg gctgcctggt gaaggactac ttccccgagc ccgtgaccgt gcctggaac    480 agcggagccc tgacctccgg cgtgcacacc ttccccgccg tgctgcagag cagcggcctg    540
tacagcctgt ccagcgtggt gacagtgccc agcagcagcc tgggcaccca gacctacatc    600
tgcaacgtga accacaagcc cagcaacacc aaggtggaca agagagtgga gcccaagagc    660
tgcgacaaga cccacacctg cccccccctgc ccagccccag agctgctggg cggacccctcc    720 gtgttcctgt tccccccaa gcccaaggac accctgatga tcagcaggac cccgaggtg    780

```
acctgcgtgg tggtggccgt gagccacgag acccagagg tgaagttcaa ctggtacgtg      840
gacggcgtgg aggtgcacaa cgccaagacc aagcccagag aggagcagta caacagcacc      900
tacagggtgg tgtccgtgct gaccgtgctg caccaggact ggctgaacgg caaggaatac      960
aagtgcaagg tctccaacaa ggccctggca gcccccatcg aaaagaccat cagcaaggcc     1020
aagggccagc cacgggagcc ccaggtgtac accctgcccc cctcccggga ggagatgacc     1080
aagaaccagg tgtccctgac ctgtctggtg aagggcttct accccagcga catcgccgtg     1140
gagtgggaga gcaacggcca gcccgagaac aactacaaga ccaccccccc agtgctggac     1200
agcgacggca gcttcttcct gtacagcaag ctgaccgtgg acaagtccag gtggcagcag     1260
ggcaacgtgt tcagctgcag cgtgatgcac gaggccctgc acaaccacta cacccagaag     1320
agcctgagcc tgtcccccgg caag                                            1344
```

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110
```

<210> SEQ ID NO 89
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
gacatcgtcc tgacacagtc tcctgacagc ctggcagtga gcctgggcga aagggcaacc       60
attaattgta gagcttccga gtccgtcgag tactatggca ctagtctgat gcagtggtac      120
cagcagaagc cagggcagcc ccctaaactg ctgatctatg cagctagcaa cgtggagtcc      180
ggagtcccag accggttctc tggaagtggg tcaggaaccg attttaccct gacaattagc      240
tccctgcagg cagaagacgt ggccgtctac tattgtcagc agagccgcaa ggacccaagc      300
acattcggag gggggaccaa agtggaaatc aag                                   333
```

<210> SEQ ID NO 90
<211> LENGTH: 218

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Asp Ile Val Leu Thr Gln Ser Pro Asp Ser Leu Ala Val Ser Leu Gly
1               5                   10                  15
Glu Arg Ala Thr Ile Asn Cys Arg Ala Ser Glu Ser Val Glu Tyr Tyr
            20                  25                  30
Gly Thr Ser Leu Met Gln Trp Tyr Gln Gln Lys Pro Gly Gln Pro Pro
        35                  40                  45
Lys Leu Leu Ile Tyr Ala Ala Ser Asn Val Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Ser Arg
                85                  90                  95
Lys Asp Pro Ser Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 91
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
gacatcgtcc tgacacagtc tcctgacagc ctggcagtga gcctgggcga aagggcaacc      60
attaattgta gagcttccga gtccgtcgag tactatggca ctagtctgat gcagtggtac     120
cagcagaagc cagggcagcc ccctaaactg ctgatctatg cagctagcaa cgtggagtcc     180
ggagtcccag accggttctc tggaagtggg tcaggaaccg attttaccct gacaattagc     240
tccctgcagg cagaagacgt ggccgtctac tattgtcagc agagccgcaa ggacccaagc     300
acattcggag ggggaccaa agtggaaatc aagcgtacgt ggccgctcc cagcgtgttc      360
atcttccccc cagcgacga gcagctgaag agcggcaccg ccagcgtggt gtgcctgctg      420
aacaacttct accccgggga ggccaaggtg cagtggaagg tggacaacgc cctgcagagc     480
ggcaacagcc aggagagcgt caccgagcag gacagcaagg actccaccta cagcctgagc     540
```

```
agcaccctga ccctgagcaa ggccgactac gagaagcata aggtgtacgc ctgcgaggtg      600
acccaccagg gcctgtccag ccccgtgacc aagagcttca cagggggcga gtgc            654
```

<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Gln Gly Asp Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115

<210> SEQ ID NO 93
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
caggtgcagc tggtgcagtc tggcgccgaa gtgaagaaac caggcgccag cgtgaaggtg     60
tcctgcaagg ccagcggcta cacctttacc agctacaaca tgcactgggt gcgccaggcc    120
cctggacagg gactggaatg gatgggcgac atctaccccg gccagggcga cacctcctac    180
aaccagaaat tcaagggcag agtgaccatg acccgggaca ccagcaccct caccgtgtac    240
atggaactga gcagcctgcg gagcgaggac accgccgtgt actactgtgc tagagtgggc    300
ggagccttcc ccatggacta ttggggccag ggcaccaccg tgaccgtgag ctca          354
```

<210> SEQ ID NO 94
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

-continued

Asn Met His Trp Val Arg Gln Ala Pro Gly Gln Gly Leu Glu Trp Met
        35                  40                  45

Gly Asp Ile Tyr Pro Gly Gln Gly Asp Thr Ser Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Ala Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 95
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
caggtgcagc tggtgcagtc tggcgccgaa gtgaagaaac caggcgccag cgtgaaggtg      60
tcctgcaagg ccagcggcta caccttacc agctacaaca tgcactgggt gcgccaggcc     120
cctggacagg gactggaatg gatgggcgac atctacccg gccagggcga cacctcctac     180
aaccagaaat tcaagggcag agtgaccatg acccgggaca ccagcacctc caccgtgtac     240
atggaactga gcagcctgcg gagcgaggac accgccgtgt actactgtgc tagagtgggc     300
ggagccttcc ccatggacta ttggggccag ggcaccaccg tgaccgtgag ctcagctagc     360
accaagggcc ccagcgtgtt ccccctggcc ccagcagca agagcaccag cggcggcaca     420
gccgccctgg gctgcctggt gaaggactac ttccccgagc ccgtgaccgt gtcctggaac     480
agcggagccc tgacctccgg cgtgcacacc ttcccgccg tgctgcagag cagcggcctg     540
tacagcctgt ccagcgtggt gacagtgccc agcagcagcc tgggcaccca gacctacatc     600
tgcaacgtga accacaagcc cagcaacacc aaggtggaca gagagtgga gcccaagagc     660
tgcgacaaga cccacacctg cccccccctgc ccagccccag agctgctggg cggaccctcc     720
gtgttcctgt tccccccaa gcccaaggac accctgatga tcagcaggac ccccgaggtg     780
acctgcgtgg tggtggccgt gagccacgag gacccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaggaatac     960
aagtgcaagg tctccaacaa ggccctggca gcccccatcg aaagaccat cagcaaggcc    1020
aagggccagc cacgggagcc ccaggtgtac accctgcccc cctcccggga ggagatgacc    1080
aagaaccagg tgtccctgac ctgtctggtg aagggcttct accccagcga catcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
agcctgagcc tgtccccccgg caag                                          1344
```

<210> SEQ ID NO 96
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Ala Ile Arg Leu Thr Gln Ser Pro Ser Ser Phe Ser Ala Ser Thr Gly
1               5                   10                  15

Asp Arg Val Thr Ile Thr Cys Arg Ala Ser Glu Ser Val Glu Tyr Tyr
            20                  25                  30

Gly Thr Ser Leu Met Gln Trp Tyr Gln Gln Lys Pro Gly Lys Ala Pro
        35                  40                  45

Lys Leu Leu Ile Tyr Ala Ala Ser Asn Val Glu Ser Gly Val Pro Ser
    50                  55                  60

```
Arg Phe Ser Gly Ser Gly Ser Gly Thr Asp Phe Thr Leu Thr Ile Ser
 65                  70                  75                  80

Ser Leu Gln Ser Glu Asp Phe Ala Thr Tyr Tyr Cys Gln Gln Ser Arg
                 85                  90                  95

Lys Asp Pro Ser Thr Phe Gly Gly Gly Thr Lys Val Glu Ile Lys
            100                 105                 110

<210> SEQ ID NO 97
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gccatcagac tgacccagag ccccagctcc tttagcgcca gcaccggcga cagagtgacc      60
atcacctgta gagccagcga gagcgtggaa tattacggca ccagcctgat gcagtggtat     120
cagcagaagc ccggcaaggc ccccaagctg ctgatctacg ccgccagcaa tgtggaaagc     180
ggcgtgccca gcagattcag cggctctggc agcggcaccg acttcaccct gacaatcagc     240
agcctgcaga gcgaggactt cgccacctac tactgccagc agagccggaa ggaccccagc     300
acatttggcg gaggcaccaa ggtggaaatc aag                                   333

<210> SEQ ID NO 98
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ala Ile Arg Leu Thr Gln Ser Pro Ser Ser Phe Ser Ala Ser Thr Gly
 1               5                  10                  15

Asp Arg Val Thr Ile Thr Cys Arg Ala Ser Glu Ser Val Glu Tyr Tyr
                20                  25                  30

Gly Thr Ser Leu Met Gln Trp Tyr Gln Gln Lys Pro Gly Lys Ala Pro
            35                  40                  45

Lys Leu Leu Ile Tyr Ala Ala Ser Asn Val Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Ser Glu Asp Phe Ala Thr Tyr Tyr Cys Gln Gln Ser Arg
                 85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 99
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
gccatcagac tgacccagag ccccagctcc tttagcgcca gcaccggcga cagagtgacc      60
atcacctgta gagccagcga gagcgtggaa tattacggca ccagcctgat gcagtggtat     120
cagcagaagc ccggcaaggc ccccaagctg ctgatctacg ccgccagcaa tgtggaaagc     180
ggcgtgccca gcagattcag cggctctggc agcggcaccg acttcaccct gacaatcagc     240
agcctgcaga gcgaggactt cgccacctac tactgccagc agagccggaa ggaccccagc     300
acatttggcg gaggcaccaa ggtggaaatc aagcgtacgg tggccgctcc cagcgtgttc     360
atcttccccc ccagcgacga gcagctgaag agcggcaccg ccagcgtggt gtgcctgctg     420
aacaacttct accccgggga ggccaaggtg cagtggaagg tggacaacgc cctgcagagc     480
ggcaacagcc aggagagcgt caccgagcag gacagcaagg actccaccta cagcctgagc     540
agcaccctga ccctgagcaa ggccgactac gagaagcata aggtgtacgc ctgcgaggtg     600
acccaccagg gcctgtccag ccccgtgacc aagagcttca caggggcga gtgc            654

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Asn Met His Trp Val Arg Gln Met Pro Gly Lys Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser
        115

<210> SEQ ID NO 101
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
caggtgcaat tggtacagtc tggcgcagaa gtaaagaaac caggagagag tttgaaaatt      60
tcctgcaagg gcagtgggta cacattcacg tcctacaata tgcactgggt gagacagatg     120
ccaggcaagg gcctggagtg gatgggagac atatacccag gcaatggaga cacaagctat     180
aatcagaaat tcaaaggaca ggtgacgatc tccgcagaca aatccatatc tacggtctac     240
ctccagtggt cctcacttaa agcctccgac accgccatgt actattgcgc tcgggtaggt     300
ggcgcgtttc caatggacta ttggggccaa gggaccacag taaccgtcag ctca           354
```

<210> SEQ ID NO 102
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
                20                  25                  30

Asn Met His Trp Val Arg Gln Met Pro Gly Lys Gly Leu Glu Trp Met
            35                  40                  45

Gly Asp Ile Tyr Pro Gly Asn Gly Asp Thr Ser Tyr Asn Gln Lys Phe
        50                  55                  60

Lys Gly Gln Val Thr Ile Ser Ala Asp Lys Ser Ile Ser Thr Val Tyr
65                  70                  75                  80

Leu Gln Trp Ser Ser Leu Lys Ala Ser Asp Thr Ala Met Tyr Tyr Cys
                85                  90                  95

Ala Arg Val Gly Gly Ala Phe Pro Met Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ala Val Ser His Glu Asp Pro
                260                 265                 270
```

Glu Val Lys Phe Asn Trp Tyr Val Asp Gly Val Glu His Asn Ala
                275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Ala Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 103
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
caggtgcaat tggtacagtc tggcgcagaa gtaaagaaac caggagagag tttgaaaatt      60
tcctgcaagg gcagtgggta cacattcacg tcctacaata tgcactgggt gagacagatg     120
ccaggcaagg gcctggagtg gatgggagac atataccagg caatggaga cacaagctat      180 aatcagaaat tcaaaggaca ggtgacgatc tccgcagaca atccatatc tacggtctac      240 ctccagtggt cctcacttaa agcctccgac accgccatgt actattgcgc tcgggtaggt     300
ggcgcgtttc caatggacta ttggggccaa gggaccacag taaccgtcag ctcagctagc     360
accaagggcc cagcgtgtt cccctggcc cccagcagca gagcaccag cggcggcaca       420 gccgccctgg gctgcctggt gaaggactac ttccccgagc ccgtgaccgt gtcctggaac     480
agcggagccc tgacctccgg cgtgcacacc ttccccgccg tgctgcagag cagcggcctg     540
tacagcctgt ccagcgtggt gacagtgccc agcagcagcc tgggcaccca gacctacatc     600
tgcaacgtga accacaagcc cagcaacacc aaggtggaca gagagtgga gcccaagagc      660 tgcgacaaga cccacacctg ccccccctgc ccagcccag agctgctggg cggaccctcc      720
gtgttcctgt tccccccaa gcccaaggac accctgatga tcagcaggac ccccgaggtg      780
acctgcgtgg tggtggccgt gagccacgag gacccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaggaatac     960
aagtgcaagg tctccaacaa ggccctggca gcccccatcg aaaagaccat cagcaaggcc    1020

```
aagggccagc cacgggagcc ccaggtgtac accctgcccc cctcccggga ggagatgacc    1080
aagaaccagg tgtccctgac ctgtctggtg aagggcttct accccagcga catcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
agcctgagcc tgtccccccgg caag                                          1344
```

<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Glu Tyr Tyr
                20                  25                  30

Gly Thr Ser Leu Met Gln Trp Tyr Gln Gln Lys Pro Gly Lys Ala Pro
            35                  40                  45

Lys Leu Leu Ile Tyr Ala Ala Ser Asn Val Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Phe Cys Gln Gln Ser Arg
                85                  90                  95

Lys Asp Pro Ser Thr Phe Gly Gly Gly Thr Lys Val Glu Ile Lys
            100                 105                 110
```

<210> SEQ ID NO 105
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
gcaatacagt tgacacagag tccttcaagt ttgtccgctt ccgttggcga ccgagtgaca     60
atcacctgta gagcatccga gtcagtggag tattatggca ctagcctgat gcagtggtat    120
cagcaaaagc cagggaaagc cccaaagctg ctgatatatg ccgcgagtaa cgtcgagtca    180
ggggtgccat caagattctc cggttccggg tccggaaccg acttcacact gaccatctct    240
tcccttcagc cagaggactt cgctacgtac ttttgccagc agtcacggaa agatccctct    300
actttcggag gtgggacaaa agtcgaaatt aaa                                 333
```

<210> SEQ ID NO 106
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Ala Ile Gln Leu Thr Gln Ser Pro Ser Ser Leu Ser Ala Ser Val Gly
```

```
                1               5              10              15
            Asp Arg Val Thr Ile Thr Cys Arg Ala Ser Glu Ser Val Glu Tyr Tyr
                               20              25              30
            Gly Thr Ser Leu Met Gln Trp Tyr Gln Gln Lys Pro Gly Lys Ala Pro
                           35              40              45
            Lys Leu Leu Ile Tyr Ala Ala Ser Asn Val Glu Ser Gly Val Pro Ser
                50              55              60
            Arg Phe Ser Gly Ser Gly Ser Gly Thr Asp Phe Thr Leu Thr Ile Ser
             65              70              75              80
            Ser Leu Gln Pro Glu Asp Phe Ala Thr Tyr Phe Cys Gln Gln Ser Arg
                           85              90              95
            Lys Asp Pro Ser Thr Phe Gly Gly Thr Lys Val Glu Ile Lys Arg
                       100             105             110
            Thr Val Ala Ala Pro Ser Val Phe Ile Phe Pro Ser Asp Glu Gln
                       115             120             125
            Leu Lys Ser Gly Thr Ala Ser Val Val Cys Leu Leu Asn Asn Phe Tyr
                       130             135             140
            Pro Arg Glu Ala Lys Val Gln Trp Lys Val Asp Asn Ala Leu Gln Ser
            145             150             155             160
            Gly Asn Ser Gln Glu Ser Val Thr Glu Gln Asp Ser Lys Asp Ser Thr
                           165             170             175
            Tyr Ser Leu Ser Ser Thr Leu Thr Leu Ser Lys Ala Asp Tyr Glu Lys
                       180             185             190
            His Lys Val Tyr Ala Cys Glu Val Thr His Gln Gly Leu Ser Ser Pro
                       195             200             205
            Val Thr Lys Ser Phe Asn Arg Gly Glu Cys
                       210             215
```

<210> SEQ ID NO 107
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
gcaatacagt tgacacagag tccttcaagt ttgtccgctt ccgttggcga ccgagtgaca    60
atcacctgta gagcatccga gtcagtggag tattatggca ctagcctgat gcagtggtat   120
cagcaaaagc cagggaaagc cccaaagctg ctgatatatg ccgcgagtaa cgtcgagtca   180
ggggtgccat caagattctc cggttccggg tccggaaccg acttcacact gaccatctct   240
tcccttcagc cagaggactt cgctacgtac ttttgccagc agtcacggaa agatccctct   300
actttcggag gtgggacaaa agtcgaaatt aaacgtacgg tggccgctcc cagcgtgttc   360
atcttccccc ccagcgacga gcagctgaag agcggcaccg ccagcgtggt gtgcctgctg   420
aacaacttct accccgggga ggccaaggtg cagtggaagg tggacaacgc cctgcagagc   480
ggcaacagcc aggagagcgt caccgagcag gacagcaagg actccaccta cagcctgagc   540
agcaccctga ccctgagcaa ggccgactac gagaagcata aggtgtacgc ctgcgaggtg   600
acccaccagg gcctgtccag ccccgtgacc aagagcttca cagggggcga gtgc         654
```

<210> SEQ ID NO 108
<211> LENGTH: 327
<212> TYPE: PRT
<213> ORGANISM: Homo sapiens

<400> SEQUENCE: 108

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 109
<211> LENGTH: 107
<212> TYPE: PRT
<213> ORGANISM: Homo sapiens

<400> SEQUENCE: 109

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 110
<211> LENGTH: 326
<212> TYPE: PRT
<213> ORGANISM: Homo sapiens

<400> SEQUENCE: 110

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser

Cys Ser Val Met His Glu Ala Leu His Asn His Tyr Thr Gln Lys Ser
305                 310                 315                 320

Leu Ser Leu Ser Leu Gly
                325

<210> SEQ ID NO 111
<211> LENGTH: 330
<212> TYPE: PRT
<213> ORGANISM: Homo sapiens

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 112
<211> LENGTH: 330
<212> TYPE: PRT
<213> ORGANISM: Homo sapiens

<400> SEQUENCE: 112

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 113
<211> LENGTH: 330
<212> TYPE: PRT
<213> ORGANISM: Homo sapiens

<400> SEQUENCE: 113

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 114
<211> LENGTH: 330
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 115
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
caggtccagc tggtccagag cggagcagag gtcaaaaagc ccggagcaag cgtgaaggtc      60
tcatgcaaag caagcggata cacatttaca tcatacaaca tgcactggat caggcaggct     120
ccaggacagg gactggagtg gatcggggac atctaccctg aaacggcga tactagctat      180 aatcagaagt tcaaaggccg ggccaccctg acagctgaca gtctactag taccgtgtat     240 atggagctga gctccctgcg gtctgaagat accgcagtgt actattgcgc cagagtcggg    300
ggggcatttc ctatggatta ttgggggcag gggactctgg tcactgtctc ctcc          354

```
<210> SEQ ID NO 116
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Ile Arg Gln Ala Pro Gly Gln Gly Leu Glu Trp Ile
        35                  40                  45

Gly Asp Ile Tyr Pro Gly Asn Gly Asp Thr Ser Tyr Asn Gln Lys Phe
    50                  55                  60

Lys Gly Arg Ala Thr Leu Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 117
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
caggtccagc tggtccagag cggagcagag gtcaaaaagc ccggagcaag cgtgaaggtc      60
tcatgcaaag caagcggata cacatttaca tcatacaaca tgcactggat caggcaggct     120
ccaggacagg gactggagtg gatcggggac atctaccctg gaaacggcga tactagctat     180
aatcagaagt tcaaaggccg ggccacccty acagctgaca agtctactag taccgtgtat     240
atggagctga gctccctgcg gtctgaagat accgcagtgt actattgcgc cagagtcggg     300
ggggcatttc ctatggatta ttgggggcag gggactctgg tcactgtctc ctccgctagc     360
accaagggcc catccgtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcacgaa gacctacacc     600
tgcaacgtag atcacaagcc cagcaacacc aaggtggaca gagagttga gtccaaatat     660
ggtccccat gcccaccatg cccagcacct gagttcctgg ggggaccatc agtcttcctg     720
ttccccccaa acccaagga cactctcatg atctcccgga cccctgaggt cacgtgcgtg     780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaa                                                     1335

<210> SEQ ID NO 118
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118

```
gacatcgtcc tgacacagtc tcctgacagc ctggcagtga gcctgggcga aagggcaacc    60
attaattgta gagcttccga gtccgtcgag tactatggca ctagtctgat gcagtggtac   120
cagcagaagc cagggcagcc ccctaaactg ctgatctatg cagctagcaa cgtggagtcc   180
ggagtcccag accggttctc tggaagtggg tcaggaaccg attttaccct gacaattagc   240
tccctgcagg cagaagacgt ggccgtctac tattgtcagc agagccgcaa ggacccaagc   300
acattcggag gggggaccaa agtggaaatc aag                                333
```

<210> SEQ ID NO 119
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119

```
gacatcgtcc tgacacagtc tcctgacagc ctggcagtga gcctgggcga aagggcaacc    60
attaattgta gagcttccga gtccgtcgag tactatggca ctagtctgat gcagtggtac   120
cagcagaagc cagggcagcc ccctaaactg ctgatctatg cagctagcaa cgtggagtcc   180
ggagtcccag accggttctc tggaagtggg tcaggaaccg attttaccct gacaattagc   240
tccctgcagg cagaagacgt ggccgtctac tattgtcagc agagccgcaa ggacccaagc   300
acattcggag gggggaccaa agtggaaatc aagcggactg ttgctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600
acccatcagg gcctgagttc accggtgaca aagagcttca cagggagag tgt           654
```

<210> SEQ ID NO 120
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

```
caggtccagc tggtccagag cggagcagag gtcaaaaagc ccggagcaag cgtgaaggtc    60
tcatgcaaag caagcggata cacatttaca tcatacaaca tgcactgggt caggcaggct   120
ccaggacagg gactggagtg gatcggggac atctaccctg aaacggcga tactagctat   180
aatcagaagt tcaaaggccg ggccaccatg acagctgaca agtctactag taccgtgtat   240
atggagctga gctccctgcg gtctgaagat accgcagtgt actattgcgc cagagtcggg   300
ggggcatttc ctatggatta ttggggggcag gggactctgg tcactgtctc ctcc         354
```

<210> SEQ ID NO 121
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Asn Met His Trp Val Arg Gln Ala Pro Gly Gln Gly Leu Glu Trp Ile
        35                  40                  45
Gly Asp Ile Tyr Pro Gly Asn Gly Asp Thr Ser Tyr Asn Gln Lys Phe
    50                  55                  60
Lys Gly Arg Ala Thr Met Thr Ala Asp Lys Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Val Gly Gly Ala Phe Pro Met Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
```

```
Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly Lys
        435                 440                 445

<210> SEQ ID NO 122
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
caggtccagc tggtccagag cggagcagag gtcaaaaagc ccggagcaag cgtgaaggtc    60
tcatgcaaag caagcggata cacatttaca tcatacaaca tgcactgggt caggcaggct   120
ccaggacagg gactggagtg gatcggggac atctaccctg gaaacggcga tactagctat   180
aatcagaagt tcaaaggccg ggccaccatg acagctgaca agtctactag taccgtgtat   240
atggagctga gctccctgcg gtctgaagat accgcagtgt actattgcgc cagagtcggg   300
ggggcatttc ctatggatta ttgggggcag gggactctgg tcactgtctc ctccgctagc   360
accaagggcc catccgtctt ccccctggcg ccctgctcca ggagcacctc cgagagcaca   420
gccgccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct gggcacgaa gacctacacc   600 tgcaacgtag atcacaagcc cagcaacacc aaggtggaca gagagttga gtccaaatat   660 ggtccccat gcccaccatg cccagcacct gagttcctgg ggggaccatc agtcttcctg   720
ttccccccaa aacccaagga cactctcatg atctcccgga cccctgaggt cacgtgcgtg   780
gtggtggacg tgagccagga agaccccgag gtccagttca actggtacgt ggatggcgtg   840
gaggtgcata atgccaagac aaagccgcgg gaggagcagt tcaacagcac gtaccgtgtg   900
gtcagcgtcc tcaccgtcct gcaccaggac tggctgaacg gcaaggagta caagtgcaag   960
gtctccaaca aaggcctccc gtcctccatc gagaaaacca tctccaaagc caaagggcag  1020
ccccgagagc cacaggtgta caccctgccc ccatcccagg aggagatgac caagaaccag  1080
gtcagcctga cctgcctggt caaaggcttc taccccagcg acatcgccgt ggagtgggag  1140
agcaatgggc agccggagaa caactacaag accacgcctc ccgtgctgga ctccgacggc  1200
tccttcttcc tctacagcag gctaaccgtg gacaagagca ggtggcagga ggggaatgtc  1260
ttctcatgct ccgtgatgca tgaggctctg cacaaccact acacacagaa gagcctctcc  1320
ctgtctctgg gtaaa                                                   1335

<210> SEQ ID NO 123
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
gacatcgtcc tgacacagtc tcctgacagc ctggcagtga gcctgggcga aagggcaacc    60
```

```
attaattgta gagcttccga gtccgtcgag tactatggca ctagtctgat gcagtggtac      120
cagcagaagc cagggcagcc ccctaaactg ctgatctatg cagctagcaa cgtggagtcc      180
ggagtcccag accggttctc tggaagtggg tcaggaaccg attttaccct gacaattagc      240
tccctgcagg cagaagacgt ggccgtctac ttttgtcagc agagccgcaa ggacccaagc      300
acattcggag gggggaccaa agtggaaatc aag                                   333

<210> SEQ ID NO 124
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gacatcgtcc tgacacagtc tcctgacagc ctggcagtga gcctgggcga aagggcaacc       60
attaattgta gagcttccga gtccgtcgag tactatggca ctagtctgat gcagtggtac      120
cagcagaagc cagggcagcc ccctaaactg ctgatctatg cagctagcaa cgtggagtcc      180
ggagtcccag accggttctc tggaagtggg tcaggaaccg attttaccct gacaattagc      240
tccctgcagg cagaagacgt ggccgtctac ttttgtcagc agagccgcaa ggacccaagc      300
acattcggag gggggaccaa agtggaaatc aagcggactg ttgctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagttc accggtgaca aagagcttca caggggagag tgt             654

<210> SEQ ID NO 125
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gcaatacagt tgacacagag tccttcaagt ttgtccgctt ccgttggcga ccgagtgaca       60
atcacctgta gagcatccga gtcagtggag tattatggca ctagcctgat gcagtggtat      120
cagcaaaagc cagggaaagc cccaaagctg ctgatatatg ccgcgagtaa cgtcgagtca      180
ggggtgccat caagattctc cggttccggg tccggaaccg acttcacact gaccatctct      240
tcccttcagc cagaggactt cgctacgtac ttttgccagc agtcacggaa agatccctct      300
actttcggag gtgggacaaa agtcgaaatt aaa                                   333

<210> SEQ ID NO 126
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gcaatacagt tgacacagag tccttcaagt ttgtccgctt ccgttggcga ccgagtgaca       60
```

```
atcacctgta gagcatccga gtcagtggag tattatggca ctagcctgat gcagtggtat    120
cagcaaaagc cagggaaagc cccaaagctg ctgatatatg ccgcgagtaa cgtcgagtca    180
ggggtgccat caagattctc cggttccggg tccggaaccg acttcacact gaccatctct    240
tcccttcagc cagaggactt cgctacgtac ttttgccagc agtcacggaa agatccctct    300
actttcggag gtgggacaaa agtcgaaatt aaacgtacgg tggcagctcc gtctgttttc    360
atctttccac ctagcgacga gcaactcaaa agtggtacag catccgtggt ttgtctgctg    420
aacaattttt accccaggga ggctaaggtc cagtggaaag tcgataacgc tcttcagtct    480
ggcaacagtc aggagagcgt cacagagcag gactctaagg atagcactta tagtctgtcc    540
tccacgctga cactgtctaa agcggattat gagaagcaca aggtttacgc ctgtgaggta    600
acgcaccaag gactctcctc cccagttacc aaatctttca acagaggaga atgt           654
```

<210> SEQ ID NO 127
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
gagattgttc ttacgcaaag tcccgccaca cttagtttgt caccaggaga gcgcgccacc     60
ctgagctgca gagcttcaga gagtgtggaa tactacggca catccctgat gcagtggtat    120
cagcagaaac caggacaggc tcctcggctg ctgatctacg cagccagcaa cgtcgagtcc    180
ggcattccag ccagattttc tgggtcagga tctggaactg actttacact gacaatctcc    240
agcctggaac ccgaggacat tgctgtgtat ttttgtcaac agtcccggaa ggaccccagt    300
acctttggag gtggaaccaa ggtagagata aag                                 333
```

<210> SEQ ID NO 128
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
gagattgttc ttacgcaaag tcccgccaca cttagtttgt caccaggaga gcgcgccacc     60
ctgagctgca gagcttcaga gagtgtggaa tactacggca catccctgat gcagtggtat    120
cagcagaaac caggacaggc tcctcggctg ctgatctacg cagccagcaa cgtcgagtcc    180
ggcattccag ccagattttc tgggtcagga tctggaactg actttacact gacaatctcc    240
agcctggaac ccgaggacat tgctgtgtat ttttgtcaac agtcccggaa ggaccccagt    300
acctttggag gtggaaccaa ggtagagata aagcgtacgg tggcagctcc gtctgttttc    360
atctttccac ctagcgacga gcaactcaaa agtggtacag catccgtggt ttgtctgctg    420
aacaattttt accccaggga ggctaaggtc cagtggaaag tcgataacgc tcttcagtct    480
ggcaacagtc aggagagcgt cacagagcag gactctaagg atagcactta tagtctgtcc    540
tccacgctga cactgtctaa agcggattat gagaagcaca aggtttacgc ctgtgaggta    600
acgcaccaag gactctcctc cccagttacc aaatctttca acagaggaga atgt           654
```

<210> SEQ ID NO 129
<211> LENGTH: 301

```
<212> TYPE: PRT
<213> ORGANISM: Homo sapiens

<400> SEQUENCE: 129

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
                35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
            210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Gly Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
            290                 295                 300

<210> SEQ ID NO 130
<211> LENGTH: 135
<212> TYPE: PRT
<213> ORGANISM: Homo sapiens

<400> SEQUENCE: 130

Met Glu Thr Asp Thr Leu Leu Leu Trp Val Leu Leu Leu Trp Val Pro
1               5                   10                  15

Gly Ser Thr Gly Ser Glu Val Glu Tyr Arg Ala Glu Val Gly Gln Asn
            20                  25                  30

Ala Tyr Leu Pro Cys Phe Tyr Thr Pro Ala Ala Pro Gly Asn Leu Val
                35                  40                  45
```

```
Pro Val Cys Trp Gly Lys Gly Ala Cys Pro Val Phe Glu Cys Gly Asn
    50                  55                  60

Val Val Leu Arg Thr Asp Glu Arg Asp Val Asn Tyr Trp Thr Ser Arg
 65                  70                  75                  80

Tyr Trp Leu Asn Gly Asp Phe Arg Lys Gly Asp Val Ser Leu Thr Ile
                 85                  90                  95

Glu Asn Val Thr Leu Ala Asp Ser Gly Ile Tyr Cys Cys Arg Ile Gln
            100                 105                 110

Ile Pro Gly Ile Met Asn Asp Glu Lys Phe Asn Leu Lys Leu Val Ile
            115                 120                 125

Lys His His His His His His
            130                 135

<210> SEQ ID NO 131
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Asn Met His Trp Val Arg Gln Ala Pro Gly Gln Gly Leu Glu Trp Ile
         35                  40                  45

Gly Asp Ile Tyr Pro Gly Gln Gly Asp Thr Ser Tyr Asn Gln Lys Phe
 50                  55                  60

Lys Gly Arg Ala Thr Met Thr Ala Asp Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His
225

<210> SEQ ID NO 132
<211> LENGTH: 218
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 132

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 133

His His His His His His
1               5

<210> SEQ ID NO 134
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

```
Asn Met His Trp Val Lys Gln Thr Pro Arg Gln Gly Leu Glu Trp Ile
             35                  40                  45

Gly Ala Ile Tyr Pro Gly Asn Gly Asp Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Phe Cys
             85                  90                  95

Ala Arg

<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Glu Tyr Tyr
             20                  25                  30

Gly Thr Ser Leu Met Gln Trp Tyr Gln Gln Lys Pro Gly Gln Pro Pro
         35                  40                  45

Lys Leu Leu Ile Tyr Ala Ala Ser Asn Val Glu Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
             85                  90                  95

Lys Val Pro Ser Thr Phe Gly Gly Gly Thr Lys Leu Glu Ile Lys
                100                 105                 110

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Ala Cys Pro Val Phe
 1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asn Asp Glu Lys Phe Asn Leu Lys Leu
 1               5

<210> SEQ ID NO 138
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 138

Ile Met Asn Asp
1

<210> SEQ ID NO 139
<211> LENGTH: 114
<212> TYPE: PRT
<213> ORGANISM: Homo sapiens

<400> SEQUENCE: 139

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr

<210> SEQ ID NO 140
<211> LENGTH: 21
<212> TYPE: PRT
<213> ORGANISM: Homo sapiens

<400> SEQUENCE: 140

Thr Pro Ala Ala Pro Gly Asn Leu Val Pro Val Cys Trp Gly Lys Gly
1               5                   10                  15

Ala Cys Pro Val Phe
            20

<210> SEQ ID NO 141
<211> LENGTH: 5
<212> TYPE: PRT
<213> ORGANISM: Homo sapiens

<400> SEQUENCE: 141

Arg Asp Val Asn Tyr
1               5

<210> SEQ ID NO 142
<211> LENGTH: 7
<212> TYPE: PRT
<213> ORGANISM: Homo sapiens

<400> SEQUENCE: 142

Glu Lys Phe Asn Leu Lys Leu
1               5
```

METHOD OF DETECTING TIM-3 USING ANTIBODY MOLECULES TO TIM-3

CROSS REFERENCE TO RELATED APPLICATIONS

This application is a divisional of U.S. application Ser. No. 15/432,819, filed Feb. 14, 2017, now U.S. Pat. No. 10,472,419, which is a divisional of U.S. application Ser. No. 14/610,837, filed Jan. 30, 2015, now U.S. Pat. No. 9,605,070, which claims the benefit of U.S. Provisional Application No. 61/934,469, filed Jan. 31, 2014, and U.S. Provisional Application No. 62/094,912, filed Dec. 19, 2014. The contents of the aforementioned applications are hereby incorporated by reference in their entirety.

GOVERNMENT SUPPORT

This invention was made with government support under grant numbers P01 AI054456 and R01 AI089955 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 26, 2015, is named C2160-700210_SL.txt and is 206,078 bytes in size.

BACKGROUND

Activation of naive CD4+ T helper cells results in the development of at least two distinct effector populations, Th1 cells and Th2 cells. See U.S. Pat. No. 7,470,428, Mosmann T R et al. (1986) *J Immunol* 136:2348-57; Mosmann T R et al. (1996) *Immunol Today* 17:138-46; Abbas A K et al. (1996) *Nature* 383:787-793. Th1 cells produce cytokines (e.g., interferon gamma, interleukin-2, tumor necrosis factor alpha, and lymphotoxin) which are commonly associated with cell-mediated immune responses against intracellular pathogens, delayed-type hypersensitivity reactions (Sher A et al. (1992) *Annu Rev Immunol* 10:385-409), and induction of organ-specific autoimmune diseases. Liblau R S et al. (1995) *Immunol Today* 16:34-38. Th2 cells produce cytokines (e.g., IL-4, IL-10, and IL-13) that are crucial for control of extracellular helminthic infections and promote atopic and allergic diseases. Sher A et al. (1992) *Annu Rev Immunol* 2327477.1 10:385-409. In addition to their distinct roles in disease, the Th1 and Th2 cells cross-regulate each other's expansion and functions. Thus, preferential induction of Th2 cells inhibits autoimmune diseases (Kuchroo V K et al. (1995) *Cell* 80:707-18; Nicholson L B et al. (1995) *Immunity* 3:397-405), and predominant induction of Th1 cells can regulate induction of asthma, atopy and allergies. Lack G et. al. (1994) *J Immunol* 152:2546-54; Hofstra C L et al. (1998) *J Immunol* 161: 5054-60.

TIM-3 is a transmembrane receptor protein that is expressed, e.g., on Th1 (T helper 1) CD4+ cells and cytotoxic CD8+ T cells that secrete IFN-γ. TIM-3 is generally not expressed on naïve T cells but rather upregulated on activated, effector T cells. TIM-3 has a role in regulating immunity and tolerance in vivo (see Hastings et al., *Eur J Immunol.* 2009 September; 39(9):2492-501). There is a need in the art for new molecules that regulate TIM-3 function and the function of TIM-3 expressing cells.

SUMMARY

Disclosed herein are antibody molecules that bind to TIM-3 (T-cell immunoglobulin domain and mucin domain 3) with high affinity and specificity. Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided. The anti-TIM-3 antibody molecules disclosed herein can be used (alone or in combination with other agents or therapeutic modalities) to treat, prevent and/or diagnose immune disorders, cancer, infectious disease, Crohn's disease, sepsis, SIRS (Systemic Inflammatory Response Syndrome), and glomerulonephritis. Thus, compositions and methods for detecting TIM-3, as well as methods for treating various disorders, including cancer and immune disorders using the anti-TIM-3 antibody molecules are disclosed herein.

Accordingly, in certain aspects, this disclosure provides an antibody molecule (e.g., an isolated or recombinant antibody molecule) having one or more (e.g., 2, 3, 4, 5, 6, 7, 8, 9, 10, 11, 12, 13, 14, 15, 16 or all) of the following properties (a), (b), (c), (d), (e), (f), (g), (h), (i), (j), (k), (l), (m), (n), (o), (p) or (q):

(a) binds to TIM-3, e.g., human TIM-3, with high affinity, e.g., with a dissociation constant ($K_D$) of less than about 100 nM, typically about 10 nM, and more typically, about 1-0.1 nM or stronger, e.g., less than about 0.2, 0.16, 0.15, 0.1, 0.075, 0.05, or 0.042 nM, (b) binds substantially to a non-human primate TIM-3, e.g., cynomolgus TIM-3, with a dissociation constant ($K_D$) of less than about 100 nM, typically about 10 nM, and more typically, about 3-0.3 nM or stronger, e.g., 1-0.1 nM or stronger, e.g., less than about 1 nM, 0.75 nM, or 0.68 nM, (c) inhibits binding of TIM-3 to a TIM-3 ligand, e.g., phosphatidylserine (PtdSer), HMGB1, or CEACAM-1, (d) enhances IFN-gamma and/or TNF-alpha secretion and/or proliferation in T cells, e.g., CD4+ or CD8+ T cells, e.g., in CD4+ T cells that were stimulated with anti-CD3/CD28 in the presence of IL-12 or in T cell-DC autologous culture assays with anti-CD3/CD28 stimulation, (e) enhances cytotoxic NK (natural killer) cell activity against a target cell (e.g., K562 cells), e.g., in an in vitro assay, (f) enhances capacity of macrophages or antigen presenting cells to stimulate a T cell response, e.g., increasing IL-12 secretion of antigen presenting cells, (g) binds specifically to an epitope on TIM-3, e.g., the same or similar epitope as the epitope recognized by an antibody molecule described herein, e.g., a murine or humanized anti-TIM-3 antibody molecule as described herein, e.g., an antibody molecule of Tables 1-4, (h) shows the same or similar binding affinity or specificity, or both, as an antibody molecule of Tables 1-4, (i) shows the same or similar binding affinity or specificity, or both, as an antibody molecule (e.g., an heavy chain variable region and light chain variable region) described in Tables 1-4, (j) shows the same or similar binding affinity or specificity, or both, as an antibody molecule (e.g., an heavy chain variable region and light chain variable region) comprising an amino acid sequence shown in Tables 1-4, (k) inhibits, e.g., competitively inhibits, the binding of a second antibody molecule to TIM-3 wherein the second antibody molecule is an antibody molecule described herein, e.g., an antibody molecule chosen from Tables 1-4, (l) binds the same (or substantially the same) or an overlapping (or substantially overlapping) epitope with a second antibody molecule to TIM-3, wherein the second antibody molecule is an antibody molecule described herein, e.g., an antibody molecule chosen from Tables 1-4, (m) competes for binding, and/or binds the same (or substantially the same) or overlapping (or substantially overlapping) epitope, with a second antibody molecule to TIM-3, wherein the second antibody molecule is an antibody molecule described herein, e.g., an antibody molecule chosen from Tables 1-4, e.g., as determined by the methods described in Example 11, (n) has one or more biological properties of an antibody molecule described herein, e.g., an antibody molecule chosen from Tables 1-4, (o) has one or more pharmacokinetic properties of an antibody molecule described herein, e.g., an antibody molecule chosen from Tables 1-4, (p) modulates (e.g., enhances or inhibits) one or more activities of TIM-3, e.g., results in one or more of: enhancing IFN-gamma and/or TNF-alpha secretion in T cells; enhancing proliferation in T cells, e.g., CD4+ or CD8+ T cells; enhancing NK cell cytotoxic activity; reducing suppressor activity of regulatory T cells (Tregs); or increasing immune stimulation properties of macrophages and/or antigen presenting cells, e.g., increasing cytokine secretion, e.g., IL-12 secretion; or (q) binds to one or more residues within: the two residues adjacent to the N-terminus of the A strand (residues Val24 and Glu25 in human TIM-3), the BC loop, the CC' loop, the F strand, the FG loop, and the G strand of TIM-3, or one or more residues within a combination of two, three, four, five or all of: the two residues adjacent to the N-terminus of the A strand (residues Val24 and Glu25 in human TIM-3), the BC loop, the CC' loop, the F strand, the FG loop, and the G strand of TIM-3, e.g., wherein the binding is assayed using ELISA or Biacore.

In some embodiments, the antibody molecule binds to TIM-3 with high affinity, e.g., with a $K_D$ that is at least about 10%, 20%, 30%, 40%, 50%, 60%, 70%, 80% or 90% lower than the $K_D$ of a murine anti-TIM-3 antibody molecule, e.g., a murine anti-TIM-3 antibody molecule described herein.

In some embodiments, the expression level of the anti-TIM-3 antibody molecule is higher, e.g., at least about 0.5, 1, 2, 3, 4, 5, 6, 7, 8, 9 or 10-fold higher, than the expression level of a murine antibody molecule, e.g., a murine or chimeric anti-TIM-3 antibody molecule described herein. In some embodiments, the antibody molecule is expressed in mammalian cells, e.g., rodent cells.

In some embodiments, the anti-TIM-3 antibody molecule reduces one or more activities of TIM-3 with an IC50 (concentration at 50% inhibition) that is lower, e.g., at least about 10%, 20%, 30%, 40%, 50%, 60%, 70%, 80% or 90% lower, than the IC50 of a murine anti-TIM-3 antibody molecule, e.g., a murine anti-TIM-3 antibody molecule described herein. In some embodiments, the TIM-3 activity is the binding of TIM-3 to one or more (e.g., one, two, three, four or all) of the TIM-3 ligands described herein, e.g., one, two or more (all) of PtdSer, CEACAM-1, or HMGB1.

In some embodiments, the anti-TIM-3 antibody molecule interacts with, e.g., binds to, a TIM-3 surface (e.g., one, two, three, five, eight, ten, fifteen, or more continuous or discontinuous (e.g., noncontiguous) amino acid residues chosen from Val24, Glu25, Thr41, Gly56, Ala57, Cys58, Pro59, Val60, Phe61, Glu121, Lys122, Phe123, Asn124, Leu125, Lys126, and/or Leu127.

In some embodiments, the anti-TIM-3 antibody molecule interacts with, e.g., binds to, a TIM-3 surface (e.g., one, two, three, five, eight, ten, fifteen, twenty, twenty-one, twenty-five, or more continuous or discontinuous (e.g., noncontiguous) amino acid residues chosen from Val24, Glu25, Tyr26, Phe39, Tyr40, Thr41, Gly56, Ala57, Cys58, Pro59, Val60, Phe61, Ser105, Gly106, Ile107, Asn119, Asp120, Glu121, Lys122, Phe123, Asn124, Leu125, Lys126, Leu127, and/or Val128, e.g., as detailed in Table 13.

In some embodiments, the anti-TIM-3 antibody molecule interacts with, e.g., binds to, a TIM-3 surface (e.g., one, two, three, five, eight, ten, fifteen, twenty, twenty-one, twenty-five, or more continuous or discontinuous (e.g., noncontiguous) amino acid residues chosen from Glu23, Val24, Glu25, Tyr26, Thr41, Pro42, Ala43, Ala44, Pro45, Gly46, Asn47, Leu48, Val49, Pro50, Val51, Cys52, Trp53, Gly54, Lys55, Gly56, Ala57, Cys58, Pro59, Val60, Phe61, Glu121, Lys122, Phe123, Asn124, Leu125, Lys126 and/or Leu127.

In some embodiments, the anti-TIM-3 antibody molecule interacts with, e.g., binds to, a TIM-3 surface (e.g., one, two, three, five, eight, ten, fifteen, twenty, twenty-one, twenty-five, or more continuous or discontinuous (e.g., noncontiguous) amino acid residues chosen from Val24, Glu25, Tyr26, Phe39, Tyr40, Thr41, Pro42, Ala43, Ala44, Pro45, Gly46, Asn47, Leu48, Val49, Pro50, Val51, Cys52, Trp53, Gly54, Lys55, Gly56, Ala57, Cys58, Pro59, Val60, Phe61, Ser105, Gly106, Ile107, Asn119, Asp120, Glu121, Lys122, Phe123, Asn124, Leu125, Lys126, Leu127, and/or Val128.

In other embodiments, the anti-TIM-3 antibody molecule competes with CEACAM-1 for binding to TIM-3. In one embodiment, the anti-TIM-3 antibody molecule interacts, e.g., binds to, one, two, or more (all) of Cys58, Asn119 and Lys122 of TIM-3, e.g., displaces or competes CEACAM-1 for binding to these residues. In one embodiment, the anti-TIM-3 antibody molecule reduces or blocks the formation of a hydrogen bond between Lys122 of TIM-3 and Asn42 of CEACAM-1, e.g., by at least about 10%, 20%, 30%, 40%, 50%, 60%, 70%, 80% or 90%, compared to the formation of a hydrogen bond between between Lys122 of TIM-3 and Asn42 of CEACAM-1 in the absence of the anti-TIM-3 antibody molecule.

In another embodiment, the anti-TIM-3 antibody molecule interacts with, e.g., binds to, a PtdSer-binding loop of TIM-3. In one embodiment, the anti-TIM-3 antibody molecule interacts with, e.g., binds to, at least two PtdSer-binding loops of TIM-3, e.g., the FG loop and CC' loop of TIM-3 (e.g., a metal ion-dependent ligand binding site (MILIBS)). For example, the carboxyl group of PtdSer can bind to the CC' loop of TIM-3 and the amino group of PtdSer can bind to the FG loop of TIM-3. In one embodiment, the anti-TIM-3 antibody molecule reduces or prevents PtdSer-mediated membrane penetration of TIM-3.

In another embodiment, the anti-TIM-3 antibody molecule competes with HMGB1 for binding to TIM-3. E.g., it reduces binding of HMGB1 to residue 62 of TIM-3 (Q in mouse, E in human TIM-3), e.g., by at least about 10%, 20%, 30%, 40%, 50%, 60%, 70%, 80% or 90%, compared to the binding of HMGB1 to residue 62 of TIM-3 in the absence of the anti-TIM-3 antibody molecule.

In yet another embodiment, the anti-TIM-3 antibody molecule does not compete with a Galectin-9 (Gal-9) ligand for binding to TIM-3.

In some embodiments, the anti-TIM-3 antibody molecule has improved stability, e.g., at least about 0.5, 1, 2, 3, 4, 5, 6, 7, 8, 9 or 10-fold more stable in vivo or in vitro, than a murine or humanized anti-TIM-3 antibody molecule, e.g., a murine or humanized anti-TIM-3 antibody molecule described herein.

In some embodiments, the anti-TIM-3 antibody molecule comprises at least one antigen-binding region, e.g., a variable region or an antigen-binding fragment thereof, from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In certain embodiments, the anti-TIM-3 antibody molecule comprises at least one, two, three, or four variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In some embodiments, the anti-TIM-3 antibody molecule comprises at least one or two heavy chain variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In certain embodiments, the anti-TIM-3 antibody molecule comprises at least one or two light chain variable regions from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In one embodiment, the anti-TIM-3 antibody molecule includes a heavy chain constant region for an IgG4, e.g., a human IgG4. In another embodiment, the human IgG4 includes a substitution (e.g., a Ser to Pro substitution) at position 228 according to EU numbering or at position 108 of SEQ ID NO: 108 or 110. In still another embodiment, the anti-TIM-3 antibody molecule includes a heavy chain constant region for an IgG1, e.g., a human IgG1. In one embodiment, the human IgG1 includes a substitution (e.g., an Asn to Ala substitution) at position 297 according to EU numbering or at position 180 of SEQ ID NO: 112. In one embodiment, the human IgG1 includes a substitution (e.g., an Asp to Ala substitution) at position 265 according to EU numbering or at position 148 of SEQ ID NO: 113, a substitution (e.g., a Pro to Ala substitution) at position 329 according to EU numbering or at position 212 of SEQ ID NO: 113, or both. In one embodiment, the human IgG1 includes a substitution (e.g., a Leu to Ala substitution) at position 234 according to EU numbering or at position 117 of SEQ ID NO: 114, a substitution (e.g., a Leu to Ala substitution) at position 235 according to EU numbering or at position 118 of SEQ ID NO: 114, or both. In one embodiment, the heavy chain constant region comprises an amino sequence set forth in Table 1-5, or a sequence substantially identical (e.g., at least 80%, 85%, 90%, 92%, 95%, 97%, 98%, 99% or higher identical) thereto.

In yet another embodiment, the anti-TIM-3 antibody molecule includes a kappa light chain constant region, e.g., a human kappa light chain constant region. In one embodiment, the light chain constant region comprises an amino sequence set forth in Table 1-5, or a sequence substantially identical (e.g., at least 80%, 85%, 90%, 92%, 95%, 97%, 98%, 99% or higher identical) thereto.

In another embodiment, the anti-TIM-3 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 1-5, or a sequence substantially identical (e.g., at least 80%, 85%, 90%, 92%, 95%, 97%, 98%, 99% or higher identical) thereto. In yet another embodiment, the anti-TIM-3 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 1-5, or a sequence substantially identical (e.g., at least 80%, 85%, 90%, 92%, 95%, 97%, 98%, 99% or higher identical) thereto. In one embodiment, the human IgG1 includes a substitution at position 297 according to EU numbering (e.g., an Asn to Ala substitution). In one embodiment, the human IgG1 includes a substitution at position 265 according to EU numbering, a substitution at position 329 according to EU numbering, or both (e.g., an Asp to Ala substitution at position 265 and/or a Pro to Ala substitution at position 329). In one embodiment, the human IgG1 includes a substitution at position 234 according to EU numbering, a substitution at position 235 according to EU numbering, or both (e.g., a Leu to Ala substitution at position 234 and/or a Leu to Ala substitution at position 235).

In another embodiment, the anti-TIM-3 antibody molecule includes a heavy chain variable domain and a constant region, a light chain variable domain and a constant region, or both, comprising the amino acid sequence of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In some embodiments, the anti-TIM-3 antibody molecule includes at least one, two, or three complementarity determining regions (CDRs) from a heavy chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4, or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In some embodiments, the anti-TIM-3 antibody molecule comprises at least one, two, or three complementarity determining regions (CDRs) from a heavy chain variable region comprising an amino acid sequence shown in Tables 1-4, or encoded by the nucleotide sequence in Tables 1-4. In one embodiment, one or more of the CDRs (or collectively all of the CDRs) have one, two, three, four, five or more changes, e.g., amino acid substitutions, insertions, or deletions, relative to the amino acid sequence shown in Tables 1-4, or encoded by a nucleotide sequence shown in Tables 1-4. In certain embodiments, the anti-TIM-3 antibody molecule includes a substitution in a heavy chain CDR, e.g., one or more substitutions in a CDR1, CDR2 and/or CDR3 of the heavy chain. In one embodiment, the anti-TIM-3 antibody molecule includes a substitution in the heavy chain CDR2 at position 55 of the heavy chain region, e.g., a substitution of an asparagine to serine, or an asparagine to glutamine, at position 55 of the heavy chain region according to Tables 1-4 (e.g., any of SEQ ID NOs: 1 or 18 for murine or humanized, unmodified; or any of SEQ ID NOs: 26, or 32 for a modified sequence).

In some embodiments, the anti-TIM-3 antibody molecule includes at least one, two, or three complementarity determining regions (CDRs) from a light chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4, or encoded by the nucleotide sequence in Tables 1-4; or a sequence substantially identical (e.g., at least 80%, 85%, 90%, 92%, 95%, 97%, 98%, 99% or higher identical) to any of the aforesaid sequences.

In certain embodiments, the anti-TIM-3 antibody molecule includes at least one, two, or three CDRs (or collectively all of the CDRs) from a light chain variable region comprising an amino acid sequence shown in Tables 1-4, or encoded by a nucleotide sequence shown in Tables 1-4. In some embodiments, one or more of the CDRs (or collectively all of the CDRs) have one, two, three, four, five, six or more changes, e.g., amino acid substitutions, insertions, or deletions, relative to the CDRs shown in Tables 1-4, or encoded by a nucleotide sequence shown in Tables 1-4. In some embodiments, the anti-TIM-3 antibody molecule includes at least one, two, or three CDRs (or collectively all of the CDRs) from a light chain variable region comprising an amino acid sequence shown in Tables 1-4, or encoded by a nucleotide sequence shown in Tables 1-4. In some embodiments, one or more of the CDRs (or collectively all of the CDRs) have one, two, three, four, five, six or more changes, e.g., amino acid substitutions, insertions, or deletions, relative to the CDRs shown in Tables 1-4, or encoded by a nucleotide sequence shown in Tables 1-4.

In some embodiments, the anti-TIM-3 antibody molecule includes at least one, two, three, four, five or six CDRs (or collectively all of the CDRs) from a heavy and light chain variable region comprising an amino acid sequence shown in Tables 1-4, or encoded by a nucleotide sequence shown in Tables 1-4. In some embodiments, one or more of the CDRs (or collectively all of the CDRs) have one, two, three, four, five, six or more changes, e.g., amino acid substitutions, insertions, or deletions, relative to the CDRs shown in Tables 1-4, or encoded by a nucleotide sequence shown in Tables 1-4.

In certain embodiments, the anti-TIM-3 antibody molecule includes all six CDRs from an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4, or closely related CDRs, e.g., CDRs which are identical or which have at least one amino acid alteration, but not more than two, three or four alterations (e.g., substitutions, deletions, or insertions, e.g., conservative substitutions). In certain embodiments, the anti-TIM-3 antibody molecule may include any CDR described herein. In certain embodiments, the anti-TIM-3 antibody molecule includes a substitution in a heavy chain CDR, e.g., one or more substitutions in a CDR1, CDR2 and/or CDR3 of the heavy chain. In one embodiment, the anti-TIM-3 antibody molecule includes a substitution in the heavy chain CDR2 at position 55 of the heavy chain region, e.g., a substitution of an asparagine to serine, or an asparagine to glutamine, at position 55 of the heavy chain region according to Tables 1-4 (e.g., any of SEQ ID NOs: 1 or 18 for murine or humanized, unmodified; or any of SEQ ID NOs: 26, or 32 for a modified sequence).

In some embodiments, the anti-TIM-3 antibody molecule includes at least one, two, or three CDRs according to Kabat et al. (e.g., at least one, two, or three CDRs according to the Kabat definition as set out in Tables 1-4) from a heavy chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Tables 1-4.

In certain embodiments, the anti-TIM-3 antibody molecule includes at least one, two, or three CDRs according to Kabat et al. (e.g., at least one, two, or three CDRs according to the Kabat definition as set out in Tables 1-4) from a light chain variable region of an antibody described herein, e.g., an antibody chosen from any of ABTIM, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Tables 1-4.

In certain embodiments, the anti-TIM-3 antibody molecule includes at least one, two, three, four, five, or six CDRs according to Kabat et al. (e.g., at least one, two, three, four, five, or six CDRs according to the Kabat definition as set out in Tables 1-4) from the heavy and light chain variable regions of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Tables 1-4.

In some embodiments, the anti-TIM-3 antibody molecule includes all six CDRs according to Kabat et al. (e.g., all six CDRs according to the Kabat definition as set out in Tables 1-4) from the heavy and light chain variable regions of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Tables 1-4. In one embodiment, the anti-TIM-3 antibody molecule may include any CDR described herein.

In some embodiments, the anti-TIM-3 antibody molecule includes at least one, two, or three Chothia hypervariable loops (e.g., at least one, two, or three hypervariable loops according to the Chothia definition as set out in Tables 1-4) from a heavy chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or at least the amino acids from those hypervariable loops that contact TIM-3; or which have at least one amino acid alteration, but not more than two, three or four alterations (e.g., substitutions, deletions, or insertions, e.g., conservative substitutions) relative to one, two, or three hypervariable loops according to Chothia et al. shown in Tables 1-4.

In certain embodiments, the anti-TIM-3 antibody molecule includes at least one, two, or three Chothia hypervariable loops (e.g., at least one, two, or three hypervariable loops according to the Chothia definition as set out in Tables 1-4) of a light chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or at least the amino acids from those hypervariable loops that contact TIM-3; or which have at least one amino acid alteration, but not more than two, three or four alterations (e.g., substitutions, deletions, or insertions, e.g., conservative substitutions) relative to one, two, or three hypervariable loops according to Chothia et al. shown in Tables 1-4.

In certain embodiments, the anti-TIM-3 antibody molecule includes at least one, two, three, four, five, or six hypervariable loops (e.g., at least one, two, three, four, five, or six hypervariable loops according to the Chothia definition as set out in Tables 1-4) from the heavy and light chain variable regions of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or at least the amino acids from those hypervariable loops that contact TIM-3; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Tables 1-4.

In some embodiments, the anti-TIM-3 antibody molecule includes all six hypervariable loops (e.g., all six hypervariable loops according to the Chothia definition as set out in Tables 1-4) of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Tables 1-4. In one embodiment, the anti-TIM-3 antibody molecule may include any hypervariable loop described herein.

In still another embodiment, the anti-TIM-3 antibody molecule includes at least one, two, or three hypervariable loops that have the same canonical structures as the corresponding hypervariable loop of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23, e.g., the same canonical structures as at least loop 1 and/or loop 2 of the heavy and/or light chain variable domains of an antibody described herein. See, e.g., Chothia et al., (1992) *J. Mol. Biol.* 227: 799-817; Tomlinson et al., (1992) *J. Mol. Biol.* 227:776-798 for descriptions of hypervariable loop canonical structures. These structures can be determined by inspection of the tables described in these references.

In certain embodiments, the anti-TIM-3 antibody molecule includes a combination of CDRs or hypervariable loops defined according to the Kabat et al. and Chothia et al.

In one embodiment, the anti-TIM-3 antibody molecule includes at least one, two or three CDRs or hypervariable loops from a heavy chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23, according to the Kabat and Chothia definition (e.g., at least one, two, or three CDRs or hypervariable loops according to the Kabat and Chothia definition as set out in Tables 1-4); or encoded by the nucleotide sequence in Tables 1-4; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Tables 1-4.

In nother embodiment, the anti-TIM-3 antibody molecule includes at least one, two or three CDRs or hypervariable loops from a light chain variable region of an antibody described herein, e.g., an antibody chosen from any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23, according to the Kabat and Chothia definition (e.g., at least one, two, or three CDRs or hypervariable loops according to the Kabat and Chothia definition as set out in Tables 1-4); or encoded by the nucleotide sequence in Tables 1-4; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Tables 1-4.

The anti-TIM-3 antibody molecule can contain any combination of CDRs or hypervariable loops according to the Kabat and Chothia definitions.

In some embodiments, the anti-TIM-3 antibody molecule includes at least one, two, or three Chothia hypervariable loops from a heavy chain variable region of an antibody described herein, e.g., an antibody of Tables 1-4, or at least the amino acids from those hypervariable loops that contact TIM-3.

In some embodiments, the anti-TIM-3 antibody molecule includes at least one, two, or three Chothia hypervariable loops from a light chain variable region of an antibody described herein, e.g., an antibody of Tables 1-4, or at least the amino acids from those hypervariable loops that contact TIM-3.

In some embodiments, the anti-TIM-3 antibody molecule includes at least one, two, or three Kabat hypervariable loops from a heavy chain variable region of an antibody described herein, e.g., an antibody of Tables 1-4, or at least the amino acids from those hypervariable loops that contact TIM-3.

In some embodiments, the anti-TIM-3 antibody molecule includes at least one, two, or three Kabat hypervariable loops from a light chain variable region of an antibody described herein, e.g., an antibody of Tables 1-4, or at least the amino acids from those hypervariable loops that contact TIM-3.

In certain embodiments, the anti-TIM-3 antibody molecule includes at least one, two, three, four, five, or six hypervariable loops from the heavy and light chain variable regions of an antibody described herein, e.g., an antibody of Tables 1-4, or at least the amino acids from those hypervariable loops that contact TIM-3.

In certain embodiments, the anti-TIM-3 antibody molecule includes all six hypervariable loops from the heavy and light chain variable regions of an antibody described herein, e.g., an antibody of Tables 1-4, or at least the amino acids from those hypervariable loops that contact TIM-3, or at least the amino acids from those hypervariable loops that contact TIM-3, or closely related hypervariable loops, e.g., hypervariable loops which are identical or which have at least one amino acid alteration, but not more than two, three or four alterations (e.g., substitutions, e.g., conservative substitutions, deletions, or insertions).

In some embodiments, the anti-TIM-3 antibody molecule includes at least one, two, or three hypervariable loops that have the same canonical structures as the corresponding hypervariable loop of an antibody described herein, e.g., an antibody of Tables 1-4, e.g., the same canonical structures as at least loop 1 and/or loop 2 of the heavy and/or light chain variable domains of an antibody described herein. See, e.g., Chothia et al., (1992) J. Mol. Biol. 227:799-817; Tomlinson et al., (1992) J. Mol. Biol. 227:776-798 for descriptions of hypervariable loop canonical structures. These structures can be determined by inspection of the tables described in these references. In an embodiment, e.g., an embodiment comprising a variable region, CDR (e.g., Chothia CDR or Kabat CDR), or other sequence referred to herein, e.g., in Tables 1-4, the antibody molecule is a monospecific antibody molecule, a bispecific antibody molecule, or is an antibody molecule that comprises an antigen binding fragment of an antibody, e.g., a half antibody or antigen binding fragment of a half antibody. In certain embodiments the antibody molecule is a bispecific antibody molecule having a first binding specificity for TIM-3 and a second binding specificity for PD-1, LAG-3, CEACAM (e.g., CEACAM-1, CEACAM-3 and/or CEACAM-5), PD-L1 or PD-L2.

In certain embodiments, the light or the heavy chain variable framework (e.g., the region encompassing at least FR1, FR2, FR3, or FR4) of the anti-TIM-3 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In some embodiments, the light or heavy chain variable framework region includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-TIM-3 antibody molecule comprises a heavy chain variable domain having at least one, two, three, four, five, six, seven, ten, fifteen, twenty or more changes, e.g., amino acid substitutions, insertions, or deletions, from an amino acid sequence of, e.g., the amino acid sequence of the FR region in the entire variable region, e.g., shown in FIG. 1A. In some embodiments, the anti-TIM-3 antibody molecule comprises a heavy chain variable domain having one or more (e.g., all) of: A at position 2, Y at position 3, S at position 7, R at position 13, V at position 37, R at position 42, V at position 72, A at position 79, or F at position 95, e.g., the amino acid sequence of the FR in the entire variable region, e.g., as shown in Figure. 1A. In some embodiments, the anti-TIM-3 antibody molecule comprises a heavy chain variable domain having 2, 3, 4, 5, 6, 7, 8, or 9 positions selected from: A at position 2, Y at position 3, S at position 7, R at position 13, V at position 37, R at position 42, V at position 72, A at position 79, or F at position 95 of the amino acid sequence of an antibody of Tables 1-4, e.g., In certain embodiments (and optionally in combination with the heavy chain substitutions described herein, e.g., in the previous paragraph), the anti-TM-3 antibody molecule comprises a light chain variable domain having at least one, two, three, four, five, six, seven, ten, fifteen, twenty or more amino acid changes, e.g., amino acid substitutions, insertions, or deletions, from an amino acid sequence of Tables 1-4, e.g., the amino acid sequence of the FR region in the entire variable region, e.g., shown in FIG. 1B. In certain embodiments, the anti-TIM-3 antibody comprises a light chain variable domain having M at position 89 of the amino acid sequence of an antibody of Tables 1-4.

In some embodiments, the heavy or light chain variable domain, or both, of the of the anti-TIM-3 antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody chosen from any of ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23; or as described in Tables 1-4; or encoded by the nucleotide sequence in Tables 1-4; or which differs at least 1 or 5 residues, but less than 40, 30, 20, or 10 residues, from a variable region of an antibody described herein. In certain embodiments, the heavy or light chain variable region, or both, of the anti-TIM-3 antibody molecule includes an amino acid sequence encoded by a nucleic acid sequence described herein or a nucleic acid that hybridizes to a nucleic acid sequence described herein (e.g., a nucleic acid sequence as shown in Tables 1-4) or its complement, e.g., under low stringency, medium stringency, or high stringency, or other hybridization condition described herein.

In certain embodiments, the anti-TIM-3 antibody molecule comprises at least one, two, three, or four antigen-binding regions, e.g., variable regions, having an amino acid sequence as set forth in Tables 1-4, or a sequence substantially identical thereto (e.g., a sequence at least about 85%, 90%, 95%, 99% or more identical thereto, or which differs by no more than 1, 2, 5, 10, or 15 amino acid residues from the sequences shown in Tables 1-4. In certain embodiments, the anti-TIM-3 antibody molecule includes a VH and/or VL domain encoded by a nucleic acid having a nucleotide sequence that encodes an antibody of Tables 1-4, or a sequence substantially identical to any one of the nucleotide sequences (e.g., a sequence at least about 85%, 90%, 95%, 99% or more identical thereto, or which differs by no more than 3, 6, 15, 30, or 45 nucleotides from the sequences shown in Tables 1-4).

In certain embodiments, the anti-TIM-3 antibody molecule comprises at least one, two, or three (e.g., all) CDRs from a heavy chain variable region having an amino acid sequence as set forth in Tables 1-4, or a sequence substantially homologous thereto (e.g., a sequence at least about 85%, 90%, 95%, 99% or more identical thereto, and/or having one, two, three or more substitutions, insertions or deletions, e.g., conserved substitutions). In some embodiments, the anti-TIM-3 antibody molecule comprises at least one, two, or three (e.g., all) CDRs from a light chain variable region having an amino acid sequence as set forth in Tables 1-4, or a sequence substantially homologous thereto (e.g., a sequence at least about 85%, 90%, 95%, 99% or more identical thereto, and/or having one, two, three or more substitutions, insertions or deletions, e.g., conserved substitutions). In certain embodiments, the anti-TIM-3 antibody molecule comprises at least one, two, three, four, five or six (e.g., all) CDRs from heavy and light chain variable regions having an amino acid sequence as set forth in Tables 1-4, or a sequence substantially homologous thereto (e.g., a sequence at least about 85%, 90%, 95%, 99% or more identical thereto, and/or having one, two, three or more substitutions, insertions or deletions, e.g., conserved substitutions).

In some embodiments, the anti-TIM-3 antibody molecule comprises at least one, two, or three (e.g., all) CDRs and/or hypervariable loops from a heavy chain variable region having an amino acid sequence of an antibody described herein, e.g., an antibody chosen from any of ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23, as summarized in Tables 1-4, or a sequence substantially identical thereto (e.g., a sequence at least about 85%, 90%, 95%, 99% or more identical thereto, and/or having one, two, three or more substitutions, insertions or deletions, e.g., conserved substitutions). In certain embodiments, the anti-TIM-3 antibody molecule comprises at least one, two, or three (e.g., all) CDRs and/or hypervariable loops from a light chain variable region having an amino acid sequence of an antibody described herein, e.g., an antibody chosen from any of ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23, as summarized in Tables 1-4, or a sequence substantially identical thereto (e.g., a sequence at least about 85%, 90%, 95%, 99% or more identical thereto, and/or having one, two, three or more substitutions, insertions or deletions, e.g., conserved substitutions). In some embodiments, the anti-TIM-3 antibody molecule comprises all six CDRs and/or hypervariable loops described herein, e.g., described in Tables 1-4.

In some embodiments, the antibody molecule has a variable region that is identical in sequence, or which differs by 1, 2, 3, or 4 amino acids from a variable region described herein (e.g., an FR region disclosed herein).

In some embodiments, the anti-TIM-3 antibody molecule is a full antibody or fragment thereof (e.g., a Fab, F(ab')$_2$, Fv, or a single chain Fv fragment (scFv)). In certain embodiments, the anti-TIM-3 antibody molecule is a monoclonal antibody or an antibody with single specificity. The anti-TIM-3 antibody molecule can also be a humanized, chimeric, camelid, shark, or in vitro-generated antibody molecule. In some embodiments, the anti-TIM-3 antibody molecule thereof is a humanized antibody molecule. The heavy and light chains of the anti-TIM-3 antibody molecule can be full-length (e.g., an antibody can include at least one or at least two complete heavy chains, and at least one or at least two complete light chains) or can include an antigen-binding fragment (e.g., a Fab, F(ab')$_2$, Fv, a single chain Fv fragment, a single domain antibody, a diabody (dAb), a bivalent or bispecific antibody or fragment thereof, a single domain variant thereof, or a camelid antibody).

In certain embodiments, the anti-TIM-3 antibody molecule is in the form of a bispecific or multispecific antibody molecule. In one embodiment, the bispecific antibody molecule has a first binding specificity to TIM-3 and a second binding specifity, e.g., a second binding specificity to PD-1, LAG-3, CEACAM (e.g., CEACAM-1, -3 and/or -5), PD-L1 or PD-L2. In one embodiment, the bispecific antibody molecule binds to TIM-3 and PD-1. In another embodiment, the bispecific antibody molecule binds to TIM-3 and LAG-3. In another embodiment, the bispecific antibody molecule binds to TIM-3 and CEACAM (e.g., CEACAM-1,-3 and/or -5). In another embodiment, the bispecific antibody molecule binds to TIM-3 and CEACAM-1. In another embodiment, the bispecific antibody molecule binds to TIM-3 and CEACAM-3. In yet another embodiment, the bispecific antibody molecule binds to TIM-3 and CEACAM-5. In another embodiment, the bispecific antibody molecule binds to TIM-3 and PD-L1. In yet another embodiment, the bispecific antibody molecule binds to TIM-3 and PD-L2. Any combination of the aforesaid molecules can be made in a multispecific antibody molecule, e.g., a trispecific antibody that includes a first binding specificity to TIM-3, and a second and third binding specifities to one or more of: PD-1, LAG-3, CEACAM (e.g., CEACAM-1, -3 and/or -5), PD-L1 or PD-L2.

In other embodiments, the anti-TIM-3 antibody molecule is used in combination with a bispecific molecule comprising one or more of: PD-1, LAG-3, CEACAM (e.g., CEACAM-1, -3 and/or -5), PD-L1 or PD-L2. In one embodiment, the bispecific antibody molecule used in combination binds to CEACAM (e.g., CEACAM-1, -3 and/or -5) and LAG-3. In another embodiment, the bispecific antibody molecule used in combination binds to CEACAM (e.g., CEACAM-1, -3 and/or -5) and PD-1. In another embodiment, the bispecific antibody molecule used in combination binds to LAG-3 and PD-1.

In certain embodiments, the anti-TIM-3 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG2 (e.g., human IgG1 or IgG2). In some embodiments, the heavy chain constant region is human IgG1. In some embodiments, the anti-TIM-3 antibody molecule has a light chain constant region chosen from, e.g., the light chain constant regions of kappa or lambda, in some embodiments kappa (e.g., human kappa). In some embodiments, the constant region is altered, e.g., mutated, to modify the properties of the anti-TIM-3 antibody molecule (e.g., to increase or decrease one or more of: Fc receptor binding, antibody glycosylation, the number of cysteine residues, effector cell function, or complement function). For example, the constant region may be mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 108 or 110; or positions 135 (M to Y), 137 (S to T), 139 (T to E), 316 (H to K) and 317 (N to F) of SEQ ID NOs: 111, 112, 113 or 114). In another embodiment, the heavy chain constant region of an IgG4, e.g., a human IgG4, is mutated at position 228 according to EU numbering (e.g., S to P), e.g., as shown in Table 5. In certain embodiments, the anti-TIM-3 antibody molecules comprises a human IgG4 mutated at position 228 according to EU numbering (e.g., S to P), e.g., as shown in Table 5; and a kappa light chain constant region, e.g., as shown in Table 5. In still another embodiment, the heavy chain constant region of an IgG1, e.g., a human IgG1, is mutated at one or more of position 297 (e.g., N to A), position 265 (e.g., D to A), position 329 (e.g., P to A), position 234 (e.g., L to A), or position 235 (e.g., L to A), all according to EU numbering, e.g., as shown in Table 5. In certain embodiments, the anti-TIM-3 antibody molecules comprises a human IgG1 mutated at one or more of the aforesaid positions, e.g., as shown in Table 5; and a kappa light chain constant region, e.g., as shown in Table 5. In some embodiments, the anti-TIM-3 antibody molecule is a humanized antibody molecule.

In some embodiments, the anti-TIM-3 antibody molecules comprise combinations of human or humanized framework regions with CDRs (complementarity determining regions).

The invention also features an antibody molecule that competes with a monoclonal antibody, e.g., an antibody molecule described herein, for binding to human TIM-3.

In certain embodiments, the monoclonal antibody comprises:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

The invention also features an antibody molecule that binds to the same (or substantially the same) or an overlapping (or substantially overlapping) epitope as a monoclonal antibody, e.g., an antibody molecule described herein, to human TIM-3.

In certain embodiments, the monoclonal antibody comprises:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

The invention also features a nucleic acid molecule that comprise one or both nucleotide sequences that encode heavy and light chain variable regions, CDRs, hypervariable loops, framework regions of the anti-TIM-3 antibody molecules, as described herein. In certain embodiments, the nucleotide sequence that encodes the anti-TIM-3 antibody molecule is codon optimized. For example, the invention features a first and second nucleic acid encoding heavy and light chain variable regions, respectively, of an anti-TIM-3 antibody molecule chosen from one or more of, e.g., any of ABTIM3, ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, ABTIM3-hum23, as summarized in Tables 1-4, or a sequence substantially identical thereto. For example, the nucleic acid can comprise a nucleotide sequence as set forth in Tables 1-4, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 1-4).

In some embodiments, nucleic acids comprising nucleotide sequences that encode heavy and light chain variable regions and CDRs of the anti-TIM-3 antibody molecules, as described herein, are disclosed. For example, the disclosure provides a first and second nucleic acid encoding heavy and light chain variable regions, respectively, of an anti-TIM-3 antibody molecule according to Tables 1-4 or a sequence substantially identical thereto. For example, the nucleic acid can comprise a nucleotide sequence encoding an an anti-TIM-3 antibody molecule according to Table 1-4, or a sequence substantially identical to that nucleotide sequence (e.g., a sequence at least about 85%, 90%, 95%, 99% or more identical thereto, or which differs by no more than 3, 6, 15, 30, or 45 nucleotides from the aforementioned nucleotide sequence.

In certain embodiments, the nucleic acid can comprise a nucleotide sequence encoding at least one, two, or three CDRs, or hypervariable loops, from a heavy chain variable region having an amino acid sequence as set forth in Tables 1-4, or a sequence substantially homologous thereto (e.g., a sequence at least about 85%, 90%, 95%, 99% or more identical thereto, and/or having one, two, three or more substitutions, insertions or deletions, e.g., conserved substitutions).

In certain embodiments, the nucleic acid can comprise a nucleotide sequence encoding at least one, two, or three CDRs, or hypervariable loops, from a light chain variable region having an amino acid sequence as set forth in Tables 1-4, or a sequence substantially homologous thereto (e.g., a sequence at least about 85%, 90%, 95%, 99% or more identical thereto, and/or having one, two, three or more substitutions, insertions or deletions, e.g., conserved substitutions).

In some embodiments, the nucleic acid can comprise a nucleotide sequence encoding at least one, two, three, four, five, or six CDRs, or hypervariable loops, from heavy and light chain variable regions having an amino acid sequence as set forth in Table 1-4, or a sequence substantially homologous thereto (e.g., a sequence at least about 85%, 90%, 95%, 99% or more identical thereto, and/or having one, two, three or more substitutions, insertions or deletions, e.g., conserved substitutions).

In some embodiments, the anti-TIM-3 antibody molecule is isolated or recombinant.

In certain aspects, this disclosure features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

In some aspects, the present disclosure provides a method of providing an antibody molecule described herein. The method may include: providing a TIM-3 antigen (e.g., an antigen comprising at least a portion of a TIM-3 epitope, e.g., the IgV domain of TIM-3); obtaining an antibody molecule that specifically binds to the TIM-3 antigen; and evaluating if the antibody molecule specifically binds to the TIM-3 antigen, or evaluating efficacy of the antibody molecule in modulating, e.g., stimulating or inhibiting, the activity of TIM-3. The method can further include administering the antibody molecule to a subject, e.g., a human or non-human animal.

In certain aspects, the disclosure provides, compositions, e.g., pharmaceutical compositions, which include a pharmaceutically acceptable carrier, excipient or stabilizer, and at least one of the anti-TIM-3 antibody molecules described herein. In one embodiment, the composition, e.g., the pharmaceutical composition, includes a combination of the antibody molecule and one or more agents, e.g., a therapeutic agent or other antibody molecule, as described herein. In some embodiments, the antibody molecule is conjugated to a label or a therapeutic agent. In some embodiments, the compositions, e.g., the pharmaceutical compositions, comprise a combination of the antibody molecule and a second agent, e.g., a therapeutic agent, or two or more of the aforesaid antibody molecules, as further described herein.

The anti-TIM-3 antibody molecules disclosed herein can inhibit, reduce or neutralize one or more activities of TIM-3, e.g., resulting in blockade or reduction of an immune checkpoint on T cells or NK cells, or reinvigoration of an immune response by modulating antigen-presenting cells. In one embodiment, the antibody molecule results in one or more of: enhancing IFN-gamma and/or TNF alpha section in T cells; enhancing proliferation in T cells, e.g., CD4+ or CD8+ T cells; enhancing NK cell cytotoxic activity; or reducing suppressor activity of regulatory T cells (Tregs) or macrophages; or increasing capacity of macrophages or dendritic cells to stimulate an immune response. Thus, such antibody molecules can be used to treat or prevent disorders where enhancing an immune response in a subject is desired.

Uses of the Anti-TIM-3 Antibody Molecules

The antibody molecules disclosed herein can modulate (e.g., enhance, stimulate, increase, inhibit, reduce or neutralize) one or more activities of TIM-3. In some embodiments, the antibody molecule results in one or more of: enhancing IFN-gamma secretion and/or proliferation in T cells or enhancing NK cell cytotoxic activity. For instance, in some embodiments, the anti-TIM-3 antibody molecule increases IFN-gamma secretion by at least 16%, 18%, 20%, 22%, 24%, 26%, 28%, or 30%, e.g., in an assay of Example 4. In certain embodiments, the anti-TIM-3 antibody molecule increases NK cell cytotoxic activity by at least about 10%, 20%, 30%, 40%, 60%, 80%, or 100%, e.g., in an assay of Example 5. For example, the anti-TIM-3 antibody molecule could increase NK cell cytotoxic activity to at least about 60% or 70% of target cells killed when E/T=5, to at least about 75% or 85% of target cells killed when E/T=12, or to at least about 85% or 95% of target cells killed when E/T=25, e.g., in an assay of Example 5.

In certain aspects, a method of modulating (e.g., stimulating or inhibiting) an immune response in a subject is provided. The method comprises administering to the subject an anti-TIM-3 antibody molecule disclosed herein, (e.g., a therapeutically effective amount of an anti-TIM-3 antibody molecule), alone or in combination with one or more agents or procedures (e.g., in combination with other immunomodulatory agents), such that the immune response in the subject is modulated. In some embodiments, the antibody molecule enhances, stimulates or increases an immune response in the subject. In some embodiments, the antibody molecule inhibits, reduces, or neutralizes an immune response in a subject.

The subject can be a mammal, e.g., a monkey, a primate, preferably a higher primate, e.g., a human (e.g., a patient having, or at risk of having, a disorder described herein). In some embodiments, the subject is in need of enhancing an immune response, and in some embodiments, the subject is in need of inhibiting an immune response. In one embodiment, the subject has, or is at risk of, having a disorder described herein, e.g., a cancer or an infectious disorder as described herein. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

In one aspect, a method of treating (e.g., one or more of reducing, inhibiting, or delaying progression) a cancer or a tumor in a subject is provided. The method comprises administering to the subject an anti-TIM-3 antibody molecule described herein, e.g., a therapeutically effective amount of an anti-TIM-3 antibody molecule, alone or in combination with one or more agents or procedures. In certain embodiments, the anti-TIM-3 antibody molecule is administered in combination with a modulator of a costimulatory molecule (e.g., an agonist of a costimulatory molecule) or a modulator of an inhibitory molecule (e.g., an inhibitor of an immune checkpoint inhibitor), e.g., as described herein.

This disclosure also provides a method of reducing or inhibiting growth of a cancer or tumor cells (e.g., treating a cancer) in a subject, comprising administering to the subject an anti-TIM-3 antibody molecule described herein, e.g., a therapeutically effective amount of an anti-TIM-3 antibody molecule, alone or in combination with a second agent, e.g., an immunomodulator (e.g., an anti-PD-1, PD-L1, LAG-3 or CEACAM-1 inhibitor (e.g., antibody), or a combination thereof.

In certain embodiments, the cancer treated with the anti-TIM-3 antibody molecule, alone or in combination with one or more immunomodulatos, includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a lung cancer (e.g., lung adenocarcinoma or a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer (e.g., hepatocellular carcinoma), a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), anal cancer, gastro-esophageal cancer (e.g., esophageal squamous cell carcinoma), mesothelioma, nasopharyngeal cancer, thyroid cancer, cervical cancer, a lymphoproliferative disease (e.g., a post-transplant lymphoproliferative disease) or a hematological cancer, (e.g., diffuse large B cell lymphoma, T-cell lymphoma, B-cell lymphoma, or a non-Hogdkin lymphoma), or a leukemia (e.g., a myeloid leukemia or a lymphoid leukemia).

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a lung adenocarcinoma, non-small cell lung cancer or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-TIM-3 antibody molecule is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In one embodiment, the cancer microenvironment has an elevated level of PD-L1 expression. Alternatively, or in combination, the cancer microenvironment can have increased IFNγ and/or CD8 expression.

In some embodiments, the subject has, or is identified as having, a tumor that has one or more of high PD-L1 level or expression, or as being Tumor Infiltrating Lymphocyte (TIL)+ (e.g., as having an increased number of TILs), or both. In certain embodiments, the subject has, or is identified as having, a tumor that has high PD-L1 level or expression and that is TIL+. In some embodiments, the methods described herein further include identifying a subject based on having a tumor that has one or more of high PD-L1 level or expression or as being TIL+, or both. In certain embodiments, the methods described herein further include identifying a subject based on having a tumor that has high PD-L1 level or expression and as being TIL+. In some embodiments, tumors that are TIL+ are positive for CD8 and IFNγ. In some embodiments, the subject has, or is identified as having, a high percentage of cells that are positive for one, two or more of PD-L1, CD8, and/or IFNγ. In certain embodiments, the subject has or is identified as having a high percentage of cells that are positive for all of PD-L1, CD8, and IFNγ.

In some embodiments, the methods described herein further include identifying a subject based on having a high percentage of cells that are positive for one, two or more of PD-L1, CD8, and/or IFNγ. In certain embodiments, the methods described herein further include identifying a subject based on having a high percentage of cells that are positive for all of PD-L1, CD8, and IFNγ. In some embodiments, the subject has, or is identified as having, one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; an esophageal cancer; a thyroid cancer; a melanoma, and/or a nasopharyngeal cancer (NPC). In certain embodiments, the methods described herein further describe identifying a subject based on having one, two or more of PD-L1, CD8, and/or IFNγ, and one or more of a lung cancer, e.g., squamous cell lung cancer or lung adenocarcinoma; a head and neck cancer; a squamous cell cervical cancer; a stomach cancer; a thyroid cancer; a melanoma, and/or a nasopharyngeal cancer.

In some embodiments, subject has, or is identified as having, a tumor that has one, two, or more of high PD-1 level or expression, high TIM-3 level or expression, and/or high level of infiltration of regulatory T cells in the tumor, e.g., an increased number or percentage of Tregs present in the tumor. In certain embodiments, the subject has, or is identified as having, a tumor that has a high level or expression of PD-1 and TIM-3, and a high level, e.g., number, or regulatory T cells in the tumor. In some embodiments, the methods described herein further include identifying a subject based on one, two or more of a high percentage of cells that are positive for PD-1, a high percentage of cells that are positive for TIM-3, and/or a high level of infiltration of regulatory T cells in the tumor, e.g., an increased number or percentage of Tregs present in the tumor. In some embodiments, the methods described herein further include identifying a subject based on one, two or more of a high percentage of cells that are positive for PD-1, a high percentage of cells that are positive for TIM-3, and/or a high level of infiltration of regulatory T cells in the tumor, e.g., an increased number or percentage of Tregs present in the tumor, and one or more of a lung cancer, e.g., non-small cell lung cancer (NSCLC); a hepatocellular cancer, e.g., hepatocellular carcinoma; or an ovarian cancer, e.g., ovarian carcinoma.

Methods and compositions disclosed herein are useful for treating metastatic lesions associated with the aforementioned cancers.

In further aspects, this disclosure provides a method of treating an infectious disease in a subject, comprising administering to a subject a therapeutically effective amount of an anti-TIM-3 antibody described herein, or antigen-binding portion thereof, alone or in combination with one or more agents or procedures (e.g., one or more immunomodulatory agents).

Still further, this disclosure provides methods of enhancing an immune response to an antigen in a subject, comprising administering to the subject: (i) the antigen; and (ii) an anti-TIM-3 antibody, or antigen-binding portion thereof, such that an immune response to the antigen in the subject is enhanced. The antigen can be, for example, a tumor antigen, a viral antigen, a bacterial antigen or an antigen from a pathogen.

The anti-TIM-3 antibody molecule can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

The anti-TIM-3 antibody molecule can be used alone in unconjugated form, or can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the anti-TIM-3 antibody can be coupled to a radioactive isotope such as an α-, β-, or γ-emitter, or a β- and γ-emitter.

Dosages and therapeutic regimens of the anti-TIM-3 antibody molecule can be determined by a skilled artisan. In certain embodiments, the anti-TIM-3 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-TIM-3 antibody molecule is administered at a dose from about 10 to 20 mg/kg every other week.

The antibody molecules described herein are preferred for use in the methods described herein, although other anti-TIM-3 antibodies can be used instead, or in combination with an anti-TIM-3 antibody molecule of the invention.

Combination Therapies

The methods and compositions described herein can be used in combination with other therapeutic modalities. In some embodiments, the methods of described herein include administering to the subject an anti-TIM-3 antibody molecule as described herein, in combination with a cytotoxic agent, in an amount effective to treat or prevent said disorder. The antibody molecule and the cytotoxic agent can be administered simultaneously or sequentially.

Any combination and sequence of the anti-TIM-3 antibody molecules and other therapeutic modalities can be used. The anti-TIM-3 antibody molecule and/or other therapeutic modalities can be administered during periods of active disorder, or during a period of remission or less active disease. The anti-TIM-3 antibody molecule and other therapeutic modalities can be administered before treatment, concurrently with treatment, post-treatment, or during remission of the disorder.

In certain embodiments, the methods and compositions described herein are administered in combination with one or more of other antibody molecules, chemotherapy, other anti-cancer therapy (e.g., targeted anti-cancer therapies, gene therapy, viral therapy, RNA therapy bone marrow transplantation, nanotherapy, or oncolytic drugs), cytotoxic agents, immune-based therapies (e.g., cytokines or cell-based immune therapies), surgical procedures (e.g., lumpectomy or mastectomy) or radiation procedures, or a combination of any of the foregoing. The additional therapy may be in the form of adjuvant or neoadjuvant therapy. In some embodiments, the additional therapy is an enzymatic inhibitor (e.g., a small molecule enzymatic inhibitor) or a metastatic inhibitor. Exemplary cytotoxic agents that can be administered in combination with include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation (e.g., gamma irradiation)). In other embodiments, the additional therapy is surgery or radiation, or a combination thereof. In other embodiments, the additional therapy is a therapy targeting one or more of PI3K/AKT/mTOR pathway, an HSP90 inhibitor, or a tubulin inhibitor.

Alternatively, or in combination with the aforesaid combinations, the methods and compositions described herein can be administered in combination with one or more of: an immunomodulator (e.g., an activator of a costimulatory molecule or an inhibitor of an inhibitory molecule, e.g., an immune checkpoint molecule); a vaccine, e.g., a therapeutic cancer vaccine; or other forms of cellular immunotherapy.

Exemplary non-limiting combinations and uses of the anti-TIM-3 antibody molecules include the following.

In certain embodiments, the anti-TIM-3 antibody molecule is administered in combination with a modulator of a costimulatory molecule or an inhibitory molecule, e.g., a co-inhibitory ligand or receptor.

In one embodiment, the anti-TIM-3 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In one embodiment, the anti-TIM-3 antibody molecule is administered in combination with an inhibitor of an inhibitory (or immune checkpoint) molecule chosen from PD-1, PD-L1, PD-L2, CTLA-4, LAG-3, CEACAM (e.g., CEACAM-1, -3 and/or -5), VISTA, BTLA, TIGIT, LAIR1, CD160, 2B4 and/or TGFR beta. Inhibition of an inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule. In one embodiment, the inhibitor is a soluble ligand (e.g., a CTLA-4-Ig), or an antibody or antibody fragment that binds to PD-L1, PD-L2 or CTLA-4. For example, the anti-TIM-3 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). In one embodiment, the anti-TIM-3 antibody molecule is administered after treatment with an anti-CTLA-4 antibody (e.g., ipilimumab) with or without a BRAF inhibitor (e.g., vemurafenib or dabrafenib).

In another embodiment, the anti-TIM-3 antibody molecule is administered in combination with an anti-TIM-3 antibody or antigen-binding fragment thereof.

In another embodiment, the anti-TIM-3 antibody molecule is administered in combination with an anti-PD-1 antibody or antigen-binding fragment thereof.

In yet other embodiments, the anti-TIM-3 antibody molecule is administered in combination with an anti-TIM-3 antibody and an anti-TIM-3 antibody (or antigen-binding fragments thereof).

In another embodiment, the anti-TIM-3 antibody molecule is administered in combination with a CEACAM inhibitor (e.g., CEACAM-1, -3 and/or -5 inhibitor), e.g., an anti-CEACAM antibody molecule. In another embodiment, the anti-TIM-3 antibody molecule is administered in combination with a CEACAM-1 inhibitor, e.g., an anti-CEACAM-1 antibody molecule. In another embodiment, the anti-TIM-3 antibody molecule is administered in combination with a CEACAM-3 inhibitor, e.g., an anti-CEACAM-3 antibody molecule. In another embodiment, the anti-TIM-31 antibody molecule is administered in combination with a CEACAM-5 inhibitor, e.g., an anti-CEACAM-5 antibody molecule.

The combination of antibodies recited herein can be administered separately, e.g., as separate antibodies or antigen-binding fragments thereof, or linked, e.g., as a bispecific or trispecific antibody molecule. In one embodiment, a bispecific antibody that includes an anti-TIM-3 antibody molecule and an anti-PD-1, anti-CEACAM (e.g., anti-CEACAM-1, -3 and/or -5), or anti-TIM-3 antibody, or an antigen-binding fragment thereof, is administered. In certain embodiments, the combination of antibodies recited herein is used to treat a cancer, e.g., a cancer as described herein (e.g., a solid tumor or a hematologic malignancy).

In other embodiments, the anti-TIM-3 antibody molecule is administered in combination with a cytokine. The cytokine can be administered as a fusion molecule to the anti-TIM-3 antibody molecule, or as separate compositions. In one embodiment, the anti-TIM-3 antibody is administered in combination with one, two, three or more cytokines, e.g., as a fusion molecule or as separate compositions. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to TIM-3), a second binding specificity to a second target (e.g., LAG-3 or PD-1), and is optionally linked to an interleukin (e.g., IL-12) domain e.g., full length IL-12 or a portion thereof. In certain embodiments, the combination of anti-TIM-3 antibody molecule and the cytokine described herein is used to treat a cancer, e.g., a cancer as described herein (e.g., a solid tumor).

In certain embodiments, the anti-TIM-3 antibody molecule is administered in combination with an antibody specific against an HLA C, e.g., an antibody specific to Killer-cell Immunoglobulin-like Receptors (also referred to herein as an "anti-KIR antibody"). In certain embodiments, the combination of anti-TIM-3 antibody molecule and anti-KIR antibody is used to treat a cancer, e.g., a cancer as described herein (e.g., a solid tumor, e.g., an advanced solid tumor).

In one embodiment, the anti-TIM-3 antibody molecule is administered in combination with a cellular immunotherapy (e.g., Provenge® (e.g., Sipuleucel-T)), and optionally in combination with cyclophosphamide. In certain embodiments, the combination of anti-TIM-3 antibody molecule, Provenge® and/or cyclophosphamide is used to treat a cancer, e.g., a cancer as described herein (e.g., a prostate cancer, e.g., an advanced prostate cancer).

In another embodiment, the anti-TIM-3 antibody molecule is administered in combination with a vaccine, e.g., a cancer vaccine, (e.g., a dendritic cell renal carcinoma (DC-RCC) vaccine). In one embodiment, the vaccine is peptide-based, DNA-based, RNA-based, or antigen-based, or a combination thereof. In embodiments, the vaccine comprises one or more peptides, nucleic acids (e.g., DNA or RNA), antigens, or a combination thereof. In certain embodiments, the combination of anti-TIM-3 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In another embodiment, the anti-TIM-3 antibody molecule is administered in combination with an adjuvant.

In yet another embodiment, the anti-TIM-3 antibody molecule is administered in combination with chemotherapy, and/or immunotherapy. For example, the anti-TIM-3 antibody molecule can be used to treat a myeloma, alone or in combination with one or more of: chemotherapy or other anti-cancer agents (e.g., thalidomide analogs, e.g., lenalidomide), an anti-PD-1 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-TIM-3 antibody molecule is used in combination with an anti-TIM-3 antibody to treat a myeloma, e.g., a multiple myeloma.

In one embodiment, the anti-TIM-3 antibody molecule is used in combination with chemotherapy to treat a lung cancer, e.g., non-small cell lung cancer. In one embodiment, the anti-TIM-3 antibody molecule is used with standard lung, e.g., NSCLC, chemotherapy, e.g., platinum doublet therapy, to treat lung cancer. In yet other embodiments, the anti-TIM-3 antibody molecule is used in combination with an indoleamine-pyrroie 2,3-dioxygenase (IDO) inhibitor (e.g., INCB24360) in a subject with advanced or metastatic cancer (e.g., a patient with metastic and recurrent NSCLC cancer).

In yet other embodiments, the anti-TIM-3 antibody molecule is used in combination with one or more of: an immune-based strategy (e.g., interleukin-2 or interferon-α), a targeting agent (e.g., a VEGF inhibitor such as a monoclonal antibody to VEGF); a VEGF tyrosine kinase inhibitor such as sunitinib, sorafenib, axitinib and pazopanib; an RNAi inhibitor; or an inhibitor of a downstream mediator of VEGF signaling, e.g., an inhibitor of the mammalian target of rapamycin (mTOR), e.g., everolimus and temsirolimus. Any of such combinations can be used to treat a renal cancer, e.g., renal cell carcinoma (RCC) (e.g., clear cell renal cell carcinoma (CCRCC)) or metastatic RCC.

In some embodiments, the anti-TIM-3 antibody molecule, e.g., the anti-TIM-3 antibody molecule described herein, is used in combination with a MEK inhibitor (e.g., a MEK inhibitor as described herein). In some embodiments, the combination of the anti-TIM-3 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage.

In another embodiment, the anti-TIM-3 antibody molecule is used in combination with one, two or all of oxaliplatin, leucovorin or 5-FU (e.g., a FOLFOX co-treatment). Alternatively or in combination, combination further includes a VEGF inhibitor (e.g., a VEGF inhibitor as disclosed herein). In some embodiments, the combination of the anti-TIM-3 antibody, the FOLFOX co-treatment, and the VEGF inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. The cancer may be at an early, intermediate or late stage.

In other embodiments, the anti-TIM-3 antibody molecule is administered with a tyrosine kinase inhibitor (e.g., axitinib) to treat renal cell carcinoma and other solid tumors.

In other embodiments, the anti-TIM-3 antibody molecule is administered with a 4-1BB receptor targeting agent (e.g., an antibody that stimulates signaling through 4-1BB (CD-137), e.g., PF-2566). In one embodiment, the anti-TIM-3 antibody molecule is administered in combination with a tyrosine kinase inhibitor (e.g., axitinib) and a 4-1BB receptor targeting agent.

The anti-TIM-3 antibody molecule can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the antibody can be coupled to a radioactive isotope such as an α-, β-, or γ-emitter, or a β- and γ-emitter.

Additional Combination Therapies

The methods and compositions described herein (e.g., anti-TIM-3 antibodies and methods of using them) can be used in combination with other agents or therapeutic modalities, e.g., a second therapeutic agent chosen from one or more of the agents listed in Table 6. In one embodiment, the methods described herein include administering to the subject an anti-TIM-3 antibody molecule as described herein (optionally in combination with one or more inhibitors of PD-1, PD-L1, PD-L2, LAG-3, CEACAM (e.g., CEACAM-1 and/or CEACAM-5), or CTLA-4)), further include administration of a second therapeutic agent chosen from one or more of the agents listed in Table 6, in an amount effective to treat or prevent a disorder, e.g., a disorder as described herein, e.g., a cancer. When administered in combination, the anti-TIM-3 antibody molecule, the additional agent (e.g., second or third agent), or all, can be administered in an amount or dose that is higher, lower or the same than the amount or dosage of each agent used individually, e.g., as a monotherapy. In certain embodiments, the administered amount or dosage of the anti-TIM-3 antibody, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the anti-TIM-3 antibody, the additional agent (e.g., second or third agent), or all, that results in a desired effect (e.g., treatment of cancer) is lower (e.g., at least 20%, at least 30%, at least 40%, or at least 50% lower).

In other embodiments, the second therapeutic agent is chosen from one or more of the agents listed in Table 6. In one embodiment, the cancer is chosen from a lung cancer (e.g., a non-small cell lung cancer (NSCLC) (e.g., a NSCLC with squamous and/or non-squamous histology, or a NSCLC adenocarcinoma), or disclosed in a publication listed in Table 6. In some embodiments, the second therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11β-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 6.

In one embodiment, the second therapeutic agent is chosen from one or more of: Compound A8, Compound A17, Compound A23, Compound A24, Compound A27, Compound A29, Compound A33, and Compound A13.

In other embodiments, the second therapeutic agent is chosen from one or more of: Compound A5, Compound A8, Compound A17, Compound A23, Compound A24, Compound A29, and Compound A40.

In other embodiments, the second therapeutic agent is chosen from one or more of: Compound A9, Compound A16, Compound A17, Compound A21, Compound A22, Compound A25, Compound 28, Compound A48, and Compound 49.

In other embodiments, the second therapeutic agent is chosen from a modulator of an apoptotic pathway, e.g., an IDH1 inhibitor, or a Bcl-2 or Bcl-XL inhibitor. In one embodiment, the second therapeutic agent is chosen from Compound A21, A14 or a combination thereof. Without being bound by theory, TIM-3 is known to interact with PtdSer, which tends to be exposed on the surface of apoptotic cells, and can cause immunosuppression. Blockade of a PtdSer-TIM-3 interaction, e.g., using an anti-TIM-3 antibody molecule as described herein may ameliorate or overcome the immunosuppression.

In other embodiments, the second therapeutic agent is an inhibitor of CSF-1R, e.g., an anti-CSF-1R antibody or small molecule inhibitor (such as Compound A15 or A33). These second therapeutic agents may inhibit macrophages (e.g., M2 macrophages). In certain embodiments, such second therapeutic agents can facilitate the conversion to M1 macrophages.

In embodiments, the second therapeutic agent is administered at a therapeutic or lower-than therapeutic dose. In certain embodiments, the concentration of the second therapeutic agent that is required to achieve inhibition, e.g., growth inhibition, is lower when the second therapeutic agent is administered in combination with the anti-TIM-3 antibody molecule than when the second therapeutic agent is administered individually. In certain embodiments, the concentration of the anti-TIM-3 antibody molecule that is required to achieve inhibition, e.g., growth inhibition, is lower when the anti-TIM-3 antibody molecule is administered in combination with the second therapeutic agent than when the anti-TIM-3 antibody molecule is administered individually. In certain embodiments, in a combination therapy, the concentration of the second therapeutic agent that is required to achieve inhibition, e.g., growth inhibition, is lower than the therapeutic dose of the second therapeutic agent as a monotherapy, e.g., 10-20%, 20-30%, 30-40%, 40-50%, 50-60%, 60-70%, 70-80%, or 80-90% lower. In certain embodiments, in a combination therapy, the concentration of the anti-TIM-3 antibody molecule that is required to achieve inhibition, e.g., growth inhibition, is lower than the therapeutic dose of the anti-TIM-3 antibody molecule as a monotherapy, e.g., 10-20%, 20-30%, 30-40%, 40-50%, 50-60%, 60-70%, 70-80%, or 80-90% lower.

Detection

In some aspects, the present disclosure provides methods for detecting the presence of TIM-3 in a sample, e.g., in vitro or in vivo (e.g., a biological sample, e.g., blood, serum, semen or urine, or a tissue biopsy, e.g., from a hyperproliferative or cancerous lesion). The methods herein can be used to evaluate (e.g., monitor treatment or progression of, diagnose and/or stage a disorder described herein, e.g., an immune disorder, a cancer, or an infectious disease, in a subject). The method may include: (i) contacting the sample with (and optionally, a reference, e.g., a control sample), or administering to the subject, an anti-TIM-3 antibody molecule as described herein, under conditions that allow interaction to occur, and (ii) detecting whether there is formation of a complex between the antibody molecule and the sample (and optionally, the reference, e.g., control, sample). Formation of the complex is indicative of the presence of TIM-3, and can indicate the suitability or need for a treatment described herein. The method can involve, e.g., an immunohistochemistry, immunocytochemistry, flow cytometry, antibody molecule complexed magnetic beads, ELISA assays, PCR-techniques (e.g., RT-PCR).

Typically, the anti-TIM-3 antibody molecule used in the in vivo and in vitro diagnostic methods is directly or indirectly labeled with a detectable substance to facilitate detection of the bound or unbound binding agent. Suitable detectable substances include various biologically active enzymes, prosthetic groups, fluorescent materials, luminescent materials, paramagnetic (e.g., nuclear magnetic resonance active) materials, and radioactive materials.

Additional embodiments provide a method of treating a cancer, comprising: identifying in a sample (e.g., a subject's sample comprising cancer cells and optionally immune cells such as TILs) the presence of one, two or all of PD-L1, CD8, or IFN-γ, thereby providing a value for one, two or all of PD-L1, CD8, and IFN-γ. The method can further include comparing the PD-L1, CD8, and/or IFN-γ values to a reference value, e.g., a control value. If the PD-L1, CD8, and/or IFN-γ values are greater than the reference value, e.g., the control values, administering a therapeutically effective amount of an anti-TIM-3 antibody (e.g., an anti-TIM-3 antibody described herein) to the subject, optionally in combination with one or more other agents, thereby treating the cancer. The cancer may be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer, or breast cancer, e.g., TN breast cancer, e.g., IM-TN breast cancer. In some embodiments, the cancer is ER+ breast cancer or pancreatic cancer.

Also provided is a method of treating a cancer, comprising: testing a sample (e.g., a subject's sample comprising cancer cells) for the presence of PD-L1, thereby identifying a PD-L1 value, comparing the PD-L1 value to a control value, and if the PD-L1 value is greater than the control value, administering a therapeutically effective amount of an anti-TIM-3 antibody (e.g., an anti-TIM-3 antibody described herein) to the subject, optionally in combination with one or more other agents, e.g., an anti-PD-1 antibody molecule, thereby treating the cancer. The cancer may be, e.g., a cancer as described herein, such as cancer is non-small cell lung (NSCLC) adenocarcinoma (ACA), NSCLC squamous cell carcinoma (SCC), or hepatocellular carcinoma (HCC).

In some aspects, the present disclosure provides diagnostic or therapeutic kits that include the anti-TIM-3 antibody molecules described herein and instructions for use.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

Figures and Tables are provided herewith.

BRIEF DESCRIPTION OF DRAWINGS

Each of the Figures is described herein in more detail.

FIGS. 1A-1B depict exemplary anti-TIM-3 antibodies. FIG. 1A provides the heavy chain and light chain variable regions of ABTIM3 (SEQ ID NOS: 1 and 2, respectively, in order of appearance). FIG. 1B provides a sequence alignment between the variable regions of ABTIM3 and murine (mouse) germline antibodies (SEQ ID NOS: 134 and 135, respectively, in order of appearance). The CDRs are boxed (depicted in white text on a black background in the priority documents).

FIGS. 2A-2E illustrate the binding and activity of various anti-TIM-3 antibodies. FIG. 2A summarizes affinity data for the murine antibody ABTIM3 and another TIM-3 binding antibody. FIG. 2B shows a binding curve of one panel of antibodies for human TIM-3 in transfected cells. FIG. 2C shows a binding curve of a second panel of antibodies, including ABTIM3 (triangles) for human TIM-3 in transfected cells. FIG. 2D shows a binding curve of ABTIM3 and other anti-TIM-3 antibodies for cynomolgus monkey TIM-3. FIG. 2E shows the affinity of several anti-TIM-3 antibodies for cynomolgus monkey TIM-3. Monoclonal antibody ABTIM3 has the highest affinity of the antibodies tested in these experiments, indicating it has good cross-reactivity with human and monkey targets.

FIG. 3A illustrates the recombinant construct used for epitope analysis. FIG. 3B shows that the anti-TIM-3 monoclonal antibody (anti-TIM-3 #3), and anti-PD-L1 control monoclonal antibodies (anti-PD-L1 #1 and #2), bind to the chimeric protein of FIG. 3A, while anti-TIM-3 #2 and ABTIM3 do not substantially bind.

FIG. 5A shows the results of a representative experiment where cells were exposed to antibodies ABTIM3, anti-TIM-3 #2, mIgG1, and anti-PD-L1 control antibody (from left to right). IFN-gamma levels were measured by flow cytometry. FIG. 5B quantifies IFN-gamma expression in cells exposed to these four antibodies.

FIG. 8A shows that humanized anti-TIM-3 antibodies bound to cells expressing huTIM-3 in a FACS assay. FIG. 8B shows that the humanized anti-TIM-3 antibodies competed with the parental murine ABTIM3 for cells expressing huTIM-3 in a FACS assay.

FIG. 9A shows the overall structure of ABTIM3-hum21 Fab binding to TIM-3. Labeled in the figure are 1) the deduced PtdSer, $Ca^{2+}$ and Galectin-9 binding sites on human TIM-3 and 2) names of the β strands and BC, FG and CC' loops. FIG. 9B shows a detailed view of ABTIM3-hum21 epitope residues on TIM-3 (shown as sticks and labeled). FIG. 9B discloses residues 56-61 ("GACPVF") as SEQ ID NO: 136 and residues 119-127 ("NDEKFNLKL") as SEQ ID NO: 137.

FIGS. 10A-10C shows the comparison of ABTIM3-hum21 epitope with CEACAM-1-binding site on human TIM-3. FIG. 10A shows the comparison of the crucial CEACAM-1-binding residues of TIM-3 (residues 117-120 ("IMND") disclosed as SEQ ID NO: 138) (left panel, grey surface, residues are labeled) and the ABTIM3-hum21 epitope (right panel, grey surface, residues that overlap with CECAM1-binding site are labeled). Since TIM-3 is oriented the same way in both panels, it is obvious that ABTIM3-hum21 epitope overlaps with CEACAM-1 binding site. FIG. 10B shows the K122 of TIM-3 forms hydrogen bond with CEACAM-1 (left panel), and is completed blocked by ABTIM3-hum21 (right panel). FIG. 10C shows two-angle views of the superimposition of TIM-3/ABTIM3-hum21 Fab and TIM-3/CEACAM-1 structures, which shows significant clash between ABTIM3-hum21 and TIM-3, indicating ABTIM3-hum21 will disrupt CEACAM-1 binding to TIM-3.

FIG. 23A shows the mean serum concentration of BTIM3-hum11 in mice after antibody administration. FIG. 23B shows the mean serum concentration of ABTIM3-hum11 in rats after antibody administration.

BRIEF DESCRIPTION OF THE TABLES

Figure 2D:
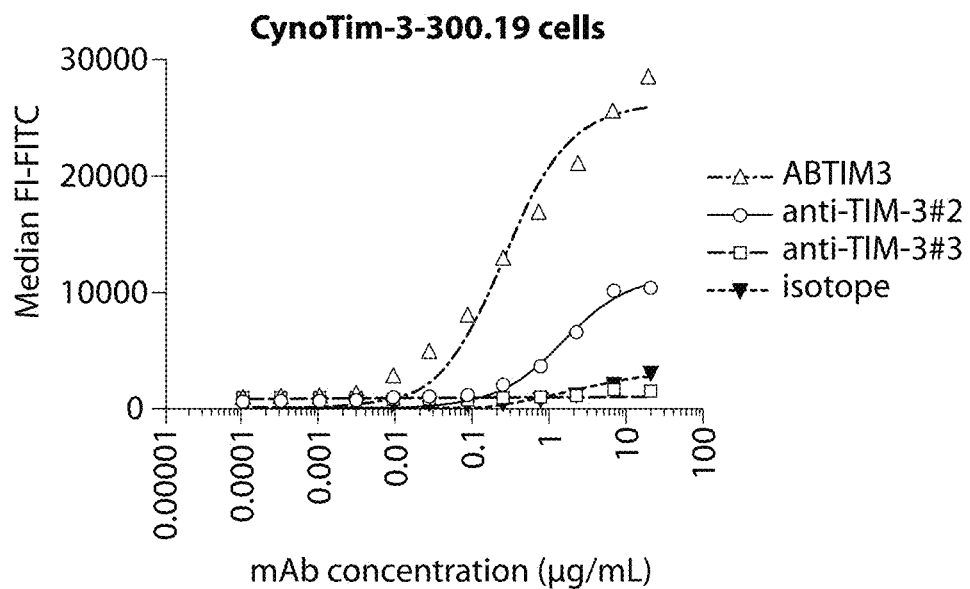

Each of the Tables is described herein in more detail.

Table 1 summarizes the sequences of the murine anti-TIM-3 antibody, ABTIM3.

Table 2 depicts the amino acid sequences of ABTIM3 heavy chain variable domain and light chain variable domain.

Table 3 depicts the amino acid sequences of ABTIM3 heavy chain CDRs and light chain CDRs.

Table 4 is a summary of the amino acid and nucleotide sequences for the murine and humanized anti-TIM-3 antibody molecules. The antibody molecules include murine ABTIM3 and humanized anti-TIM-3 antibodies: ABTIM3-hum01, ABTIM3-hum02, ABTIM3-hum03, ABTIM3-hum04, ABTIM3-hum05, ABTIM3-hum06, ABTIM3-hum07, ABTIM3-hum08, ABTIM3-hum09, ABTIM3-hum10, ABTIM3-hum11, ABTIM3-hum12, ABTIM3-hum13, ABTIM3-hum14, ABTIM3-hum15, ABTIM3-hum16, ABTIM3-hum17, ABTIM3-hum18, ABTIM3-hum19, ABTIM3-hum20, ABTIM3-hum21, ABTIM3-hum22, and ABTIM3-hum23. The amino acid and nucleotide sequences of the heavy and light chain CDRs, the amino acid and nucleotide sequences of the heavy and light chain variable regions, and the amino acid and nucleotide sequences of the heavy and light chains are shown in this Table.

Table 5 depicts the constant region amino acid sequences of human IgG heavy chains and human kappa light chain.

Table 6 is a summary of selected therapeutic agents that can be administered in combination with the anti-TIM-3 antibody molecules and other immunomodulators (e.g., one or more of: an activator of a costimulatory molecule and/or an inhibitor of an immune checkpoint molecule) described herein. Table 6 provides from left to right the following: the Compound Designation of the second therapeutic agent, the Compound structure, and Patent publication(s) disclosing the Compound.

Table 7 summarizes the $K_D$ values for anti-TIM-3 antibody binding to activated PBMCs.

Table 8 summarizes the $K_D$ values for anti-TIM-3 antibody binding to PD-L1 IgV/TIM-3 mucin construct.

Table 9 summarizes the $K_D$ values for a panel of humanized anti-TIM-3 antibodies as measured by Biacore assay.

Table 10 summarizes the $K_D$ values for anti-TIM-3 antibody binding to cells expressing human TIM-3.

Table 11 summarizes the $K_D$ values for anti-TIM-3 antibody binding to TIM-3-Ig.

Table 12 summarizes the amino acid sequences used for crystal structure determination.

Table 13 summarizes the amino acids in TIM-3 and anti-TIM-3 antibody that participate in the binding interaction.

Table 14 summarizes the Biacore competition assay cycles.

Table 15 summerizes the results from Biacore competition assay.

Table 16 summerizes the pharmacokinetic properties of ABTIM3-hum11.

DETAILED DESCRIPTION

T-cell immunoglobulin domain and mucin domain 3 (TIM-3, also known as Hepatitis A virus cellular receptor 2, and HAVCR2) is a cell surface protein expressed, e.g., on activated CD4+ and CD8+ T cells, natural regulatory T cells (nTregs), NK cells, and innate cells, e.g., macrophages, monocytes and dendritic cells (DCs). TIM-3 is generally not expressed on naïve T cells, but rather upregulated on activated, effector T cells, e.g., on a PD-1+ subset of cells. TIM-3 is also expressed on tissue site natural regulatory cells and in murine models. TIM-3+ Tregs have been shown to have a more suppressive phenotype while TIM-3+ Tregs have also been shown to correlate with disease severity in NSCLC, hepatocellular and ovarian carcinoma. TIM-3 is constitutively expressed on DCs, monocytes/macrophages and NK cells, and blockade of TIM-3 has been shown to correlate with increased cytotoxicity in NK cells; increased secretion of IL-12/TNF-α by monocytes/macrophages; and increased NF-κB expression in DCs. Blockade of TIM-3 (partially alone and additively or synergistically in combination with PD-1 pathway blockade) has shown anti-tumor efficacy in several preclinical cancer models, including CT26 colon carcinoma (Sakuishi et al., *J Exp Med.* 2010; 207(10):2187-94), WT3 sarcoma and TRAMP-C1 prostate carcinoma (Ngiow et al., *Cancer Res.* 2011; 71(10):3540-3551). Recent studies have highlighted TIM-3 as an important player in the T effector cell exhaustion and suppression that takes place in chronic immune conditions such as infection, e.g., bacterial or viral, and cancer in both humans and experimental models. TIM-3 has been described as an inhibitory receptor in the immunological synapse, and blocking of TIM-3 may enhance immune response against infection and cancer.

Blockade of TIM-3 has been shown to restore activity in effector cells, such as cytokine secretion and proliferation. In virally exhausted cell populations, e.g., cells infected with HCV, TIM-3-expressing cells (TIM3+ cells) express less TNF-alpha and IFN-gamma cytokines than TIM-3 negative cells in both effector cell populations, CD4+ and CD8+ T cells (Golden-Mason et al., 2009, *J. Virol*, 83:9122). Blockade of TIM-3 restores proliferation in CD8+ T cells from an HIV patient, or in cells that recapitulate viral exhaustion (Jones et al., 2008, *J. Exp. Med.*, 205:2763), or proliferation and IFN-γ and/or TNF-α secretion in NY-ESO-1 specific T cells from PBMCs from metastatic patients (Fourcade et al., 2010, *J. Exp. Med.*, 207:2175). TIM-3 blockade may also diminish the suppressor activity of regulatory T cells. TIM-3+ T cells have been found to be concentrated in tumors, and contribute to the immunosuppressive tumor environment (Sakuishi et al., 2013, *Oncoimmunology*, 2:e23849; Gao et al., 2012, *Plos One*; and Yan et al., 2013, *Plos One*). Thus, blockade of TIM-3, e.g., by antibodies that inhibit TIM-3 function, can improve the immune response against infection and anti-tumor immunity.

TIM-3 has also been implicated in regulating immune response through macrophage activity. Blockade of TIM-3 leads to an increase in TLR-mediated IL-12 production (Zhang et al., 2010, *J Leukoc Biol*, 91:189). Thus, TIM-3 blockade may increase immune stimulation properties of macrophages to enhance immune response against infection and anti-tumor activity.

TIM-3 has five reported ligands: Galectin-9 (Gal-9), phosphatidylserine (PtdSer), HMGB1, Semaphorin-4A, and CEACAM-1. S-type lectin galectin-9 can inhibit TIM-3-associated Th1 effector function and induce apoptosis on TIM-3-expressing T cells in murine models. PtdSer usually resides on the intracellular side of the plasma membrane, but is flipped to the extracellular side during apoptosis. PtdSer binds a preserved cleft in all three human TIM family members (TIM-1, 3, 4). Inhibition of PtdSer binding to TIM-3 may activate T-cell response. Galectin-9 is secreted by tumor cells and can contribute to evasion from anti-tumor immunity. DNA alarmin HMGB1, for which TIM-3 may act as a "sink," can prevent the HMGB1/RAGE interactions that stimulate innate immunity. Semaphorin-4A and CEACAM-1 (another immune checkpoint molecule whose inhibition can enhance immune response) can interact with TIM-3 both in cis as a heterodimer on T cells and in trans as a ligand. Interaction between CEACAM-1 and TIM-3 may help mediate block immune response signaling. Co-blockade of TIM-3 and CEACAM-1 in CT26 colon carcinoma showed similar efficacy to that seen for co-blockade of PD-L1 and TIM-3.

The TIM-3 cytoplasmic tail has seven sites for tyrosine phosphorylation and no known inhibitory (i.e., ITIM) motifs, which suggests that TIM-3 could co-stimulate with the T cell receptor, leading to functional exhaustion through increased T cell signaling. TIM-3 can interact with Fyn and facilitate accumulation of receptor phosphatases CD148 and CD45 at the immunologic synapse. The presence of CEACAM-1 as a co-receptor in the TIM-3/CEACAM-1 heterodimer suggests that this co-expression may lead to inhibitory signaling in T cells via the ITIM motif in the CEACAM-1 cytoplasmic tail which has been shown to interact with both SHP1 and SHP2.

Disclosed herein are antibody molecules that bind to TIM-3 with high affinity and specificity. In one embodiment, humanized antibodies against TIM-3 are disclosed. Additional aspects of the invention include nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided. The anti-TIM-3 antibody molecules disclosed herein can be used (alone or in combination with other agents or therapeutic modalities) to treat, prevent and/or diagnose immune disorders, cancer, infectious disease, Crohn's disease, sepsis, SIRS (Systemic Inflammatory Response Syndrome), and glomerulonephritis. Thus, compositions and methods for detecting TIM-3, as well as methods for treating various disorders, including cancer and immune disorders using the anti-TIM-3 antibody molecules are disclosed herein.

The term "TIM-3" include isoforms, mammalian, e.g., human TIM-3, species homologs of human TIM-3, and analogs comprising at least one common epitope with TIM-3. The amino acid sequence of TIM-3, e.g, human TIM-3, is known in the art, e.g., Sabatos et al., 2003. *Nat Immunol*, 4(11):1102.

Definitions

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a some embodiments, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are suitable conditions and the ones that should be used unless otherwise specified.

It is understood that the molecules described herein may have additional conservative or non-essential amino acid substitutions, which do not have a substantial effect on their functions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein.

The terms "nucleic acid," "nucleic acid sequence," "nucleotide sequence," or "polynucleotide sequence," and "polynucleotide" are used interchangeably.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the compositions and methods herein are described in further detail below. Additional definitions are set out throughout the specification.

Antibody Molecules

In some embodiments, the antibody molecule binds to a mammalian, e.g., human, TIM-3. For example, the antibody molecule binds specifically to an epitope, e.g., linear or conformational epitope, (e.g., an epitope as described herein) on TIM-3. In some embodiments, the epitope is at least a portion of the IgV domain of human or cynomolgus TIM-3.

As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobulin chain. In an embodiment, an antibody molecule comprises an antigen bindng or functional fragment of a full length antibody, or a full length immunoglobulin chain.

In an embodiment, an antibody molecule is a monospecific antibody molecule and binds a single epitope. E.g., a monospecific antibody molecule having a plurality of immunoglobulin variable domain sequences, each of which binds the same or substantially the same epitope.

In an embodiment, an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule, In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment the first and second epitopes do not overlap or do not substantially overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody molecule comprises a half antibody having binding specificity for a first epitope and a half antibody having binding specificity for a second epitope. In an embodiment, a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope. In an embodiment the first epitope is located on TIM-3 and the second epitope is located on a PD-1, LAG-3, CEACAM (e.g., CEACAM-1, CEACAM-3 and/or CEACAM-5), PD-L1, or PD-L2.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The preparation of antibody molecules can be monoclonal or polyclonal. An antibodymolecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of:

Fc receptor binding, antibody glycosylation, the number of cysteine residues, effector cell function, or complement function).

The antibodies disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR). The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In some embodiments, the following definitions are used: AbM definition of CDR1 of the heavy chain variable domain and Kabat definitions for the other CDRs. In certain embodiments, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to a TIM-3 polypeptide, or an epitope thereof. With respect to proteins (or protein mimetics), the antigen-binding site typically includes one or more loops (of at least, e.g., four amino acids or amino acid mimics) that form an interface that binds to the TIM-3 polypeptide. Typically, the antigen-binding site of an antibody molecule includes at least one or two CDRs, or more typically at least three, four, five or six CDRs.

The terms "compete" or "cross-compete" are used interchangeably herein to refer to the ability of an antibody molecule to interfere with binding of an anti-TIM-3 antibody molecule, e.g., an anti-TIM-3 antibody molecule provided herein, to a target, e.g., human TIM-3. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-TIM-3 antibody molecule is said to compete for binding to the target with a second anti-TIM-3 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

As used herein, the term "epitope" refers to the moieties of an antigen (e.g., human TIM-3) that specifically interact with an antibody molecule. Such moieties, referred to herein as epitopic determinants, typically comprise, or are part of, elements such as amino acid side chains or sugar side chains. An epitopic determinant can be defined by methods known in the art or disclosed herein, e.g., by crystallography or by hydrogen-deuterium exchange. At least one or some of the moieties on the antibody molecule, that specifically interact with an epitopic determinant, are typically located in a CDR(s). Typically an epitope has a specific three dimensional structural characteristics. Typically an epitope has specific charge characteristics. Some epitopes are linear epitopes while others are conformational epitopes.

In an embodiment, an epitopic determinant is a moiety on the antigen, e.g., such as amino acid side chain or sugar side chain, or part thereof, which, when the antigen and antibody molecule are co-crystallized, is within a predetermined distance, e.g., within 5 Angstroms, of a moiety on the antibody molecule, referred to herein as a "crystallographic epitopic determinant." The crystallographic epitopic determinants of an epitope are collectively refered to as the "crystallographic epitope."

A first antibody molecule binds the same epitope as a second antibody molecule (e.g., a reference antibody molecule, e.g., an antibody molecule disclosed herein, e.g., ABTIM3-hum21, ABTIM-hum11 or ABTIM3-hum03) if the first antibody specifically interacts with the same epitopic determinants on the antigen as does the second or reference antibody, e.g., when interaction is measured in the same way for both the antibody and the second or reference antibody. Epitopes that overlap share at least one epitopic determinant. A first antibody molecule binds an overlapping epitope with a second antibody molecule (e.g., a reference antibody molecule, e.g., an antibody disclosed herein, e.g., ABTIM3-hum21, ABTIM-hum11 or ABTIM3-hum03) when both antibody molecules specifically interact with a common epitopic determinant. A first and a second antibody molecule (e.g., a reference antibody molecule, e.g., an antibody molecule disclosed herein, e.g., ABTIM3-hum21, ABTIM-hum11 or ABTIM3-hum03) bind substantially overlapping epitopes if at least half of the epitopic determinants of the second or reference antibody are found as epitopic determinants in the epitope of the first antibody. A first and a second antibody molecule (e.g., a reference antibody molecule, e.g., an antibody molecule disclosed herein, e.g., ABTIM3-hum21, ABTIM-hum11 or ABTIM3-hum03) bind substantially the same epitope if the first antibody molecule binds at least half of the core epitopic determinants of the epitope of the second or reference antibody, wherein the core epitopic determinants are defined by crystallography and hydrogen-deuterium exchange, e.g., including residues Val24, Glu25, Thr41, Glu121, Lys122, Phe123, Asn124, Leu125, Lys126, Leu127, Val128, Gly56, Ala57, Cys58, Pro59, Va160, and Phe61 of human TIM-3.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., Cancer Immunol. Immunother., 32:180-190 (1990)) and also because of potential allergic reactions (see, e.g., LoBuglio et al., *Hybridoma*, 5:5117-5123 (1986)).

The antibody molecule can be a polyclonal or a monoclonal antibody. In other embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. *International* Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In some embodiments, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In certain embodiments, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are also contemplated. Antibodies generated in a non-human organism, e.g., a rat or mouse, and then modified, e.g., in the variable framework or constant region, to decrease antigenicity in a human are also contemplated.

Chimeric antibodies can be produced by any suitable recombinant DNA technique. Several are known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to TIM-3. In some embodiments, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In some embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has effector function and can fix complement. In other embodiments the antibody does not recruit effector cells or fix complement. In certain embodiments, the antibody has reduced or no ability to bind an Fc receptor. For example, it may be an isotype or subtype, fragment or other mutant, which does not support binding to an Fc receptor, e.g., it has a mutagenized or deleted Fc receptor binding region.

The antibody constant region is altered in some embodiments. Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In some embodiments, the only amino acids in the anti-TIM-3 antibody molecule are canonical amino acids. In some embodiments, the anti-TIM-3 antibody molecule comprises naturally-occurring amino acids; analogs, derivatives and congeners thereof; amino acid analogs having variant side chains; and/or all stereoisomers of any of any of the foregoing. The anti-TIM-3 antibody molecule may comprise the D- or L-optical isomers of amino acids and peptidomimetics.

A polypeptide of an anti-TIM-3 antibody molecule may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-TIM-3 antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., immunomodulatory, immunostimularoty, cytotoxic, or cytostatic) agent or moiety. Radioactive isotopes can be used in diagnostic or therapeutic applications. Radioactive isotopes that can be coupled to the anti-TIM-3 antibodies include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In some embodiments, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent.

Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some aspects, this disclosure provides a method of providing a target binding molecule that specifically binds to a TIM-3 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98, or 99% identical to) a corresponding portion of a human target protein, but differing by at least one amino acid (e.g., at least one, two, three, four, five, six, seven, eight, or nine amino acids); obtaining an antibody molecule that specifically binds to the antigen; and evaluating efficacy of the binding agent in modulating activity of the target protein. The method can further include administering the binding agent (e.g., antibody molecule) or a derivative (e.g., a humanized antibody molecule) to a human subject.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments crosslinked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837, 821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with cross-linkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005, 079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO00006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

In other embodiments, the anti-TIM-3 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21. In one embodiment, a bispecific antibody molecule has a first binding specificity to a first target (e.g., to TIM-3), a second binding specificity to a second target (e.g., LAG-3 or PD-1), and is optionally linked to an interleukin (e.g., IL-12) domain e.g., full length IL-12 or a portion thereof. In other embodiments, the anti-TIM-3 antibody molecule is fused to another protein e.g., one, two or more cytokines, e.g., as a fusion molecule. In other embodiments, the fusion molecule comprises one or more proteins, e.g., one, two or more cytokines. In one embodiment, the cytokine is an interleukin (IL) chosen from one, two, three or more of IL-1, IL-2, IL-12, IL-15 or IL-21.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

Exemplary Anti-TIM-3 Antibody Molecules

In certain embodiments, the anti-TIM-3 antibody comprises:

(a) a heavy chain variable region (VH) comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14;

(b) a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;

(c) a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14;

(d) a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;

(e) a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14; or (f) a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

In certain embodiments, the antibody molecule comprises a VH comprising a VHCDR1 amino acid sequence chosen from SEQ ID NO: 9; a VHCDR2 amino acid sequence of SEQ ID NO: 10; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14.

In certain embodiments, the antibody molecule comprises a VH comprising a VHCDR1 amino acid sequence chosen from SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

In certain embodiments, the antibody molecule comprises a VH comprising a VHCDR1 amino acid sequence chosen from SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14.

In certain embodiments, the antibody molecule comprises a VH comprising a VHCDR1 amino acid sequence chosen from SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

In certain embodiments, the antibody molecule comprises a VH comprising a VHCDR1 amino acid sequence chosen from SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14.

In certain embodiments, the antibody molecule comprises a VH comprising a VHCDR1 amino acid sequence chosen from SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

In certain embodiments, the anti-TIM-3 antibody molecule comprises:

(i) a heavy chain variable region (VH) comprising a VHCDR1 amino acid sequence chosen from SEQ ID NO: 3 or SEQ ID NO: 9; a VHCDR2 amino acid sequence of SEQ ID NO: 4 or SEQ ID NO: 10; and a VHCDR3 amino acid sequence of SEQ ID NO: 5; and (ii) a light chain variable region (VL) comprising a VLCDR1 amino acid sequence of SEQ ID NO: 6 or SEQ ID NO: 12, a VLCDR2 amino acid sequence of SEQ ID NO: 7 or SEQ ID NO: 13, and a VLCDR3 amino acid sequence of SEQ ID NO: 8 or SEQ ID NO: 14.

In other embodiments, the anti-TIM-3 antibody molecule comprises:

(i) a heavy chain variable region (VH) comprising a VHCDR1 amino acid sequence chosen from SEQ ID NO: 3 or SEQ ID NO: 9; a VHCDR2 amino acid sequence of SEQ ID NO: 24 or SEQ ID NO: 25; and a VHCDR3 amino acid sequence of SEQ ID NO: 5; and (ii) a light chain variable region (VL) comprising a VLCDR1 amino acid sequence of SEQ ID NO: 6 or SEQ ID NO: 12, a VLCDR2 amino acid sequence of SEQ ID NO: 7 or SEQ ID NO: 13, and a VLCDR3 amino acid sequence of SEQ ID NO: 8 or SEQ ID NO: 14.

In other embodiments, the anti-TIM-3 antibody molecule comprises:

(i) a heavy chain variable region (VH) comprising a VHCDR1 amino acid sequence chosen from SEQ ID NO: 3 or SEQ ID NO: 9; a VHCDR2 amino acid sequence of SEQ ID NO: 30 or SEQ ID NO: 31; and a VHCDR3 amino acid sequence of SEQ ID NO: 5; and (ii) a light chain variable region (VL) comprising a VLCDR1 amino acid sequence of SEQ ID NO: 6 or SEQ ID NO: 12, a VLCDR2 amino acid sequence of SEQ ID NO: 7 or SEQ ID NO: 13, and a VLCDR3 amino acid sequence of SEQ ID NO: 8 or SEQ ID NO: 14.

In embodiments of the aforesaid antibody molecules, the VHCDR1 comprises the amino acid sequence of SEQ ID NO: 3. In other embodiments, the VHCDR1 comprises the amino acid sequence of SEQ ID NO: 9.

In embodiments of the aforesaid antibody molecules, the VHCDR2 comprises the amino acid sequence of SEQ ID NO: 4. In other embodiments, the VHCDR2 comprises the amino acid sequence of SEQ ID NO: 10. In other embodiments, the VHCDR2 comprises the amino acid sequence of SEQ ID NO: 24. In other embodiments, the VHCDR2 comprises the amino acid sequence of SEQ ID NO: 25. In other embodiments, the VHCDR2 comprises the amino acid sequence of SEQ ID NO: 30. In other embodiments, the VHCDR2 comprises the amino acid sequence of SEQ ID NO: 31.

In other embodiments, the aforesaid antibody molecules comprise a heavy chain variable domain comprising an amino acid sequence at least 85% identical to any of SEQ ID NOs: 1, 16, 26, 32, 36, 44, 48, 52, 60, 68, 72, 76, 80, 84, 92, or 100.

In other embodiments, the aforesaid antibody molecules comprise a heavy chain variable domain comprising the amino acid sequence of SEQ ID NO: 1, 16, 26, 32, 36, 44, 48, 52, 60, 68, 72, 76, 80, 84, 92, or 100.

In other embodiments, the aforesaid antibody molecules comprise a light chain variable domain comprising an amino acid sequence at least 85% identical to any of SEQ ID NOs: 2, 20, 40, 56, 64, 88, 96, or 104.

In other embodiments, the aforesaid antibody molecules comprise a light chain variable domain comprising the amino acid sequence of SEQ ID NO: 2, 20, 40, 56, 64, 88, 96, or 104.

In other embodiments, the aforesaid antibody molecules comprise a heavy chain variable domain comprising the amino acid sequence of SEQ ID NO: 1.

In other embodiments, the aforesaid antibody molecules comprise a heavy chain variable domain comprising the amino acid sequence of SEQ ID NO: 16.

In other embodiments, the aforesaid antibody molecules comprise a heavy chain comprising the amino acid sequence of SEQ ID NO: 18.

In other embodiments, the aforesaid antibody molecules comprise a heavy chain variable domain comprising the amino acid sequence of SEQ ID NO: 26.

In other embodiments, the aforesaid antibody molecules comprise a heavy chain comprising the amino acid sequence of SEQ ID NO: 28.

In other embodiments, the aforesaid antibody molecules comprise a heavy chain variable domain comprising the amino acid sequence of SEQ ID NO: 32.

In other embodiments, the aforesaid antibody molecules comprise a heavy chain comprising the amino acid sequence of SEQ ID NO: 34.

In other embodiments, the aforesaid antibody molecules comprise a heavy chain variable domain comprising the amino acid sequence of SEQ ID NO: 36.

In other embodiments, the aforesaid antibody molecules comprise a heavy chain comprising the amino acid sequence of SEQ ID NO: 38.

In other embodiments, the aforesaid antibody molecules comprise a heavy chain variable domain comprising the amino acid sequence of SEQ ID NO: 44.

In other embodiments, the aforesaid antibody molecules comprise a heavy chain comprising the amino acid sequence of SEQ ID NO: 46.

In other embodiments, the aforesaid antibody molecules comprise a heavy chain variable domain comprising the amino acid sequence of SEQ ID NO: 48.

In other embodiments, the aforesaid antibody molecules comprise a heavy chain comprising the amino acid sequence of SEQ ID NO: 50.

In other embodiments, the aforesaid antibody molecules comprise a heavy chain variable domain comprising the amino acid sequence of SEQ ID NO: 52.

In other embodiments, the aforesaid antibody molecules comprise a heavy chain comprising the amino acid sequence of SEQ ID NO: 54.

In other embodiments, the aforesaid antibody molecules comprise a heavy chain variable domain comprising the amino acid sequence of SEQ ID NO: 60.

In other embodiments, the aforesaid antibody molecules comprise a heavy chain comprising the amino acid sequence of SEQ ID NO: 62.

In other embodiments, the aforesaid antibody molecules comprise a heavy chain variable domain comprising the amino acid sequence of SEQ ID NO: 68.

In other embodiments, the aforesaid antibody molecules comprise a heavy chain comprising the amino acid sequence of SEQ ID NO: 70.

In other embodiments, the aforesaid antibody molecules comprise a heavy chain variable domain comprising the amino acid sequence of SEQ ID NO: 72.

In other embodiments, the aforesaid antibody molecules comprise a heavy chain comprising the amino acid sequence of SEQ ID NO: 74.

In other embodiments, the aforesaid antibody molecules comprise a heavy chain variable domain comprising the amino acid sequence of SEQ ID NO: 76.

In other embodiments, the aforesaid antibody molecules comprise a heavy chain comprising the amino acid sequence of SEQ ID NO: 78.

In other embodiments, the aforesaid antibody molecules comprise a heavy chain variable domain comprising the amino acid sequence of SEQ ID NO: 80.

In other embodiments, the aforesaid antibody molecules comprise a heavy chain comprising the amino acid sequence of SEQ ID NO: 82.

In other embodiments, the aforesaid antibody molecules comprise a heavy chain variable domain comprising the amino acid sequence of SEQ ID NO: 84.

In other embodiments, the aforesaid antibody molecules comprise a heavy chain comprising the amino acid sequence of SEQ ID NO: 86.

In other embodiments, the aforesaid antibody molecules comprise a heavy chain variable domain comprising the amino acid sequence of SEQ ID NO: 92.

In other embodiments, the aforesaid antibody molecules comprise a heavy chain comprising the amino acid sequence of SEQ ID NO: 94.

In other embodiments, the aforesaid antibody molecules comprise a heavy chain variable domain comprising the amino acid sequence of SEQ ID NO: 100.

In other embodiments, the aforesaid antibody molecules comprise a heavy chain comprising the amino acid sequence of SEQ ID NO: 102.

In other embodiments, the aforesaid antibody molecules comprise a heavy chain comprising the amino acid sequence of SEQ ID NO: 116.

In other embodiments, the aforesaid antibody molecules comprise a heavy chain comprising the amino acid sequence of SEQ ID NO: 121.

In other embodiments, the aforesaid antibody molecules comprise a light chain variable domain comprising the amino acid sequence of SEQ ID NO: 2.

In other embodiments, the aforesaid antibody molecules comprise a light chain variable domain comprising the amino acid sequence of SEQ ID NO: 20.

In other embodiments, the aforesaid antibody molecules comprise a light chain comprising the amino acid sequence of SEQ ID NO: 22.

In other embodiments, the aforesaid antibody molecules comprise a light chain variable domain comprising the amino acid sequence of SEQ ID NO: 40.

In other embodiments, the aforesaid antibody molecules comprise a light chain comprising the amino acid sequence of SEQ ID NO: 42.

In other embodiments, the aforesaid antibody molecules comprise a light chain variable domain comprising the amino acid sequence of SEQ ID NO: 56.

In other embodiments, the aforesaid antibody molecules comprise a light chain comprising the amino acid sequence of SEQ ID NO: 58.

In other embodiments, the aforesaid antibody molecules comprise a light chain variable domain comprising the amino acid sequence of SEQ ID NO: 64.

In other embodiments, the aforesaid antibody molecules comprise a light chain comprising the amino acid sequence of SEQ ID NO: 66.

In other embodiments, the aforesaid antibody molecules comprise a light chain variable domain comprising the amino acid sequence of SEQ ID NO: 88.

In other embodiments, the aforesaid antibody molecules comprise a light chain comprising the amino acid sequence of SEQ ID NO: 90.

In other embodiments, the aforesaid antibody molecules comprise a light chain variable domain comprising the amino acid sequence of SEQ ID NO: 96.

In other embodiments, the aforesaid antibody molecules comprise a light chain comprising the amino acid sequence of SEQ ID NO: 98.

In other embodiments, the aforesaid antibody molecules comprise a light chain variable domain comprising the amino acid sequence of SEQ ID NO: 104.

In other embodiments, the aforesaid antibody molecules comprise a light chain comprising the amino acid sequence of SEQ ID NO: 106.

In other embodiments, the aforesaid antibody molecules comprise a heavy chain variable domain comprising the amino acid sequence of SEQ ID NO: 1 and a light chain variable domain comprising the amino acid sequence of SEQ ID NO: 2.

In other embodiments, the aforesaid antibody molecules comprise a heavy chain variable domain comprising the amino acid sequence of SEQ ID NO: 16 and a light chain variable domain comprising the amino acid sequence of SEQ ID NO: 20.

In other embodiments, the aforesaid antibody molecules comprise a heavy chain variable domain comprising the amino acid sequence of SEQ ID NO: 26 and a light chain variable domain comprising the amino acid sequence of SEQ ID NO: 20.

In other embodiments, the aforesaid antibody molecules comprise a heavy chain variable domain comprising the amino acid sequence of SEQ ID NO: 32 and a light chain variable domain comprising the amino acid sequence of SEQ ID NO: 20.

In other embodiments, the aforesaid antibody molecules comprise a heavy chain variable domain comprising the amino acid sequence of SEQ ID NO: 36 and a light chain variable domain comprising the amino acid sequence of SEQ ID NO: 40.

In other embodiments, the aforesaid antibody molecules comprise a heavy chain variable domain comprising the amino acid sequence of SEQ ID NO: 44 and a light chain variable domain comprising the amino acid sequence of SEQ ID NO: 40.

In other embodiments, the aforesaid antibody molecules comprise a heavy chain variable domain comprising the amino acid sequence of SEQ ID NO: 48 and a light chain variable domain comprising the amino acid sequence of SEQ ID NO: 40.

In other embodiments, the aforesaid antibody molecules comprise a heavy chain variable domain comprising the amino acid sequence of SEQ ID NO: 36 and a light chain variable domain comprising the amino acid sequence of SEQ ID NO: 20.

In other embodiments, the aforesaid antibody molecules comprise a heavy chain variable domain comprising the amino acid sequence of SEQ ID NO: 16 and a light chain variable domain comprising the amino acid sequence of SEQ ID NO: 40.

In other embodiments, the aforesaid antibody molecules comprise a heavy chain variable domain comprising the amino acid sequence of SEQ ID NO: 52 and a light chain variable domain comprising the amino acid sequence of SEQ ID NO: 56.

In other embodiments, the aforesaid antibody molecules comprise a heavy chain variable domain comprising the amino acid sequence of SEQ ID NO: 60 and a light chain variable domain comprising the amino acid sequence of SEQ ID NO: 56.

In other embodiments, the aforesaid antibody molecules comprise a heavy chain variable domain comprising the amino acid sequence of SEQ ID NO: 52 and a light chain variable domain comprising the amino acid sequence of SEQ ID NO: 64.

In other embodiments, the aforesaid antibody molecules comprise a heavy chain variable domain comprising the amino acid sequence of SEQ ID NO: 60 and a light chain variable domain comprising the amino acid sequence of SEQ ID NO: 64.

In other embodiments, the aforesaid antibody molecules comprise a heavy chain variable domain comprising the amino acid sequence of SEQ ID NO: 68 and a light chain variable domain comprising the amino acid sequence of SEQ ID NO: 64.

In other embodiments, the aforesaid antibody molecules comprise a heavy chain variable domain comprising the amino acid sequence of SEQ ID NO: 72 and a light chain variable domain comprising the amino acid sequence of SEQ ID NO: 64.

In other embodiments, the aforesaid antibody molecules comprise a heavy chain variable domain comprising the amino acid sequence of SEQ ID NO: 76 and a light chain variable domain comprising the amino acid sequence of SEQ ID NO: 56.

In other embodiments, the aforesaid antibody molecules comprise a heavy chain variable domain comprising the amino acid sequence of SEQ ID NO: 80 and a light chain variable domain comprising the amino acid sequence of SEQ ID NO: 56.

In other embodiments, the aforesaid antibody molecules comprise a heavy chain variable domain comprising the amino acid sequence of SEQ ID NO: 68 and a light chain variable domain comprising the amino acid sequence of SEQ ID NO: 56.

In other embodiments, the aforesaid antibody molecules comprise a heavy chain variable domain comprising the amino acid sequence of SEQ ID NO: 72 and a light chain variable domain comprising the amino acid sequence of SEQ ID NO: 56.

In other embodiments, the aforesaid antibody molecules comprise a heavy chain variable domain comprising the amino acid sequence of SEQ ID NO: 76 and a light chain variable domain comprising the amino acid sequence of SEQ ID NO: 64.

In other embodiments, the aforesaid antibody molecules comprise a heavy chain variable domain comprising the amino acid sequence of SEQ ID NO: 80 and a light chain variable domain comprising the amino acid sequence of SEQ ID NO: 64.

In other embodiments, the aforesaid antibody molecules comprise a heavy chain variable domain comprising the amino acid sequence of SEQ ID NO: 84 and a light chain variable domain comprising the amino acid sequence of SEQ ID NO: 88.

In other embodiments, the aforesaid antibody molecules comprise a heavy chain variable domain comprising the amino acid sequence of SEQ ID NO: 92 and a light chain variable domain comprising the amino acid sequence of SEQ ID NO: 96.

In other embodiments, the aforesaid antibody molecules comprise a heavy chain variable domain comprising the amino acid sequence of SEQ ID NO: 100 and a light chain variable domain comprising the amino acid sequence of SEQ ID NO: 104.

In other embodiments, the aforesaid antibody molecules comprise a heavy chain comprising the amino acid sequence of SEQ ID NO: 18 and a light chain comprising the amino acid sequence of SEQ ID NO: 22.

In other embodiments, the aforesaid antibody molecules comprise a heavy chain comprising the amino acid sequence of SEQ ID NO: 28 and a light chain comprising the amino acid sequence of SEQ ID NO: 22.

In other embodiments, the aforesaid antibody molecules comprise a heavy chain comprising the amino acid sequence of SEQ ID NO: 34 and a light chain comprising the amino acid sequence of SEQ ID NO: 22.

In other embodiments, the aforesaid antibody molecules comprise a heavy chain comprising the amino acid sequence of SEQ ID NO: 38 and a light chain comprising the amino acid sequence of SEQ ID NO: 42.

In other embodiments, the aforesaid antibody molecules comprise a heavy chain comprising the amino acid sequence of SEQ ID NO: 46 and a light chain comprising the amino acid sequence of SEQ ID NO: 42.

In other embodiments, the aforesaid antibody molecules comprise a heavy chain comprising the amino acid sequence of SEQ ID NO: 50 and a light chain comprising the amino acid sequence of SEQ ID NO: 42.

In other embodiments, the aforesaid antibody molecules comprise a heavy chain comprising the amino acid sequence of SEQ ID NO: 116 and a light chain comprising the amino acid sequence of SEQ ID NO: 22.

In other embodiments, the aforesaid antibody molecules comprise a heavy chain comprising the amino acid sequence of SEQ ID NO: 121 and a light chain comprising the amino acid sequence of SEQ ID NO: 42.

In other embodiments, the aforesaid antibody molecules comprise a heavy chain comprising the amino acid sequence of SEQ ID NO: 54 and a light chain comprising the amino acid sequence of SEQ ID NO: 58.

In other embodiments, the aforesaid antibody molecules comprise a heavy chain comprising the amino acid sequence of SEQ ID NO: 62 and a light chain comprising the amino acid sequence of SEQ ID NO: 58.

In other embodiments, the aforesaid antibody molecules comprise a heavy chain comprising the amino acid sequence of SEQ ID NO: 54 and a light chain comprising the amino acid sequence of SEQ ID NO: 66.

In other embodiments, the aforesaid antibody molecules comprise a heavy chain comprising the amino acid sequence of SEQ ID NO: 62 and a light chain comprising the amino acid sequence of SEQ ID NO: 66.

In other embodiments, the aforesaid antibody molecules comprise a heavy chain comprising the amino acid sequence of SEQ ID NO: 70 and a light chain comprising the amino acid sequence of SEQ ID NO: 66.

In other embodiments, the aforesaid antibody molecules comprise a heavy chain comprising the amino acid sequence of SEQ ID NO: 74 and a light chain comprising the amino acid sequence of SEQ ID NO: 66.

In other embodiments, the aforesaid antibody molecules comprise a heavy chain comprising the amino acid sequence of SEQ ID NO: 78 and a light chain comprising the amino acid sequence of SEQ ID NO: 58.

In other embodiments, the aforesaid antibody molecules comprise a heavy chain comprising the amino acid sequence of SEQ ID NO: 82 and a light chain comprising the amino acid sequence of SEQ ID NO: 58.

In other embodiments, the aforesaid antibody molecules comprise a heavy chain comprising the amino acid sequence of SEQ ID NO: 70 and a light chain comprising the amino acid sequence of SEQ ID NO: 58.

In other embodiments, the aforesaid antibody molecules comprise a heavy chain comprising the amino acid sequence of SEQ ID NO: 74 and a light chain comprising the amino acid sequence of SEQ ID NO: 58.

In other embodiments, the aforesaid antibody molecules comprise a heavy chain comprising the amino acid sequence of SEQ ID NO: 78 and a light chain comprising the amino acid sequence of SEQ ID NO: 66.

In other embodiments, the aforesaid antibody molecules comprise a heavy chain comprising the amino acid sequence of SEQ ID NO: 82 and a light chain comprising the amino acid sequence of SEQ ID NO: 66.

In other embodiments, the aforesaid antibody molecules comprise a heavy chain comprising the amino acid sequence of SEQ ID NO: 86 and a light chain comprising the amino acid sequence of SEQ ID NO: 90.

In other embodiments, the aforesaid antibody molecules comprise a heavy chain comprising the amino acid sequence of SEQ ID NO: 94 and a light chain comprising the amino acid sequence of SEQ ID NO: 98.

In other embodiments, the aforesaid antibody molecules comprise a heavy chain comprising the amino acid sequence of SEQ ID NO: 102 and a light chain comprising the amino acid sequence of SEQ ID NO: 106.

In other embodiments, the aforesaid antibody molecules are chosen from a Fab, F(ab')$_2$, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In some embodiments, the anti-TIM-3 antibody molecule comprises the CDR2 of the VH region of SEQ ID NO: 1, using the Kabat or Chothia definitions of CDRs. In some embodiments, the anti-TIM-3 antibody molecule comprises the CDR2 and one or both of CDR1 and CDR3 of the VH region of SEQ ID NO: 1, using the Kabat or Chothia definitions of CDRs. In some embodiments, the anti-TIM-3 antibody molecule comprises CDR2 of the VH region of SEQ ID NO: 1 in combination with another 1, 2, 3, 4, or 5 (e.g., collectively all) CDRs found in SEQ ID NO: 1 or SEQ ID NO: 2, using the Kabat of Chothia definitions of CDRs. In some embodiments, the anti-TIM-3 antibody molecule comprises the VHCDR2 of SEQ ID NO: 4. For instance, the anti-TIM-3 antibody molecule may comprise the VHCDR2 of SEQ ID NO: 4 in combination with one or both of the VHCDR1 of SEQ ID NO: 3 and the VHCDR3 of SEQ ID NO: 5. As a further example, the anti-TIM-3 antibody molecule may comprise the VHCDR2 of SEQ ID NO: 4 in combination with another 1, 2, 3, 4, or 5 (e.g., collectively all) CDRs selected from SEQ ID NOS: 3, 5, 6, 7, and 8.

In some embodiments, the anti-TIM-3 antibody molecule comprises the CDR3 of the VL region of SEQ ID NO: 2, using the Kabat or Chothia definitions of CDRs. In some embodiments, the anti-TIM-3 antibody molecule comprises the CDR3 and one or both of CDR1 and CDR2 of the VL region of SEQ ID NO: 2, using the Kabat or Chothia definitions of CDRs. In some embodiments, the anti-TIM-3 antibody molecule comprises CDR3 of the VL region of SEQ ID NO: 2 in combination with another 1, 2, 3, 4, or 5 (e.g., collectively all) CDRs found in SEQ ID NO: 1 or SEQ ID NO: 2, using the Kabat of Chothia definitions of CDRs. In some embodiments, the anti-TIM-3 antibody molecule comprises the VLCDR3 of SEQ ID NO: 8. For instance, the anti-TIM-3 antibody molecule may comprise the VLCDR3 of SEQ ID NO: 8 in combination with one or both of the VHCDR1 of SEQ ID NO: 6 and the VHCDR2 of SEQ ID NO: 7. As a further example, the anti-TIM-3 antibody molecule may comprise the VLCDR3 of SEQ ID NO: 8 in combination with another 1, 2, 3, 4, or 5 (e.g., collectively all) CDRs selected from SEQ ID NOs: 3-7.

In some embodiments, the anti-TIM-3 antibody molecule comprises the CDR2 of the VH region of SEQ ID NO: 1 and the CDR3 of the VL region of SEQ ID NO: 2, optionally in combination with an additional 1, 2, 3, or 4 (e.g., collectively all) CDRs found in SEQ ID NO: 1 and SEQ ID NO: 2, using the Kabat or Chothia definitions of CDRs. In certain embodiments, the anti-TIM-3 antibody molecule comprises the VHCDR2 of SEQ ID NO: 4 and the VLCDR3 of SEQ ID NO: 8, optionally in combination with an additional 1, 2, 3, or 4 (e.g., collectively all) CDRs selected from SEQ ID NOS: 3, 5, 6, or 7.

In some embodiments, the anti-TIM-3 antibody molecule comprises a heavy chain constant region, a light chain constant region, and heavy and light chain variable regions of Tables 1-4 (e.g., SEQ ID NO: 1 and SEQ ID NO: 2). In certain embodiments, the anti-TIM-3 antibody molecule comprises a heavy chain constant region, a light chain constant region, and 1, 2, 3, 4, 5, or 6 (e.g., all) CDRs of Tables 1-4.

In some embodiments, the anti-TIM-3 antibody molecule comprises the sequence of all or a portion of the heavy chain of SEQ ID NO: 1. For instance, in some embodiments, the anti-TIM-3 antibody molecule comprises amino acids 1-98, 1-107, or 1-118 of SEQ ID NO: 1. In some embodiments, the anti-TIM-3 antibody molecule comprises amino acids 1-98 of SEQ ID NO: 1, a hCDR3 region (e.g., SEQ ID NO: 5 or a sequence substantially identical thereto), and a VHFW4 region (e.g., a human VHFW4 region, a homologous region of human D or J sequences, amino acids 108-118 of SEQ ID NO: 1, or a sequence substantially identical thereto). In some embodiments, the VHFW4 region has no more than 1 or 2 positions of non-identity relative to amino acids 108-118 of SEQ ID NO: 1. In some embodiments, the VHFW4 region has no more than 3, 4, 5, 6, 7, 8, 9, or 10 positions of non-identity relative to amino acids 108-118 of SEQ ID NO: 1. In some embodiments the hCDR3 region has no more than 1 or 2 positions of non-identity relative to SEQ ID NO: 5.

In other embodiments, the aforesaid antibody molecules are capable of binding to human TIM-3 with a dissociation constant ($K_D$) of less than 0.5 nM.

In some embodiments, the anti-TIM-3 antibody molecule is capable of independently binding to human TIM-3 and cynomolgus monkey TIM-3 with high affinity. In some embodiments, high affinity refers to a $K_D$ of less than 5, 2, 1, 0.5, 0.4, 0.3, 0.2, or 0.1 nM, e.g., about 0.3 to 0.01 nM, e.g., about 0.2 to 0.05 nM, e.g., as measured by a Biacore method.

In other embodiments, the aforesaid antibody molecules bind to cynomolgus TIM-3 with a $K_D$ of less than 10, 5, 4, 3, 2, or 1 nM, e.g., as measured by a Biacore method, FACS analysis, or ELISA.

In other embodiments, the aforesaid antibody molecules bind to human TIM-3 with a KD of less than 5, 2, 1, 0.5, 0.4, 0.3, 0.2, or 0.1 nM, e.g., as measured by a Biacore method, FACS analysis, or ELISA.

In embodiments, the aforesaid antibody molecules do not bind to mouse TIM-3.

In some embodiments, the antibody molecule binds to a mammalian, e.g., human, TIM-3. For example, the antibody molecule binds specifically to an epitope, e.g., linear or conformational epitope, (e.g., an epitope as described herein) on TIM-3. In some embodiments, the epitope is at least a portion of the IgV domain of human or cynomolgus TIM-3. In certain aspects, it is advantageous to identify an antibody that binds with high affinity to the human and cynomolgus homologs of a protein of interest. This desirable cross-reactivity allows the same antibody (or two antibodies with the same CDRs or variable regions) to be tested in an animal model and then administered to human patients as a therapeutic.

In certain embodiments, the aforesaid antibody molecules are not cross-reactive with mouse TIM-3. In certain embodiments, the aforesaid antibody molecules are less cross-reactive with rat TIM-3. For example, the cross-reactivity can be measured by a Biacore method or a binding assay using cells that expresses TIM-3 (e.g., human TIM-3-expressing 300.19 cells). In other embodiments, the aforesaid antibody molecules bind an extracellular Ig-like domain (e.g., IgV domain) of TIM-3.

In some embodiments, the aforesaid anti-TIM-3 antibody molecules bind to one or more residues within: the two residues adjacent to the N-terminus of the A strand, the BC loop, the CC' loop, the F strand, the FG loop, and the G strand of TIM-3, or one or more (e.g., two, five, ten, fifteen, twenty, twenty-five, thirty, thirty-five, or all) residues within two or more of the two residues adjacent to the N-terminus of the A strand, the BC loop, the CC' loop, the F strand, the FG loop, or the G strand of TIM-3. The F strand of TIM-3 comprises residues G106 to I112; the G strand of TIM-3 comprises residues E121 to K130; the FG loop of TIM-3 comprises the residues between the F strand and the G strand, e.g., comprising residues Q113 to D120; the BC loop of TIM-3 comprises the residues between the B strand and the C strand, e.g., comprising residues P37 to P50; the two residues adjacent to the N-terminus of the A strand comprises residues V24 and E25; the CC' loop comprises the residues between the C strand and the C' strand, e.g., comprising residues G56 to N65. In other embodiments, the aforesaid anti-TIM-3 antibody molecules bind to one or more residues within: the A strand, the EF loop, the C strand, the C'C" loop, or the C" strand. The A strand comprises residues Y26 to E29; the EF loop comprises the residues between the E strand and the F strand, e.g., comprising residues E98 to S105; the C strand comprises residues V51 to K55; the C'C" loop comprises the residues between the C' strand and the C" strand, e.g., comprising residues D71 to D74; and the C" strand comprises residues V75 to W78. The numbering for the residues of TIM-3 is described, e.g., in FIG. 18. In an embodiment, the anti-TIM-3 antibody molecules bind to one or more (e.g., two, five, ten, fifteen, twenty, twenty-five, thirty, thirty-five, or all) residues in the F strand, the G strand, and the CC' loop of TIM-3.

In some embodiments, the aforesaid anti-TIM-3 antibody molecules reduce or inhibit plasma membrane penetration or PtdSer-dependent membrane penetration of TIM-3. In some embodiments, the aforesaid anti-TIM-3 antibody molecules reduce or inhibit binding to TIM-3 ligand PtdSer. In some embodiments, the aforesaid anti-TIM-3 antibody molecules reduce or inhibit binding to TIM-3 ligand HMGB1. In some embodiments, the aforesaid anti-TIM-3 antibody molecules reduce or inhibit binding to TIM-3 ligand CEACAM-1. In some embodiments, the aforesaid anti-TIM-3 antibody molecules reduce or inhibit binding to TIM-3 ligand Semaphorin-4A. In some embodiments, the aforesaid anti-TIM-3 antibody molecules do not reduce or inhibit binding to TIM-3 ligand Galectin-9.

In some embodiments, the anti-TIM-3 antibody molecule interacts with, e.g., binds to, a TIM-3 surface (e.g., one, two, three, five, eight, ten, fifteen, or more continuous or discontinuous (e.g., noncontiguous) amino acid residues chosen from Val24, Glu25, Thr41, Gly56, Ala57, Cys58, Pro59, Val60, Phe61, Glu121, Lys122, Phe123, Asn124, Leu125, Lys126, and/or Leu127.

In some embodiments, the anti-TIM-3 antibody molecule interacts with, e.g., binds to, a TIM-3 surface (e.g., one, two, three, five, eight, ten, fifteen, twenty, twenty-one, twenty-five, or more continuous and discontinuous (e.g., noncontiguous) amino acid residues chosen from Val24, Glu25, Tyr26, Phe39, Tyr40, Thr41, Gly56, Ala57, Cys58, Pro59, Val60, Phe61, Ser105, Gly106, Ile107, Asn119, Asp120, Glu121, Lys122, Phe123, Asn124, Leu125, Lys126, Leu127, and/or Val128, e.g., as detailed in Table 13.

In some embodiments, the anti-TIM-3 antibody molecule interacts with, e.g., binds to, a TIM-3 surface (e.g., one, two, three, five, eight, ten, fifteen, twenty, twenty-one, twenty-five, or more continuous or discontinuous (e.g., noncontiguous) amino acid residues chosen from Glu23, Val24, Glu25, Tyr26, Thr41, Pro42, Ala43, Ala44, Pro45, Gly46, Asn47, Leu48, Val49, Pro50, Val51, Cys52, Trp53, Gly54, Lys55, Gly56, Ala57, Cys58, Pro59, Val60, Phe61, Glu121, Lys122, Phe123, Asn124, Leu125, Lys126, and/or Leu127.

In some embodiments, the anti-TIM-3 antibody molecule interacts with, e.g., binds to, a TIM-3 surface (e.g., one, two, three, five, eight, ten, fifteen, twenty, twenty-one, twenty-five, or more continuous or discontinuous (e.g., noncontiguous) amino acid residues chosen from Val24, Glu25, Tyr26, Phe39, Tyr40, Thr41, Pro42, Ala43, Ala44, Pro45, Gly46, Asn47, Leu48, Val49, Pro50, Val51, Cys52, Trp53, Gly54, Lys55, Gly56, Ala57, Cys58, Pro59, Val60, Phe61, Ser105, Gly106, Ile107, Asn119, Asp120, Glu121, Lys122, Phe123, Asn124, Leu125, Lys126, Leu127, and/or Val128.

In other embodiments, the anti-TIM-3 antibody molecule competes with CEACAM-1 for binding to TIM-3. In one embodiment, the anti-TIM-3 antibody molecule interacts, e.g., binds to, one, two, or more (all) of C58, N119 and K122 of TIM-3, e.g., displaces or competes CEACAM-1 for binding to these residues. In one embodiment, the anti-TIM-3 antibody molecule reduces or blocks the formation of a hydrogen bond between K122 of TIM-3 and N42 of CEACAM-1. With respect to CEACAM-1, it has been shown that CEACAM-1 is a ligand for TIM-3 and is required for its ability to mediate T-cell inhibition, which may have important role in regulating autoimmunity and anti-tumour immunity (Huang, et al. (2014) *Nature* doi: 10.1038/nature13848). Inhibition of an interaction between TIM-3 and CEACAM-1 can be used with the other immunomodulators described herein (e.g., anti-PD-1 inhibitor) to enhance an immune response against a cancer.

In another embodiment, the anti-TIM-3 antibody molecule interacts with, e.g., binds to, a PtdSer-binding loop of TIM-3, e.g., the human TIM-3 IgV domain. In one embodiment, the anti-TIM-3 antibody molecule interacts with, e.g., binds to, at least two PtdSer-binding loops of TIM-3, e.g., the FG loop and CC' loop of TIM-3 (e.g., a metal ion-dependent ligand binding site (MILIBS)). For example, the carboxyl group of PtdSer can bind to the CC' loop of TIM-3 and the amino group of PtdSer can bind to the FG loop of TIM-3. In one embodiment, the anti-TIM-3 antibody molecule reduces or prevents PtdSer-mediated membrane penetration of TIM-3 Thus, the anti-TIM-3 antibody molecule may reduce engagement of TIM-3-expressing cells and/or penetration into the membrane of apoptotic cells (which can display PtdSer) for engulfment.

In another embodiment, the anti-TIM-3 antibody molecule competes with HMGB1 for bind to TIM-3. E.g., it reduces binding of HMGB1 to residue 62 of TIM-3 (Q in mouse, E in human TIM-3). With respect to HMGB1, it has been reported to interact with TIM-3 to help tumor-associated dendritic cells suppress nucleic acid-mediated innate immune response (Chiba et al., (2012) *Nat. Immunol.* 13(9): 832-842). Thus, the anti-TIM-3 antibody molecule may enhance nucleic acid-mediated innate immune response.

In yet another embodiment, the anti-TIM-3 antibody molecule does not compete with or reduce a Galectin-9 (Gal-9) ligand to binding to TIM-3.

In embodiments, the anti-TIM-3 antibody molecule is a monospecific antibody molecule or a bispecific antibody molecule. In embodiments, the antibody molecule has a first binding specificity for TIM-3 and a second binding specifity for PD-1, LAG-3, CEACAM (e.g., CEACAM-1 and/or CEACAM-5), PD-L1 or PD-L2. In embodiments, the antibody molecule comprises an antigen binding fragment of an antibody, e.g., a half antibody or antigen binding framgment of a half antibody.

In other embodiments, the aforesaid antibody molecules are capable of enhancing an antigen-specific T cell response.

Provided herein is an isolated nucleic acid molecule encoding the above antibody molecule, vectors and host cells thereof. The nucleic acid molecule includes but is not limited to RNA, genomic DNA and cDNA.

In embodiments, the isolated nucleic acid encodes the antibody heavy chain variable region or light chain variable region, or both, of any the aforesaid antibody molecules.

In other embodiments, the isolated nucleic acid comprises a nucleotide sequence encoding a heavy chain variable domain, wherein the nucleotide sequence is at least 85% identical to any of SEQ ID NOs: 11, 17, 29, 33, 37, 45, 49, 53, 61, 69, 73, 77, 81, 85, 93, 101, 115, or 120.

In other embodiments, the isolated nucleic acid comprises a nucleotide sequence encoding a heavy chain variable domain, wherein the nucleotide sequence comprises any of SEQ ID NOs: 11, 17, 27, 33, 37, 45, 49, 53, 61, 69, 73, 77, 81, 85, 93, 101, 115, or 120.

In other embodiments, the isolated nucleic acid comprises a nucleotide sequence encoding a heavy chain, wherein the nucleotide sequence is at least 85% identical to any of SEQ ID NOs: 19, 29, 35, 39, 47, 51, 55, 63, 71, 75, 79, 83, 87, 95, 103, 117, or 122.

In other embodiments, the isolated nucleic acid comprises a nucleotide sequence encoding a heavy chain, wherein the nucleotide sequence comprises any of SEQ ID NOs: 19, 29, 35, 39, 47, 51, 55, 63, 71, 75, 79, 83, 87, 95, 103, 117 or 122.

In other embodiments, the isolated nucleic acid comprises a nucleotide sequence encoding a light chain variable domain, wherein the nucleotide sequence is at least 85% identical to any of SEQ ID NOs: 15, 21, 41, 57, 65, 89, 97, 105, 118, 123, 125, or 127.

In other embodiments, the isolated nucleic acid comprises a nucleotide sequence encoding a light chain variable domain, wherein the nucleotide sequence comprises any of SEQ ID NOs: 15, 21, 41, 57, 65, 89, 97, 105, 118, 123, 125, or 127.

In other embodiments, the isolated nucleic acid comprises a nucleotide sequence encoding a light chain, wherein the nucleotide sequence is at least 85% identical to any of SEQ ID NOs: 23, 43, 59, 67, 91, 99, 107, 119, 124, 126, or 128.

In other embodiments, the isolated nucleic acid comprises a nucleotide sequence encoding a light chain, wherein the nucleotide sequence comprises any of SEQ ID NOs: 23, 43, 59, 67, 91, 99, 107, 119, 124, 126, or 128.

Pharmaceutical Compositions and Kits

In some aspects, this disclosure provides compositions, e.g., pharmaceutically acceptable compositions, which include an anti-TIM-3 antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In some embodiments, the antibody molecule is administered by intravenous infusion or injection. In certain embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods. Several are known in the art, and for many therapeutic applications, an appropriate route/mode of administration is intravenous injection or infusion. In an embodiment, the antibody molecules can be administered by intravenous infusion at a rate of more than 20 mg/min, e.g., 20-40 mg/min, and preferably greater than or equal to 40 mg/min to reach a dose of about 35 to 440 mg/m$^2$, preferably about 70 to 310 mg/m$^2$, and more preferably, about 110 to 130 mg/m$^2$. In an embodiment, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic compositions can also be administered with medical devices, and several are known in the art.

Dosage regimens are adjusted to provide the desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody molecule is 0.1-30 mg/kg, more preferably 1-25 mg/kg. Dosages and therapeutic regimens of the anti-TIM-3 antibody molecule can be determined by a skilled artisan. In certain embodiments, the anti-TIM-3 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-TIM-3 antibody molecule is administered at a dose from about 10 to 20 mg/kg every other week. The antibody molecule can be administered by intravenous infusion at a rate of more than 20 mg/min, e.g., 20-40 mg/min, and preferably greater than or equal to 40 mg/min to reach a dose of about 35 to 440 mg/m$^2$, preferably about 70 to 310 mg/m$^2$, and more preferably, about 110 to 130 mg/m$^2$. In embodiments, the infusion rate of about 110 to 130 mg/m$^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions herein may include a "therapeutically effective amount" or a "prophylactically effective amount" of an antibody molecule. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the antibody molecule is outweighed by the therapeutically beneficial effects. A "therapeutically effective dosage" preferably inhibits a measurable parameter by at least about 20%, more preferably by at least about 40%, even more preferably by at least about 60%, and still more preferably by at least about 80% relative to untreated subjects. The measurable parameter may be, e.g., tumor growth rate or pathogen growth rate. The ability of a compound to inhibit a measurable parameter can be evaluated in an animal model system predictive of efficacy in the corresponding human disease. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within this disclosure is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject.

Uses of Anti-TIM-3 Antibody Molecules

TIM-3 is a coinhibitory protein expressed, e.g., on activated T helper 1 (Th1) CD4+ and cytotoxic CD8+ T cells that secrete IFN-γ. TIM-3 is largely co-expressed on PD-1+ exhausted T cells as shown in preclinical models of cancer and viral exhaustion. Co-blockade of these pathways can restore effector T cell function (e.g., IFN-γ secretion, proliferation) in several models as well as human PBMCs derived from metastatic melanoma patients and patients with HIV or HCV. TIM-3 is also enriched on Fox-P3+ natural regulatory T cells (and FoxP3-negative induced regulatory cells), and the nTreg expression correlates with disease severity in NSCLC, hepatocellular and ovarian carcinoma. In mouse models, TIM-3+ nTregs have been shown to be more immunosuppressive (secrete higher levels of IL-10 and TGF-β).

In addition, TIM-3 can play an important role on innate immune cells, including NK cells, monocytes/macrophages and dendritic cells (DCs). TIM-3 is constitutively expressed on macrophages and DCs, and blockade can enhance TNF-α secretion from human monocytes and increase NF-κB expression in a mouse dendritic cell line. TIM-3 can also contribute to expansion of myeloid-derived suppressor cells (MDSCs). Constitutive expression of TIM-3 on macrophages is associated with less IL-12 secretion, and downregulation of TIM-3 post-TLR activation can lead to enhanced IL-12 and subsequent effector T cell responses.

The antibody molecules disclosed herein have in vitro and in vivo diagnostic, as well as therapeutic and prophylactic utilities. In some embodiments, the antibody molecules modulate (e.g., enhance or inhibit) an immune response in a subject by binding TIM-3. For example, these molecules can be administered to cells in culture, in vitro or ex vivo, or to a subject, e.g., a human subject, e.g., in vivo, to modulate (e.g., enhance or inhibit) immunity.

Accordingly, in some aspects, the disclosure provides a method of modifying an immune response in a subject comprising administering to the subject an antibody molecule described herein, such that the immune response in the subject is modified. In some embodiments, the immune response is enhanced, stimulated or up-regulated. In certain embodiments, the immune response is inhibited or down-regulated. For example, these antibody molecules can be administered to cells in culture, e.g. in vitro or ex vivo, or in a subject, e.g., in vivo, to treat, prevent, and/or diagnose a variety of disorders, such as cancers, immune disorders, and infectious diseases.

As used herein, the term "subject" is intended to include human and non-human animals. In some embodiments, the subject is a human subject, e.g., a human patient having a disorder or condition characterized by abnormal TIM-3 functioning. Generally, the subject has at least some TIM-3 protein, including the TIM-3 epitope that is bound by the antibody molecule, e.g., a high enough level of the protein and epitope to support antibody binding to TIM-3. The term "non-human animals" includes mammals and non-mammals, such as non-human primates. In some embodiments, the subject is a human. In some embodiments, the subject is a human patient in need of enhancement of an immune response. The methods and compositions described herein are suitable for treating human patients having a disorder that can be treated by modulating (e.g., augmenting or inhibiting) an immune response.

Methods of Treating Immune Disorders

TIM-3 is a transmembrane receptor expressed on T cells, e.g., CD4+ T cells, CD8+ T cells, regulatory T cells, and differentiated Th1 cells. TIM-3-dependent trafficking of Th1 cells to target tissue can be inhibited with soluble TIM-3 (see U.S. Pat. No. 7,470,428). Accordingly, modulating TIM-3 function may reduce T-cell trafficking into a target tissue, e.g., in subjects with autoimmune disease. TIM-3 may play an important role in the induction of autoimmune diseases by regulating macrophage activation and/or function. Accordingly, in certain embodiments, the anti-TIM-3 antibody molecules described herein are suitable for use in downregulating an unwanted immune response, e.g., treating autoimmune diseases.

Furthermore, as described in the Examples herein, anti-TIM-3 antibodies can stimulate NK cell-mediated killing of target cells, and can enhance IFN-gamma secretion and proliferation of CD4+ T cells. Accordingly, in certain embodiments, the anti-TIM-3 antibody molecules described herein are suitable for use in stimulating a desired immune response, e.g., an immune response against a cancer cell or pathogen.

The anti-TIM-3 antibodies described herein may be used for treating immune disorders, especially T lymphocyte-related disorders, including, but not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis (e.g., IgA nephropathy), certain pathogen susceptibilities such as helminthic (e.g., leishmaniasis).

In certain embodiments, the anti-TIM-3 antibody is used to modulate T cell function, e.g., CD4+ T cells, CD8+ T cells, Tregs, Th17, and Th1 function. In some embodiments, the anti-TIM-3 antibody molecule causes TIM-3 blockade, and is used to treat an immune disorder which is not a Th1-dependent disease (see Schroll et al., Am J Pathol 2010 April; 176(4):1716-1742). In certain embodiments, the anti-TIM-3 antibody molecule does not cause TIM-3 blockade.

In some aspects, the present disclosure provides methods of administering an anti-TIM-3 antibody molecule, resulting in promoting or reducing T-cell trafficking to a target tissue, promoting or inhibiting antigen-presenting cell (APC) activation.

In some embodiments the subject is in need of treatment for an autoimmune disease. Autoimmune disease include those in which a subject's own antibodies react with host tissue or in which immune effector T cells are autoreactive to endogenous self-peptides and cause destruction of tissue. Thus an immune response is mounted against a subject's own antigens, referred to as self-antigens. Autoimmune diseases include but are not limited to rheumatoid arthritis, Crohn's disease e.g., pediatric Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, autoimmune diabetes mellitus (type 1 diabetes mellitus; insulin-dependent diabetes mellitus), atherosclerosis, and Alzheimer's disease.

In some aspects, an anti-TIM-3 antibody molecule described herein is administered to treat an unwanted immune response to an allergen. Examples of natural animal and plant allergens include proteins specific to the following genuses: Canine (*Canis familiaris*); Dermatophagoides (e.g., *Dermatophagoides farinae*); Felis (*Felis domesticus*); Ambrosia (*Ambrosia artemiisfolia;* Lolium (e.g., *Lolium perenne* or *Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g., *Plantago lanceolata*); Parietaria (e.g., *Parietaria officinalis* or *Parietaria judaica*); Blattella (e.g., *Blattella germanica*); Apis (e.g., *Apis multiflorum*); Cupressus (e.g., *Cupressus sempervirens, Cupressus arizonica* and *Cupressus macrocarpa*); Juniperus (e.g., *Juniperus sabinoides, Juniperus virginiana, Juniperus communis* and *Juniperus ashei*); Thuya (e.g., *Thuya orientalis*); Chamaecyparis (e.g., *Chamaecyparis obtusa*); Periplaneta (e.g., *Periplaneta americana*); Agropyron (e.g., *Agropyron repens*); Secale (e.g., *Secale cereale*); Triticum (e.g., *Triticum aestivum*); Dactylis (e.g., *Dactylis glomerata*); Festuca (e.g., *Festuca elatior*); Poa (e.g., *Poa pratensis* or *Poa compressa*); Avena (e.g., *Avena sativa*); Holcus (e.g., *Holcus lanatus*); Anthoxanthum (e.g., *Anthoxanthum odoratum*); Arrhenatherum (e.g., *Arrhenatherum elatius*); Agrostis (e.g., *Agrostis alba*); Phleum (e.g., *Phleum pratense*); Phalaris (e.g., *Phalaris arundinacea*); Paspalum (e.g., *Paspalum notatum*); Sorghum (e.g., *Sorghum halepensis*); and Bromus (e.g., *Bromus inermis*).

In some embodiments, the anti-TIM-3 antibody molecule is administered to treat multiple sclerosis, Crohn's disease, sepsis, SIRS (Systemic Inflammatory Response Syndrome), or glomerulonephritis.

Methods of Treating Cancer

In some aspects, the present disclosure provides methods of administering an anti-TIM-3 antibody molecule to treat cancer. While not wishing to be bound by theory, in some embodiments, an anti-TIM-3 antibody molecule stimulates a patient's immune system to recognize and destroy cancer cells, thereby treating the cancer. In some embodiments, the cancer to be treated expresses TIM-3, and the anti-TIM-3 antibody molecule targets the cancer cells or cells in the cancer microenvironment.

In some aspects, the present disclosure relates to treatment of a subject in vivo using an anti-TIM-3 antibody molecule such that growth of cancerous tumors is inhibited. An anti-TIM-3 antibody may be used alone to inhibit the growth of cancerous tumors. Alternatively, an anti-TIM-3 antibody may be used in combination with one or more of: a standard cancer treatment (e.g., for cancer or infectious disorders), or another antibody or antigen-binding fragment thereof, an immunomodulator (e.g., an activator of a costimulatory molecule or an inhibitor of an inhibitory molecule); a vaccine, (e.g., a cancer vaccine); or other forms of cellular immunotherapy, as described below.

Accordingly, in some embodiments, the disclosure provides a method of inhibiting growth of tumor cells in a subject, comprising administering to the subject a therapeutically effective amount of an anti-TIM-3 antibody molecule described herein.

In some embodiments, the methods are suitable for the treatment of cancer in vivo. To achieve antigen-specific enhancement of immunity, the anti-TIM-3 antibody molecule can be administered together with an antigen of interest. When antibodies to TIM-3 are administered in combination with one or more agents, the combination can be administered in either order or simultaneously.

Types of Cancer

In certain aspects, a method of treating a subject, e.g., reducing or ameliorating, a hyperproliferative condition or disorder (e.g., a cancer), e.g., solid tumor, a hematological cancer, a soft tissue tumor, or a metastatic lesion, in a subject is provided. The method includes administering to the subject one or more anti-TIM-3 antibody molecules described herein, alone or in combination with other agents or therapeutic modalities.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas) of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions described herein.

Exemplary cancers whose growth can be inhibited using the antibody molecules disclosed herein include cancers typically responsive to immunotherapy. Non-limiting examples of suitable cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, refractory or recurrent malignancies can be treated using the antibody molecules described herein.

Cancers include, but are not limited to, basal cell carcinoma, biliary tract cancer; bladder cancer; bone cancer; brain and CNS cancer; primary CNS lymphoma; neoplasm of the central nervous system (CNS); breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia (including acute myeloid leukemia, chronic myeloid leukemia, acute lymphoblastic leukemia, chronic lymphocytic leukemia, chronic or acute leukemias); liver cancer; lung cancer (e.g., small cell and non-small cell); lymphoma including Hodgkin's and non-Hodgkin's lymphoma; lymphocytic lymphoma; melanoma, e.g., cutaneous or intraocular malignant melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, hepatocarcinoma, cancer of the anal region, carcinoma of the fallopian tubes, carcinoma of the vagina, carcinoma of the vulva, cancer of the small intestine, cancer of the endocrine system, cancer of the parathyroid gland, cancer of the adrenal gland, sarcoma of soft tissue, cancer of the urethra, cancer of the penis, solid tumors of childhood, spinal axis tumor, brain stem glioma, pituitary adenoma, Kaposi's sarcoma, epidermoid cancer, squamous cell cancer, T-cell lymphoma, environmentally induced cancers including those induced by asbestos, as well as other carcinomas and sarcomas, and combinations of said cancers.

In some embodiments, the cancer treated with the antibody molecules, includes but is not limited to, solid tumors, hematological cancers, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), genitals and genitourinary tract (e.g., renal, urothelial, bladder cells), pharynx, CNS (e.g., brain, neural or glial cells), skin (e.g., melanoma), and pancreas, as well as adenocarcinomas which include malignancies such as most colon cancers, rectal cancer, renal-cell carcinoma, liver cancer, non-small cell-carcinoma of the lung, cancer of the small intestine and cancer of the esophagus. Methods and compositions disclosed herein are also useful for treating metastatic lesions associated with the aforementioned cancers.

While not wishing to be bound by theory, in some embodiments, a patient is more likely to respond to treatment with an immunomodulator (optionally in combination with one or more agents as described herein) if the patient has a cancer that highly expresses PD-L1, and/or the cancer is infiltrated by anti-tumor immune cells, e.g., TILs. The anti-tumor immunce cells may be positive for CD8, PD-L1, and/or IFN-γ; thus levels of CD8, PD-L1, and/or IFN-γ can serve as a readout for levels of TILs in the microenvironment. In certain embodiments, the cancer microenvironment is referred to as triple-positive for PD-L1/CD8/IFN-γ.

Accordingly, in certain aspects, this application provides methods of determining whether a tumor sample is positive for one or more of PD-L1, CD8, and IFN-γ, and if the tumor sample is positive for one or more, e.g., two, or all three, of the markers, then administering to the patient a therapeutically effective amount of an anti-PD-1 antibody molecule, optionally in combination with one or more other immunomodulators or anti-cancer agents, e.g., an anti-TIM3 antibody as described herein.

In the following indications, a large fraction of patients are triple-positive for PD-L1/CD8/IFN-γ: Lung cancer (squamous); lung cancer (adenocarcinoma); head and neck cancer; stomach cancer; NSCLC; HNSCC; gastric cancers (e.g., MSIhi and/or EBV+); CRC (e.g., MSIhi); nasopharyngeal cancer (NPC); cervical cancer (e.g., squamous); thyroid cancer e.g., papillary thyroid; melanoma; TN breast cancer; and DLBCL (Diffuse Large B-Cell Lymphoma). In breast cancer generally and in colon cancer generally, a moderate fraction of patients is triple-positive for PD-L1/CD8/IFN-γ. In the following indications, a small fraction of patients are triple-positive for PD-L1/CD8/IFN-γ: ER+ breast cancer, and pancreatic cancer. These findings are discussed further in Example 9. Regardless of whether a large or small fraction of patients is triple-positive for these markers, screening the patients for these markers allows one to identify a fraction of patients that has an especially high likelihood of responding favorably to therapy with a PD-1 antibody (e.g., a blocking PD-1 antibody), optionally in combination with one or more other immunomodulators (e.g., an anti-TIM-3 antibody molecule described herein, an anti-LAG-3 antibody molecule, or an anti-PD-L1 antibody molecule) and/or anti-cancer agents, e.g., those listed in Table 6 and disclosed in the publications listed in Table 6.

In some embodiments, the cancer sample is classified as triple-positive for PDL1/CD8/IFN-γ. This measurement can roughly be broken down into two thresholds: whether an individual cell is classified as positive, and whether the sample as a whole is classified as positive. First, one can measure, within an individual cell, the level of PD-L1, CD8, and/or IFN-γ. In some embodiments, a cell that is positive for one or more of these markers is a cell that has a higher level of the marker compared to a control cell or a reference value. For example, in some embodiments, a high level of PD-L1 in a given cell is a level higher than the level of PD-L1 in a corresponding non-cancerous tissue in the patient. As another example, in some embodiments, a high level of CD8 or IFN-γ in a given cell is a level of that protein typically seen in a TIL. Second, one can also measure the percentage of cells in the sample that are positive for PD-L1, CD8, and/or IFN-γ. (It is not necessary for a single cell to express all three markers.) In some embodiments, a triple positive sample is one that has a high percentage of cells, e.g., higher than a reference value or higher than a control sample, that are positive for these markers.

In other embodiments, one can measure the levels of PDL1, CD8, and/or IFN-γ overall in the sample. In this case, a high level of CD8 or IFN-γ in the sample can be the level of that protein typically seen in a tumor infiltrated with TIL. Similarly, a high level of PD-L1 can be the level of that protein typically seen in a tumor sample, e.g., a tumor microenvironment.

The identification of subsets of patients that are triple-positive for PD-L1/CD8/IFN-γ, as shown in Example 10 herein, reveals certain sub-populations of patients that are likely to be especially responsive to PD-1 antibody therapy. For instance, many IM-TN (immunomodulatory, triple negative) breast cancer patients are triple-positive for PDL1/CD8/IFN-γ. IM-TN breast cancer is described in, e.g., Brian D. Lehmann et al., "Identification of human triple-negative breast cancer subtypes and preclinical models for selection of targeted therapies", *J Clin Invest*. Jul. 1, 2011; 121(7): 2750-2767. Triple-negative breast cancers are those that do not express estrogen receptor (ER), progesterone receptor (PR) and Her2/neu. These cancers are difficult to treat because they are typically not responsive to agents that target ER, PR, and Her2/neu. Triple-negative breast cancers can be further subdivided into different classes, one of which is immunomodulatory. As described in Lehmann et al., IM-TN breast cancer is enriched for factors involved in immune cell processes, for example, one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing. Accordingly, in some embodiments, the cancer treated is a cancer that is, or is determined to be, positive for one or more marker of IM-TN breast cancer, e.g., a factor that promotes one or more of immune cell signaling (e.g., TH1/TH2 pathway, NK cell pathway, B cell receptor signaling pathway, DC pathway, and T cell receptor signaling), cytokine signaling (e.g., cytokine pathway, IL-12 pathway, and IL-7 pathway), antigen processing and presentation, signaling through core immune signal transduction pathways (e.g., NFKB, TNF, and JAK/STAT signaling), genes involved in T-cell function, immune transcription, interferon (IFN) response and antigen processing.

As another example, it is shown herein that a subset of colon cancer patients having high MSI (microsatellite instability) is also triple-positive for PD-L1/CD8/IFN-γ. Accordingly, in some embodiments, a PD-1 antibody, optionally in combination with one or more immunomodulators such as a TIM-3 antibody described herein, a LAG-3 antibody, or PD-L1 antibody, and one or more anti-cancer agents, e.g., an anti-cancer agent described in Table 6 or in a publication in Table 6, is administered to a patient who has, or who is identified as having, colon cancer with high MSI, thereby treating the cancer. In some embodiments, a cell with high MSI is a cell having MSI at a level higher than a reference value or a control cell, e.g., a non-cancerous cell of the same tissue type as the cancer.

As another example, it is shown herein that a subset of gastric cancer patients having high MSI, and/or which is EBV+, is also triple-positive for PD-L1/CD8/IFN-γ. Accordingly, in some embodiments, a PD-1 antibody, optionally in combination with one or more immunomodulators such as a TIM-3 antibody described herein, a LAG-3 antibody, or PD-L1 antibody, and one or more anti-cancer agents, e.g., an anti-cancer agent described in Table 6 or in a publication in Table 6 is administered to a patient who has, or who is identified as having, gastric cancer with high MSI and/or EBV+, thereby treating the cancer. In some embodiments, a cell with high MSI is a cell having MSI at a level higher than a reference value or a control cell, e.g., a non-cancerous cell of the same tissue type as the cancer.

Additionally disclosed herein are methods of assaying a cancer for PD-L1, and then treating the cancer with a PD-1 antibody, optionally in combination with one or more immunomodulators such as a TIM-3 antibody described herein, a LAG-3 antibody, or PD-L1 antibody. As described in Example 10 herein, a cancer sample can be assayed for PD-L1 protein levels or mRNA levels. A sample having levels of PD-L1 (protein or mRNA) higher than a reference value or a control cell (e.g., a non-cancerous cell) can be classified as PD-L1 positive. Accordingly, in some embodiments, a PD-1 antibody (optionally in combination with one or more anti-cancer agents, optionally in combination with one or more immunomodulators such as a TIM-3 antibody described herein, a LAG-3 antibody, or PD-L1 antibody) is administered to a patient who has, or who is identified as having, a cancer that is PD-L1 positive. The cancer may be, e.g., non-small cell lung (NSCLC) adenocarcinoma (ACA), NSCLC squamous cell carcinoma (SCC), or hepatocellular carcinoma (HCC).

Based on, e.g, Example 9 herein, it was found that certain gastric cancers that are triple-positive for PDL1/CD8/IFN-γ are also positive for PIK3CA. Accordingly, in some embodiments, a cancer can be treated with an anti-PD-1 antibody molecule (optionally in combination with one or more immunomodulators, e.g., an anti-LAG-3 antibody molecule, an anti-TIM-3 antibody molecule as described herein, or an anti-PD-L1 antibody molecule) and an agent that inhibits PIK3CA. Exemplary agents in this category are described in Stein R C (September 2001). "Prospects for phosphoinositide 3-kinase inhibition as a cancer treatment". Endocrine-related *Cancer* 8 (3): 237-48 and Marone R, Cmiljanovic V, Giese B, Wymann M P (January 2008). "Targeting phosphoinositide 3-kinase: moving towards therapy". *Biochimica et Biophysica Acta* 1784 (1): 159-85.

Based on, e.g., Example 9 herein, CRC, e.g., a patient that has (or is identified as having) MSI-high CRC may be treated with a PD-1 antibody, optionally in combination with a therapeutic that targets one or more of TIM-3, e.g., anti-TIM-3 antibody described herein, LAG-3, RNF43, and BRAF. For instance, these cancers may be treated with a PD-1 antibody, optionally in combination with one or more therapeutics that target one or more of TIM-3, LAG-3, PD-1, RNF43, and BRAF. In embodiments, the one or more therapeutics include an immunomodulators such as an anti-TIM-3 antibody described herein, an anti-LAG-3 antibody molecule, and an anti-cancer agent described in Table 6 or a publication listed in Table 6. LAG-3 inhibitors, e.g., antibodies, are described herein. RNF43 can be inhibited, e.g., with an antibody, small molecule (e.g., 2-(2',3-dimethyl-[2,4'-bipyridin]-5-yl)-N-(5-(pyrazin-2-yl)pyridin-2-yl)acetamide (Compound A28)), siRNA, or a Rspo ligand or derivative thereof. BRAF inhibitors (e.g., vemurafenib or dabrafenib) are described herein.

Based on, e.g, Example 9 herein, a patient that has (or is identified as having) a squamous cell lung cancer may be treated with a PD-1 antibody molecule in combination with a therapeutic that targets TIM-3, e.g., a TIM-3 antibody molecule, LAG-3, e.g., a LAG-3 antibody molecule, and optionally with one or more anti-cancer agents, e.g., an anti-cancer agent described in Table 6 or in a publication in Table 6.

In some embodiments, a subject that has (or is identified as having) a squamous cell lung cancer may be treated with a PD-1 antibody, optionally in combination with a therapeutic that targets TIM-3, e.g., a TIM-3 antibody described herein.

Based on, e.g, Example 9 herein, a patient that has (or is identified as having) a thyroid cancer may be treated with a PD-1 antibody molecule, optionally in combination with a therapeutic that targets BRAF, and optionally in combination with one or more immunomodulators, e.g., an anti-LAG-3 antibody molecule, an anti-TIM-3 antibody molecule described herein, and an anti-PD-L1 antibody molecule. BRAF inhibitors (e.g., vemurafenib or dabrafenib) are described herein, e.g., in Table 6 and the publications listed in Table 6.

In other embodiments, the cancer is a hematological malignancy or cancer including but is not limited to a leukemia or a lymphoma. For example, a anti-TIM-3 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In some embodiments, the anti-TIM-3 antibody molecule is used to treat a cancer that expresses TIM-3. TIM-3-expressing cancers include cervical cancer (Cao et al., *PLoS One*. 2013; 8(1):e53834), lung cancer (Zhuang et al., *Am J Clin Pathol*. 2012; 137(6):978-985) (e.g., non-small cell lung cancer), acute myeloid leukemia (Kikushige et al., *Cell Stem Cell*. 2010 Dec. 3; 7(6):708-17), diffuse large B cell lymphoma, melanoma (Fourcade et al., *JEM* 2010; 207 (10): 2175), renal cancer (e.g., renal cell carcinoma (RCC), e.g., kidney clear cell carcinoma, kidney papillary cell carcinoma, or metastatic renal cell carcinoma), squamous cell carcinoma, esophageal squamous cell carcinoma, nasopharyngeal carcinoma, colorectal cancer, breast cancer (e.g., a breast cancer that does not express one, two or all of estrogen receptor, progesterone receptor, or Her2/neu, e.g., a triple negative breast cancer), mesothelioma, hepatocellular carcinoma, and ovarian cancer. The TIM-3-expressing cancer may be a metastatic cancer. In other embodiments, the anti-TIM-3 antibody molecule is used to treat a cancer that is characterized by macrophage activity or high expression of macrophage cell markers. In an embodiment, the anti-TIM-3 antibody molecule is used to treat a cancer that is characterized by high expression of one or more of the following macrophage cell markers: LILRB4 (macrophage inhibitory receptor), CD14, CD16, CD68, MSR1, SIGLEC1, TREM2, CD163, ITGAX, ITGAM, CD11b, or CD11c. Examples of such cancers include, but are not limited to, diffuse large B-cell lymphoma, glioblastoma multiforme, kidney renal clear cell carcinoma, pancreatic adenocarcinoma, sarcoma, liver heptocellular carcinoma, lung adenocarcinoma, kidney renal papillary cell carcinoma, skin cutaneous melanoma, brain lower grade glioma, lung squamous cell carcinoma, ovarian serious cystadenocarcinoma, head and neck squamous cell carcinoma, breast invasive carcinoma, acute myeloid leukemia, cervical squamous cell carcinoma, endocervical adenocarcinoma, uterine carcinoma, colorectal cancer, uterine corpus endometrial carcinoma, thyroid carcinoma, bladder urothelial carcinoma, adrenocortical carcinoma, kidney chromophobe, and prostate adenocarcinoma.

In one embodiment, the cancer is a lung cancer, e.g., a lung adenocarcinoma.

In another embodiment, the cancer is a renal cancer, e.g., a renal cell carcinoma (RCC) (e.g., a kidney clear cell carcinoma or a kidney papillary cell carcinoma), or a metastatic lesion thereof.

In yet another embodiment, the cancer is a mesothelioma.

In yet another embodiment, the cancer is a nasopharyngeal carcinoma (NPC).

In yet another embodiment, the cancer is a hematological cancer (e.g., a myeloid leukemia, e.g., acute myeloid leukemia (AML)).

In yet another embodiment, the cancer is a lymphoma (e.g., diffuse large B cell lymphoma).

In yet another embodiment, the cancer is a breast cancer, e.g., triple negative (TN) and/or immunomodulatory subtype.

In yet another embodiment, the cancer is glioblastoma multiforme.

In yet another embodiment, the cancer is an ovarian cancer (e.g., ovarian carcinoma).

In certain embodiments, the cancer is a solid tumor and the antibody molecule is administered in combination with an anti-LAG-3 or anti-PD-1 antibody molecule.

Combination of Anti-TIM-3 Antibodies with Cancer Vaccines

Antibody molecules to TIM-3 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF, DNA-based vaccines, RNA-based vaccines, and viral transduction-based vaccines. The cancer vaccine may be prophylactic or therapeutic.

In some embodiments, therapy with an anti-TIM-3 antibody molecule is combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. U.S.A.* 90: 3539-43).

Anti-TIM-3 antibody molecules can be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et. al. (1994) *Science* 266: 2011-2013). (These somatic tissues may be protected from immune attack by various means). Tumor antigens may also be "neo-antigens" expressed in cancer cells because of somatic mutations that alter protein sequence or create fusion proteins between two unrelated sequences (e.g., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV), and Epstein-Barr virus (EBV). Another form of tumor specific antigen which may be used in conjunction with an anti-TIM-3 antibody is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with an anti-TIM-3 therapy to activate more potent anti-tumor responses.

Alternatively or in combination, the combination further includes an inhibitor or activator of an immune checkpoint modulator, e.g., a LAG-3 inhibitor (e.g., an anti-TIM-3 antibody molecule), a PD-L1 inhibitor (e.g., an anti-PD-L1 antibody molecule), a PD-1 inhibitor (e.g., an anti-PD-1 antibody molecule), or a CTLA-4 inhibitor (e.g., an anti-CTLA-4 antibody), or any combination thereof.

TIM-3 blockade may also be combined with a standard cancer treatment. TIM-3 blockade may be effectively combined with chemotherapeutic regimes. In these instances, it may be possible to reduce the dose of chemotherapeutic reagent administered (Mokyr, M. et al. (1998) *Cancer Research* 58: 5301-5304). In certain embodiments, the methods and compositions described herein are administered in combination with one or more of other antibody molecules, chemotherapy, other anti-cancer therapy (e.g., targeted anti-cancer therapies, or oncolytic drugs), cytotoxic agents, immune-based therapies (e.g., cytokines), surgical and/or radiation procedures. Exemplary cytotoxic agents that can be administered in combination with include anti-microtubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

Alternatively, or in combination with the aforesaid combinations, the methods and compositions described herein can be administered in combination with one or more of: an immunomodulator (e.g., an activator of a costimulatory molecule or an inhibitor of an inhibitory molecule); a vaccine, e.g., a therapeutic cancer vaccine; or other forms of cellular immunotherapy.

Exemplary non-limiting combinations and uses of the anti-TIM-3 antibody molecules include the following.

In certain embodiments, the anti-TIM-3 antibody molecule is administered in combination with a modulator of a costimulatory molecule or an inhibitory molecule, e.g., a co-inhibitory ligand or receptor.

In one embodiment, the anti-TIM-3 antibody molecule is administered in combination with a modulator, e.g., agonist, of a costimulatory molecule. In one embodiment, the agonist of the costimulatory molecule is chosen from an agonist (e.g., an agonistic antibody or antigen-binding fragment thereof, or soluble fusion) of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand.

In another embodiment, the anti-TIM-3 antibody molecule is used in combination with a costimulatory molecule, e.g., an agonist associated with a positive signal that includes a costimulatory domain of CD28, CD27, ICOS and GITR.

Exemplary GITR agonists include, e.g., GITR fusion proteins and anti-GITR antibodies (e.g., bivalent anti-GITR antibodies), such as, a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.:WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In one embodiment, the anti-TIM-3 antibody molecule is administered in combination with an inhibitor of an immune checkpoint molecule (or immune inhibitory molecule). The term "immune checkpoints" as used herein refers to a group of molecules on the cell surface of immune cells, e.g., CD4 and CD8 T cells that can serve as "brakes" to downmodulate or inhibit an immune response, e.g., an anti-tumor immune response. Immune checkpoint molecules include, but are not limited to, Programmed Death 1 (PD-1), PD-L1, Cytotoxic T-Lymphocyte Antigen 4 (CTLA-4), B7-H1, B7-H3, B7-H4, OX-40, 4-1BB CD137), CD40, T-cell immunoglobulin domain and mucin domain-3 (TIM-3), and Lymphocyte-activation gene 3 (LAG-3), among others. Immunotherapeutic agents that can act as inhibitors of immune checkpoint molecules useful in combination with the anti-PD-1 molecules described herein, include, but are not limited to, inhibitors of PD-L1, PD-L2, CTLA-4, TIM-3, LAG-3, VISTA, BTLA, TIGIT, LAIR1, CD160, 2B4, CEACAM (e.g., CEACAM-1, CEACM-3, and/or CEACAM-5), and/or TGFR beta. Inhibition of an immune inhibitory molecule can be performed by inhibition at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand, or an antibody or antigen-binding fragment thereof, that binds to the inhibitory molecule.

In one embodiment, the inhibitor is a soluble ligand (e.g., a CTLA-4-Ig or a TIM-3-Ig), or an antibody or antibody fragment that binds to CTLA-4. For example, the anti-TIM-3 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer). Exemplary anti-CTLA-4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). In one embodiment, the anti-TIM-3 antibody molecule is administered after treatment, e.g., after treatment of a melanoma, with an anti-CTLA-4 antibody (e.g., ipilimumab) with or without a BRAF inhibitor (e.g., vemurafenib or dabrafenib). Exemplary doses that can be use include a dose of anti-TIM-3 antibody molecule of about 1 to 30 mg/kg, 1 to 20 mg/kg, or 1 to 10 mg/kg, e.g., 3 mg/kg, and a dose of an anti-CTLA-4 antibody, e.g., ipilimumab, of about 3 mg/kg.

In certain embodiments, immune checkpoint molecules, e.g., PD-1, LAG-3, TIM-3, CEACAM-1/-5, can regulate T-cell function to promote tumoral immune escape. Thus, the anti-TIM-3 antibodies described herein can be used in combination with one or more inhibitors of these immune inhibitor molecules to enhance an anti-tumor response. The combination of antibodies recited herein can be administered separately, e.g., as separate antibodies, or linked, e.g., as a bispecific or trispecific antibody molecule.

In one embodiment, the anti-TIM-3 antibody molecule is administered in combination with an anti-TIM-3 antibody or an antigen-binding fragment thereof. In another embodiment, the anti-TIM-3 antibody molecule is administered in combination with an anti-PD-1 antibody or antigen-binding fragment thereof. In yet other embodiments, the anti-TIM-3 antibody molecule is administered in combination with an anti-TIM-3 antibody and an anti-PD-1 antibody, or antigen-binding fragments thereof. In one embodiment, a bispecific antibody that includes an anti-TIM-3 antibody molecule and an anti-PD-1 or anti-TIM-3 antibody, or antigen-binding fragment thereof, is administered. In certain embodiments, the combination of antibodies recited herein is used to treat a cancer, e.g., a cancer as described herein (e.g., a solid tumor). The efficacy of the aforesaid combinations can be tested in animal models known in the art. For example, the animal models to test the effect of anti-PD-1 and anti-LAG-3 are described, e.g., in Woo et al. (2012) *Cancer Res.* 72(4):917-27).

In some embodiments, the inhibitors of the TIM-3 and PD-1 molecules (e.g., anti-TIM-3 and anti-PD-1 antibody molecules) are administered in combination, e.g., to treat cancer. In some embodiments, the subject is a patient who has progressed (e.g., experienced tumor growth) during therapy with a PD-1 inhibitor (e.g., an antibody molecule as described herein) and/or a PD-L1 inhibitor (e.g., an anti-PD-L1 antibody molecule). In some embodiments, therapy with the PD-1 antibody molecule and/or PD-L1 antibody molecule is continued, and a TIM-3 immune inhibitory molecule (e.g., antibody) is added to the therapy.

In other embodiments, the anti-TIM-3 antibody molecule is administered in combination with a CEACAM inhibitor (e.g., CEACAM-1, CEACAM-3, and/or CEACAM-5 inhibitor). In one embodiment, the inhibitor of CEACAM is an anti-CEACAM antibody molecule. In one embodiment, the anti-TIM-3 antibody molecule is administered in combination with a CEACAM-1 inhibitor, e.g., an anti-CEACAM-1 antibody molecule. In another embodiment, the anti-TIM-3 antibody molecule is administered in combination with a CEACAM-3 inhibitor, e.g., an anti-CEACAM-3 antibody molecule. In another embodiment, the anti-TIM-3 antibody molecule is administered in combination with a CEACAM-5 inhibitor, e.g., an anti-CEACAM-5 antibody molecule. Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal.pone.0021146), or cross-reacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature* doi:10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

In some embodiments, the PD-1 and TIM-3 immune inhibitory molecules (e.g., antibody molecules) are administered in combination with each other, e.g., to treat cancer. In some embodiments, the patient is a patient who progressed (e.g., experienced tumor growth) during therapy with a PD-1 inhibitor (e.g., an antibody molecule as described herein) and/or a PDL1 inhibitor (e.g., antibody molecule). In some embodiments, therapy with the PD-1 antibody molecule and/or PDL1 antibody molecule is continued, and a TIM-3 immune inhibitory molecule (e.g., antibody) is added to the therapy.

In some embodiments, the TIM-3 and LAG-3 immune inhibitory molecules (e.g., antibody molecules) are administered in combination with each other, e.g., to treat cancer. In some embodiments, the patient is a patient who progressed (e.g., experienced tumor growth) during therapy with a TIM-3 inhibitor (e.g., an antibody molecule as described herein) and/or a PD-1 inhibitor (e.g., antibody molecule). In some embodiments, therapy with the anti-TIM-3 antibody molecule and/or PDL1 antibody molecule is continued, and a LAG-3 immune inhibitory molecule (e.g., antibody) is added to the therapy.

In other embodiments, the anti-TIM-3 antibody molecule is administered in combination with a cytokine, e.g., interleukin-21, interleukin-2, or interleukin 15. In certain embodiments, the combination of anti-TIM-3 antibody molecule and cytokine described herein is used to treat a cancer, e.g., a cancer as described herein (e.g., a solid tumor or melanoma).

Exemplary immunomodulators that can be used in combination with anti-TIM-3 antibody molecules include, but are not limited to, e.g., afutuzumab (available from Roche®); pegfilgrastim (Neulasta®); lenalidomide (CC-5013, Revlimid®); thalidomide (Thalomid®), actimid (CC4047); and cytokines, e.g., IL-21 or IRX-2 (mixture of human cytokines including interleukin 1, interleukin 2, and interferon γ, CAS 951209-71-5, available from IRX Therapeutics).

In yet other embodiments, the anti-TIM-3 antibody molecule is used in combination with an indoleamine-pyrrole 2,3-dioxygenase (IDO) inhibitor (e.g., INCB24360) in a subject with advanced or metastatic cancer (e.g., a patient with metastic and recurrent NSCL cancer).

In other embodiments, the anti-TIM-3 antibody molecules are administered to a subject in conjunction with (e.g., before, simultaneously or following) one or more of: bone marrow transplantation, T cell ablative therapy using chemotherapy agents such as, fludarabine, external-beam radiation therapy (XRT), cyclophosphamide, and/or antibodies such as OKT3 or CAMPATH. In one embodiment, the anti-TIM-3 antibody molecules are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive the anti-TIM-3 antibody molecules. In an additional embodiment, the anti-TIM-3 antibody molecules are administered before or following surgery.

Another example of a combination is an anti-TIM-3 antibody in combination with decarbazine for the treatment of melanoma. Without being bound by theory, the combined use of TIM-3 blockade and chemotherapy is believed to be facilitated by cell death, that is a consequence of the cytotoxic action of most chemotherapeutic compounds, which can result in increased levels of tumor antigen in the antigen presentation pathway. Other combination therapies that may result in synergy with TIM-3 blockade through cell death are radiation, surgery, and hormone deprivation. Each of these protocols creates a source of tumor antigen in the host. Angiogenesis inhibitors may also be combined with TIM-3 blockade. Inhibition of angiogenesis leads to tumor cell death which may feed tumor antigen into host antigen presentation pathways.

TIM-3 blocking antibodies can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the use of TIM-3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies or antigen-binding fragments thereof to each of these entities may be used in combination with anti-TIM-3 antibody molecules to counteract the effects of the immunosuppressive agent and favor tumor immune responses by the host.

Other antibodies which may be used to activate host immune responsiveness can be used in combination with anti-TIM-3 antibody molecules. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjunction with PD-1 antibodies (Ito, N. et al. (2000) *Immunobiology* 201 (5) 527-40). Antibodies to T cell costimulatory molecules such as CTLA-4 (e.g., U.S. Pat. No. 5,811,097), OX-40 (Weinberg, A. et al. (2000) *Immunol* 164: 2160-2169), 4-1BB (Melero, I. et al. (1997) *Nature Medicine* 3: 682-685 (1997), and ICOS (Hutloff, A. et al. (1999) *Nature* 397: 262-266) may also provide for increased levels of T cell activation.

Additional exemplary standard of care treatments are described in the section entitled "Combination Therapies" below.

In all of the methods described herein, TIM-3 blockade can be combined with other forms of immunotherapy such as cytokine treatment (e.g., interferons, GM-CSF, G-CSF, IL-2, IL-21), or bispecific antibody therapy, which provides for enhanced presentation of tumor antigens (see e.g., Holliger (1993) *Proc. Natl. Acad. Sci. USA* 90:6444-6448; Poljak (1994) *Structure* 2:1121-1123).

Methods of administering the antibody molecules are known in the art and are described below. Suitable dosages of the molecules used will depend on the age and weight of the subject and the particular drug used. Dosages and therapeutic regimens of the anti-TIM-3 antibody molecule can be determined by a skilled artisan. In certain embodiments, the anti-TIM-3 antibody molecule is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the anti-TIM-3 antibody molecule is administered at a dose of about 1 mg/kg, about 3 mg/kg, about 10 mg/kg, about 15 mg/kg, about 20 mg/kg, about 25 mg/kg or about 30 mg/kg. In some embodiments, the anti-TIM-3 antibody molecule is administered at a dose of about 1-3 mg/kg, about 3-10 mg/kg, about 3-15 mg/kg, about 10-15 mg/kg, about 10-20 mg/kg, about 10-25 mg/kg, or about 20-30 mg/kg. In some embodiments, the anti-TIM-3 antibody molecule is administered at a dose of about 0.5-2, 2-4, 2-5, or 5-15 mg/kg. The dosing schedule can vary from e.g., once a week to once every 2, 3, or 4 weeks. In one embodiment, the anti-TIM-3 antibody molecule is administered at a dose from about 10 to 20 mg/kg every other week.

The antibody molecules can be used by themselves or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Anti-TIM-3 antibody molecules may also be combined with standard cancer treatments. For instance, anti-TIM-3 antibody molecules may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is an anti-TIM-3 antibody molecule in combination with decarbazine for the treatment of melanoma. Another example of such a combination is an anti-TIM-3 antibody molecule in combination with interleukin-2 (IL-2) for the treatment of melanoma. In some embodiments the anti-TIM-3 antibody molecule can be combined with IL-21. While not wishing to be bound by theory, one scientific rationale behind the combined use of anti-TIM-3 antibody molecule therapy and chemotherapy is that cell death, that is a consequence of the cytotoxic action of most chemotherapeutic compounds, should result in increased levels of tumor antigen in the antigen presentation pathway. Other combination therapies that may result in synergy with anti-TIM-3 antibody molecule therapy through cell death are radiation, surgery, and hormone deprivation. Each of these protocols creates a source of tumor antigen in the host. Angiogenesis inhibitors may also be combined with anti-TIM-3 antibody molecule therapy. Inhibition of angiogenesis leads to tumor cell death which may feed tumor antigen into host antigen presentation pathways.Anti-TIM-3 antibody molecules can also be used in combination with bispecific antibodies. Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the use of anti-TIM-3 antibody molecules. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies to each of these entities may be used in combination with anti-TIM-3 antibody molecules to counteract the effects of the immunosuppressive agent and favor tumor immune responses by the host.

Other antibodies which may be used to activate host immune responsiveness can be used in combination with anti-TIM-3 antibody molecules. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with anti-TIM-3 antibody molecules (see Ito, N. et al. (2000) Immunobiology 201 (5) 527-40). Activating antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Additional Combination Therapies

The anti-TIM-3 antibody molecule can be used in combination with other therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

By "in combination with," it is not intended to imply that the therapy or the therapeutic agents must be administered at the same time and/or formulated for delivery together, although these methods of delivery are within the scope described herein. The anti-TIM-3 antibody molecules can be administered concurrently with, prior to, or subsequent to, one or more other additional therapies or therapeutic agents. The anti-TIM-3 antibody molecule and the other agent or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In certain embodiments, the anti-TIM-3 antibody molecules described herein are administered in combination with one or more other inhibitors of TIM-3 or other immune checkpoint molecules, e.g., PD-1, PD-L1, PD-L2, CEACAM (e.g., CEACAM-1, CEACAM-3, or CEACAM-5), or LAG-3.

In certain embodiments, the anti-TIM-3 antibody molecules described herein are administered in combination with one or more other inhibitors of PD-1, PD-L1 and/or PD-L2 known in the art. The antagonist may be an antibody, an antigen binding fragment thereof, an immunoadhesin, a fusion protein, or oligopeptide. In some embodiments, the anti-PD-1 antibody is chosen from MDX-1106, Merck 3475 or CT-011. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 binding antagonist is chosen from YW243.55.S70, MPDL3280A, MEDI-4736, MSB-0010718C, or MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634.

MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. In other embodiments, the anti-PD-1 antibody is pembrolizumab. Pembrolizumab (Trade name Keytruda formerly lambrolizumab—also known as MK-3475) disclosed, e.g., in Hamid, O. et al. (2013) *New England Journal of Medicine* 369 (2): 134-44. AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, U.S. Pat. No. 2010/028330, and/or U.S. Pat. No. 2012/0114649.

In some embodiments, the anti-PD-1 antibody is MDX-1106. Alternative names for MDX-1106 include MDX-1106-04, ONO-4538, BMS-936558 or Nivolumab. In some embodiments, the anti-PD-1 antibody is Nivolumab (CAS Registry Number: 946414-94-4). Nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pembrolizumab (Trade name Keytruda formerly lambrolizumab—also known as MK-3475; Merck) is a humanized IgG4 monoclonal antibody that binds to PD-1. Lambrolizumab and other humanized anti-PD-1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1105 (also referred to as BMS-936559, and, e.g., anti-PD-L1 binding agents disclosed in WO2007/005874).

Cancer Therapies

Exemplary combinations of anti-TIM-3 antibody molecules (alone or in combination with other stimulatory agents) and standard of care for cancer, include at least the following. In certain embodiments, the anti-TIM-3 antibody molecule, e.g., the anti-TIM-3 antibody molecule described herein, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids that can be used in combination with the anti-PD-1 antibody molecules, alone or in combination with another immunomodulator (e.g., an anti- LAG-3, anti-PD-L1 or anti-TIM-3 antibody molecule), include, but ate not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with the anti-TIM-3 antibody molecules, alone or in combination with another immunomodulator (e.g., an anti-LAG-3, anti-PD-L1 or anti-PD-1 antibody molecule), include, but ate not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments, the anti-TIM-3 antibody molecule, e.g., the anti-TIM-3 antibody molecule described herein, is used, alone or in combination with another immunomodulator (e.g., an anti-LAG-3, anti-PD-1 or anti-PD-L1 antibody molecule), in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®)), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib.

In certain embodiments, the anti-TIM-3 antibody molecule, e.g., the anti-TIM-3 antibody molecule described herein, is used, alone or in combination with another immunomodulator (e.g., an anti-LAG-3, anti-PD-1 or anti-PD-L1 antibody molecule), in combination with a Vascular Endothelial Growth Factor (VEGF) receptor inhibitors, including but not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) *Cancer Res.* 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006009360, 20050186208, 20030206899, 20030190317, 20030203409, and 20050112126; and Popkov et al, *Journal of Immunological Methods* 288: 149-164 (2004). Other antibodies include those that bind to a functional epitope on human VEGF comprising of residues F17, Ml 8, D19, Y21, Y25, Q89, 191, K101, El 03, and C104 or, alternatively, comprising residues F17, Y21, Q22, Y25, D63, 183 and Q89.

In some embodiments, the anti-TIM-3 antibody molecule, e.g., the anti-TIM-3 antibody molecule described herein, is used, alone or in combination with another immunomodulator (e.g., an anti-LAG-3, anti-PD-1 or anti-PD-L1 antibody molecule), in combination with a PI3K inhibitor. In one embodiment, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235).

In some embodiments, the anti-TIM-3 antibody molecules described herein is used, alone or in combination with another immunomodulator (e.g., an anti-LAG-3, anti-PD-1 or anti-PD-L1 antibody molecule), in combination with a mTOR inhibitor, e.g., one or more mTOR inhibitors chosen from one or more of rapamycin, temsirolimus (TORISEL®), AZD8055, BEZ235, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.0$^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1), and XL765.

In some embodiments, the anti-TIM-3 antibody molecule, e.g., the anti-TIM-3 antibody molecule described herein, is used, alone or in combination with another immunomodulator (e.g., an anti-LAG-3, anti-PD-1 or anti-PD-L1 antibody molecule), in combination with a BRAF inhibitor, e.g., GSK2118436, RG7204, PLX4032, GDC-0879, PLX4720, and sorafenib tosylate (Bay 43-9006).

In some embodiments, the anti-TIM-3 antibody molecule, e.g., the anti-TIM-3 antibody molecule described herein, is used, alone or in combination with another immunomodulator (e.g., an anti-LAG-3, anti-PD-1 or anti-PD-L1 antibody molecule), in combination with a MEK inhibitor. In some embodiments, the combination of the anti-TIM-3 antibody and the MEK inhibitor is used to treat a cancer (e.g., a cancer described herein). In some embodiments, the cancer treated with the combination is chosen from a melanoma, a colorectal cancer, a non-small cell lung cancer, an ovarian cancer, a breast cancer, a prostate cancer, a pancreatic cancer, a hematological malignancy or a renal cell carcinoma. In certain embodiments, the cancer includes a BRAF mutation (e.g., a BRAF V600E mutation), a BRAF wildtype, a KRAS wildtype or an activating KRAS mutation. The cancer may be at an early, intermediate or late stage. Any MEK inhibitor can be used in combination including, but not limited to, ARRY-142886, G02442104 (also known as GSK1120212), RDEA436, RDEA119/BAY 869766, AS703026, G00039805 (also known as AZD-6244 or selumetinib), BIX 02188, BIX 02189, CI-1040 (PD-184352), PD0325901, PD98059, U0126, GDC-0973 (Methanone, [3,4-difluoro-2-[(2-fluoro-4-iodophenyl)amino]phenyl][3-hydroxy-3-(25)-2-piperidinyl-1-azetidinyl]-), G-38963, G02443714 (also known as AS703206), or a pharmaceutically acceptable salt or solvate thereof. Additional examples of MEK inhibitors are disclosed in WO 2013/019906, WO 03/077914, WO 2005/121142, WO 2007/04415, WO 2008/024725 and WO 2009/085983, the contents of which are incorporated herein by reference.

In some embodiments, the anti-TIM-3 antibody molecule, e.g., the anti-TIM-3 antibody molecule described herein, is used, alone or in combination with another immunomodulator (e.g., an anti-LAG-3, anti-PD-1 or anti-PD-L1 antibody molecule), in combination with a JAK2 inhibitor, e.g., CEP-701, INCB18424, CP-690550 (tasocitinib).

In some embodiments, the pharmaceutical composition described herein is used, alone or in combination with another immunomodulator (e.g., an anti-LAG-3, anti-PD-L1 or anti-PD-1 antibody molecule), in combination with paclitaxel or a paclitaxel agent, e.g., TAXOL®, protein-bound paclitaxel (e.g., ABRAXANE®). Exemplary paclitaxel agents include, but are not limited to, nanoparticle albumin-bound paclitaxel (ABRAXANE, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Anti-TIM-3 antibody molecules, alone or in combination with another immunomodulator (e.g., an anti-LAG-3, anti-PD-1 or anti-PD-L1 antibody molecule), can be administered in combination with one or more of the existing modalities for treating cancers, including, but not limited to: surgery; radiation therapy (e.g., external-beam therapy which involves three dimensional, conformal radiation therapy where the field of radiation is designed, local radiation (e.g., radition directed to a preselected target or organ), or focused radiation). Focused radiation can be selected from the group consisting of stereotactic radiosurgery, fractionated stereotactic radiosurgery, and intensity-modulated radiation therapy. The focused radiation can have a radiation source selected from the group consisting of a particle beam (proton), cobalt-60 (photon), and a linear accelerator (x-ray), e.g., as decribed in WO 2012/177624.

In certain embodiments, the anti-TIM-3 antibody molecule, alone or in combination with another immunomodulator (e.g., an anti-LAG-3, anti-PD-1 or anti-PD-L1 antibody molecule), is administered in combination with an antibody against a Killer-cell Immunoglobulin-like Receptors (also referred to herein as an "anti-KIR antibody"), a pan-KIR antibody, or an anti-NKG2D antibody, and an anti-MICA antibody. In certain embodiments, the combination of anti-TIM-3 antibody molecule and anti-KIR antibody, pan-KIR antibody, or an anti-NKG2D antibody described herein is used to treat a cancer, e.g., a cancer as described herein (e.g., a solid tumor, e.g., an advanced solid tumor).

In one embodiment, the anti-TIM-3 antibody molecule, alone or in combination with another immunomodulator (e.g., an anti-LAG-3, anti-PD-1 or anti-PD-L1 antibody molecule), is administered in combination with a cellular immunotherapy (e.g., Provenge (e.g., Sipuleucel)), and optionally in combination with cyclophosphamide. In certain embodiments, the combination of anti-TIM-3 antibody molecule, Provenge and/or cyclophosphamide is used to treat a cancer, e.g., a cancer as described herein (e.g., a prostate cancer, e.g., an advanced prostate cancer).

In another embodiment, the anti-TIM-3 antibody molecule, alone or in combination with another immunomodulator (e.g., an anti-LAG-3, anti-PD-1 or anti-PD-L1 antibody molecule), is administered in combination with a vaccine, e.g., a dendritic cell renal carcinoma (DC-RCC) vaccine. In certain embodiments, the combination of anti-TIM-3 antibody molecule and the DC-RCC vaccine is used to treat a cancer, e.g., a cancer as described herein (e.g., a renal carcinoma, e.g., metastatic renal cell carcinoma (RCC) or clear cell renal cell carcinoma (CCRCC)).

In yet another embodiment, the anti-TIM-3 antibody molecule, alone or in combination with another immunomodulator (e.g., an anti-LAG-3, anti-PD-1 or anti-PD-L1 antibody molecule), is administered in combination with chemotherapy, and/or immunotherapy. For example, the anti-TIM-3 antibody molecule can be used to treat a myeloma, alone or in combination with one or more of: chemotherapy or other anti-cancer agents (e.g., thalidomide analogs, e.g., lenalidomide), an anti-PD-1 antibody, tumor antigen-pulsed dendritic cells, fusions (e.g., electrofusions) of tumor cells and dendritic cells, or vaccination with immunoglobulin idiotype produced by malignant plasma cells. In one embodiment, the anti-TIM-3 antibody molecule is used in combination with an anti-PD-1 antibody to treat a myeloma, e.g., a multiple myeloma.

In one embodiment, the anti-TIM-3 antibody molecule, alone or in combination with another immunomodulator (e.g., an anti-LAG-3, anti-PD-1 or anti-PD-L1 antibody molecule), is used in combination with chemotherapy to treat a lung cancer, e.g., non-small cell lung cancer. In one embodiment, the anti-TIM-3 antibody molecule is used with platinum doublet therapy to treat lung cancer.

In yet another embodiment, the anti-TIM-3 antibody molecule, alone or in combination with another immunomodulator (e.g., an anti-LAG-3, anti-PD-1 or anti-PD-L1 antibody molecule), is used to treat a renal cancer, e.g., renal cell carcinoma (RCC) (e.g., clear cell renal cell carcinoma (CCRCC) or metastatic RCC. The anti-TIM-3 antibody molecule can be administered in combination with one or more of: an immune-based strategy (e.g., interleukin-2 or interferon-α), a targeted agent (e.g., a VEGF inhibitor such as a monoclonal antibody to VEGF); a VEGF tyrosine kinase inhibitor such as sunitinib, sorafenib, axitinib and pazopanib; an RNAi inhibitor), or an inhibitor of a downstream mediator of VEGF signaling, e.g., an inhibitor of the mammalian target of rapamycin (mTOR), e.g., everolimus and temsirolimus.

An example of suitable therapeutics for use in combination with the anti-TIM-3 antibody molecules described herein, alone or in combination with another immunomodulator (e.g., an anti-LAG-3, anti-PD-1 or anti-PD-L1 antibody molecule), for treatment of pancreatic cancer includes, but is not limited to, a chemotherapeutic agent, e.g., paclitaxel or a paclitaxel agent (e.g., a paclitaxel formulation such as TAXOL, an albumin-stabilized nanoparticle paclitaxel formulation (e.g., ABRAXANE) or a liposomal paclitaxel formulation); gemcitabine (e.g., gemcitabine alone or in combination with AXP107-11); other chemotherapeutic agents such as oxaliplatin, 5-fluorouracil, capecitabine, rubitecan, epirubicin hydrochloride, NC-6004, cisplatin, docetaxel (e.g., TAXOTERE), mitomycin C, ifosfamide; interferon; tyrosine kinase inhibitor (e.g., EGFR inhibitor (e.g., erlotinib, panitumumab, cetuximab, nimotuzumab); HER2/neu receptor inhibitor (e.g., trastuzumab); dual kinase inhibitor (e.g., bosutinib, saracatinib, lapatinib, vandetanib); multikinase inhibitor (e.g., sorafenib, sunitinib, XL184, pazopanib); VEGF inhibitor (e.g., bevacizumab, AV-951, brivanib); radioimmunotherapy (e.g., XR303); cancer vaccine (e.g., GVAX, survivin peptide); COX-2 inhibitor (e.g., celecoxib); IGF-1 receptor inhibitor (e.g., AMG 479, MK-0646); mTOR inhibitor (e.g., everolimus, temsirolimus); IL-6 inhibitor (e.g., CNTO 328); cyclin-dependent kinase inhibitor (e.g., P276-00, UCN-01); Altered Energy Metabolism-Directed (AEMD) compound (e.g., CPI-613); HDAC inhibitor (e.g., vorinostat); TRAIL receptor 2 (TR-2) agonist (e.g., conatumumab); MEK inhibitor (e.g., AS703026, selumetinib, GSK1120212); Raf/MEK dual kinase inhibitor (e.g., RO5126766); Notch signaling inhibitor (e.g., MK0752); monoclonal antibody-antibody fusion protein (e.g., L19IL2); curcumin; HSP90 inhibitor (e.g., tanespimycin, STA-9090); rIL-2; denileukin diftitox; topoisomerase 1 inhibitor (e.g., irinotecan, PEP02); statin (e.g., simvastatin); Factor VIIa inhibitor (e.g., PCI-27483); AKT inhibitor (e.g., RX-0201); hypoxia-activated prodrug (e.g., TH-302); metformin hydrochloride, gamma-secretase inhibitor (e.g., RO4929097); ribonucleotide reductase inhibitor (e.g., 3-AP); immunotoxin (e.g., HuC242-DM4); PARP inhibitor (e.g., KU-0059436, veliparib); CTLA-4 inhbitor (e.g., CP-675,206, ipilimumab); AdV-tk therapy; proteasome inhibitor (e.g., bortezomib (Velcade), NPI-0052); thiazolidinedione (e.g., pioglitazone); NPC-1C; Aurora kinase inhibitor (e.g., R763/AS703569), CTGF inhibitor (e.g., FG-3019); siG12D LODER; and radiation therapy (e.g., tomotherapy, stereotactic radiation, proton therapy), surgery, and a combination thereof. In certain embodiments, a combination of paclitaxel or a paclitaxel agent, and gemcitabine can be used with the anti-TIM-3 antibody molecules described herein.

An example of suitable therapeutics for use in combination with the anti-TIM-3 antibody molecules, alone or in combination with another immunomodulator (e.g., an anti-LAG-3, anti-PD-1 or anti-PD-L1 antibody molecule), for treatment of small cell lung cancer includes, but is not limited to, a chemotherapeutic agent, e.g., etoposide, carboplatin, cisplatin, oxaliplatin, irinotecan, topotecan, gemcitabine, liposomal SN-38, bendamustine, temozolomide, belotecan, NK012, FR901228, flavopiridol); tyrosine kinase inhibitor (e.g., EGFR inhibitor (e.g., erlotinib, gefitinib, cetuximab, panitumumab); multikinase inhibitor (e.g., sorafenib, sunitinib); VEGF inhibitor (e.g., bevacizumab, vandetanib); cancer vaccine (e.g., GVAX); Bcl-2 inhibitor (e.g., oblimersen sodium, ABT-263); proteasome inhibitor (e.g., bortezomib (Velcade), NPI-0052), paclitaxel or a paclitaxel agent; docetaxel; IGF-1 receptor inhibitor (e.g., AMG 479); HGF/SF inhibitor (e.g., AMG 102, MK-0646); chloroquine; Aurora kinase inhibitor (e.g., MLN8237); radioimmunotherapy (e.g., TF2); HSP90 inhibitor (e.g., tanespimycin, STA-9090); mTOR inhibitor (e.g., everolimus); Ep-CAM-/CD3-bispecific antibody (e.g., MT110); CK-2 inhibitor (e.g., CX-4945); HDAC inhibitor (e.g., belinostat); SMO antagonist (e.g., BMS 833923); peptide cancer vaccine, and radiation therapy (e.g., intensity-modulated radiation therapy (IMRT), hypofractionated radiotherapy, hypoxia-guided radiotherapy), surgery, and combinations thereof.

An example of suitable therapeutics for use in combination with the anti-TIM-3 antibody molecules, alone or in combination with another immunomodulator (e.g., an anti-LAG-3, anti-PD-1 or anti-PD-L1 antibody molecule), for treatment of non-small cell lung cancer includes, but is not limited to, a chemotherapeutic agent, e.g., vinorelbine, cisplatin, docetaxel, pemetrexed disodium, etoposide, gemcitabine, carboplatin, liposomal SN-38, TLK286, temozolomide, topotecan, pemetrexed disodium, azacitidine, irinotecan, tegafur-gimeracil-oteracil potassium, sapacitabine); tyrosine kinase inhibitor (e.g., EGFR inhibitor (e.g., erlotinib, gefitinib, cetuximab, panitumumab, necitumumab, PF-00299804, nimotuzumab, RO5083945), MET inhibitor (e.g., PF-02341066, ARQ 197), PI3K kinase inhibitor (e.g., XL147, GDC-0941), Raf/MEK dual kinase inhibitor (e.g., RO5126766), PI3K/mTOR dual kinase inhibitor (e.g., XL765), SRC inhibitor (e.g., dasatinib), dual inhibitor (e.g., BIBW 2992, GSK1363089, ZD6474, AZD0530, AG-013736, lapatinib, MEHD7945A, linifanib), multikinase inhibitor (e.g., sorafenib, sunitinib, pazopanib, AMG 706, XL184, MGCD265, BMS-690514, R935788), VEGF inhibitor (e.g., endostar, endostatin, bevacizumab, cediranib, BIBF 1120, axitinib, tivozanib, AZD2171), cancer vaccine (e.g., BLP25 liposome vaccine, GVAX, recombinant DNA and adenovirus expressing L523S protein), Bcl-2 inhibitor (e.g., oblimersen sodium), proteasome inhibitor (e.g., bortezomib, carfilzomib, NPI-0052, MLN9708), paclitaxel or a paclitaxel agent, docetaxel, IGF-1 receptor inhibitor (e.g., cixutumumab, MK-0646, OSI 906, CP-751,871, BIIB022), hydroxychloroquine, HSP90 inhibitor (e.g., tanespimycin, STA-9090, AUY922, XL888), mTOR inhibitor (e.g., everolimus, temsirolimus, ridaforolimus), Ep-CAM-/CD3-bispecific antibody (e.g., MT110), CK-2 inhibitor (e.g., CX-4945), HDAC inhibitor (e.g., MS 275, LBH589, vorinostat, valproic acid, FR901228), DHFR inhibitor (e.g., pralatrexate), retinoid (e.g., bexarotene, tretinoin), antibody-drug conjugate (e.g., SGN-15), bisphosphonate (e.g., zoledronic acid), cancer vaccine (e.g., belagenpumatucel-L), low molecular weight heparin (LMWH) (e.g., tinzaparin, enoxaparin), GSK1572932A, melatonin, talactoferrin, dimesna, topoisomerase inhibitor (e.g., amrubicin, etoposide, karenitecin), nelfinavir, cilengitide, ErbB3 inhibitor (e.g., MM-121, U3-1287), survivin inhibitor (e.g., YM155, LY2181308), eribulin mesylate, COX-2 inhibitor (e.g., celecoxib), pegfilgrastim, Polo-like kinase 1 inhibitor (e.g., BI 6727), TRAIL receptor 2 (TR-2) agonist (e.g., CS-1008), CNGRC peptide (SEQ ID NO: 225)-TNF alpha conjugate, dichloroacetate (DCA), HGF inhibitor (e.g., SCH 900105), SAR240550, PPAR-gamma agonist (e.g., CS-7017), gamma-secretase inhibitor (e.g., RO4929097), epigenetic therapy (e.g., 5-azacitidine), nitroglycerin, MEK inhibitor (e.g., AZD6244), cyclin-dependent kinase inhibitor (e.g., UCN-01), cholesterol-Fus1, antitubulin agent (e.g., E7389), farnesyl-OH-transferase inhibitor (e.g., lonafarnib), immunotoxin (e.g., BB-10901, SS1 (dsFv) PE38), fondaparinux, vascular-disrupting agent (e.g., AVE8062), PD-L1 inhibitor (e.g., MDX-1105, MDX-1106), beta-glucan, NGR-hTNF, EMD 521873, MEK inhibitor (e.g., GSK1120212), epothilone analog (e.g., ixabepilone), kinesin-spindle inhibitor (e.g., 4SC-205), telomere targeting agent (e.g., KML-001), P70 pathway inhibitor (e.g., LY2584702), AKT inhibitor (e.g., MK-2206), angiogenesis inhibitor (e.g., lenalidomide), Notch signaling inhibitor (e.g., OMP-21M18), radiation therapy, surgery, and combinations thereof.

An example of suitable therapeutics for use in combination with the anti-TIM-3 antibody molecules, alone or in combination with another immunomodulator (e.g., an anti-LAG-3, anti-PD-1 or anti-PD-L1 antibody molecule), for treatment of ovarian cancer includes, but is not limited to, a chemotherapeutic agent (e.g., paclitaxel or a paclitaxel agent; docetaxel; carboplatin; gemcitabine; doxorubicin; topotecan; cisplatin; irinotecan, TLK286, ifosfamide, olaparib, oxaliplatin, melphalan, pemetrexed disodium, SJG-136, cyclophosphamide, etoposide, decitabine); ghrelin antagonist (e.g., AEZS-130), immunotherapy (e.g., APC8024, oregovomab, OPT-821), tyrosine kinase inhibitor (e.g., EGFR inhibitor (e.g., erlotinib), dual inhibitor (e.g., E7080), multikinase inhibitor (e.g., AZD0530, JI-101, sorafenib, sunitinib, pazopanib), ON 01910.Na), VEGF inhibitor (e.g., bevacizumab, BIBF 1120, cediranib, AZD2171), PDGFR inhibitor (e.g., IMC-3G3), paclitaxel, topoisomerase inhibitor (e.g., karenitecin, Irinotecan), HDAC inhibitor (e.g., valproate, vorinostat), folate receptor inhibitor (e.g., farletuzumab), angiopoietin inhibitor (e.g., AMG 386), epothilone analog (e.g., ixabepilone), proteasome inhibitor (e.g., carfilzomib), IGF-1 receptor inhibitor (e.g., OSI 906, AMG 479), PARP inhibitor (e.g., veliparib, AG014699, iniparib, MK-4827), Aurora kinase inhibitor (e.g., MLN8237, ENMD-2076), angiogenesis inhibitor (e.g., lenalidomide), DHFR inhibitor (e.g., pralatrexate), radioimmunotherapeutic agnet (e.g., Hu3S193), statin (e.g., lovastatin), topoisomerase 1 inhibitor (e.g., NKTR-102), cancer vaccine (e.g., p53 synthetic long peptides vaccine, autologous OC-DC vaccine), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 6727), gamma-secretase inhibitor (e.g., RO4929097), Wee-1 inhibitor (e.g., MK-1775), antitubulin agent (e.g., vinorelbine, E7389), immunotoxin (e.g., denileukin diftitox), SB-485232, vascular-disrupting agent (e.g., AVE8062), integrin inhibitor (e.g., EMD 525797), kinesin-spindle inhibitor (e.g., 4SC-205), revlimid, HER2 inhibitor (e.g., MGAH22), ErrB3 inhibitor (e.g., MM-121), radiation therapy; and combinations thereof.

In one exemplary embodiment, the anti-TIM-3 antibody molecule, alone or in combination with another immunomodulator (e.g., an anti-LAG-3, anti-PD-1 or anti-PD-L1 antibody molecule), is used to treat a myeloma, alone or in combination with one or more of: chemotherapy or other anti-cancer agents (e.g., thalidomide analogs, e.g., lenalidomide), HSCT (Cook, R. (2008) *J Manag Care Pharm.* 14(7 Suppl):19-25), an anti-TIM3 antibody (Hallett, W H D et al. (2011) *J of American Society for Blood and Marrow Transplantation* 17(8):1133-145), tumor antigen-pulsed dendritic cells, fusions (e.g., electrofusions) of tumor cells and dendritic cells, or vaccination with immunoglobulin idiotype produced by malignant plasma cells (reviewed in Yi, Q. (2009) *Cancer J.* 15(6):502-10).

In yet another embodiment, the anti-TIM-3 antibody molecule, alone or in combination with another immunomodulator (e.g., an anti-LAG-3, anti-PD-1 or anti-PD-L1 antibody molecule), is used to treat a renal cancer, e.g., renal cell carcinoma (RCC) or metastatic RCC. The anti-TIM-3 antibody molecule can be administered in combination with one or more of: an immune-based strategy (e.g., interleukin-2 or interferon-α), a targeted agent (e.g., a VEGF inhibitor such as a monoclonal antibody to VEGF, e.g., bevacizumab (Rini, B. I. et al. (2010) *J. Clin. Oncol.* 28(13):2137-2143)); a VEGF tyrosine kinase inhibitor such as sunitinib, sorafenib, axitinib and pazopanib (reviewed in Pal. S. K. et al. (2014) *Clin. Advances in Hematology & Oncology* 12(2):90-99)); an RNAi inhibitor), or an inhibitor of a downstream mediator of VEGF signaling, e.g., an inhibitor of the mammalian target of rapamycin (mTOR), e.g., everolimus and temsirolimus (Hudes, G. et al. (2007) *N. Engl. J. Med.* 356(22):2271-2281, Motzer, R. J. et al. (2008) *Lancet* 372: 449-456).

An example of suitable therapeutics for use in combination with the anti-TIM-3 antibody molecules described herein, alone or in combination with another immunomodulator (e.g., an anti-LAG-3, anti-PD-1 or anti-PD-L1 antibody molecule), for treatment of chronic myelogenous leukemia (AML) according to the invention includes, but is not limited to, a chemotherapeutic (e.g., cytarabine, hydroxyurea, clofarabine, melphalan, thiotepa, fludarabine, busulfan, etoposide, cordycepin, pentostatin, capecitabine, azacitidine, cyclophosphamide, cladribine, topotecan), tyrosine kinase inhibitor (e.g., BCR/ABL inhibitor (e.g., imatinib, nilotinib), ON 01910.Na, dual inhibitor (e.g., dasatinib, bosutinib), multikinase inhibitor (e.g., DCC-2036, ponatinib, sorafenib, sunitinib, RGB-286638)), interferon alfa, steroids, apoptotic agent (e.g., omacetaxine mepesuccinat), immunotherapy (e.g., allogeneic CD4+ memory Th1-like T cells/microparticle-bound anti-CD3/anti-CD28, autologous cytokine induced killer cells (CIK), AHN-12), CD52 targeting agent (e.g., alemtuzumab), HSP90 inhibitor (e.g., tanespimycin, STA-9090, AUY922, XL888), mTOR inhibitor (e.g., everolimus), SMO antagonist (e.g., BMS 833923), ribonucleotide reductase inhibitor (e.g., 3-AP), JAK-2 inhibitor (e.g., INCB018424), Hydroxychloroquine, retinoid (e.g., fenretinide), cyclin-dependent kinase inhibitor (e.g., UCN-01), HDAC inhibitor (e.g., belinostat, vorinostat, JNJ-26481585), PARP inhibitor (e.g., veliparib), MDM2 antagonist (e.g., RO5045337), Aurora B kinase inhibitor (e.g., TAK-901), radioimmunotherapy (e.g., actinium-225-labeled anti-CD33 antibody HuM195), Hedgehog inhibitor (e.g., PF-04449913), STAT3 inhibitor (e.g., OPB-31121), KB004, cancer vaccine (e.g., AG858), bone marrow transplantation, stem cell transplantation, radiation therapy, and combinations thereof.

An example of suitable therapeutics for use in combination with the anti-TIM-3 antibody molecules, alone or in combination with another immunomodulator (e.g., an anti-LAG-3, anti-PD-1 or anti-PD-L1 antibody molecule), for treatment of chronic lymphocytic leukemia (CLL) includes, but is not limited to, a chemotherapeutic agent (e.g., fludarabine, cyclophosphamide, doxorubicin, vincristine, chlorambucil, bendamustine, chlorambucil, busulfan, gemcitabine, melphalan, pentostatin, mitoxantrone, 5-azacytidine, pemetrexed disodium), tyrosine kinase inhibitor (e.g., EGFR inhibitor (e.g., erlotinib), BTK inhibitor (e.g., PCI-32765), multikinase inhibitor (e.g., MGCD265, RGB-286638), CD-20 targeting agent (e.g., rituximab, ofatumumab, RO5072759, LFB-R603), CD52 targeting agent (e.g., alemtuzumab), prednisolone, darbepoetin alfa, lenalidomide, Bcl-2 inhibitor (e.g., ABT-263), immunotherapy (e.g., allogeneic CD4+ memory Th1-like T cells/microparticle-bound anti-CD3/anti-CD28, autologous cytokine induced killer cells (CIK)), HDAC inhibitor (e.g., vorinostat, valproic acid, LBH589, JNJ-26481585, AR-42), XIAP inhibitor (e.g., AEG35156), CD-74 targeting agent (e.g., milatuzumab), mTOR inhibitor (e.g., everolimus), AT-101, immunotoxin (e.g., CAT-8015, anti-Tac(Fv)-PE38 (LMB-2)), CD37 targeting agent (e.g., TRU-016), radioimmunotherapy (e.g., 131-tositumomab), hydroxychloroquine, perifosine, SRC inhibitor (e.g., dasatinib), thalidomide, PI3K delta inhibitor (e.g., CAL-101), retinoid (e.g., fenretinide), MDM2 antagonist (e.g., RO5045337), plerixafor, Aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), hypoxia-activated prodrug (e.g., TH-302), paclitaxel or a paclitaxel agent, HSP90 inhibitor, AKT inhibitor (e.g., MK2206), HMG-CoA inhibitor (e.g., simvastatin), GNKG186, radiation therapy, bone marrow transplantation, stem cell transplantation, and a combination thereof.

An example of suitable therapeutics for use in combination with the anti-TIM-3 antibody molecules described herein, alone or in combination with another immunomodulator (e.g., an anti-LAG-3, anti-PD-1 or anti-PD-L1 antibody molecule), for treatment of acute lymphocytic leukemia (ALL) includes, but is not limited to, a chemotherapeutic agent (e.g., prednisolone, dexamethasone, vincristine, asparaginase, daunorubicin, cyclophosphamide, cytarabine, etoposide, thioguanine, mercaptopurine, clofarabine, liposomal annamycin, busulfan, etoposide, capecitabine, decitabine, azacitidine, topotecan, temozolomide), tyrosine kinase inhibitor (e.g., BCR/ABL inhibitor (e.g., imatinib, nilotinib), ON 01910.Na, multikinase inhibitor (e.g., sorafenib)), CD-20 targeting agent (e.g., rituximab), CD52 targeting agent (e.g., alemtuzumab), HSP90 inhibitor (e.g., STA-9090), mTOR inhibitor (e.g., everolimus, rapamycin), JAK-2 inhibitor (e.g., INCB018424), HER2/neu receptor inhibitor (e.g., trastuzumab), proteasome inhibitor (e.g., bortezomib), methotrexate, asparaginase, CD-22 targeting agent (e.g., epratuzumab, inotuzumab), immunotherapy (e.g., autologous cytokine induced killer cells (CIK), AHN-12), blinatumomab, cyclin-dependent kinase inhibitor (e.g., UCN-01), CD45 targeting agent (e.g., BC8), MDM2 antagonist (e.g., RO5045337), immunotoxin (e.g., CAT-8015, DT2219ARL), HDAC inhibitor (e.g., JNJ-26481585), JVRS-100, paclitaxel or a paclitaxel agent, STAT3 inhibitor (e.g., OPB-31121), PARP inhibitor (e.g., veliparib), EZN-2285, radiation therapy, steroid, bone marrow transplantation, stem cell transplantation, or a combination thereof.

An example of suitable therapeutics for use in combination with the anti-TIM-3 antibody molecules described herein, alone or in combination with another immunomodulator (e.g., an anti-LAG-3, anti-PD-1 or anti-PD-L1 antibody molecule), for treatment of acute myeloid leukemia (AML) includes, but is not limited to, a chemotherapeutic agent (e.g., cytarabine, daunorubicin, idarubicin, clofarabine, decitabine, vosaroxin, azacitidine, clofarabine, ribavirin, CPX-351, treosulfan, elacytarabine, azacitidine), tyrosine kinase inhibitor (e.g., BCR/ABL inhibitor (e.g., imatinib, nilotinib), ON 01910.Na, multikinase inhibitor (e.g., midostaurin, SU 11248, quizartinib, sorafinib)), immunotoxin (e.g., gemtuzumab ozogamicin), DT3881L3 fusion protein, HDAC inhibitor (e.g., vorinostat, LBH589), plerixafor, mTOR inhibitor (e.g., everolimus), SRC inhibitor (e.g., dasatinib), HSP90 inhbitor (e.g., STA-9090), retinoid (e.g., bexarotene, Aurora kinase inhibitor (e.g., BI 811283), JAK-2 inhibitor (e.g., INCB018424), Polo-like kinase inhibitor (e.g., BI 6727), cenersen, CD45 targeting agent (e.g., BC8), cyclin-dependent kinase inhibitor (e.g., UCN-01), MDM2 antagonist (e.g., RO5045337), mTOR inhibitor (e.g., everolimus), LY573636-sodium, ZRx-101, MLN4924, lenalidomide, immunotherapy (e.g., AHN-12), histamine dihydrochloride, radiation therapy, bone marrow transplantation, stem cell transplantation, and a combination thereof.

An example of suitable therapeutics for use in combination with the anti-TIM-3 antibody molecules described herein, alone or in combination with another immunomodulator (e.g., an anti-LAG-3, anti-PD-1 or anti-PD-L1 antibody molecule), for treatment of multiple myeloma (MM) includes, but is not limited to, a chemotherapeutic agent (e.g., melphalan, amifostine, cyclophosphamide, doxorubicin, clofarabine, bendamustine, fludarabine, adriamycin, SyB L-0501), thalidomide, lenalidomide, dexamethasone, prednisone, pomalidomide, proteasome inhibitor (e.g., bortezomib, carfilzomib, MLN9708), cancer vaccine (e.g., GVAX), CD-40 targeting agent (e.g., SGN-40, CHIR-12.12), perifosine, zoledronic acid, Immunotherapy (e.g., MAGE-A3, NY-ESO-1, HuMax-CD38), HDAC inhibitor (e.g., vorinostat, LBH589, AR-42), aplidin, cycline-dependent kinase inhibitor (e.g., PD-0332991, dinaciclib), arsenic trioxide, CB3304, HSP90 inhibitor (e.g., KW-2478), tyrosine kinase inhibitor (e.g., EGFR inhibitor (e.g., cetuximab), multikinase inhibitor (e.g., AT9283)), VEGF inhibitor (e.g., bevacizumab), plerixafor, MEK inhibitor (e.g., AZD6244), IPH2101, atorvastatin, immunotoxin (e.g., BB-10901), NPI-0052, radioimmunotherapeutic (e.g., yttrium Y 90 ibritumomab tiuxetan), STAT3 inhibitor (e.g., OPB-31121), MLN4924, Aurora kinase inhibitor (e.g., ENMD-2076), IMGN901, ACE-041, CK-2 inhibitor (e.g., CX-4945), radiation therapy, bone marrow transplantation, stem cell transplantation, and a combination thereof.

An example of suitable therapeutics for use in combination with the anti-TIM-3 antibody molecules, alone or in combination with another immunomodulator (e.g., an anti-LAG-3, anti-PD-1 or anti-PD-L1 antibody molecule), for treatment of prostate cancer includes, but is not limited to, a chemotherapeutic agent (e.g., docetaxel, carboplatin, fludarabine), abiraterone, hormonal therapy (e.g., flutamide, bicalutamide, nilutamide, cyproterone acetate, ketoconazole, aminoglutethimide, abarelix, degarelix, leuprolide, goserelin, triptorelin, buserelin), tyrosine kinase inhibitor (e.g., dual kinase inhibitor (e.g., lapatanib), multikinase inhibitor (e.g., sorafenib, sunitinib)), VEGF inhibitor (e.g., bevacizumab), TAK-700, cancer vaccine (e.g., BPX-101, PEP223), lenalidomide, TOK-001, IGF-1 receptor inhibitor (e.g., cixutumumab), TRC105, Aurora A kinase inhibitor (e.g., MLN8237), proteasome inhibitor (e.g., bortezomib), OGX-011, radioimmunotherapy (e.g., HuJ591-GS), HDAC inhibitor (e.g., valproic acid, SB939, LBH589), hydroxychloroquine, mTOR inhibitor (e.g., everolimus), dovitinib lactate, diindolylmethane, efavirenz, OGX-427, genistein, IMC-3G3, bafetinib, CP-675,206, radiation therapy, surgery, or a combination thereof.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of HNSCC includes, but is not limited to, one or both of Compound A8 as described herein (or a compound described in PCT Publication No. WO2010/029082) and cetuximab (e.g., Erbitux, marketed by BMS). In some embodiments, the therapeutic (e.g., the Compound A8 or compound related to A8) is a PI3K modulator, e.g., a PI3K inhibitor. In some embodiments, the therapeutic (e.g., cetuximab) modulates, e.g., inhibits, EGFR. In some embodiments, the cancer has, or is identified as having, elevated levels or activity of PI3K or EGFR compared to a control cell or reference value.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of gastric cancer, e.g., MSI-high and/or EBV+ gastric cancer, includes, but is not limited to, Compound A8 as described herein (or a compound described in PCT Publication No. WO2010/029082). In some embodiments, the therapeutic (e.g., the Compound A8 or compound related to A8) is a PI3K modulator, e.g., a PI3K inhibitor. In some embodiments, the cancer has, or is identified as having, elevated levels or activity of PI3K compared to a control cell or reference value.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of gastric cancer, e.g., MSI-high and/or RNF43-inactivated gastric cancer, includes, but is not limited to, Compound A28 as described herein (or a compound described in PCT Publication No. WO2010/101849). In some embodiments, the therapeutic (e.g., the Compound A28 or compound related to A28) is a modulator, e.g., inhibitor, of porcupine. In some embodiments, the cancer has, or is identified as having, elevated levels or activity of porcupine compared to a control cell or reference value.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of GI stromal tumor (GIST), includes, but is not limited to, Compound A16 as described herein (or a compound described in PCT Publication No. WO1999/003854). In some embodiments, the therapeutic (e.g., the Compound A16 or compound related to A16) is a modulator, e.g., inhibitor, of a tyrosine kinase. In some embodiments, the cancer has, or is determined to have, elevated levels or activity of a tyrosine kinase compared to a control cell or reference value.

An example of suitable therapeutics for use in combination with the anti-TIM-3 antibody molecules, alone or in combination with another immunomodulator (e.g., an anti- LAG-3, anti-PD-L1 or anti-PD-1 antibody molecule), for treatment of NSCLC, e.g., squamous or adenocarcinoma, includes, but is not limited to, one or both of Compound A17 as described herein (or a compound described in U.S. Pat. Nos. 7,767,675 and 8,420,645) and Compound A23 as described herein (or a compound described in PCT Publication No. WO2003/077914). In some embodiments, the compound (e.g., the Compound A17 or compound related to A17) modulates, e.g., inhibits, c-MET. In some embodiments, the compound (e.g., the Compound A23 or compound related to A23) modulates, e.g., inhibits, Alk. In some embodiments, the cancer has, or is determined to have, elevated levels or activity of one or both of c-MET or Alk compared to a control cell or reference value. In some embodiments, the cancer has, or is identified as having, a mutation in EGFR.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of melanoma (e.g., NRAS melanoma) includes, but is not limited to, one or both of Compound A24 as described herein (or a compound described in U.S. Pat. Nos. 8,415,355 and 8,685,980) and Compound A34 as described herein (or a compound described in PCT Publication No. WO2003/077914). In some embodiments, the compound (e.g., the Compound A24 or compound related to A24) modulates, e.g., inhibits, one or more of JAK and CDK4/6. In some embodiments, the compound (e.g., the Compound A34 or compound related to A34) modulates, e.g., inhibits, MEK. In some embodiments, the cancer has, or is identified as having, elevated levels or activity of one or more of JAK, CDK4/6, and MEK compared to a control cell or reference value.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of melanoma (e.g., NRAS melanoma) includes, but is not limited to, one or both of Compound A29 as described herein (or a compound described in PCT Publication No. WO2011/025927) and Compound A34 as described herein (or a compound described in PCT Publication No. WO2003/077914). In some embodiments, the compound (e.g., the Compound A29 or compound related to A29) modulates, e.g., inhibits, BRAF. In some embodiments, the compound (e.g., the Compound A34 or compound related to A34) modulates, e.g., inhibits, MEK. In some embodiments, the cancer has, or is identified as having, elevated levels or activity of one or both of BRAF and MEK compared to a control cell or reference value.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of squamous NSCLC includes, but is not limited to, Compound A5 as described herein (or a compound described in U.S. Pat. No. 8,552,002). In some embodiments, the compound (e.g., the Compound A5 or compound related to A5) modulates, e.g., inhibits, FGFR. In some embodiments, the cancer has, or is identified as having, elevated levels or activity of FGFR compared to a control cell or reference value.

An example of suitable therapeutics for use in combination with the anti-TIM-3 antibody molecules, alone or in combination with another immunomodulator (e.g., an anti-LAG-3, anti-PD-L1 or anti-PD-1 antibody molecule), for treatment of colorectal cancer includes, but is not limited to, one or both of Compound A29 as described herein (or a compound PCT Publication No. WO2011/025927) and cetuximab (e.g., Erbitux, marketed by BMS). In some embodiments, the therapeutic (e.g., the Compound A29 or compound related to A29) modulates, e.g., inhibits, BRAF. In some embodiments, the therapeutic (e.g., cetuximab) modulates, e.g., inhibits EGFR. In some embodiments, the cancer has, or is identified as having, elevated levels or activity of BRAF or EGFR compared to a control cell or reference value.

This disclosure also provides a method of treating cancer with Compound A8, cetuximab, and a TIM-3 antibody molecule (optionally in combination with a PD-1 antibody molecule or LAG-3 antibody molecule). In some embodiments, the patient is first treated with Compound A8 and cetuximab. This treatment continues for an amount of time, e.g., a predetermined amount of time, e.g., about 1, 2, 4, 6, 8, 10, or 12 months. Next, the TIM-3 antibody molecule (optionally in combination with a PD-1 antibody molecule or LAG-3 antibody molecule) is administered. The TIM-3 antibody can optionally be administered in combination with cetuximab.

In some embodiments, the patient is first treated with all three of Compound A8, cetuximab, and a TIM-3 antibody molecule (optionally in combination with a PD-1 antibody molecule or LAG-3 antibody molecule). This treatment continues for an amount of time, e.g., a predetermined amount of time, e.g., about 6, 8, 10, or 12 months. Next, the Compound A8 and/or cetuximab can be tapered off, so that the maintenance phase involves treatment with the TIM-3 antibody molecule (e.g., as a monotherapy, or in combination with a PD-1 antibody molecule or LAG-3 antibody molecule) but not Compound A8 or cetuximab.

In other embodiments, the three compounds (Compound A8, cetuximab, and a TIM-3 antibody molecule, optionally in combination with a PD-1 antibody molecule or LAG-3 antibody molecule) are given sequentially at the outset of the treatment. For instance, Compound A8 and cetuximab can be given first, as described above. Next, the TIM-3 antibody molecule (optionally in combination with a PD-1 antibody molecule or LAG-3 antibody molecule) is added to the regimen. Next, the Compound A8 and/or cetuximab can be tapered off as described above.

Exemplary doses for the three (or more) agent regimens are as follows. The TIM-3 antibody molecule can be administered, e.g., at a dose of about 1 to 40 mg/kg, e.g., 1 to 30 mg/kg, e.g., about 5 to 25 mg/kg, about 10 to 20 mg/kg, about 1 to 5 mg/kg, or about 3 mg/kg. In some embodiments, the Compound A8 is administered at a dose of approximately 200-300, 300-400, or 200-400 mg. In some embodiments, the cetuximab is administered at a 400 mg/m2 initial dose as a 120-minute intravenous infusion followed by 250 mg/m2 weekly infused over 60 minutes. In embodiments, one or more of the Compound A8, cetuximab, and TIM-3 antibody molecule is administered at a dose that is lower than the dose at which that agent is typically administered as a monotherapy, e.g., about 0-10%, 10-20%, 20-30%, 30-40%, 40-50%, 50-60%, 60-70%, 70-80%, or 80-90% lower than the dose at which that agent is typically administered as a monotherapy. In embodiments, the one or more of the Compound A8, cetuximab, and TIM-3 antibody molecule is administered at a dose that is lower than the dose of that agent recited in this paragraph, e.g., about 0-10%, 10-20%, 20-30%, 30-40%, 40-50%, 50-60%, 60-70%, 70-80%, or 80-90% lower than the dose of that agent recited in this paragraph. In certain embodiments, the concentration of the Compound A8 that is required to achieve inhibition, e.g., growth inhibition, is lower when the Compound A8 is administered in combination with one or both of the cetuximab and TIM-3 antibody molecule than when the Compound A8 is administered individually. In certain embodiments, the concentration of the cetuximab that is required to achieve inhibition, e.g., growth inhibition, is lower when the cetuximab is administered in combination with one or both of the Compound A8 and TIM-3 antibody molecule than when the cetuximab is administered individually. In certain embodiments, the concentration of the TIM-3 antibody molecule that is required to achieve inhibition, e.g., growth inhibition, is lower when the TIM-3 antibody molecule is administered in combination with one or both of the cetuximab and Compound A8 than when the TIM-3 antibody molecule is administered individually.

Additionally disclosed herein is a method of treating cancer with the anti-TIM-3 antibody molecules, alone or in combination with another immunomodulator (e.g., an anti-LAG-3, anti-PD-L1 or anti-PD-1 antibody molecule), and a targeted anti-cancer agent, e.g., an agent that targets one or more proteins. In some embodiments, the anti-TIM-3 antibody molecule (and optionally other immunomodulator(s)) are administered first, and the targeted anti-cancer agent is administered second. The length of time between administration of the anti-TIM-3 antibody molecule and the targeted anti-cancer agent can be, e.g., 10, 20, or 30 minutes, 1, 2, 4, 6, or 12 hours, or 1, 2, 3, 4, 5, 6, or 7 days, or any span of time within this range. In certain embodiments, the anti-TIM-3 antibody molecule is administered repeatedly over a period of time (e.g., 1, 2, 3, 4, 5, or 6 days, or 1, 2, 4, 8, 12, 16, or 20 weeks, or any span of time within this range) before the targeted anti-cancer agent is administered. In other embodiments, the anti-TIM-3 antibody molecule and the targeted anti-cancer agent are administered at substantially the same time.

Methods of Treating Infectious Diseases

Other methods of the invention are used to treat patients that have been exposed to particular toxins or pathogens. Based on, at least, the Examples herein, anti-TIM-3 antibodies can stimulate NK cell mediated killing of target cells and can enhances IFN-gamma secretion and proliferation of CD4+ T cells. Accordingly, in certain embodiments, the anti-TIM-3 antibody molecules described herein are suitable for use in stimulating an immune response against an infectious agent. Accordingly, another aspect of the invention provides a method of treating an infectious disease in a subject comprising administering to the subject an anti-TIM-3 antibody molecule, such that the subject is treated for the infectious disease. In the treatment of infection (e.g., acute and/or chronic), administration of the anti-TIM-3 antibody molecules can be combined with conventional treatments in addition to or in lieu of stimulating natural host immune defenses to infection. Natural host immune defenses to infection include, but are not limited to inflammation, fever, antibody-mediated host defense, T-lymphocyte-mediated host defenses, including lymphokine secretion and cytotoxic T-cells (especially during viral infection), complement mediated lysis and opsonization (facilitated phagocytosis), and phagocytosis. The ability of the anti-TIM-3 antibody molecules to reactivate dysfunctional T-cells would be useful to treat chronic infections, in particular those in which cell-mediated immunity is important for complete recovery.

Certain methods described herein are used to treat patients that have been exposed to particular toxins or pathogens. Some aspects provides a method of treating an infectious disease in a subject comprising administering to the subject an anti-TIM-3 antibody molecule, such that the subject is treated for the infectious disease.

Similar to its application to tumors as discussed in the previous section, aIn embodiments, the anti-TIM-3 antibody molecules can be used alone, or as an adjuvant, in combination with vaccines, to stimulate the immune response to, e.g., pathogens or toxins. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas Aeruginosa*. Anti-TIM-3 antibody molecule therapy is also useful against established infections by agents such as HIV that present altered antigens over the course of the infections.

Accordingly, in some embodiments an anti-TIM-3 antibody molecule is used to treat a subject that has an infection or is at risk of having an infection. An infection refers to, e.g., a disease or condition attributable to the presence in a host of a foreign organism or agent that reproduces within the host. Infections typically involve breach of a normal mucosal or other tissue barrier by an infectious organism or agent. A subject that has an infection is a subject having objectively measurable infectious organisms or agents present in the subject's body. A subject at risk of having an infection is a subject that is predisposed to develop an infection. Such a subject can include, for example, a subject with a known or suspected exposure to an infectious organism or agent. A subject at risk of having an infection also can include a subject with a condition associated with impaired ability to mount an immune response to an infectious organism or agent, e.g., a subject with a congenital or acquired immunodeficiency, a subject undergoing radiation therapy or chemotherapy, a subject with a burn injury, a subject with a traumatic injury, a subject undergoing surgery or other invasive medical or dental procedure.

Infections are broadly classified as bacterial, viral, fungal, or parasitic based on the category of infectious organism or agent involved. Other less common types of infection include, e.g., infections involving rickettsiae, mycoplasmas, and agents causing scrapie, bovine spongiform encephalopthy (BSE), and prion diseases (e.g., kuru and Creutzfeldt-Jacob disease). Examples of bacteria, viruses, fungi, and parasites which cause infection are well known in the art. An infection can be acute, subacute, chronic, or latent, and it can be localized or systemic. Furthermore, an infection can be predominantly intracellular or extracellular during at least one phase of the infectious organism's or agent's life cycle in the host.

Viruses

Examples of viruses that have been found to cause infections in humans include but are not limited to: Retroviridae (e.g., human immunodeficiency viruses, such as HIV-1 (also referred to as HTLV-III), HIV-2, LAV or HTLV-III/LAV, or HIV-III, and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., corona-viruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=enterally transmitted; class 2=parenterally transmitted (i.e., Hepatitis C); Norwalk and related viruses, and astroviruses). Some examples of pathogenic viruses causing infections treatable by methods herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

For infections resulting from viral causes, the anti-TIM-3 antibody molecules can be combined by application simultaneous with, prior to or subsequent to application of standard therapies for treating viral infections. Such standard therapies vary depending upon type of virus, although in almost all cases, administration of human serum containing antibodies (e.g., IgA, IgG) specific to the virus can be effective.

Some examples of pathogenic viruses causing infections treatable by methods include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, arboviral encephalitis virus, and ebolaviruses (e.g., BDBV, EBOV, RESTV, SUDV and TAFV).

In one embodiment, the infection is an influenza infection. Influenza infection can result in fever, cough, myalgia, headache and malaise, which often occur in seasonal epidemics. Influenza is also associated with a number of postinfectious disorders, such as encephalitis, myopericarditis, Goodpasture's syndrome, and Reye's syndrome. Influenza infection also suppresses normal pulmonary antibacterial defenses, such that patient's recovering from influenza have an increased risk of developing bacterial pneumonia. Influenza viral surface proteins show marked antigenic variation, resulting from mutation and recombination. Thus, cytolytic T lymphocytes are the host's primary vehicle for the elimination of virus after infection. Influenza is classified into three primary types: A, B and C. Influenza A is unique in that it infects both humans and many other animals (e.g., pigs, horses, birds and seals) and is the principal cause of pandemic influenza. Also, when a cell is infected by two different influenza A strains, the segmented RNA genomes of two parental virus types mix during replication to create a hybrid replicant, resulting in new epidemic strains. Influenza B does not replicate in animals and thus has less genetic variation and influenza C has only a single serotype.

Most conventional therapies are palliatives of the symptoms resulting from infection, while the host's immune response actually clears the disease. However, certain strains (e.g., influenza A) can cause more serious illness and death. Influenza A may be treated both clinically and prophylactically by the administration of the cyclic amines inhibitors amantadine and rimantadine, which inhibit viral replication. However, the clinical utility of these drugs is limited due to the relatively high incidence of adverse reactions, their narrow anti-viral spectrum (influenza A only), and the propensity of the virus to become resistant. The administration of serum IgG antibody to the major influenza surface proteins, hemagglutinin and neuraminidase can prevent pulmonary infection, whereas mucosal IgA is required to prevent infection of the upper respiratory tract and trachea. The most effective current treatment for influenza is vaccination with the administration of virus inactivated with formalin or β-propiolactone.

In another embodiment, the infection is a hepatitis infection, e.g., a Hepatitis B or C infection.

Hepatitis B virus (HB-V) is the most infectious known bloodborne pathogen. It is a major cause of acute and chronic heptatis and hepatic carcinoma, as well as life-long, chronic infection. Following infection, the virus replicates in hepatocytes, which also then shed the surface antigen HBsAg. The detection of excessive levels of HBsAg in serum is used a standard method for diagnosing a hepatitis B infection. An acute infection may resolve or it can develop into a chronic persistent infection. Current treatments for chronic HBV include α-interferon, which increases the expression of class I human leukocyte antigen (HLA) on the surface of hepatocytes, thereby facilitating their recognition by cytotoxic T lymphocytes. Additionally, the nucleoside analogs ganciclovir, famciclovir and lamivudine have also shown some efficacy in the treatment of HBV infection in clinical trials. Additional treatments for HBV include pegylated α-interferon, adenofvir, entecavir and telbivudine. While passive immunity can be conferred through parental administration of anti-HBsAg serum antibodies, vaccination with inactivated or recombinant HBsAg also confers resistance to infection. The anti-TIM-3 antibody molecules may be combined with conventional treatments for hepatitis B infections for therapeutic advantage.

Hepatitis C virus (HC-V) infection may lead to a chronic form of hepatitis, resulting in cirrhosis. While symptoms are similar to infections resulting from Hepatitis B, in distinct contrast to HB-V, infected hosts can be asymptomatic for 10-20 years. The anti-TIM-3 antibody molecule can be administered as a monotherapy, or combined with the standard of care for hepatitis C infection. For example, the anti-TIM-3 antibody molecule can be administered with one or more of Sovaldi (sofosbuvir) Olysio (simeprevir), plus ribavirin or pegylated interferon. Although regimens that include Incivek (telaprevir) or Victrelis (boceprevir) plus ribavirin and pegylated interferon are also approved, they are associated with increased side effects and longer duration of treatment and are therefore not considered preferred regimens.

Conventional treatment for HC-V infection includes the administration of a combination of α-interferon and ribavirin. A promising potential therapy for HC-V infection is the protease inhibitor telaprevir (VX-960). Additional treatments include: anti-PD-1 antibody (MDX-1106, Medarex), bavituximab (an antibody that binds anionic phospholipid phosphatidylserine in a B2-glycoprotein I dependent manner, Peregrine Pharmaceuticals), anti-HPV viral coat protein E2 antibod(y)(ies) (e.g., ATL 6865–Ab68+Ab65, XTL Pharmaceuticals) and Civacir® (polyclonal anti-HCV human immune globulin). The anti-PD-L1 antibodies of the invention may be combined with one or more of these treatments for hepatitis C infections for therapeutic advantage. Protease, polymerase and NSSA inhibitors which may be used in combination with the anti-TIM-3 antibody molecules to specifically treat Hepatitis C infection include those described in US 2013/0045202, incorporated herein by reference.

In another embodiment, the infection is a measles virus. After an incubation of 9-11 days, hosts infected with the measles virus develop fever, cough, coryza and conjunctivitis. Within 1-2 days, an erythematous, maculopapular rash develop, which quickly spreads over the entire body. Because infection also suppresses cellular immunity, the host is at greater risk for developing bacterial superinfections, including otitis media, pneumonia and postinfectious encephalomyelitis. Acute infection is associated with significant morbidity and mortality, especially in malnourished adolescents.

Treatment for measles includes the passive administration of pooled human IgG, which can prevent infection in non-immune subjects, even if given up to one week after exposure. However, prior immunization with live, attenuated virus is the most effective treatment and prevents disease in more than 95% of those immunized. As there is one serotype of this virus, a single immunization or infection typically results in protection for life from subsequent infection.

In a small proportion of infected hosts, measles can develop into SSPE, which is a chronic progressive neurologic disorder resulting from a persistent infection of the central nervous system. SSPE is caused by clonal variants of measles virus with defects that interfere with virion assembly and budding. For these patients, reactivation of T-cells with the anti-TIM-3 antibody molecules so as to facilitate viral clearance would be desirable.

In another embodiment, the infection is HIV. HIV attacks CD4+ cells, including T-lymphocytes, monocyte-macrophages, follicular dendritic cells and Langerhan's cells, and $CD4^+$ helper/inducer cells are depleted. As a result, the host acquires a severe defect in cell-mediated immunity. Infection with HIV results in AIDS in at least 50% of individuals, and is transmitted via sexual contact, administration of infected blood or blood products, artificial insemination with infected semen, exposure to blood-containing needles or syringes and transmission from an infected mother to infant during childbirth.

A host infected with HIV may be asymptomatic, or may develop an acute illness that resembling mononucleosis—fever, headache, sore throat, malaise and rash. Symptoms can progress to progressive immune dysfunction, including persistent fever, night sweats, weight loss, unexplained diarrhea, eczema, psoriasis, seborrheic dermatitis, herpes zoster, oral candidiasis and oral hairy leukoplakia. Opportunistic infections by a host of parasites are common in patients whose infections develop into AIDS.

Treatments for HIV include antiviral therapies including nucleoside analogs, zidovudine (AST) either alone or in combination with didanosine or zalcitabine, dideoxyinosine, dideoxycytidine, lamivudine, stavudine; reverse transcriptive inhibitors such as delavirdine, nevirapine, loviride, and proteinase inhibitors such as saquinavir, ritonavir, indinavir and nelfinavir. The anti-TIM-3 antibody molecules may be combined with conventional treatments for HIV infections for therapeutic advantage.

In another embodiment, the infection is a Cytomegalovirus (CMV). CMV infection is often associated with persistent, latent and recurrent infection. CMV infects and remains latent in monocytes and granulocyte-monocyte progenitor cells. The clinical symptoms of CMV include mononucleosis-like symptoms (i.e., fever, swollen glands, malaise), and a tendancy to develop allergic skin rashes to antibiotics. The virus is spread by direct contact. The virus is shed in the urine, saliva, semen and to a lesser extent in other body fluids. Transmission can also occur from an infected mother to her fetus or newborn and by blood transfusion and organ transplants. CMV infection results in general impairment of cellular immunity, characterized by impaired blastogenic responses to nonspecific mitogens and specific CMV antigens, diminished cytotoxic ability and elevation of CD8 lymphocyte number of $CD4^+$ lymphocytes.

Treatments of CMV infection include the anti-virals ganciclovir, foscarnet and cidovir, but these drugs are typically only prescribed in immunocompromised patients. The anti-TIM-3 antibody molecules may be combined with conventional treatments for cytomegalovirus infections for therapeutic advantage.

In another embodiment, the infection is Epstein-Barr virus (EBV). EBV can establish persistent and latent infections and primarily attacks B cells. Infection with EBV results in the clinical condition of infectious mononucleosis, which includes fever, sore throat, often with exudate, generalized lymphadenopathy and splenomegaly. Hepatitis is also present, which can develop into jaundice.

While typical treatments for EBV infections are palliative of symptoms, EBV is associated with the development of certain cancers such as Burkitt's lymphoma and nasopharyngeal cancer. Thus, clearance of viral infection before these complications result would be of great benefit. The anti-TIM-3 antibody molecules may be combined with conventional treatments for Epstein-Barr virus infections for therapeutic advantage.

In another embodiment, the infection is Herpes simplex virus (HSV). HSV is transmitted by direct contact with an infected host. A direct infection may be asymptomatic, but typically result in blisters containing infectious particles. The disease manifests as cycles of active periods of disease, in which lesions appear and disappear as the viral latently infect the nerve ganglion for subsequent outbreaks. Lesions may be on the face, genitals, eyes and/or hands. In some case, an infection can also cause encephalitis.

Treatments for herpes infections are directed primarily to resolving the symptomatic outbreaks, and include systemic antiviral medicines such as: acyclovir (e.g., Zovirax®), valaciclovir, famciclovir, penciclovir, and topical medications such as docosanol (Abreva®), tromantadine and zilactin. The clearance of latent infections of herpes would be of great clinical benefit. The anti-TIM-3 antibody molecules may be combined with conventional treatments for herpes virus infections for therapeutic advantage.

In another embodiment, the infection is Human T-lymphotrophic virus (HTLV-1, HTLV-2). HTLV is transmitted via sexual contact, breast feeding or exposure to contaminated blood. The virus activates a subset of Tx cells called Th1 cells, resulting in their overproliferation and overproduction of Th1 related cytokines (e.g., IFN-γ and TNF-α). This in turn results in a suppression of Th2 lymphocytes and reduction of Th2 cytokine production (e.g., IL-4, IL-5, IL-10 and IL-13), causing a reduction in the ability of an infected host to mount an adequate immune response to invading organisms requiring a Th2-dependent response for clearnance (e.g., parasitic infections, production of mucosal and humoral antibodies).

HTLV infections cause lead to opportunistic infections resulting in bronchiectasis, dermatitis and superinfections with *Staphylococcus* spp. and *Strongyloides* spp. resulting in death from polymicrobial sepsis. HTLV infection can also lead directly to adult T-cell leukemia/lymphoma and progressive demyelinating upper motor neuron disease known as HAM/TSP. The clearance of HTLV latent infections would be of great clinical benefit. The anti-TIM-3 antibody molecules may be combined with conventional treatments for HTLV infections for therapeutic advantage.

In another embodiment, the infection is Human papilloma virus (HPV). HPV primarily affects keratinocytes and occurs in two forms: cutaneous and genital. Transmission is believed to occur through direct contact and/or sexual activity. Both cutaneous and genital HPV infection, can result in warts and latent infections and sometimes recurring infections, which are controlled by host immunity which controls the symptoms and blocks the appearance of warts, but leaves the host capable of transmitting the infection to others.

Infection with HPV can also lead to certain cancers, such as cervical, anal, vulvar, penile and oropharynial cancer. There are no known cures for HPV infection, but current treatment is topical application of Imiquimod, which stimulates the immune system to attack the affected area. The clearance of HPV latent infections would be of great clinical benefit. The anti-TIM-3 antibodies of the invention may be combined with conventional treatments for HPV infections for therapeutic advantage.

In another embodiment, the infection is Ebola virus (EBOV). EBOV is one of five known viruses within the Ebolavirus genus. EBOV causes severe and often fatal hemorrhagic fever in humans and mammals, known as Ebola virus disease (EVD). Transmission occurs through contact with blood, secretions, organs, or other boldily fluids of infected patients. Currently, there is no proven treatment or vaccine.

Bacterial Infections

Bacteria include both Gram negative and Gram positive bacteria. Examples of Gram positive bacteria include, but are not limited to *Pasteurella* species, Staphylococci species, and *Streptococcus* species. Examples of Gram negative bacteria include, but are not limited to, *Escherichia coli*, *Pseudomonas* species, and *Salmonella* species. Specific examples of infectious bacteria include but are not limited to: *Helicobacter* pyloris, *Borrelia burgdorferi*, *Legionella* pneumophilia, Mycobacteria spp. (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic spp.), *Streptococcus pneumoniae*, pathogenic *Campylobacter* spp., *Enterococcus* spp., *Haemophilus influenzae, Bacillus anthracis, Corynebacterium diphtheriae, Corynebacterium* spp., *Erysipelothrix rhusiopathiae, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Mycobacterium leprae, Rickettsia*, and *Actinomyces israelii*. Some examples of pathogenic bacteria causing infections treatable by methods herein include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic bacteria causing infections treatable by methods of the invention include syphilis, *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lymes disease bacteria. The anti-TIM-3 antibody molecules can be used in combination with existing treatment modalities for the aforesaid infections. For example, Treatments for syphilis include penicillin (e.g., penicillin G.), tetracycline, doxycycline, ceftriaxone and azithromycin.

Lyme disease, caused by *Borrelia burgdorferi* is transmitted into humans through tick bites. The disease manifests initially as a localized rash, followed by flu-like symptoms including malaise, fever, headache, stiff neck and arthralgias. Later manifestations can include migratory and polyarticular arthritis, neurologic and cardiac involvement with cranial nerve palsies and radiculopathy, myocarditis and arrhythmias. Some cases of Lyme disease become persistent, resulting in irreversible damage analogous to tertiary syphilis. Current therapy for Lyme disease includes primarily the administration of antibiotics. Antibiotic-resistant strains may be treated with hydroxychloroquine or methotrexate. Antibiotic refractory patients with neuropathic pain can be treated with gabapentin. Minocycline may be helpful in late/chronic Lyme disease with neurological or other inflammatory manifestations.

Other forms of borreliois, such as those resulting from *B. recurentis, B. hermsii, B. turicatae, B. parikeri, B. hispanica, B. duttonii* and *B. persica*, as well leptospirosis (E.g., *L. interrogans*), typically resolve spontaneously unless blood titers reach concentrations to cause intrahepatic obstruction.

Fungi and Parasites

Examples of fungi include: *Aspergillus* spp., *Blastomyces dermatitidis, Candida albicans*, other *Candida* spp., *Coccidioides immitis, Cryptococcus neoformans, Histoplasma capsulatum, Chlamydia trachomatis, Nocardia* spp., *Pneumocystis carinii*. Some examples of pathogenic fungi causing infections treatable by methods herein include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Parasites include but are not limited to blood-borne and/or tissues parasites such as *Babesia microti, Babesia divergens, Entamoeba histolytica, Giardia lamblia, Leishmania tropica, Leishmania* spp., *Leishmania braziliensis, Leishmania donovani, Plasmodium falciparum, Plasmodium malariae, Plasmodium ovale, Plasmodium vivax*, and *Toxoplasma gondii, Trypanosoma gambiense* and *Trypanosoma rhodesiense* (African sleeping sickness), *Trypanosoma cruzi* (Chagas' disease), and *Toxoplasma gondii*, flat worms, round worms. Some examples of pathogenic parasites causing infections treatable by methods herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

Some examples of pathogenic fungi causing infections treatable by methods of the invention include *Candida* (*albicans, krusei, glabrata, tropicalis*, etc.), *Cryptococcus neoformans, Aspergillus (fumigatus, niger*, etc.), Genus Mucorales (*mucor, absidia, rhizophus*), *Sporothrix schenkii, Blastomyces dermatitidis, Paracoccidioides brasiliensis, Coccidioides immitis* and *Histoplasma capsulatum.*

Some examples of pathogenic parasites causing infections treatable by methods described herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

In some embodiments, the infectious disease is chosen from hepatitis (e.g., hepatis C infection), or sepsis.

In all of the above methods, anti-TIM-3 antibody molecule therapy can be combined with other forms of immunotherapy such as cytokine treatment (e.g., interferons, GM-CSF, G-CSF, IL-2, IL-21), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123).

Methods of administering various antibody molecules are known in the art and are described below. Suitable dosages of the antibody molecules used will depend on the age and weight of the subject and the particular drug used. The antibody molecules can be used as competitive agents for ligand binding to inhibit or reduce an undesirable interaction.

The antibody molecules can be used by themselves or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Additional Combination Therapies

The anti-TIM-3 antibody molecules can be used in combination with other therapies. For example, the combination therapy can include an anti-TIM-3 antibody molecule co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Anti-TIM-3 antibody molecules can be administered in combination with one or more of the existing modalities for treating cancers, including, but not limited to: surgery; radiation therapy (e.g., external-beam therapy which involves three dimensional, conformal radiation therapy where the field of radiation is designed.

In certain aspects, the anti-TIM-3 antibody is co-administered with a second agent that acts on TIM-3 or another element of a TIM-3 pathway.

In some embodiments, e.g., when treating infectious disease, the anti-TIM-3 antibody may be co-administered with, e.g., an antibiotic, an anti-viral agent, or an anti-fungal agent.

In some embodiments, e.g., when treating Crohn's disease, the anti-TIM-3 antibody may be co-administered with, e.g. an anti-inflammatory drug such as 5-aminosalicylic acid (5-ASA), prednisone, or hydrocortisone; purine analogs such as azathioprine; antimetabolites such as methotrexate; TNF-alpha inhibitors, e.g., a monoclonal antibody to tumor necrosis factor alpha (TNF-α), e.g., infliximab, adalimumab, or certolizumab; or integrin inhibitors, e.g., a monoclonal antibody to alpha-4-integrin, e.g., natalizumab.

In some embodiments, e.g., when treating multiple sclerosis, the anti-TIM-3 antibody may be co-administered with, e.g. an interferon such as interferon beta-la, interferon beta-lb, an interferon analog, a random amino acid polymer such as glatiramer acetate; a type II topoisomerase inhibitor such as mitoxantrone; an integrin inhibitor, e.g., a monoclonal antibody to alpha-4-integrin, e.g., natalizumab; a sphingosine 1-phosphate receptor modulator, e.g., fingolimod; a pyrimidines synthesis inhibitor, e.g., a dihydroorotate dehydrogenase inhibitor such as teriflunomide; and other immunomodulatory agents such as dimethyl fumarate.

In some embodiments, e.g., when treating sepsis, the anti-TIM-3 antibody may be co-administered with, e.g. antibiotics; vasopressors such as norepinephrine or dopamine; steroids; Recombinant activated protein C (drotrecogin alpha); intravenous fluids; and ventilation.

In some embodiments, e.g., when treating SIRS (Systemic Inflammatory Response Syndrome) the anti-TIM-3 antibody may be co-administered with, e.g. antibiotics; steroids; antioxidants; or intravenous fluids.

In some embodiments, e.g., when treating glomerulonephritis, the anti-TIM-3 antibody may be co-administered with, e.g., steroids; an alkylating agent such as cyclophosphamide; or a purine analog such as azathioprine.

Combinations of TIM-3 antibody molecules with one or more second therapeutics are provided herein. Many of the combinations in this section are useful in treating cancer, but other indications are also described. This section focuses on combinations of anti-TIM-3 antibody molecules, optionally in combination with one or more immunomodulators (e.g., an anti-PD-1 antibody molecule, an anti-LAG-3 antibody molecule, or an anti-PD-L1 antibody molecule), with one or more of the agents described in Table 6. In the combinations herein below, in one embodiment, the anti-TIM-3 antibody molecule comprises (i) a heavy chain variable region (VH) comprising a VHCDR1 amino acid sequence chosen from SEQ ID NO: 3 or SEQ ID NO: 9; a VHCDR2 amino acid sequence of SEQ ID NO: 4, SEQ ID NO: 10, SEQ ID NO: 24, SEQ ID NO: 25, SEQ ID NO: 30, or SEQ ID NO: 31; and a VHCDR3 amino acid sequence of SEQ ID NO: 5; and (ii) a light chain variable region (VL) comprising a VLCDR1 amino acid sequence of SEQ ID NO: 6 or SEQ ID NO: 12, a VLCDR2 amino acid sequence of SEQ ID NO: 7 or SEQ ID NO: 13, and a VLCDR3 amino acid sequence of SEQ ID NO: 8 or SEQ ID NO: 14.

In one embodiment, the anti-TIM-3 antibody molecule, e.g., an anti-TIM-3 antibody molecule as described herein, alone or in combination with one or more other immunomodulators, is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is disclosed in Table 6, or in a publication recited in Table 6, e.g., in the A1 row of Table 6. In one embodiment, the PKC inhibitor is Sotrastaurin (Compound A1) or a compound disclosed in PCT Publication No. WO 2005/039549. In one embodiment, a TIM-3 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In certain embodiments, Sotrastaurin (Compound A1) is administered at a dose of about 20 to 600 mg, e.g., about 200 to about 600 mg, about 50 mg to about 450 mg, about 100 mg to 400 mg, about 150 mg to 350 mg, or about 200 mg to 300 mg, e.g., about 50 mg, 100 mg, 150 mg, 200 mg, 300 mg, 400 mg, 500 mg, or 600 mg. The dosing schedule can vary from e.g., every other day to daily, twice or three times a day.

In one embodiment, the anti-TIM-3 antibody molecule, e.g., an anti-TIM-3 antibody molecule as described herein, alone or in combination with one or more other immunomodulators, is used in combination with a BCR-ABL inhibitor, TASIGNA (Compound A2, or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, a TIM-3 antibody molecule is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension.

In one embodiment, the BCR-ABL inhibitor or TASIGNA is administered at a dose of about 300 mg (e.g., twice daily, e.g., for newly diagnosed Ph+ CML-CP), or about 400 mg, e.g., twice daily, e.g., for resistant or intolerant Ph+ CML-CP and CML-AP). BCR-ABL inhibitor or a Compound A2 is administered at a dose of about 300-400 mg.

In another embodiment, the anti-TIM-3 antibody molecule, e.g., an anti-TIM-3 antibody molecule as described herein, alone or in combination with one or more other immunomodulators, is used in combination with an HSP90 inhibitor, such as 5-(2,4-dihydroxy-5-isopropylphenyl)-N-ethyl-4-(4-(morpholinomethyl)phenyl)isoxazole-3-carboxamide (Compound A3), or a compound disclosed in PCT Publication No. WO 2010/060937 or WO 2004/072051, to treat a disorder, e.g., a disorder described herein. In one embodiment, the HSP90 inhibitor is 5-(2,4-dihydroxy-5-isopropylphenyl)-N-ethyl-4-(4-(morpholinomethyl)phenyl) isoxazole-3-carboxamide (Compound A3), or a compound disclosed in PCT Publication No. WO 2010/060937 or WO 2004/072051. In one embodiment, a TIM-3 antibody molecule is used in combination with 5-(2,4-dihydroxy-5-isopropylphenyl)-N-ethyl-4-(4-(morpholinomethyl)phenyl) isoxazole-3-carboxamide (Compound A3), or a compound as described in PCT Publication No. WO 2010/060937 or WO 2004/072051, to treat a disorder such as a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the anti-TIM-3 antibody molecule, e.g., an anti-TIM-3 antibody molecule as described herein, alone or in combination with one or more other immunomodulators, is used in combination with an inhibitor of PI3K and/or mTOR, Dactolisib (Compound A4) or 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806, to treat a disorder, e.g., a disorder described herein. In one embodiment, the PI3K and/or mTOR inhibitor is Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound disclosed in PCT Publication No. WO 2006/122806. In one embodiment, a TIM-3 antibody molecule is used in combination with Dactolisib (Compound A4), 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), or a compound described in PCT Publication No. WO 2006/122806, to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the anti-TIM-3 antibody molecule, e.g., an anti-TIM-3 antibody molecule as described herein, alone or in combination with one or more other immunomodulators, is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, a TIM-3 antibody molecule is used in combination with Compound A5, or a compound as described in U.S. Pat. No. 8,552,002, to treat a disorder such as a digestive/gastrointestinal cancer, a hematological cancer, or a solid tumor.

In one embodiment, the FGFR inhibitor or 3-(2,6-dichloro-3,5-dimethoxyphenyl)-1-(6-((4-(4-ethylpiperazin-1-yl)phenyl)amino)pyrimidin-4-yl)-1-methylurea (Compound A5) is administered at a dose of about 100-125 mg (e.g., per day), e.g., about 100 mg or about 125 mg.

In another embodiment, the anti-TIM-3 antibody molecule, e.g., an anti-TIM-3 antibody molecule as described herein, alone or in combination with one or more other immunomodulators, is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, a TIM-3 antibody molecule is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer.

In one embodiment, the PI3K inhibitor or Buparlisib (Compound A6) is administered at a dose of about 100 mg (e.g., per day).

In another embodiment, the anti-TIM-3 antibody molecule, e.g., an anti-TIM-3 antibody molecule as described herein, alone or in combination with one or more other immunomodulators, is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386 to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, a TIM-3 antibody molecule is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis.

In one embodiment, the FGFR inhibitor or 8-(2,6-difluoro-3,5-dimethoxyphenyl)-N-(4-((dimethylamino)methyl)-1H-imidazol-2-yl)quinoxaline-5-carboxamide (Compound A7) is administered at a dose of e.g., from approximately 3 mg to approximately 5 g, more preferably from approximately 10 mg to approximately 1.5 g per person per day, optionally divided into 1 to 3 single doses which may, for example, be of the same size.

In another embodiment, the anti-TIM-3 antibody molecule, e.g., an anti-TIM-3 antibody molecule as described herein, alone or in combination with one or more other immunomodulators, is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, a TIM-3 antibody molecule is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer.

In one embodiment, the PI3K inhibitor or (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) is administered at a dose of about 150-300, 200-300, 200-400, or 300-400 mg (e.g., per day), e.g., about 200, 300, or 400 mg.

In another embodiment, the anti-TIM-3 antibody molecule, e.g., an anti-TIM-3 antibody molecule as described herein, alone or in combination with one or more other immunomodulators, is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is a compound disclosed in PCT Publication No. WO 2010/149755. In one embodiment, a TIM-3 antibody molecule is used in combination with a compound disclosed in PCT Publication No. WO 2010/149755, to treat prostate cancer.

In another embodiment, the anti-TIM-3 antibody molecule, e.g., an anti-TIM-3 antibody molecule as described herein, alone or in combination with one or more other immunomodulators, is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786 to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, a TIM-3 antibody molecule is used in combination with (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCTPublication No. WO 2011/076786, to treat a disorder such as a solid tumor.

In one embodiment, the HDM2 inhibitor or (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) is administered at a dose of about 400 to 700 mg, e.g., administered three times weekly, 2 weeks on and one week off. In some embodiments, the dose is about 400, 500, 600, or 700 mg; about 400-500, 500-600, or 600-700 mg, e.g., administered three times weekly.

In another embodiment, the anti-TIM-3 antibody molecule, e.g., an anti-TIM-3 antibody molecule as described herein, alone or in combination with one or more other immunomodulators, is used in combination with an iron chelating agent, Deferasirox (also known as EXJADE; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, a TIM-3 antibody molecule is used in combination with Deferasirox (Compound A11), or a compound disclosed in PCT Publication No. WO 1997/049395, to treat iron overload, hemochromatosis, or myelodysplasia.

In another embodiment, the anti-TIM-3 antibody molecule, e.g., an anti-TIM-3 antibody molecule as described herein, alone or in combination with one or more other immunomodulators, is used in combination with an aromatase inhibitor, Letrozole (also known as FEMARA; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, a TIM-3 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the anti-TIM-3 antibody molecule, e.g., an anti-TIM-3 antibody molecule as described herein, alone or in combination with one or more other immunomodulators, is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826 to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, a TIM-3 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the anti-TIM-3 antibody molecule, e.g., an anti-TIM-3 antibody molecule as described herein, alone or in combination with one or more other immunomodulators, is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, a TIM-3 antibody molecule is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, anti-TIM-3 antibody molecule, e.g., an anti-TIM-3 antibody molecule as described herein, alone or in combination with one or more other immunomodulators, is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, anti-TIM-3 antibody molecule, e.g., an anti-TIM-3 antibody molecule as described herein, is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In another embodiment, the anti-TIM-3 antibody molecule, e.g., an anti-TIM-3 antibody molecule as described herein, alone or in combination with one or more other immunomodulators, is used in combination with an apoptosis inducer and/or an angiogenesis inhibitor, such as Imatinib mesylate (also known as GLEEVEC; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, a TIM-3 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In certain embodiments, Imatinib mesylate (Compound A16) is administered at a dose of about 100 to 1000 mg, e.g., about 200 mg to 800 mg, about 300 mg to 700 mg, or about 400 mg to 600 mg, e.g., about 200 mg, 300 mg, 400 mg, 500 mg, 600 mg, or 700 mg. The dosing schedule can vary from e.g., every other day to daily, twice or three times a day. In one embodiment, Imatinib mesylate is administered at an oral dose from about 100 mg to 600 mg daily, e.g., about 100 mg, 200 mg, 260 mg, 300 mg, 400 mg, or 600 mg daily.

In another embodiment, the anti-TIM-3 antibody molecule, e.g., an anti-TIM-3 antibody molecule as described herein, alone or in combination with one or more other immunomodulators, is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, a TIM-3 antibody molecule is used in combination with 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia.

In one embodiment, the JAK inhibitor or a 2-fluoro-N-methyl-4-(7-(quinolin-6-ylmethyl)imidazo[1,2-b][1,2,4]triazin-2-yl)benzamide (Compound A17), or a dihydrochloric salt thereof is administered at a dose of about 400-600 mg (e.g., per day), e.g., about 400, 500, or 600 mg, or about 400-500 or 500-600 mg.

In another embodiment, the anti-TIM-3 antibody molecule, e.g., an anti-TIM-3 antibody molecule as described herein, alone or in combination with one or more other immunomodulators, is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, a TIM-3 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia.

In one embodiment, the JAK inhibitor or Ruxolitinib Phosphate (Compound A18) is administered at a dose of about 15-25 mg, e.g., twice daily. In some embodiments, the dose is about 15, 20, or 25 mg, or about 15-20 or 20-25 mg.

In another embodiment, the anti-TIM-3 antibody molecule, e.g., an anti-TIM-3 antibody molecule as described herein, alone or in combination with one or more other immunomodulators, is used in combination with a deacetylase (DAC) inhibitor, Panobinostat (Compound A19), or a compound disclosed in PCT Publication No. WO 2014/072493 to treat a disorder, e.g., a disorder described herein. In one embodiment, the DAC inhibitor is Panobinostat (Compound A19) or a compound disclosed in PCT Publication No. WO 2014/072493. In one embodiment, a TIM-3 antibody molecule is used in combination with Panobinostat (Compound A19), a compound disclosed in PCT Publication No. WO 2014/072493, to treat a disorder such as a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer, a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer.

In one embodiment, the DAC inhibitor or Panobinostat (Compound A19) is administered at a dose of about 20 mg (e.g., per day).

In another embodiment, the anti-TIM-3 antibody molecule, e.g., an anti-TIM-3 antibody molecule as described herein, alone or in combination with one or more other immunomodulators, is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, a TIM-3 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the anti-TIM-3 antibody molecule, e.g., an anti-TIM-3 antibody molecule as described herein, alone or in combination with one or more other immunomodulators, is used in combination with a IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, a TIM-3 antibody molecule is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a breast cancer, an ovarian cancer, a pancreatic cancer, or a hematopoiesis disorder.

In one embodiment, the IAP inhibitor or (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 is administered at a dose of approximately 1800 mg, e.g., once weekly.

In another embodiment, the anti-TIM-3 antibody molecule, e.g., an anti-TIM-3 antibody molecule as described herein, alone or in combination with one or more other immunomodulators, is used in combination a Smoothened (SMO) inhibitor, Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder, e.g., a disorder described herein. In one embodiment, the SMO inhibitor is Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120. In one embodiment, a TIM-3 antibody molecule is used in combination with Sonidegib phosphate (Compound A22), (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2007/131201 or WO 2010/007120 to treat a disorder such as a cancer, a medulloblastoma, a small cell lung cancer, a prostate cancer, a basal cell carcinoma, a pancreatic cancer, or an inflammation.

In certain embodiments, Sonidegib phosphate (Compound A22) is administered at a dose of about 20 to 500 mg, e.g., about 40 mg to 400 mg, about 50 mg to 300 mg, or about 100 mg to 200 mg, e.g., about 50 mg, 100 mg, 150 mg, 200 mg, 250 mg, or 300 mg. The dosing schedule can vary from e.g., every other day to daily, twice or three times a day.

In another embodiment, the anti-TIM-3 antibody molecule, e.g., an anti-TIM-3 antibody molecule as described herein, alone or in combination with one or more other immunomodulators, is used in combination with an Alk inhibitor, ceritinib (also known as ZYKADIA; Compound A23) or a compound disclosed in PCT Publication No. WO 2007/131201 to treat a disorder, e.g., a disorder described herein. In one embodiment, the Alk inhibitor is ceritinib (Compound A23) or a compound disclosed in PCT Publication No. WO 2007/131201. In one embodiment, a TIM-3 antibody molecule is used in combination with ceritinib (Compound A23) or a compound disclosed in PCT Publication No. WO 2007/131201, to treat a disorder such as non-small cell lung cancer or solid tumors.

In one embodiment, the Alk inhibitor or ceritinib (Compound A23) is administered at a dose of approximately 750 mg, e.g., once daily.

In another embodiment, the anti-TIM-3 antibody molecule, e.g., an anti-TIM-3 antibody molecule as described herein, alone or in combination with one or more other immunomodulators, is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. No. 8,415,355 or 8,685,980. In one embodiment, a TIM-3 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. No. 8,415,355 or 8,685,980, to treat a disorder such as a lymphoma, a neurologic cancer, a melanoma, a breast cancer, or a solid tumor.

In one embodiment, the JAK and/or CDK4/6 inhibitor or 7-cyclopentyl-N,N-dimethyl-2-((5-(piperazin-1-yl)pyridin-2-yl)amino)-7H-pyrrolo[2,3-d]pyrimidine-6-carboxamide (Compound A24) is administered at a dose of approximately 200-600 mg, e.g., per day. In one embodiment, the compound is administered at a dose of about 200, 300, 400, 500, or 600 mg, or about 200-300, 300-400, 400-500, or 500-600 mg.

In another embodiment, the antibody molecule, e.g., an anti-TIM-3 antibody molecule as described herein, alone or in combination with one or more other immunomodulators, is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, a TIM-3 antibody molecule is used in combination with human monoclonal antibody molecule (Compound A26) described in U.S. Pat. No. 7,867,493 to treat a disorder such as, a cancer, a prostate cancer, or a breast cancer.

In another embodiment, the anti-TIM-3 antibody molecule, e.g., an anti-TIM-3 antibody molecule as described herein, alone or in combination with one or more other immunomodulators, is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, a TIM-3 antibody molecule is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the anti-TIM-3 antibody molecule, e.g., an anti-TIM-3 antibody molecule as described herein, alone or in combination with one or more other immunomodulators, is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, a TIM-3 antibody molecule is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer).

In certain embodiments, 2-(2',3-dimethyl-[2,4'-bipyridin]-5-yl)-N-(5-(pyrazin-2-yl)pyridin-2-yl)acetamide (Compound A28) is administered at a dose of about 1 to 50 mg, e.g., about 2 mg to 45 mg, about 3 mg to 40 mg, about 5 mg to 35 mg, 5 mg to 10 mg, or about 10 mg to 30 mg, e.g., about 2 mg, 5 mg, 10 mg, 20 mg, 30 mg, or 40 mg. The dosing schedule can vary from e.g., every other day to daily, twice or three times a day.

In another embodiment, the anti-TIM-3 antibody molecule, e.g., an anti-TIM-3 antibody molecule as described herein, alone or in combination with one or more other immunomodulators, is used in combination with a BRAF inhibitor, Encorafenib (Compound A29), or a compound disclosed in PCT Publication No. WO 2011/025927 to treat a disorder, e.g., a disorder described herein. In one embodiment, the BRAF inhibitor is Encorafenib (Compound A29) or a compound disclosed in PCT Publication No. WO 2011/025927. In one embodiment, a TIM-3 antibody molecule is used in combination with Encorafenib (Compound A29), or a compound disclosed in PCT Publication No. WO 2011/025927, to treat a disorder such as a non-small cell lung cancer, a melanoma, or a colorectal cancer.

In one embodiment, the BRAF inhibitor or Encorafenib (Compound A29) is administered at a dose of about 200-300, 200-400, or 300-400 mg, e.g., per day. In one embodiment, the compound is administered at a dose of about 200, about 300 or about 400 mg.

In another embodiment, the anti-TIM-3 antibody molecule, e.g., an anti-TIM-3 antibody molecule as described herein, alone or in combination with one or more other immunomodulators, is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, a TIM-3 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the anti-TIM-3 antibody molecule, e.g., an anti-TIM-3 antibody molecule as described herein, alone or in combination with one or more other immunomodulators, is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, a TIM-3 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In some embodiments, Compound A31 is a human monoclonal antibody molecule.

In one embodiment, the HER3 inhibitor or Compound A31 is administered at a dose of about 3, 10, 20, or 40 mg/kg, e.g., once weekly (QW). In one embodiment, the compound is administered at a dose of about 3-10, 10-20, or 20-40 mg/kg.

In another embodiment, the anti-TIM-3 antibody molecule, e.g., an anti-TIM-3 antibody molecule as described herein, alone or in combination with one or more other immunomodulators, is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, a TIM-3 antibody molecule is used in combination with Compound A32, or a compound as described in Table 6, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425.

In another embodiment, the anti-TIM-3 antibody molecule, e.g., an anti-TIM-3 antibody molecule as described herein, alone or in combination with one or more other immunomodulators, is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, a TIM-3 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In embodiments, Compound A33 is a monoclonal antibody molecule against M-CSF or a fragment (e.g., Fab fragment) thereof. In embodiments, the M-CSF inhibitor or Compound A33 is administered at an average dose of about 10 mg/kg.

In another embodiment, the anti-TIM-3 antibody molecule, e.g., an anti-TIM-3 antibody molecule as described herein, alone or in combination with one or more other immunomodulators, is used in combination with a MEK inhibitor, Binimetinib (Compound A34), or a compound disclosed in PCT Publication No. WO 2003/077914 to treat a disorder, e.g., a disorder described herein. In one embodiment, the MEK inhibitor is Binimetinib (Compound A34), or a compound disclosed in PCT Publication No. WO 2003/077914. In one embodiment, a TIM-3 antibody molecule is used in combination with Binimetinib (Compound A34), or a compound disclosed in PCT Publication No. WO 2003/077914, to treat a disorder such as a non-small cell lung cancer, a multisystem genetic disorder, a melanoma, an ovarian cancer, a digestive/gastrointestinal cancer, a rheumatoid arthritis, or a colorectal cancer.

In one embodiment, the MEK inhibitor or Binimetinib (Compound A34) is administered at a dose of about 45 mg, e.g., twice daily.

In another embodiment, the anti-TIM-3 antibody molecule, e.g., an anti-TIM-3 antibody molecule as described herein, alone or in combination with one or more other immunomodulators, is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein. In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, a TIM-3 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related mascular degeration, a diabetic complication, or a dermatologic disorder.

In another embodiment, the anti-TIM-3 antibody molecule, e.g., an anti-TIM-3 antibody molecule as described herein, alone or in combination with one or more other immunomodulators, is used in combination with a TOR inhibitor (e.g., mTOR inhibitor), Everolimus (also known as AFINITOR; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, a TIM-3 antibody molecule is used in combination with Everolimus (Compound A36) to treat a disorder such as an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer, or a bladder cancer.

In one embodiment, the TOR inhibitor or Everolimusis (Compound A36) administered at a dose of about 2.5-20 mg/day. In one embodiment, the compound is administered at a dose of about 2.5, 5, 10, or 20 mg/day, e.g., about 2.5-5, 5-10, or 10-20 mg/day.

In another embodiment, the anti-TIM-3 antibody molecule, e.g., an anti-TIM-3 antibody molecule as described herein, alone or in combination with one or more other immunomodulators, is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein. In one embodiment, the inhibitor of one or more of VEGFR-2, PDGFR-beta, KIT or Raf kinase C is 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377. In one embodiment, a TIM-3 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37), or a compound disclosed in PCT Publication No. WO 2007/030377, to treat a disorder such as a cancer, a melanoma, or a solid tumor.

In another embodiment, the anti-TIM-3 antibody molecule, e.g., an anti-TIM-3 antibody molecule as described herein, alone or in combination with one or more other immunomodulators, is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, a TIM-3 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a nurologic cancer, a skin cancer (e.g., a melanoma), a pancreatic cancer, a liver cancer, Cushing's syndrome, a gastrointestinal disorder, acromegaly, a liver and biliary tract disorder, or liver cirrhosis.

In another embodiment, the anti-TIM-3 antibody molecule, e.g., an anti-TIM-3 antibody molecule as described herein, alone or in combination with one or more other immunomodulators, is used in combination a signal transduction modulator and/or angiogenesis inhibitor, Dovitinib (Compound A39) or a compound disclosed in PCT Publication No. WO 2009/115562 to treat a disorder, e.g., a disorder described herein. In one embodiment, the signal transduction modulator and/or angiogenesis inhibitor is Dovitinib (Compound A39) or a compound disclosed in PCT Publication No. WO 2009/115562. In one embodiment, a TIM-3 antibody molecule is used in combination with Dovitinib (Compound A39), or a compound disclosed in PCT Publication No. WO 2009/115562, to treat a disorder such as a cancer, a respiratory/thoracic cancer, a multiple myeloma, a prostate cancer, a non-small cell lung cancer, an endocrine cancer, or a neurological genetic disorder.

In another embodiment, the anti-TIM-3 antibody molecule, e.g., an anti-TIM-3 antibody molecule as described herein, alone or in combination with one or more other immunomodulators, is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, a TIM-3 antibody molecule is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor.

In one embodiment, the EGFR inhibitor or (R,E)-N-(7-chloro-1-(1-(4-(dimethylamino)but-2-enoyl)azepan-3-yl)-1H-benzo[d]imidazol-2-yl)-2-methylisonicotinamide (Compound A40) is administered at a dose of 150-250 mg, e.g., per day. In one embodiment, the compound is administered at a dose of about 150, 200, or 250 mg, or about 150-200 or 200-250 mg.

In another embodiment, the anti-TIM-3 antibody molecule, e.g., an anti-TIM-3 antibody molecule as described herein, alone or in combination with one or more other immunomodulators, is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687 to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, a TIM-3 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the anti-TIM-3 antibody molecule, e.g., an anti-TIM-3 antibody molecule as described herein, alone or in combination with one or more other immunomodulators, is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-$N^4$-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-N$^2$-(2-fluoro-5-methyl-4-(1-(tetrahydro-2H-pyran-4-yl)piperidin-4-yl)phenyl)-N$^4$-(5-methyl-1H-pyrazol-3-yl) pyrimidine-2,4-diamine (Compound A44), 5-chloro-N2-(4-(1-ethylpiperidin-4-yl)-2-fluoro-5-methylphenyl)-N$^4$-(5-methyl-1H-pyrazol-3-yl)pyrimidine-2,4-diamine (Compound A45), or a compound disclosed in PCT Publication No. WO 2010/002655. In one embodiment, a TIM-3 antibody molecule is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-N$^2$-(2-fluoro-5-methyl-4-(1-(tetrahydro-2H-pyran-4-yl)piperidin-4-yl)phenyl)-N$^4$-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-N$^4$-(5-methyl-1H-pyrazol-3-yl)pyrimidine-2,4-diamine (Compound A45), or a compound disclosed in PCT Publication No. WO 2010/002655, to treat a disorder such as a cancer or a sarcoma.

In another embodiment, the anti-TIM-3 antibody molecule, e.g., an anti-TIM-3 antibody molecule as described herein, alone or in combination with one or more other immunomodulators, is used in combination with a P-Glycoprotein 1 inhibitor, Valspodar (also known as AMDRAY; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, a TIM-3 antibody molecule is used in combination with Valspodar (Compound A46), or a compound disclosed in EP 296122, to treat a disorder such as a cancer or a drug-resistant tumor.

In another embodiment, the anti-TIM-3 antibody molecule, e.g., an anti-TIM-3 antibody molecule as described herein, alone or in combination with one or more other immunomodulators, is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, a TIM-3 antibody molecule is used in combination with Vatalanib succinate (Compound A47), or a compound disclosed in EP 296122, to treat cancer.

In another embodiment, the anti-TIM-3 antibody molecule, e.g., an anti-TIM-3 antibody molecule as described herein, alone or in combination with one or more other immunomodulators, is used in combination with an IDH inhibitor or a compound disclosed in WO2014/141104 to treat a disorder, e.g., a disorder described herein. In one embodiment, the IDH inhibitor is a compound disclosed in PCT Publication No. WO2014/141104. In one embodiment, a TIM-3 antibody molecule is used in combination with a compound disclosed in WO2014/141104 to treat a disorder such as a cancer.

In another embodiment, the anti-TIM-3 antibody molecule, e.g., an anti-TIM-3 antibody molecule as described herein, alone or in combination with one or more other immunomodulators, is used in combination with a BCL-ABL inhibitor or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, a TIM-3 antibody molecule is used in combination with a compound disclosed in PCT Publication No. WO2013/171639, WO2013/171640, WO2013/171641, or WO2013/171642 to treat a disorder such as a cancer.

In another embodiment, the anti-TIM-3 antibody molecule, e.g., an anti-TIM-3 antibody molecule as described herein, alone or in combination with one or more other immunomodulators, is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In one embodiment, a TIM-3 antibody molecule is used in combination with a compound disclosed in PCT Publication No. WO2014/151616 to treat a disorder such as a cancer.

In another embodiment, the anti-TIM-3 antibody molecule, e.g., an anti-TIM-3 antibody molecule as described herein, alone or in combination with one or more other immunomodulators, is used in combination with an ERK1/2 ATP competitive inhibitor or a compound disclosed in International Patent Application No. PCT/US2014/062913 to treat a disorder, e.g., a disorder described herein. In one embodiment, the ERK1/2 ATP competitive inhibitor is a compound disclosed in International Patent Application No. PCT/US2014/062913. In one embodiment, a TIM-3 antibody molecule is used in combination with Compound A51 or a compound disclosed in International Patent Application No. PCT/US2014/062913 to treat a disorder such as a cancer.

In some embodiments, the TIM-3 antibody molecule is administerd in combination with one or more agents selected from, Compound A8, Compound A17, Compound A23, Compound A24, Compound A27, Compound A29, and Compound A33.

In some embodiments, a TIM-3 antibody molecule is administered in combination with an anti-cancer agent having a known activity in an immune cell assay, e.g., in one or more of a huMLR assay, a T cell proliferation assay, and a B-cell proliferation assay. Exemplary assays are described below. Based on the assay, an IC50 for can be calculated for each test agent. In embodiments, the anti-cancer agent has an IC50 of, e.g., 0-1 µM, 1-4 µM, or greater than 4 µM, e.g., 4-10 µM or 4-20 µM. In embodiments, the second therapeutic agent is chosen from one or more of: Compound A9, Compound A16, Compound A17, Compound A21, Compound A22, Compound A25, Compound A28, Compound A48, and Compound 49.

In some embodiments, the Compound A28 (or a compound related to Compound A28) is administered at a dose of approximately 5-10 or 10-30 mg. In some embodiments, the Compound A22 (or compound related to Compound A22) is administered at a dose of about 200 mg. In some embodiments, the Compound A17 (or compound related to Compound A17) is administered at a dose of approximately 400-600 mg. In some embodiments, the Compound A16 (or compound related to Compound A16) is administered at a dose of approximately 400-600 mg PO qDay. In some embodiments, the Compound A29 (or compound related to Compound A29) is administered at a dose of approximately 200-400 or 300-400 mg. In some embodiments, the Compound A24 (or compound related to Compound A24) is administered at a dose of approximately 200-600 mg. In some embodiments, the Compound A23 (ceritinib) (or compound related to ceritinib) is administered at a dose of approximately 750 mg once daily. In some embodiments, the Compound A8 (or compound related to Compound A8) is administered at a dose of approximately 200-400 or 300-400 mg. In some embodiments, the Compound A5 (or compound related to Compound A5) is administered at a dose of approximately 100-125 mg. In some embodiments, the Compound A6 (or compound related to Compound A6) is administered at a dose of about 100 mg. In some embodiments, the Compound A1 (or compound related to Compound A1) is administered at a dose of approximately 200-300 or 200-600 mg. In some embodiments, the Compound A40 (or compound related to Compound A40) is administered at a dose of approximately 150-250 mg. In embodiments, the Compound A10 (or compound related to Compound A10) is administered at a dose of approximately 400 to 700 mg, e.g., administered three times weekly, 2 weeks on and one week off. In embodiments, the BCR-ABL inhibitor is administered at a dose of approximately 20 mg bid-80 mg bid.

Exemplary huMLR assay and B or T cell proliferation assays are provided below.

Human Mixed Lymphocyte Reaction

The Mixed Lymphocyte Reaction (MLR) is a functional assay which measures the proliferative response of lymphocytes from one individual (the responder) to lymphocytes from another individual (the stimulator). To perform an allogeneic MLR, peripheral blood mononuclear cells (PBMC) from three donors were isolated from buffy-coats of unknown HLA type (Kantonspital Blutspendezentrum from Bern and Aarau, Switzerland). The cells were prepared at 2.105 in 0.2 mL of culture medium containing RPMI 1640 GlutaMAX™ with 10% fetal calf serum (FCS), 100U penicillin/100 µg streptomycin, 50 µM 2-Mercaptoethanol. Individual 2-way reactions were set up by mixing PBMC from two different donors at a 1:1 ratio and co-cultures were done in triplicates in flat-bottomed 96-well tissue culture plates for 6 days at 37° C., 5% $CO_2$, in presence or not of an 8-point concentration range of test compounds. Cells were pulsed with 3H-TdR (1 µCi/0.2 mL) for the last 16h of culture and incorporated radioactivity was used as a measure of cell proliferation. The concentration that inhibited 50% of the maximal huMLR response (IC50) was calculated for each compound. Cyclosporine was used as a positive control of huMLR inhibition.

Human B Cell Proliferation Assay

PBMC were freshly isolated by Ficoll-Paque density gradient from human blood and subjected to negative B-cell isolation. B cells were resuspended in culture medium (RPMI 1640, HEPES, 10% FCS, 50m/mL gentamicine, 50 µM 2-Mercaptoethanol, 1×ITS (Insulin, Transferrin and Sodium Selenite), 1× Non-Essential Amino-Acids) at a concentration of 9.104 per well in a flat-bottom 96-well culture plate. B cell stimulation was performed by human anti-IgM antibody molecule (30 ug/mL) and IL-4 (75 ng/mL) or by CD40 ligand (3 ug/mL) and IL-4 (75 ng/mL) in presence or not of a 7-point concentration range of test compounds. After 72h of culture at 37° C., 10% $CO_2$, cells were pulsed with 3H-TdR (1 µCi/well) for the last 6h of culture. B cells were then harvested and the incorporation of thymidine was measured using a scintillation counter. Of each duplicate treatment, the mean was calculated and these data were plotted in XLfit 4 to determine the respective IC50 values.

Human T Cell Proliferation Assay

PBMC were freshly isolated by Ficoll-Paque density gradient from human blood and subjected to negative isolation of T cells. T cells were prepared in culture medium (RPMI 1640, HEPES, 10% FCS, 50m/mL gentamicine, 50 µM 2-Mercaptoethanol, 1×ITS (Insulin, Transferrin and Sodium Selenite), 1× Non-Essential Amino-Acids) at a concentration of 8.104 per well in a flat-bottom 96-well culture plate. T cell stimulation was performed by human anti-CD3 antibody molecule (10 ug/mL) or by human anti-CD3 antibody molecule (5m/mL) and anti-CD28 antibody molecule (1m/mL) in presence or not of a 7-point concentration range of test compounds. After 72h of culture at 37° C., 10% $CO_2$, cells were pulsed with 3H-TdR (1 µCi/well) for the last 6h of culture. Cell proliferation was measured by the incorporation of thymidine allowing IC50 determination for each tested compound.

Down-Modulators of the Immune System

In an alternative embodiment, the anti-TIM-3 antibody molecules disclosed herein are used to produce anti-idiotypic peptides or antibodies (Wallmann, J. et al. (2010) "Anti-Ids in Allergy: Timeliness of a Classic Concept," *World Allergy Organiz. J.* 3(6):195-201; Nardi, M. et al. (2000) "Antiidiotype Antibody Against Platelet Anti-Gpiiia Contributes To The Regulation Of Thrombocytopenia In HIV-1-ITP Patients," *J. Exp. Med.* 191(12):2093-2100) or mimetics (Zang, Y. C. et al. (2003) "Human Anti-Idiotypic T Cells Induced By TCR Peptides Corresponding To A Common CDR3Sequence Motif In Myelin Basic Protein-Reactive T Cells," *Int. Immunol.* 15(9):1073-1080; Loiarro, M. et al. (Epub 2010 Apr. 8) "Targeting TLR/IL-1R Signalling In Human Diseases," *Mediators Inflamm.* 2010:674363) of TIM-3. Such molecules serve as surrogates for TIM-3, and thus their administration to a subject down-modulates the immune system of such subject by mimicking or facilitating ligand-TIM-3 binding. Such molecules have utility in the treatment of graft vs. host disease. Similarly, agonist antibodies that i) enhance binding between such antibodies and such receptor/ligand or ii) trigger signal transduction when bound directly to a TIM-3 ligand or TIM-3, have utility as agonists of TIM-3 signaling and thus have utility in the treatment of inflammation and autoimmune disease, by directly or indirectly agonizing receptor activity.

Bispecific antibodies, exhibiting immunospecific binding to both TIM-3 and TIM-3 ligands are capable of binding to both APC and T-cells, and thus facilitate the co-localization of APCs and T-cells. Such co-localization facilitates the ability of such cells to bind together via TIM-3 ligand and TIM-3 molecules that are not complexed with antibody, or by co-inhibitory molecules. Such binding provides down modulation of the immune system of the recipient.

Down-modulation of the immune system is desirable in the treatment of inflammatory and auto-immune diseases, and graft vs. host disease (GvHD). Examples of autoimmune disorders that may be treated by administering the antibodies of the present invention include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the antibodies and antigen-binding fragments of the present invention have utility in the treatment of inflammatory and autoimmune diseases.

Diagnostic Uses

In some aspects, the present disclosure provides a diagnostic method for detecting the presence of a TIM-3 protein in vitro (e.g., in a biological sample, such as a tissue biopsy, e.g., from a cancerous tissue) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma, tissue, biopsy) or a control subject with an antibody molecule described herein; and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of TIM-3 in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids such as blood, or tissue samples.

Complex formation between the antibody molecule and TIM-3 can be detected by measuring or visualizing either the antibody molecule bound to the TIM-3 antigen or unbound antibody molecule. Any suitable detection assays can be used, and conventional detection assays include an enzyme-linked immunosorbent assays (ELISA), a radioimmunoassay (RIA) or tissue immunohistochemistry. Alternative to labeling the antibody molecule, the presence of TIM-3 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of TIM-3 in the sample is inversely proportional to the amount of labeled standard bound to the antibody molecule.

In some aspects, the present disclosure provides methods of using an anti-TIM-3 antibody molecule to diagnose sepsis, SIRS (Systemic Inflammatory Response Syndrome), preeclampsia, or glomerulonephritis. Sepsis is often accompanied by a downregulation of TIM-3 (Yang et al., J Immunol. 2013 Mar. 1; 190(5):2068-79) so lowered levels of TIM-3 are indicative of sepsis while normal levels of TIM-3 are an indication that sepsis is not present. In SIRS and preeclampsia, TIM-3 levels are downregulated in peripheral lymphocytes (Miko et al., PLoS ONE 8(8): e71811), so lowered levels of TIM-3 are indicative of SIRS or preeclampsia, while normal levels of TIM-3 are an indication that SIRS and preeclampsia are not present. In glomerulonephritis, TIM-3 can be upregulated (see Schroll et al., Am J Pathol 2010 April; 176(4):1716-1742) so elevated levels of TIM-3 are indicative of glomerulonephritis, while normal levels are an indication that glomerulonephritis is not present.

Nucleic Acids

The present disclosure also features nucleic acids comprising nucleotide sequences that encode heavy and light chain variable regions and CDRs of the anti-TIM-3 antibody molecules, as described herein. For example, the present disclosure features a first and second nucleic acid encoding heavy and light chain variable regions, respectively, of an anti-TIM-3 antibody molecule chosen from one or more of the antibody molecules disclosed herein, e.g., an antibody of Tables 1-4. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences provided in Tables 1-4.

In certain embodiments, the nucleic acid can comprise a nucleotide sequence encoding at least one, two, or three CDRs from a heavy chain variable region having an amino acid sequence as set forth in Tables 1-4, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, or three CDRs from a light chain variable region having an amino acid sequence as set forth in Tables 1-4, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, three, four, five, or six CDRs from heavy and light chain variable regions having an amino acid sequence as set forth in Tables 1-4, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in Tables 1-4, a sequence substantially homologous thereto (e.g., a sequence at least about 85%, 90%, 95%, 99% or more identical thereto, and/or capable of hybridizing under the stringency conditions described herein). In some embodiments, the nucleic acid can comprise a nucleotide sequence encoding at least one, two, or three CDRs from a light chain variable region having the nucleotide sequence as set forth in Tables 1-4, or a sequence substantially homologous thereto (e.g., a sequence at least about 85%, 90%, 95%, 99% or more identical thereto, and/or capable of hybridizing under the stringency conditions described herein). In certain embodiments, the nucleic acid can comprise a nucleotide sequence encoding at least one, two, three, four, five, or six CDRs from heavy and light chain variable regions having the nucleotide sequence as set forth in Tables 1-4, or a sequence substantially homologous thereto (e.g., a sequence at least about 85%, 90%, 95%, 99% or more identical thereto, and/or capable of hybridizing under the stringency conditions described herein). The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

In some aspects, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising nucleotide sequences encoding an antibody molecule described herein. In some embodiments, the vectors comprise nucleotides encoding an antibody molecule described herein. In some embodiments, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The present disclosure also provides host cells comprising a nucleic acid encoding an antibody molecule as described herein.

In some embodiments, the host cells are genetically engineered to comprise nucleic acids encoding the antibody molecule.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Exemplary sequences of anti-TIM-3 antibodies are described in the Tables 1-4 below.

TABLE 1

Summary of the sequences of the murine antibody ABTIM3.

| Antibody designation | SEQ ID NO | Description |
|---|---|---|
| ABTIM3 | 1 | VH amino acid sequence |
| | 2 | VL amino acid sequence |
| | 3 | VHCDR1 amino acid sequence |
| | 4 | VHCDR2 amino acid sequence |
| | 5 | VHCDR3 amino acid sequence |
| | 6 | VLCDR1 amino acid sequence |
| | 7 | VLCDR2 amino acid sequence |
| | 8 | VLCDR3 amino acid sequence |

TABLE 2

Depiction of the amino acid sequences of the murine antibody ABTIM3 heavy chain variable domain and light chain variable domain. CDRs are shown in white text on a black background.

| SEQ ID NO | Sequence |
|---|---|
| 1 | QVQLQQPGAE LVKPGASVKM SCKASGYTFT SYNMHWIKQT PGQGLEWIGD IYPGNGDTSY NQKFKGKATL TADKSSSTVY MQLSSLTSED SAVYYCARVG GAFPMDYWGQ GTSVTVSS |
| 2 | DIVLTQSPAS LAVSLGQRAT ISCRASESVE YYGTSLMQWY QQKPGQPPKL LIYAASNVES GVPARFSGSG SGTDFSLNIH PVEEDDIAIY FCQQSRKDPS TFGGGTKLEI K |

TABLE 3

Depiction of the amino acid sequences of the murine antibody ABTIM3 heavy chain CDRs and light chain CDRs.

| SEQ ID NO | Sequence |
|---|---|
| 3 | SYNMH |
| 4 | DIYPGNGDTSYNQKFKG |
| 5 | VGGAFPMDY |
| 6 | RASESVEYYGTSLMQ |
| 7 | AASNVES |
| 8 | QQSRKDPST |

Exemplary sequences of anti-TIM-3 antibodies are described in Table 4. The antibody molecules include murine ABTIM3, and humanized antibody molecules. The amino acid and nucleotide sequences of the heavy and light chain CDRs, the heavy and light chain variable regions, and the heavy and light chains are shown.

TABLE 4

Summary of the sequences of exemplary anti-TIM-3 antibodies.

| Hybridoma clone | | |
|---|---|---|
| ABTIM3 | | |
| SEQ ID NO: 3 (Kabat) | HCDR1 | SYNMH |
| SEQ ID NO: 4 (Kabat) | HCDR2 | DIYPGNGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 10 (Chothia) | HCDR2 | YPGNGD |

TABLE 4-continued

Summary of the sequences of exemplary anti-TIM-3 antibodies.

Hybridoma
clone

| | | |
|---|---|---|
| SEQ ID NO: 5 (Chothia) | HCDR3 | VGGAFPMDY |
| SEQ ID NO: 1 | VH | QVQLQQPGAELVKPGASVKMSCKASGYTFTSYNMHWIKQTPGQGLEWIGDIY PGNGDTSYNQKFKGKATLTADKSSSTVYMQLSSLTSEDSAVYYCARVGGAFP MDYWGQGTSVTVSS |
| SEQ ID NO: 11 | DNA VH | CAGGTGCAACTGCAGCAGCCTGGGGCTGAGCTGGTGAAGCCTGGGGCCTCAG TGAAGATGTCCTGCAAGGCTTCTGGCTACACATTTACCAGTTACAATATGCA CTGGATAAAGCAGACACCTGGACAGGGCCTGGAATGGATTGGAGATATTTAT CCAGGAAATGGTGATACTTCCTACAATCAGAAATTCAAAGGCAAGGCCACAT TGACTGCAGACAAATCCTCCAGCACAGTCTACATGCAGCTCAGCAGCCTGAC ATCTGAGGACTCTGCGGTCTATTACTGTGCAAGAGTGGGGGGTGCCTTTCCT ATGGACTACTGGGGTCAAGGAACCTCAGTCACCGTCTCCTCA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 2 | VL | DIVLTQSPASLAVSLGQRATISCRASESVEYYGTSLMQWYQQKPGQPPKLLI YAASNVESGVPARFSGSGSGTDFSLNIHPVEEDDIAIYFCQQSRKDPSTFGG GTKLEIK |
| SEQ ID NO: 15 | DNA VL | GACATTGTGCTCACCCAATCTCCAGCTTCTTTGGCTGTGTCTCTAGGGCAGA GAGCCACCATCTCCTGCAGAGCCAGTGAAAGTGTTGAATATTATGGCACAAG TTTAATGCAGTGGTACCAACAGAAACCAGGACAGCCACCCAAACTCCTCATC TATGCTGCATCCAACGTAGAATCTGGGGTCCCTGCCAGGTTTAGTGGCAGTG GGTCTGGGACAGACTTCAGCCTCAACATCCATCCTGTGGAGGAGGATGATAT TGCAATATATTTCTGTCAGCAAAGTAGGAAGGATCCTTCGACGTTCGGTGGA GGCACCAAGCTGGAGATCAAA |

ABTIM3-hum01

| | | |
|---|---|---|
| SEQ ID NO: 3 (Kabat) | HCDR1 | SYNMH |
| SEQ ID NO: 4 (Kabat) | HCDR2 | DIYPGNGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 10 (Chothia) | HCDR2 | YPGNGD |

TABLE 4-continued

Summary of the sequences of exemplary anti-TIM-3 antibodies.

Hybridoma clone

| | | |
|---|---|---|
| SEQ ID NO: 5 (Chothia) | HCDR3 | VGGAFPMDY |
| SEQ ID NO: 16 | VH | QVQLVQSGAEVKKPGASVKVSCKASGYTFTSYNMHWVRQAPGQGLEWIGDIY PGNGDTSYNQKFKGRATMTADKSTSTVYMELSSLRSEDTAVYYCARVGGAFP MDYWGQGTLVTVSS |
| SEQ ID NO: 17 | DNA VH | CAGGTGCAGCTGGTGCAGTCAGGCGCCGAAGTGAAGAAACCCGGCGCTAGTG TGAAAGTCTCTTGTAAAGCTAGTGGCTACACCTTCACTAGCTATAATATGCA CTGGGTTCGCCAGGCCCCAGGGCAGGGCCTCGAGTGGATCGGCGATATCTAC CCCGGGAACGGCGACACTAGTTATAATCAGAAGTTTAAGGGTAGAGCTACTA TGACCGCCGATAAGTCTACTAGCACCGTCTATATGGAACTGAGTTCCCTGAG GTCTGAGGACACCGCCGTCTACTACTGCGCTAGAGTGGGCGGAGCCTTCCCT ATGGACTACTGGGGTCAAGGCACCCTGGTCACCGTGTCTAGC |
| SEQ ID NO: 18 | Heavy Chain | QVQLVQSGAEVKKPGASVKVSCKASGYTFTSYNMHWVRQAPGQGLEWIGDIY PGNGDTSYNQKFKGRATMTADKSTSTVYMELSSLRSEDTAVYYCARVGGAFP MDYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLG |
| SEQ ID NO: 19 | DNA Heavy Chain | CAGGTGCAGCTGGTGCAGTCAGGCGCCGAAGTGAAGAAACCCGGCGCTAGTG TGAAAGTCTCTTGTAAAGCTAGTGGCTACACCTTCACTAGCTATAATATGCA CTGGGTTCGCCAGGCCCCAGGGCAGGGCCTCGAGTGGATCGGCGATATCTAC CCCGGGAACGGCGACACTAGTTATAATCAGAAGTTTAAGGGTAGAGCTACTA TGACCGCCGATAAGTCTACTAGCACCGTCTATATGGAACTGAGTTCCCTGAG GTCTGAGGACACCGCCGTCTACTACTGCGCTAGAGTGGGCGGAGCCTTCCCT ATGGACTACTGGGGTCAAGGCACCCTGGTCACCGTGTCTAGCGCTAGCACTA AGGGCCCGTCCGTGTTCCCCCTGGCACCTTGTAGCCGGAGCACTAGCGAATC CACCGCTGCCCTCGGCTGCCTGGTCAAGGATTACTTCCCGGAGCCCGTGACC GTGTCCTGGAACAGCGGAGCCCTGACCTCCGGAGTGCACACCTTCCCCGCTG TGCTGCAGAGCTCCGGGCTGTACTCGCTGTCGTCGGTGGTCACGGTGCCTTC ATCTAGCCTGGGTACCAAGACCTACACTTGCAACGTGGACCACAAGCCTTCC AACACTAAGGTGGACAAGCGCGTCGAATCGAAGTACGGCCCACCGTGCCCGC CTTGTCCCGCGCCGGAGTTCCTCGGCGGTCCCTCGGTCTTTCTGTTCCCACC GAAGCCCAAGGACACTTTGATGATTTCCCGCACCCCTGAAGTGACATGCGTG GTCGTGGACGTGTCACAGGAAGATCCGGAGGTGCAGTTCAATTGGTACGTGG ATGGCGTCGAGGTGCACAACGCCAAAACCAAGCCGAGGGAGGAGCAGTTCAA CTCCACTTACCGCGTCGTGTCCGTGCTGACGGTGCTGCATCAGGACTGGCTG AACGGGAAGGAGTACAAGTGCAAAGTGTCCAACAAGGGACTTCCTAGCTCAA TCGAAAAGACCATCTCGAAAGCCAAGGGACAGCCCCGGGAACCCCAAGTGTA TACCCTGCCACCGAGCCAGGAAGAAATGACTAAGAACCAAGTCTCATTGACT TGCCTTGTGAAGGGCTTCTACCCATCGGATATCGCCGTGGAATGGGAGTCCA ACGGCCAGCCGGAAAACAACTACAAGACCACCCCTCCGGTGCTGGACTCAGA CGGATCCTTCTTCCTCTACTCGCGGCTGACCGTGGATAAGAGCAGATGGCAG GAGGGAAATGTGTTCAGCTGTTCTGTGATGCATGAAGCCCTGCACAACCACT ACACTCAGAAGTCCCTGTCCCTCTCCCTGGGA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |

TABLE 4-continued

Summary of the sequences of exemplary anti-TIM-3 antibodies.

Hybridoma clone

| | | |
|---|---|---|
| SEQ ID NO: 14 (Chothia) | LCDR3 | SRKDPS |
| SEQ ID NO: 20 | VL | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIK |
| SEQ ID NO: 21 | DNA VL | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTACTGTCAGCAGTCTAGGAAGGACCCTAGCACCTTCGGCGGA GGCACTAAGGTCGAGATTAAG |
| SEQ ID NO: 22 | Light Chain | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 23 | DNA Light Chain | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTACTGTCAGCAGTCTAGGAAGGACCCTAGCACCTTCGGCGGA GGCACTAAGGTCGAGATTAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |
| ABTIM3-hum02 | | |
| SEQ ID NO: 3 (Kabat) | HCDR1 | SYNMH |
| SEQ ID NO: 24 (Kabat) | HCDR2 | DIYPGSGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 25 (Chothia) | HCDR2 | YPGSGD |
| SEQ ID NO: 5 (Chothia) | HCDR3 | VGGAFPMDY |
| SEQ ID NO: 26 | VH | QVQLVQSGAEVKKPGASVKVSCKASGYTFTSYNMHWVRQAPGQGLEWIGDIY PGSGDTSYNQKFKGRATMTADKSTSTVYMELSSLRSEDTAVYYCARVGGAFP MDYWGQGTLVTVSS |
| SEQ ID NO: 27 | DNA VH | CAGGTGCAGCTGGTGCAGTCAGGCGCCGAAGTGAAGAAACCCGGCGCTAGTG TGAAAGTTAGCTGTAAAGCTAGTGGCTACACCTTCACTAGCTATAATATGCA CTGGGTTCGCCAGGCCCCAGGTCAAGGCCTCGAGTGGATCGGCGATATCTAC CCCGGTAGCGGCGACACTAGTTATAATCAGAAGTTTAAGGGTAGAGCTACTA TGACCGCCGATAAGTCTACTAGCACCGTCTATATGGAACTGAGTTCCCTGAG GTCTGAAGATACCGCCGTCTACTACTGCGCTAGAGTGGGCGGAGCCTTCCCT ATGGGACTACTGGGGTCAAGGCACCCTGGTCACCGTGTCTAGC |

TABLE 4-continued

Summary of the sequences of exemplary anti-TIM-3 antibodies.

Hybridoma clone

| | | |
|---|---|---|
| SEQ ID NO: 28 | Heavy Chain | QVQLVQSGAEVKKPGASVKVSCKASGYTFTSYNMHWVRQAPGQGLEWIGDIY PGSGDTSYNQKFKGRATMTADKSTSTVYMELSSLRSEDTAVYYCARVGGAFP MDYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLG |
| SEQ ID NO: 29 | DNA Heavy Chain | CAGGTGCAGCTGGTGCAGTCAGGCGCCGAAGTGAAGAAACCCGGCGCTAGTG TGAAAGTTAGCTGTAAAGCTAGTGGCTACACCTTCACTAGCTATAATATGCA CTGGGTTCGCCAGGCCCCAGGTCAAGGCCTCGAGTGGATCGGCGATATCTAC CCCGGTAGCGGCGACACTAGTTATAATCAGAAGTTTAAGGGTAGAGCTACTA TGACCGCCGATAAGTCTACTAGCACCGTCTATATGGAACTGAGTTCCCTGAG GTCTGAAGATACCGCCGTCTACTACTGCGCTAGAGTGGGCGGAGCCTTCCCT ATGGACTACTGGGGTCAAGGCACCCTGGTCACCGTGTCTAGCGCTAGCACTA AGGGCCCGTCCGTGTTCCCCCTGGCACCTTGTAGCCGGAGCACTAGCGAATC CACCGCTGCCCTCGGCTGCCTGGTCAAGGATTACTTCCCGGAGCCCGTGACC GTGTCCTGGAACAGCGGAGCCCTGACCTCCGGAGTGCACACCTTCCCCGCTG TGCTGCAGAGCTCCGGGCTGTACTCGCTGTCGTCGGTGGTCACGGTGCCTTC ATCTAGCCTGGGTACCAAGACCTACACTTGCAACGTGGACCACAAGCCTTCC AACACTAAGGTGGACAAGCGCGTCGAATCGAAGTACGGCCCACCGTGCCCGC CTTGTCCCGCGCCGGAGTTCCTCGGCGGTCCCTCGGTCTTTCTGTTCCCACC GAAGCCCAAGGACACTTTGATGATTTCCCGCACCCCTGAAGTGACATGCGTG GTCGTGGACGTGTCACAGGAAGATCCGGAGGTGCAGTTCAATTGGTACGTGG ATGGCGTCGAGGTGCACAACGCCAAAACCAAGCCGAGGGAGGAGCAGTTCAA CTCCACTTACCGCGTCGTGTCCGTGCTGACGGTGCTGCATCAGGACTGGCTG AACGGGAAGGAGTACAAGTGCAAAGTGTCCAACAAGGGACTTCCTAGCTCAA TCGAAAAGACCATCTCGAAAGCAAGGGACAGCCCCGGGAACCCCAAGTGTA TACCCTGCCACCGAGCCAGGAAGAAATGACTAAGAACCAAGTCTCATTGACT TGCCTTGTGAAGGGCTTCTACCCATCGGATATCGCCGTGGAATGGGAGTCCA ACGGCCAGCCGGAAAACAACTACAAGACCACCCCTCCGGTGCTGGACTCAGA CGGATCCTTCTTCCTCTACTCGCGGCTGACCGTGGATAAGAGCAGATGGCAG GAGGGAAATGTGTTCAGCTGTTCTGTGATGCATGAAGCCCTGCACAACCACT ACACTCAGAAGTCCCTGTCCCTCTCCCTGGGA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 20 | VL | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIK |
| SEQ ID NO: 21 | DNA VL | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTACTGTCAGCAGTCTAGGAAGGACCCTAGCACCTTCGGCGGA GGCACTAAGGTCGAGATTAAG |
| SEQ ID NO: 22 | Light Chain | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG |

TABLE 4-continued

Summary of the sequences of exemplary anti-TIM-3 antibodies.

Hybridoma clone

| | | |
|---|---|---|
| | | GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 23 | DNA<br>Light<br>Chain | GATATCGTCCTGACTCAGTCACCCGATAGCCTGGCCGTCAGCCTGGGCGAGC<br>GGGCTACTATTAACTGTAGAGCTAGTGAATCAGTCGAGTACTACGGCACTAG<br>CCTGATGCAGTGGTATCAGCAGAAGCCCGGTCAACCCCCTAAGCTGCTGATC<br>TACGCCGCCTCTAACGTGGAATCAGGCGTGCCCGATAGGTTTAGCGGTAGCG<br>GTAGTGGCACCGACTTCACCCTGACTATTAGTAGCCTGCAGGCCGAGGACGT<br>GGCCGTCTACTACTGTCAGCAGTCTAGGAAGGACCCTAGCACCTTCGGCGGA<br>GGCACTAAGGTCGAGATTAAGCGTACGGTGGCCGCTCCCAGCGTGTTCATCT<br>TCCCCCCCAGCGACGAGCAGCTGAAGAGCGGCACCGCCAGCGTGGTGCCT<br>GCTGAACAACTTCTACCCCCGGGAGGCCAAGGTGCAGTGGAAGGTGGACAAC<br>GCCCTGCAGAGCGGCAACAGCCAGGAGAGCGTCACCGAGCAGGACAGCAAGG<br>ACTCCACCTACAGCCTGAGCAGCACCCTGACCCTGAGCAAGGCCGACTACGA<br>GAAGCATAAGGTGTACGCCTGCGAGGTGACCCACCAGGGCCTGTCCAGCCCC<br>GTGACCAAGAGCTTCAACAGGGGCGAGTGC |

ABTIM3-hum03

| | | |
|---|---|---|
| SEQ ID<br>NO: 3<br>(Kabat) | HCDR1 | SYNMH |
| SEQ ID<br>NO: 30<br>(Kabat) | HCDR2 | DIYPGQGDTSYNQKFKG |
| SEQ ID<br>NO: 5<br>(Kabat) | HCDR3 | VGGAFPMDY |
| SEQ ID<br>NO: 9<br>(Chothia) | HCDR1 | GYTFTSY |
| SEQ ID<br>NO: 31<br>(Chothia) | HCDR2 | YPGQGD |
| SEQ ID<br>NO: 5<br>(Chothia) | HCDR3 | VGGAFPMDY |
| SEQ ID<br>NO: 32 | VH | QVQLVQSGAEVKKPGASVKVSCKASGYTFTSYNMHWVRQAPGQGLEWIGDIY<br>PGQGDTSYNQKFKGRATMTADKSTSTVYMELSSLRSEDTAVYYCARVGGAFP<br>MDYWGQGTLVTVSS |
| SEQ ID<br>NO: 33 | DNA VH | CAGGTGCAGCTGGTGCAGTCAGGCGCCGAAGTGAAGAAACCCGGCGCTAGTG<br>TGAAAGTTAGCTGTAAAGCTAGTGGCTATACTTTCACTTCTTATAATATGCA<br>CTGGGTCCGCCAGGCCCCAGGTCAAGGCCTCGAGTGGATCGGCGATATCTAC<br>CCCGGTCAAGGCGACACTTCCTATAATCAGAAGTTTAAGGGTAGAGCTACTA<br>TGACCGCCGATAAGTCTACTTCTACCGTCTATATGGAACTGAGTTCCCTGAG<br>GTCTGAGGACACCGCCGTCTACTACTGCGCTAGAGTGGGCGGAGCCTTCCCA<br>ATGGACTACTGGGGTCAAGGCACCCTGGTCACCGTGTCTAGC |
| SEQ ID<br>NO: 34 | Heavy<br>Chain | QVQLVQSGAEVKKPGASVKVSCKASGYTFTSYNMHWVRQAPGQGLEWIGDIY<br>PGQGDTSYNQKFKGRATMTADKSTSTVYMELSSLRSEDTAVYYCARVGGAFP<br>MDYWGQGTLVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLG |
| SEQ ID<br>NO: 35 | DNA<br>Heavy<br>Chain | CAGGTGCAGCTGGTGCAGTCAGGCGCCGAAGTGAAGAAACCCGGCGCTAGTG<br>TGAAAGTTAGCTGTAAAGCTAGTGGCTATACTTTCACTTCTTATAATATGCA<br>CTGGGTCCGCCAGGCCCCAGGTCAAGGCCTCGAGTGGATCGGCGATATCTAC<br>CCCGGTCAAGGCGACACTTCCTATAATCAGAAGTTTAAGGGTAGAGCTACTA<br>TGACCGCCGATAAGTCTACTTCTACCGTCTATATGGAACTGAGTTCCCTGAG<br>GTCTGAGGACACCGCCGTCTACTACTGCGCTAGAGTGGGCGGAGCCTTCCCA<br>ATGGACTACTGGGGTCAAGGCACCCTGGTCACCGTGTCTAGCGCTAGCACTA<br>AGGGCCCGTCCGTGTTCCCCCTGGCACCTTGTAGCCGGAGCACTAGCGAATC<br>CACCGCTGCCCTCGGCTGCCTGGTCAAGGATTACTTCCCGGAGCCCGTGACC |

TABLE 4-continued

Summary of the sequences of exemplary anti-TIM-3 antibodies.

Hybridoma
clone

```
             GTGTCCTGGAACAGCGGAGCCCTGACCTCCGGAGTGCACACCTTCCCCGCTG
             TGCTGCAGAGCTCCGGGCTGTACTCGCTGTCGTCGGTGGTCACGGTGCCTTC
             ATCTAGCCTGGGTACCAAGACCTACACTTGCAACGTGGACCACAAGCCTTCC
             AACACTAAGGTGGACAAGCGCGTCGAATCGAAGTACGCCCACCGTGCCCGC
             CTTGTCCCGCGCCGGAGTTCCTCGGCGGTCCCTCGGTCTTTCTGTTCCCACC
             GAAGCCCAAGGACACTTTGATGATTTCCCGCACCCCTGAAGTGACATGCGTG
             GTCGTGGACGTGTCACAGGAAGATCCGGAGGTGCAGTTCAATTGGTACGTGG
             ATGGCGTCGAGGTGCACAACGCCAAAACCAAGCCGAGGGAGGAGCAGTTCAA
             CTCCACTTACCGCGTCGTGTCCGTGCTGACGGTGCTGCATCAGGACTGGCTG
             AACGGGAAGGAGTACAAGTGCAAAGTGTCCAACAAGGGACTTCCTAGCTCAA
             TCGAAAAGACCATCTCGAAAGCCAAGGGACAGCCCCGGGAACCCCAAGTGTA
             TACCCTGCCACCGAGCCAGGAAGAAATGACTAAGAACCAAGTCTCATTGACT
             TGCCTTGTGAAGGGCTTCTACCCATCGGATATCGCCGTGGAATGGGAGTCCA
             ACGGCCAGCCGGAAAACAACTACAAGACCACCCCTCCGGTGCTGGACTCAGA
             CGGATCCTTCTTCCTCTACTCGCGGCTGACCGTGGATAAGAGCAGATGGCAG
             GAGGGAAATGTGTTCAGCTGTTCTGTGATGCATGAAGCCCTGCACAACCACT
             ACACTCAGAAGTCCCTGTCCCTCTCCCTGGGA
```

| SEQ ID NO: 6 (Kabat) | LCDR1 | RASESVEYYGTSLMQ |
|---|---|---|
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 20 | VL | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIK |
| SEQ ID NO: 21 | DNA VL | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTACTGTCAGCAGTCTAGGAAGGACCCTAGCACCTTCGGCGGA GGCACTAAGGTCGAGATTAAG |
| SEQ ID NO: 22 | Light Chain | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 23 | DNA Light Chain | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTACTGTCAGCAGTCTAGGAAGGACCCTAGCACCTTCGGCGGA GGCACTAAGGTCGAGATTAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

TABLE 4-continued

Summary of the sequences of exemplary anti-TIM-3 antibodies.

Hybridoma clone

ABTIM3-hum04

| | | |
|---|---|---|
| SEQ ID NO: 3 (Kabat) | HCDR1 | SYNMH |
| SEQ ID NO: 4 (Kabat) | HCDR2 | DIYPGNGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 10 (Chothia) | HCDR2 | YPGNGD |
| SEQ ID NO: 5 (Chothia) | HCDR3 | VGGAFPMDY |
| SEQ ID NO: 36 | VH | QVQLVQSGAEVKKPGASVKVSCKASGYTFTSYNMHWIRQAPGQGLEWIGDIY PGNGDTSYNQKFKGRATLTADKSTSTVYMELSSLRSEDTAVYYCARVGGAFP MDYWGQGTLVTVSS |
| SEQ ID NO: 37 | DNA VH | CAGGTGCAGCTGGTGCAGTCAGGCGCCGAAGTGAAGAAACCCGGCGCTAGTG TGAAAGTTTCTTGTAAAGCTAGTGGCTACACCTTCACTAGCTATAATATGCA CTGGATTAGACAGGCCCCAGGGCAGGGCCTCGAGTGGATCGGCGATATCTAC CCCGGGAACGGCGACACTAGTTATAATCAGAAGTTTAAGGGTAGAGCTACCC TGACCGCCGATAAGTCTACTAGCACCGTCTATATGGAACTGAGTTCCCTGAG GTCTGAGGACACCGCCGTCTACTACTGCGCTAGAGTGGGCGGAGCCTTCCCT ATGGACTACTGGGGCAGGGCACCCTGGTCACCGTGTCTAGC |
| SEQ ID NO: 38 | Heavy Chain | QVQLVQSGAEVKKPGASVKVSCKASGYTFTSYNMHWIRQAPGQGLEWIGDIY PGNGDTSYNQKFKGRATLTADKSTSTVYMELSSLRSEDTAVYYCARVGGAFP MDYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLG |
| SEQ ID NO: 39 | DNA Heavy Chain | CAGGTGCAGCTGGTGCAGTCAGGCGCCGAAGTGAAGAAACCCGGCGCTAGTG TGAAAGTTTCTTGTAAAGCTAGTGGCTACACCTTCACTAGCTATAATATGCA CTGGATTAGACAGGCCCCAGGGCAGGGCCTCGAGTGGATCGGCGATATCTAC CCCGGGAACGGCGACACTAGTTATAATCAGAAGTTTAAGGGTAGAGCTACCC TGACCGCCGATAAGTCTACTAGCACCGTCTATATGGAACTGAGTTCCCTGAG GTCTGAGGACACCGCCGTCTACTACTGCGCTAGAGTGGGCGGAGCCTTCCCT ATGGACTACTGGGGCAGGGCACCCTGGTCACCGTGTCTAGCGCTAGCACTA AGGGCCCGTCCGTGTTCCCCCTGGCACCTTGTAGCCGGAGCACTAGCGAATC CACCGCTGCCCTCGGCTGCCTGGTCAAGGATTACTTCCCGGAGCCCGTGACC GTGTCCTGGAACAGCGGAGCCCTGACCTCCGGAGTGCACACCTTCCCCGCTG TGCTGCAGAGCTCCGGGCTGTACTCGCTGTCGTCGGTGGTCACGGTGCCTTC ATCTAGCCTGGGTACCAAGACCTACACTTGCAACGTGGACCACAAGCCTTCC AACACTAAGGTGGACAAGCGCGTCGAATCGAAGTACGGCCCACCGTGCCCGC CTTGTCCCGCGCCGGAGTTCCTCGGCGGTCCCTCGGTCTTTCTGTTCCCACC GAAGCCCAAGGACACTTTGATGATTTCCCGCACCCCTGAAGTGACATGCGTG GTCGTGGACGTGTCACAGGAAGATCCGGAGGTGCAGTTCAATTGGTACGTGG ATGGCGTCGAGGTGCACAACGCCAAAACCAAGCCGAGGGAGGAGCAGTTCAA CTCCACTTACCGCGTCGTGTCCGTGCTGACGGTGCTGCATCAGGACTGGCTG AACGGGAAGGAGTACAAGTGCAAGGTCTCCAACAAGGGACTTCCTAGCTCAA TCGAAAAGACCATCTCGAAAGCCAAGGGACAGCCCCGGGAACCCCAAGTGTA TACCCTGCCACCGAGCCAGGAAGAAATGACTAAGAACCAAGTCTCATTGACT TGCCTTGTGAAGGGCTTCTACCCATCGGATATCGCCGTGGAATGGGAGTCCA ACGGCCAGCCGGAAAACAACTACAAGACCACCCCTCCGGTGCTGGACTCAGA CGGATCCTTCTTCCTCTACTCGCGGCTGACCGTGGATAAGAGCAGATGGCAG GAGGGAAATGTGTTCAGCTGTTCTGTGATGCATGAAGCCCTGCACAACCACT ACACTCAGAAGTCCCTGTCCCTCTCCCTGGGA |

TABLE 4-continued

Summary of the sequences of exemplary anti-TIM-3 antibodies.

Hybridoma clone

| | | |
|---|---|---|
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 40 | VL | DIVLTQSPDSLAVSLGERATINCRASESVEYYGTSLMQWYQQKPGQPPKLLI YAASNVESGVPDRFSGSGSGTDFTLTISSLQAEDVAVYFCQQSRKDPSTFGG GTKVEIK |
| SEQ ID NO: 41 | DNA VL | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTTCTGTCAGCAGTCTAGGAAGGACCCTAGCACCTTCGGCGGA GGCACTAAGGTCGAGATTAAG |
| SEQ ID NO: 42 | Light Chain | DIVLTQSPDSLAVSLGERATINCRASESVEYYGTSLMQWYQQKPGQPPKLLI YAASNVESGVPDRFSGSGSGTDFTLTISSLQAEDVAVYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 43 | DNA Light Chain | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTTCTGTCAGCAGTCTAGGAAGGACCCTAGCACCTTCGGCGGA GGCACTAAGGTCGAGATTAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

ABTIM3-hum05

| | | |
|---|---|---|
| SEQ ID NO: 3 (Kabat) | HCDR1 | SYNMH |
| SEQ ID NO: 24 (Kabat) | HCDR2 | DIYPGSGDTSYNQKFKG |
| SEQ ID NO: 5 (Kabat) | HCDR3 | VGGAFPMDY |
| SEQ ID NO: 9 (Chothia) | HCDR1 | GYTFTSY |

TABLE 4-continued

Summary of the sequences of exemplary anti-TIM-3 antibodies.

Hybridoma clone

| | | |
|---|---|---|
| SEQ ID NO: 25 (Chothia) | HCDR2 | YPGSGD |
| SEQ ID NO: 5 (Chothia) | HCDR3 | VGGAFPMDY |
| SEQ ID NO: 44 | VH | QVQLVQSGAEVKKPGASVKVSCKASGYTFTSYNMHWIRQAPGQGLEWIGDIYPGSGDTSYNQKFKGRATLTADKSTSTVYMELSSLRSEDTAVYYCARVGGAFPMDYWGQGTLVTVSS |
| SEQ ID NO: 45 | DNA VH | CAGGTGCAGCTGGTGCAGTCAGGCGCCGAAGTGAAGAAACCCGGCGCAAGCGTTAAAGTCTCATGTAAAGCTAGTGGCTACACCTTCACTAGCTATAATATGCACTGGATTAGACAGGCCCCAGGGCAAGGCCTGGAGTGGATCGGCGATATCTACCCCGGTAGCGGCGACACTAGTTATAATCAGAAGTTTAAGGGTAGAGCTACCCTGACCGCCGATAAGTCTACTAGCACCGTCTATATGGAACTGAGTTCCCTGAGGAGTGAAGACACCGCCGTCTACTACTGCGCTAGAGTGGGCGGAGCCTTCCCTATGGACTACTGGGGTCAAGGCACCCTGGTCACCGTGTCAAGC |
| SEQ ID NO: 46 | Heavy Chain | QVQLVQSGAEVKKPGASVKVSCKASGYTFTSYNMHWIRQAPGQGLEWIGDIYPGSGDTSYNQKFKGRATLTADKSTSTVYMELSSLRSEDTAVYYCARVGGAFPMDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| SEQ ID NO: 47 | DNA Heavy Chain | CAGGTGCAGCTGGTGCAGTCAGGCGCCGAAGTGAAGAAACCCGGCGCAAGCGTTAAAGTCTCATGTAAAGCTAGTGGCTACACCTTCACTAGCTATAATATGCACTGGATTAGACAGGCCCCAGGGCAAGGCCTGGAGTGGATCGGCGATATCTACCCCGGTAGCGGCGACACTAGTTATAATCAGAAGTTTAAGGGTAGAGCTACCCTGACCGCCGATAAGTCTACTAGCACCGTCTATATGGAACTGAGTTCCCTGAGGAGTGAAGACACCGCCGTCTACTACTGCGCTAGAGTGGGCGGAGCCTTCCCTATGGACTACTGGGGTCAAGGCACCCTGGTCACCGTGTCAAGCGCTAGCACTAAGGGCCCGTCCGTGTTCCCCCTGGCACCTTGTAGCCGGAGCACTAGCGAATCCACCGCTGCCCTCGGCTGCCTGGTCAAGGATTACTTCCCGGAGCCCGTGACCGTGTCCTGGAACAGCGGAGCCCTGACCTCCGGAGTGCACACCTTCCCGCTGTGCTGCAGAGCTCCGGGCTGTACTCGCTGTCGTCGGTGGTCACGGTGCCTTCATCTAGCCTGGGTACCAAGACCTACACTTGCAACGTGGACCACAAGCCTTCCAACACTAAGGTGGACAAGCGCGTCGAATCGAAGTACGCCCACCGTGCCCGCCTTGTCCCGCGCCGGAGTTCCTCGGCGGTCCCTCGGTCTTTCTGTTCCCACCGAAGCCCAAGGACACTTTGATGATTTCCCGCACCCCTGAAGTGACATGCGTGGTCGTGGACGTGTCACAGGAAGATCCGGAGGTGCAGTTCAATTGGTACGTGGATGGCGTCGAGGTGCACAACGCCAAAACCAAGCCGAGGGAGGAGCAGTTCAACTCCACTTACCGCGTCGTGTCCGTGCTGACGGTGCTGCATCAGGACTGGCTGAACGGGAAGGAGTACAAGTGCAAAGTGTCCAACAAGGGACTTCCTAGCTCAATCGAAAAGACCATCTCGAAAGCCAAGGGACAGCCCCGGGAACCCCAAGTGTATACCCTGCCACCGAGCCAGGAAGAAATGACTAAGAACCAAGTCTCATTGACTTGCCTTGTGAAGGGCTTCTACCCATCGGATATCGCCGTGGAATGGGAGTCCAACGGCCAGCCGGAAAACAACTACAAGACCACCCCTCCGGTGCTGGACTCAGACGGATCCTTCTTCCTCTACTCGCGGCTGACCGTGGATAAGAGCAGATGGCAGGAGGGAAATGTGTTCAGCTGTTCTGTGATGCATGAAGCCCTGCACAACCACTACACTCAGAAGTCCCTGTCCCTCTCCCTGGGA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |

TABLE 4-continued

Summary of the sequences of exemplary anti-TIM-3 antibodies.

Hybridoma
clone

| | | |
|---|---|---|
| SEQ ID NO: 13 (Chothia) | LCDR2 | AAS |
| SEQ ID NO: 14 (Chothia) | LCDR3 | SRKDPS |
| SEQ ID NO: 40 | VL | DIVLTQSPDSLAVSLGERATINCRASESVEYYGTSLMQWYQQKPGQPPKLLI YAASNVESGVPDRFSGSGSGTDFTLTISSLQAEDVAVYFCQQSRKDPSTFGG GTKVEIK |
| SEQ ID NO: 41 | DNA VL | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTTCTGTCAGCAGTCTAGGAAGGACCCTAGCACCTTCGGCGGA GGCACTAAGGTCGAGATTAAG |
| SEQ ID NO: 42 | Light Chain | DIVLTQSPDSLAVSLGERATINCRASESVEYYGTSLMQWYQQKPGQPPKLLI YAASNVESGVPDRFSGSGSGTDFTLTISSLQAEDVAVYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 43 | DNA Light Chain | GATATCGTCCTGACTCAGTCACCCGATAGCCTGGCCGTCAGCCTGGGCGAGC GGGCTACTATTAACTGTAGAGCTAGTGAATCAGTCGAGTACTACGGCACTAG CCTGATGCAGTGGTATCAGCAGAAGCCCGGTCAACCCCCTAAGCTGCTGATC TACGCCGCCTCTAACGTGGAATCAGGCGTGCCCGATAGGTTTAGCGGTAGCG GTAGTGGCACCGACTTCACCCTGACTATTAGTAGCCTGCAGGCCGAGGACGT GGCCGTCTACTTCTGTCAGCAGTCTAGGAAGGACCCTAGCACCTTCGGCGGA GGCACTAAGGTCGAGATTAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

ABTIM3-hum06

| | | |
|---|---|---|
| SEQ ID NO: 3 (Kabat) | HCDR1 | SYNMH |
| SEQ ID NO: 30 (Kabat) | HCDR2 | DIYPGQGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 31 (Chothia) | HCDR2 | YPGQGD |
| SEQ ID NO: 5 (Chothia) | HCDR3 | VGGAFPMDY |
| SEQ ID NO: 48 | VH | QVQLVQSGAEVKKPGASVKVSCKASGYTFTSYNMHWIRQAPGQGLEWIGDIY PGQGDTSYNQKFKGRATLTADKSTSTVYMELSSLRSEDTAVYYCARVGGAFP MDYWGQGTLVTVSS |
| SEQ ID NO: 49 | DNA VH | CAGGTGCAGCTGGTGCAGTCAGGCGCCGAAGTGAAGAAACCCGGCGCTAGTG TGAAAGTCTCTTGTAAAGCTAGTGGCTACACCTTCACTAGCTATAATATGCA CTGGATTAGACAGGCCCCAGGTCAAGGCCTCGAGTGGATCGGCGATATCTAC CCCGGTCAAGGCGACACTAGTTATAATCAGAAGTTTAAGGGTAGAGCTACCC |

TABLE 4-continued

Summary of the sequences of exemplary anti-TIM-3 antibodies.

Hybridoma
clone

|  |  |  |
|---|---|---|
|  |  | TGACCGCCGATAAGTCTACTAGCACCGTCTATATGGAACTGAGTTCCCTGAG<br>GTCTGAGGACACCGCCGTCTACTACTGCGCTAGAGTGGGCGGAGCCTTCCCT<br>ATGGACTACTGGGGTCAAGGCACCCTGGTCACCGTGTCTAGC |
| SEQ ID<br>NO: 50 | Heavy<br>Chain | QVQLVQSGAEVKKPGASVKVSCKASGYTFTSYNMHWIRQAPGQGLEWIGDIY<br>PGQGDTSYNQKFKGRATLTADKSTSTVYMELSSLRSEDTAVYYCARVGGAFP<br>MDYWGQGTLVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLG |
| SEQ ID<br>NO: 51 | DNA<br>Heavy<br>Chain | CAGGTGCAGCTGGTGCAGTCAGGCGCCGAAGTGAAGAAACCCGGCGCTAGTG<br>TGAAAGTCTCTTGTAAAGCTAGTGGCTACACCTTCACTAGCTATAATATGCA<br>CTGGATTAGACAGGCCCCAGGTCAAGGCCTCGAGTGGATCGGCGATATCTAC<br>CCCGGTCAAGGCGACACTAGTTATAATCAGAAGTTTAAGGGTAGAGCTACCC<br>TGACCGCCGATAAGTCTACTAGCACCGTCTATATGGAACTGAGTTCCCTGAG<br>GTCTGAGGACACCGCCGTCTACTACTGCGCTAGAGTGGGCGGAGCCTTCCCT<br>ATGGACTACTGGGGTCAAGGCACCCTGGTCACCGTGTCTAGCGCTAGCACTA<br>AGGGCCCGTCCGTGTTCCCCCTGGCACCTTGTAGCCGGAGCACTAGCGAATC<br>CACCGCTGCCCTCGGCTGCCTGGTCAAGGATTACTTCCCGGAGCCCGTGACC<br>GTGTCCTGGAACAGCGGAGCCCTGACCTCCGGAGTGCACACCTTCCCCGCTG<br>TGCTGCAGAGCTCCGGGCTGTACTCGCTGTCGTCGGTGGTCACGGTGCCTTC<br>ATCTAGCCTGGGTACCAAGACCTACACTTGCAACGTGACCACAAGCCTTCC<br>AACACTAAGGTGGACAAGCGCGTCGAATCGAAGTACGGCCCACCGTGCCCGC<br>CTTGTCCCGCGCCGGAGTTCCTCGGCGGTCCCTCGGTCTTTCTGTTCCCACC<br>GAAGCCCAAGGACACTTTGATGATTTCCCGCACCCCTGAAGTGACATGCGTG<br>GTCGTGGACGTGTCACAGGAAGATCCGGAGGTGCAGTTCAATTGGTACGTGG<br>ATGGCGTCGAGGTGCACAACGCCAAAACCAAGCCGAGGGAGGAGCAGTTCAA<br>CTCCACTTACCGCGTCGTGTCCGTGCTGACGGTGCTGCATCAGGACTGGCTG<br>AACGGGAAGGAGTACAAGTGCAAAGTGTCCAACAAGGGACTTCCTAGCTCAA<br>TCGAAAAGACCATCTCGAAAGCCAAGGGACAGCCCCGGGAACCCCAAGTGTA<br>TACCCTGCCACCGAGCCAGGAAGAAATGACTAAGAACCAAGTCTCATTGACT<br>TGCCTTGTGAAGGGCTTCTACCCATCGGATATCGCCGTGGAATGGGAGTCCA<br>ACGGCCAGCCGGAAAACAACTACAAGACCACCCCTCCGGTGCTGGACTCAGA<br>CGGATCCTTCTTCCTCTACTCGCGGCTGACCGTGGATAAGAGCAGATGGCAG<br>GAGGGAAATGTGTTCAGCTGTTCTGTGATGCATGAAGCCCTGCACAACCACT<br>ACACTCAGAAGTCCCTGTCCCTCTCCCTGGGA |
| SEQ ID<br>NO: 6<br>(Kabat) | LCDR1 | RASESVEYYGTSLMQ |
| SEQ ID<br>NO: 7<br>(Kabat) | LCDR2 | AASNVES |
| SEQ ID<br>NO: 8<br>(Kabat) | LCDR3 | QQSRKDPST |
| SEQ ID<br>NO: 12<br>(Chothia) | LCDR1 | SESVEYYGTSL |
| SEQ ID<br>NO: 13<br>(Chothia) | LCDR2 | AAS |
| SEQ ID<br>NO: 14<br>(Chothia) | LCDR3 | SRKDPS |
| SEQ ID<br>NO: 40 | VL | DIVLTQSPDSLAVSLGERATINCRASESVEYYGTSLMQWYQQKPGQPPKLLI<br>YAASNVESGVPDRFSGSGSGTDFTLTISSLQAEDVAVYFCQQSRKDPSTFGG<br>GTKVEIK |
| SEQ ID<br>NO: 41 | DNA VL | GATATCGTCCTGACTCAGTCACCCGATAGCCTGGCCGTCAGCCTGGGCGAGC<br>GGGCTACTATTAACTGTAGAGCTAGTGAATCAGTCGAGTACTACGGCACTAG<br>CCTGATGCAGTGGTATCAGCAGAAGCCCGGTCAACCCCCTAAGCTGCTGATC<br>TACGCCGCCTCTAACGTGGAATCAGGCGTGCCCGATAGGTTTAGCGGTAGCG<br>GTAGTGGCACCGACTTCACCCTGACTATTAGTAGCCTGCAGGCCGAGGACGT |

TABLE 4-continued

Summary of the sequences of exemplary anti-TIM-3 antibodies.

Hybridoma clone

| | | |
|---|---|---|
| | | GGCCGTCTACTTCTGTCAGCAGTCTAGGAAGGACCCTAGCACCTTCGGCGGA<br>GGCACTAAGGTCGAGATTAAG |
| SEQ ID<br>NO: 42 | Light<br>Chain | DIVLTQSPDSLAVSLGERATINCRASESVEYYGTSLMQWYQQKPGQPPKLLI<br>YAASNVESGVPDRFSGSGSGTDFTLTISSLQAEDVAVYFCQQSRKDPSTFGG<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 43 | DNA<br>Light<br>Chain | GATATCGTCCTGACTCAGTCACCCGATAGCCTGGCCGTCAGCCTGGGCGAGC<br>GGGCTACTATTAACTGTAGAGCTAGTGAATCAGTCGAGTACTACGGCACTAG<br>CCTGATGCAGTGGTATCAGCAGAAGCCCGGTCAACCCCCTAAGCTGCTGATC<br>TACGCCGCCTCTAACGTGGAATCAGGCGTGCCCGATAGGTTTAGCGGTAGCG<br>GTAGTGGCACCGACTTCACCCTGACTATTAGTAGCCTGCAGGCCGAGGACGT<br>GGCCGTCTACTTCTGTCAGCAGTCTAGGAAGGACCCTAGCACCTTCGGCGGA<br>GGCACTAAGGTCGAGATTAAGCGTACGGTGGCCGCTCCCAGCGTGTTCATCT<br>TCCCCCCCAGCGACGAGCAGCTGAAGAGCGGCACCGCCAGCGTGGTGTGCCT<br>GCTGAACAACTTCTACCCCCGGGAGGCCAAGGTGCAGTGGAAGGTGGACAAC<br>GCCCTGCAGAGCGGCAACAGCCAGGAGAGCGTCACCGAGCAGGACAGCAAGG<br>ACTCCACCTACAGCCTGAGCAGCACCCTGACCCTGAGCAAGGCCGACTACGA<br>GAAGCATAAGGTGTACGCCTGCGAGGTGACCCACCAGGGCCTGTCCAGCCCC<br>GTGACCAAGAGCTTCAACAGGGGCGAGTGC |

ABTIM3-hum07

| | | |
|---|---|---|
| SEQ ID<br>NO: 3<br>(Kabat) | HCDR1 | SYNMH |
| SEQ ID<br>NO: 4<br>(Kabat) | HCDR2 | DIYPGNGDTSYNQKFKG |
| SEQ ID<br>NO: 5<br>(Kabat) | HCDR3 | VGGAFPMDY |
| SEQ ID<br>NO: 9<br>(Chothia) | HCDR1 | GYTFTSY |
| SEQ ID<br>NO: 10<br>(Chothia) | HCDR2 | YPGNGD |
| SEQ ID<br>NO: 5<br>(Chothia) | HCDR3 | VGGAFPMDY |
| SEQ ID<br>NO: 36 | VH | QVQLVQSGAEVKKPGASVKVSCKASGYTFTSYNMHWIRQAPGQGLEWIGDIY<br>PGNGDTSYNQKFKGRATLTADKSTSTVYMELSSLRSEDTAVYYCARVGGAFP<br>MDYWGQGTLVTVSS |
| SEQ ID<br>NO: 115 | DNA VH | CAGGTCCAGCTGGTCCAGAGCGGAGCAGAGGTCAAAAAGCCCGGAGCAAGCG<br>TGAAGGTCTCATGCAAAGCAAGCGGATACACATTTACATCATACAACATGCA<br>CTGGATCAGGCAGGCTCCAGGACAGGGACTGGAGTGGATCGGGGACATCTAC<br>CCTGGAAACGGCGATACTAGCTATAATCAGAAGTTCAAAGGCCGGGCCACCC<br>TGACAGCTGACAAGTCTACTAGTACCGTGTATATGGAGCTGAGCTCCCTGCG<br>GTCTGAAGATACCGCAGTGTACTATTGCGCCAGAGTCGGGGGGGGCATTTCCT<br>ATGGATTATTGGGGCAGGGGACTCTGGTCACTGTCTCCTCC |
| SEQ ID<br>NO: 116 | Heavy<br>Chain | QVQLVQSGAEVKKPGASVKVSCKASGYTFTSYNMHWIRQAPGQGLEWIGDIY<br>PGNGDTSYNQKFKGRATLTADKSTSTVYMELSSLRSEDTAVYYCARVGGAFP<br>MDYWGQGTLVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLGK |
| SEQ ID<br>NO: 117 | DNA<br>Heavy<br>Chain | CAGGTCCAGCTGGTCCAGAGCGGAGCAGAGGTCAAAAAGCCCGGAGCAAGCG<br>TGAAGGTCTCATGCAAAGCAAGCGGATACACATTTACATCATACAACATGCA<br>CTGGATCAGGCAGGCTCCAGGACAGGGACTGGAGTGGATCGGGGACATCTAC<br>CCTGGAAACGGCGATACTAGCTATAATCAGAAGTTCAAAGGCCGGGCCACCC |

TABLE 4-continued

Summary of the sequences of exemplary anti-TIM-3 antibodies.

Hybridoma
clone

|  |  |  |
|---|---|---|
|  |  | TGACAGCTGACAAGTCTACTAGTACCGTGTATATGGAGCTGAGCTCCCTGCG<br>GTCTGAAGATACCGCAGTGTACTATTGCGCCAGAGTCGGGGGGGCATTTCCT<br>ATGGATTATTGGGGCAGGGGACTCTGGTCACTGTCTCCTCCGCTAGCACCA<br>AGGGCCCATCCGTCTTCCCCCTGGCGCCCTGCTCCAGGAGCACCTCCGAGAG<br>CACAGCCGCCCTGGGCTGCCTGGTCAAGGACTACTTCCCCGAACCGGTGACG<br>GTGTCGTGGAACTCAGGCGCCCTGACCAGCGGCGTGCACACCTTCCCGGCTG<br>TCCTACAGTCCTCAGGACTCTACTCCCTCAGCAGCGTGGTGACCGTGCCCTC<br>CAGCAGCTTGGGCACGAAGACCTACACCTGCAACGTAGATCACAAGCCCAGC<br>AACACCAAGGTGGACAAGAGAGTTGAGTCCAAATATGGTCCCCCATGCCCAC<br>CATGCCCAGCACCTGAGTTCCTGGGGGGACCATCAGTCTTCCTGTTCCCCCC<br>AAAACCCAAGGACACTCTCATGATCTCCCGGACCCCTGAGGTCACGTGCGTG<br>GTGGTGGACGTGAGCCAGGAAGACCCCGAGGTCCAGTTCAACTGGTACGTGG<br>ATGGCGTGGAGGTGCATAATGCCAAGACAAAGCCGCGGGAGGAGCAGTTCAA<br>CAGCACGTACCGTGTGGTCAGCGTCCTCACCGTCCTGCACCAGGACTGGCTG<br>AACGGCAAGGAGTACAAGTGCAAGGTCTCCAACAAAGGCCTCCCGTCCTCCA<br>TCGAGAAAACCATCTCCAAAGCCAAAGGGCAGCCCCGAGAGCCACAGGTGTA<br>CACCCTGCCCCCATCCCAGGAGGAGATGACCAAGAACCAGGTCAGCCTGACC<br>TGCCTGGTCAAAGGCTTCTACCCCAGCGACATCGCCGTGGAGTGGGAGAGCA<br>ATGGGCAGCCGGAGAACAACTACAAGACCACGCCTCCCGTGCTGGACTCCGA<br>CGGCTCCTTCTTCCTCTACAGCAGGCTAACCGTGGACAAGAGCAGGTGGCAG<br>GAGGGGAATGTCTTCTCATGCTCCGTGATGCATGAGGCTCTGCACAACCACT<br>ACACACAGAAGAGCCTCTCCCTGTCTCTGGGTAAA |
| SEQ ID<br>NO: 6<br>(Kabat) | LCDR1 | RASESVEYYGTSLMQ |
| SEQ ID<br>NO: 7<br>(Kabat) | LCDR2 | AASNVES |
| SEQ ID<br>NO: 8<br>(Kabat) | LCDR3 | QQSRKDPST |
| SEQ ID<br>NO: 12<br>(Chothia) | LCDR1 | SESVEYYGTSL |
| SEQ ID<br>NO: 13<br>(Chothia) | LCDR2 | AAS |
| SEQ ID<br>NO:14<br>(Chothia) | LCDR3 | SRKDPS |
| SEQ ID<br>NO: 20 | VL | DIVLTQSPDSLAVSLGERATINCRASESVEYYGTSLMQWYQQKPGQPPKLLI<br>YAASNVESGVPDRFSGSGSGTDFTLTISSLQAEDVAVYYCQQSRKDPSTFGG<br>GTKVEIK |
| SEQ ID<br>NO: 118 | DNA VL | GACATCGTCCTGACACAGTCTCCTGACAGCCTGGCAGTGAGCCTGGGCGAAA<br>GGGCAACCATTAATTGTAGAGCTTCCGAGTCCGTCGAGTACTATGGCACTAG<br>TCTGATGCAGTGGTACCAGCAGAAGCCAGGGCAGCCCCCTAAACTGCTGATC<br>TATGCAGCTAGCAACGTGGAGTCCGGAGTCCCAGACCGGTTCTCTGGAAGTG<br>GGTCAGGAACCGATTTTACCCTGACAATTAGCTCCCTGCAGGCAGAAGACGT<br>GGCCGTCTACTATTGTCAGCAGAGCCGCAAGGACCCAAGCACATTCGGAGGG<br>GGGACCAAAGTGGAAATCAAG |
| SEQ ID<br>NO: 22 | Light<br>Chain | DIVLTQSPDSLAVSLGERATINCRASESVEYYGTSLMQWYQQKPGQPPKLLI<br>YAASNVESGVPDRFSGSGSGTDFTLTISSLQAEDVAVYYCQQSRKDPSTFGG<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 119 | DNA<br>Light<br>Chain | GACATCGTCCTGACACAGTCTCCTGACAGCCTGGCAGTGAGCCTGGGCGAAA<br>GGGCAACCATTAATTGTAGAGCTTCCGAGTCCGTCGAGTACTATGGCACTAG<br>TCTGATGCAGTGGTACCAGCAGAAGCCAGGGCAGCCCCCTAAACTGCTGATC<br>TATGCAGCTAGCAACGTGGAGTCCGGAGTCCCAGACCGGTTCTCTGGAAGTG<br>GGTCAGGAACCGATTTTACCCTGACAATTAGCTCCCTGCAGGCAGAAGACGT<br>GGCCGTCTACTATTGTCAGCAGAGCCGCAAGGACCCAAGCACATTCGGAGGG<br>GGGACCAAAGTGGAAATCAAGCGGACTGTTGCTGCACCATCTGTCTTCATCT<br>TCCCGCCATCTGATGAGCAGTTGAAATCTGGAACTGCCTCTGTTGTGTGCCT<br>GCTGAATAACTTCTATCCCAGAGAGGCCAAAGTACAGTGGAAGGTGGATAAC<br>GCCCTCCAATCGGGTAACTCCCAGGAGAGTGTCACAGAGCAGGACAGCAAGG |

TABLE 4-continued

Summary of the sequences of exemplary anti-TIM-3 antibodies.

Hybridoma
clone

ACAGCACCTACAGCCTCAGCAGCACCCTGACGCTGAGCAAAGCAGACTACGA
GAAACACAAAGTCTACGCCTGCGAAGTCACCCATCAGGGCCTGAGTTCACCG
GTGACAAAGAGCTTCAACAGGGGAGAGTGT

ABTIM3-hum08

| | | |
|---|---|---|
| SEQ ID NO: 3 (Kabat) | HCDR1 | SYNMH |
| SEQ ID NO: 4 (Kabat) | HCDR2 | DIYPGNGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 10 (Chothia) | HCDR2 | YPGNGD |
| SEQ ID NO: 5 (Chothia) | HCDR3 | VGGAFPMDY |
| SEQ ID NO: 16 | VH | QVQLVQSGAEVKKPGASVKVSCKASGYTFTSYNMHWVRQAPGQGLEWIGDIY PGNGDTSYNQKFKGRATMTADKSTSTVYMELSSLRSEDTAVYYCARVGGAFP MDYWGQGTLVTVSS |
| SEQ ID NO: 120 | DNA VH | CAGGTCCAGCTGGTCCAGAGCGGAGCAGAGGTCAAAAAGCCCGGAGCAAGCG TGAAGGTCTCATGCAAAGCAAGCGGATACACATTTACATCATACAACATGCA CTGGGTCAGGCAGGCTCCAGGACAGGGACTGGAGTGGATCGGGGACATCTAC CCTGGAAACGGCGATACTAGCTATAATCAGAAGTTCAAAGGCCGGGCCACCA TGACAGCTGACAAGTCTACTAGTACCGTGTATATGGAGCTGAGCTCCCTGCG GTCTGAAGATACCGCAGTGTACTATTGCGCCAGAGTCGGGGGGGCATTTCCT ATGGATTATTGGGGCAGGGGACTCTGGTCACTGTCTCCTCC |
| SEQ ID NO: 121 | Heavy Chain | QVQLVQSGAEVKKPGASVKVSCKASGYTFTSYNMHWVRQAPGQGLEWIGDIY PGNGDTSYNQKFKGRATMTADKSTSTVYMELSSLRSEDTAVYYCARVGGAFP MDYWGQGTLVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 122 | DNA Heavy Chain | CAGGTCCAGCTGGTCCAGAGCGGAGCAGAGGTCAAAAAGCCCGGAGCAAGCG TGAAGGTCTCATGCAAAGCAAGCGGATACACATTTACATCATACAACATGCA CTGGGTCAGGCAGGCTCCAGGACAGGGACTGGAGTGGATCGGGGACATCTAC CCTGGAAACGGCGATACTAGCTATAATCAGAAGTTCAAAGGCCGGGCCACCA TGACAGCTGACAAGTCTACTAGTACCGTGTATATGGAGCTGAGCTCCCTGCG GTCTGAAGATACCGCAGTGTACTATTGCGCCAGAGTCGGGGGGGCATTTCCT ATGGATTATTGGGGCAGGGGACTCTGGTCACTGTCTCCTCCGCTAGCACCA AGGGCCCATCCGTCTTCCCCCTGGCGCCCTGCTCCAGGAGCACCTCCGAGAG CACAGCCGCCCTGGGCTGCCTGGTCAAGGACTACTTCCCCGAACCGGTGACG GTGTCGTGGAACTCAGGCGCCCTGACCAGCGGCGTGCACACCTTCCCGGCTG TCCTACAGTCCTCAGGACTCTACTCCCTCAGCAGCGTGGTGACCGTGCCCTC CAGCAGCTTGGGCACGAAGACCTACACCTGCAACGTAGATCACAAGCCCAGC AACACCAAGGTGGACAAGAGAGTTGAGTCCAAATATGGTCCCCCATGCCCAC CATGCCCAGCACCTGAGTTCCTGGGGGGACCATCAGTCTTCCTGTTCCCCCC AAAACCCAAGGACACTCTCATGATCTCCCGGACCCCTGAGGTCACGTGCGTG GTGGTGGACGTGAGCCAGGAAGACCCCGAGGTCCAGTTCAACTGGTACGTGG ATGGCGTGGAGGTGCATAATGCCAAGACAAAGCCGCGGGAGGAGCAGTTCAA CAGCACGTACCGTGTGGTCAGCGTCCTCACCGTCCTGCACCAGGACTGGCTG AACGGCAAGGAGTACAAGTGCAAGGTCTCCAACAAAGGCCTCCCGTCCTCCA TCGAGAAAACCATCTCCAAAGCCAAAGGGCAGCCCCGAGAGCCACAGGTGTA CACCCTGCCCCCATCCCAGGAGGAGATGACCAAGAACCAGGTCAGCCTGACC TGCCTGGTCAAAGGCTTCTACCCCAGCGACATCGCCGTGGAGTGGGAGAGCA ATGGGCAGCCGGAGAACAACTACAAGACCACGCCTCCCGTGCTGGACTCCGA |

TABLE 4-continued

Summary of the sequences of exemplary anti-TIM-3 antibodies.

Hybridoma clone

|   |   |   |
|---|---|---|
|   |   | CGGCTCCTTCTTCCTCTACAGCAGGCTAACCGTGGACAAGAGCAGGTGGCAG<br>GAGGGGAATGTCTTCTCATGCTCCGTGATGCATGAGGCTCTGCACAACCACT<br>ACACACAGAAGAGCCTCTCCCTGTCTCTGGGTAAA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 40 | VL | DIVLTQSPDSLAVSLGERATINCRASESVEYYGTSLMQWYQQKPGQPPKLLI<br>YAASNVESGVPDRFSGSGSGTDFTLTISSLQAEDVAVYFCQQSRKDPSTFGG<br>GTKVEIK |
| SEQ ID NO: 123 | DNA VL | GACATCGTCCTGACACAGTCTCCTGACAGCCTGGCAGTGAGCCTGGGCGAAA<br>GGGCAACCATTAATTGTAGAGCTTCCGAGTCCGTCGAGTACTATGGCACTAG<br>TCTGATGCAGTGGTACCAGCAGAAGCCAGGGCAGCCCCCTAAACTGCTGATC<br>TATGCAGCTAGCAACGTGGAGTCCGGAGTCCCAGACCGGTTCTCTGGAAGTG<br>GGTCAGGAACCGATTTTACCCTGACAATTAGCTCCCTGCAGGCAGAAGACGT<br>GGCCGTCTACTTTTGTCAGCAGAGCCGCAAGGACCCAAGCACATTCGGAGGG<br>GGGACCAAAGTGGAAATCAAG |
| SEQ ID NO: 42 | Light Chain | DIVLTQSPDSLAVSLGERATINCRASESVEYYGTSLMQWYQQKPGQPPKLLI<br>YAASNVESGVPDRFSGSGSGTDFTLTISSLQAEDVAVYFCQQSRKDPSTFGG<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID NO: 124 | DNA Light Chain | GACATCGTCCTGACACAGTCTCCTGACAGCCTGGCAGTGAGCCTGGGCGAAA<br>GGGCAACCATTAATTGTAGAGCTTCCGAGTCCGTCGAGTACTATGGCACTAG<br>TCTGATGCAGTGGTACCAGCAGAAGCCAGGGCAGCCCCCTAAACTGCTGATC<br>TATGCAGCTAGCAACGTGGAGTCCGGAGTCCCAGACCGGTTCTCTGGAAGTG<br>GGTCAGGAACCGATTTTACCCTGACAATTAGCTCCCTGCAGGCAGAAGACGT<br>GGCCGTCTACTTTTGTCAGCAGAGCCGCAAGGACCCAAGCACATTCGGAGGG<br>GGGACCAAAGTGGAAATCAAGCGGACTGTTGCTGCACCATCTGTCTTCATCT<br>TCCCGCCATCTGATGAGCAGTTGAAATCTGGAACTGCCTCTGTTGTGTGCCT<br>GCTGAATAACTTCTATCCCAGAGAGGCCAAAGTACAGTGGAAGGTGGATAAC<br>GCCCTCCAATCGGGTAACTCCCAGGAGAGTGTCACAGAGCAGGACAGCAAGG<br>ACAGCACCTACAGCCTCAGCAGCACCCTGACGCTGAGCAAAGCAGACTACGA<br>GAAACACAAAGTCTACGCCTGCGAAGTCACCCATCAGGGCCTGAGTTCACCG<br>GTGACAAAGAGCTTCAACAGGGGAGAGTGT |
| ABTIM3-hum09 |   |   |
| SEQ ID NO: 3 (Kabat) | HCDR1 | SYNMH |
| SEQ ID NO: 4 (Kabat) | HCDR2 | DIYPGNGDTSYNQKFKG |
| SEQ ID NO: 5 (Kabat) | HCDR3 | VGGAFPMDY |

TABLE 4-continued

Summary of the sequences of exemplary anti-TIM-3 antibodies.

Hybridoma clone

| | | |
|---|---|---|
| SEQ ID NO: 9 (Chothia) | HCDR1 | GYTFTSY |
| SEQ ID NO: 10 (Chothia) | HCDR2 | YPGNGD |
| SEQ ID NO: 5 (Chothia) | HCDR3 | VGGAFPMDY |
| SEQ ID NO: 52 | VH | QVQLVQSGAEVKKPGSSVKVSCKASGYTFTSYNMHWVRQAPGQGLEWMGDIY PGNGDTSYNQKFKGRVTITADKSTSTVYMELSSLRSEDTAVYYCARVGGAFP MDYWGQGTTVTVSS |
| SEQ ID NO: 53 | DNA VH | CAGGTGCAGCTGGTGCAGTCAGGCGCCGAAGTGAAGAAACCCGGCTCTAGCG TGAAAGTTTCTTGTAAAGCTAGTGGCTACACCTTCACTAGCTATAATATGCA CTGGGTTCGCCAGGCCCCAGGGCAAGGCCTCGAGTGGATGGGCGATATCTAC CCCGGGAACGGCGACACTAGTTATAATCAGAAGTTTAAGGGTAGAGTCACTA TCACCGCCGATAAGTCTACTAGCACCGTCTATATGGAACTGAGTTCCCTGAG GTCTGAGGACACCGCCGTCTACTACTGCGCTAGAGTGGGCGGAGCCTTCCCT ATGGACTACTGGGGTCAAGGCACTACCGTGACCGTGTCTAGC |
| SEQ ID NO: 54 | Heavy Chain | QVQLVQSGAEVKKPGSSVKVSCKASGYTFTSYNMHWVRQAPGQGLEWMGDIY PGNGDTSYNQKFKGRVTITADKSTSTVYMELSSLRSEDTAVYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLG |
| SEQ ID NO: 55 | DNA Heavy Chain | CAGGTGCAGCTGGTGCAGTCAGGCGCCGAAGTGAAGAAACCCGGCTCTAGCG TGAAAGTTTCTTGTAAAGCTAGTGGCTACACCTTCACTAGCTATAATATGCA CTGGGTTCGCCAGGCCCCAGGGCAAGGCCTCGAGTGGATGGGCGATATCTAC CCCGGGAACGGCGACACTAGTTATAATCAGAAGTTTAAGGGTAGAGTCACTA TCACCGCCGATAAGTCTACTAGCACCGTCTATATGGAACTGAGTTCCCTGAG GTCTGAGGACACCGCCGTCTACTACTGCGCTAGAGTGGGCGGAGCCTTCCCT ATGGACTACTGGGGTCAAGGCACTACCGTGACCGTGTCTAGCGCTAGCACTA AGGGCCCCGTCCGTGTTCCCCCTGGCACCTTGTAGCCGGAGCACTAGCGAATC CACCGCTGCCCTCGGCTGCCTGGTCAAGGATTACTTCCCGGAGCCCGTGACC GTGTCCTGGAACAGCGGAGCCCTGACCTCCGGAGTGCACACCTTCCCCGCTG TGCTGCAGAGCTCCGGGCTGTACTCGCTGTCGTCGGTGGTCACGGTGCCTTC ATCTAGCCTGGGTACCAAGACCTACACTTGCAACGTGGACCACAAGCCTTCC AACACTAAGGTGGACAAGCGCGTCGAATCGAAGTACGGCCCACCGTGCCCGC CTTGTCCCGCGCCGGAGTTCCTCGGCGGTCCCTCGGTCTTTCTGTTCCCACC GAAGCCCAAGGACACTTTGATGATTTCCCGCACCCCTGAAGTGACATGCGTG GTCGTGGACGTGTCACAGGAAGATCCGGAGGTGCAGTTCAATTGGTACGTGG ATGGCGTCGAGGTGCACAACGCCAAAACCAAGCCGAGGGAGGACAGTTCAA CTCCACTTACCGCGTCGTGTCCGTGCTGACGGTGCTGCATCAGGACTGGCTG AACGGGAAGGAGTACAAGTGCAAGTGTCCAACAAGGGACTTCCTAGCTCAA TCGAAAAGACCATCTCGAAAGCCAAGGGACAGCCCCGGGAACCCCAAGTGTA TACCCTGCCACCGAGCCAGGAAGAAATGACTAAGAACCAAGTCTCATTGACT TGCCTTGTGAAGGGCTTCTACCCATCGGATATCGCCGTGGAATGGGAGTCCA ACGGCCAGCCGGAAAACAACTACAAGACCACCCCTCCGGTGCTGGACTCAGA CGGATCCTTCTTCCTCTACTCGCGGCTGACCGTGGATAAGAGCAGATGGCAG GAGGGAAATGTGTTCAGCTGTTCTGTGATGCATGAAGCCCTGCACAACCACT ACACTCAGAAGTCCCTGTCCCTCTCCCTGGGA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |

TABLE 4-continued

Summary of the sequences of exemplary anti-TIM-3 antibodies.

Hybridoma clone

| SEQ ID NO: 12 (Chothia) | LCDR1 | SESVEYYGTSL |
|---|---|---|
| SEQ ID NO: 13 (Chothia) | LCDR2 | AAS |
| SEQ ID NO: 14 (Chothia) | LCDR3 | SRKDPS |
| SEQ ID NO: 56 | VL | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIK |
| SEQ ID NO: 57 | DNA VL | GAGATCGTCCTGACTCAGTCACCCGCTACCCTGAGCCTGAGCCCTGGCGAGA GAGCTACACTGAGCTGTAGAGCTAGTGAATCAGTCGAGTACTACGGCACTAG CCTGATGCAGTGGTATCAGCAGAAGCCCGGTCAAGCCCCTAGACTGCTGATC TACGCCGCCTCTAACGTGGAATCAGGGATCCCCGCTAGGTTTAGCGGTAGCG GTAGTGGCACCGACTTCACCCTGACTATCTCTAGCCTGGAACCCGAGGATAT CGCCGTCTACTTCTGTCAGCAGTCTAGGAAGGACCCTAGCACCTTCGGCGGA GGCACTAAGGTCGAGATTAAG |
| SEQ ID NO: 58 | Light Chain | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 59 | DNA Light Chain | GAGATCGTCCTGACTCAGTCACCCGCTACCCTGAGCCTGAGCCCTGGCGAGA GAGCTACACTGAGCTGTAGAGCTAGTGAATCAGTCGAGTACTACGGCACTAG CCTGATGCAGTGGTATCAGCAGAAGCCCGGTCAAGCCCCTAGACTGCTGATC TACGCCGCCTCTAACGTGGAATCAGGGATCCCCGCTAGGTTTAGCGGTAGCG GTAGTGGCACCGACTTCACCCTGACTATCTCTAGCCTGGAACCCGAGGATAT CGCCGTCTACTTCTGTCAGCAGTCTAGGAAGGACCCTAGCACCTTCGGCGGA GGCACTAAGGTCGAGATTAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

ABTIM3-hum10

| SEQ ID NO: 3 (Kabat) | HCDR1 | SYNMH |
|---|---|---|
| SEQ ID NO: 4 (Kabat) | HCDR2 | DIYPGNGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 10 (Chothia) | HCDR2 | YPGNGD |
| SEQ ID NO: 5 (Chothia) | HCDR3 | VGGAFPMDY |
| SEQ ID NO: 60 | VH | EVQLVQSGAEVKKPGESLKISCKGSGYTFTSYNMHWVRQMPGKGLEWMGDIY PGNGDTSYNQKFKGQVTISADKSISTVYLQWSSLKASDTAMYYCARVGGAFP MDYWGQGTTVTVSS |

TABLE 4-continued

Summary of the sequences of exemplary anti-TIM-3 antibodies.

Hybridoma clone

| SEQ ID NO: 61 | DNA VH | GAAGTGCAGCTGGTGCAGTCAGGCGCCGAAGTGAAGAAGCCCGGCGAGTCAC<br>TGAAGATTAGCTGTAAAGGTTCAGGCTACACCTTCACTAGCTATAATATGCA<br>CTGGGTCCGCCAGATGCCCGGGAAAGGCCTCGAGTGGATGGGCGATATCTAC<br>CCCGGGAACGGCGACACTAGTTATAATCAGAAGTTTAAGGGGCAAGTCACAA<br>TTAGCGCCGATAAGTCTATTAGCACCGTCTACCTGCAGTGGTCTAGCCTGAA<br>GGCTAGTGACACCGCTATGTACTACTGCGCTAGAGTGGGCGGAGCCTTCCCT<br>ATGGACTACTGGGGTCAAGGCACTACCGTGACCGTGTCTAGC |
|---|---|---|
| SEQ ID NO: 62 | Heavy Chain | EVQLVQSGAEVKKPGESLKISCKGSGYTFTSYNMHWVRQMPGKGLEWMGDIY<br>PGNGDTSYNQKFKGQVTISADKSISTVYLQWSSLKASDTAMYYCARVGGAFP<br>MDYWGQGTTVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLG |
| SEQ ID NO: 63 | DNA Heavy Chain | GAAGTGCAGCTGGTGCAGTCAGGCGCCGAAGTGAAGAAGCCCGGCGAGTCAC<br>TGAAGATTAGCTGTAAAGGTTCAGGCTACACCTTCACTAGCTATAATATGCA<br>CTGGGTCCGCCAGATGCCCGGGAAAGGCCTCGAGTGGATGGGCGATATCTAC<br>CCCGGGAACGGCGACACTAGTTATAATCAGAAGTTTAAGGGGCAAGTCACAA<br>TTAGCGCCGATAAGTCTATTAGCACCGTCTACCTGCAGTGGTCTAGCCTGAA<br>GGCTAGTGACACCGCTATGTACTACTGCGCTAGAGTGGGCGGAGCCTTCCCT<br>ATGGACTACTGGGGTCAAGGCACTACCGTGACCGTGTCTAGCGCTAGCACTA<br>AGGGCCCGTCCGTGTTCCCCCTGGCACCTTGTAGCCGGAGCACTAGCGAATC<br>CACCGCTGCCCTCGGCTGCCTGGTCAAGGATTACTTCCCGGAGCCCGTGACC<br>GTGTCCTGGAACAGCGGAGCCCTGACCTCCGGAGTGCACACCTTCCCGCTG<br>TGCTGCAGAGCTCCGGGCTGTACTCGCTGTCGTCGGTGGTCACGGTGCCTTC<br>ATCTAGCCTGGGTACCAAGACCTACACTTGCAACGTGGACCACAAGCCTTCC<br>AACACTAAGGTGGACAAGCGCGTCGAATCGAAGTACGCCCACCGTGCCCGC<br>CTTGTCCCGCCGGAGTTCCTCGGCGGTCCCTCGGTCTTTCTGTTCCCACC<br>GAAGCCCAAGGACACTTTTGATGATTTCCCGCACCCCTGAAGTGACATGCGTG<br>GTCGTGGACGTGTCACAGGAAGATCCGGAGGTGCAGTTCAATTGGTACGTGG<br>ATGGCGTCGAGGTGCACAACGCCAAAACCAAGCCGAGGGAGGAGCAGTTCAA<br>CTCCACTTACCGCGTCGTGTCCGTGCTGACGGTGCTGCATCAGGACTGGCTG<br>AACGGGAAGGAGTACAAGTGCAAAGTGTCCAACAAGGGACTTCCTAGCTCAA<br>TCGAAAAGACCATCTCGAAAGCCAAGGGACAGCCCCGGGAACCCCAAGTGTA<br>TACCCTGCCACCGAGCCAGGAAGAAATGACTAAGAACCAAGTCTCATTGACT<br>TGCCTTGTGAAGGGCTTCTACCCATCGGATATCGCCGTGGAATGGGAGTCCA<br>ACGGCCAGCCGGAAAACAACTACAAGACCACCCCTCCGGTGCTGGACTCAGA<br>CGGATCCTTCTTCCTCTACTCGCGGCTGACCGTGGATAAGAGCAGATGGCAG<br>GAGGGAAATGTGTTCAGCTGTTCTGTGATGCATGAAGCCCTGCACAACCACT<br>ACACTCAGAAGTCCCTGTCCCTCTCCCTGGGA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 56 | VL | EIVLTQSPATLSLSPGERATLSCRASESVEYYGTSLMQWYQQKPGQAPRLLI<br>YAASNVESGIPARFSGSGSGTDFTLTISSLEPEDIAVYFCQQSRKDPSTFGG<br>GTKVEIK |
| SEQ ID NO: 57 | DNA VL | GAGATCGTCCTGACTCAGTCACCCGCTACCCTGAGCCTGAGCCCTGGCGAGA<br>GAGCTACACTGAGCTGTAGAGCTAGTGAATCAGTCGAGTACTACGGCACTAG |

TABLE 4-continued

Summary of the sequences of exemplary anti-TIM-3 antibodies.

Hybridoma
clone

|  |  |  |
|---|---|---|
|  |  | CCTGATGCAGTGGTATCAGCAGAAGCCCGGTCAAGCCCCTAGACTGCTGATC<br>TACGCCGCCTCTAACGTGGAATCAGGGATCCCCGCTAGGTTTAGCGGTAGCG<br>GTAGTGGCACCGACTTCACCCTGACTATCTCTAGCCTGGAACCCGAGGATAT<br>CGCCGTCTACTTCTGTCAGCAGTCTAGGAAGGACCCTAGCACCTTCGGCGGA<br>GGCACTAAGGTCGAGATTAAG |
| SEQ ID<br>NO: 58 | Light<br>Chain | EIVLTQSPATLSLSPGERATLSCRASESVEYYGTSLMQWYQQKPGQAPRLLI<br>YAASNVESGIPARFSGSGSGTDFTLTISSLEPEDIAVYFCQQSRKDPSTFGG<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 59 | DNA<br>Light<br>Chain | GAGATCGTCCTGACTCAGTCACCCGCTACCCTGAGCCTGAGCCCTGGCGAGA<br>GAGCTACACTGAGCTGTAGAGCTAGTGAATCAGTCGAGTACTACGGCACTAG<br>CCTGATGCAGTGGTATCAGCAGAAGCCCGGTCAAGCCCCTAGACTGCTGATC<br>TACGCCGCCTCTAACGTGGAATCAGGGATCCCCGCTAGGTTTAGCGGTAGCG<br>GTAGTGGCACCGACTTCACCCTGACTATCTCTAGCCTGGAACCCGAGGATAT<br>CGCCGTCTACTTCTGTCAGCAGTCTAGGAAGGACCCTAGCACCTTCGGCGGA<br>GGCACTAAGGTCGAGATTAAGCGTACGGTGGCCGCTCCCAGCGTGTTCATCT<br>TCCCCCCCAGCGACGAGCAGCTGAAGAGCGGCACCGCCAGCGTGGTGTGCCT<br>GCTGAACAACTTCTACCCCCGGGAGGCCAAGGTGCAGTGGAAGGTGGACAAC<br>GCCCTGCAGAGCGGCAACAGCCAGGAGAGCGTCACCGAGCAGGACAGCAAGG<br>ACTCCACCTACAGCCTGAGCAGCACCCTGACCCTGAGCAAGGCCGACTACGA<br>GAAGCATAAGGTGTACGCCTGCGAGGTGACCCACCAGGGCCTGTCCAGCCCC<br>GTGACCAAGAGCTTCAACAGGGGCGAGTGC |

ABTIM3-hum11

| SEQ ID<br>NO: 3<br>(Kabat) | HCDR1 | SYNMH |
|---|---|---|
| SEQ ID<br>NO: 4<br>(Kabat) | HCDR2 | DIYPGNGDTSYNQKFKG |
| SEQ ID<br>NO: 5<br>(Kabat) | HCDR3 | VGGAFPMDY |
| SEQ ID<br>NO: 9<br>(Chothia) | HCDR1 | GYTFTSY |
| SEQ ID<br>NO: 10<br>(Chothia) | HCDR2 | YPGNGD |
| SEQ ID<br>NO: 5<br>(Chothia) | HCDR3 | VGGAFPMDY |
| SEQ ID<br>NO: 52 | VH | QVQLVQSGAEVKKPGSSVKVSCKASGYTFTSYNMHWVRQAPGQGLEWMGDIY<br>PGNGDTSYNQKFKGRVTITADKSTSTVYMELSSLRSEDTAVYYCARVGGAFP<br>MDYWGQGTTVTVSS |
| SEQ ID<br>NO: 53 | DNA VH | CAGGTGCAGCTGGTGCAGTCAGGCGCCGAAGTGAAGAAACCCGGCTCTAGCG<br>TGAAAGTTTCTTGTAAAGCTAGTGGCTACACCTTCACTAGCTATAATATGCA<br>CTGGGTTCGCCAGGCCCCAGGGCAAGGCCTCGAGTGGATGGGCGATATCTAC<br>CCCGGGAACGGCGACACTAGTTATAATCAGAAGTTTAAGGGTAGAGTCACTA<br>TCACCGCCGATAAGTCTACTAGCACCGTCTATATGGAACTGAGTTCCCTGAG<br>GTCTGAGGACACCGCCGTCTACTACTGCGCTAGAGTGGGCGGAGCCTTCCCT<br>ATGGACTACTGGGGTCAAGGCACTACCGTGACCGTGTCTAGC |
| SEQ ID<br>NO: 54 | Heavy<br>Chain | QVQLVQSGAEVKKPGSSVKVSCKASGYTFTSYNMHWVRQAPGQGLEWMGDIY<br>PGNGDTSYNQKFKGRVTITADKSTSTVYMELSSLRSEDTAVYYCARVGGAFP<br>MDYWGQGTTVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLG |

TABLE 4-continued

Summary of the sequences of exemplary anti-TIM-3 antibodies.

Hybridoma
clone

| SEQ ID NO: 55 | DNA Heavy Chain | CAGGTGCAGCTGGTGCAGTCAGGCGCCGAAGTGAAGAAACCCGGCTCTAGCG
TGAAAGTTTCTTGTAAAGCTAGTGGCTACACCTTCACTAGCTATAATATGCA
CTGGGTTCGCCAGGCCCCAGGGCAAGGCCTCGAGTGGATGGGCGATATCTAC
CCCGGGAACGGCGACACTAGTTATAATCAGAAGTTTAAGGGTAGAGTCACTA
TCACCGCCGATAAGTCTACTAGCACCGTCTATATGGAACTGAGTTCCCTGAG
GTCTGAGGACACCGCCGTCTACTACTGCGCTAGAGTGGGCGGAGCCTTCCCT
ATGGACTACTGGGGTCAAGGCACTACCGTGACCGTGTCTAGCGCTAGCACTA
AGGGCCCGTCCGTGTTCCCCCTGGCACCTTGTAGCCGGAGCACTAGCGAATC
CACCGCTGCCCTCGGCTGCCTGGTCAAGGATTACTTCCCGGAGCCCGTGACC
GTGTCCTGGAACAGCGGAGCCCTGACCTCCGGAGTGCACACCTTCCCCGCTG
TGCTGCAGAGCTCCGGGCTGTACTCGCTGTCGTCGGTGGTCACGGTGCCTTC
ATCTAGCCTGGGTACCAAGACCTACACTTGCAACGTGGACCACAAGCCTTCC
AACACTAAGGTGGACAAGCGCGTCGAATCGAAGTACGCCCACCGTGCCCGC
CTTGTCCCGCGCCGGAGTTCCTCGGCGGTCCCTCGGTCTTTCTGTTCCCACC
GAAGCCCAAGGACACTTTGATGATTTCCCGCACCCCTGAAGTGACATGCGTG
GTCGTGGACGTGTCACAGGAAGATCCGGAGGTGCAGTTCAATTGGTACGTGG
ATGGCGTCGAGGTGCACAACGCCAAAACCAAGCCGAGGGAGGAGCAGTTCAA
CTCCACTTACCGTGTCGTGTCCGTGCTGACGGTGCTGCATCAGGACTGGCTG
AACGGGAAGGAGTACAAGTGCAAAGTGTCCAACAAGGGACTTCCTAGCTCAA
TCGAAAAGACCATCTCGAAAGCCAAGGGACAGCCCCGGGAACCCCAAGTGTA
TACCCTGCCACCGAGCCAGGAAGAAATGACTAAGAACCAAGTCTCATTGACT
TGCCTTGTGAAGGGCTTCTACCCATCGGATATCGCCGTGGAATGGGAGTCCA
ACGGCCAGCCGGAAAACAACTACAAGACCACCCCTCCGGTGCTGGACTCAGA
CGGATCCTTCTTCCTCTACTCGCGGCTGACCGTGGATAAGAGCAGATGGCAG
GAGGGAAATGTGTTCAGCTGTTCTGTGATGCATGAAGCCCTGCACAACCACT
ACACTCAGAAGTCCCTGTCCCTCTCCCTGGGA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 64 | VL | AIQLTQSPSSLSASVGDRVTITCRASESVEYYGTSLMQWYQQKPGKAPKLLI
YAASNVESGVPSRFSGSGSGTDFTLTISSLQPEDFATYFCQQSRKDPSTFGG
GTKVEIK |
| SEQ ID NO: 65 | DNA VL | GCTATTCAGCTGACTCAGTCACCTAGTAGCCTGAGCGCTAGTGTGGGCGATA
GAGTGACTATCACCTGTAGAGCTAGTGAATCAGTCGAGTACTACGGCACTAG
CCTGATGCAGTGGTATCAGCAGAAGCCCGGGAAAGCCCCTAAGCTGCTGATC
TACGCCGCCTCTAACGTGGAATCAGGCGTGCCCTCTAGGTTTAGCGGTAGCG
GTAGTGGCACCGACTTCACCCTGACTATCTCTAGCCTGCAGCCCGAGGACTT
CGCTACCTACTTCTGTCAGCAGTCTAGGAAGGACCCTAGCACCTTCGGCGGA
GGCACTAAGGTCGAGATTAAG |
| SEQ ID NO: 66 | Light Chain | AIQLTQSPSSLSASVGDRVTITCRASESVEYYGTSLMQWYQQKPGKAPKLLI
YAASNVESGVPSRFSGSGSGTDFTLTISSLQPEDFATYFCQQSRKDPSTFGG
GTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSP
VTKSFNRGEC |
| SEQ ID NO: 67 | DNA Light Chain | GCTATTCAGCTGACTCAGTCACCTAGTAGCCTGAGCGCTAGTGTGGGCGATA
GAGTGACTATCACCTGTAGAGCTAGTGAATCAGTCGAGTACTACGGCACTAG
CCTGATGCAGTGGTATCAGCAGAAGCCCGGGAAAGCCCCTAAGCTGCTGATC
TACGCCGCCTCTAACGTGGAATCAGGCGTGCCCTCTAGGTTTAGCGGTAGCG
GTAGTGGCACCGACTTCACCCTGACTATCTCTAGCCTGCAGCCCGAGGACTT |

TABLE 4-continued

Summary of the sequences of exemplary anti-TIM-3 antibodies.

Hybridoma
clone

|  |  |  |
|---|---|---|
|  |  | CGCTACCTACTTCTGTCAGCAGTCTAGGAAGGACCCTAGCACCTTCGGCGGA<br>GGCACTAAGGTCGAGATTAAGCGTACGGTGGCCGCTCCCAGCGTGTTCATCT<br>TCCCCCCCAGCGACGAGCAGCTGAAGAGCGGCACCGCCAGCGTGGTGTGCCT<br>GCTGAACAACTTCTACCCCCGGGAGGCCAAGGTGCAGTGGAAGGTGGACAAC<br>GCCCTGCAGAGCGGCAACAGCCAGGAGAGCGTCACCGAGCAGGACAGCAAGG<br>ACTCCACCTACAGCCTGAGCAGCACCCTGACCCTGAGCAAGGCCGACTACGA<br>GAAGCATAAGGTGTACGCCTGCGAGGTGACCCACCAGGGCCTGTCCAGCCCC<br>GTGACCAAGAGCTTCAACAGGGGCGAGTGC |

ABTIM3-hum12

| SEQ ID<br>NO: 3<br>(Kabat) | HCDR1 | SYNMH |
|---|---|---|
| SEQ ID<br>NO: 4<br>(Kabat) | HCDR2 | DIYPGNGDTSYNQKFKG |
| SEQ ID<br>NO: 5<br>(Kabat) | HCDR3 | VGGAFPMDY |
| SEQ ID<br>NO: 9<br>(Chothia) | HCDR1 | GYTFTSY |
| SEQ ID<br>NO: 10<br>(Chothia) | HCDR2 | YPGNGD |
| SEQ ID<br>NO: 5<br>(Chothia) | HCDR3 | VGGAFPMDY |
| SEQ ID<br>NO: 60 | VH | EVQLVQSGAEVKKPGESLKISCKGSGYTFTSYNMHWVRQMPGKGLEWMGDIY<br>PGNGDTSYNQKFKGQVTISADKSISTVYLQWSSLKASDTAMYYCARVGGAFP<br>MDYWGQGTTVTVSS |
| SEQ ID<br>NO: 61 | DNA VH | GAAGTGCAGCTGGTGCAGTCAGGCGCCGAAGTGAAGAAGCCCGGCGAGTCAC<br>TGAAGATTAGCTGTAAAGGTTCAGGCTACACCTTCACTAGCTATAATATGCA<br>CTGGGTCCGCCAGATGCCCGGGAAAGGCCTCGAGTGGATGGGCGATATCTAC<br>CCCGGGAACGGCGACACTAGTTATAATCAGAAGTTTAAGGGGCAAGTCACAA<br>TTAGCGCCGATAAGTCTATTAGCACCGTCTACCTGCAGTGGTCTAGCCTGAA<br>GGCTAGTGACACCGCTATGTACTACTGCGCTAGAGTGGGCGGAGCCTTCCCT<br>ATGGACTACTGGGGTCAAGGCACTACCGTGACCGTGTCTAGC |
| SEQ ID<br>NO: 62 | Heavy<br>Chain | EVQLVQSGAEVKKPGESLKISCKGSGYTFTSYNMHWVRQMPGKGLEWMGDIY<br>PGNGDTSYNQKFKGQVTISADKSISTVYLQWSSLKASDTAMYYCARVGGAFP<br>MDYWGQGTTVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLG |
| SEQ ID<br>NO: 63 | DNA<br>Heavy<br>Chain | GAAGTGCAGCTGGTGCAGTCAGGCGCCGAAGTGAAGAAGCCCGGCGAGTCAC<br>TGAAGATTAGCTGTAAAGGTTCAGGCTACACCTTCACTAGCTATAATATGCA<br>CTGGGTCCGCCAGATGCCCGGGAAAGGCCTCGAGTGGATGGGCGATATCTAC<br>CCCGGGAACGGCGACACTAGTTATAATCAGAAGTTTAAGGGGCAAGTCACAA<br>TTAGCGCCGATAAGTCTATTAGCACCGTCTACCTGCAGTGGTCTAGCCTGAA<br>GGCTAGTGACACCGCTATGTACTACTGCGCTAGAGTGGGCGGAGCCTTCCCT<br>ATGGACTACTGGGGTCAAGGCACTACCGTGACCGTGTCTAGCGCTAGCACTA<br>AGGGCCCGTCCGTGTTCCCCCTGGCACCTTGTAGCGGGAGCACTAGCGAATC<br>CACCGCTGCCCTCGGCTGCCTGGTCAAGGATTACTTCCCGGAGCCCGTGACC<br>GTGTCCTGGAACAGCGGAGCCCTGACCTCCGGAGTGCACACCTTCCCCGCTG<br>TGCTGCAGAGCTCCGGCTGTACTCGCTGTCGTCGGTGGTCACGGTGCCTTC<br>ATCTAGCCTGGGTACCAAGACCTACACTTGCAACGTGGACCACAAGCCTTCC<br>AACACTAAGGTGGACAAGCGCGTCGAATCGAAGTACGGCCCACCGTGCCCGC<br>CTTGTCCCGCGCGGAGTTCCTCGGCGGTCCCTCGGTCTTTCTGTTCCCACC<br>GAAGCCCAAGGACACTTTGATGATTTCCCGCACCCCTGAAGTGACATGCGTG<br>GTCGTGGACGTGTCACAGGAAGATCCGGAGGTGCAGTTCAATTGGTACGTGG<br>ATGGCGTCGAGGTGCACAACGCCAAAACCAAGCCGAGGGAGGAGCAGTTCAA<br>CTCCACTTACCGCGTCGTGTCCGTGCTGACGGTGCTGCATCAGGACTGGCTG |

TABLE 4-continued

Summary of the sequences of exemplary anti-TIM-3 antibodies.

Hybridoma
clone

| | | |
|---|---|---|
| | | AACGGGAAGGAGTACAAGTGCAAAGTGTCCAACAAGGGACTTCCTAGCTCAA<br>TCGAAAAGACCATCTCGAAAGCCAAGGGACAGCCCCGGGAACCCCAAGTGTA<br>TACCCTGCCACCGAGCCAGGAAGAAATGACTAAGAACCAAGTCTCATTGACT<br>TGCCTTGTGAAGGGCTTCTACCCATCGGATATCGCCGTGGAATGGGAGTCCA<br>ACGGCCAGCCGGAAAACAACTACAAGACCACCCCTCCGGTGCTGGACTCAGA<br>CGGATCCTTCTTCCTCTACTCGCGGCTGACCGTGGATAAGAGCAGATGGCAG<br>GAGGGAAATGTGTTCAGCTGTTCTGTGATGCATGAAGCCCTGCACAACCACT<br>ACACTCAGAAGTCCCTGTCCCTCTCCCTGGGA |
| SEQ ID<br>NO: 6<br>(Kabat) | LCDR1 | RASESVEYYGTSLMQ |
| SEQ ID<br>NO: 7<br>(Kabat) | LCDR2 | AASNVES |
| SEQ ID<br>NO: 8<br>(Kabat) | LCDR3 | QQSRKDPST |
| SEQ ID<br>NO: 12<br>(Chothia) | LCDR1 | SESVEYYGTSL |
| SEQ ID<br>NO: 13<br>(Chothia) | LCDR2 | AAS |
| SEQ ID<br>NO: 14<br>(Chothia) | LCDR3 | SRKDPS |
| SEQ ID<br>NO: 64 | VL | AIQLTQSPSSLSASVGDRVTITCRASESVEYYGTSLMQWYQQKPGKAPKLLI<br>YAASNVESGVPSRFSGSGSGTDFTLTISSLQPEDFATYFCQQSRKDPSTFGG<br>GTKVEIK |
| SEQ ID<br>NO: 65 | DNA VL | GCTATTCAGCTGACTCAGTCACCTAGTAGCCTGAGCGCTAGTGTGGGCGATA<br>GAGTGACTATCACCTGTAGAGCTAGTGAATCAGTCGAGTACTACGGCACTAG<br>CCTGATGCAGTGGTATCAGCAGAAGCCCGGGAAAGCCCCTAAGCTGCTGATC<br>TACGCCGCCTCTAACGTGGAATCAGGCGTGCCCTCTAGGTTTAGCGGTAGCG<br>GTAGTGGCACCGACTTCACCCTGACTATCTCTAGCCTGCAGCCCGAGGACTT<br>CGCTACCTACTTCTGTCAGCAGTCTAGGAAGGACCCTAGCACCTTCGGCGGA<br>GGCACTAAGGTCGAGATTAAG |
| SEQ ID<br>NO: 66 | Light<br>Chain | AIQLTQSPSSLSASVGDRVTITCRASESVEYYGTSLMQWYQQKPGKAPKLLI<br>YAASNVESGVPSRFSGSGSGTDFTLTISSLQPEDFATYFCQQSRKDPSTFGG<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 67 | DNA<br>Light<br>Chain | GCTATTCAGCTGACTCAGTCACCTAGTAGCCTGAGCGCTAGTGTGGGCGATA<br>GAGTGACTATCACCTGTAGAGCTAGTGAATCAGTCGAGTACTACGGCACTAG<br>CCTGATGCAGTGGTATCAGCAGAAGCCCGGGAAAGCCCCTAAGCTGCTGATC<br>TACGCCGCCTCTAACGTGGAATCAGGCGTGCCCTCTAGGTTTAGCGGTAGCG<br>GTAGTGGCACCGACTTCACCCTGACTATCTCTAGCCTGCAGCCCGAGGACTT<br>CGCTACCTACTTCTGTCAGCAGTCTAGGAAGGACCCTAGCACCTTCGGCGGA<br>GGCACTAAGGTCGAGATTAAGCGTACGGTGGCCGCTCCCAGCGTGTTCATCT<br>TCCCCCCCAGCGACGAGCAGCTGAAGAGCGGCACCGCCAGCGTGGTGTGCCT<br>GCTGAACAACTTCTACCCCGGGAGGCCAAGGTGCAGTGGAAGGTGGACAAC<br>GCCCTGCAGAGCGGCAACAGCCAGGAGAGCGTCACCGAGCAGGACAGCAAGG<br>ACTCCACCTACAGCCTGAGCAGCACCCTGACCCTGAGCAAGGCCGACTACGA<br>GAAGCATAAGGTGTACGCCTGCGAGGTGACCCACCAGGGCCTGTCCAGCCCC<br>GTGACCAAGAGCTTCAACAGGGGCGAGTGC |

ABTIM3-hum13

| | | |
|---|---|---|
| SEQ ID<br>NO: 3<br>(Kabat) | HCDR1 | SYNMH |
| SEQ ID<br>NO: 24<br>(Kabat) | HCDR2 | DIYPGSGDTSYNQKFKG |

TABLE 4-continued

Summary of the sequences of exemplary anti-TIM-3 antibodies.

Hybridoma clone

| | | |
|---|---|---|
| SEQ ID NO: 5 (Kabat) | HCDR3 | VGGAFPMDY |
| SEQ ID NO: 9 (Chothia) | HCDR1 | GYTFTSY |
| SEQ ID NO: 25 (Chothia) | HCDR2 | YPGSGD |
| SEQ ID NO: 5 (Chothia) | HCDR3 | VGGAFPMDY |
| SEQ ID NO: 68 | VH | QVQLVQSGAEVKKPGSSVKVSCKASGYTFTSYNMHWVRQAPGQGLEWMGDIY PGSGDTSYNQKFKGRVTITADKSTSTVYMELSSLRSEDTAVYYCARVGGAFP MDYWGQGTTVTVSS |
| SEQ ID NO: 69 | DNA VH | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCAGTGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCA |
| SEQ ID NO: 70 | Heavy Chain | QVQLVQSGAEVKKPGSSVKVSCKASGYTFTSYNMHWVRQAPGQGLEWMGDIY PGSGDTSYNQKFKGRVTITADKSTSTVYMELSSLRSEDTAVYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 71 | DNA Heavy Chain | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCAGTGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCTACAA AGGGCCCCTCCGTCTTTCCACTCGCGCCGTGCTCTCGCTCCACCTCAGAGTC AACTGCCGCTCTGGGTTGCCTGGTCAAGGACTACTTCCCAGAGCCGGTGACA GTGAGCTGGAACAGTGGGGCCCTGACATCCGGCGTTCATACCTTCCCCGCAG TCCTCCAGTCCTCAGGCCTGTATTCCCTGAGCAGCGTTGTCACAGTGCCCTC CAGCTCTCTTGGCACGAAAACCTACACATGCAACGTTGATCATAAGCCGTCT AATACCAAGGTGGATAAAAGAGTGGAGAGCAAGTACGGCCCACCCTGCCCGC CTTGCCCAGCTCCGGAGTTCCTGGGCGGACCATCCGTTTTCTTGTTTCCACC CAAACCTAAAGACACTCTGATGATTTCCCGAACCCCTGAAGTGACTTGCGTT GTGGTGGACGTCTCCCAGGAGGACCCAGAAGTGCAATTCAACTGGTACGTGG ACGGGGTGGAGGTGCACAATGCAAAAACCAAACCAAGGGAGGAACAGTTTAA TTCAACATATAGGGTTGTGTCTGTGCTGACGGTTCTGCATCAGGACTGGCTG AACGGAAAGGAATACAAGTGCAAGGTGTCCAACAAAGGACTGCCAAGCTCTA TCGAGAAAACAATCTCTAAGGCCAAGGGACAACCTAGAGAGCCCCAAGTTTA CACCCTGCCACCATCACAGGAAGAGATGACCAAAAATCAGGTGAGCTTGACA TGCCTGGTGAAGGGCTTCTACCCTAGCGATATTGCGGTTGAGTGGGAGTCAA ATGGCCAGCCTGAGAACAACTATAAGACTACTCCTCCCGTGCTGGACTCCGA CGGGAGCTTTTTCCTGTATTCCAGGCTTACAGTCGATAAGAGCAGATGGCAA GAGGGGAATGTGTTTTCCTGCTCCGTGATGCACGAGGCTCTCCATAACCATT ATACTCAGAAAAGTCTCTCTCTGTCACTGGGCAAA |
| SEQ ID NO: 6 (Kabat) | LCDR1 | RASESVEYYGTSLMQ |
| SEQ ID NO: 7 (Kabat) | LCDR2 | AASNVES |

TABLE 4-continued

Summary of the sequences of exemplary anti-TIM-3 antibodies.

Hybridoma clone

| | | |
|---|---|---|
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 64 | VL | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG GTKVEIK |
| SEQ ID NO: 125 | DNA VL | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAA |
| SEQ ID NO: 66 | Light Chain | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 126 | DNA Light Chain | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAACGTACGGTGGCAGCTCCGTCTGTTTTCATCT TTCCACCTAGCGACGAGCAACTCAAAAGTGGTACAGCATCCGTGGTTTGTCT GCTGAACAATTTTTACCCCAGGGAGGCTAAGGTCCAGTGGAAAGTCGATAAC GCTCTTCAGTCTGGCAACAGTCAGGAGAGCGTCACAGAGCAGGACTCTAAGG ATAGCACTTATAGTCTGTCCTCCACGCTGACACTGTCTAAAGCGGATTATGA GAAGCACAAGGTTTACGCCTGTGAGGTAACGCACCAAGGACTCTCCTCCCCA GTTACCAAATCTTTCAACAGAGGAGAATGT |

ABTIM3-hum14

| | | |
|---|---|---|
| SEQ ID NO: 3 (Kabat) | HCDR1 | SYNMH |
| SEQ ID NO: 30 (Kabat) | HCDR2 | DIYPGQGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 31 (Chothia) | HCDR2 | YPGQGD |
| SEQ ID NO: 5 (Chothia) | HCDR3 | VGGAFPMDY |

TABLE 4-continued

Summary of the sequences of exemplary anti-TIM-3 antibodies.

Hybridoma clone

| SEQ ID NO: 72 | VH | QVQLVQSGAEVKKPGSSVKVSCKASGYTFTSYNMHWVRQAPGQGLEWMGDIY PGQGDTSYNQKFKGRVTITADKSTSTVYMELSSLRSEDTAVYYCARVGGAFP MDYWGQGTTVTVSS |
|---|---|---|
| SEQ ID NO: 73 | DNA VH | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCCAGGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCA |
| SEQ ID NO: 74 | Heavy Chain | QVQLVQSGAEVKKPGSSVKVSCKASGYTFTSYNMHWVRQAPGQGLEWMGDIY PGQGDTSYNQKFKGRVTITADKSTSTVYMELSSLRSEDTAVYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 75 | DNA Heavy Chain | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCCAGGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCAGCCTCTACAA AGGGCCCCTCCGTCTTTCCACTCGCGCCGTGCTCTCGCTCCACCTCAGAGTC AACTGCCGCTCTGGGTTGCCTGGTCAAGGACTACTTCCCAGAGCCGGTGACA GTGAGCTGGAACAGTGGGGCCCTGACATCCGGCGTTCATACCTTCCCCGCAG TCCTCCAGTCCTCAGGCCTGTATTCCCTGAGCAGCGTTGTCACAGTGCCCTC CAGCTCTCTTGGCACGAAAACCTACACATGCAACGTTGATCATAAGCCGTCT AATACCAAGGTGGATAAAAGAGTGGAGAGCAAGTACGGCCCACCCTGCCCGC CTTGCCCAGCTCCGGAGTTCCTGGGCGGACCATCCGTTTTCTTGTTTCCACC CAAACCTAAAGACACTCTGATGATTTCCCGAACCCCTGAAGTGACTTGCGTT GTGGTGGACGTCTCCCAGGAGGACCCAGAAGTGCAATTCAACTGGTACGTGG ACGGGGTGGAGGTGCACAATGCAAAAACCAAACCAAGGGAGGAACAGTTTAA TTCAACATATAGGGTTGTGTCTGTGCTGACGGTTCTGCATCAGGACTGGCTG AACGGAAAGGAATACAAGTGCAAGGTGTCCAACAAAGGACTGCCAAGCTCTA TCGAGAAAACAATCTCTAAGGCCAAGGGACAACCTAGAGAGCCCCAAGTTTA CACCCTGCCACCATCACAGGAAGAGATGACCAAAAATCAGGTGAGCTTGACA TGCCTGGTGAAGGGCTTCTACCCTAGCGATATTGCGGTTGAGTGGGAGTCAA ATGGCCAGCCTGAGAACAACTATAAGACTACTCCTCCCGTGCTGGACTCCGA CGGGAGCTTTTTCCTGTATTCCAGGCTTACAGTCGATAAGAGCAGATGGCAA GAGGGGAATGTGTTTTCCTGCTCCGTGATGCACGAGGCTCTCCATAACCATT ATACTCAGAAAAGTCTCTCTCTGTCACTGGGCAAA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |

TABLE 4-continued

Summary of the sequences of exemplary anti-TIM-3 antibodies.

Hybridoma
clone

| SEQ ID NO: 64 | VL | AIQLTQSPSSLSASVGDRVTITCRASESVEYYGTSLMWYQQKPGKAPKLLI YAASNVESGVPSRFSGSGSGTDFTLTISSLQPEDFATYFCQQSRKDPSTFGG GTKVEIK |
| --- | --- | --- |
| SEQ ID NO: 125 | DNA VL | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAA |
| SEQ ID NO: 66 | Light Chain | AIQLTQSPSSLSASVGDRVTITCRASESVEYYGTSLMWYQQKPGKAPKLLI YAASNVESGVPSRFSGSGSGTDFTLTISSLQPEDFATYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 126 | DNA Light Chain | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAACGTACGGTGGCAGCTCCGTCTGTTTTCATCT TTCCACCTAGCGACGAGCAACTCAAAAGTGGTACAGCATCCGTGGTTTGTCT GCTGAACAATTTTTACCCCAGGGAGGCTAAGGTCCAGTGGAAAGTCGATAAC GCTCTTCAGTCTGGCAACAGTCAGGAGAGCGTCACAGAGCAGGACTCTAAGG ATAGCACTTATAGTCTGTCCTCCACGCTGACACTGTCTAAAGCGGATTATGA GAAGCACAAGGTTTACGCCTGTGAGGTAACGCACCAAGGACTCTCCTCCCCA GTTACCAAATCTTTCAACAGAGGAGAATGT |

ABTIM3-hum15

| SEQ ID NO: 3 (Kabat) | HCDR1 | SYNMH |
| --- | --- | --- |
| SEQ ID NO: 24 (Kabat) | HCDR2 | DIYPGSGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 25 (Chothia) | HCDR2 | YPGSGD |
| SEQ ID NO: 5 (Chothia) | HCDR3 | VGGAFPMDY |
| SEQ ID NO: 76 | VH | EVQLVQSGAEVKKPGESLKISCKGSGYTFTSYNMHWVRQMPGKGLEWMGDIY PGSGDTSYNQKFKGQVTISADKSISTVYLQWSSLKASDTAMYYCARVGGAFP MDYWGQGTTVTVSS |
| SEQ ID NO: 77 | DNA VH | GAAGTTCAATTGGTACAGTCTGGCGCAGAAGTAAAGAAACCAGGAGAGAGTT TGAAAATTTCCTGCAAGGGCAGTGGGTACACATTCACGTCCTACAATATGCA CTGGGTGAGACAGATGCCAGGCAAGGGCCTGGAGTGGATGGGAGACATATAC CCAGGCAGTGGAGACACAAGCTATAATCAGAAATTCAAAGGACAGGTGACGA TCTCCGCAGACAAATCCATATCTACGGTCTACCTCCAGTGGTCCTCACTTAA AGCCTCCGACACCGCCATGTACTATTGCGCTCGGGTAGGTGGCGCGTTTCCA ATGGACTATTGGGGCCAAGGGACCACAGTAACCGTCAGCTCA |
| SEQ ID NO: 78 | Heavy Chain | EVQLVQSGAEVKKPGESLKISCKGSGYTFTSYNMHWVRQMPGKGLEWMGDIY PGSGDTSYNQKFKGQVTISADKSISTVYLQWSSLKASDTAMYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS |

TABLE 4-continued

Summary of the sequences of exemplary anti-TIM-3 antibodies.

Hybridoma clone

| | | |
|---|---|---|
| | | NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 79 | DNA Heavy Chain | GAAGTTCAATTGGTACAGTCTGGCGCAGAAGTAAAGAAACCAGGAGAGAGTT TGAAAATTTCCTGCAAGGGCAGTGGGTACACATTCACGTCCTACAATATGCA CTGGGTGAGACAGATGCCAGGCAAGGGCCTGGAGTGGATGGGAGACATATAC CCAGGCAGTGGAGACACAAGCTATAATCAGAAATTCAAAGGACAGGTGACGA TCTCCGCAGACAAATCCATATCTACGGTCTACCTCCAGTGGTCCTCACTTAA AGCCTCCGACACCGCCATGTACTATTGCGCTCGGGTAGGTGGCGCGTTTCCA ATGGACTATTGGGGCCAAGGGACCACAGTAACCGTCAGCTCAGCCTCTACAA AGGGCCCCTCCGTCTTTCCACTCGCGCCGTGCTCTCGCTCCACCTCAGAGTC AACTGCCGCTCTGGGTTGCCTGGTCAAGGACTACTTCCCAGAGCCGGTGACA GTGAGCTGGAACAGTGGGGCCCTGACATCCGGCGTTCATACCTTCCCGCAG TCCTCCAGTCCTCAGGCCTGTATTCCCTGAGCAGCGTTGTCACAGTGCCCTC CAGCTCTCTTGGCACGAAAACCTACACATGCAACGTTGATCATAAGCCGTCT AATACCAAGGTGGATAAAAGAGTGGAGAGCAAGTACGGCCCACCCTGCCCGC CTTGCCCAGCTCCGGAGTTCCTGGGCGGACCATCCGTTTTCTTGTTTCCACC CAAACCTAAAGACACTCTGATGATTTCCCGAACCCCTGAAGTGACTTGCGTT GTGGTGGACGTCTCCCAGGAGGACCCAGAAGTGCAATTCAACTGGTACGTGG ACGGGGTGGAGGTGCACAATGCAAAAACCAAACCAAGGGGAGGAACAGTTTAA TTCAACATATAGGGTTGTGTCTGTGCTGACGGTTCTGCATCAGGACTGGCTG AACGAAAGGAATACAAGTGCAAGGTGTCCAACAAAGGACTGCCAAGCTCTA TCGAGAAAACAATCTCTAAGGCCAAGGGACAACCTAGAGAGCCCCAAGTTTA CACCCTGCCACCATCACAGGAAGAGATGACCAAAAATCAGGTGAGCTTGACA TGCCTGGTGAAGGGCTTCTACCCTAGCGATATTGCGGTTGAGTGGGAGTCAA ATGGCCAGCCTGAGAACAACTATAAGACTACTCCTCCCGTGCTGGACTCCGA CGGGAGCTTTTTCCTGTATTCCAGGCTTACAGTCGATAAGAGCAGATGGCAA GAGGGGAATGTGTTTTCCTGCTCCGTGATGCACGAGGCTCTCCATAACCATT ATACTCAGAAAAGTCTCTCTCTGTCACTGGGCAAA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 56 | VL | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIK |
| SEQ ID NO: 127 | DNA VL | GAGATTGTTCTTACGCAAAGTCCCGCCACACTTAGTTTGTCACCAGGAGAGC GCGCCACCCTGAGCTGCAGAGCTTCAGAGAGTGTGGAATACTACGGCACATC CCTGATGCAGTGGTATCAGCAGAAACCAGGACAGGCTCCTCGGCTGCTGATC TACGCAGCCAGCAACGTCGAGTCCGGCATTCCAGCCAGATTTTCTGGGTCAG GATCTGGAACTGACTTTACACTGACAATCTCCAGCCTGGAACCCGAGGACAT TGCTGTGTATTTTTGTCAACAGTCCCGGAAGGACCCCAGTACCTTTGGAGGT GGAACCAAGGTAGAGATAAAG |
| SEQ ID NO: 58 | Light Chain | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |

TABLE 4-continued

Summary of the sequences of exemplary anti-TIM-3 antibodies.

Hybridoma
clone

| SEQ ID NO: 128 | DNA Light Chain | GAGATTGTTCTTACGCAAAGTCCCGCCACACTTAGTTTGTCACCAGGAGAGC<br>GCGCCACCCTGAGCTGCAGAGCTTCAGAGAGTGTGGAATACTACGGCACATC<br>CCTGATGCAGTGGTATCAGCAGAAACCAGGACAGGCTCCTCGGCTGCTGATC<br>TACGCAGCCAGCAACGTCGAGTCCGGCATTCCAGCCAGATTTTCTGGGTCAG<br>GATCTGGAACTGACTTTACACTGACAATCTCCAGCCTGGAACCCGAGGACAT<br>TGCTGTGTATTTTGTCAACAGTCCCGGAAGGACCCCAGTACCTTTGGAGGT<br>GGAACCAAGGTAGAGATAAAGCGTACGGTGGCAGCTCCGTCTGTTTTCATCT<br>TTCCACCTAGCGACGAGCAACTCAAAAGTGGTACAGCATCCGTGGTTTGTCT<br>GCTGAACAATTTTTACCCCAGGGAGGCTAAGGTCCAGTGGAAAGTCGATAAC<br>GCTCTTCAGTCTGGCAACAGTCAGGAGAGCGTCACAGAGCAGGACTCTAAGG<br>ATAGCACTTATAGTCTGTCCTCCACGCTGACACTGTCTAAAGCGGATTATGA<br>GAAGCACAAGGTTTACGCCTGTGAGGTAACGCACCAAGGACTCTCCTCCCCA<br>GTTACCAAATCTTTCAACAGAGGAGAATGT |

ABTIM3-hum16

| SEQ ID NO: 3 (Kabat) | HCDR1 | SYNMH |
| SEQ ID NO: 30 (Kabat) | HCDR2 | DIYPGQGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 31 (Chothia) | HCDR2 | YPGQGD |
| SEQ ID NO: 5 (Chothia) | HCDR3 | VGGAFPMDY |
| SEQ ID NO: 80 | VH | EVQLVQSGAEVKKPGESLKISCKGSGYTFTSYNMHWVRQMPGKGLEWMGDIY<br>PGQGDTSYNQKFKGQVTISADKSISTVYLQWSSLKASDTAMYYCARVGGAFP<br>MDYWGQGTTVTVSS |
| SEQ ID NO: 81 | DNA VH | GAAGTTCAATTGGTACAGTCTGGCGCAGAAGTAAAGAAACCAGGAGAGAGTT<br>TGAAAATTTCCTGCAAGGGCAGTGGGTACACATTCACGTCCTACAATATGCA<br>CTGGGTGAGACAGATGCCAGGCAAGGGCCTGGAGTGGATGGGAGACATATAC<br>CCAGGCCAGGGAGACACAAGCTATAATCAGAAATTCAAAGGACAGGTGACGA<br>TCTCCGCAGACAAATCCATATCTACGGTCTACCTCCAGTGGTCCTCACTTAA<br>AGCCTCCGACACCGCCATGTACTATTGCGCTCGGGTAGGTGGCGCGTTTCCA<br>ATGGACTATTGGGGCCAAGGGACCACAGTAACCGTCAGCTCA |
| SEQ ID NO: 82 | Heavy Chain | EVQLVQSGAEVKKPGESLKISCKGSGYTFTSYNMHWVRQMPGKGLEWMGDIY<br>PGQGDTSYNQKFKGQVTISADKSISTVYLQWSSLKASDTAMYYCARVGGAFP<br>MDYWGQGTTVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLGK |
| SEQ ID NO: 83 | DNA Heavy Chain | GAAGTTCAATTGGTACAGTCTGGCGCAGAAGTAAAGAAACCAGGAGAGAGTT<br>TGAAAATTTCCTGCAAGGGCAGTGGGTACACATTCACGTCCTACAATATGCA<br>CTGGGTGAGACAGATGCCAGGCAAGGGCCTGGAGTGGATGGGAGACATATAC<br>CCAGGCCAGGGAGACACAAGCTATAATCAGAAATTCAAAGGACAGGTGACGA<br>TCTCCGCAGACAAATCCATATCTACGGTCTACCTCCAGTGGTCCTCACTTAA<br>AGCCTCCGACACCGCCATGTACTATTGCGCTCGGGTAGGTGGCGCGTTTCCA<br>ATGGACTATTGGGGCCAAGGGACCACAGTAACCGTCAGCTCAGCCTCTACAA<br>AGGGCCCCTCCGTCTTTCCACTCGCCGTGCTCTCGCTCCACCTCAGAGTC<br>AACTGCCGCTCTGGGTTGCCTGGTCAAGGACTACTTCCCAGAGCCGGTGACA<br>GTGAGCTGGAACAGTGGGGCCCTGACATCCGGCGTTCATACCTTCCCCGCAG<br>TCCTCCAGTCCTCAGGCCTGTATTCCCTGAGCAGCGTTGTCACAGTGCCCTC<br>CAGCTCTCTTGGCACGAAAACCTACACATGCAACGTTGATCATAAGCCGTCT<br>AATACCAAGGTGGATAAAAGAGTGGAGAGCAAGTACGGCCCACCCTGCCCGC |

TABLE 4-continued

Summary of the sequences of exemplary anti-TIM-3 antibodies.

Hybridoma clone

|  |  |  |
|---|---|---|
|  |  | CTTGCCCAGCTCCGGAGTTCCTGGGCGGACCATCCGTTTTCTTGTTTCCACC<br>CAAACCTAAAGACACTCTGATGATTTCCCGAACCCCTGAAGTGACTTGCGTT<br>GTGGTGGACGTCTCCCAGGAGGACCCAGAAGTGCAATTCAACTGGTACGTGG<br>ACGGGGTGGAGGTGCACAATGCAAAAACAAACCAAGGGAGGAACAGTTTAA<br>TTCAACATATAGGGTTGTGTCTGTGCTGACGGTTCTGCATCAGGACTGGCTG<br>AACGGAAAGGAATACAAGTGCAAGGTGTCCAACAAAGGACTGCCAAGCTCTA<br>TCGAGAAAACAATCTCTAAGGCCAAGGGACAACCTAGAGAGCCCCAAGTTTA<br>CACCCTGCCACCATCACAGGAAGAGATGACCAAAAATCAGGTGAGCTTGACA<br>TGCCTGGTGAAGGGCTTCTACCCTAGCGATATTGCGGTTGAGTGGGAGTCAA<br>ATGGCCAGCCTGAGAACAACTATAAGACTACTCCTCCCGTGCTGGACTCCGA<br>CGGGAGCTTTTTCCTGTATTCCAGGCTTACAGTCGATAAGAGCAGATGGCAA<br>GAGGGGAATGTGTTTTCCTGCTCCGTGATGCACGAGGCTCTCCATAACCATT<br>ATACTCAGAAAAGTCTCTCTCTGTCACTGGGCAAA |
| SEQ ID<br>NO: 6<br>(Kabat) | LCDR1 | RASESVEYYGTSLMQ |
| SEQ ID<br>NO: 7<br>(Kabat) | LCDR2 | AASNVES |
| SEQ ID<br>NO: 8<br>(Kabat) | LCDR3 | QQSRKDPST |
| SEQ ID<br>NO: 12<br>(Chothia) | LCDR1 | SESVEYYGTSL |
| SEQ ID<br>NO: 13<br>(Chothia) | LCDR2 | AAS |
| SEQ ID<br>NO: 14<br>(Chothia) | LCDR3 | SRKDPS |
| SEQ ID<br>NO: 56 | VL | EIVLTQSPATLSLSPGERATLSCRASESVEYYGTSLMQWYQQKPGQAPRLLI<br>YAASNVESGIPARFSGSGSGTDFTLTISSLEPEDIAVYFCQQSRKDPSTFGG<br>GTKVEIK |
| SEQ ID<br>NO: 127 | DNA VL | GAGATTGTTCTTACGCAAAGTCCCGCCACACTTAGTTTGTCACCAGGAGAGC<br>GCGCCACCCTGAGCTGCAGAGCTTCAGAGAGTGTGGAATACTACGGCACATC<br>CCTGATGCAGTGGTATCAGCAGAAACCAGGACAGGCTCCTCGGCTGCTGATC<br>TACGCAGCCAGCAACGTCGAGTCCGGCATTCCAGCCAGATTTTCTGGGTCAG<br>GATCTGGAACTGACTTTACACTGACAATCTCCAGCCTGGAACCCGAGGACAT<br>TGCTGTGTATTTTTGTCAACAGTCCCGGAAGGACCCCAGTACCTTTGGAGGT<br>GGAACCAAGGTAGAGATAAAG |
| SEQ ID<br>NO: 58 | Light<br>Chain | EIVLTQSPATLSLSPGERATLSCRASESVEYYGTSLMQWYQQKPGQAPRLLI<br>YAASNVESGIPARFSGSGSGTDFTLTISSLEPEDIAVYFCQQSRKDPSTFGG<br>GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 128 | DNA<br>Light<br>Chain | GAGATTGTTCTTACGCAAAGTCCCGCCACACTTAGTTTGTCACCAGGAGAGC<br>GCGCCACCCTGAGCTGCAGAGCTTCAGAGAGTGTGGAATACTACGGCACATC<br>CCTGATGCAGTGGTATCAGCAGAAACCAGGACAGGCTCCTCGGCTGCTGATC<br>TACGCAGCCAGCAACGTCGAGTCCGGCATTCCAGCCAGATTTTCTGGGTCAG<br>GATCTGGAACTGACTTTACACTGACAATCTCCAGCCTGGAACCCGAGGACAT<br>TGCTGTGTATTTTTGTCAACAGTCCCGGAAGGACCCCAGTACCTTTGGAGGT<br>GGAACCAAGGTAGAGATAAAGCGTACGGTGGCAGCTCCGTCTGTTTTCATCT<br>TTCCACCTAGCGACGAGCAACTCAAAAGTGGTACAGCATCCGTGGTTTGTCT<br>GCTGAACAATTTTTACCCCAGGGAGGCTAAGGTCCAGTGGAAAGTCGATAAC<br>GCTCTTCAGTCTGGCAACAGTCAGGAGAGCGTCACAGAGCAGGACTCTAAGG<br>ATAGCACTTATAGTCTGTCCTCCACGCTGACACTGTCTAAAGCGGATTATGA<br>GAAGCACAAGGTTTACGCCTGTGAGGTAACGCACCAAGGACTCTCCTCCCCA<br>GTTACCAAATCTTTCAACAGAGGAGAATGT |

ABTIM3-hum17

| SEQ ID<br>NO: 3<br>(Kabat) | HCDR1 | SYNMH |

TABLE 4-continued

Summary of the sequences of exemplary anti-TIM-3 antibodies.

Hybridoma
clone

| | | |
|---|---|---|
| SEQ ID NO: 24 (Kabat) | HCDR2 | DIYPGSGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 25 (Chothia) | HCDR2 | YPGSGD |
| SEQ ID NO: 5 (Chothia) | HCDR3 | VGGAFPMDY |
| SEQ ID NO: 68 | VH | QVQLVQSGAEVKKPGSSVKVSCKASGYTFTSYNMHWVRQAPGQGLEWMGDIY PGSGDTSYNQKFKGRVTITADKSTSTVYMELSSLRSEDTAVYYCARVGGAFP MDYWGQGTTVTVSS |
| SEQ ID NO: 69 | DNA VH | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCAGTGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCA |
| SEQ ID NO: 70 | Heavy Chain | QVQLVQSGAEVKKPGSSVKVSCKASGYTFTSYNMHWVRQAPGQGLEWMGDIY PGSGDTSYNQKFKGRVTITADKSTSTVYMELSSLRSEDTAVYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 71 | DNA Heavy Chain | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCAGTGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCAGCCTCTACAA AGGGCCCCTCCGTCTTTCCACTCGCGCCGTGCTCTCGCTCCACCTCAGAGTC AACTGCCGCTCTGGGTTGCCTGGTCAAGGACTACTTCCCAGAGCCGGTGACA GTGAGCTGGAACAGTGGGGCCCTGACATCCGGCGTTCATACCTTCCCCGCAG TCCTCCAGTCCTCAGGCCTGTATTCCCTGAGCAGCGTTGTCACAGTGCCCTC CAGCTCTCTTGGCACGAAAACCTACACATGCAACGTTGATCATAAGCCGTCT AATACCAAGGTGGATAAAAGAGTGGAGAGCAAGTACGGCCCACCCTGCCCGC CTTGCCCAGCTCCGGAGTTCCTGGGCGGACCATCCGTTTTCTTGTTTCCACC CAAACCTAAAGACACTCTGATGATTTCCCGAACCCCTGAAGTGACTTGCGTT GTGGTGGACGTCTCCCAGGAGGACCCAGAAGTGCAATTCAACTGGTACGTGG ACGGGGTGGAGGTGCACAATGCAAAAACCAAACCAAGGGAGGAACAGTTTAA TTCAACATATAGGGTTGTGTCTGTGCTGACGGTTCTGCATCAGGACTGGCTG AACGGAAAGGAATACAAGTGCAAGGTGTCCAACAAAGGACTGCCAAGCTCTA TCGAGAAAACAATCTCTAAGGCCAAGGGACAACCTAGAGAGCCCCAAGTTTA CACCCTGCCACCATCACAGGAAGAGATGACCAAAAATCAGGTGAGCTTGACA TGCCTGGTGAAGGGCTTCTACCCTAGCGATATTGCGGTTGAGTGGGAGTCAA ATGGCCAGCCTGAGAACAACTATAAGACTACTCCTCCCGTGCTGGACTCCGA CGGGAGCTTTTTCCTGTATTCCAGGCTTACAGTCGATAAGAGCAGATGGCAA GAGGGGAATGTGTTTTCCTGCTCCGTGATGCACGAGGCTCTCCATAACCATT ATACTCAGAAAAGTCTCTCTCTGTCACTGGGCAAA |
| SEQ ID NO: 6 (Kabat) | LCDR1 | RASESVEYYGTSLMQ |

TABLE 4-continued

Summary of the sequences of exemplary anti-TIM-3 antibodies.

Hybridoma clone

| SEQ ID NO: 7 (Kabat) | LCDR2 | AASNVES |
| --- | --- | --- |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 56 | VL | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIK |
| SEQ ID NO: 127 | DNA VL | GAGATTGTTCTTACGCAAAGTCCCGCCACACTTAGTTTGTCACCAGGAGAGC GCGCCACCCTGAGCTGCAGAGCTTCAGAGAGTGTGGAATACTACGGCACATC CCTGATGCAGTGGTATCAGCAGAAACCAGGACAGGCTCCTCGGCTGCTGATC TACGCAGCCAGCAACGTCGAGTCCGGCATTCCAGCCAGATTTTCTGGGTCAG GATCTGGAACTGACTTTACACTGACAATCTCCAGCCTGGAACCCGAGGACAT TGCTGTGTATTTTTGTCAACAGTCCCGGAAGGACCCCAGTACCTTTGGAGGT GGAACCAAGGTAGAGATAAAG |
| SEQ ID NO: 58 | Light Chain | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 128 | DNA Light Chain | GAGATTGTTCTTACGCAAAGTCCCGCCACACTTAGTTTGTCACCAGGAGAGC GCGCCACCCTGAGCTGCAGAGCTTCAGAGAGTGTGGAATACTACGGCACATC CCTGATGCAGTGGTATCAGCAGAAACCAGGACAGGCTCCTCGGCTGCTGATC TACGCAGCCAGCAACGTCGAGTCCGGCATTCCAGCCAGATTTTCTGGGTCAG GATCTGGAACTGACTTTACACTGACAATCTCCAGCCTGGAACCCGAGGACAT TGCTGTGTATTTTTGTCAACAGTCCCGGAAGGACCCCAGTACCTTTGGAGGT GGAACCAAGGTAGAGATAAAGCGTACGGTGGCAGCTCCGTCTGTTTTCATCT TTCCACCTAGCGACGAGCAACTCAAAAGTGGTACAGCATCCGTGGTTTGTCT GCTGAACAATTTTTACCCCAGGGAGGCTAAGGTCCAGTGGAAAGTCGATAAC GCTCTTCAGTCTGGCAACAGTCAGGAGAGCGTCACAGAGCAGGACTCTAAGG ATAGCACTTATAGTCTGTCCTCCACGCTGACACTGTCTAAAGCGGATTATGA GAAGCACAAGGTTTACGCCTGTGAGGTAACGCACCAAGGACTCTCCTCCCCA GTTACCAAATCTTTCAACAGAGGAGAATGT |

ABTIM3-hum18

| SEQ ID NO: 3 (Kabat) | HCDR1 | SYNMH |
| --- | --- | --- |
| SEQ ID NO: 30 (Kabat) | HCDR2 | DIYPGQGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 31 (Chothia) | HCDR2 | YPGQGD |

TABLE 4-continued

Summary of the sequences of exemplary anti-TIM-3 antibodies.

Hybridoma
clone

| | | |
|---|---|---|
| SEQ ID NO: 5 (Chothia) | HCDR3 | VGGAFPMDY |
| SEQ ID NO: 72 | VH | QVQLVQSGAEVKKPGSSVKVSCKASGYTFTSYNMHWVRQAPGQGLEWMGDIY PGQGDTSYNQKFKGRVTITADKSTSTVYMELSSLRSEDTAVYYCARVGGAFP MDYWGQGTTVTVSS |
| SEQ ID NO: 73 | DNA VH | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCCAGGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCA |
| SEQ ID NO: 74 | Heavy Chain | QVQLVQSGAEVKKPGSSVKVSCKASGYTFTSYNMHWVRQAPGQGLEWMGDIY PGQGDTSYNQKFKGRVTITADKSTSTVYMELSSLRSEDTAVYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 75 | DNA Heavy Chain | CAGGTGCAATTGGTTCAGTCAGGAGCAGAAGTTAAGAAGCCAGGATCATCCG TCAAGGTGTCCTGCAAAGCATCTGGCTACACCTTCACCAGCTACAATATGCA CTGGGTCCGACAAGCCCCTGGGCAGGGCTTGGAGTGGATGGGAGACATTTAC CCCGGCCAGGGTGACACTTCCTATAACCAGAAGTTCAAGGGCCGAGTCACTA TTACCGCTGACAAGTCCACCTCCACAGTCTACATGGAACTCTCTTCTCTGAG ATCCGAGGACACTGCCGTCTATTACTGCGCTCGCGTGGGCGGTGCTTTCCCA ATGGACTATTGGGGACAGGGCACAACCGTGACCGTCAGCTCAGCCTCTACAA AGGGCCCCTCCGTCTTTCCACTCGCGCCGTGCTCTCGCTCCACCTCAGAGTC AACTGCCGCTCTGGGTTGCCTGGTCAAGGACTACTTCCCAGAGCCGGTGACA GTGAGCTGGAACAGTGGGGCCCTGACATCGGCGTTCATACCTTCCCCGCAG TCCTCCAGTCCTCAGGCCTGTATTCCCTGAGCAGCGTTGTCACAGTGCCCTC CAGCTCTCTTGGCACGAAAACCTACACATGCAACGTTGATCATAAGCCGTCT AATACCAAGGTGGATAAAAGAGTGGAGAGCAAGTACGGCCCACCCTGCCCGC CTTGCCCAGCTCCGGAGTTCCTGGGCGGACCATCCGTTTTCTTGTTTCCACC CAAACCTAAAGACACTCTGATGATTTCCCGAACCCCTGAAGTGACTTGCGTT GTGGTGGACGTCTCCCAGGAGGACCCAGAAGTGCAATTCAACTGGTACGTGG ACGGGGTGGAGGTGCACAATGCAAAACCAAACCAAGGGAGGAACAGTTTAA TTCAACATATAGGGTTGTGTCTGTGCTGACGGTTCTGCATCAGGACTGGCTG AACGGAAAGGAATACAAGTGCAAGGTGTCCAACAAAGGACTGCCAAGCTCTA TCGAGAAACAATCTCTAAGGCCAAGGGACAACCTAGAGAGCCCCAAGTTTA CACCCTGCCACCATCACAGGAAGAGATGACCAAAAATCAGGTGAGCTTGACA TGCCTGGTGAAGGGCTTCTACCCTAGCGATATTGCGGTTGAGTGGGAGTCAA ATGGCCAGCCTGAGAACAACTATAAGACTACTCCTCCCGTGCTGGACTCCGA CGGGAGCTTTTTCCTGTATTCCAGGCTTACAGTCGATAAGAGCAGATGGCAA GAGGGGAATGTGTTTTCCTGCTCCGTGATGCACGAGGCTCTCCATAACCATT ATACTCAGAAAAGTCTCTCTCTGTCACTGGGCAAA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |

TABLE 4-continued

Summary of the sequences of exemplary anti-TIM-3 antibodies.

Hybridoma clone

| SEQ ID NO: 14 (Chothia) | LCDR3 | SRKDPS |
| --- | --- | --- |
| SEQ ID NO: 56 | VL | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIK |
| SEQ ID NO: 127 | DNA VL | GAGATTGTTCTTACGCAAAGTCCCGCCACACTTAGTTTGTCACCAGGAGAGC GCGCCACCCTGAGCTGCAGAGCTTCAGAGAGTGTGGAATACTACGGCACATC CCTGATGCAGTGGTATCAGCAGAAACCAGGACAGGCTCCTCGGCTGCTGATC TACGCAGCCAGCAACGTCGAGTCCGGCATTCCAGCCAGATTTTCTGGGTCAG GATCTGGAACTGACTTTACACTGACAATCTCCAGCCTGGAACCCGAGGACAT TGCTGTGTATTTTTGTCAACAGTCCCGGAAGGACCCCAGTACCTTTGGAGGT GGAACCAAGGTAGAGATAAAG |
| SEQ ID NO: 58 | Light Chain | EIVLTQSPATLSLSPGERATLSCRASESVEYYGTSLMQWYQQKPGQAPRLLI YAASNVESGIPARFSGSGSGTDFTLTISSLEPEDIAVYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 128 | DNA Light Chain | GAGATTGTTCTTACGCAAAGTCCCGCCACACTTAGTTTGTCACCAGGAGAGC GCGCCACCCTGAGCTGCAGAGCTTCAGAGAGTGTGGAATACTACGGCACATC CCTGATGCAGTGGTATCAGCAGAAACCAGGACAGGCTCCTCGGCTGCTGATC TACGCAGCCAGCAACGTCGAGTCCGGCATTCCAGCCAGATTTTCTGGGTCAG GATCTGGAACTGACTTTACACTGACAATCTCCAGCCTGGAACCCGAGGACAT TGCTGTGTATTTTTGTCAACAGTCCCGGAAGGACCCCAGTACCTTTGGAGGT GGAACCAAGGTAGAGATAAAGCGTACGGTGGCAGCTCCGTCTGTTTTCATCT TTCCACCTAGCGACGAGCAACTCAAAAGTGGTACAGCATCCGTGGTTTGTCT GCTGAACAATTTTTACCCCAGGGAGGCTAAGGTCCAGTGGAAAGTCGATAAC GCTCTTCAGTCTGGCAACAGTCAGGAGAGCGTCACAGAGCAGGACTCTAAGG ATAGCACTTATAGTCTGTCCTCCACGCTGACACTGTCTAAAGCGGATTATGA GAAGCACAAGGTTTACGCCTGTGAGGTAACGCACCAAGGACTCTCCTCCCCA GTTACCAAATCTTTCAACAGAGGAGAATGT |

ABTIM3-hum19

| SEQ ID NO: 3 (Kabat) | HCDR1 | SYNMH |
| --- | --- | --- |
| SEQ ID NO: 24 (Kabat) | HCDR2 | DIYPGSGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 25 (Chothia) | HCDR2 | YPGSGD |
| SEQ ID NO: 5 (Chothia) | HCDR3 | VGGAFPMDY |
| SEQ ID NO: 76 | VH | EVQLVQSGAEVKKPGESLKISCKGSGYTFTSYNMHWVRQMPGKGLEWMGDIY PGSGDTSYNQKFKGQVTISADKSISTVYLQWSSLKASDTAMYYCARVGGAFP MDYWGQGTTVTVSS |
| SEQ ID NO: 77 | DNA VH | GAAGTTCAATTGGTACAGTCTGGCGCAGAAGTAAAGAAACCAGGAGAGAGTT TGAAAATTTCCTGCAAGGGCAGTGGGTACACATTCACGTCCTACAATATGCA CTGGGTGAGACAGATGCCAGGCAAGGGCCTGGAGTGGATGGGAGACATATAC CCAGGCAGTGGAGACACAAGCTATAATCAGAAATTCAAAGGACAGGTGACGA TCTCCGCAGACAAATCCATATCTACGGTCTACCTCCAGTGGTCCTCACTTAA AGCCTCCGACACCGCCATGTACTATTGCGCTCGGGTAGGTGGCGCGTTTCCA ATGGACTATTGGGGCCAAGGGACCACAGTAACCGTCAGCTCA |

TABLE 4-continued

Summary of the sequences of exemplary anti-TIM-3 antibodies.

| Hybridoma clone | | |
|---|---|---|
| SEQ ID NO: 78 | Heavy Chain | EVQLVQSGAEVKKPGESLKISCKGSGYTFTSYNMHWVRQMPGKGLEWMGDIY PGSGDTSYNQKFKGQVTISADKSISTVYLQWSSLKASDTAMYYCARVGGAFP MDYWGQGTTVTVSSASTKGPSVFPLAPCSRSTSESTAALGCLVKDYFPEPVT VSWNSGALTSGVHTFPAVLQSSGLYSLSSVVTVPSSSLGTKTYTCNVDHKPS NTKVDKRVESKYGPPCPPCPAPEFLGGPSVFLFPPKPKDTLMISRTPEVTCV VVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSRWQ EGNVFSCSVMHEALHNHYTQKSLSLSLGK |
| SEQ ID NO: 79 | DNA Heavy Chain | GAAGTTCAATTGGTACAGTCTGGCGCAGAAGTAAAGAAACCAGGAGAGAGTT TGAAAATTTCCTGCAAGGGCAGTGGGTACACATTCACGTCCTACAATATGCA CTGGGTGAGACAGATGCCAGGCAAGGGCCTGGAGTGGATGGGAGACATATAC CCAGGCAGTGGAGACACAAGCTATAATCAGAAATTCAAAGGACAGGTGACGA TCTCCGCAGACAAATCCATATCTACGGTCTACCTCCAGTGGTCCTCACTTAA AGCCTCCGACACCGCCATGTACTATTGCGCTCGGGTAGGTGGCGCGTTTCCA ATGGACTATTGGGGCCAAGGGACCACAGTAACCGTCAGCTCAGCCTCTACAA AGGGCCCCTCCGTCTTTCCACTCGCGCCGTGCTCTCGCTCCACCTCAGAGTC AACTGCCGCTCTGGGTTGCCTGGTCAAGGACTACTTCCCAGAGCCGGTGACA GTGAGCTGGAACAGTGGGGCCCTGACATCCGGCGTTCATACCTTCCCCGCAG TCCTCCAGTCCTCAGGCCTGTATTCCCTGAGCAGCGTTGTCACAGTGCCCTC CAGCTCTCTTGGCACGAAAACCTACACATGCAACGTTGATCATAAGCCGTCT AATACCAAGGTGGATAAAAGAGTGGAGAGCAAGTACGGCCCACCCTGCCCGC CTTGCCCAGCTCCGGAGTTCCTGGGCGGACCATCCGTTTTCTTGTTTCCACC CAAACCTAAAGACACTCTGATGATTTCCCGAACCCCTGAAGTGACTTGCGTT GTGGTGGACGTCTCCCAGGAGGACCCAGAAGTGCAATTCAACTGGTACGTGG ACGGGGTGGAGGTGCACAATGCAAAAACCAAACCAAGGGAGGAACAGTTTAA TTCAACATATAGGGTTGTGTCTGTGCTGACGGTTCTGCATCAGGACTGGCTG AACGGAAAGGAATACAAGTGCAAGGTGTCCAACAAAGGACTGCCAAGCTCTA TCGAGAAAACAATCTCTAAGGCCAAGGGACAACCTAGAGAGCCCCAAGTTTA CACCCTGCCACCATCACAGGAAGAGATGACCAAAAATCAGGTGAGCTTGACA TGCCTGGTGAAGGGCTTCTACCCTAGCGATATTGCGGTTGAGTGGGAGTCAA ATGGCCAGCCTGAGAACAACTATAAGACTACTCCTCCCGTGCTGGACTCCGA CGGGAGCTTTTTCCTGTATTCCAGGCTTACAGTCGATAAGAGCAGATGGCAA GAGGGGAATGTGTTTTCCTGCTCCGTGATGCACGAGGCTCTCCATAACCATT ATACTCAGAAAAGTCTCTCTCTGTCACTGGGCAAA |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 64 | VL | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG GTKVEIK |
| SEQ ID NO: 125 | DNA VL | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAA |
| SEQ ID NO: 66 | Light Chain | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG |

TABLE 4-continued

Summary of the sequences of exemplary anti-TIM-3 antibodies.

Hybridoma clone

| | | |
|---|---|---|
| | | GTKVEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| SEQ ID<br>NO: 126 | DNA<br>Light<br>Chain | GCAATACAGTTGACACAGAGTCCTTCAAGTTTGTCCGCTTCCGTTGGCGACC<br>GAGTGACAATCACCTGTAGAGCATCCGAGTCAGTGGAGTATTATGGCACTAG<br>CCTGATGCAGTGGTATCAGCAAAAGCCAGGGAAAGCCCCAAAGCTGCTGATA<br>TATGCCGCGAGTAACGTCGAGTCAGGGGTGCCATCAAGATTCTCCGGTTCCG<br>GGTCCGGAACCGACTTCACACTGACCATCTCTTCCCTTCAGCCAGAGGACTT<br>CGCTACGTACTTTTGCCAGCAGTCACGGAAAGATCCCTCTACTTTCGGAGGT<br>GGGACAAAAGTCGAAATTAAACGTACGGTGGCAGCTCCGTCTGTTTTCATCT<br>TTCCACCTAGCGACGAGCAACTCAAAAGTGGTACAGCATCCGTGGTTTGTCT<br>GCTGAACAATTTTTACCCCAGGGAGGCTAAGGTCCAGTGGAAAGTCGATAAC<br>GCTCTTCAGTCTGGCAACAGTCAGGAGAGCGTCACAGAGCAGGACTCTAAGG<br>ATAGCACTTATAGTCTGTCCTCCACGCTGACACTGTCTAAAGCGGATTATGA<br>GAAGCACAAGGTTTACGCCTGTGAGGTAACGCACCAAGGACTCTCCTCCCCA<br>GTTACCAAATCTTTCAACAGAGGAGAATGT |

ABTIM3-hum20

| | | |
|---|---|---|
| SEQ ID<br>NO: 3<br>(Kabat) | HCDR1 | SYNMH |
| SEQ ID<br>NO: 30<br>(Kabat) | HCDR2 | DIYPGQGDTSYNQKFKG |
| SEQ ID<br>NO: 5<br>(Kabat) | HCDR3 | VGGAFPMDY |
| SEQ ID<br>NO: 9<br>(Chothia) | HCDR1 | GYTFTSY |
| SEQ ID<br>NO: 31<br>(Chothia) | HCDR2 | YPGQGD |
| SEQ ID<br>NO: 5<br>(Chothia) | HCDR3 | VGGAFPMDY |
| SEQ ID<br>NO: 80 | VH | EVQLVQSGAEVKKPGESLKISCKGSGYTFTSYNMHWVRQMPGKGLEWMGDIY<br>PGQGDTSYNQKFKGQVTISADKSISTVYLQWSSLKASDTAMYYCARVGGAFP<br>MDYWGQGTTVTVSS |
| SEQ ID<br>NO: 81 | DNA VH | GAAGTTCAATTGGTACAGTCTGGCGCAGAAGTAAAGAAACCAGGAGAGAGTT<br>TGAAAATTTCCTGCAAGGGCAGTGGGTACACATTCACGTCCTACAATATGCA<br>CTGGGTGAGACAGATGCCAGGCAAGGGCCTGGAGTGGATGGGAGACATATAC<br>CCAGGCCAGGGAGACACAAGCTATAATCAGAAATTCAAAGGACAGGTGACGA<br>TCTCCGCAGACAAATCCATATCTACGGTCTACCTCCAGTGGTCCTCACTTAA<br>AGCCTCCGACACCGCCATGTACTATTGCGCTCGGGTAGGTGGCGCGTTTCCA<br>ATGGACTATTGGGGCCAAGGGACCACAGTAACCGTCAGCTCA |
| SEQ ID<br>NO: 82 | Heavy<br>Chain | EVQLVQSGAEVKKPGESLKISCKGSGYTFTSYNMHWVRQMPGKGLEWMGDIY<br>PGQGDTSYNQKFKGQVTISADKSISTVYLQWSSLKASDTAMYYCARVGGAFP<br>MDYWGQGTTVTVSSASTKGPSVFPLAPCSRSTSESTAALGCLVKDYFPEPVT<br>VSWNSGALTSGVHTFPAVLQSSGLYSLSSVVTVPSSSLGTKTYTCNVDHKPS<br>NTKVDKRVESKYGPPCPPCPAPEFLGGPSVFLFPPKPKDTLMISRTPEVTCV<br>VVDVSQEDPEVQFNWYVDGVEVHNAKTKPREEQFNSTYRVVSVLTVLHQDWL<br>NGKEYKCKVSNKGLPSSIEKTISKAKGQPREPQVYTLPPSQEEMTKNQVSLT<br>CLVKGFYPSDIAVEWESNGQPENNYKTTPPVLDSDGSFFLYSRLTVDKSRWQ<br>EGNVFSCSVMHEALHNHYTQKSLSLSLGK |
| SEQ ID<br>NO: 83 | DNA<br>Heavy<br>Chain | GAAGTTCAATTGGTACAGTCTGGCGCAGAAGTAAAGAAACCAGGAGAGAGTT<br>TGAAAATTTCCTGCAAGGGCAGTGGGTACACATTCACGTCCTACAATATGCA<br>CTGGGTGAGACAGATGCCAGGCAAGGGCCTGGAGTGGATGGGAGACATATAC<br>CCAGGCCAGGGAGACACAAGCTATAATCAGAAATTCAAAGGACAGGTGACGA<br>TCTCCGCAGACAAATCCATATCTACGGTCTACCTCCAGTGGTCCTCACTTAA<br>AGCCTCCGACACCGCCATGTACTATTGCGCTCGGGTAGGTGGCGCGTTTCCA<br>ATGGACTATTGGGGCCAAGGGACCACAGTAACCGTCAGCTCAGCCTCTACAA<br>AGGGCCCCTCCGTCTTTCCACTCGCGCCGTGCTCTCGCTCCACCTCAGAGTC<br>AACTGCCGCTCTGGGTTGCCTGGTCAAGGACTACTTCCCAGAGCCGGTGACA |

TABLE 4-continued

Summary of the sequences of exemplary anti-TIM-3 antibodies.

Hybridoma
clone

```
GTGAGCTGGAACAGTGGGGCCCTGACATCCGGCGTTCATACCTTCCCCGCAG
TCCTCCAGTCCTCAGGCCTGTATTCCCTGAGCAGCGTTGTCACAGTGCCCTC
CAGCTCTCTTGGCACGAAAACCTACACATGCAACGTTGATCATAAGCCGTCT
AATACCAAGGTGGATAAAAGAGTGGAGAGCAAGTACGCCCACCCTGCCCGC
CTTGCCCAGCTCCGGAGTTCCTGGGCGGACCATCCGTTTTCTTGTTTCCACC
CAAACCTAAAGACACTCTGATGATTTCCCGAACCCCTGAAGTGACTTGCGTT
GTGGTGGACGTCTCCCAGGAGGACCCAGAAGTGCAATTCAACTGGTACGTGG
ACGGGGTGGAGGTGCACAATGCAAAAACCAAACCAAGGGAGGAACAGTTTAA
TTCAACATATAGGGTTGTGTCTGTGCTGACGGTTCTGCATCAGGACTGGCTG
AACGGAAAGGAATACAAGTGCAAGGTGTCCAACAAAGGACTGCCAAGCTCTA
TCGAGAAACAATCTCTAAGGCCAAGGGACAACCTAGAGAGCCCCAAGTTTA
CACCCTGCCACCATCACAGGAAGAGATGACCAAAAATCAGGTGAGCTTGACA
TGCCTGGTGAAGGGCTTCTACCCTAGCGATATTGCGGTTGAGTGGGAGTCAA
ATGGCCAGCCTGAGAACAACTATAAGACTACTCCTCCCGTGCTGGACTCCGA
CGGGAGCTTTTTCCTGTATTCCAGGCTTACAGTCGATAAGAGCAGATGGCAA
GAGGGGAATGTGTTTTCCTGCTCCGTGATGCACGAGGCTCTCCATAACCATT
ATACTCAGAAAAGTCTCTCTCTGTCACTGGGCAAA
```

| | | |
|---|---|---|
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 64 | VL | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG GTKVEIK |
| SEQ ID NO: 125 | DNA VL | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAA |
| SEQ ID NO: 66 | Light Chain | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 126 | DNA Light Chain | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAACGTACGGTGGCAGCTCCGTCTGTTTTCATCT TTCCACCTAGCGACGAGCAACTCAAAAGTGGTACAGCATCCGTGGTTTGTCT GCTGAACAATTTTTACCCCAGGGAGGCTAAGGTCCAGTGGAAAGTCGATAAC GCTCTTCAGTCTGGCAACAGTCAGGAGAGCGTCACAGAGCAGGACTCTAAGG ATAGCACTTATAGTCTGTCCTCCACGCTGACACTGTCTAAAGCGGATTATGA GAAGCACAAGGTTTACGCCTGTGAGGTAACGCACCAAGGACTCTCCTCCCCA GTTACCAAATCTTTCAACAGAGGAGAATGT |

TABLE 4-continued

Summary of the sequences of exemplary anti-TIM-3 antibodies.

Hybridoma clone

ABTIM3-hum21

| | | |
|---|---|---|
| SEQ ID NO: 3 (Kabat) | HCDR1 | SYNMH |
| SEQ ID NO: 30 (Kabat) | HCDR2 | DIYPGQGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 31 (Chothia) | HCDR2 | YPGQGD |
| SEQ ID NO: 5 (Chothia) | HCDR3 | VGGAFPMDY |
| SEQ ID NO: 84 | VH | QVQLVQSGAEVKKPGASVKVSCKASGYTFTSYNMHWVRQAPGQGLEWIGDIY PGQGDTSYNQKFKGRATMTADKSTSTVYMELSSLRSEDTAVYYCARVGGAFP MDYWGQGTLVTVSS |
| SEQ ID NO: 85 | DNA VH | CAGGTGCAATTGGTGCAGAGCGGAGCAGAGGTCAAAAAGCCCGGAGCAAGCG TGAAGGTCTCATGCAAAGCAAGCGGATACACATTTACATCATACAACATGCA CTGGGTCAGGCAGGCTCCAGGACAGGGACTGGAGTGGATCGGGGACATCTAC CCTGGACAGGGCGATACTAGCTATAATCAGAAGTTCAAAGGCCGGGCCACCA TGACAGCTGACAAGTCTACTAGTACCGTGTATATGGAACTGAGCTCCCTGCG GTCTGAAGATACCGCAGTGTACTATTGCGCCAGAGTCGGGGGGGCATTTCCT ATGGATTATTGGGGGCAGGGGACTCTGGTCACTGTCAGCTCA |
| SEQ ID NO: 86 | Heavy Chain | QVQLVQSGAEVKKPGASVKVSCKASGYTFTSYNMHWVRQAPGQGLEWIGDIY PGQGDTSYNQKFKGRATMTADKSTSTVYMELSSLRSEDTAVYYCARVGGAFP MDYWGQGTLVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKRVEPKSCDKTHTCPPCPAPELLGGPSVFLFPPKPKDTLMISRTPEV TCVVVAVSHEDPEVKFNWYVDGVEVHNAKTKPREEQYNSTYRVVSVLTVLHQ DWLNGKEYKCKVSNKALAAPIEKTISKAKGQPREPQVYTLPPSREEMTKNQV SLTCLVKGFYPSDIAVEWESNGQPENNYKTTPPVLDSDGSFFLYSKLTVDKS RWQQGNVFSCSVMHEALHNHYTQKSLSLSPGK |
| SEQ ID NO: 87 | DNA Heavy Chain | CAGGTGCAATTGGTGCAGAGCGGAGCAGAGGTCAAAAAGCCCGGAGCAAGCG TGAAGGTCTCATGCAAAGCAAGCGGATACACATTTACATCATACAACATGCA CTGGGTCAGGCAGGCTCCAGGACAGGGACTGGAGTGGATCGGGGACATCTAC CCTGGACAGGGCGATACTAGCTATAATCAGAAGTTCAAAGGCCGGGCCACCA TGACAGCTGACAAGTCTACTAGTACCGTGTATATGGAACTGAGCTCCCTGCG GTCTGAAGATACCGCAGTGTACTATTGCGCCAGAGTCGGGGGGGCATTTCCT ATGGATTATTGGGGGCAGGGGACTCTGGTCACTGTCAGCTCAGCTAGCACCA AGGGCCCCAGCGTGTTCCCCCTGGCCCCCAGCAGCAAGAGCACCAGCGGCGG CACAGCCGCCCTGGGCTGCCTGGTGAAGGACTACTTCCCCGAGCCCGTGACC GTGTCCTGGAACAGCGGAGCCCTGACCTCCGGCGTGCACACCTTCCCCGCCG TGCTGCAGAGCAGCGGCCTGTACAGCCTGTCCAGCGTGGTGACAGTGCCCAG CAGCAGCCTGGGCACCCAGACCTACATCTGCAACGTGAACCACAAGCCCAGC AACACCAAGGTGGACAAGAGAGTGGAGCCCAAGAGCTGCGACAAGACCCACA CCTGCCCCCCCTGCCCAGCCCCAGAGCTGCTGGGCGGACCCTCCGTGTTCCT GTTCCCCCCCAAGCCCAAGGACACCCTGATGATCAGCAGGACCCCCGAGGTG ACCTGCGTGGTGGTGGCCGTGAGCCACGAGGACCCAGAGGTGAAGTTCAACT GGTACGTGGACGGCGTGGAGGTGCACAACGCCAAGACCAAGCCCAGAGAGGA GCAGTACAACAGCACCTACAGGGTGGTGTCCGTGCTGACCGTGCTGCACCAG GACTGGCTGAACGGCAAGGAATACAAGTGCAAGGTCTCCAACAAGGCCCTGG CAGCCCCCATCGAAAAGACCATCAGCAAGGCCAAGGGCCAGCCACGGGAGCC CCAGGTGTACACCCTGCCCCCCTCCCGGGAGGAGATGACCAAGAACCAGGTG TCCCTGACCTGTCTGGTGAAGGGCTTCTACCCCAGCGACATCGCCGTGGAGT GGGAGAGCAACGGCCAGCCCGAGAACAACTACAAGACCACCCCCCCAGTGCT GGACAGCGACGGCAGCTTCTTCCTGTACAGCAAGCTGACCGTGGACAAGTCC AGGTGGCAGCAGGGCAACGTGTTCAGCTGCAGCGTGATGCACGAGGCCCTGC ACAACCACTACACCCAGAAGAGCCTGAGCCTGTCCCCCGGCAAG |

TABLE 4-continued

Summary of the sequences of exemplary anti-TIM-3 antibodies.

Hybridoma clone

| | | |
|---|---|---|
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |
| SEQ ID NO: 13 (Chothia) | LCDR2 | AAS |
| SEQ ID NO: 14 (Chothia) | LCDR3 | SRKDPS |
| SEQ ID NO: 88 | VL | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIK |
| SEQ ID NO: 89 | DNA VL | GACATCGTCCTGACACAGTCTCCTGACAGCCTGGCAGTGAGCCTGGGCGAAA GGGCAACCATTAATTGTAGAGCTTCCGAGTCCGTCGAGTACTATGGCACTAG TCTGATGCAGTGGTACCAGCAGAAGCCAGGGCAGCCCCCTAAACTGCTGATC TATGCAGCTAGCAACGTGGAGTCCGGAGTCCCAGACCGGTTCTCTGGAAGTG GGTCAGGAACCGATTTTACCCTGACAATTAGCTCCCTGCAGGCAGAAGACGT GGCCGTCTACTATTGTCAGCAGAGCCGCAAGGACCCAAGCACATTCGGAGGG GGGACCAAAGTGGAAATCAAG |
| SEQ ID NO: 90 | Light Chain | DIVLTQSPDSLAVSLGERATINCRASESVEYYGTSLMQWYQQKPGQPPKLLI YAASNVESGVPDRFSGSGSGTDFTLTISSLQAEDVAVYYCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 91 | DNA Light Chain | GACATCGTCCTGACACAGTCTCCTGACAGCCTGGCAGTGAGCCTGGGCGAAA GGGCAACCATTAATTGTAGAGCTTCCGAGTCCGTCGAGTACTATGGCACTAG TCTGATGCAGTGGTACCAGCAGAAGCCAGGGCAGCCCCCTAAACTGCTGATC TATGCAGCTAGCAACGTGGAGTCCGGAGTCCCAGACCGGTTCTCTGGAAGTG GGTCAGGAACCGATTTTACCCTGACAATTAGCTCCCTGCAGGCAGAAGACGT GGCCGTCTACTATTGTCAGCAGAGCCGCAAGGACCCAAGCACATTCGGAGGG GGGACCAAAGTGGAAATCAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

ABTIM3-hum22

| | | |
|---|---|---|
| SEQ ID NO: 3 (Kabat) | HCDR1 | SYNMH |
| SEQ ID NO: 30 (Kabat) | HCDR2 | DIYPGQGDTSYNQKFKG |
| SEQ ID NO: 5 (Kabat) | HCDR3 | VGGAFPMDY |
| SEQ ID NO: 9 (Chothia) | HCDR1 | GYTFTSY |

TABLE 4-continued

Summary of the sequences of exemplary anti-TIM-3 antibodies.

Hybridoma
clone

| SEQ ID NO: 31 (Chothia) | HCDR2 | YPGQGD |
|---|---|---|
| SEQ ID NO: 5 (Chothia) | HCDR3 | VGGAFPMDY |
| SEQ ID NO: 92 | VH | QVQLVQSGAEVKKPGASVKVSCKASGYTFTSYNMHWVRQAPGQGLEWMGDIY PGQGDTSYNQKFKGRVTMTRDTSTSTVYMELSSLRSEDTAVYYCARVGGAFP MDYWGQGTTVTVSS |
| SEQ ID NO: 93 | DNA VH | CAGGTGCAGCTGGTGCAGTCTGGCGCCGAAGTGAAGAAACCAGGCGCCAGCG TGAAGGTGTCCTGCAAGGCCAGCGGCTACACCTTTACCAGCTACAACATGCA CTGGGTGCGCCAGGCCCCTGGACAGGGACTGGAATGGATGGGCGACATCTAC CCCGGCCAGGGCGACACCTCCTACAACCAGAAATTCAAGGGCAGAGTGACCA TGACCCGGGACACCAGCACCTCCACCGTGTACATGGAACTGAGCAGCCTGCG GAGCGAGGACACCGCCGTGTACTACTGTGCTAGAGTGGGCGGAGCCTTCCCC ATGGACTATTGGGGCCAGGGCACCACCGTGACCGTGAGCTCA |
| SEQ ID NO: 94 | Heavy Chain | QVQLVQSGAEVKKPGASVKVSCKASGYTFTSYNMHWVRQAPGQGLEWMGDIY PGQGDTSYNQKFKGRVTMTRDTSTSTVYMELSSLRSEDTAVYYCARVGGAFP MDYWGQGTTVTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKRVEPKSCDKTHTCPPCPAPELLGGPSVFLFPPKPKDTLMISRTPEV TCVVVAVSHEDPEVKFNWYVDGVEVHNAKTKPREEQYNSTYRVVSVLTVLHQ DWLNGKEYKCKVSNKALAAPIEKTISKAKGQPREPQVYTLPPSREEMTKNQV SLTCLVKGFYPSDIAVEWESNGQPENNYKTTPPVLDSDGSFFLYSKLTVDKS RWQQGNVFSCSVMHEALHNHYTQKSLSLSPGK |
| SEQ ID NO: 95 | DNA Heavy Chain | CAGGTGCAGCTGGTGCAGTCTGGCGCCGAAGTGAAGAAACCAGGCGCCAGCG TGAAGGTGTCCTGCAAGGCCAGCGGCTACACCTTTACCAGCTACAACATGCA CTGGGTGCGCCAGGCCCCTGGACAGGGACTGGAATGGATGGGCGACATCTAC CCCGGCCAGGGCGACACCTCCTACAACCAGAAATTCAAGGGCAGAGTGACCA TGACCCGGGACACCAGCACCTCCACCGTGTACATGGAACTGAGCAGCCTGCG GAGCGAGGACACCGCCGTGTACTACTGTGCTAGAGTGGGCGGAGCCTTCCCC ATGGACTATTGGGGCCAGGGCACCACCGTGACCGTGAGCTCAGCTAGCACCA AGGGCCCCAGCGTGTTCCCCCTGGCCCCCAGCAGCAAGAGCACCAGCGGCGG CACAGCCGCCCTGGGCTGCCTGGTGAAGGACTACTTCCCCGAGCCCGTGACC GTGTCCTGGAACAGCGGAGCCCTGACCTCCGGCGTGCACACCTTCCCCGCCG TGCTGCAGAGCAGCGGCCTGTACAGCCTGTCCAGCGTGGTGACAGTGCCCAG CAGCAGCCTGGGCACCCAGACCTACATCTGCAACGTGAACCACAAGCCCAGC AACACCAAGGTGGACAAGAGAGTGGAGCCCAAGAGCTGCGACAAGACCCACA CCTGCCCCCCCTGCCCAGCCCCAGAGCTGCTGGGCGGACCCTCCGTGTTCCT GTTCCCCCCCAAGCCCAAGGACACCCTGATGATCAGCAGGACCCCCGAGGTG ACCTGCGTGGTGGTGGCCGTGAGCCACGAGGACCCAGAGGTGAAGTTCAACT GGTACGTGGACGGCGTGGAGGTGCACAACGCCAAGACCAAGCCCAGAGAGGA GCAGTACAACAGCACCTACAGGGTGGTGTCCGTGCTGACCGTGCTGCACCAG GACTGGCTGAACGGCAAGGAATACAAGTGCAAGGTCTCCAACAAGGCCCTGG CAGCCCCCATCGAAAAGACCATCAGCAAGGCCAAGGGCCAGCCACGGGAGCC CCAGGTGTACACCCTGCCCCCCTCCCGGGAGGAGATGACCAAGAACCAGGTG TCCCTGACCTGTCTGGTGAAGGGCTTCTACCCCAGCGACATCGCCGTGGAGT GGGAGAGCAACGGCCAGCCCGAGAACAACTACAAGACCACCCCCCCAGTGCT GGACAGCGACGGCAGCTTCTTCCTGTACAGCAAGCTGACCGTGGACAAGTCC AGGTGGCAGCAGGGCAACGTGTTCAGCTGCAGCGTGATGCACGAGGCCCTGC ACAACCACTACACCCAGAAGAGCCTGAGCCTGTCCCCCGGCAAG |
| SEQ ID NO: 6 (Kabat) | LCDR1 | RASESVEYYGTSLMQ |
| SEQ ID NO: 7 (Kabat) | LCDR2 | AASNVES |
| SEQ ID NO: 8 (Kabat) | LCDR3 | QQSRKDPST |
| SEQ ID NO: 12 (Chothia) | LCDR1 | SESVEYYGTSL |

TABLE 4-continued

Summary of the sequences of exemplary anti-TIM-3 antibodies.

Hybridoma clone

| | | |
|---|---|---|
| SEQ ID NO: 13 (Chothia) | LCDR2 | AAS |
| SEQ ID NO: 14 (Chothia) | LCDR3 | SRKDPS |
| SEQ ID NO: 96 | VL | AIRLTQSPSSFSASTGDRVTITCRASESVEYYGTSLMQWYQQKPGKAPKLLI YAASNVESGVPSRFSGSGSGTDFTLTISSLQSEDFATYYCQQSRKDPSTFGG GTKVEIK |
| SEQ ID NO: 97 | DNA VL | GCCATCAGACTGACCCAGAGCCCCAGCTCCTTTAGCGCCAGCACCGGCGACA GAGTGACCATCACCTGTAGAGCCAGCGAGAGCGTGGAATATTACGGCACCAG CCTGATGCAGTGGTATCAGCAGAAGCCCGGCAAGGCCCCCAAGCTGCTGATC TACGCCGCCAGCAATGTGGAAAGCGGCGTGCCCAGCAGATTCAGCGGCTCTG GCAGCGGCACCGACTTCACCCTGACAATCAGCAGCCTGCAGAGCGAGGACTT CGCCACCTACTACTGCCAGCAGAGCCGGAAGGACCCCAGCACATTTGGCGGA GGCACCAAGGTGGAAATCAAG |
| SEQ ID NO: 98 | Light Chain | AIRLTQSPSSFSASTGDRVTITCRASESVEYYGTSLMQWYQQKPGKAPKLLI YAASNVESGVPSRFSGSGSGTDFTLTISSLQSEDFATYYCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 99 | DNA Light Chain | GCCATCAGACTGACCCAGAGCCCCAGCTCCTTTAGCGCCAGCACCGGCGACA GAGTGACCATCACCTGTAGAGCCAGCGAGAGCGTGGAATATTACGGCACCAG CCTGATGCAGTGGTATCAGCAGAAGCCCGGCAAGGCCCCCAAGCTGCTGATC TACGCCGCCAGCAATGTGGAAAGCGGCGTGCCCAGCAGATTCAGCGGCTCTG GCAGCGGCACCGACTTCACCCTGACAATCAGCAGCCTGCAGAGCGAGGACTT CGCCACCTACTACTGCCAGCAGAGCCGGAAGGACCCCAGCACATTTGGCGGA GGCACCAAGGTGGAAATCAAGCGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

ABTIM3-hum23

| | | |
|---|---|---|
| SEQ ID NO: 3 (Kabat) | HCDR1 | SYNMH |
| SEQ ID NO: 4 (Kabat) | HCDR2 | DIYPGNGDTSYNQKFKG |
| SEQ ID NO: 5 (Kabat) | HCDR3 | VGGAFPMDY |
| SEQ ID NO: 9 (Chothia) | HCDR1 | GYTFTSY |
| SEQ ID NO: 10 (Chothia) | HCDR2 | YPGNGD |
| SEQ ID NO: 5 (Chothia) | HCDR3 | VGGAFPMDY |
| SEQ ID NO: 100 | VH | QVQLVQSGAEVKKPGESLKISCKGSGYTFTSYNMHWVRQMPGKGLEWMGDIY PGNGDTSYNQKFKGQVTISADKSISTVYLQWSSLKASDTAMYYCARVGGAFP MDYWGQGTTVTVSS |
| SEQ ID NO: 101 | DNA VH | CAGGTGCAATTGGTACAGTCTGGCGCAGAAGTAAAGAAACCAGGAGAGAGTT TGAAAATTTCCTGCAAGGGCAGTGGGTACACATTCACGTCCTACAATATGCA CTGGGTGAGACAGATGCCAGGCAAGGGCCTGGAGTGGATGGGAGACATATAC CCAGGCAATGGAGACACAAGCTATAATCAGAAATTCAAGGACAGGTGACGA |

TABLE 4-continued

Summary of the sequences of exemplary anti-TIM-3 antibodies.

Hybridoma
clone

|  |  |  |
|---|---|---|
|  |  | TCTCCGCAGACAAATCCATATCTACGGTCTACCTCCAGTGGTCCTCACTTAA<br>AGCCTCCGACACCGCCATGTACTATTGCGCTCGGGTAGGTGGCGCGTTTCCA<br>ATGGACTATTGGGGCCAAGGGACCACAGTAACCGTCAGCTCA |
| SEQ ID<br>NO: 102 | Heavy<br>Chain | QVQLVQSGAEVKKPGESLKISCKGSGYTFTSYNMHWVRQMPGKGLEWMGDIY<br>PGNGDTSYNQKFKGQVTISADKSISTVYLQWSSLKASDTAMYYCARVGGAFP<br>MDYWGQGTTVTVSSASTKGPSVFPLAPSSKSTSGGTAALGCLVKDYFPEPVT<br>VSWNSGALTSGVHTFPAVLQSSGLYSLSSVVTVPSSSLGTQTYICNVNHKPS<br>NTKVDKRVEPKSCDKTHTCPPCPAPELLGGPSVFLFPPKPKDTLMISRTPEV<br>TCVVVAVSHEDPEVKFNWYVDGVEVHNAKTKPREEQYNSTYRVVSVLTVLHQ<br>DWLNGKEYKCKVSNKALAAPIEKTISKAKGQPREPQVYTLPPSREEMTKNQV<br>SLTCLVKGFYPSDIAVEWESNGQPENNYKTTPPVLDSDGSFFLYSKLTVDKS<br>RWQQGNVFSCSVMHEALHNHYTQKSLSLSPGK |
| SEQ ID<br>NO: 103 | DNA<br>Heavy<br>Chain | CAGGTGCAATTGGTACAGTCTGGCGCAGAAGTAAAGAAACCAGGAGAGAGTT<br>TGAAAATTTCCTGCAAGGGCAGTGGGTACACATTCACGTCCTACAATATGCA<br>CTGGGTGAGACAGATGCCAGGCAAGGGCCTGGAGTGGATGGGAGACATATAC<br>CCAGGCAATGGAGACACAAGCTATAATCAGAAATTCAAAGGACAGGTGACGA<br>TCTCCGCAGACAAATCCATATCTACGGTCTACCTCCAGTGGTCCTCACTTAA<br>AGCCTCCGACACCGCCATGTACTATTGCGCTCGGGTAGGTGGCGCGTTTCCA<br>ATGGACTATTGGGGCCAAGGGACCACAGTAACCGTCAGCTCAGCTAGCACCA<br>AGGGCCCCAGCGTGTTCCCCCTGGCCCCAGCAGCAAGAGCACCAGCGGCGG<br>CACAGCCGCCCTGGGCTGCCTGGTGAAGGACTACTTCCCCGAGCCCGTGACC<br>GTGTCCTGGAACAGCGGAGCCCTGACCTCCGGCGTGCACACCTTCCCGCCG<br>TGCTGCAGAGCAGCGGCCTGTACAGCCTGTCCAGCGTGGTGACAGTGCCCAG<br>CAGCAGCCTGGGCACCCAGACCTACATCTGCAACGTGAACCACAAGCCCAGC<br>AACACCAAGGTGGACAAGAGAGTGGAGCCCAAGAGCTGCGACAAGACCCACA<br>CCTGCCCCCCTGCCCAGCCCCAGAGCTGCTGGGCGGACCCTCCGTGTTCCT<br>GTTCCCCCCAAGCCCAAGGACACCCTGATGATCAGCAGGACCCCCGAGGTG<br>ACCTGCGTGGTGGTGGCCGTGAGCCACGAGGACCCAGAGGTGAAGTTCAACT<br>GGTACGTGGACGGCGTGGAGGTGCACAACGCCAAGACCAAGCCCAGAGAGGA<br>GCAGTACAACAGCACCTACAGGGTGGTGTCCGTGCTGACCGTGCTGCACCAG<br>GACTGGCTGAACGGCAAGGAATACAAGTGCAAGGTCTCCAACAAGGCCCTGG<br>CAGCCCCCATCGAAAAGACCATCAGCAAGGCCAAGGGCCAGCCACGGGAGCC<br>CCAGGTGTACACCCTGCCCCCCTCCCGGGAGGAGATGACCAAGAACCAGGTG<br>TCCCTGACCTGTCTGGTGAAGGGCTTCTACCCCAGCGACATCGCCGTGGAGT<br>GGGAGAGCAACGGCCAGCCCGAGAACAACTACAAGACCACCCCCCCAGTGCT<br>GGACAGCGACGGCAGCTTCTTCCTGTACAGCAAGCTGACCGTGGACAAGTCC<br>AGGTGGCAGCAGGGCAACGTGTTCAGCTGCAGCGTGATGCACGAGGCCCTGC<br>ACAACCACTACACCCAGAAGAGCCTGAGCCTGTCCCCCGGCAAG |
| SEQ ID<br>NO: 6<br>(Kabat) | LCDR1 | RASESVEYYGTSLMQ |
| SEQ ID<br>NO: 7<br>(Kabat) | LCDR2 | AASNVES |
| SEQ ID<br>NO: 8<br>(Kabat) | LCDR3 | QQSRKDPST |
| SEQ ID<br>NO: 12<br>(Chothia) | LCDR1 | SESVEYYGTSL |
| SEQ ID<br>NO: 13<br>(Chothia) | LCDR2 | AAS |
| SEQ ID<br>NO: 14<br>(Chothia) | LCDR3 | SRKDPS |
| SEQ ID<br>NO: 104 | VL | AIQLTQSPSSLSASVGDRVTITCRASESVEYYGTSLMQWYQQKPGKAPKLLI<br>YAASNVESGVPSRFSGSGSGTDFTLTISSLQPEDFATYFCQQSRKDPSTFGG<br>GTKVEIK |
| SEQ ID<br>NO: 105 | DNA VL | GCAATACAGTTGACACAGAGTCCTTCAAGTTTGTCCGCTTCCGTTGGCGACC<br>GAGTGACAATCACCTGTAGAGCATCCGAGTCAGTGGAGTATTATGGCACTAG<br>CCTGATGCAGTGGTATCAGCAAAAGCCAGGGAAAGCCCCAAAGCTGCTGATA<br>TATGCCGCGAGTAACGTCGAGTCAGGGGTGCCATCAAGATTCTCCGGTTCCG<br>GGTCCGGAACCGACTTCACACTGACCATCTCTTCCCTTCAGCCAGAGGACTT |

TABLE 4-continued

Summary of the sequences of exemplary anti-TIM-3 antibodies.

| Hybridoma clone | | | |
|---|---|---|---|
| | | | CGCTACGTACTTTTGCCAGCAGTCACGGAAAGATCCCTCTACTTTCGGAGGT GGGACAAAAGTCGAAATTAAA |
| SEQ ID NO: 106 | Light Chain | | AIQLTQSPSSLSASVGDRVTITCRASESVEYYGTSLMQWYQQKPGKAPKLLI YAASNVESGVPSRFSGSGSGTDFTLTISSLQPEDFATYFCQQSRKDPSTFGG GTKVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| SEQ ID NO: 107 | DNA Light Chain | | GCAATACAGTTGACACAGAGTCCTTCAAGTTTGTCCGCTTCCGTTGGCGACC GAGTGACAATCACCTGTAGAGCATCCGAGTCAGTGGAGTATTATGGCACTAG CCTGATGCAGTGGTATCAGCAAAAGCCAGGGAAAGCCCCAAAGCTGCTGATA TATGCCGCGAGTAACGTCGAGTCAGGGGTGCCATCAAGATTCTCCGGTTCCG GGTCCGGAACCGACTTCACACTGACCATCTCTTCCCTTCAGCCAGAGGACTT CGCTACGTACTTTTGCCAGCAGTCACGGAAAGATCCCTCTACTTTCGGAGGT GGGACAAAAGTCGAAATTAAACGTACGGTGGCCGCTCCCAGCGTGTTCATCT TCCCCCCCAGCGACGAGCAGCTGAAGAGCGGCACCGCCAGCGTGGTGTGCCT GCTGAACAACTTCTACCCCCGGGAGGCCAAGGTGCAGTGGAAGGTGGACAAC GCCCTGCAGAGCGGCAACAGCCAGGAGAGCGTCACCGAGCAGGACAGCAAGG ACTCCACCTACAGCCTGAGCAGCACCCTGACCCTGAGCAAGGCCGACTACGA GAAGCATAAGGTGTACGCCTGCGAGGTGACCCACCAGGGCCTGTCCAGCCCC GTGACCAAGAGCTTCAACAGGGGCGAGTGC |

TABLE 5

Constant region amino acid sequences of human IgG heavy chains and human kappa light chain HC  IgG4 (S228P) mutant constant region amino acid sequence (EU Numbering)
ASTKGPSVFP LAPCSRSTSE STAALGCLVK DYFPEPVTVS WNSGALTSGV HTFPAVLQSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLGK (SEQ ID NO: 108)

LC  Human kappa constant region amino acid sequence
RTVAAPSVFI FPPSDEQLKS GTASVVCLLN NFYPREAKVQ WKVDNALQSG NSQESVTEQD
SKDSTYSLSS TLTLSKADYE KHKVYACEVT HQGLSSPVTK
SFNRGEC (SEQ ID NO: 109)

HC  IgG4 (S228P) mutant constant region amino acid sequence lacing C-terminal lysine (K) (EU Numbering)
ASTKGPSVFP LAPCSRSTSE STAALGCLVK DYFPEPVTVS WNSGALTSGV HTFPAVLQSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLG (SEQ ID NO: 110)

HC  IgG1 wild type
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPELLGG
PSVFLFPPKP KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPGK (SEQ ID NO: 111)

HC  IgG1 (N297A) mutant constant region amino acid sequence (EU Numbering)
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPELLGG
PSVFLFPPKP KDTLMISRTP EVTCVVVDVS HEDPEVKFNW YVDGVEVHNA KTKPREEQYA
STYRVVSVLT VLHQDWLNGK EYKCKVSNKA LPAPIEKTIS KAKGQPREPQ VYTLPPSREE
MTKNQVSLTC LVKGFYPSDI AVEWESNGQP ENNYKTTPPV LDSDGSFFLY SKLTVDKSRW
QQGNVFSCSV MHEALHNHYT QKSLSLSPGK (SEQ ID NO: 112)

HC  IgG1 (D265A, P329A) mutant constant region amino acid sequence (EU Numbering)
ASTKGPSVFP LAPSSKSTSG GTAALGCLVK DYFPEPVTVS WNSGALTSGV HTFPAVLQSS
GLYSLSSVVT VPSSSLGTQT YICNVNHKPS NTKVDKRVEP KSCDKTHTCP PCPAPELLGG TABLE 5-continued Constant region amino acid sequences of human IgG heavy chains and human kappa light chain

```
    PSVFLFPPKP KDTLMISRTP EVTCVVVAVS HEDPEVKFNW YVDGVEVHNA KTKPREEQYN
    STYRVVSVLT VLHQDWLNGK EYKCKVSNKA LAAPIEKTIS KAKGQPREPQ VYTLPPSREE
    MTKNQVSLTC LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 113)

HC  IgG1 (L234A, L235A) mutant constant region amino acid sequence
    (EU Numbering)
    ASTKGPSVFP LAPSSKSTSG GTAALGCLVK DYFPEPVTVS WNSGALTSGV HTFPAVLQSS
    GLYSLSSVVT VPSSSLGTQT YICNVNHKPS NTKVDKRVEP KSCDKTHTCP PCPAPEAAGG
    PSVFLFPPKP KDTLMISRTP EVTCVVVDVS HEDPEVKFNW YVDGVEVHNA KTKPREEQYN
    STYRVVSVLT VLHQDWLNGK EYKCKVSNKA LPAPIEKTIS KAKGQPREPQ VYTLPPSREE
    MTKNQVSLTC LVKGFYPSDI AVEWESNGQP ENNYKTTPPV LDSDGSFFLY SKLTVDKSRW
    QQGNVFSCSV MHEALHNHYT QKSLSLSPGK (SEQ ID NO: 114)
```

TABLE 6

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A1 | Sotrastaurin | 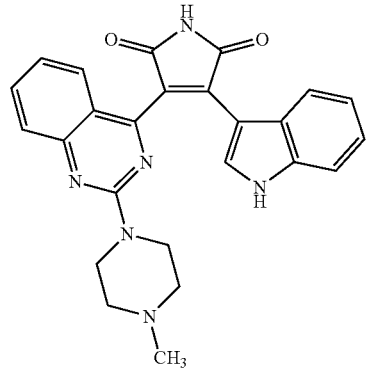 [SMILES: CN1CCN(c2nc(C3=C(c4c[nH]c5ccccc45)C(=O)NC3=O)c3ccccc3n2)CC1] | EP 1682103 US 2007/142401 WO 2005/039549 |
| A2 | Nilotinib HCl monohydrate TASIGNA ® | 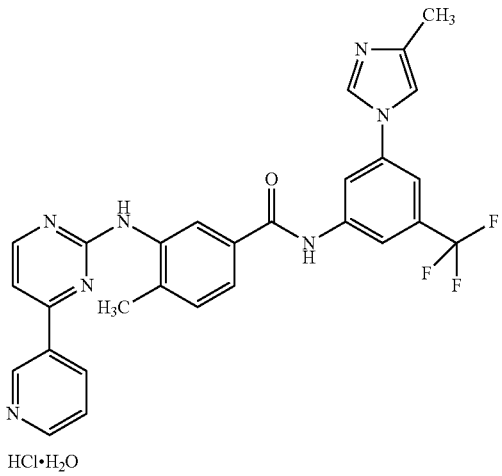 HCl·H₂O | WO 2004/005281 US 7,169,791 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A3 | | 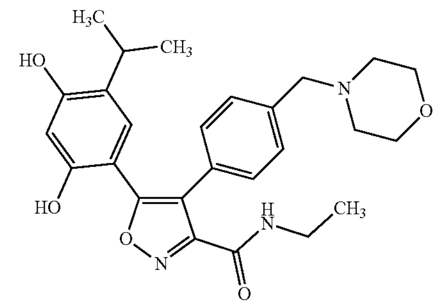 [SMILES: CCNC(=O)c1noc(-c2cc(C(C)C)c(O)cc2O)c1-c1ccc(CN2CCOCC2)cc1] | WO 2010/060937<br>WO 2004/072051<br>EP 1611112<br>US 8,450,310 |
| A4 | Dactolisib | 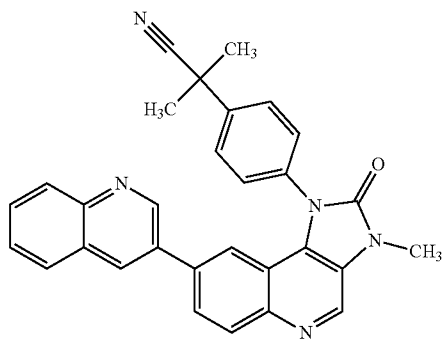 [SMILES: Cn1c(=O)n(-c2ccc(C(C)(C)C#N)cc2)c2c3cc(-c4cnc5ccccc5c4)ccc3ncc21] | WO 2006/122806 |
| A5 | | 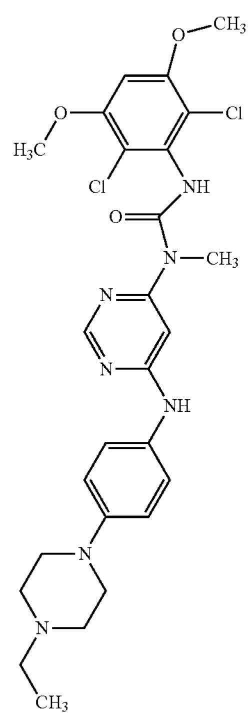 [SMILES: CCN1CCN(c2ccc(Nc3cc(N(C)C(=O)Nc4c(Cl)c(OC)cc(OC)c4Cl)ncn3)cc2)CC1] | US 8,552,002 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A6 | Buparlisib | 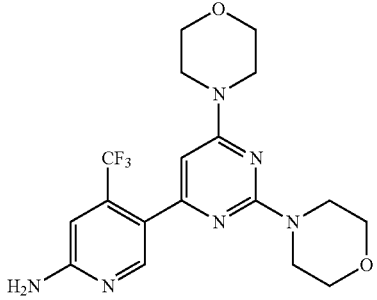 [SMILES: Nc1cc(C(F)(F)F)c(-c2cc(N3CCOCC3)nc(N3CCOCC3)n2)cn1] | WO 2007/084786 |
| A7 | | 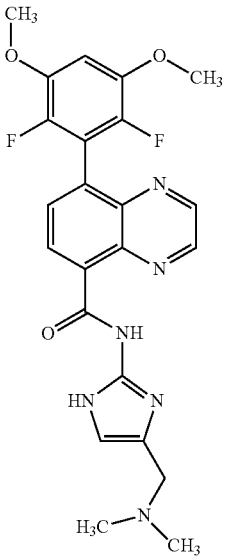 [SMILES: COc1cc(OC)c(F)c(-c2ccc(C(=O)Nc3nc(CN(C)C)c[nH]3)c3nccnc23)c1F] | WO 2009/141386 US 2010/0105667 |
| A8 | | 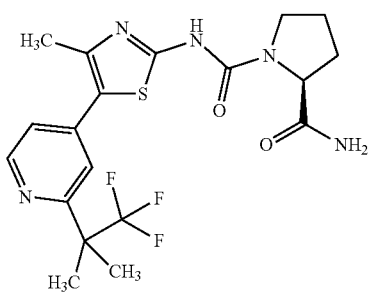 [SMILES: Cc1nc(NC(=O)N2CCC[C@H]2C(N)=O)sc1-c1ccnc(C(C)(C)C(F)(F)F)c1] | WO 2010/029082 |
| A9 | | CYP17 inhibitor | WO 2010/149755 US 8,263,635 B2 EP 2445903 B1 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A10 | | 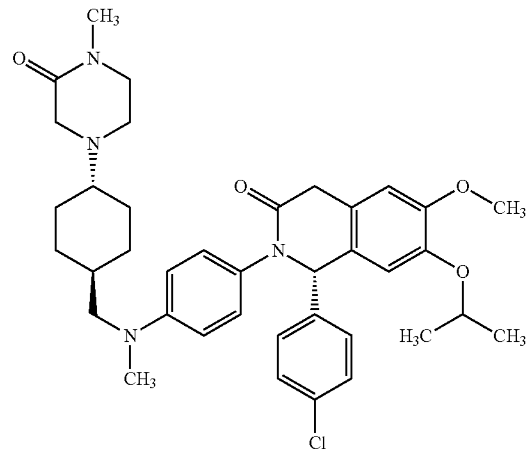 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |
| A11 | Deferasirox EXJADE ® | 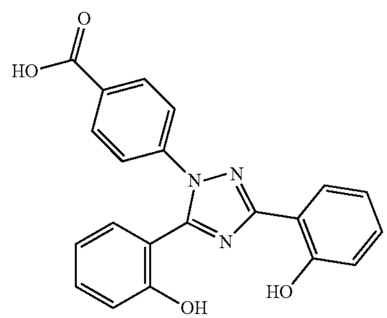 [SMILES: O=C(O)c1ccc(-n2nc(-c3ccccc3O)nc2-c2ccccc2O)cc1] | WO 1997/049395 |
| A12 | Letrozole FEMARA ® | 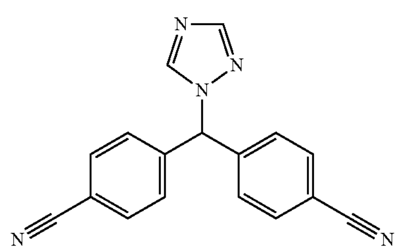 [SMILES: N#Cc1ccc(C(c2ccc(C#N)cc2)n2cncn2)cc1] | US 4,978,672 |
| A13 | | 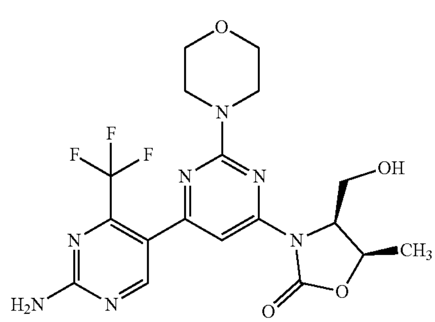 [SMILES: C[C@H]1OC(=O)N(c2cc(-c3cnc(N)nc3C(F)(F)F)nc(N3CCOCC3)n2)[C@H]1CO] | WO 2013/124826 US 2013/0225574 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A14 | | 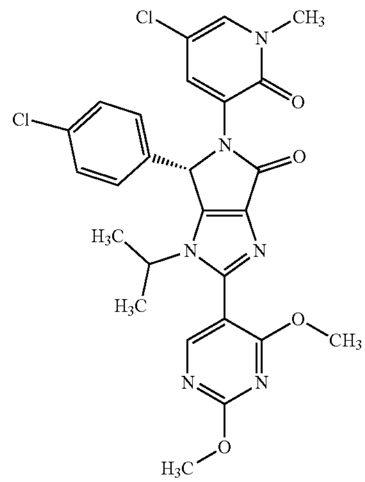 [SMILES: COc1ncc(-c2nc3c(n2C(C)C)[C@H](c2ccc(Cl)cc2)N(c2cc(Cl)cn(C)c2=O)C3=O)c(OC)n1] | WO 2013/111105 |
| A15 | | 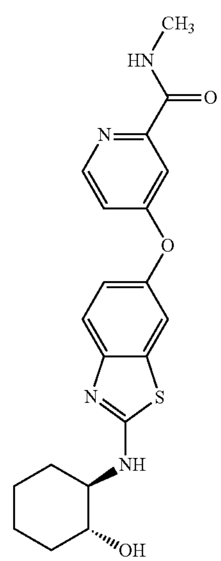 [SMILES: CNC(=O)c1cc(Oc2ccc3nc(N[C@@H]4CCCC[C@H]4O)sc3c2)ccn1] | WO 2005/073224 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A16 | Imatinib mesylate GLEEVEC ® | 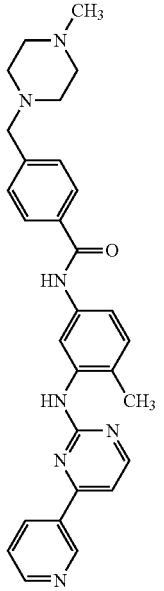<br>Mesylate | WO 1999/003854 |
| A17 | | 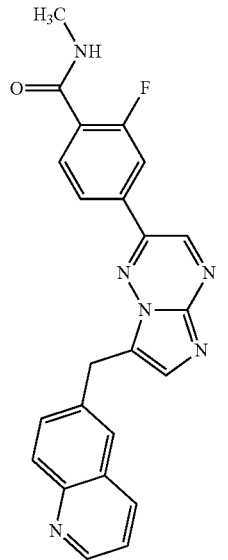<br>Dihydrochloric salt | EP 2099447<br>US 7,767,675<br>US 8,420,645 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A18 | Ruxolitinib Phosphate JAKAFI® | 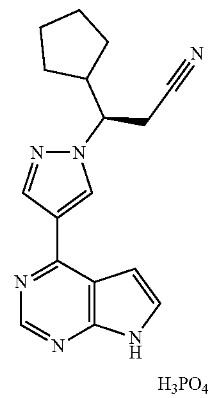 | WO 2007/070514<br>EP 2474545<br>US 7,598,257<br>WO 2014/018632 |
| A19 | Panobinostat | 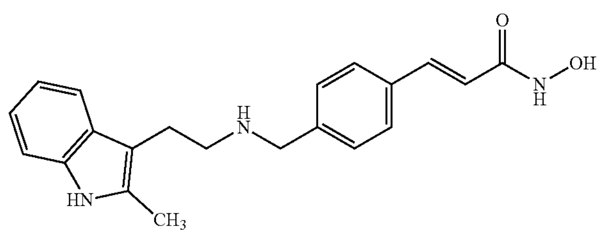 [SMILES: Cc1[nH]c2ccccc2c1CCNCc1ccc(/C=C/C(=O)NO)cc1] | WO 2014/072493<br>WO 2002/022577<br>EP 1870399 |
| A20 | Osilodrostat | 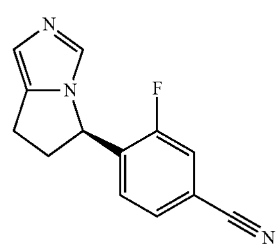 [SMILES: N#Cc1ccc([C@H]2CCc3cncn32)c(F)c1] | WO 2007/024945 |
| A21 | | 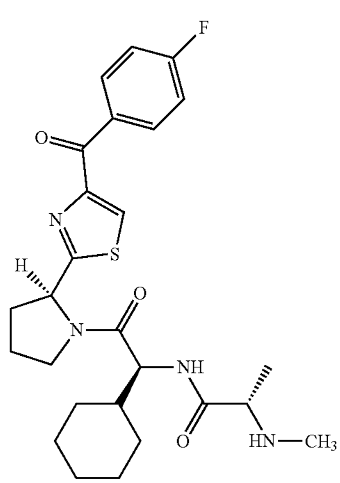 [SMILES: CN[C@@H](C)C(=O)N[C@H](C(=O)N1CCC[C@H]1c1nc(C(=O)c2ccc(F)cc2)cs1)C1CCCCC1] | WO 2008/016893<br>EP 2051990<br>US 8,546,336 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A22 | Sonidegib phosphate | 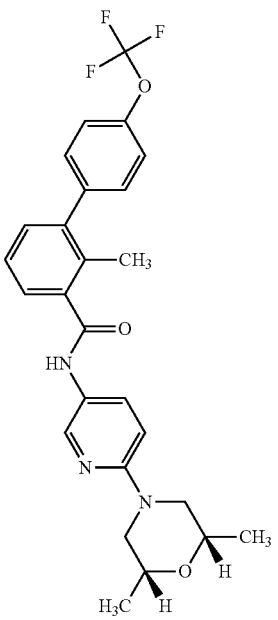 [SMILES: Cc1c(C(=O)Nc2ccc(N3C[C@@H](C)O[C@@H](C)C3)nc2)cccc1-c1ccc(OC(F)(F)F)cc1] | WO 2007/131201<br>EP 2021328<br>US 8,178,563 |
| A23 | ceritinib ZYKADIA™ | 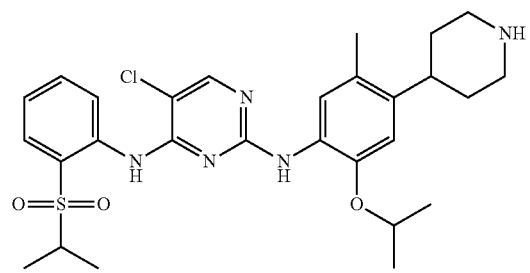 [SMILES: Cc1cc(Nc2ncc(Cl)c(Nc3ccccc3S(=O)(=O)C(C)C)n2)c(OC(C)C)cc1C1CCNCC1] | WO 2008/073687<br>US 8,039,479 |
| A24 | | 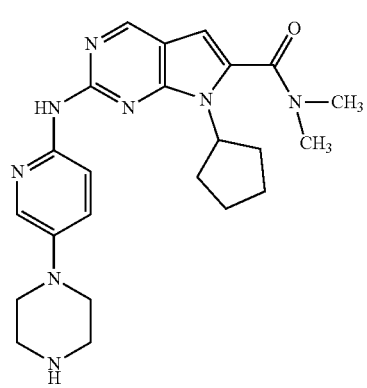 [SMILES: CN(C)C(=O)c1cc2cnc(Nc3ccc(N4CCNCC4)cn3)nc2n1C1CCCC1] | US 8,415,355<br>US 8,685,980 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A25 | | *(structure)* | WO 2010/007120 |
| A26 | | Human monoclonal antibody to PRLR | US 7,867,493 |
| A27 | | *(structure)* | WO 2010/026124<br>EP 2344474<br>US 2010/0056576<br>WO 2008/106692 |
| A28 | | *(structure)* | WO 2010/101849 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A29 | Encorafenib | 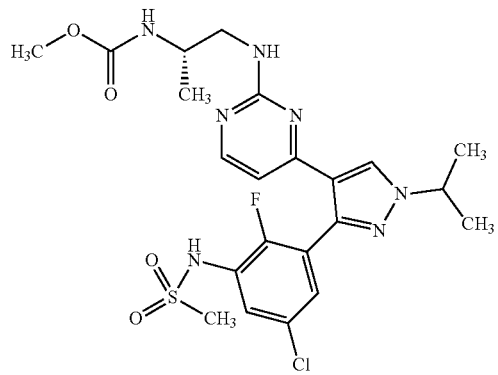 [SMILES: COC(=O)N[C@@H](C)CNc1nccc(-c2cn(C(C)C)nc2-c2cc(Cl)cc(NS(C)(=O)=O)c2F)n1] | WO 2011/025927 |
| A30 | | 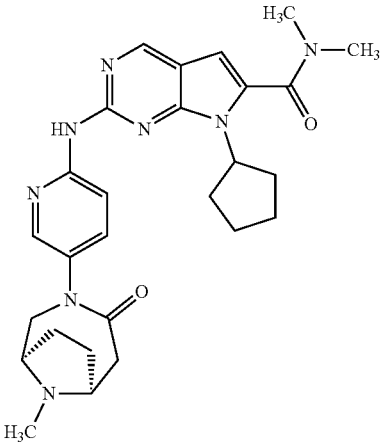 [SMILES: CN(C)C(=O)c1cc2cnc(Nc3ccc(N4C[C@H]5CC[C@@H](CC4=O)N5C)cn3)nc2n1C1CCCC1] | WO 2011/101409 |
| A31 | | Human monoclonal antibody to HER3 | WO 2012/022814<br>EP 2606070<br>US 8,735,551 |
| A32 | | Antibody Drug Conjugate (ADC) | WO 2014/160160<br>Ab: 12425 (see Table 1, paragraph [00191])<br>Linker: SMCC (see paragraph [00117]<br>Payload: DM1 (see paragraph [00111]<br>See also Claim 29 |
| A33 | | Monoclonal antibody or Fab to M-CSF | WO 2004/045532 |
| A34 | Binimetinib | 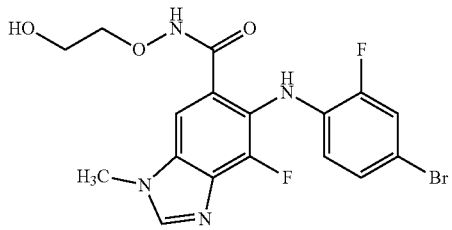 [SMILES: Cn1cnc2c(F)c(Nc3ccc(Br)cc3F)c(C(=O)NOCCO)cc21] | WO 2003/077914 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A35 | Midostaurin | 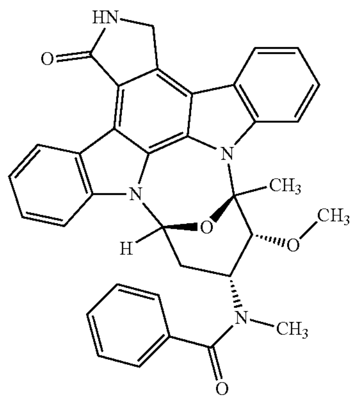 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] | WO 2003/037347<br>EP 1441737<br>US 2012/252785 |
| A36 | Everolimus<br>AFINITOR ® | 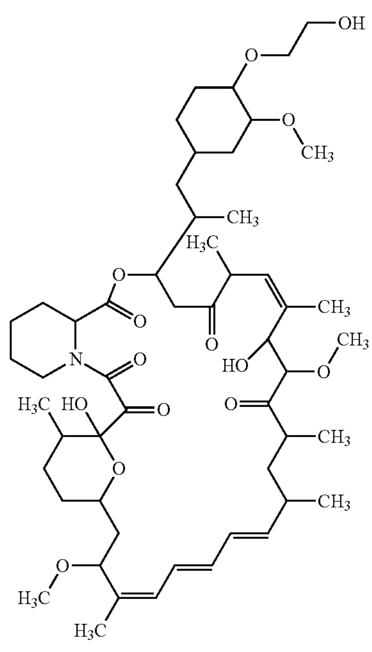 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A37 | | 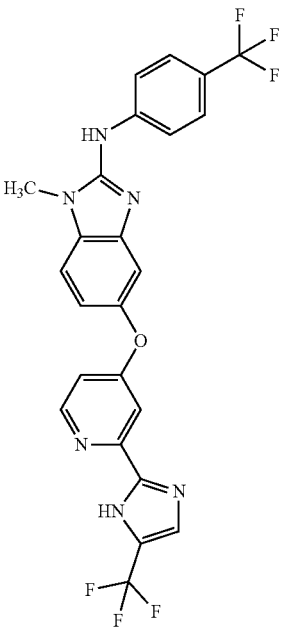 [SMILES: Cn1c(Nc2ccc(C(F)(F)F)cc2)nc2cc(Oc3ccnc(-c4ncc(C(F)(F)F)[nH]4)c3)ccc21] | WO 2007/030377<br>US 7,482,367 |
| A38 | Pasireotide diaspartate SIGNIFOR ® | 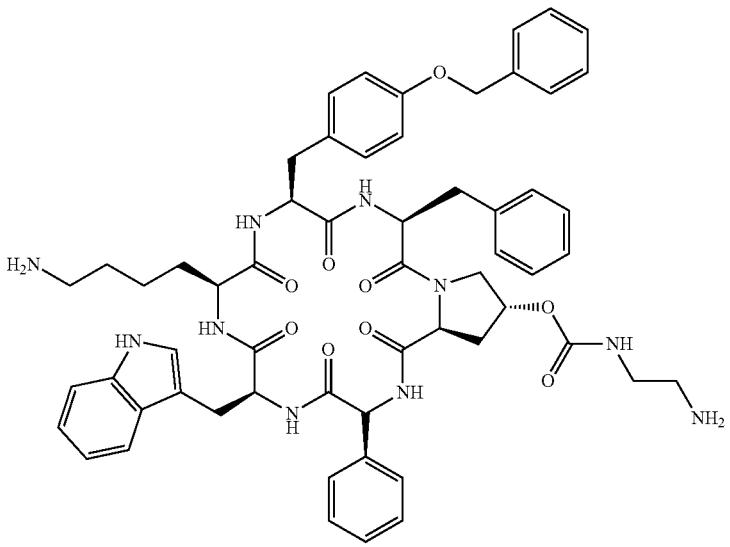 | WO 2002/010192<br>US 7,473,761 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A39 | Dovitinib | 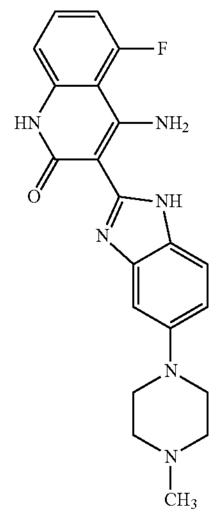 [SMILES: CN1CCN(c2ccc3[nH]c(-c4c(N)c5c(F)cccc5[nH]c4=O)nc3c2)CC1] | WO 2009/115562<br>US 8,563,556 |
| A40 | | 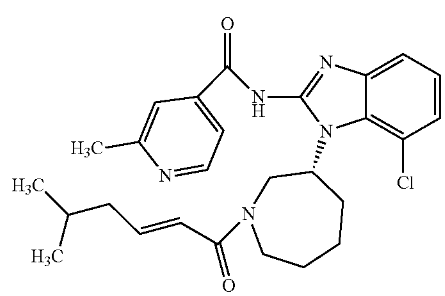 [SMILES: Cc1cc(C(=O)Nc2nc3cccc(Cl)c3n2[C@@H]2CCCCN(C(=O)/C=C/CC(C)C)C2)ccn1] | WO 2013/184757 |
| A41 | | 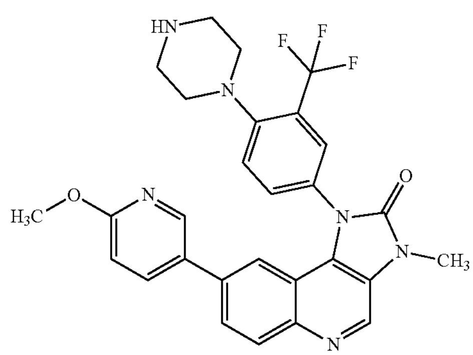 | WO 02006/122806 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A42 | | 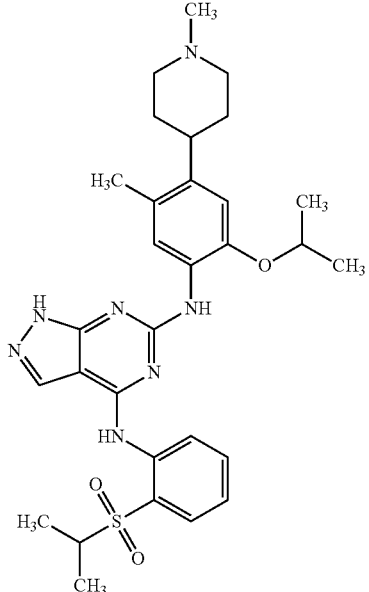 [SMILES: Cc1cc(Nc2nc(Nc3ccccc3S(=O)(=O)C(C)C)c3cn[nH]c3n2)c(OC(C)C)cc1C1CCN(C)CC1] | WO 2008/073687<br>US 8,372,858 |
| A43 | | 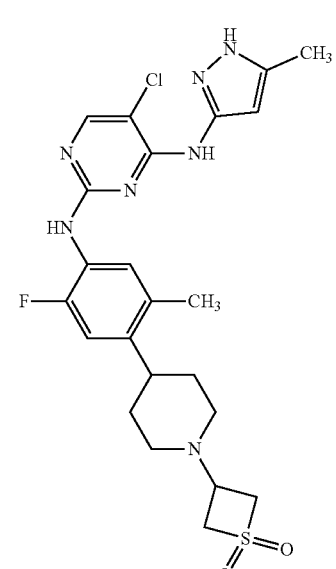 | WO 2010/002655<br>US 8,519,129 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A44 | | 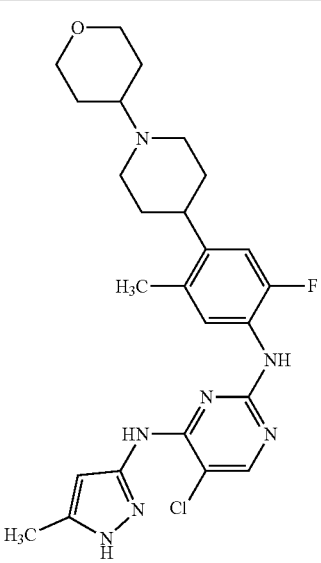 [SMILES: Cc1cc(Nc2nc(Nc3cc(C)c(C4CCN(C5CCOCC5)CC4)cc3F)ncc2Cl)n[nH]1] | WO 2010/002655<br>US 8,519,129 |
| A45 | | 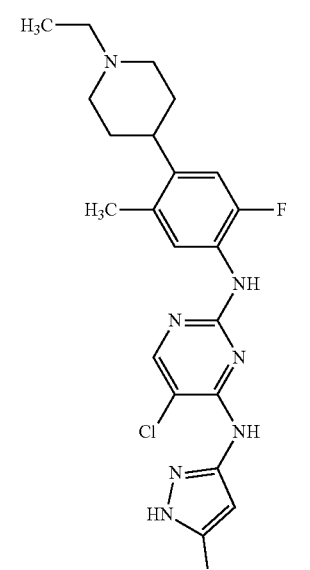 | WO 2010/002655 |

TABLE 6-continued

Selected therapeutic agents that can be administered in combination with the anti-TIM-3 antibody molecules, e.g., as a single agent or in combination with other immunomodulators described herein. Each publication listed in this Table is herein incorporated by reference in its entirety, including all structural formulae therein.

| Compound No. | Generic Name Tradename | Compound Structure | Patents/Patent Application Publications |
|---|---|---|---|
| A46 | Valspodar AMDRAY ™ | 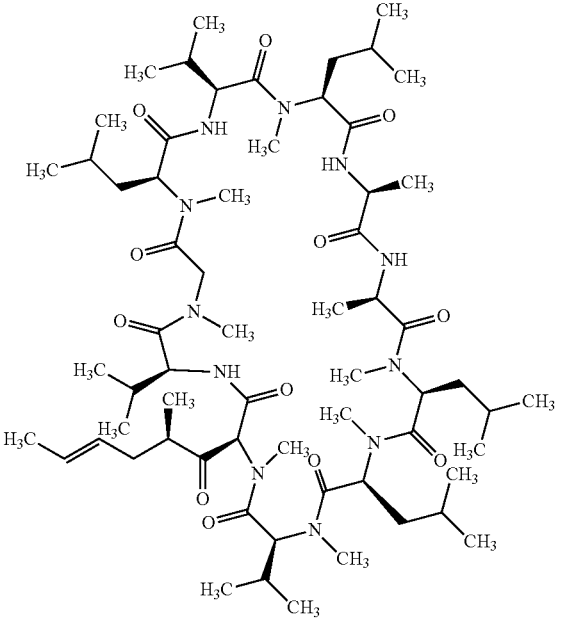 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | EP 296122 |
| A47 | Vatalanib succinate | 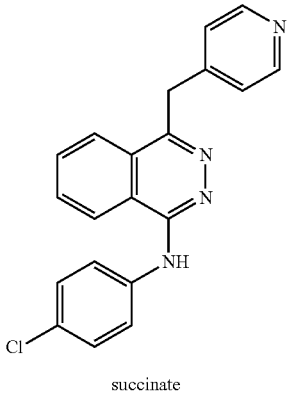 [SMILES: Clc1ccc(Nc2nnc(Cc3ccncc3)c3ccccc23)cc1]<br>succinate | WO 98/35958 |
| A48 | | IDH inhibitor | WO 2014/141104 |
| A49 | | BCR-ABL inhibitor | WO 2013/171639<br>WO 2013/171640<br>WO 2013/171641<br>WO 2013/171642 |
| A50 | | cRAF inhibitor | WO 2014/151616 |
| A51 | | ERK 1/2 ATP competitive inhibitor | PCT/US2014/062913 |

Table 7. See Examples.
Table 8. See Examples.
Table 9. See Examples.
Table 10. See Examples.
Table 11. See Examples.
Table 12. See Examples.
Table 13. See Examples.
Table 14. See Examples.
Table 15. See Examples.
Table 16. See Examples.

EXAMPLES

Example 1. Characterization of ABTIM3 and Other Anti-TIM-3 Antibodies

Figure 2E:
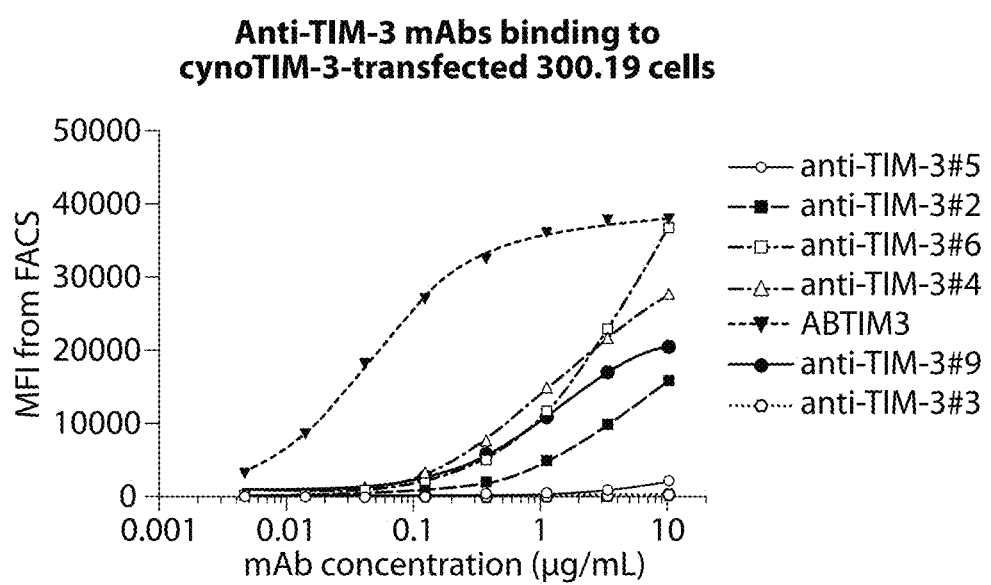

Panels of anti-TIM-3 antibodies were assayed for binding to TIM-3 expressing cells. The dissociation constants ($K_D$) of two such antibodies, ABTIM3 and anti-TIM-3 #2, as measured by surface plasmon resonance, is summarized in FIG. 2A. In FIGS. 2B and 2C, the binding of various anti-TIM-3 antibodies, including ABTIM3, to cells transfected with human TIM-3 was measured using flow cytometry. Next, three antibodies, ABTIM3, anti-TIM-3 #2, and anti-TIM-3 #3, and a control antibody were assayed for the ability to bind cynomolgus TIM-3 in cells transfected with cynoTIM-3. FIG. 2D shows that ABTIM3 has the strongest affinity for cynomolgus TIM-3 out of the three antibodies tested. FIG. 2E tests seven anti-human-TIM-3 antibodies for the ability to bind cynomolgus TIM-3, and shows that ABTIM3 binds with the highest affinity. Overall, the experiments indicate that ABTIM3 has strong (sub-nanomolar) affinity for both human and cynomolgus TIM-3.

The ability of three anti-TIM-3 antibodies, including ABTIM3, to bind to human TIM-4 expressed in CHO cells and murine TIM-3 expressed in cells was also measured by flow cytometry. Human TIM-3 has about 23% sequence identity with human TIM-4. Murine TIM-3 has about 66% sequence identity with human TIM-3 and 64% sequence identity with cynomolgus TIM-3. The results from these assays show that ABTIM3 does not bind to human TIM-4. ABTIM3 is also not cross-reactive with murine TIM-3. Taken together with the binding assay results described above, ABTIM3 antibody is specific for human and cynomolgus TIM-3.

In a cross-blocking experiment, ABTIM3 was shown to cross-block anti-TIM-3 #2, suggesting that these antibodies bind to epitopes that are near each other, and possibly overlap, although the two epitopes are not necessarily identical.

The ability of TIM-3 antibodies, e.g., ABTIM3, to bind to activated PBMCs expressing TIM-3 was also assessed. Whole human PBMCs from a donor were stimulated for 10 days with platebound CD3/CD28 (1 µg/ml each), in the presence of 10 ng/ml recombinant human IL-12. Cells were ficolled to remove dead cells and reactivated for three days with the same stimulus. Antibodies that bind to TIM-3, e.g., ABTIM3 and anti-TIM-3 #2, were compared, and anti-PD-1, anti-PD-L1, and anti-LAG-3 antibodies, and mouse IgG1 were used as control antibodies. Cells were incubated with the antibodies at various concentrations from 0.001 to 100 µg/ml, and the antibody binding to the cells was analyzed by flow cytometry. Cells were gated for CD4 or CD8 positive populations, and mean fluorescence intensity (MFI) for each antibody and concentration was plotted on a graph. Dissociation constant ($K_D$) values were then calculated. The results from the assays are shown in Table 7 below.

TABLE 7

$K_D$ values for anti-TIM-3 binding to activated PBMCs

| Antibody | CD4 gated PBMCs $K_D$ | CD8 gated PBMCs $K_D$ |
| --- | --- | --- |
| ABTIM3 | 0.29 nM | 0.30 nM |
| Anti-TIM-3 #2 | 2.84 nM | 3.14 nM |
| Anti-PD-L1 control | 0.20 nM | 0.30 nM |
| Anti-LAG-3 control | | 2.33 nM |
| Anti-PD-1 control | 22.8 nM | 85.9 nM |

These results demonstrate that ABTIM3 was able to bind to TIM-3 expressed on activated PBMCs.

Example 2. Domain Analysis of Anti-TIM-3 Antibody Binding to TIM-3

Figure 3A:
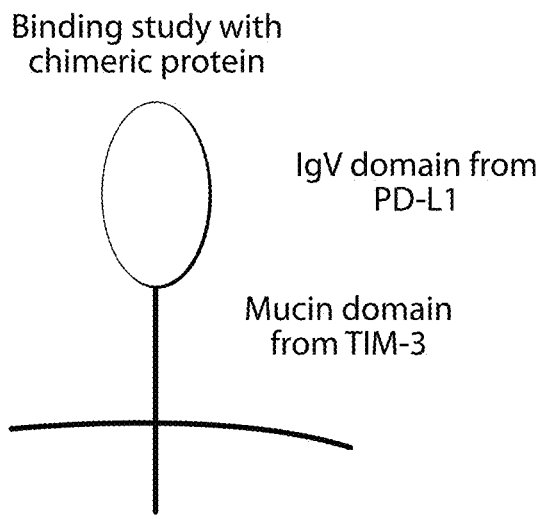
FIGS. 3A-3B show that anti-TIM-3 monoclonal antibodies, including and ABTIM3, bind to the IgV domain, while 4A4 binds to the mucin domain.
Figure 3B:
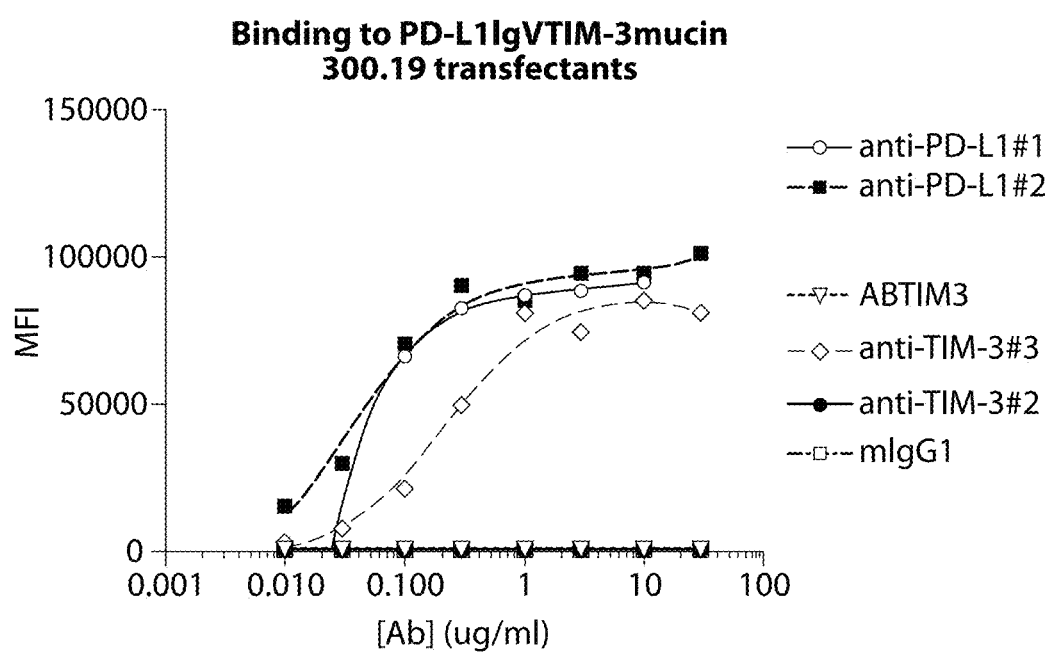

TIM-3 has an extracellular IgV domain and a mucin domain. The regions of TIM-3 bound by each of five anti-TIM-3 antibodies was determined using a recombinant construct that replaced the IgV domain of TIM-3 with the IgV domain of PD-1, and this construct is depicted in FIG. 3A. FIG. 3B shows that the anti-TIM-3 monoclonal antibody (anti-TIM-3 #3), and two anti-PD-L1 control monoclonal antibodies (anti-PD-L1 #1 and #2), bind to the chimeric protein of FIG. 3A, while anti-TIM-3 #2 and ABTIM3 do not substantially bind. This result suggests that the anti-TIM-3 monoclonal antibodies anti-TIM-3 #2 and ABTIM3 bind to the IgV domain of TIM-3, while anti-TIM-3 #3 binds to the mucin domain of TIM-3. The dissociation constant ($K_D$) values were calculated for each tested antibody for the recombinant construct are shown in Table 8.

TABLE 8

$K_D$ values for binding to PD-L1 IgV/TIM-3 mucin construct

| Antibody | Antigen | $K_D$ |
| --- | --- | --- |
| Anti-PD-L1 #1 | PD-L1 IgV domain | 0.52 nM |
| Anti-PD-L1 #2 | PD-L1 IgV domain | 0.38 nM |
| Anti-TIM-3 #3 | TIM-3 mucin domain | 2.71 nM |
| Anti-TIM-3 #2 | TIM-3 | No binding to the chimeric protein |
| ABTIM3 | TIM-3 | No binding to the chimeric protein |

Example 3. TIM-3 Binding to PtdSer is Blocked by Anti-TIM-3 Antibodies

Figure 4:
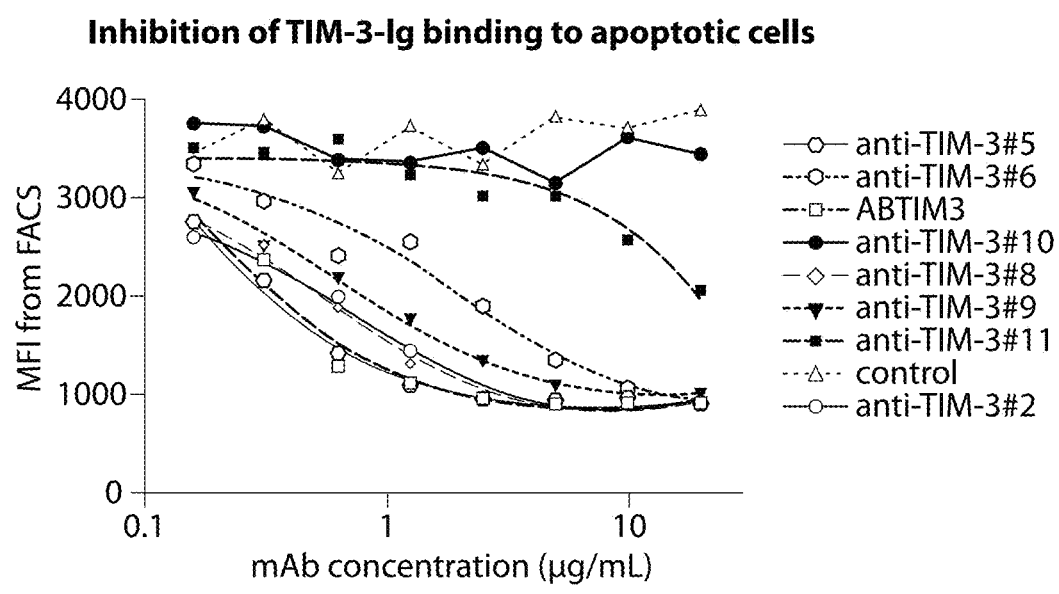
FIG. 4 illustrates that anti-TIM-3 antibodies anti-TIM-3 #2 and ABTIM3 block binding of TIM-3 to PtdSer (phosphatidylserine).

TIM-3 binds to PtdSer (phosphatidylserine), a lipid that is typically present on the surface of apoptotic cells and not normal cells. Anti-CD95-treated WR19L (Fas) cells were cultured under conditions that promote PtdSer accumulation on the cell surface (flipping of PtdSer from the inner membrane to external exposure upon induction of apoptosis). TIM-3-Ig (huTIM-3 extracellular domain fused to an Ig Fc region) was added to the cells, and binding of TIM-3-Ig to the cells was assayed in the presence of various antibodies. As shown in FIG. 4, several anti-TIM-3 mAbs, including ABTIM3, anti-TIM-3 #5, and anti-TIM-3 #2, inhibit the binding of TIM-3 to PtdSer.

Figure 5A:
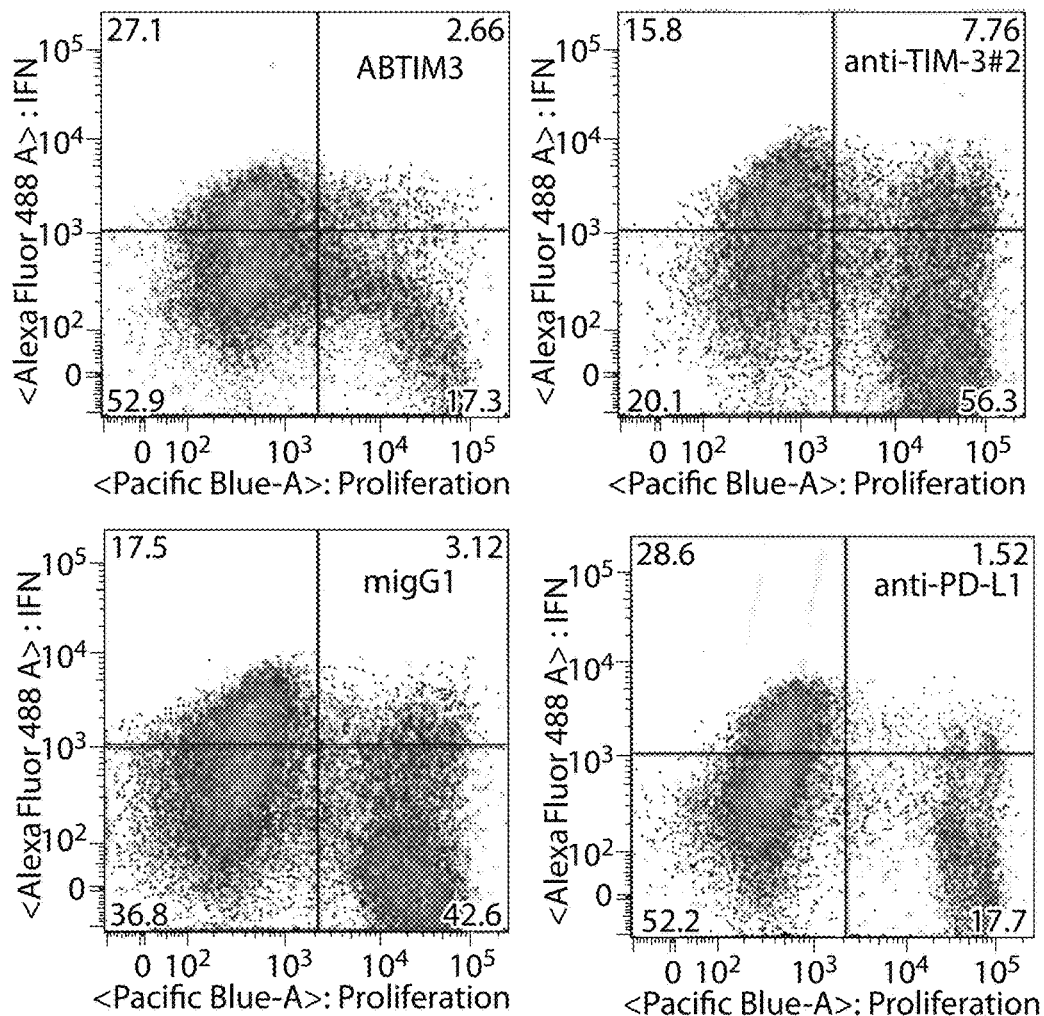
FIGS. 5A-5B illustrate that the anti-TIM-3 antibody ABTIM3 enhances IFN-gamma secretion and proliferation in IL-12 Stimulated CD4+ T Cells.
Figure 5B:
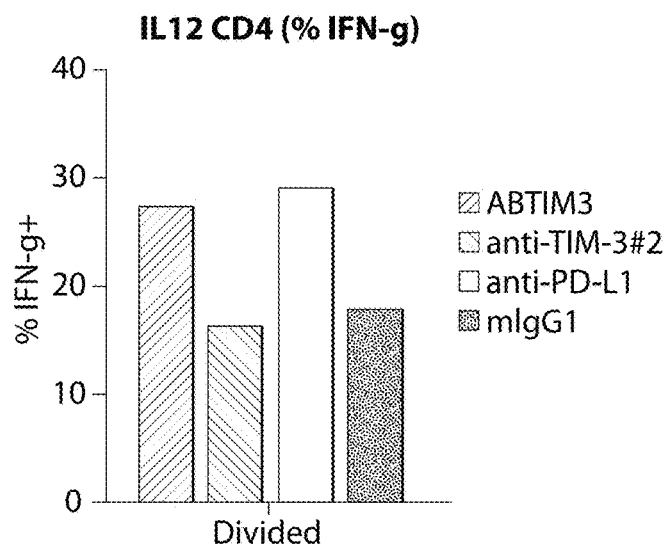
Figure 6:
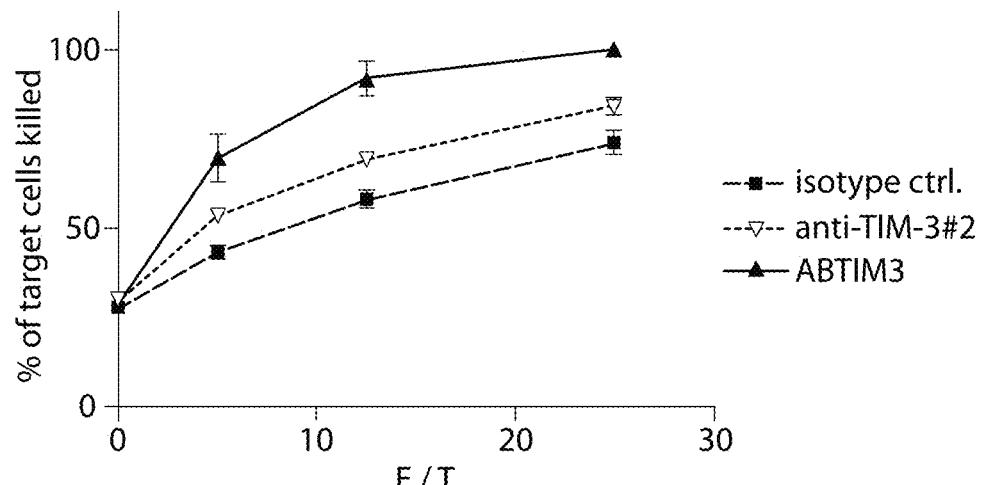
FIG. 6 shows that a ABTIM3 blockade enhances in vitro cytotoxic activity of purified NK cells.

Example 4. IFN-Gamma Secretion of CD4+ Cells is Enhanced by Anti-TIM-3 Antibodies The ability of four antibodies to enhance IFN-gamma secretion and proliferation of IL-12 stimulated CD4+ cells was assayed. This assay used the observation that a high dose of IL-12 induces expression of TIM-3 and yields an exhausted phenotype in T cells (see Yang et al., J. Clin. Invest. 122:4 p1271 2012). FIG. 5A shows four panels, each of which indicates the results of an experiment where cells were exposed to an antibody selected from ABTIM3, anti-TIM-3 #2, mIgG1, and anti-PD-L1 antibody (anti-PD-L1 control). After PMA/ionomycin restimulation and fixation and permeabilization of cells, the resulting IFN-gamma levels were measured by flow cytometry (y axis) and proliferation was measured by CFSE fluorescence (x axis). FIG. 5B quantifies IFN-gamma expression in cells exposed to these four antibodies. From left to right, the bars in FIG. 5B correspond to antibodies ABTIM3, anti-TIM-3 #2, anti-PD-L1 control, and mIgG1.

Example 5. TIM-3 Blockade Enhances In Vitro Functional Activity

5.1 TIM-3 Blockade Enhances In Vitro Cytotoxic Activity of Purified NK Cells TIM-3 is highly expressed endogenously on NK (natural killer) cells; its expression is further induced on activated NK cells. TIM-3 may act to restrain NK cell function, as do other inhibitory receptors. See Ndhlovu et al., Blood 119: 3734, 2012, and Silva et al., Cancer Immunol Res 2:410, 2014. Accordingly, the ability of ABTIM3 and other anti-TIM-3 antibodies to enhance NK cell cytotoxic activity was assayed.

In this assay, NK cells were purified from whole blood by negative bead selection and then incubated with antibody (10 µg/mL) at 37° C. After 1 hour, target K562 cells were added. After a 4-hour incubation at 37° C., the percent of K562 cell killing was measured. Antibody ABTIM3 resulted in elevated levels of K523 cell killing relative to anti-TIM-3 #2 or the isotype control.

5.2 TIM-3 Blockade Increases Proliferation from Autologous T-DC Co-Cultures

TIM-3 can be expressed on dendritic cells (DCs) and T cells. Naïve T cells and dendritic cells were isolated from donor samples. Naïve T cells and conventional DCs were cocultured for four days in the presence of anti-CD3/CD28. ABTIM3 was added at varying doses, 0.01 µg/mL, 0.1 µg/mL, 1 µg/mL, 5 µg/mL, and 25 µg/mL, to the co-culture. Cell proliferation was detected by a CFSE proliferation assay, which relies on dilution of CFSE staining to detect proliferating cells.

Figure 22:
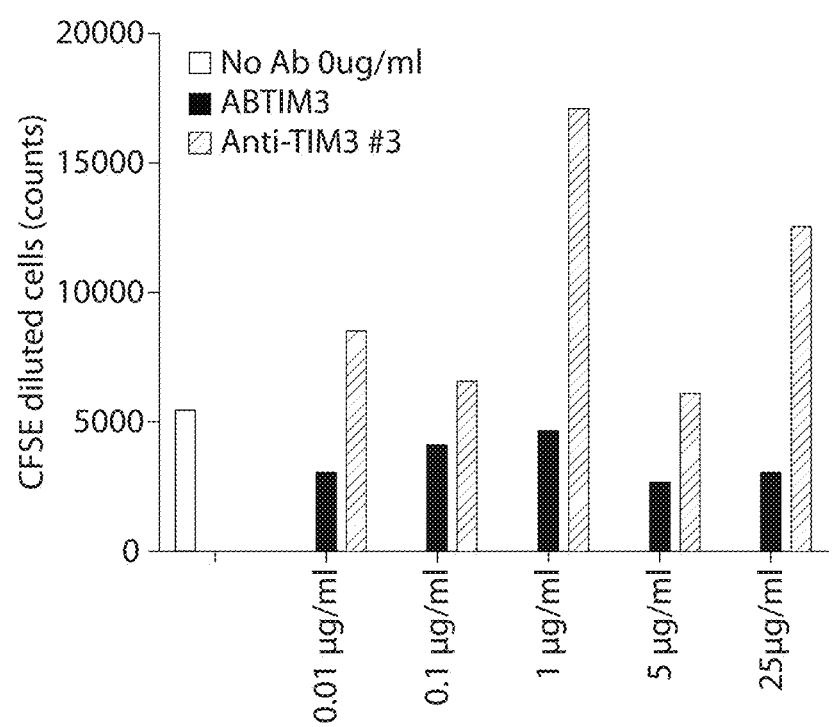
FIG. 22 shows that ABTIM3 increases proliferation in a co-culture containing dendritic cells and T cells (DC-T co-culture). DC-T co-cultures were incubated with no antibody or a titrated dilution series (0.01-25 µg/mL) of the following antibodies mouse IgG1 (control), ABTIM3 or anti-TIM3 #3 antibody.

As shown in FIG. 22, the presence of ABTIM3 at every tested dosage resulted in an increase in proliferating cells, as represented by CFSE-diluted cells, compared to no antibody and the mouse isotype (IgG1) control.

Example 6. Characterization of Humanized Anti-TIM-3 Antibody

6.1 Generation of Humanized Anti-TIM-3 Antibodies

The murine anti-TIM-3 antibody ABTIM3 was humanized by grafting the CDRs, e.g., provided in Table 3, to human IgG4 constant region, with a stabilized hinge region containing the S228P mutation. Additional modifications were made to the CDR2 of the heavy chain by mutating the putative deamidation site from N at position 6 of HCDR (Kabat), or position 4 of the HCDR2 (Chothia) to S or Q to remove the deamidation site. Other modifications included using alternative frameworks. The unique heavy chains and light chains combined in various combinations to generate a small library of unique humanized mAbs.

6.2 Binding Assays

Figure 7:
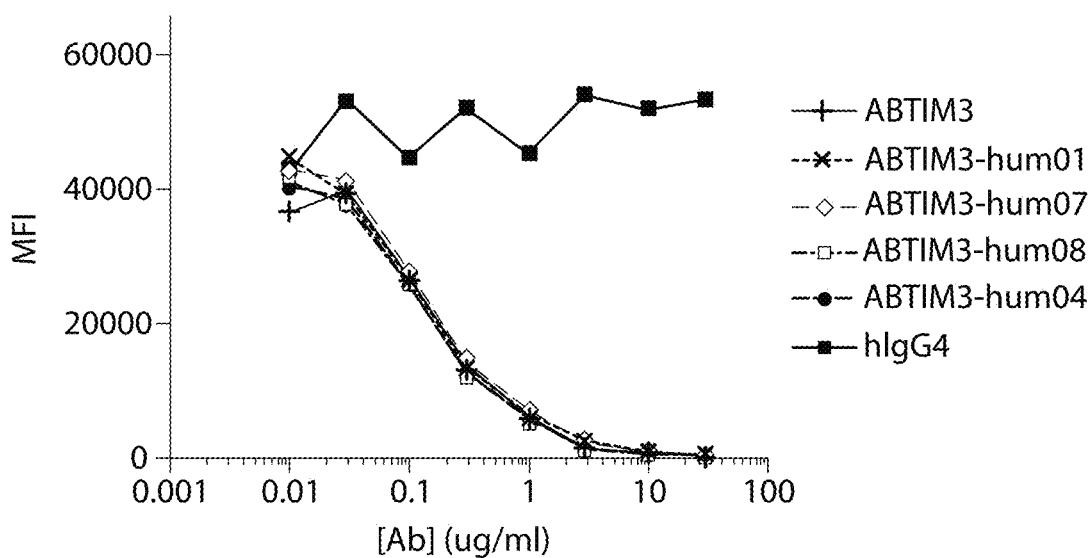
FIG. 7 shows that humanized anti-TIM-3 antibodies competed for binding with the parent murine ABTIM3 antibody in a FACS assay.

The binding capability of the humanized mAbs generated were tested by competition binding with the parent murine anti-TIM-3 antibody in a fluorescence-activated sorting assay. A representative graph depicting the results from the FACs-based competition assay comparing the binding between the parent murine anti-TIM-3 antibody and 4 humanized anti-TIM-3 antibodies (ABTIM3-hum01, ABTIM3-hum04, ABTIM3-hum07, and ABTIM3-hum08), and hIgG4 control is shown in FIG. 7.

The results from multiple surface plasmon resonance Biacore binding assays for a panel of humanized anti-TIM-3 antibodies are summarized in Table 9.

TABLE 9

Biacore $K_D$ values for a panel of anti-TIM-3 antibodies

| Clone | KD (nM) 4.7.14 | KD (nM) 4.29.14 | KD (nM) 5.1.14 | KD (nM) 5.30.14 |
|---|---|---|---|---|
| ABTIM3-hum02 | | 0.308 | 0.269 | 0.174 |
| ABTIM3-hum03 | | 0.351 | 0.16 | 0.314 |
| ABTIM3-hum05 | | 0.313 | 0.279 | 0.332 |
| ABTIM3-hum06 | | 0.498 | 0.214 | 0.364 |
| ABTIM3-hum09 | | | | 0.161 |
| ABTIM3-hum10 | | | | 0.107 |
| ABTIM3-hum11 | | | | 0.194 |
| ABTIM3-hum12 | | | | 0.355 |
| ABTIM-hum01 | | | | 0.23 |
| ABTIM-hum04 | | | | 0.172 |
| ABTIM3-hum01 | 0.103 | | 0.114 | 0.193 |
| ABTIM3-hum07 | 0.135 | | 0.199 | 0.196 |
| ABTIM3-hum08 | 0.123 | | 0.309 | 0.175 |
| ABTIM3-hum04 | 0.216 | | | |

All of the tested humanized mAbs were demonstrated to have relatively the same affinity as each other and the parent murine anti-TIM-3 antibody, within 0.1-0.5 nM $K_D$.

6.3 Binding to TIM-3 Expressing Cells

Figure 8A:
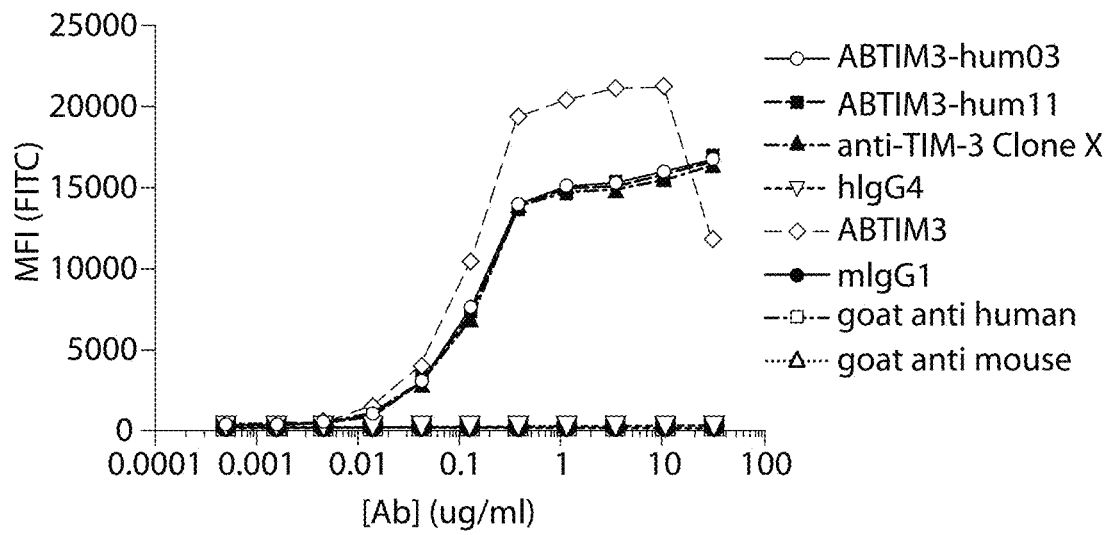
FIGS. 8A-8B illustrate that humanized anti-TIM-3 antibodies bind to cells expressing human TIM-3.

The humanized anti-TIM-3 antibodies were assayed for binding to TIM-3 expressing cells using fluorescence activated cell sorting and Biacore assays, described in Example 1. In FIG. 8A, the binding of various humanized anti-TIM-3 antibodies to cells transfected with human TIM-3 was measured using flow cytometry. ABTIM3 was used as a positive control. Negative controls include hIgG4, goat anti-human, and goat anti-mouse secondary Ab-FITC. The results from the flow cytometry competition assay were used to determine the dissociation constant ($K_D$) for cells expressing human TIM-3, as shown in Table 10 below.

TABLE 10

$K_D$ values for binding to cells expressing huTIM-3.

| Antibody | $K_D$ (nM) |
|---|---|
| ABTIM3-hum03 | 0.887 |
| ABTIM3-hum11 | 0.906 |
| ABTIM3-hum21 | 0.917 |
| ABTIM3 | 1.04 |

Figure 8B:
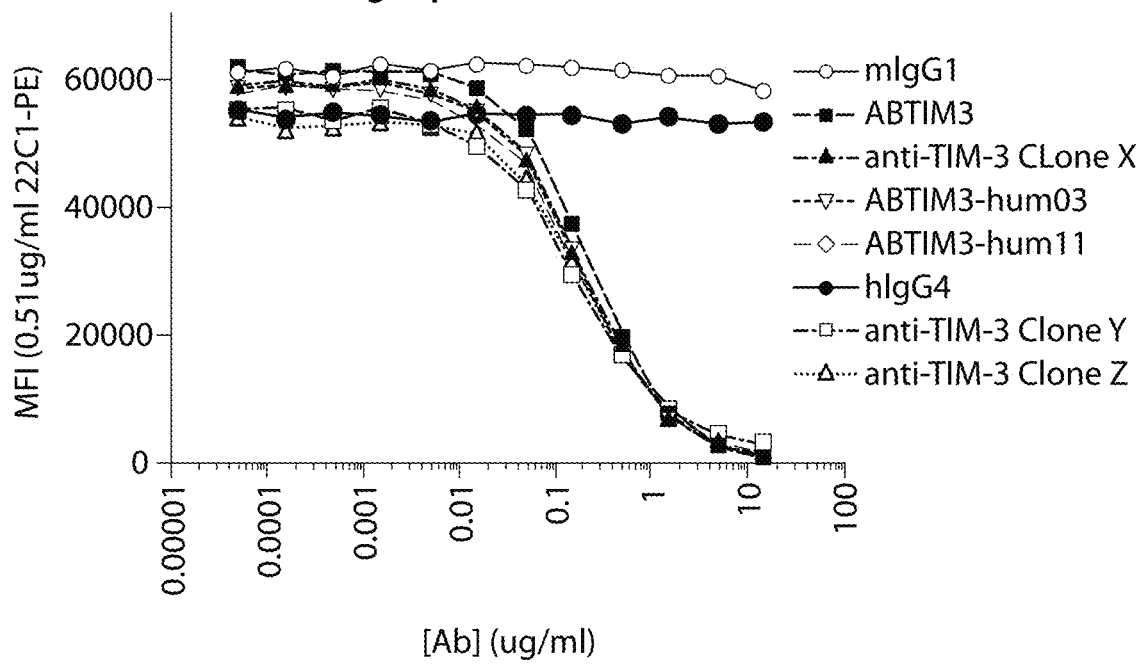

A competition binding assay was also performed to assess binding of the humanized anti-TIM-3 antibodies, ABTIM3-hum03 and ABTIM3-hum11, to cells expressing human TIM-3, while in the presence of the parental murine antibody, ABTIM3. As shown in FIG. 8B, the humanized anti-TIM-3 antibodies competed with ABTIM3.

The $K_D$ values for two humanized anti-TIM-3 antibodies for recombinant TIM-3-Ig fusion proteins were assayed by surface plasmon resonance in a Biacore assay, as shown in Table 11.

TABLE 11

Biacore $K_D$ values for TIM-3-Ig

| | | cynoTIM-3/Fc | huTIM-3/his | mTIM-3/his | ratTIM-3/Fc |
|---|---|---|---|---|---|
| ABTIM3-hum03 | KD(M) | 1.04E−09 | 1.24E−10 | | |
| | KD(M) | 3.89E−09 | 1.84E−10 | | 5.10E−08 |
| | KD(M) | 3.08E−09 | 7.58E−11 | | |
| | Mean KD (M) | 2.67E−09 | 1.28E−10 | | |

TABLE 11-continued

Biacore $K_D$ values for TIM-3-Ig

| | | cynoTIM-3/Fc | huTIM-3/his | mTIM-3/his | ratTIM-3/Fc |
|---|---|---|---|---|---|
| ABTIM3-hum11 | KD(M) | 1.24E-09 | 1.55E-10 | | |
| | KD(M) | 3.14E-09 | 2.26E-10 | | |
| | KD(M) | 5.04E-09 | 1.09E-10 | | 2.97E-07 |
| | Mean KD (M) | 3.14E-09 | 1.63E-10 | | |

These results show that the humanized TIM-3 antibodies have similar binding affinity with human and cynomolgus proteins. The humanized TIM-3 antibodies showed very weak binding affinity to rat TIM-3/Fc protein, in the order of 1/1000 compared to the binding affinity with huTIM-3/Fc.

Example 7: X-Ray Crystal Structure of the Human TIM-3/ABTIM3-Hum21 Fab Complex

The crystal structure of a human TIM-3 (IgV domain, SEQ ID NO: 220, Table 12) bound to the Fab fragment of a humanized anti-TIM-3 antibody ABTIM3-hum21 (SEQ ID NO: 221 and 222, Table 12) was determined. As detailed below, TIM-3 was co-expressed with MGB220 Fab in mammalian cells to produce purified complex. Protein crystallography was then employed to generate atomic resolution data for TIM-3 bound to ABTIM3-hum21 Fab to define the epitope. ABTIM3-hum21, a humanized antibody from a parental murine antibody, comprises an IgG1 framework and the variable heavy chain of SEQ ID NO: 84, and the variable light chain of SEQ ID NO: 88. ABTIM3-hum21 differs by only one amino acid in heavy chain CDR2 from other humanized anti-TIM antibodies described herein and this different amino acid (Gln55) is far away (>6 Å) from the epitope and thus would not change antigen binding, which indicates that the crystal structure results obtained are applicable to the other humanized antibodies described herein.

7.1 Protein Production

The sequences of TIM-3 and ABTIM3-hum21 Fab produced for crystallography are shown in Table 12. The construct of TIM-3 comprises residues 22 to 130 (underlined) of human TIM-3 (UniProt identifier Q8TDQ0, SEQ ID NO: 129), along with N- and C-terminal residues from recombinant expression vector (shown in lower case letters, SEQ ID NO: 130). The N-terminal signal sequence from mouse IgG kappa light chain was used for secreted expression of TIM-3 and was cleaved during expression, leaving intact N-terminus of TIM-3. The C-terminus of TIM-3 was fused with a 6× His tag (SEQ ID NO: 133) for purification. For ABTIM3-hum21 Fab, the sequences of heavy (SEQ ID NO: 131) and light (SEQ ID NO: 132) chains are shown.

TABLE 12

Amino acid sequences used for crystal structure determination

| Construct | Amino acid sequence | SEQ ID NO |
|---|---|---|
| Human TIM-3 (Q8TDQ0) | MFSHLPFDCVLLLLLLLLTRS<u>SEVEYRAEVGQNAYLPCF</u><br><u>YTPAAPGNLVPVCWGKGACPVFECGNVVLRTDERDVNY</u><br><u>WTSRYWLNGDFRKGDVSLTIENVTLADSGIYCCRIQIPGI</u><br><u>MNDEKFNLKLVIKPAKVTPAPTRQRDFTAAFPRMLTTRG</u><br>HGPAETQTLGSLPDINLTQISTLANELRDSRLANDLRDSG<br>ATIRIGIYIGAGICAGLALALIFGALIFKWYSHSKEKIQNLS<br>LISLANLPPSGLANAVAEGIRSEENIYTIEENVYEVEEPNE<br>YYCYVSSRQQPSQPLGCRFAMP | 129 |
| Human TIM-3 expression construct | metdtlllwvlllwvpgstgSEVEYRAEVGQNAYLPCFYTPAAPGN<br>LVPVCWGKGACPVFECGNVVLRTDERDVNYWTSRYWL<br>NGDFRKGDVSLTIENVTLADSGIYCCRIQIPGIMNDEKFN<br>LKLVIKhhhhhh | 130 |
| ABTIM3-hum21 Fab heavy chain | QVQLVQSGAEVKKPGASVKVSCKASGYTFTSYNMHWV<br>RQAPGQGLEWIGDIYPGQGDTSYNQKFKGRATMTADKS<br>TSTVYMELSSLRSEDTAVYYCARVGGAFPMDYWGQGTL<br>VTVSSASTKGPSVFPLAPSSKSTSGGTAALGCLVKDYFPE<br>PVTVSWNSGALTSGVHTFPAVLQSSGLYSLSSVVTVPSSS<br>LGTQTYICNVNHKPSNTKVDKRVEPKSCDKTH | 131 |
| ABTIM3-hum21 Fab light chain | DIVLTQSPDSLAVSLGERATINCRASESVEYYGTSLMQW<br>YQQKPGQPPKLLIYAASNVESGVPDRFSGSGSGTDFTLTI<br>SSLQAEDVAVYYCQQSRKDPSTFGGGTKVEIKRTVAAPS<br>VFIFPPSDEQLKSGTASVVCLLNNFYPREAKVQWKVDNA<br>LQSGNSQESVTEQDSKDSTYSLSSTLTLSKADYEKHKVY<br>ACEVTHQGLSSPVTKSFNRGEC | 132 |

TIM-3 was co-expressed with ABTIM3-hum21 Fab in Expi293® cells to produce complex for crystallography. In detail, 0.3 mg of plasmid encoding TIM-3 was mixed with 0.15 mg of plasmid encoding the heavy chain of ABTIM3-hum21 Fab and 0.15 mg of plasmid encoding the light chain of ABTIM3-hum21 Fab, diluted into 30 mls of Opti-MEM® I medium (Life Technologies), and incubated with 1.5 mgs of Polyethylenimine (Polysciences) in 30 mls of the same medium for 30 min. The mixture was then added into 0.6 L of Expi293® cells growing in suspension in Expi293® Expression medium (Life Technologies) at 2 million cells/ml at 37° C. with 8% of CO2 for transfection. After 5 days, the medium containing TIM-3/ABTIM3-HUM21 Fab complex was harvested by centrifugation. Five mls of Ni-NTA resin was added into the medium and kept stirring at 4° C. overnight. The next day the beads were packed into a gravity column and washed with 25 mM Hepes pH 7.4, 150 mM NaCl (HBS) supplemented with 20 mM of imidazole. The complex was eluted with 3 column volumes (CV) of HBS with 500 mM of imidazole, and then dialyzed in HBS at 4° C. overnight. The next day, the complex was incubated with 1/10 (w/w) of PNGaseF (purified in-house) at 37° C. overnight to remove N-linked glycosylation. After deglycosylation, the mixture was bound back to 5 mls of Ni-NTA resin, washed with HBS to remove PNGaseF and eluted with HBS plus 500 mM of imidazole. The eluate was then concentrated and loaded onto HiLoad 16/600 Superdex 75 PG (GE Healthcare) size exclusion column equilibrated in HBS. Peak fractions containing purified TIM-3/ABTIM3-hum21 Fab complex were analyzed by SDS-PAGE, pooled and concentrated for crystallization.

7.2 Crystallization and Structure Determination

TIM-3/ABTIM3-hum21 Fab complex was concentrated to 12.5 mg/ml, centrifuged at 20,000 g for 10 min, and screened for crystallization. Crystals for data collection were grown by hanging drop vapor diffusion at 20° C. In detail, 0.1 µl of the TIM-3/ABTIM3-hum21 Fab complex was mixed with 0.1 µl of reservoir solution containing 0.04 M potassium phosphate monobasic, 16% (w/v) PEG 8000 and 20% (v/v) Glycerol. The drop was then equilibrated against 45 µl of the same reservoir solution. Before data collection, the crystals were flash cooled in liquid nitrogen.

Diffraction data were collected at beamline 17-ID at the Advanced Photon Source (Argonne National Laboratory, USA), and processed using Autoproc (version 1.1.5, Global Phasing, LTD). The data of TIM-3/ABTIM3-hum21 Fab was processed to 2.0 Å in space group $P2_1$ with cell dimensions a=84.3 Å, b=93.0 Å, c=85.3 Å, alpha=90°, beta=114°, and gamma=90°. The structure of the complex was solved by molecular replacement using Phaser (version 2.5.5, McCoy et al., (2007) J. Appl. Cryst. 40:658-674) with structures of mouse TIM-3 (PDB ID: 3KAA) and a Fab (in-house structure) as search models. The final model was built in COOT (version 0.6 pre, Emsley & Cowtan (2004) Acta Cryst. D 60:2126-2132) and refined using Phenix (version 1.9, Afonine et al., (2012) Acta Cryst. D 68:352-367). The $R_{work}$ and $R_{free}$ values were 17.5% and 22.1%, respectively; and the root-mean-square (r.m.s) deviation values of bond lengths and bond angles are 0.007 Å and 1.1°, respectively.

Epitope was defined as residues of TIM-3 that contain atoms within 5 Å to any atom in ABTIM3-hum21 Fab, identified by CONTACT in CCP4 program suite (version 6.2.0, Winn et al., (2011) Acta. Cryst. D 67:235-242) and listed in Table 13. There are 2 copies of TIM-3/ABTIM3-hum21 Fab complexes in the asymmetric unit (the smallest unique unit in the crystal), only those antibody-contacting residues that are common in both copies are listed as epitope residues.

7.3 Epitope of ABTIM3-Hum21 on TIM-3

The crystal structure of the TIM-3/ABTIM3-hum21 Fab complex was used to identify the epitope of ABTIM3-hum21 on TIM-3. The interaction surface on TIM-3 by ABTIM3-hum21 was formed by several continuous and discontinuous (i.e. noncontiguous) sequences: namely residues Val24, Glu25, Tyr26, Phe39, Tyr40, Thr41, Gly56, Ala57, Cys58, Pro59, Val60, Phe61, Ser105, Gly106, Ile107, Asn119, Asp120, Glu121, Lys122, Phe123, Asn124, Leu125, Lys126, Leu127, and Val128 as detailed in Table 13. These residues form the exemplary three-dimensional conformational epitope that is recognized by ABTIM3-hum21 (FIG. 9).

TABLE 13

Interactions between human TIM-3 and ABTIM3-hum21. TIM-3 residues are numbered as in UniProt entry Q8TDQ0 (SEQ ID NO: 219). The antibody residues are numbered based upon their linear amino acid sequence (SEQ ID NO: 221 and 222) and corresponding chains are labeled ("H" for heavy chain, "L" for light chain). TIM-3 residues shown here have at least one atom within 5 Å to an atom in ABTIM3-hum21, to account for potential water mediated interactions.

| TIM-3 | | ABTIM3-hum21 | | |
|---|---|---|---|---|
| Amino acid | Number | Amino acid | Number | Chain |
| Val | 24 | Ala | 102 | H |
|  |  | Asp | 98 | L |
| Glu | 25 | Tyr | 31 | L |
|  |  | Arg | 96 | L |
| Tyr | 26 | Tyr | 31 | L |
| Phe | 39 | Ser | 31 | H |
|  |  | Tyr | 52 | H |
| Tyr | 40 | Ser | 31 | H |
|  |  | Thr | 28 | H |
| Thr | 41 | Thr | 28 | H |
| Gly | 56 | Thr | 34 | L |
| Ala | 57 | Phe | 103 | H |
|  |  | Thr | 34 | L |
|  |  | Asn | 57 | L |
|  |  | Tyr | 53 | L |
|  |  | Ala | 54 | L |
| Cys | 58 | Tyr | 53 | L |
|  |  | Asn | 57 | L |
| Pro | 59 | Asn | 57 | L |
|  |  | Tyr | 53 | L |
| Val | 60 | Asn | 57 | L |
|  |  | Tyr | 53 | L |
|  |  | Val | 58 | L |
|  |  | Ser | 60 | L |
|  |  | Glu | 59 | L |
| Phe | 61 | Ser | 60 | L |
| Ser | 105 | Tyr | 32 | L |
| Gly | 106 | Tyr | 31 | L |
|  |  | Tyr | 32 | L |
| Ile | 107 | Phe | 103 | H |
|  |  | Thr | 34 | L |
|  |  | Tyr | 31 | L |
|  |  | Leu | 36 | L |
| Asn | 119 | Ser | 60 | L |
| Asp | 120 | Tyr | 32 | H |
| Glu | 121 | Tyr | 32 | H |
|  |  | Thr | 28 | H |
| Lys | 122 | Tyr | 32 | H |
|  |  | Gly | 100 | H |
|  |  | Tyr | 53 | L |
|  |  | Glu | 59 | L |
| Phe | 123 | Gly | 100 | H |
|  |  | Gly | 101 | H |
|  |  | Tyr | 32 | L |
| Asn | 124 | Phe | 103 | H |
|  |  | Ala | 102 | H |

TABLE 13-continued

Interactions between human TIM-3 and ABTIM3-hum21. TIM-3 residues are numbered as in UniProt entry Q8TDQ0 (SEQ ID NO: 219). The antibody residues are numbered based upon their linear amino acid sequence (SEQ ID NO: 221 and 222) and corresponding chains are labeled ("H" for heavy chain, "L" for light chain). TIM-3 residues shown here have at least one atom within 5 Å to an atom in ABTIM3-hum21, to account for potential water mediated interactions.

| TIM-3 | | ABTIM3-hum21 | | |
|---|---|---|---|---|
| Amino acid | Number | Amino acid | Number | Chain |
|  |  | Pro | 104 | H |
|  |  | Tyr | 53 | L |
| Leu | 125 | Ala | 102 | H |
| Lys | 126 | Ala | 102 | H |
|  |  | Tyr | 31 | L |
|  |  | Leu | 36 | L |
|  |  | Ser | 95 | L |
|  |  | Lys | 97 | L |
| Leu | 127 | Tyr | 31 | L |
| Val | 128 | Tyr | 31 | L |
|  |  | Tyr | 32 | L |

7.4 ABTIM3-Hum21 v.s. TIM-3 Ligands

The identification of the epitope of TIM-3 recognized by the anti-TIM-3 antibody indicates that binding of some of the TIM-3 ligands may be disrupted by antibody binding. The known ligands of TIM-3 include CEACAM-1, phosphatidylserine (PtdSer), HMGB1, and Galectin-9 (Gal-9).

With respect to CEACAM-1, a recent study has showed that CEACAM-1 is a ligand for TIM-3 required for its ability to mediate T-cell inhibition, and this interaction has a crucial role in regulating autoimmunity and anti-tumour immunity (Huang et al., (2014) Nature). The same study also identified, both biochemically and structurally, the crucial amino acid residues of TIM-3 mediating its binding to CEACAM-1 (FIG. 10A). The ABTIM3-hum21 epitope on TIM-3 overlaps with these CEACAM-1-binding residues (FIG. 10A), including C58, N119 and K122. For example, K122 forms hydrogen bond N42 of CEACAM-1, but is complete blocked by ABTIM3-hum21 (FIG. 10B). Superimposition of the crystal structures obtained from the TIM-3/ABTIM3-hum21 Fab and the TIM-3/CEACAM-1 (PDB ID: 4QYC) complexes results in a significant clash between ABTIM3-hum21 and CEACAM-1 (FIG. 10C). Altogether, these data suggests that ABTIM3-hum21 disrupts CEACAM-1 binding.

Figure 11:
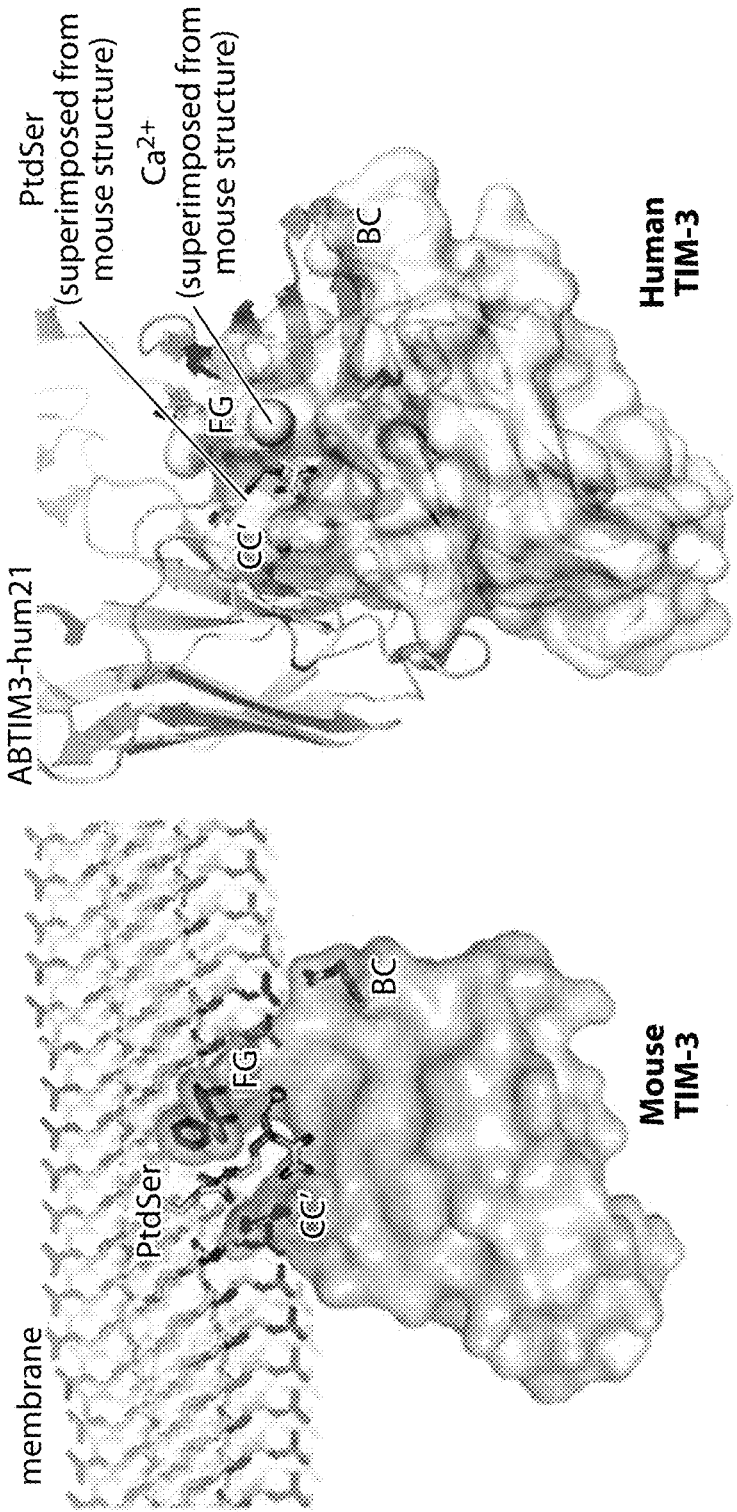
FIG. 11 illustrates the comparison of PtdSer-mediated membrane penetration of moue TIM-3 (left panel) and binding of ABTIM3-hum21 to human TIM-3 (right panel). The two TIM-3 structures are oriented the same way. The attacking angle of ABTIM3-hum21 is similar to the orientation of the membrane penetrated by TIM-3, which suggests that ABTIM3-hum21 will prevent PtdSer-mediated penetration of TIM-3.

With respect to PtdSer, the FG loop and CC' loop of TIM-3 form a pocket (often referred to as the metal ion-dependent ligand binding site (MILIBS)) that has been shown by crystal structure to bind $Ca^{2+}$ and PtdSer simultaneously (DeKruyff, et al., (2010) J Immunol. 184(4):1918-1930). This binding is thought to help TIM-3-expressing cells engage and penetrate the membrane of apoptotic cells (which displays PtdSer) for engulfment. The crystal structure of TIM-3/ABTIM3-hum21 Fab indicates that ABTIM3-hum21 binds the PtdSer-binding loops of the human TIM-3 IgV domain; and the attacking angle of the antibody suggests it will prevent PtdSer-mediated membrane penetration of TIM-3 (FIG. 11).

With respect to HMGB1, it has been reported to interact with TIM-3 to help tumor-associated dendritic cells suppress nucleic acid-mediated innate immune response (Chiba et al., (2012) Nat. Immunol. 13(9):832-842). The amino acid residue at position 62 of TIM-3 (Q in mouse, E in human TIM-3) has been shown to be important for mouse HMGB1 binding to mouse TIM-3. E62 is not present in the ABTIM3-hum21 epitope, though it is very close to the two epitope residues V60 and F61, thus there is a chance that ABTIM3-hum21 can block HMGB1 binding depending on the attacking angle of HMGB1 to TIM-3.

Figures 9A, 9B:
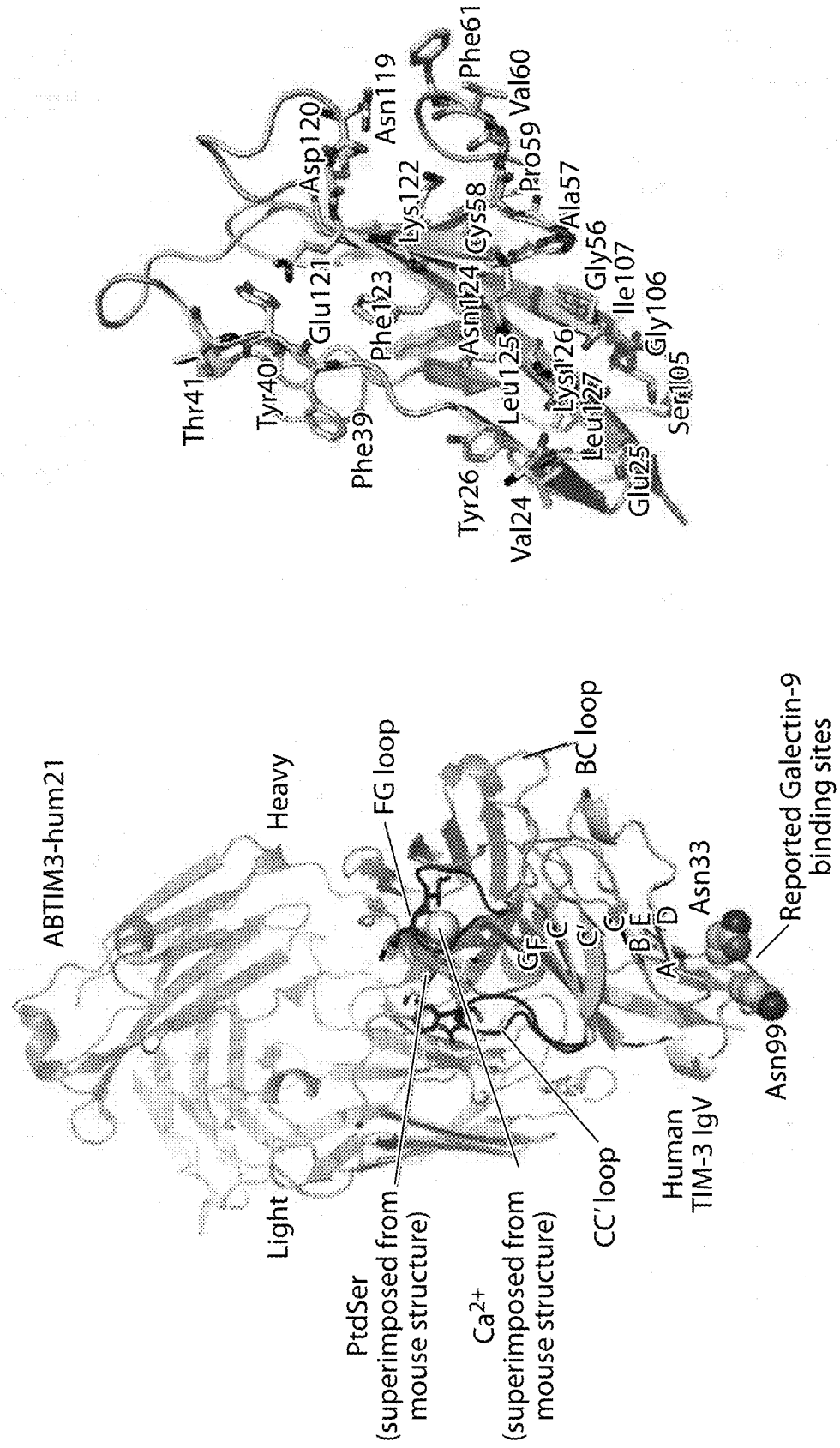
FIGS. 9A-9B illustrate the structure of ABTIM3-hum21 Fab binding to TIM-3.

With respect to Gal-9, it has been shown to bind mouse TIM-3 to negatively regulate Th1-immune response (Zhu et al., (2005) Nat. Immunol. 6(12):1245-1252). However, it has also been reported that human TIM-3 on T cells does not act as a receptor for Gal-9 (Leitner et al., (2013) PLoS Pathog. 9(3):e1003253). From the crystal structure of human TIM-3/ABTIM3-hum21 Fab, half of the proposed Gal-9 binding site in mouse TIM-3 is not conserved in human TIM-3 (N74 and N90 in mouse TIM-3 become D74 and R89 in human TIM-3), i.e. this half-site in human TIM-3 will not be able to bind Gal-9. The left-over half site (N33 and N99 in human TIM-3) is conserved but is far away from the ABTIM3-hum21 epitope on TIM-3 (FIG. 9A). Therefore, even if Gal-9 is a ligand of human TIM-3, ABTIM3-hum21 will not disrupt the binding of Gal-9 to human TIM-3.

7.5 Hydrogen-Deuterium Exchange Experimental Setup

HDx/MS experiments were performed using methods similar to those described in the literature (Chalmers et al., (2006) Anal. Chem. 78(4):1005-1014). The experiments were performed on a Waters HDx/MS platform, which includes a LEAP autosampler, nanoACQUITY UPLC and Synapt G2 mass spectrometer. The deuterium buffer used to label the protein backbone of human TIM-3 (aa22-135; SEQ ID NO: 139) was 25 mM HEPES, 150 mM NaCl, 5 mM $CaCl_2$) pH7.4 with deterium; the overall percentage of deuterium in the solution was 94.2%. For human TIM-3 (aa22-135) deuterium labeling experiments in the absence of antibody, 300 pmol of human TIM-3 (aa22-135), volume of 7.7 µl, was diluted using 100 µl of the deuterium buffer in a chilled tube and incubated for 15 minutes on a rotator at 4° C. The labeling reaction was then quenched with 100 µl of chilled quench buffer at 2° C. for five minutes followed by injected onto the LC-MS system for automated pepsin digestion and peptide analysis.

For human TIM-3 (aa22-135) deuterium labeling experiments in the presence of antibodies, 400 pmol of ABTIM3-hum03 or ABTIM3-hum11 was first immobilized on Thermo Protein G Plus beads and cross-linked using disuccinimidyl suberate (DSS). To perform the labeling experiments, the antibody beads (containing 400 pmol antibody) were incubated with 300 pmol human TIM-3 (aa22-135) for 25 minutes at 4° C. After 25 minutes the beads were washed with 200 µl of HEPES buffer. Then 200 µl of chilled deuterium buffer (87.5% deuterium) was added and the complex was incubated for 15 minutes at 4° C. After 15 minutes, the deuterium buffer was spun out and the labeling reaction was quenched with 200 µl of chilled quench buffer on ice for 4 minutes. After spinning the sample for 30 seconds in a centrifuge, the quenched solution was injected onto the LC-MS system for automated pepsin digestion and peptide analysis.

All deuterium exchange experiments were quenched using 1 M TCEP and 6 M urea (pH 2.6). After quenching, the exchanged antigen was subjected to on-line pepsin digestion using a Poroszyme Immobilized Pepsin column (2.1×30 mm) at 12° C. followed by trapping on a Waters Vanguard HSS T3 trapping column. Peptides were eluted from the trapping column and separated on a Waters BEH C18 1×100 mm column (maintained at 1° C.) at a flow rate of 40 µl/min using a binary 8.4 minute gradient of 2 to 35% B (mobile phase A was 99.9% water and 0.1% formic acid; mobile phase B was 99.9% acetonitrile and 0.1% formic acid).

7.6 Hydrogen-Deuterium Exchange Results

Figure 18:
FIG. 18 shows the peptides that are monitored in HDx-MS experiments on the human TIM-3 (residues 23 to 135 ("SEVEYRAEVGQNAYLPCFYTPAAPGNLVPVCWGK-GACPVFECGNVVLRTDERDVNY WTSRYWLNGD-FRKGDVSLTIENVTLADSGIYC-CRIQIPGIMNDEKFNLKLVIKPAKVT") as SEQ ID NO: 139). Each bar represents a peptide.
Figure 19:
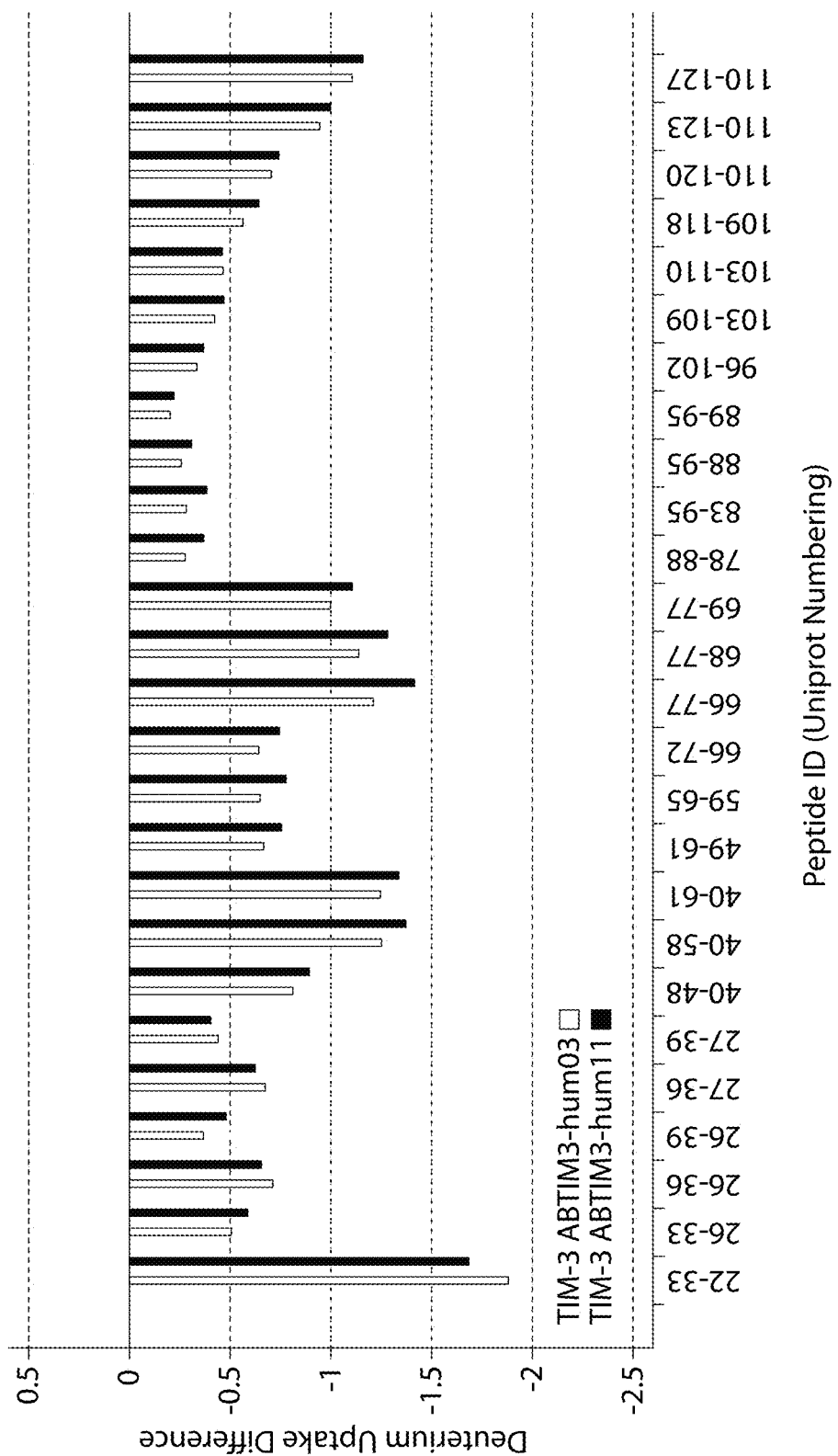
FIG. 19 illustrates the difference in deuterium uptake for the TIM-3 ABTIM3-hum03 complex (grey bars) and the TIM-3 ABTIM3-hum11 complex (black bars) for amino acids 22 through 127. All differences are relative to the deuterium uptake of unbound TIM-3 (control).

For human TIM-3 93% of the sequence was monitored by deuterium exchange as shown in FIG. 18. In this figure each bar represents a peptide that is monitored in all deuterium exchange experiments. For differential experiments between antibody bound and unbound states it is informative to examine the difference in deuterium uptake between the two states. In FIG. 19 a negative value indicates that the TIM-3-antibody complex undergoes less deuterium uptake relative to TIM-3 alone. A decrease in deuterium uptake can be due to protection of the region from exchangeable deuterium or stabilization of the hydrogen bonding network. In contrast, a positive value indicates that the complex undergoes more deuterium uptake relative to TIM-3 alone. An increase in deuterium uptake can be due to destabilization of hydrogen bonding networks (i.e. localized unfolding of the protein).

ABTIM3-hum03 shares identical CDRs with ABTIM3-hum11 except that ABTIM3-hum03 has a glutamine at position 55 in HCDR2 while ABTIM3-hum11 has an asparagine at position 55 in HCDR2. ABTIM3-hum03 shares the same CDR regions with ABTIM3-hum21. One expects these antiboides to have the same epitope on TIM-3. From FIG. 19 one observes that ABTIM3-hum03 and ABTIM3-hum11 exhihit the same protection profile which is consistent with the two antibodies sharing the same epitope. Closer examination of FIG. 19 reveals that when TIM-3 is complexed with either of the two antibodies that many regions of TIM-3 undero significant protection, typically defined as proection less than or equal to −0.5 Da (Houde et al. (2010) J. Pharma. Sci. 100(6): 2071-2086). The observation of broad protection suggests that binding of either of the two antibodies to the TIM-3 antigen cause a broad based stabilization of hydrogen bonding networks in TIM-3. This broad protection is in addition to the protection that results from solvent sheilding of the epitope at the antibody-antigen interface. Given the significant amount of broad protection, it is useful to rank order the most protected regions of TIM-3 upon antibody binding to delineat the regions likely to be involved in the epitope. TIM-3 regions that are the most protected upon ABTIM3-hum03 or ABTIM3-hum 11 binding include the regions 23-25 (EVE), 41-61 (TPAAPGNLVPVCWGK-GACPVF, SEQ ID NO: 140), 73-77 (RDVNY, SEQ ID NO: 141), and 121-127 (EKFNLKL, SEQ ID NO: 142). Comparing these protected regions to the X-ray crstyal structure data summarized in Table 13 shows consistent agreement indicating that the epitope determined by X-ray crystal structure is present in solution.

Example 8: TIM-3 Expression in Cancer

TIM-3 is expressed in various cancers. In this example, several different analysis methods were used to identify cancers with TIM-3 expression in which therapeutic benefit could be achieved by an anti-TIM-3 antibody.

8.1 Immunohistochemical Staining of Tumors

ABTIM-3 was used to stain various tumor tissues. TIM-3 tumor expression was identified in esophageal squamous cell carcinoma, primary and metastatic renal cell carcinoma, colorectal cancer, and leukemic stem cells in AML.

8.2 Expression Analysis in TCGA and ICGC Databases

Figure 12:
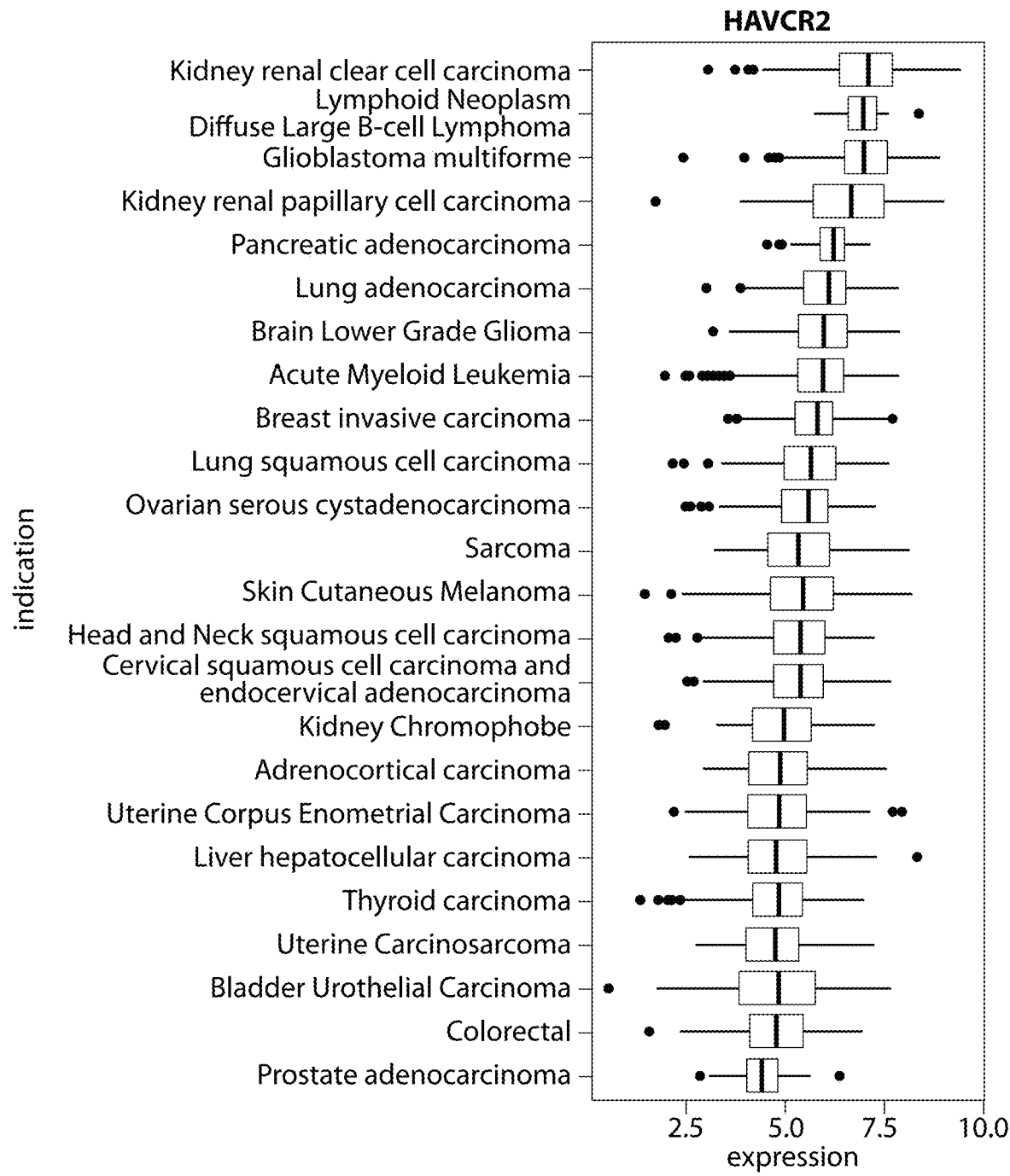
FIG. 12 shows the cancer indications with the highest expression of TIM-3 (HAVCR2) from the TCGA database.

Overall TIM-3 expression was compared in the The Cancer Genome Atlas (TCGA) database and the International Cancer Genome Consortium (ICGC) database. The following cancers were identified as among the highest expressors of TIM-3: diffuse large B cell lymphoma (DLBCL), kidney renal clear cell carcinoma (KIRC), glioblastoma multiforme (GBM), nasopharyngeal carcinoma (NPC), lung adenocarcinoma (LUAD), kidney renal papillary cell carcinoma (KIRP), mesothelioma (MESO), acute myeloid leukemia (AML), and in breast cancer, triple negative (TN) immunomodulatory (IM) subtype (FIG. 12).

Next, cancers were identified that were characterized by high TIM-3 expression in conjunction with high expression of other immune cell markers. The other immune cell markers include: T cell marker CD3e, T regulatory cell marker FoxP3, natural killer cell marker NKp30, macrophage marker CD68, and dendritic cell marker CD11c. As shown in FIG. 12, cancer indications with high expression of TIM-3 and the other immune cell marker were identified. "High" expression was quantified by $3^{rd}$ quartile (or top 25%) expressors across more than 34,000 cases. For TIM-3 and CD3e, the top indications were diffuse large B cell lymphoma (DLBCL), nasopharyngeal carcinoma (NPC), and kidney renal clear cell carcinoma (KIRC). For TIM-3 and FoxP3, the top indications were diffuse large B cell lymphoma (DLBCL), nasopharyngeal carcinoma (NPC), and lung adenocarcinoma (LUAD). For TIM-3 and NKp30, the top indications were diffuse large B cell lymphoma (DLBCL), nasopharyngeal carcinoma (NPC), and acute myeloid leukemia (AML). For TIM-3 and CD68, the top indications were diffuse large B cell lymphoma (DLBCL), kidney renal clear cell carcinoma (KIRC), and kidney renal papillary cell carcinoma (KIRP). For TIM-3 and CD11c, the top indications were diffuse large B cell lymphoma (DLBCL), mesothelioma (MESO) (though only a small sample was assessed), and kidney renal papillary cell carcinoma (KIRP).

Figure 13:
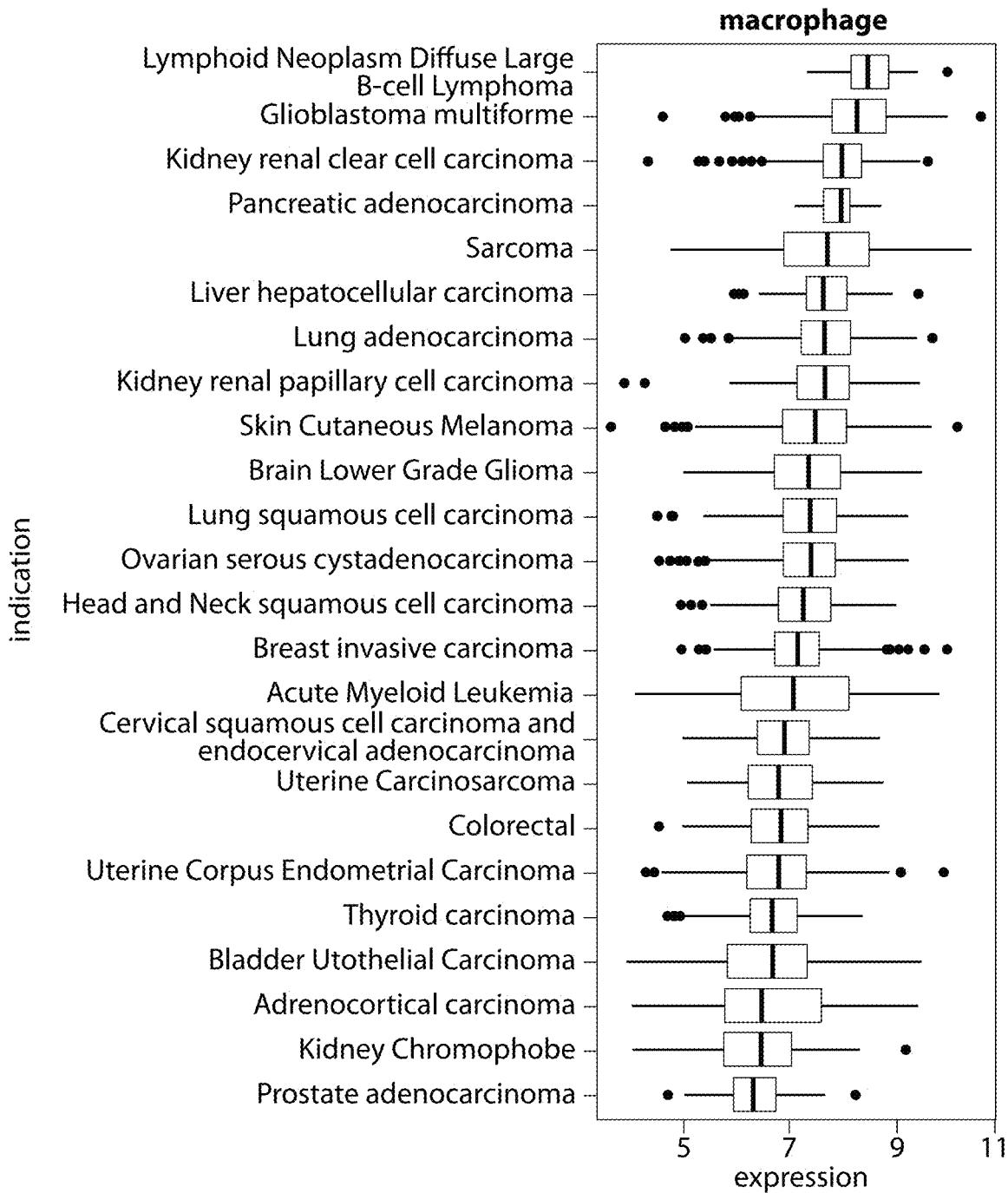
FIG. 13 shows the cancer indications with the highest expression of a macrophage expression signature from the TCGA database.

A comparison was also performed of the correlation between TIM-3 or PD-1 to T cell associated or macrophage associated markers in the TCGA database. The analysis revealed correlation between TIM-3 expression and both T cell associated markers (e.g., ZAP70, CD3D, CD3G, CD8B, GZMH, GZMK, and ITK) and macrophage associated markers (e.g., LILRB4, MRC1, MSR1, SIGLEC1, TREM2, CD163, ITGAX, and ITGAM), however, TIM-3 expression is more associated with macrophage markers, especially inhibitory receptors on macrophages (e.g., LILRB4). Expression of a macrophage signature, e.g., macrophage associated markers (e.g., LILRB4, MRC1, MSR1, SIGLEC1, TREM2, CD163, ITGAX, and ITGAM) was determined for various cancers and were organized for the highest expressors of the macrophage signature in FIG. 13. The cancer indications with high expression of the macrophage signature are also the same indications with high expression of TIM-3.

Example 9: Patient Selection Based on PDL1/CD8/IFN-γ Status

Figure 14:
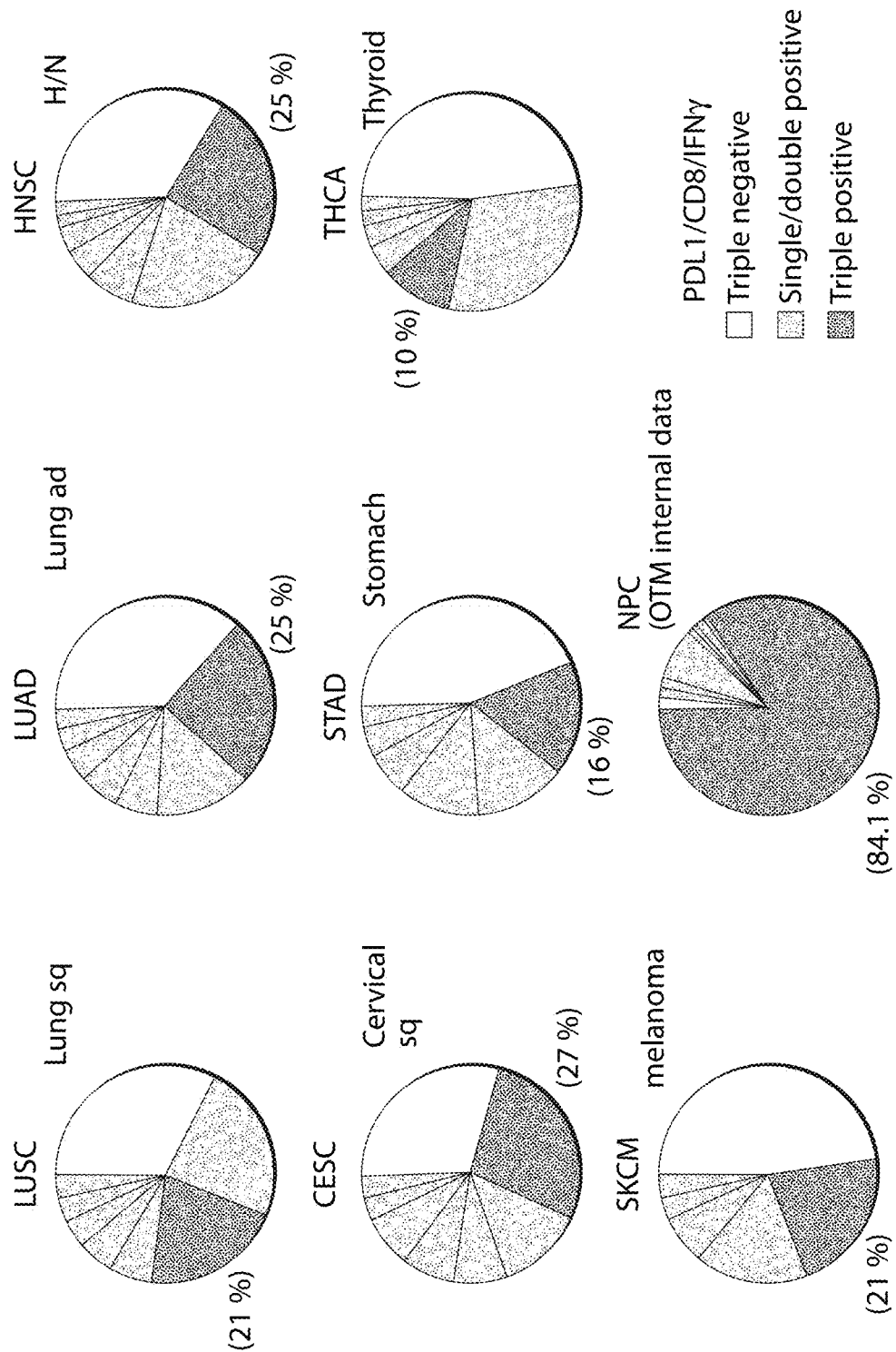
FIG. 14 shows exemplary cancers having relatively high proportions of patients that are triple-positive for PD-L1/CD8/IFN-γ.

For each of several types of cancer, samples from multiple patients were tested for PDL1/CD8/IFN-γ status. Each sample was classified as: triple-negative for PDL1/CD8/IFN-γ, single or double positive for these markers, or triple-positive for these markers. FIG. 14 shows that in this experiment, within a population of patients, the following types of cancer are frequently triple-positive for PDL1/CD8/IFN-γ: Lung cancer (squamous), lung cancer (adenocarcinoma), head and neck cancer, cervical cancer (squamous), stomach cancer, thyroid cancer, melanoma, and nasopharyngeal cancer. Patients having these types of cancer are good candidates for therapy with anti PD-1 antibodies and combination therapies as described herein. The likelihood of successful treatment can be further boosted by determining which patients are triple-positive for PDL1/CD8/IFN-γ, and treating the triple-positive patients with anti-TIM-3 antibodies, alone or in combination with one or more immodulators (e.g., a PD-1 inhibitor or a PD-L1 inhibitor), and/or combination therapies, as described herein.

Figure 15:
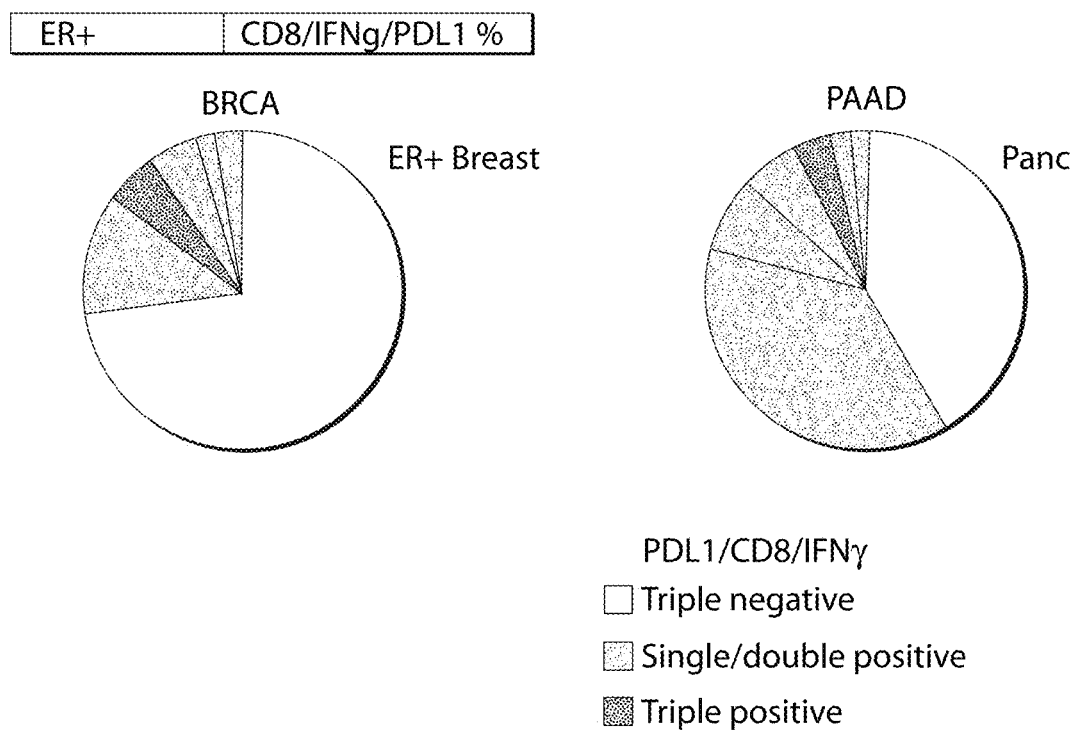
FIG. 15 shows exemplary ER+ breast cancer and pancreatic cancer having relatively low proportions for patients that are triple positive for PD-L1/CD8/IFN-γ.

FIG. 15 shows that within a population of patients, the following types of cancer are rarely triple positive for PDL1/CD8/IFN-γ: ER+ breast cancer and pancreatic cancer. Notably, even in cancers that are generally not positive for for PDL1/CD8/IFN-γ, one can increase the likelihood of successful treatment by determining which patients are triple-positive for PDL1/CD8/IFN-γ, and treating the triple-positive patients with anti-TIM-3 antibodies, alone or in combination with one or more immodulators (e.g., a PD-1 inhibitor or a PD-L1 inhibitor), and/or combination therapies, as described herein.

Figure 16:
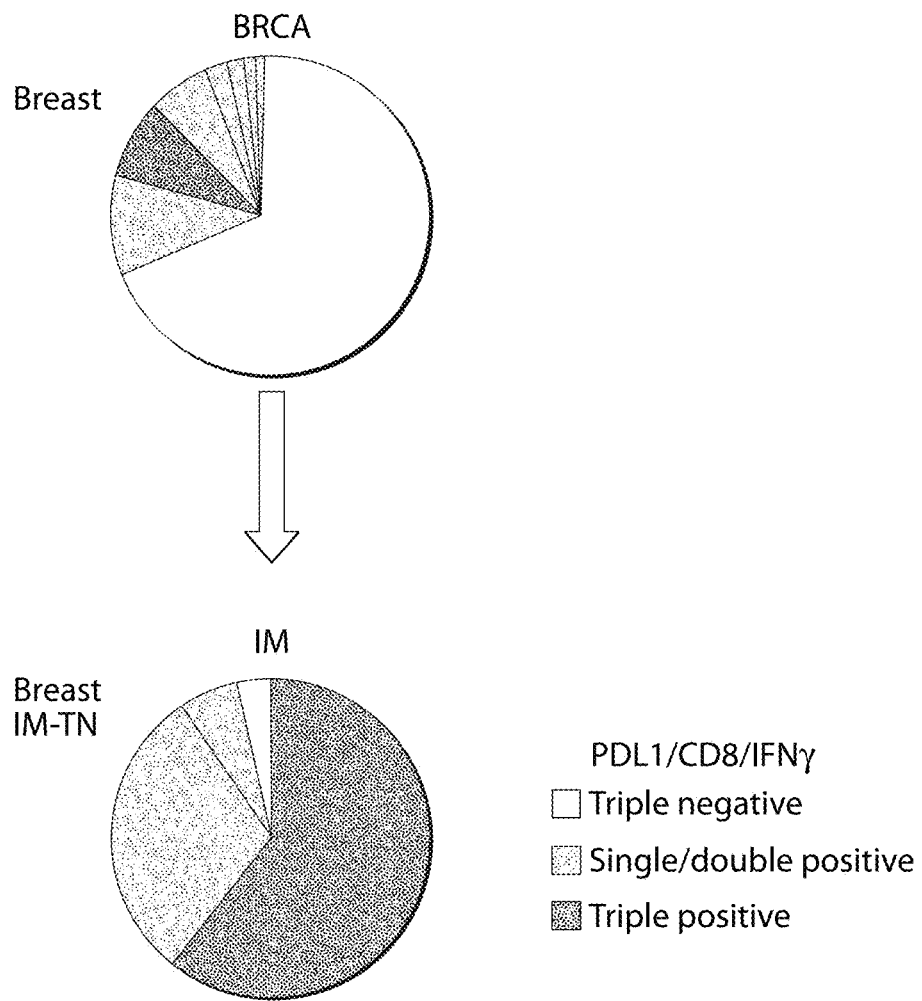
FIG. 16 shows the proportion of exemplary breast cancer patients that are triple positive for PD-L1/CD8/IFN-γ.

FIG. 16 shows the proportion of breast cancer patients that are triple positive for PDL1/CD8/IFN-γ. Considering breast cancer in general, the proportion of triple-positives is somewhat low. However, when one focuses only on IM-TN breast cancer, it can be seen that a much larger percentage of patients is triple positive for PDL1/CD8/IFN-γ. IM-TN breast cancer is particularly difficult to treat with conventional therapies. The discovery that IM-TN breast cancer is often triple-postive for PDL1/CD8/IFN-γ opens up new avenues of therapy for this cancer with anti-TIM-3 antibodies, alone or in combination with one or more immodulators (e.g., a PD-1 inhibitor or a PD-L1 inhibitor), and/or combination therapies, as described herein.

Figure 17:
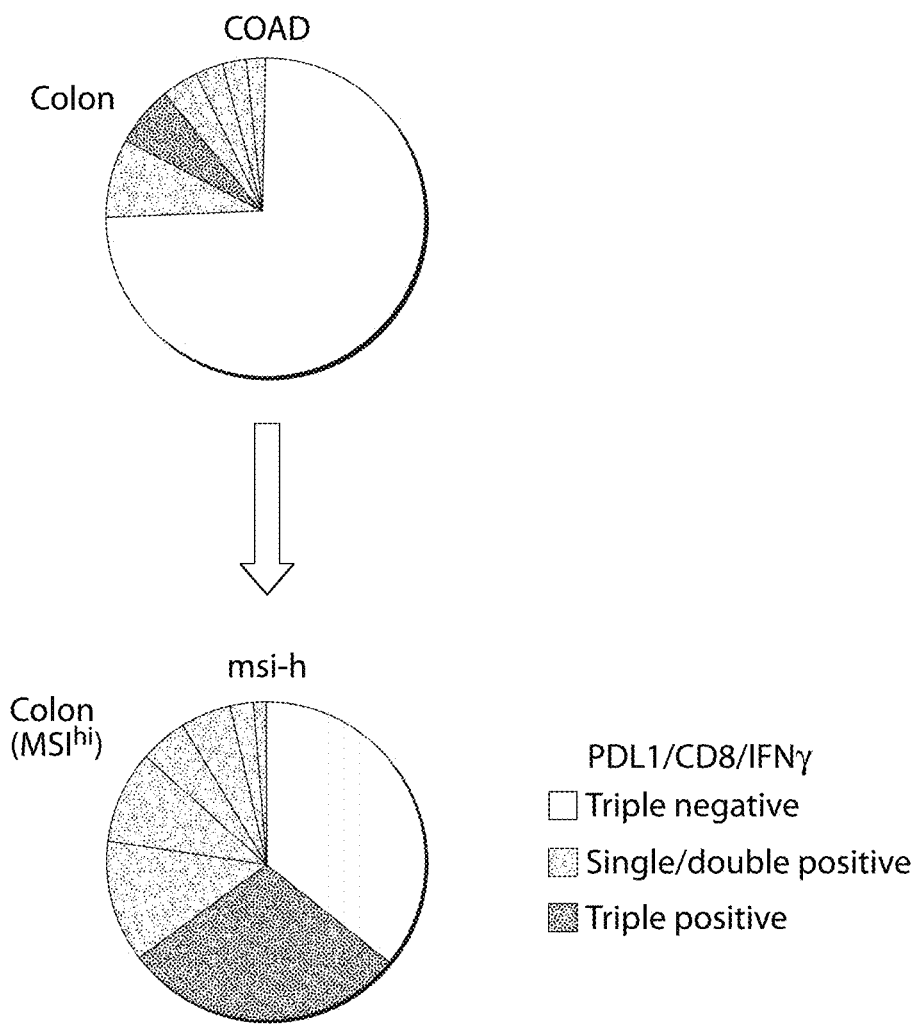
FIG. 17 shows the proportion of exemplary colon cancer patients that are triple positive for PD-L1/CD8/IFN-γ.

FIG. 17 shows the proportion of colon cancer patients that are triple positive for PDL1/CD8/IFN-γ. Considering colon cancer in general, the proportion of triple-positive is somewhat low. However, when one focuses only on MSI-high (high microsatellite instability) breast cancer, it can be seen that a much larger percentage of patients is triple positive for PDL1/CD8/IFN-γ. MSI levels can be assayed using, e.g., commercially available PCR-based methods.

Gastric cancer samples were tested for levels of PDL1/CD8/IFN-γ (data not shown). It was found that in MSI-high or EBV+ gastric cancers, about 49% were positive for PDL1, and a high proportion of the PDL1-positive cells were triple positive for PDL1/CD8/IFN-γ. It was also found that a proportion of PDL1-positive cells and PDL1/CD8/IFN-γ positive cells were also positive for PIK3CA. This finding suggests that these cancers may be treated with an anti-TIM-3 antibody, alone or in combination with one or more immodulators (e.g., a PD-1 inhibitor or a PD-L1 inhibitor), optionally in combination with a PIK3 therapeutic.

MSI-high CRC samples were tested for a combination of markers (data not shown). It was found that in MSI-high CRC samples, a high proportion of the PDL1/CD8/IFN-γ samples are also positive for LAG-3, PD-1 (also called PDCD1), RNF43, and BRAF. This finding suggests that these cancers may be treated with an anti-TIM-3 antibody, optionally in combination with a therapeutic that targets one or more of LAG-3, PDCD1, RNF43, and BRAF.

Squamous cell lung cancers were tested for a combination of markers (data not shown). It was found that in squamous cell lung cancer samples, a high proportion of the PDL1/CD8/IFN-γ samples are also positive for LAG-3. This finding suggests that these cancers may be treated with an anti-TIM-3 antibody, optionally in combination with a therapeutic that targets LAG-3, e.g., a LAG-3 antibody.

Papillary thyroid cancers were tested for a combination of markers including the BRAF V600E mutation (data not shown). It was found that a high proportion of thyroid cancer samples that are positive for PDL1 are also positive for BRAF V600E. This finding suggests that these cancers may be treated with an anti-TIM-3 antibody, alone or in combination with one or more immodulators (e.g., a PD-1 inhibitor or a PD-L1 inhibitor), optionally in combination with a therapeutic that targets BRAF.

Example 10: Patient Selection Based on PD-L1 Status

To enable broad examination of cancer indications for PD-1/PD-L1 based therapies, we evaluated PD-L1 expression at both the protein and mRNA level in human cancers including both lung and hepatic tumors.

PD-L1 protein expression was evaluated in a set of formalin-fixed paraffin-embedded non-small cell lung (NSCLC) adenocarcinoma (ACA), NSCLC squamous cell carcinoma (SCC), and hepatocellular carcinoma (HCC) tumors by immunohistochemistry (IHC). PD-L1 expression was scored semi-quantitatively by a manual histo-score (H-score) methodology based on staining intensity and percentage of positive tumor cells. In our IHC analysis, PD-L1 positivity (PD-L1+) was defined as an H-score 20. In parallel, PD-L1 mRNA expression data was examined from The Cancer Genome Atlas (TCGA) in these same indications (503 NSCLC ACA, 489 NSCLC SCC, and 191 HCC) and analyzed by comparing the expression in matched normal tissues from TCGA.

With RNAseq analysis, data was calculated as log 2 (RPKM+0.1) after RSEM normalization, utilizing OmicSoft RNASeq pipelines across TCGA tumor indications. The expression of PD-L1 is elevated in NSCLC ACA and SCC, relative to that in HCC. By overlaying the distributions and comparing the expression levels across all indications in TCGA, we ranked overexpression profiles for PD-L1 and found the TCGA HCC cohort to have much reduced PD-L1 mRNA levels, with a median level of −0.8 compared to 1.3 for ACA and 1.5 for SCC, which amounts to more than a 2-fold change of median level expression. With RNAseq, our analysis defines 50% of NSCLC adenocarcinoma, 54% of NSCLC squamous cell carcinoma, and 6% of HCC as high expressers for PD-L1.

Tumor cell PD-L1 protein expression was measured in 45 lung adenocarcinoma (ACA) samples, 47 lung squamous cell carcinoma (SCC) samples, and 36 hepatocellular carcinoma (HCC) samples. 16/45 (35.6%) lung ACA, 21/47 (44.7%) lung SCC were PD-L1 positive. In contrast, PD-L1 positivity was seen in only 2/36 (5.6%) HCC samples.

In summary, with IHC and RNAseq analysis in large and independent human NSCLC and HCC sample sets, we have found PD-L1 expression to be more enriched in NSCLC than in HCC. Within NSCLC, there are comparable findings between adenocarcinoma and squamous cell carcinomas. Importantly, amongst the large number of samples (128 for IHC and 1183 for RNAseq) in the 3 indications, very good concordance is observed between protein- and mRNA-based analyses. Our finding thus establishes the basis for large scale mRNA-based data mining in TCGA for indications and patient segments that may be enriched for responses to PD-1/PD-L1- and/or TIM-3 based immune therapies.

Example 11: Competition Assays Indicate Humanized Anti-TIM3 Antibodies Bind to a Similar Epitope As described above, the epitope of TIM-3 recognized by ABTIM3-hum21 was determined by x-ray crystallography studies. ABTIM3-hum21 differs by only one amino acid in the heavy chain CDR2 from the other humanized anti-TIM3 antibodies described herein, and this different amino acid (Gln55) is far away (>6 Å) from the epitope and thus would not be expected to change antigen binding. Two different competition assays were performed to compare epitope binding between ABTIM3-hum21 and two other humanized anti-TIM3 antibodies, ABTIM3-hum03 and ABTIM3-hum11. The results of both competition assays show that both ABTIM3-hum04 and ABTIM3-hum11 effectively compete with ABTIM3-hum03 for binding to TIM3, thus demonstrating that ABTIM3-hum03 and ABTIM3-hum11 also bind to a similar epitope as ABTIM3-hum21, e.g., the epitope as described herein.

11.1 Flow Cytometry Competition Assay $K_D$ of ABTMI3-hum21 was determined by labeling ABTIM3-hum21 with phycoerythrin, incubated with 300.19 hTIM-3 expressing cells, and a binding curve was established to determine a $K_D$ of 2.15.

Titrated concentrations of unlabelled hIgG1(isotype control), ABTIM3-hum21 (positive control), ABTIM3-hum11 or ABTIM3-hum03 were mixed with ABTIM3-hum21 at its $K_D$ and incubated with 300.19 hTIM-3 expressing cells at 4° C. for 3 hours. Cells were washed twice and run on an LSRFortessa flow cytometer. Data was analyzed in FlowJo and MFI (PE) values were plotted and graphed in GraphPad (Prism) software. The experiment was performed twice.

Figure 20:
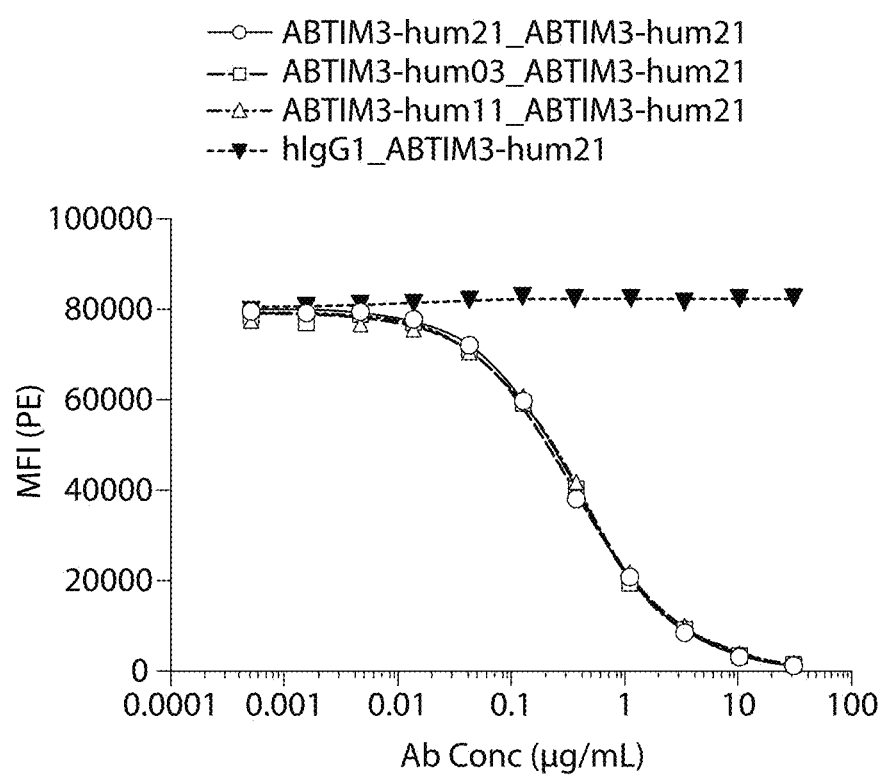
FIG. 20 shows the competition between ABTIM3-hum21 and ABTIM3-hum03 and ABTIM3-hum11 for binding to human TIM3, as determined by flow cytometry assay.

The results of the competition assay demonstrate that ABTIM3-hum11 and ABTIM3-hum03 (but not isotype control) both competed with ABTIM3-hum21 for binding with human TIM3 expressed on the 300.19 cells (FIG. 20). $K_D$ for ABTIM3-hum11 and ABTIM3-hum03 was calculated from the binding curves; the calculated $K_D$ for ABTIM3-hum11 was 2.276 nM and the calculated $K_D$ for ABTIM3-hum03 was 2.413 nM. These results demonstrate that ABTIM3-hum11 and ABTIM3-hum03 bind to a similar or the same epitope as ABTIM3-hum21.

11.2 Biacore Competition Assay hTIM-3/his antigen was captured by immobilized anti-His antibody (RU10000) on a CM5 chip. The first antibody was injected to reach saturation (>90%). Then the second antibody was injected to assess whether a second binding event occurs. Occurrence of a second binding event indicates that the two tested antibodies have different epitopes. Lack of a second binding event, indicates that the two antibodies may recognize and bind to the same epitope. Control assays were run where a test antibody was run with human IgG1 isotype control, or where the test antibody was run as the first and second antibody (e.g., self-self cycle) to observe the baseline of a binding event. Table 14 summarizes the Biacore cycles run and indicates which antibodies were used as the first and second antibody in each cycle.

TABLE 14

Summary of Biacore competition assay cycles

| Cycles | 1st Antibody | 2nd Antibody |
|---|---|---|
| 1 | huIgG1 | huIgG1 |
| 2 | huIgG1 | ABTIM3-hum21 |
| 3 | huIgG1 | ABTIM3-hum03 |
| 4 | huIgG1 | ABTIM3-hum11 |
| 5 | ABTIM3-hum21 | huIgG1 |
| 6 | ABTIM3-hum21 | ABTIM3-hum21 |
| 7 | ABTIM3-hum21 | ABTIM3-hum03 |
| 8 | ABTIM3-hum21 | ABTIM3-hum11 |
| 9 | ABTIM3-hum03 | huIgG1 |
| 10 | ABTIM3-hum03 | ABTIM3-hum21 |

TABLE 14-continued

Summary of Biacore competition assay cycles

| Cycles | 1st Antibody | 2nd Antibody |
|---|---|---|
| 11 | ABTIM3-hum03 | ABTIM3-hum03 |
| 12 | ABTIM3-hum03 | ABTIM3-hum11 |
| 13 | ABTIM3-hum11 | huIgG1 |
| 14 | ABTIM3-hum11 | ABTIM3-hum21 |
| 15 | ABTIM3-hum11 | ABTIM3-hum03 |
| 16 | ABTIM3-hum11 | ABTIM3-hum11 |

Figure 21:
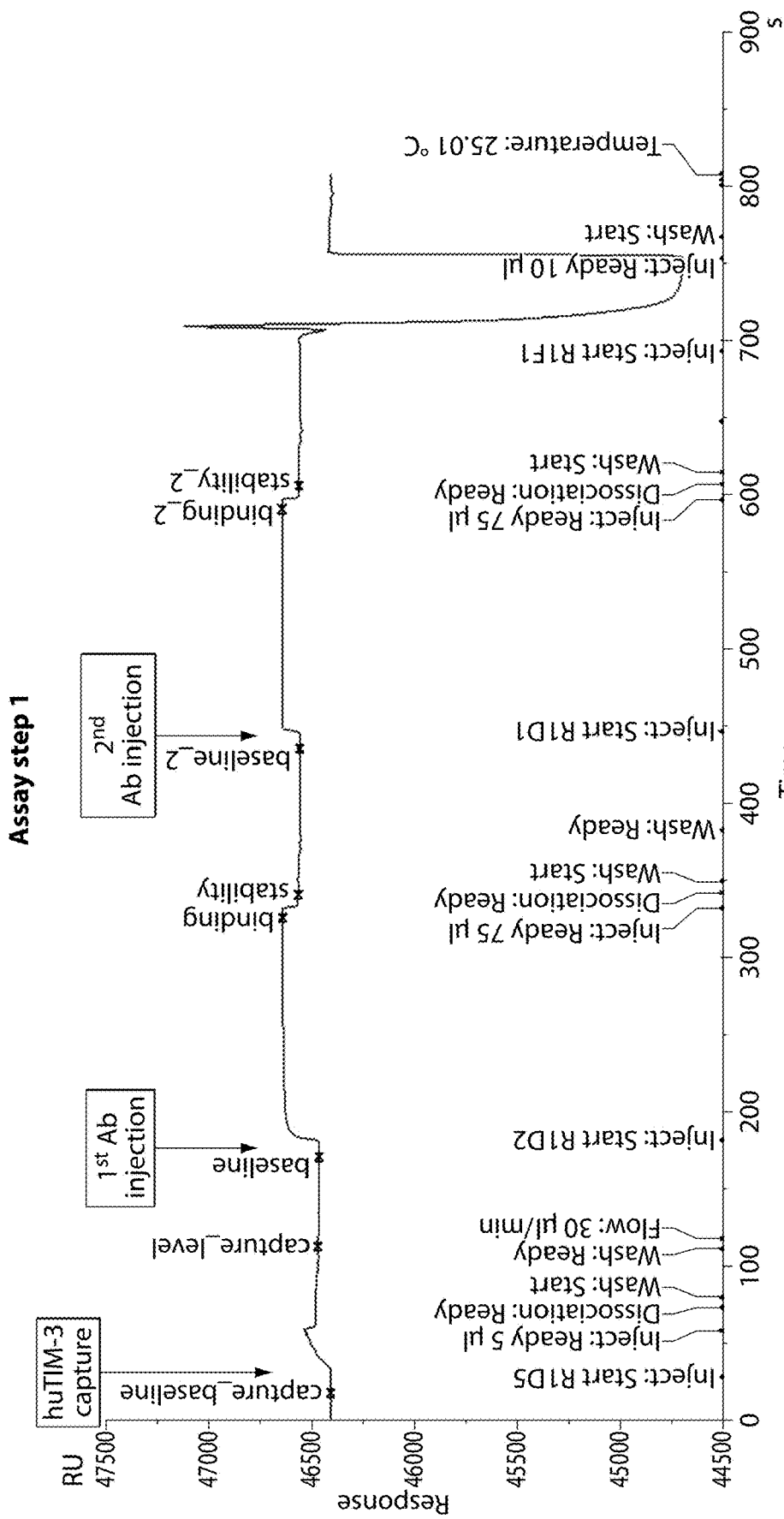
FIG. 21 shows a representative sensogram from a Biacore competition assay testing the competition between a $1^{st}$ antibody and a $2^{nd}$ antibody for immobilized human TIM-3.

Detection of the baseline and first and second binding events are recorded as RU (resonance units) and can be presented in a sensogram. A typical sensogram is shown in FIG. 21, where a binding event is shown after the 1st antibody injection. After a wash, the second antibody is injected and a second binding may be detected. Significant changes in RU indicate a binding event. A summary of the changes in RU detected from the 1st and 2nd antibody injections from the Biacore competition assay is shown in Table 15.

TABLE 15

Summary of results from Biacore competition assay

| | | 2nd Antibody Injection | | |
|---|---|---|---|---|
| 1st Antibody Injection | huIgG1 | ABTIM3-hum21 | ABTIM3-hum03 | ABTIM3-hum11 |
| huIgG1 | 0.27 | 3.6 | 88.2 | 86.3 | 83.2 |
| ABTIM3-hum21 | 95.85 | 4.5 | 6.6 | 7.6 | 8.1 |
| ABTIM3-hum03 | 93.33 | 4.5 | 6.9 | 7.3 | 8.5 |
| ABTIM3-hum11 | 93.48 | 3.8 | NA[1] | 5.3 | 7.2 |

[1]No value was calculated from the sensogram, due to an unknown fluid problem.

The results shown above demonstrate that injection of ABTIM3-hum21, ABTIM3-hum03, and ABTIM3-hum11 during the first antibody injection results in a binding event. Injection of ABTIM3-hum21, ABTIM3-hum03, and ABTIM3-hum11 as the second antibody after injection is human IgG1 control antibody results in a second binding event. However, injection of any of the anti-TIM3 antibodies tested here as the first and second antibodies did not result in a second binding event, demonstrating that for each pair of 1st and 2nd antibodies tested, there was competition for binding to the same TIM3 epitope. These results indicate that ABTIM3-hum21, ABTIM3-hum03, and ABTIM3-hum11 bind to a similar or the same epitope on human TIM3.

Example 12: Pharmacokinetic Properties of ABTIM3-Hum11

Figure 23A:
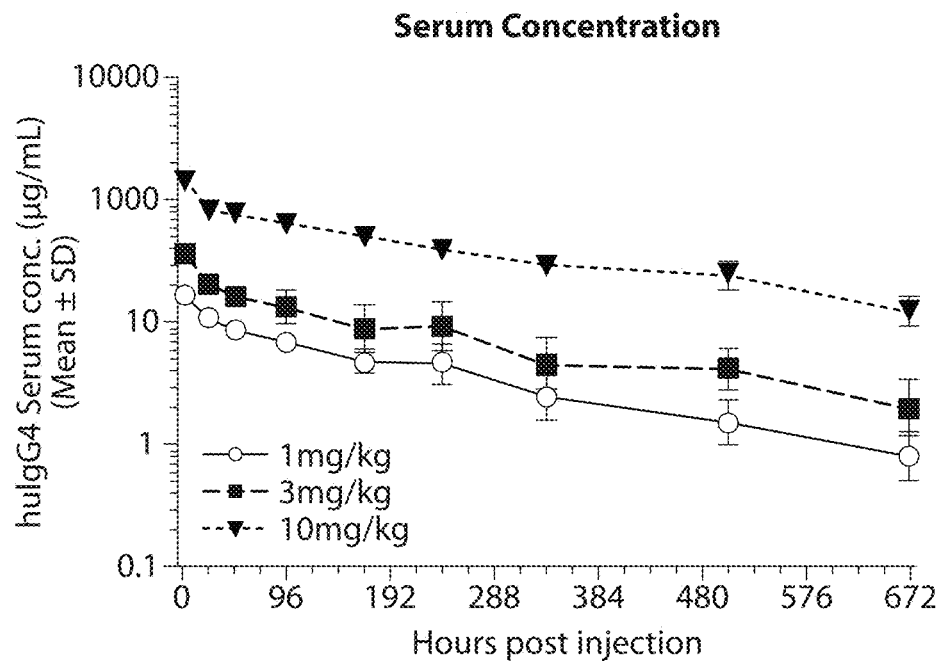
FIGS. 23A-23B show the concentration of ABTIM3-hum11 detected in the serum over time in rodents. The indicated dosages were injected into mice or rats, and the concentration of antibody in the blood was calculated at the indicated time points.
Figure 23B:
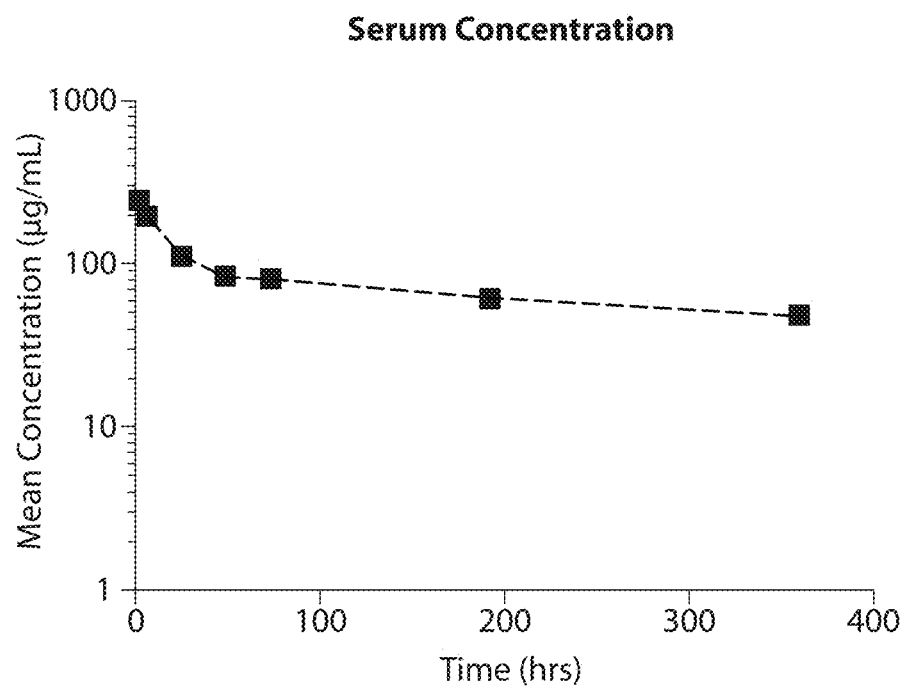

Various pharmacokinetic properties of ABTIM3-hum11 were assessed in mouse and rat models. ABTIM3-hum11 was injected intravenously into mice at varying doses, 1 mg/kg, 3 mg/kg, and 10 mg/kg. Blood samples were obtained at various timepoints between 0 and 672 hours (0-28 days). 10 mg/kg ABTIM3-hum11 was injected intravenously into rats, and blood samples were obtained at various time points from 0-400 hours (0-16 days). The concentration of ABTIM3-hum11 present in the serum was determined (FIGS. 23A and 23B). The results showed that ABTIM3-hum11 is stable in both mouse and rat serum. Table 16 shows additional pharmacokinetic properties determined, including halflife (T1/2), peak serum concentration (Cmax), AUC up to the last measurable concentration (AUClast), and AUC as extrapolated to infinity (AUCinf).

TABLE 16

Summary of pharmacokinetic properties of ABTIM3-hum11

| Species | Dose (mg/kg) | | T½ (hr) | Cmax (µg/mL) | AUClast (hr*µg/mL) | AUCinf (hr*µg/mL) |
|---|---|---|---|---|---|---|
| Mouse | 1 | N | 3 | 3 | 3 | 3 |
| | | Mean | 142.3 | 17.3 | 1507.8 | 1571.4 |
| | | STD | 96.9 | 0.7 | 337.9 | 439.5 |
| | 3 | N | 3 | 3 | 3 | 3 |
| | | Mean | 266.1 | 37.2 | 4617.9 | 5369.0 |
| | | STD | 73.1 | 2.3 | 2109.8 | 2496.1 |
| | 10 | N | 3 | 3 | 3 | 3 |
| | | Mean | 254.9 | 147.5 | 23906.5 | 28621.7 |
| | | STD | 39.2 | 13.2 | 4369.8 | 6314.1 |
| Rat | 10 | N | 3 | 3 | 3 | 3 |
| | | Mean | 400.8 | 243.4 | 26032.3 | 53767.1 |
| | | STD | 75.9 | 19.1 | 895.8 | 5362.6 |

In a toxicity study, three naïve mice were administered a single dose by intravenous injection at 1 mg/kg, 3 mg/kg, or 10 mg/kg of ABTIM3-hum11. After 28 days, no adverse events were observed, indicating that ABTIM3 antibody is tolerable in mouse models.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the compositions and methods herein have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of detecting T-cell immunoglobulin domain and mucin domain 3 (TIM-3) in a biological sample or a subject, comprising (i) contacting the sample or the subject with an antibody molecule capable of binding to human TIM-3 under conditions that allow interaction of the antibody molecule and a TIM-3 polypeptide to occur, and (ii) detecting formation of a complex between the antibody molecule and the sample or the subject;

wherein the antibody molecule comprises:
  (a) a heavy chain variable region (VH) comprising a VHCDR1 amino acid sequence of SEQ ID NO: 9; a VHCDR2 amino acid sequence of SEQ ID NO: 10; and a VHCDR3 amino acid sequence of SEQ ID NO: 5; and a light chain variable region (VL) comprising a VLCDR1 amino acid sequence of SEQ ID NO: 12, a VLCDR2 amino acid sequence of SEQ ID NO: 13, and a VLCDR3 amino acid sequence of SEQ ID NO: 14;
  (b) a VH comprising a VHCDR1 amino acid sequence of SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;
  (c) a VH comprising a VHCDR1 amino acid sequence of SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14;
  (d) a VH comprising a VHCDR1 amino acid sequence of SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8;
  (e) a VH comprising a VHCDR1 amino acid sequence of SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14; or
  (f) a VH comprising a VHCDR1 amino acid sequence of SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

2. The method of claim 1, wherein the method further comprises:
  (i) contacting a reference sample or subject with the antibody molecule; and
  (ii) detecting formation of a complex between the antibody molecule and the reference sample or subject.

3. The method of claim 1, wherein the antibody molecule comprises a VH comprising a VHCDR1 amino acid sequence of SEQ ID NO: 9; a VHCDR2 amino acid sequence of SEQ ID NO: 10; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14.

4. The method of claim 1, wherein the antibody molecule comprises a VH comprising a VHCDR1 amino acid sequence of SEQ ID NO: 3; a VHCDR2 amino acid sequence of SEQ ID NO: 4; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

5. The method of claim 1, wherein the antibody molecule comprises a VH comprising a VHCDR1 amino acid sequence of SEQ ID NO: 9; a VHCDR2 amino acid sequence of SEQ ID NO: 25; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14.

6. The method of claim 1, wherein the antibody molecule comprises a VH comprising a VHCDR1 amino acid sequence of SEQ ID NO: 3; a VHCDR2 amino acid sequence of SEQ ID NO: 24; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

7. The method of claim 1, wherein the antibody molecule comprises a VH comprising a VHCDR1 amino acid sequence of SEQ ID NO: 9; a VHCDR2 amino acid sequence of SEQ ID NO: 31; and a VHCDR3 amino acid sequence of SEQ ID NO: 5; and a VL comprising a VLCDR1 amino acid sequence of SEQ ID NO: 12, a VLCDR2 amino acid sequence of SEQ ID NO: 13, and a VLCDR3 amino acid sequence of SEQ ID NO: 14.

8. The method of claim 1, wherein the antibody molecule comprises a VH comprising a VHCDR1 amino acid sequence of SEQ ID NO: 3; a VHCDR2 amino acid sequence of SEQ ID NO: 30; and a VHCDR3 amino acid sequence of SEQ ID NO: 5; and a VL comprising a VLCDR1 amino acid sequence of SEQ ID NO: 6, a VLCDR2 amino acid sequence of SEQ ID NO: 7, and a VLCDR3 amino acid sequence of SEQ ID NO: 8.

9. The method of claim 1, wherein the antibody molecule is a humanized antibody molecule.

10. The method of claim 1, wherein the antibody molecule comprises a VH comprising an amino acid sequence at least 85% identical to any of SEQ ID NOs: 1, 16, 26, 32, 36, 44, 48, 52, 60, 68, 72, 76, 80, 84, 92, or 100.

11. The method of claim 1, wherein the antibody molecule comprises a VH comprising an amino acid sequence of SEQ ID NO: 1, 16, 26, 32, 36, 44, 48, 52, 60, 68, 72, 76, 80, 84, 92, or 100.

12. The method of claim 1, wherein the antibody molecule comprises a VL comprising an amino acid sequence at least 85% identical to any of SEQ ID NOs: 2, 20, 40, 56, 64, 88, 96, or 104.

13. The method of claim 1, wherein the antibody molecule comprises a VL comprising the amino acid sequence of SEQ ID NO: 2, 20, 40, 56, 64, 88, 96, or 104.

14. The method of claim 1, wherein the antibody molecule comprises:

(a) a VH comprising the amino acid sequence of SEQ ID NO: 1 and a VL comprising the amino acid sequence of SEQ ID NO: 2;
(b) a VH comprising the amino acid sequence of SEQ ID NO: 16 and a VL comprising the amino acid sequence of SEQ ID NO: 20;
(c) a VH comprising the amino acid sequence of SEQ ID NO: 26 and a VL comprising the amino acid sequence of SEQ ID NO: 20;
(d) a VH comprising the amino acid sequence of SEQ ID NO: 32 and a VL comprising the amino acid sequence of SEQ ID NO: 20;
(e) a VH comprising the amino acid sequence of SEQ ID NO: 36 and a VL comprising the amino acid sequence of SEQ ID NO: 40;
(f) a VH comprising the amino acid sequence of SEQ ID NO: 44 and a VL comprising the amino acid sequence of SEQ ID NO: 40;
(g) a VH comprising the amino acid sequence of SEQ ID NO: 48 and a VL comprising the amino acid sequence of SEQ ID NO: 40;
(h) a VH comprising the amino acid sequence of SEQ ID NO: 36 and a VL comprising the amino acid sequence of SEQ ID NO: 20;
(i) a VH comprising the amino acid sequence of SEQ ID NO: 16 and a VL comprising the amino acid sequence of SEQ ID NO: 40;
(j) a VH comprising the amino acid sequence of SEQ ID NO: 52 and a VL comprising the amino acid sequence of SEQ ID NO: 56;
(k) a VH comprising the amino acid sequence of SEQ ID NO: 60 and a VL comprising the amino acid sequence of SEQ ID NO: 56;
(l) a VH comprising the amino acid sequence of SEQ ID NO: 52 and a VL comprising the amino acid sequence of SEQ ID NO: 64;
(m) a VH comprising the amino acid sequence of SEQ ID NO: 60 and a VL comprising the amino acid sequence of SEQ ID NO: 64;
(n) a VH comprising the amino acid sequence of SEQ ID NO: 68 and a VL comprising the amino acid sequence of SEQ ID NO: 64;
(o) a VH comprising the amino acid sequence of SEQ ID NO: 72 and a VL comprising the amino acid sequence of SEQ ID NO: 64;
(p) a VH comprising the amino acid sequence of SEQ ID NO: 76 and a VL comprising the amino acid sequence of SEQ ID NO: 56;
(q) a VH comprising the amino acid sequence of SEQ ID NO: 80 and a VL comprising the amino acid sequence of SEQ ID NO: 56;
(r) a VH comprising the amino acid sequence of SEQ ID NO: 68 and a VL comprising the amino acid sequence of SEQ ID NO: 56;
(s) a VH comprising the amino acid sequence of SEQ ID NO: 72 and a VL comprising the amino acid sequence of SEQ ID NO: 56;
(t) a VH comprising the amino acid sequence of SEQ ID NO: 76 and a VL comprising the amino acid sequence of SEQ ID NO: 64;
(u) a VH comprising the amino acid sequence of SEQ ID NO: 80 and a VL comprising the amino acid sequence of SEQ ID NO: 64;
(v) a VH comprising the amino acid sequence of SEQ ID NO: 84 and a VL comprising the amino acid sequence of SEQ ID NO: 88;
(w) a VH comprising the amino acid sequence of SEQ ID NO: 92 and a VL comprising the amino acid sequence of SEQ ID NO: 96; or
(x) a VH comprising the amino acid sequence of SEQ ID NO: 100 and a VL comprising the amino acid sequence of SEQ ID NO: 104.

15. The method of claim 1, wherein the antibody molecule comprises:
(a) a heavy chain comprising the amino acid sequence of SEQ ID NO: 18 and a light chain comprising the amino acid sequence of SEQ ID NO: 22;
(b) a heavy chain comprising the amino acid sequence of SEQ ID NO: 28 and a light chain comprising the amino acid sequence of SEQ ID NO: 22;
(c) a heavy chain comprising the amino acid sequence of SEQ ID NO: 34 and a light chain comprising the amino acid sequence of SEQ ID NO: 22;
(d) a heavy chain comprising the amino acid sequence of SEQ ID NO: 38 and a light chain comprising the amino acid sequence of SEQ ID NO: 42;
(e) a heavy chain comprising the amino acid sequence of SEQ ID NO: 46 and a light chain comprising the amino acid sequence of SEQ ID NO: 42;
(f) a heavy chain comprising the amino acid sequence of SEQ ID NO: 50 and a light chain comprising the amino acid sequence of SEQ ID NO: 42;
(g) a heavy chain comprising the amino acid sequence of SEQ ID NO: 116 and a light chain comprising the amino acid sequence of SEQ ID NO: 22;
(h) a heavy chain comprising the amino acid sequence of SEQ ID NO: 121 and a light chain comprising the amino acid sequence of SEQ ID NO: 42;
(i) a heavy chain comprising the amino acid sequence of SEQ ID NO: 54 and a light chain comprising the amino acid sequence of SEQ ID NO: 58;
(j) a heavy chain comprising the amino acid sequence of SEQ ID NO: 62 and a light chain comprising the amino acid sequence of SEQ ID NO: 58;
(k) a heavy chain comprising the amino acid sequence of SEQ ID NO: 54 and a light chain comprising the amino acid sequence of SEQ ID NO: 66;
(l) a heavy chain comprising the amino acid sequence of SEQ ID NO: 62 and a light chain comprising the amino acid sequence of SEQ ID NO: 66;
(m) a heavy chain comprising the amino acid sequence of SEQ ID NO: 70 and a light chain comprising the amino acid sequence of SEQ ID NO: 66;
(n) a heavy chain comprising the amino acid sequence of SEQ ID NO: 74 and a light chain comprising the amino acid sequence of SEQ ID NO: 66;
(o) a heavy chain comprising the amino acid sequence of SEQ ID NO: 78 and a light chain comprising the amino acid sequence of SEQ ID NO: 58;
(p) a heavy chain comprising the amino acid sequence of SEQ ID NO: 82 and a light chain comprising the amino acid sequence of SEQ ID NO: 58;
(r) a heavy chain comprising the amino acid sequence of SEQ ID NO: 70 and a light chain comprising the amino acid sequence of SEQ ID NO: 58;
(s) a heavy chain comprising the amino acid sequence of SEQ ID NO: 74 and a light chain comprising the amino acid sequence of SEQ ID NO: 58;
(t) a heavy chain comprising the amino acid sequence of SEQ ID NO: 78 and a light chain comprising the amino acid sequence of SEQ ID NO: 66;

(u) a heavy chain comprising the amino acid sequence of SEQ ID NO: 82 and a light chain comprising the amino acid sequence of SEQ ID NO: 66;
(v) a heavy chain comprising the amino acid sequence of SEQ ID NO: 86 and a light chain comprising the amino acid sequence of SEQ ID NO: 90;
(w) a heavy chain comprising the amino acid sequence of SEQ ID NO: 94 and a light chain comprising the amino acid sequence of SEQ ID NO: 98; or
(x) a heavy chain comprising the amino acid sequence of SEQ ID NO: 102 and a light chain comprising the amino acid sequence of SEQ ID NO: 106.

16. The method of claim 1, wherein the antibody molecule comprises a heavy chain constant region of IgG1, IgG2, IgG3, and IgG4.

17. The method of claim 1, wherein the antibody molecule comprises a light chain constant region of kappa or lambda.

18. The method of claim 1, wherein the antibody molecule is a Fab, F(ab')2, Fv, or a single chain Fv fragment (scFv).

19. The method of claim 1, wherein the antibody molecule comprises a human IgG4 heavy chain constant region with a Serine to Proline mutation at position 108 of SEQ ID NO: 108 or 110 and a kappa light chain constant region.

20. The method of claim 1, wherein the antibody molecule comprises one or more of:
(i) a human IgG1 heavy chain constant region with an Asparagine to Alanine mutation at position 180 of SEQ ID NO: 112 and a kappa light chain constant region;
(ii) a human IgG1 heavy chain constant region with an Aspartate to Alanine mutation at position 148 of SEQ ID NO: 113 and Proline to Alanine mutation at position 212 of SEQ ID NO: 113, and a kappa light chain constant region; or
(iii) a human IgG1 heavy chain constant region with a Leucine to Alanine mutation at position 117 of SEQ ID NO: 114 and Leucine to Alanine mutation at position 118 of SEQ ID NO: 114, and a kappa light chain constant region.

\* \* \* \* \*